(12) United States Patent
Lee et al.

(10) Patent No.: US 12,410,186 B2
(45) Date of Patent: Sep. 9, 2025

(54) COMPOUND, ORGANIC OPTOELECTRONIC ELEMENT, AND DISPLAY DEVICE

(71) Applicant: LT MATERIALS CO., LTD., Yongin-Si (KR)

(72) Inventors: Nam-Jin Lee, Osan-si (KR); Young-Jin Lee, Osan-si (KR); Won-Jang Jeong, Hwaseong-si (KR)

(73) Assignee: LT MATERIALS CO., LTD., Yongin (KR)

(*) Notice: Subject to any disclaimer, the term of this patent is extended or adjusted under 35 U.S.C. 154(b) by 916 days.

(21) Appl. No.: 17/426,754

(22) PCT Filed: Jan. 30, 2020

(86) PCT No.: PCT/KR2020/001417
§ 371 (c)(1),
(2) Date: Jul. 29, 2021

(87) PCT Pub. No.: WO2020/159249
PCT Pub. Date: Aug. 6, 2020

(65) Prior Publication Data
US 2022/0098217 A1 Mar. 31, 2022

(30) Foreign Application Priority Data
Jan. 30, 2019 (KR) .................. 10-2019-0012107

(51) Int. Cl.
*C07D 519/00* (2006.01)
*C07D 498/04* (2006.01)
(Continued)

(52) U.S. Cl.
CPC ......... *C07D 519/00* (2013.01); *C07D 498/04* (2013.01); *C07D 513/04* (2013.01);
(Continued)

(58) Field of Classification Search
CPC .. C07D 519/00; C07D 498/04; C07D 513/04; C07F 9/28; H10K 85/622; H10K 85/654; H10K 85/6574; H10K 50/18; H10K 50/16
(Continued)

(56) References Cited

U.S. PATENT DOCUMENTS 4,356,429 A 10/1982 Tang
8,968,887 B2 3/2015 Ma et al.
(Continued)

FOREIGN PATENT DOCUMENTS

| CN | 107501336 A | 12/2017 |
| CN | 108276452 A | 7/2018 |

(Continued)

OTHER PUBLICATIONS

International Search Report (PCT/ISA/210) issued in PCT/KR2020/001417 mailed on May 12, 2020.
(Continued)

*Primary Examiner* — Ruiyun Zhang
(74) *Attorney, Agent, or Firm* — Birch, Stewart, Kolasch & Birch, LLP

(57) ABSTRACT

The present application relates to a compound represented by Chemical Formula 1, an organic optoelectronic diode and a display device.
(Continued)

[Chemical Formula 1]

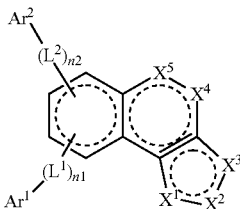

In Chemical Formula 1, each substituent has the same definition as in the specification.

5 Claims, 3 Drawing Sheets

(51) Int. Cl.
C07D 513/04 (2006.01)
C07F 9/28 (2006.01)
H10K 85/60 (2023.01)
H10K 50/16 (2023.01)
H10K 50/18 (2023.01)

(52) U.S. Cl.
CPC ............ *C07F 9/28* (2013.01); *H10K 85/622* (2023.02); *H10K 85/626* (2023.02); *H10K 85/654* (2023.02); *H10K 85/6572* (2023.02); *H10K 85/6574* (2023.02); *H10K 50/16* (2023.02); *H10K 50/18* (2023.02)

(58) Field of Classification Search
USPC .......................................................... 428/1.1
See application file for complete search history.

(56) References Cited

U.S. PATENT DOCUMENTS

| | | |
|---|---|---|
| 2012/0010237 A1 | 1/2012 | Riscoe et al. |
| 2013/0033172 A1 | 2/2013 | Huang et al. |
| 2014/0027741 A1 | 1/2014 | Park et al. |
| 2015/0191478 A1 | 7/2015 | Seo et al. |
| 2016/0347715 A1 | 12/2016 | David et al. |
| 2017/0096422 A1 | 4/2017 | Tsukamoto et al. |
| 2020/0227650 A1 | 7/2020 | Kim et al. |

FOREIGN PATENT DOCUMENTS

| | | |
|---|---|---|
| CN | 108299512 A | 7/2018 |
| KR | 10-2013-0067274 A | 6/2013 |
| KR | 10-2014-0013962 A | 2/2014 |
| TW | 201410662 A | 3/2014 |
| WO | WO 2012/167237 A2 | 12/2012 |
| WO | WO 2015/095780 A1 | 6/2015 |
| WO | WO 2015/146929 A1 | 10/2015 |
| WO | WO 2019/004584 A1 | 1/2019 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials", Advanced Materials, 1994, vol. 6, No. 9, pp. 677-679.

[FIG. 1]
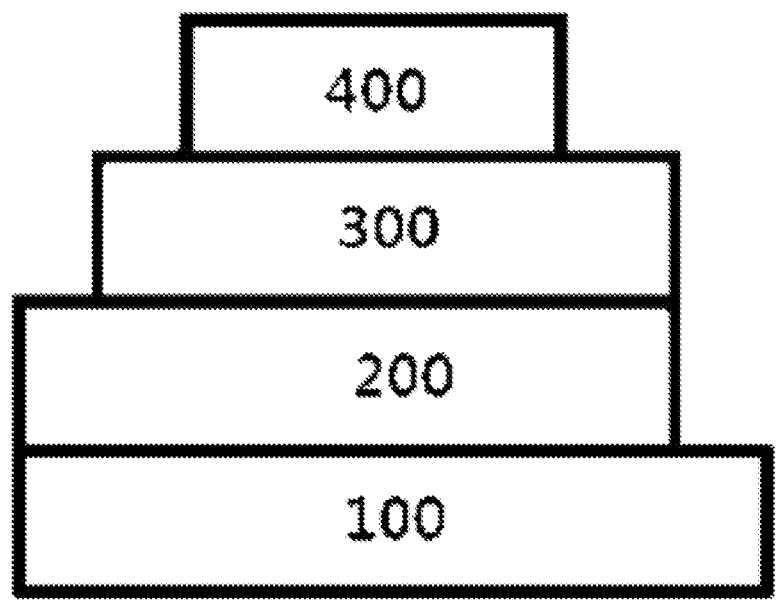

【FIG. 2】
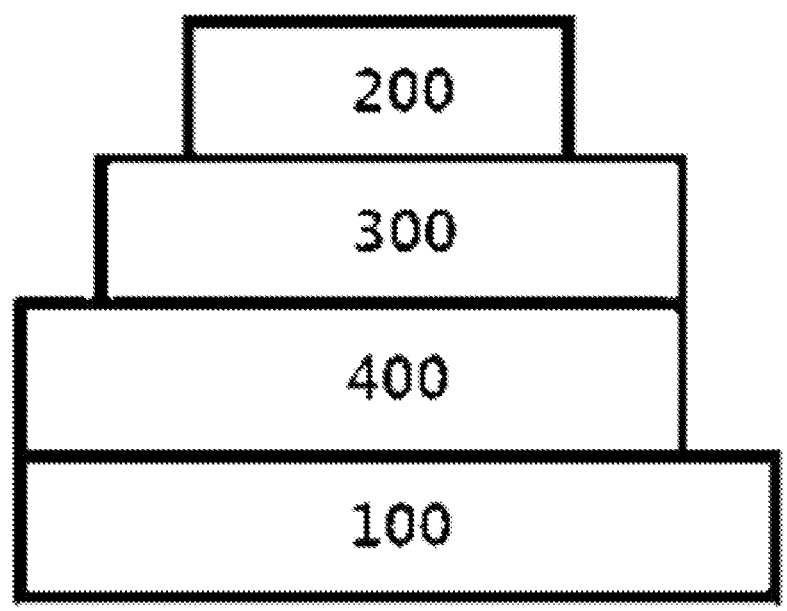

[FIG. 3]
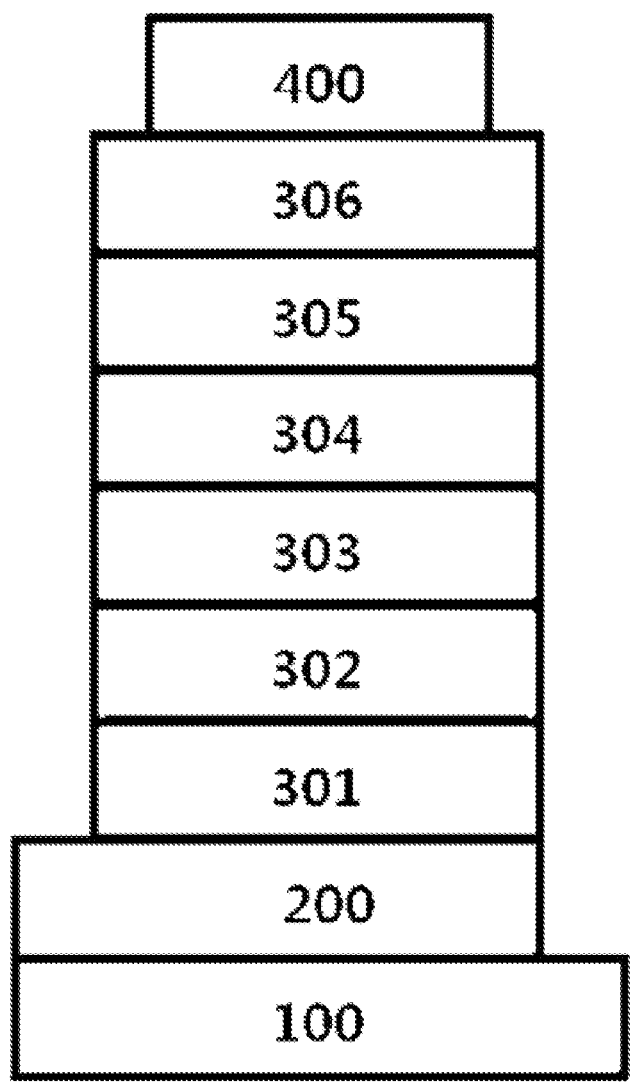

COMPOUND, ORGANIC OPTOELECTRONIC ELEMENT, AND DISPLAY DEVICE

TECHNICAL FIELD

This application claims priority to and the benefits of Korean Patent Application No. 10-2019-0012107, filed with the Korean Intellectual Property Office on Jan. 30, 2019, the entire contents of which are incorporated herein by reference.

The present application relates to a compound, an organic optoelectronic diode and a display device.

BACKGROUND ART

An organic optoelectronic diode is a device capable of interconverting electrical energy and light energy.

An organic optoelectronic diode may be divided into two types depending on the operating principle. One is an optoelectronic diode in which excitons formed by light energy are separated into electrons and holes and electrical energy is generated while the electrons and the holes are each transferred to different electrodes, and the other one is a light emitting diode generating light energy from electrical energy by supplying a voltage or a current to electrodes.

Examples of the organic optoelectronic diode may comprise an organic photoelectric diode, an organic light emitting diode, an organic solar cell, an organic photo conductor drum and the like.

Among these, an organic light emitting diode (OLED) has received much attention recently as demands for flat panel display devices have increased. An organic light emitting diode is a device converting electrical energy to light, and performance of an organic light emitting diode is greatly affected by organic materials disposed between electrodes.

An organic light emitting diode has a structure disposing an organic thin film between two electrodes. When a voltage is applied to an organic light emitting diode having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used.

In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting diode.

DISCLOSURE

Technical Problem

One embodiment of the present specification is directed to providing a compound capable of obtaining an organic optoelectronic diode with high efficiency and long lifetime.

Another embodiment of the present specification is directed to providing an organic optoelectronic diode comprising the compound.

Still another embodiment of the present specification is directed to providing a display device comprising the organic optoelectronic diode.

Technical Solution

One embodiment of the present disclosure provides a compound represented by the following Chemical Formula 1.

[Chemical Formula 1]

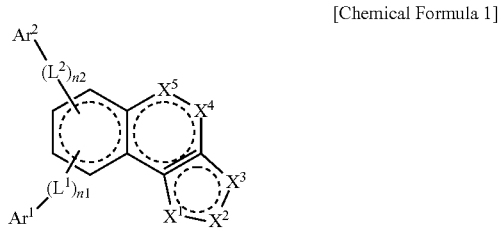

In Chemical Formula 1, any one of $X^4$ and $X^5$ is —N—, and the other one is —$C(L^2)_{n3}Ar^3$—, $Ar^3$ is hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $X^1$ to $X^3$ are each independently —$C(L^4)_{n4}Ar^4$—; —$C(L^5)_{n5}Ar^5$—; —O—; or —S—, and any one of $X^1$ to $X^3$ is —O—; or —S—, $Ar^4$ and $Ar^5$ are each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $Ar^1$ and $Ar^2$ are each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $L^1$ to $L^5$ are each independently a single bond; a substituted or unsubstituted C6 to C60 arylene group; or a substituted or unsubstituted C2 to C60 heteroarylene group, R and R' are each independently hydrogen; a substituted or unsubstituted C1 to C60 alkyl group; a substituted or unsubstituted C6 to C60 aryl group; or a substituted or unsubstituted C2 to C60 heteroaryl group, n1 to n5 are each independently one of integers of 0 to 4, and at least any one of $Ar^1$ to $Ar^5$ is a substituent having electron properties; or a substituent having hole properties.

The compound may be represented by the following Chemical Formula 2.

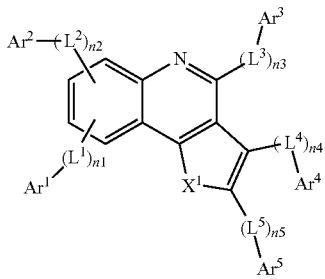

[Chemical Formula 2]

In Chemical Formula 2, $X^1$ is —O—; or —S—, $Ar^1$ to $Ar^5$ are each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $L^1$ to $L^5$ are each independently a single bond; a substituted or unsubstituted C6 to C60 arylene group; or a substituted or unsubstituted C2 to C60 heteroarylene group, n1 to n5 are each independently one of integers of 0 to 4, R and R' are each independently hydrogen; a substituted or unsubstituted C1 to C60 alkyl group; a substituted or unsubstituted C6 to C60 aryl group; or a substituted or unsubstituted C2 to C60 heteroaryl group, and at least any one of $Ar^1$ to $Ar^5$ is a substituent having electron properties; or a substituent having hole properties.

The compound may be represented by the following Chemical Formula 3.

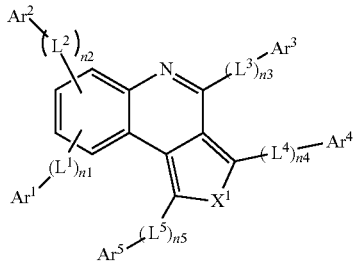

[Chemical Formula 3]

In Chemical Formula 3, $X^1$ is —O—; or —S—, $Ar^1$ to $Ar^5$ are each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $L^1$ to $L^5$ are each independently a single bond; a substituted or unsubstituted C6 to C60 arylene group; or a substituted or unsubstituted C2 to C60 heteroarylene group, n1 to n5 are each independently one of integers of 0 to 4, R and R' are each independently hydrogen; a substituted or unsubstituted C1 to C60 alkyl group; a substituted or unsubstituted C6 to C60 aryl group; or a substituted or unsubstituted C2 to C60 heteroaryl group, and at least any one of $Ar^1$ to $Ar^5$ is a substituent having electron properties; or a substituent having hole properties.

The compound may be represented by the following Chemical Formula 4.

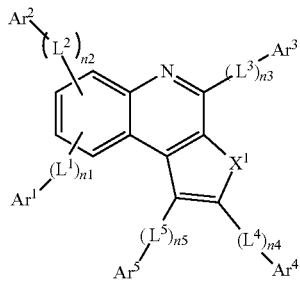

[Chemical Formula 4]

In Chemical Formula 4, $X^1$ is —O—; or —S—, $Ar^1$ to $Ar^5$ are each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $L^1$ to $L^5$ are each independently a single bond; a substituted or unsubstituted C6 to C60 arylene group; or a substituted or unsubstituted C2 to C60 heteroarylene group, n1 to n5 are each independently one of integers of 0 to 4, R and R' are each independently hydrogen; a substituted or unsubstituted C1 to C60 alkyl group; a substituted or unsubstituted C6 to C60 aryl group; or a substituted or unsubstituted C2 to C60 heteroaryl group, and at least any one of $Ar^1$ to $Ar^5$ is a substituent having electron properties; or a substituent having hole properties.

Another embodiment of the present specification provides an organic optoelectronic diode comprising an anode and a cathode facing each other, and at least one organic layer disposed between the anode and the cathode, wherein the organic layer comprises the compound.

Still another embodiment of the present specification provides a display device comprising the organic optoelectronic diode.

Advantageous Effects

An organic optoelectronic diode with high efficiency and long lifetime can be obtained.

DESCRIPTION OF DRAWINGS

FIG. 1 to FIG. 3 are sectional diagrams each illustrating an organic light emitting diode according to one embodiment of the present specification.

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, embodiments of the present disclosure will be described in detail. However, these are for illustrative purposes only, and the present disclosure is not limited thereto, and is only defined by the category of claims to describe later.

In the present specification, "substituted or unsubstituted" means being substituted with one or more substituents selected from the group consisting of deuterium; a halogen group; —CN; a C1 to C60 linear or branched alkyl group; a C2 to C60 linear or branched alkenyl group; a C2 to C60 linear or branched alkynyl group; a C3 to C60 monocyclic or polycyclic cycloalkyl group; a C2 to C60 monocyclic or polycyclic heterocycloalkyl group; a C6 to C60 monocyclic or polycyclic aryl group; a C2 to C60 monocyclic or polycyclic heteroaryl group; —SiRR'R"; —P(=O)RR'; a C1 to C20 alkylamine group; a C6 to C60 monocyclic or polycyclic arylamine group; a C2 to C60 monocyclic or polycyclic heteroarylamine group, and a substituted or unsubstituted alkoxy group, or being unsubstituted, or being substituted with a substituent bonding two or more of the substituents, or being unsubstituted, or being substituted with a substituent linking two or more substituents selected from among the above-mentioned substituents, or being unsubstituted. In addition, these may further form a ring with adjacent substituents.

For example, the "substituent linking two or more substituents" may comprise a biphenyl group. In other words, a biphenyl group may be an aryl group, or interpreted as a substituent linking two phenyl groups. The additional substituents may be further substituted. R, R' and R" are the same as or different from each other, and each independently hydrogen; deuterium; —CN; a substituted or unsubstituted C1 to C60 linear or branched alkyl group; a substituted or unsubstituted C3 to C60 monocyclic or polycyclic cycloalkyl group; a substituted or unsubstituted C6 to C60 monocyclic or polycyclic aryl group; or a substituted or unsubstituted C2 to C60 monocyclic or polycyclic heteroaryl group.

According to one embodiment of the present application, the "substituted or unsubstituted" means being substituted with one or more substituents selected from the group consisting of deuterium, a halogen group, —CN, —SiRR'R", —P(=O)RR', a C1 to C20 linear or branched alkyl group, a C6 to C60 monocyclic or polycyclic aryl group and a C2 to C60 monocyclic or polycyclic heteroaryl group, or being unsubstituted, and R, R' and R" are the same as or different from each other and each independently hydrogen; deuterium; —CN; a C1 to C60 alkyl group unsubstituted or substituted with deuterium, a halogen group, —CN, a C1 to C20 alkyl group, a C6 to C60 aryl group and a C2 to C60 heteroaryl group; a C3 to C60 cycloalkyl group unsubstituted or substituted with deuterium, halogen, —CN, a C1 to C20 alkyl group, a C6 to C60 aryl group and a C2 to C60 heteroaryl group; a C6 to C60 aryl group unsubstituted or substituted with deuterium, halogen, —CN, a C1 to C20 alkyl group, a C6 to C60 aryl group and a C2 to C60 heteroaryl group; or a C2 to C60 heteroaryl group unsubstituted or substituted with deuterium, halogen, —CN, a C1 to C20 alkyl group, a C6 to C60 aryl group and a C2 to C60 heteroaryl group.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may comprise fluorine, chlorine, bromine or iodine.

In the present specification, the alkyl group comprises a C1 to C60 linear or branched, and may be further substituted with other substituents. The number of carbon atoms of the alkyl group may be from 1 to 60, specifically from 1 to 40, specifically from 1 to 20 and more specifically from 1 to 10. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises a C2 to C60 linear or branched, and may be further substituted with other substituents. The number of carbon atoms of the alkenyl group may be from 2 to 60, specifically from 2 to 40, and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises a C2 to C60 linear or branched, and may be further substituted with other substituents. The number of carbon atoms of the alkynyl group may be from 2 to 60, specifically from 2 to 40, and more specifically from 2 to 20.

In the present specification, the cycloalkyl group comprises a C3 to C60 monocyclic or polycyclic, and may be further substituted with other substituents. Herein, the polycyclic means a group in which the cycloalkyl group is directly linked to or fused with another cyclic group. Herein, the another cyclic group may be a cycloalkyl group, but may also comprise other types of cyclic groups such as a heterocycloalkyl group, an aryl group and a heteroaryl group. The number of carbon atoms of the cycloalkyl group may be from 3 to 60, specifically from 3 to 40, and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4 methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group may comprise a C1 to C10 alkoxy group, and more specifically, a methoxy group, an ethoxy group, a propoxy group, a butoxy group, a pentoxy group and the like.

In the present specification, the silyl group may be represented by —SiRR'R", and R, R' and R" have the same definitions as above. More specifically, a dimethylsilyl group, a diethylsilyl group, a methylethylsilyl group and the like may be included.

In the present specification, the phosphine oxide group may be represented by —P(=O)RR', and R and R' have the same definitions as above. More specifically, —P(=O) dimethyl, —P(=O)diethyl, —P(=O)methylethyl and the like may be included.

In the present specification, the fluorenyl group means a substituent comprising various substituents at the number 9 position. Specifically, a concept comprising a fluorenyl group in which the number 9 position is substituted with two hydrogens, two alkyl groups, two aryl groups or two heteroaryl groups may be used. More specifically, a 9-di-H-fluorenyl group, a 9-di-methyl-fluorenyl group, a 9-di-phenyl-fluorenyl group or the like may be used.

In the present specification, the heterocycloalkyl group comprises O, S, Se, N or Si as a heteroatom, comprises a C2 to C60 monocyclic or polycyclic, and may be further substituted with other substituents. Herein, the polycyclic means a group in which the heterocycloalkyl group is directly linked to or fused with another cyclic group. Herein, the another cyclic group may be a heterocycloalkyl group, but may also comprise other types of cyclic groups such as a cycloalkyl group, an aryl group and a heteroaryl group. The number of carbon atoms of the heterocycloalkyl group may be from 2 to 60, specifically from 2 to 40, and more specifically from 3 to 20.

In the present specification, the aryl group comprises a C6 to C60 monocyclic or polycyclic, and may be further substituted with other substituents. Herein, the polycyclic means a group in which the aryl group is directly linked to or fused with another cyclic group. Herein, the another cyclic group may be an aryl group, but may also comprise other types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40, specifically from 6 to 30 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof and the like, but are not limited thereto.

In the present specification, the spiro group is a group comprising a spiro structure, and may be from C15 to C60. For example, the Spiro group may comprise a structure in which a 2,3-dihydro-1H-indene group or a cyclohexane group spiro-bonds to a fluorenyl group. Specifically, the Spiro group may comprise any one of the groups of the following structural formulae.

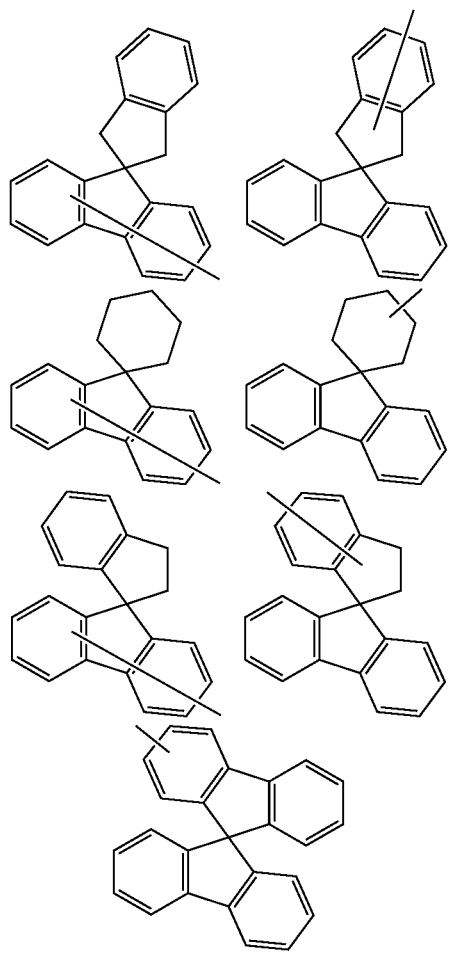

In the present specification, the heteroaryl group comprises S, O, Se, N or Si as a heteroatom, comprises a C2 to C60 monocyclic or polycyclic, and may be further substituted with other substituents. Herein, the polycyclic means a group in which the heteroaryl group is directly linked to or fused with another cyclic group. Herein, the another cyclic group may be a heteroaryl group, but may also comprise other types of cyclic groups such as a cycloalkyl group, a heterocycloalkyl group and an aryl group. The number of carbon atoms of the heteroaryl group may be from 2 to 60, specifically from 2 to 40, specifically from 2 to 30 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinozolinyl group, a naphthyridyl group, an acridinyl group, a phenanthridinyl group, an imidazopyridinyl group, diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, 9,10-dihydroacridinyl group, a phenanthrazinyl group, a phenothiathiazinyl group, a phthalazinyl group, a naphthyridinyl group, a phenanthrolinyl group, a benzo[c][1,2,5]thiadiazolyl group, 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means an aryl group having two bonding sites, that is, a divalent group. Descriptions on the aryl group provided above may be applied thereto except for each being a divalent group. In addition, the heteroarylene group means a heteroaryl group having two bonding sites, that is, a divalent group. Descriptions on the heteroaryl group provided above may be applied thereto except for each being a divalent group.

In the present specification, hole properties refer to properties capable of forming holes by donating electrons when applying an electric field, and means properties of, by having conducting properties along the HOMO level, facilitating injection of holes formed in an anode to a light emitting layer, migration of holes formed in a light emitting layer to an anode and migration in the light emitting layer.

Substituents having hole properties comprise a substituted or unsubstituted C6 to C60 aryl group having hole properties, a substituted or unsubstituted C2 to C60 heteroaryl group having hole properties, a substituted or unsubstituted arylamine group, a substituted or unsubstituted heteroarylamine group, or the like.

More specifically, the substituted or unsubstituted C6 to C60 aryl group having hole properties may be a substituted or unsubstituted phenyl group, a substituted or unsubstituted naphthyl group, a substituted or unsubstituted phenanthrenyl group, a substituted or unsubstituted anthracenyl group, a substituted or unsubstituted fluorenyl group, a substituted or unsubstituted triphenylenyl group, a substituted or unsubstituted spiro-fluorenyl group, a substituted or unsubstituted terphenyl group, a substituted or unsubstituted pyrenyl group, a substituted or unsubstituted perylenyl group, or a combination thereof.

More specifically, the substituted or unsubstituted C2 to C60 heteroaryl group having hole properties is a substituted or unsubstituted carbazolyl group, a substituted or unsubstituted dibenzofuranyl group, a substituted or unsubstituted dibenzothiophenyl group, a substituted or unsubstituted indolecarbazolyl group, or the like.

The aryl group or the heteroaryl group, a substituent bonding to the nitrogen of the substituted or unsubstituted arylamine group and the substituted or unsubstituted heteroarylamine group may be, more specifically, a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

In addition, electron properties refer to properties capable of receiving electrons when applying an electric field, and means properties of, by having conducting properties along the LUMO level, facilitating injection of electrons formed in a cathode to a light emitting layer, migration of electrons formed in a light emitting layer to a cathode and migration in the light emitting layer.

The substituted or unsubstituted C2 to C60 heteroaryl group having electron properties may be a substituted or unsubstituted imidazolyl group, a substituted or unsubstituted tetrazolyl group, a substituted or unsubstituted quinolinylene group, a substituted or unsubstituted isoquinolinylene group, a substituted or unsubstituted pyridinylene group, a substituted or unsubstituted pyrimidinylene group, a substituted or unsubstituted triazinylene group, a substituted or unsubstituted furanyl group, a substituted or unsubstituted benzofuranyl group, a substituted or unsubstituted isofuranyl group, a substituted or unsubstituted benzoisofuranyl group, a substituted or unsubstituted oxazoline group, a substituted or unsubstituted benzoxazoline group, a substituted or unsubstituted oxadiazoline group, a substituted or unsubstituted benzoxadiazoline group, a substituted or unsubstituted oxatriazolyl group, a substituted or unsubstituted thiophenyl group, a substituted or unsubstituted benzothiophenyl group, a substituted or unsubstituted isothiazoline group, a substituted or unsubstituted benzoisothiazoline group, a substituted or unsubstituted thiazoline group, a substituted or unsubstituted benzothiazoline group, a substituted or unsubstituted pyridazinyl group, a substituted or unsubstituted benzopyridazinyl group, a substituted or unsubstituted pyrazinyl group, a substituted or unsubstituted benzopyrazinyl group, a substituted or unsubstituted phthalazinyl group, a substituted or unsubstituted benzoquinolinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

More specifically, the substituted or unsubstituted C2 to C60 heteroaryl group having electron properties may be any one of the following Chemical Formulae X-1 to X-5.

[Chemical Formula X-1]

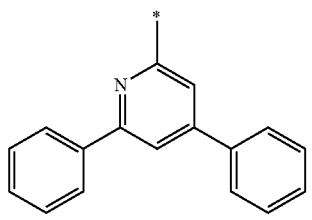

[Chemical Formula X-2]

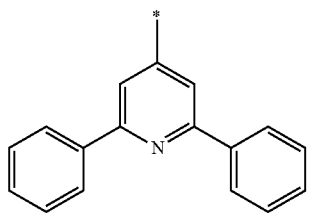

[Chemical Formula X-3]

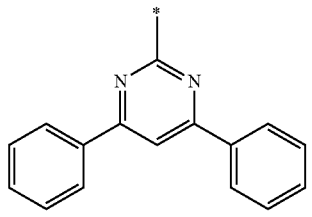

[Chemical Formula X-4]

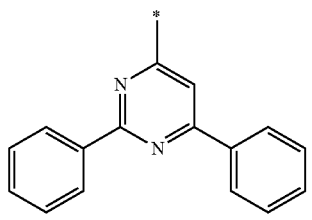

[Chemical Formula X-5]

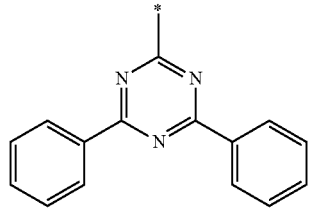

In one embodiment of the present application, $L^n$ may be a direct bond (or a single bond); a substituted or unsubstituted arylene group; or a substituted or unsubstituted heteroarylene group.

In another embodiment, $L^n$ may be a direct bond; a substituted or unsubstituted C6 to C60 arylene group; or a substituted or unsubstituted C2 to C60 heteroarylene group.

In another embodiment, $L^n$ may be a direct bond; a substituted or unsubstituted C6 to C40 arylene group; or a substituted or unsubstituted C2 to C40 heteroarylene group.

In $L^n$, n means a number for distinguishing substituents.

Hereinafter, a compound according to one embodiment will be described.

The compound according to one embodiment is represented by the following Chemical Formula 1.

[Chemical Formula 1]

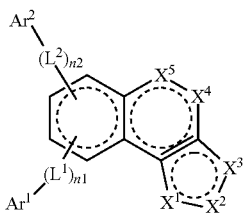

In Chemical Formula 1,
any one of $X^4$ and $X^5$ is —N—, and the other one is —C($L^3$)$_{n3}$Ar$^3$—, $Ar^3$ is hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $X^1$ to $X^3$ are each independently any one of —C($L^4$)$_{n4}$Ar$^4$; —C($L^5$)$_{n5}$Ar$^5$—; —O—; or —S—, and any one of $X^1$ to $X^3$ is —O—; or —S—, $Ar^4$ and $Ar^5$ are each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $Ar^1$ and $Ar^2$ are each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $L^1$ to $L^5$ are each independently a single bond; a substituted or unsubstituted C6 to C60 arylene group; or a substituted or unsubstituted C2 to C60 heteroarylene group, R and R' are each independently hydrogen; a substituted or unsubstituted C1 to C60 alkyl group; a substituted or unsubstituted C6 to C60 aryl group; or a substituted or unsubstituted C2 to C60 heteroaryl group, n1 to n5 are each independently one of integers of 0 to 4, at least any one of $Ar^1$ to $Ar^5$ is a substituent having electron properties; or a substituent having hole properties.

The compound represented by Chemical Formula 1 has a structure in which the substituent having electron properties or hole properties bonds to the fused ring that is a core.

The compound corresponding to Chemical Formula 1 of the present application allows the fused ring corresponding to the core structure to have an expanded HOMO/LUMO electron cloud, and, by adjusting the HOMO/LUMO energy level therethrough, hole/electron injection and hole/electron transfer abilities are further enhanced, and as a result, a driving voltage of a device using the same may be lowered.

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting diode to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and thereby has excellent thermal stability. Such an increase in the thermal stability becomes an important factor in providing driving stability to a device.

More specifically, the compound may be represented by any one of the following Chemical Formulae 2 to 4.

[Chemical Formula 2]

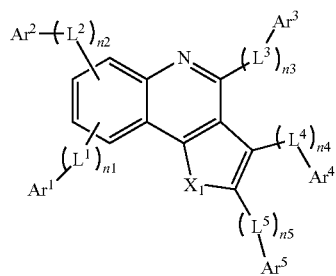

[Chemical Formula 3]

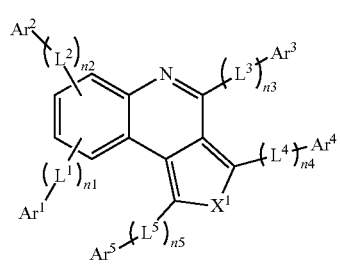

[Chemical Formula 4]

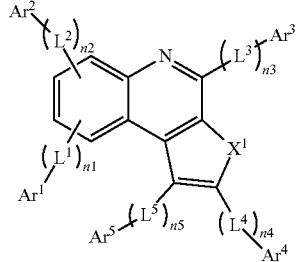

In Chemical Formulae 2 to 4, $X^1$ is —O—; or —S—, $Ar^1$ to $Ar^5$ are each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, $L^1$ to $L^5$ are each independently a single bond; a substituted or unsubstituted C6 to C60 arylene group; or a substituted or unsubstituted C2 to C60 heteroarylene group, n1 to n5 are each independently one of integers of 0 to 4, R and R' are each independently hydrogen; a substituted or unsubstituted C1 to C60 alkyl group; a substituted or unsubstituted C6 to C60 aryl group; or a substituted or unsubstituted C2 to C60 heteroaryl group, and at least any one of $Ar^1$ to $Ar^5$ is a substituent having electron properties; or a substituent having hole properties.

In one embodiment of the present application, $L^1$ to $L^5$ may be each independently a single bond; a substituted or unsubstituted C6 to C60 arylene group; or a substituted or unsubstituted C2 to C60 heteroarylene group.

In another embodiment, $L^1$ to $L^5$ may be each independently a single bond; a substituted or unsubstituted C6 to C40 arylene group; or a substituted or unsubstituted C2 to C40 heteroarylene group.

In another embodiment, $L^1$ to $L^5$ may be each independently a single bond; a C6 to C40 arylene group unsubstituted or substituted with a C2 to C40 heteroaryl group; or a C2 to C40 heteroarylene group unsubstituted or substituted with a C6 to C40 aryl group.

In another embodiment, $L^1$ to $L^5$ may be each independently a single bond; a substituted or unsubstituted phenylene group; a substituted or unsubstituted biphenylene group; a substituted or unsubstituted anthracene group; a substituted or unsubstituted divalent pyrimidine group; a substituted or unsubstituted divalent pyridine group; or a substituted or unsubstituted divalent triazine group.

In another embodiment, $L^1$ to $L^5$ may be each independently a single bond; a phenylene group unsubstituted or substituted with a carbazole group; a biphenylene group; an anthracene group; a divalent pyrimidine group unsubstituted or substituted with a phenyl group; a divalent pyridine group unsubstituted or substituted with a phenyl group; or a divalent triazine group unsubstituted or substituted with a phenyl group.

In one embodiment of the present application, $Ar^1$ to $Ar^5$ may be each independently hydrogen; deuterium; a cyano group; —P(=O)RR'; a substituted or unsubstituted C1 to C60 alkyl group; a substituted or unsubstituted C6 to C60 aryl group; or a substituted or unsubstituted C2 to C60 heteroaryl group.

In another embodiment, $Ar^1$ to $Ar^5$ may be each independently hydrogen; a cyano group; —P(=O)RR'; a substituted or unsubstituted C6 to C60 aryl group; or a substituted or unsubstituted C2 to C60 heteroaryl group.

In another embodiment, $Ar^1$ to $Ar^5$ may be each independently hydrogen; a cyano group; —P(=O)RR'; a substituted or unsubstituted C6 to C40 aryl group; or a substituted or unsubstituted C2 to C40 heteroaryl group.

In another embodiment, $Ar^1$ to $Ar^5$ may be each independently hydrogen; a cyano group; —P(=O)RR'; a C6 to C40 aryl group unsubstituted or substituted with one or more substituents selected from the group consisting of a C6 to C40 aryl group and a C2 to C40 heteroaryl group; or a C2 to C40 heteroaryl group unsubstituted or substituted with one or more substituents selected from the group consisting of a C6 to C40 aryl group and a C2 to C40 heteroaryl group.

In another embodiment, $Ar^1$ to $Ar^5$ may be each independently hydrogen; a cyano group; —P(=O)RR'; a substituted or unsubstituted phenyl group; a substituted or unsubstituted naphthyl group; a substituted or unsubstituted triphenylenyl group; a substituted or unsubstituted anthracenyl group; a substituted or unsubstituted terphenyl group; a substituted or unsubstituted pyridine group; a substituted or unsubstituted triazine group; a substituted or unsubstituted pyrimidine group; a substituted or unsubstituted quinazoline group; a substituted or unsubstituted phenanthroline group; a substituted or unsubstituted benzimidazole group; a substituted or unsubstituted benzoxazole group; a substituted or unsubstituted carbazole group; a substituted or unsubstituted dibenzofuran group; or a substituted or unsubstituted dibenzothiophene group.

In another embodiment, $Ar^1$ to $Ar^5$ may be each independently hydrogen; a cyano group; —P(=O)RR'; a phenyl group unsubstituted or substituted with a carbazole group; a naphthyl group; a triphenylenyl group; an anthracenyl group unsubstituted or substituted with a naphthyl group; a terphenyl group; a pyridine group unsubstituted or substituted with a pyridine group; a triazine group unsubstituted or substituted with one or more substituents selected from the group consisting of a phenyl group, a biphenyl group, a triphenylenyl group, a dibenzofuran group and a dibenzothiophene group; a pyrimidine group unsubstituted or substituted with one or more substituents selected from the group consisting of a phenyl group, a biphenyl group, a triphenylenyl group, a dibenzofuran group and a dibenzothiophene group; a quinazoline group unsubstituted or substituted with a phenyl group or a biphenyl group; a phenanthroline group unsubstituted or substituted with a phenyl group; a benzimidazole group unsubstituted or substituted with a phenyl group; a benzoxazole group; a carbazole group; a dibenzofuran group; or a dibenzothiophene group.

In one embodiment of the present application, $Ar^1$ and $Ar^2$ may be hydrogen.

In one embodiment of the present application, Chemical Formula 2 may be represented by any one of the following Chemical Formulae 2-1 to 2-3.

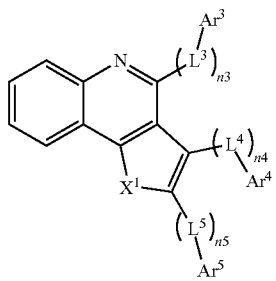

[Chemical Formula 2-1]

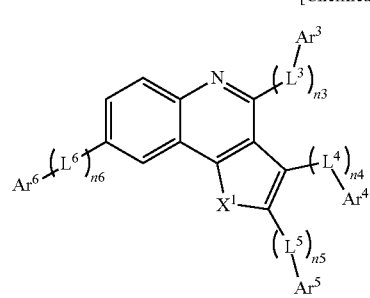

[Chemical Formula 2-2]

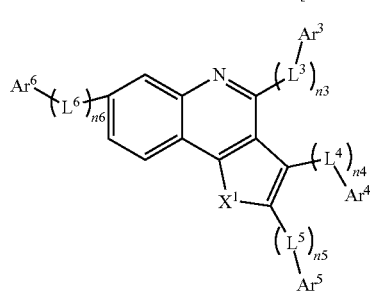

[Chemical Formula 2-3]

In Chemical Formulae 2-1 to 2-3, $X^1$, $Ar^3$ to $Ar^5$, $L^3$ to $L^5$, n3 to n5 have the same definitions as in Chemical Formula 2, $Ar^6$ is a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, R and R' are each independently hydrogen; a substituted or unsubstituted C1 to C60 alkyl group; a substituted or unsubstituted C6 to C60 aryl group; or a substituted or unsubstituted C2 to C60 heteroaryl group, $L^6$ is a single bond; a substituted or unsubstituted C6 to C60 arylene group; or a substituted or unsubstituted C2 to C60 heteroarylene group, at least any one of $Ar^3$ to $Ar^6$ is a substituent having electron properties; or a substituent having hole properties, and n6 is one of integers of 0 to 4.

In one embodiment of the present application, Chemical Formula 3 may be represented by any one of the following Chemical Formulae 3-1 to 3-3.

[Chemical Formula 3-1]

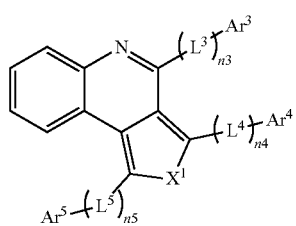

[Chemical Formula 3-2]

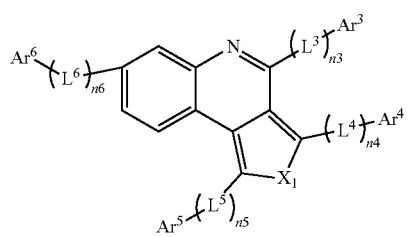

[Chemical Formula 3-3]

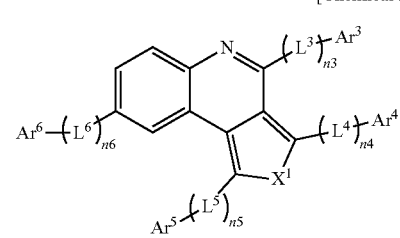

In Chemical Formulae 3-1 to 3-3, $X^1$, $Ar^3$ to $Ar^5$, $L^3$ to $L^5$, n3 to n5 have the same definitions as in Chemical Formula 3, $Ar^6$ is a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, R and R' are each independently hydrogen; a substituted or unsubstituted C1 to C60 alkyl group; a substituted or unsubstituted C6 to C60 aryl group; or a substituted or unsubstituted C2 to C60 heteroaryl group, $L^6$ is a single bond; a substituted or unsubstituted C6 to C60 arylene group; or a substituted or unsubstituted C2 to C60 heteroarylene group, at least any one of $Ar^3$ to $Ar^6$ is a substituent having electron properties; or a substituent having hole properties, and n6 is one of integers of 0 to 4.

In one embodiment of the present application, Chemical Formula 4 may be represented by any one of the following Chemical Formulae 4-1 to 4-3.

[Chemical Formula 4-1]

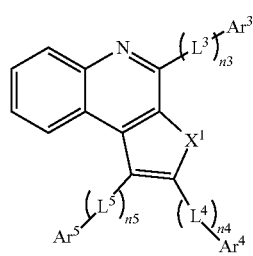

[Chemical Formula 4-2]

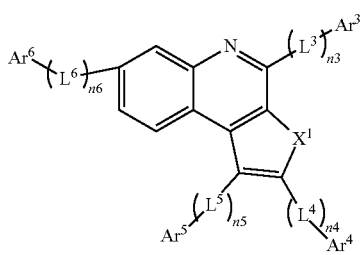

[Chemical Formula 4-3]

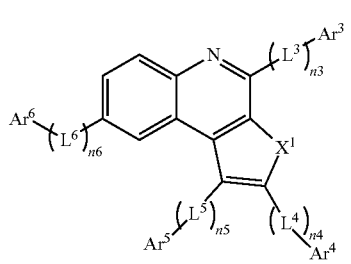

In Chemical Formulae 4-1 to 4-3, $X^1$, $Ar^3$ to $Ar^5$, $L^3$ to $L^5$, n3 to n5 have the same definitions as in Chemical Formula 4, $Ar^6$ is a cyano group; —P(=O)RR'; a substituted or unsubstituted C1 to C60 alkyl group; a substituted or unsubstituted C6 to C60 aryl group; or a substituted or unsubstituted C2 to C60 heteroaryl group, R and R' are each independently hydrogen; a substituted or unsubstituted C1 to C60 alkyl group; a substituted or unsubstituted C6 to C60 aryl group; or a substituted or unsubstituted C2 to C60 heteroaryl group, $L^6$ is a single bond; a substituted or unsubstituted C6 to C60 arylene group; or a substituted or unsubstituted C2 to C60 heteroarylene group, at least any one of $Ar^3$ to $Ar^6$ is a substituent having electron properties; or a substituent having hole properties, and n6 is one of integers of 0 to 4.

In the examples described above, the descriptions on the substituent having electron properties overlap with the descriptions on the substituent provided above, and are not repeated.

In the examples described above, the descriptions on the substituent having hole properties also overlap with the descriptions provided above.

More specifically, the substituent having hole properties may be any one of the following Chemical Formulae 5-1 to 5-4.

[Chemical Formula 5-1]

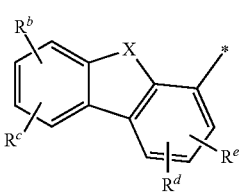

-continued

[Chemical Formula 5-2]
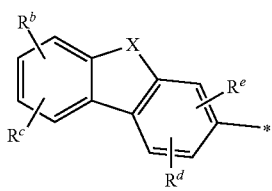

[Chemical Formula 5-3]
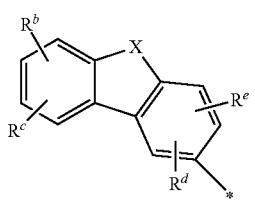

[Chemical Formula 5-4]
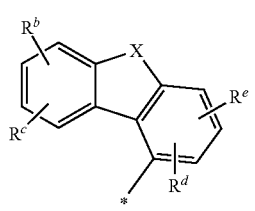

In Chemical Formula 5-1 to Chemical Formula 5-4,
X is —O— or —S—, and $R^b$ to $R^e$ are hydrogen, deuterium, a cyano group or a substituted or unsubstituted C1 to C60 alkyl group.

In Chemical Formulae 5-1 to 5-4, means a bonding position.

Chemical Formulae 5-1 to 5-4 may be selected considering hole and electron properties of the whole compound.

In one embodiment of the present application, the substituent having electron properties; or the substituent having hole properties may be —P(=O)RR'; a substituted or unsubstituted triphenylenyl group; a substituted or unsubstituted anthracenyl group; a substituted or unsubstituted terphenyl group; a substituted or unsubstituted pyridine group; a substituted or unsubstituted triazine group; a substituted or unsubstituted pyrimidine group; a substituted or unsubstituted quinazoline group; a substituted or unsubstituted phenanthroline group; a substituted or unsubstituted benzimidazole group; a substituted or unsubstituted benzoxazole group; a substituted or unsubstituted carbazole group; a substituted or unsubstituted dibenzofuran group; or a substituted or unsubstituted dibenzothiophene group.

In another embodiment, the substituent having electron properties; or the substituent having hole properties may be —P(=O)RR'; a triphenylenyl group; an anthracenyl group unsubstituted or substituted with a naphthyl group; a terphenyl group; a pyridine group unsubstituted or substituted with a pyridine group; a triazine group unsubstituted or substituted with one or more substituents selected from the group consisting of a phenyl group, a biphenyl group, a triphenylenyl group, a dibenzofuran group and a dibenzothiophene group; a pyrimidine group unsubstituted or substituted with one or more substituents selected from the group consisting of a phenyl group, a biphenyl group, a triphenylenyl group, a dibenzofuran group and a dibenzothiophene group; a quinazoline group unsubstituted or substituted with a phenyl group or a biphenyl group; a phenanthroline group unsubstituted or substituted with a phenyl group; a benzimidazole group unsubstituted or substituted with a phenyl group; a benzoxazole group; a carbazole group; a dibenzofuran group; or a dibenzothiophene group.

In one embodiment of the present application, R and R' may be each independently hydrogen; a substituted or unsubstituted C1 to C60 alkyl group; a substituted or unsubstituted C6 to C60 aryl group; or a substituted or unsubstituted C2 to C60 heteroaryl group.

In another embodiment, R and R' may be each independently a substituted or unsubstituted C6 to C60 aryl group.

In another embodiment, R and R' may be each independently a substituted or unsubstituted C6 to C40 aryl group.

In another embodiment, R and R' may be each independently a C6 to C40 monocyclic or polycyclic aryl group.

In another embodiment, R and R' may be each independently a C6 to C20 monocyclic or polycyclic aryl group.

In another embodiment, R and R' may be each independently a C6 to C20 polycyclic aryl group.

In another embodiment, R and R' may be a phenyl group.

The substituted or unsubstituted C6 to C60 aryl group bonding to the core of the compound represented by Chemical Formula 1 may be any one of substituents of the following Group II.

[Group II]
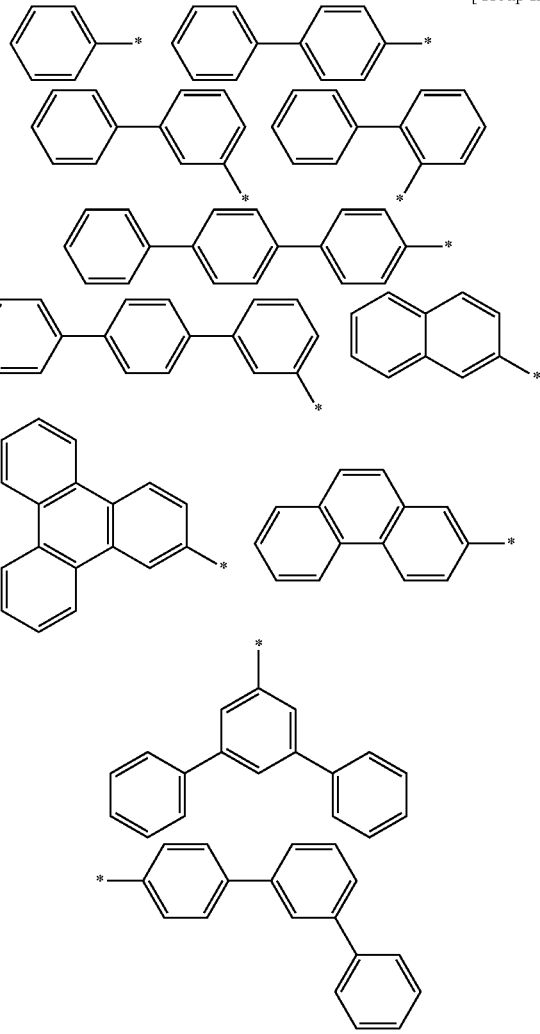

In Group II, * means a bonding position.

When the aryl group is a biphenyl or a substituted or unsubstituted fluorenyl group, the monoamine having aromatic group and fluorenyl group-type substituents continuous through two or more direct bonds has high hole mobility, and a low driving value is obtained even when used in a hole transfer layer.

The compound of the one example described above may be represented by any one of compounds of the following Group I.

[Group I]

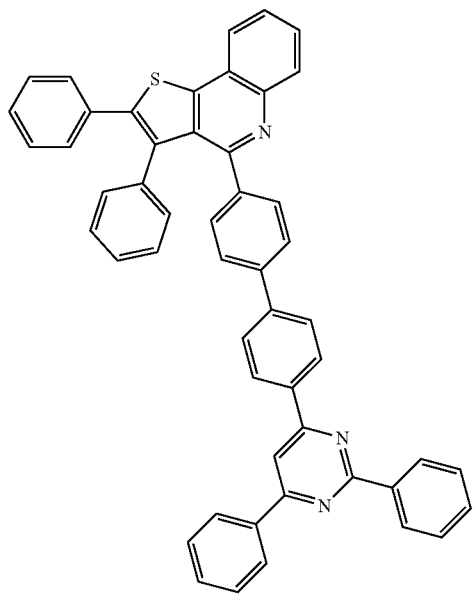

1

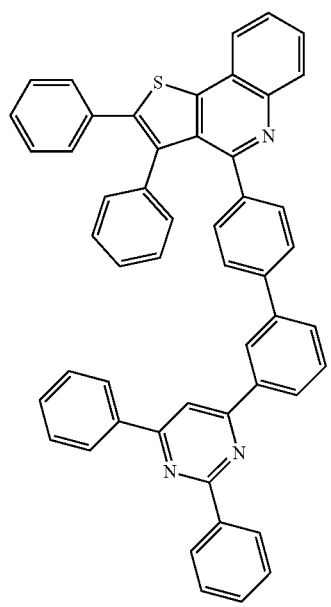

2

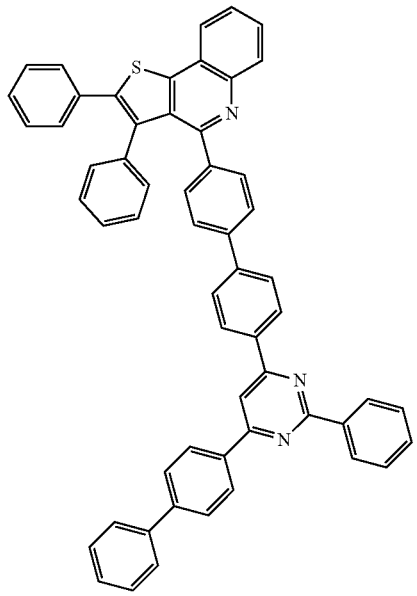

3

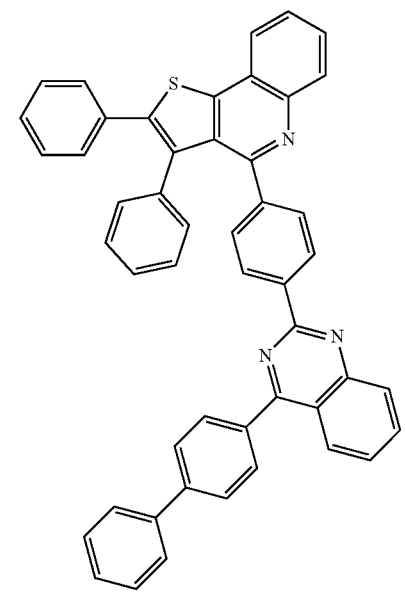

4

5
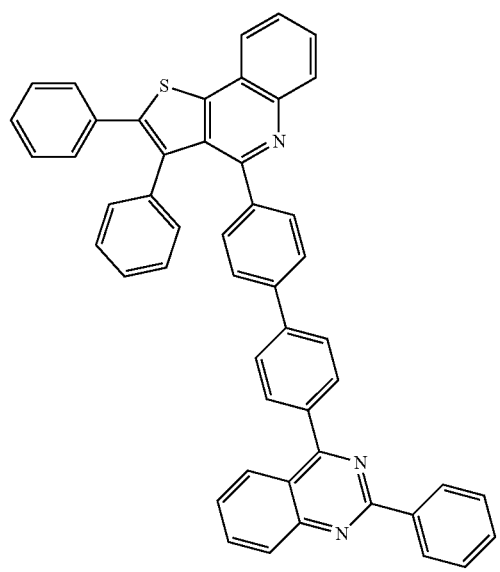
6
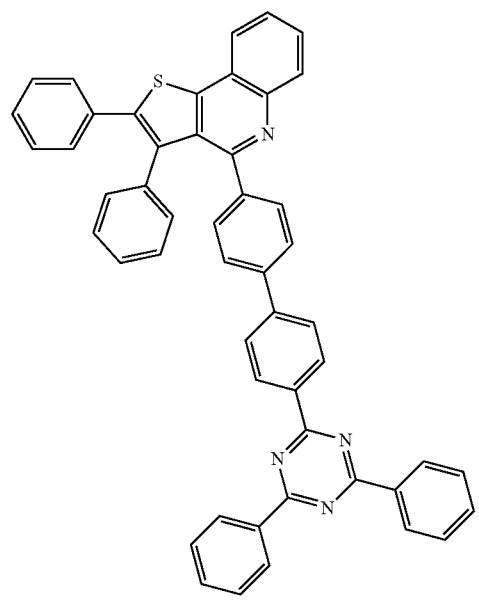
7
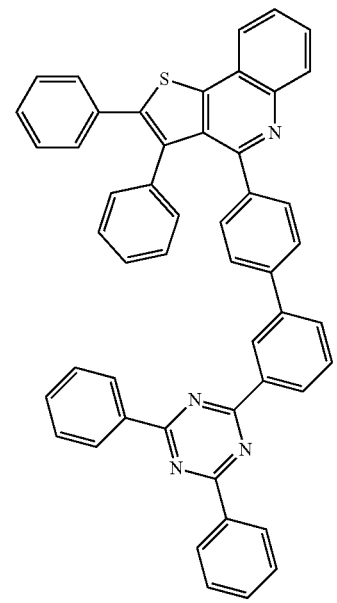
8
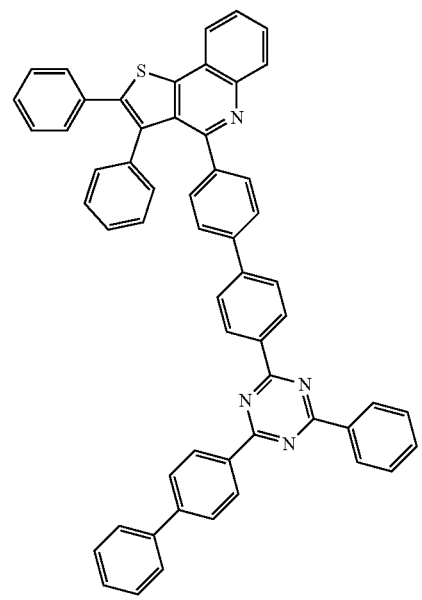

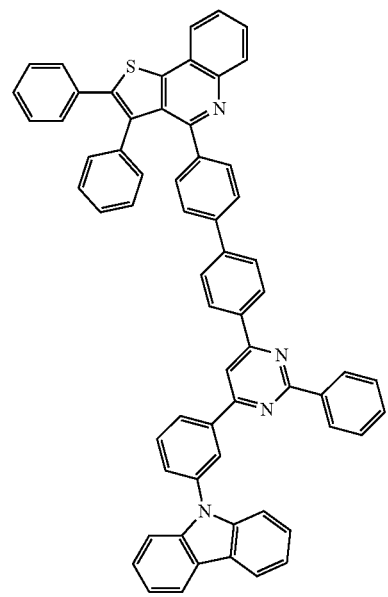
9
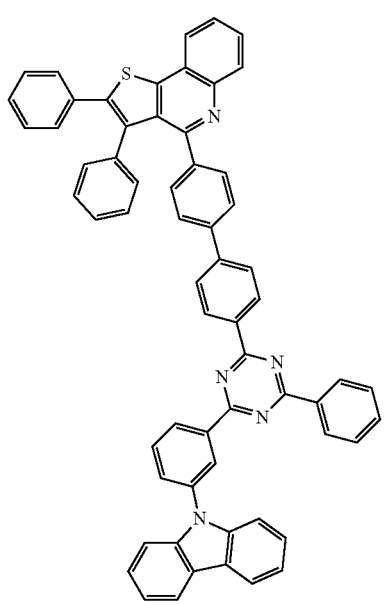
10
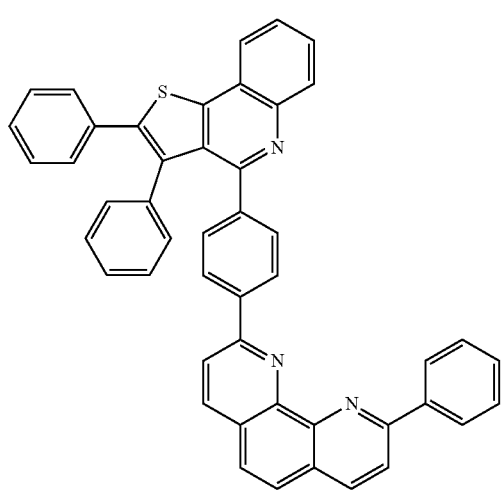
11
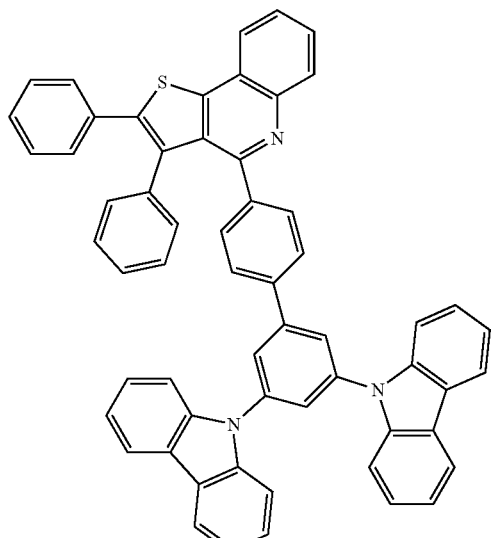
12
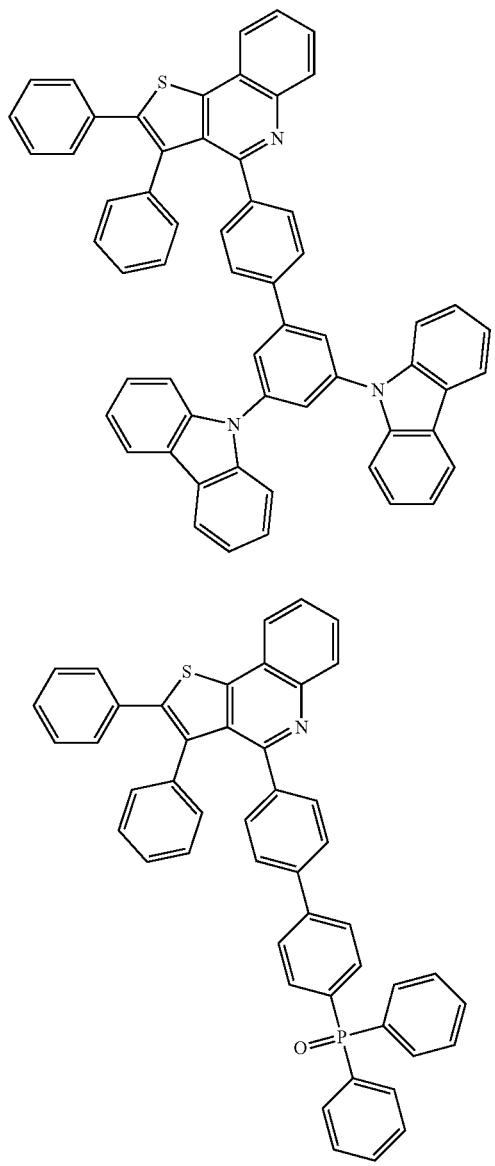
13
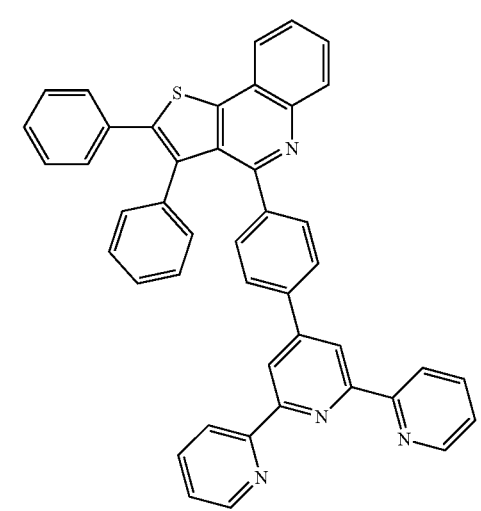
14

15
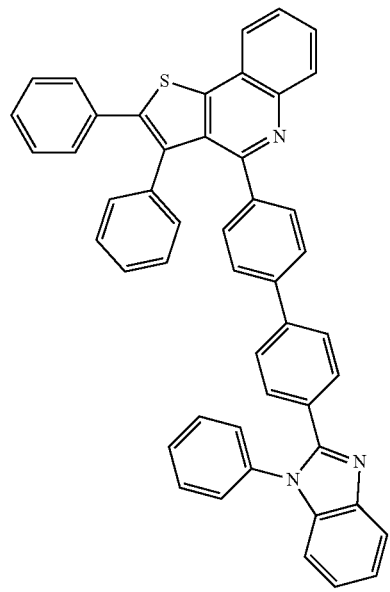
16
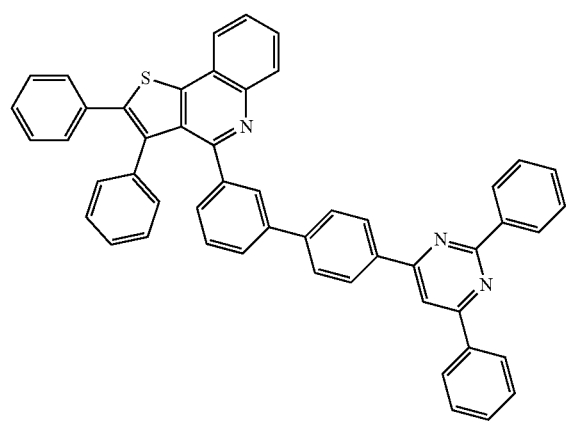
17
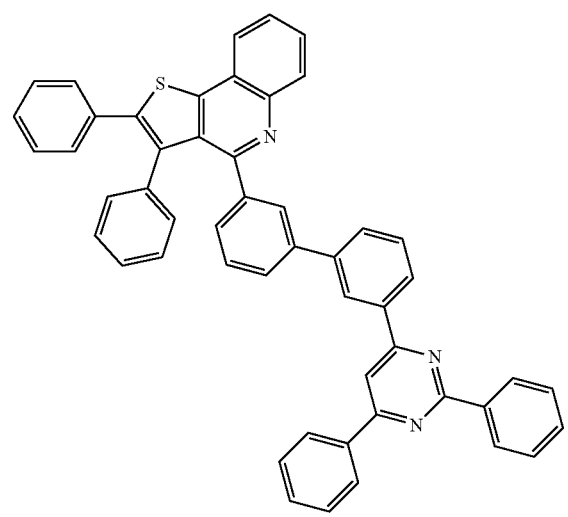
18
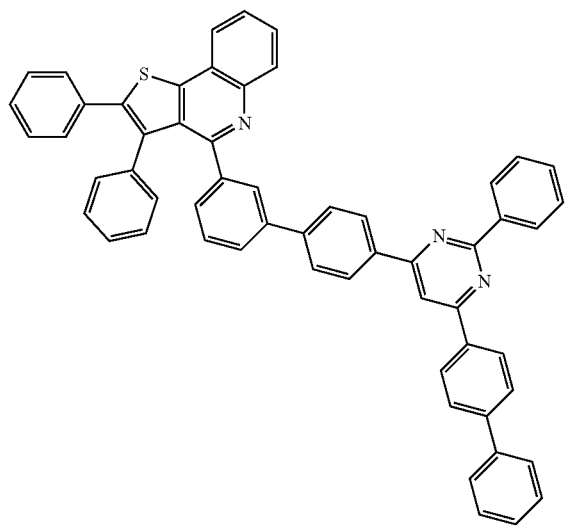
19
20

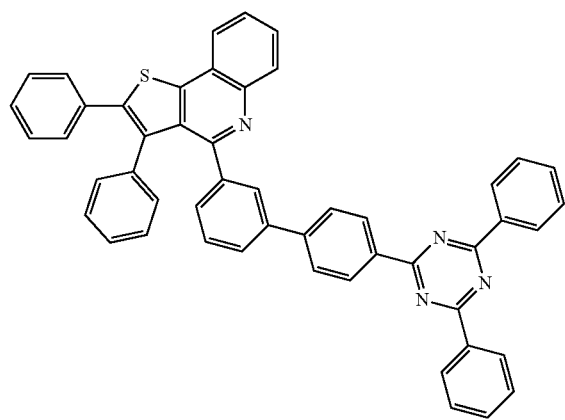
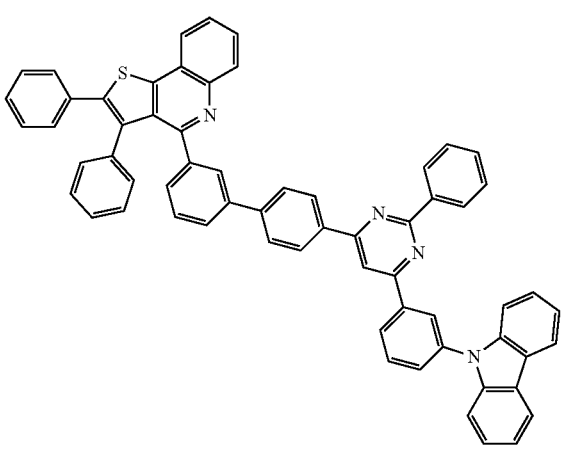
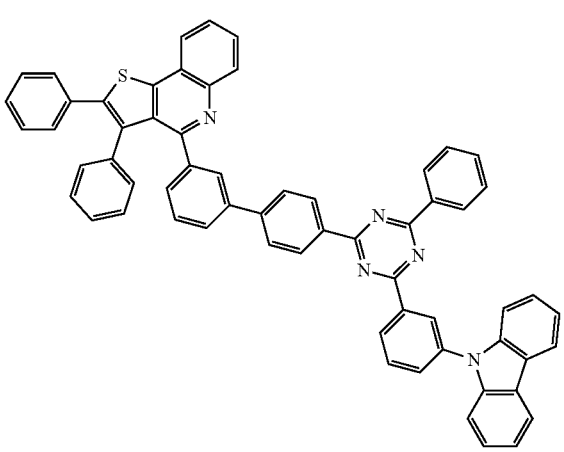

27
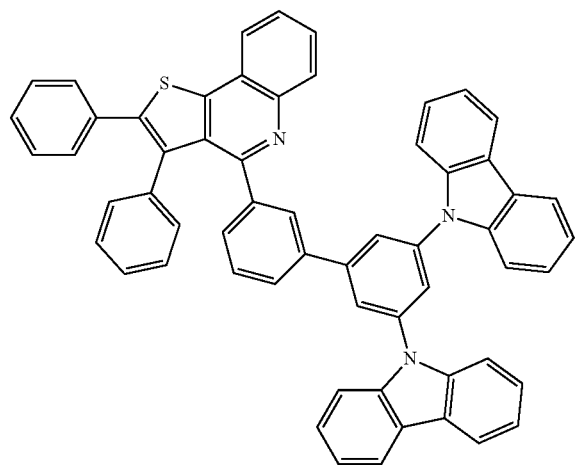
28
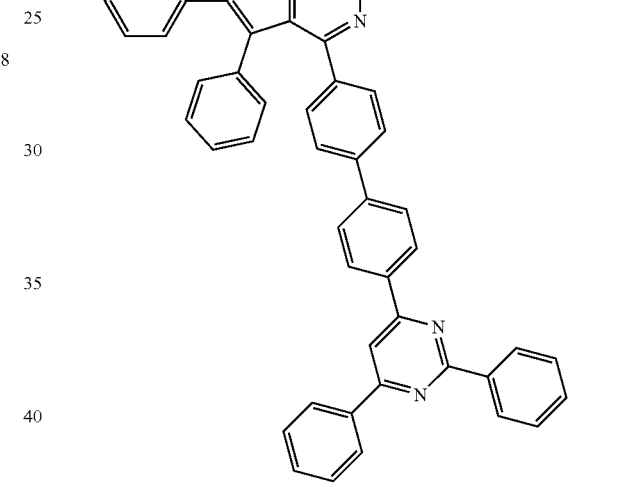
30
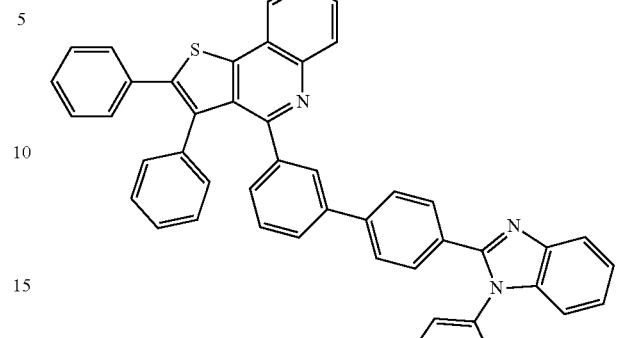
31
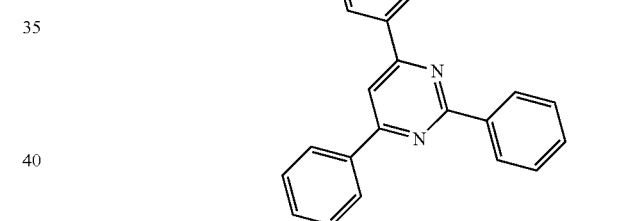
29
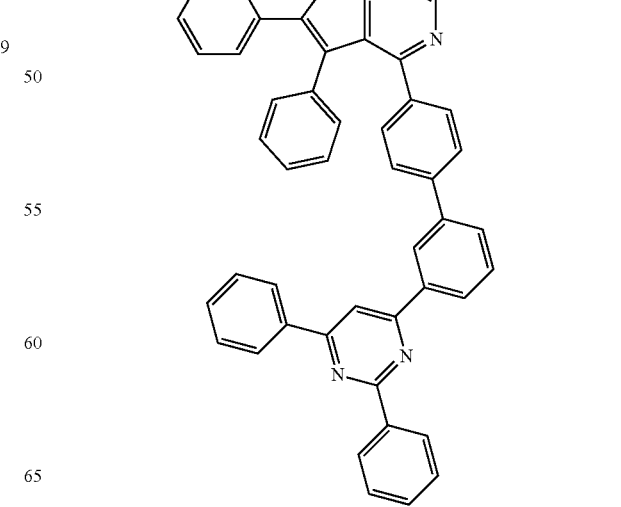
32

33
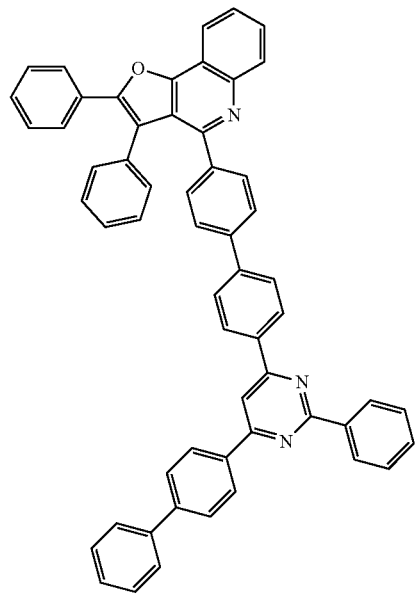
34
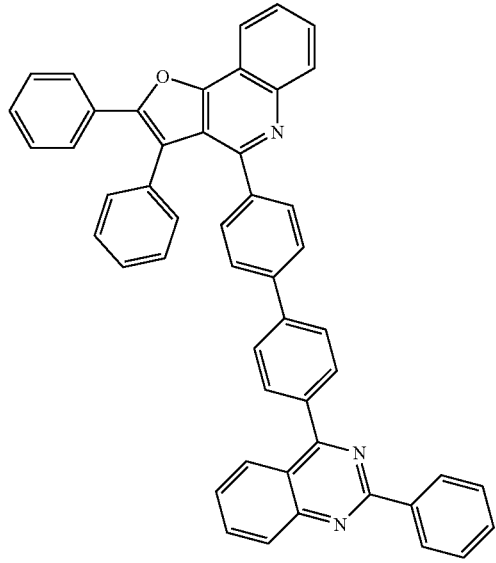
35
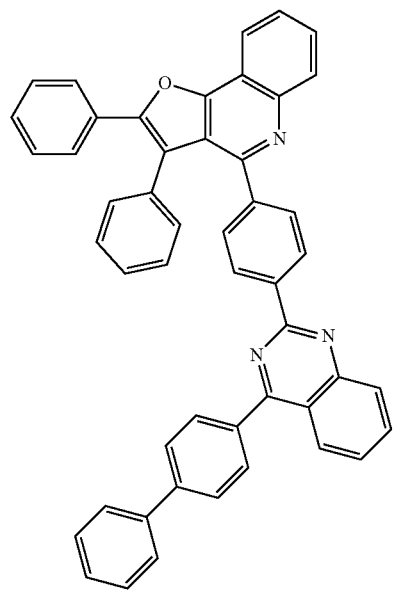
36
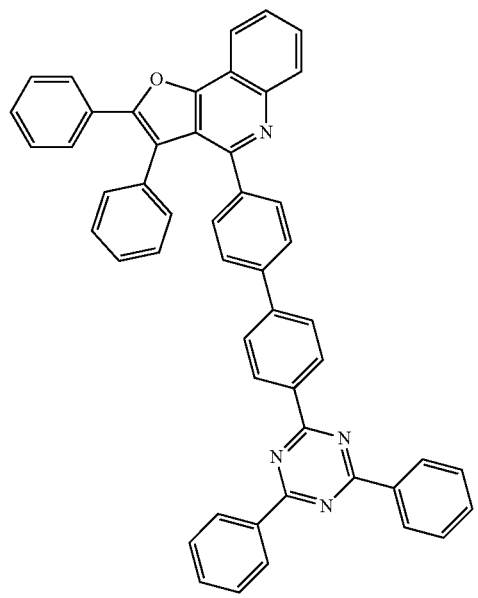

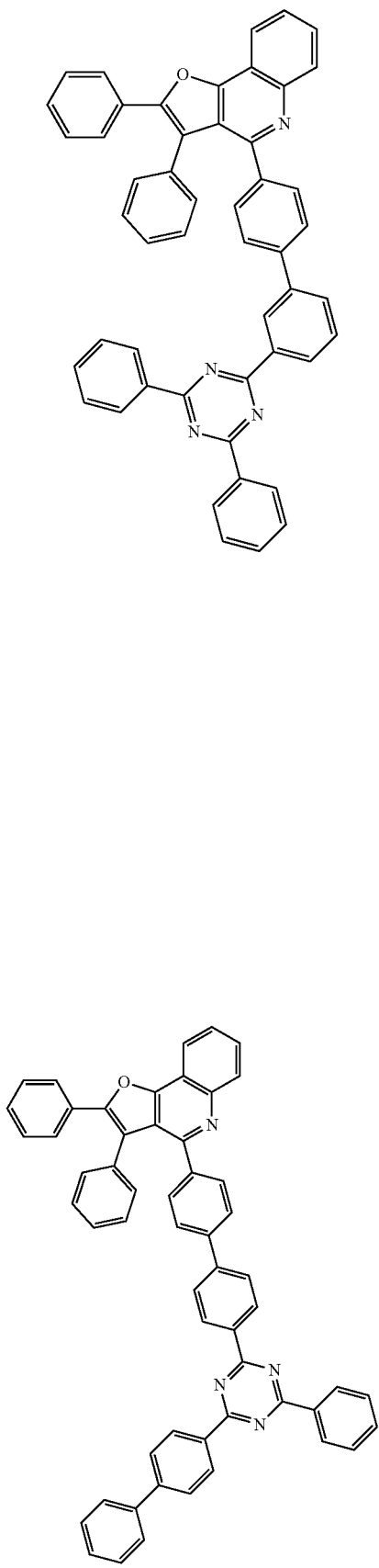
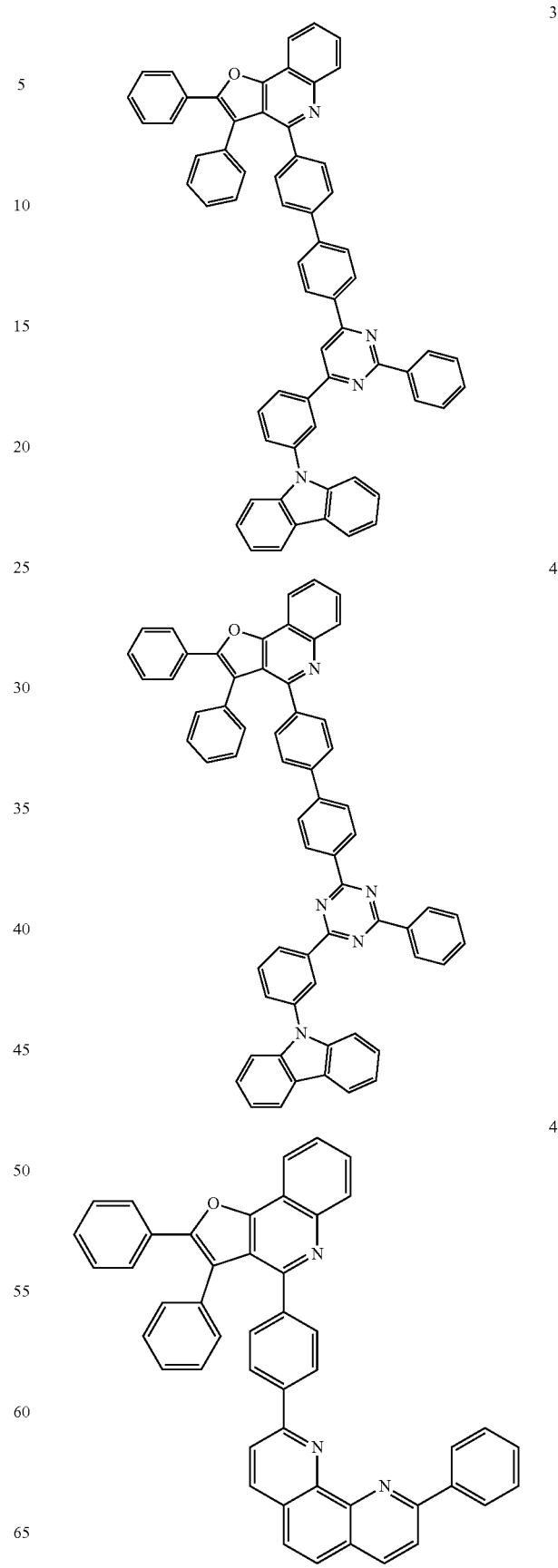

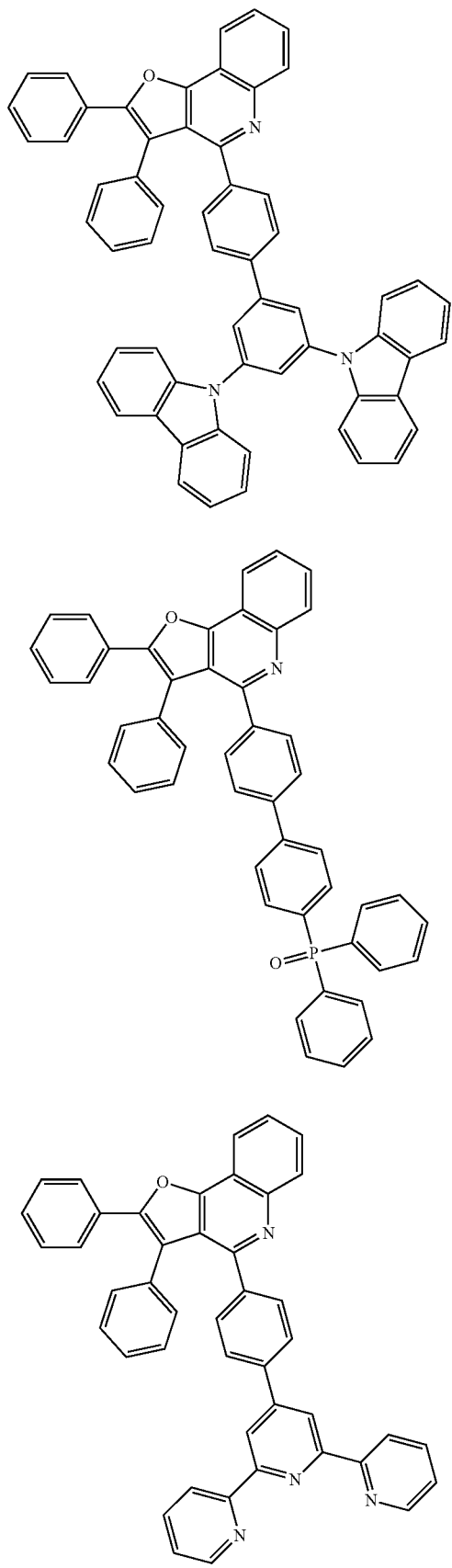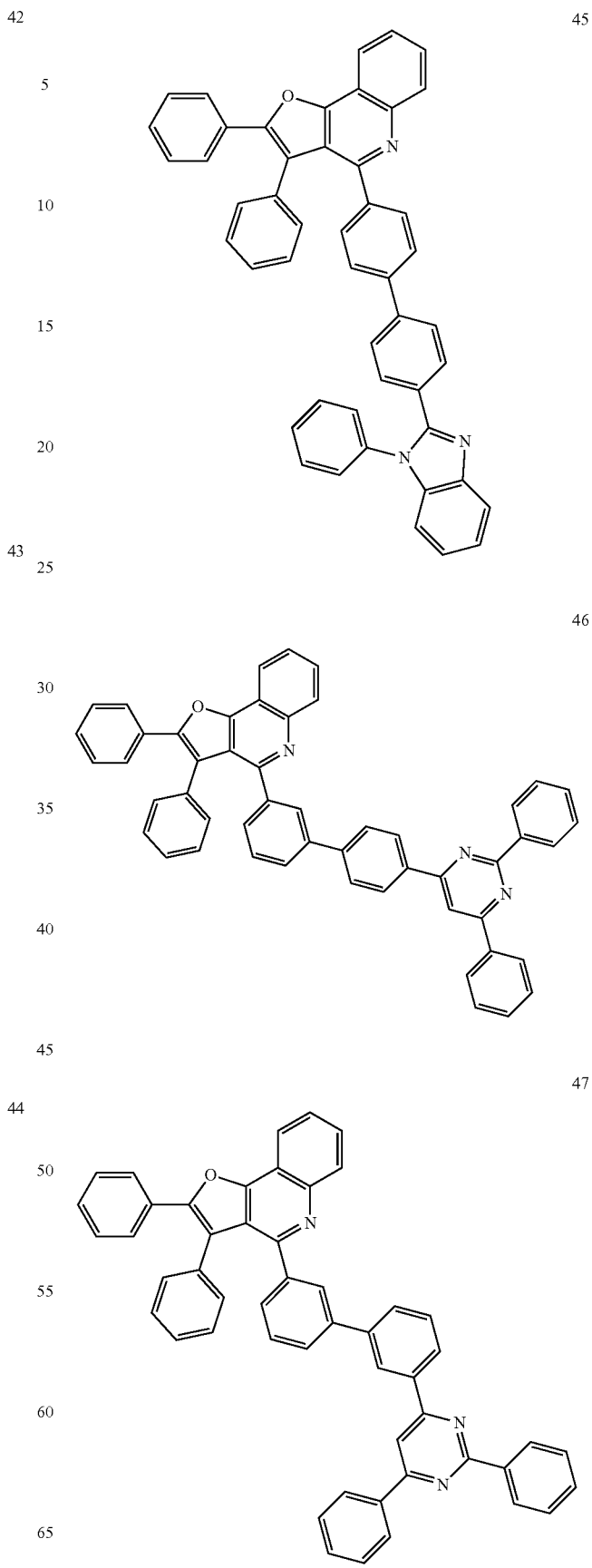

48
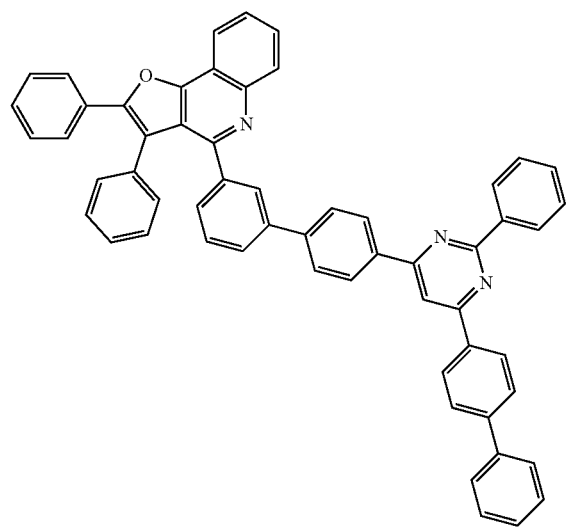
49
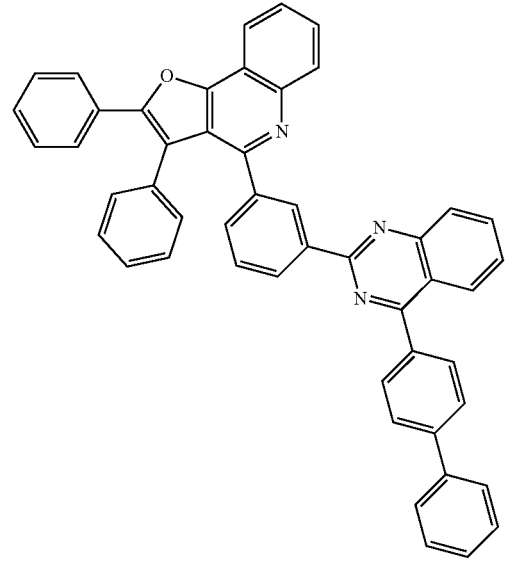
50
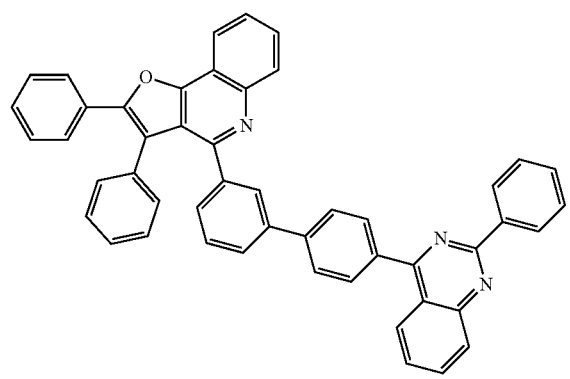
51
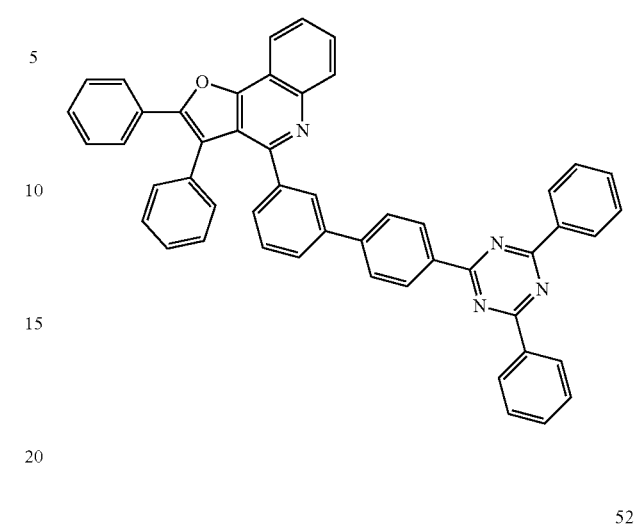
52
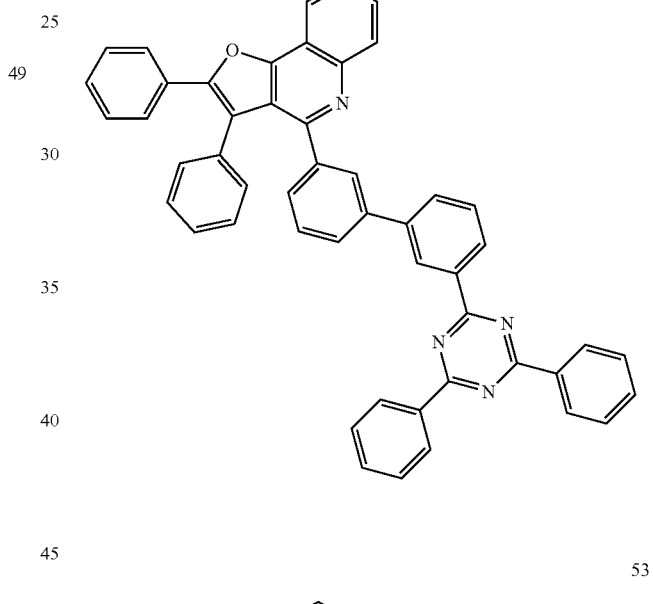
53
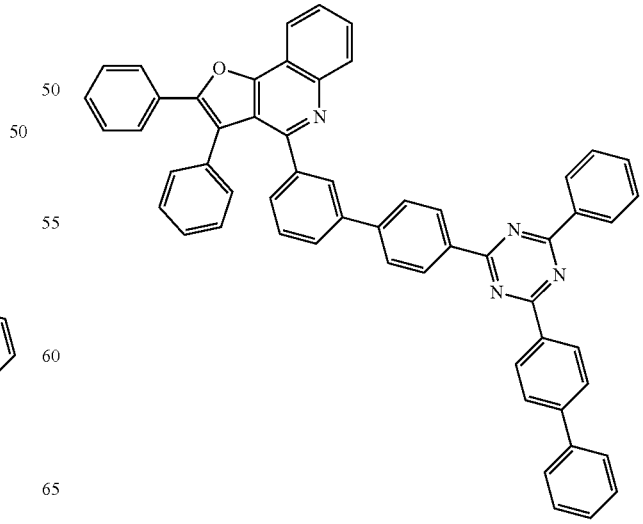

54
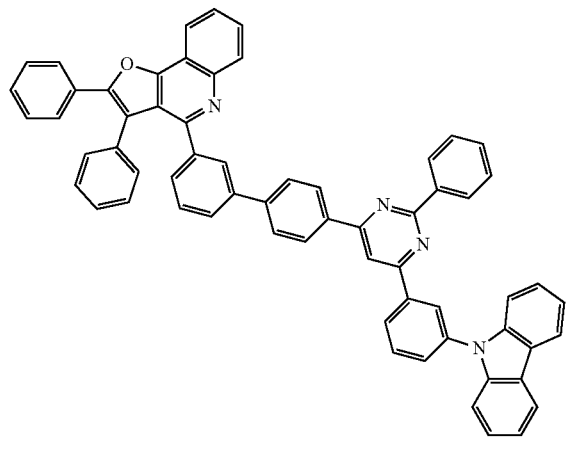
55
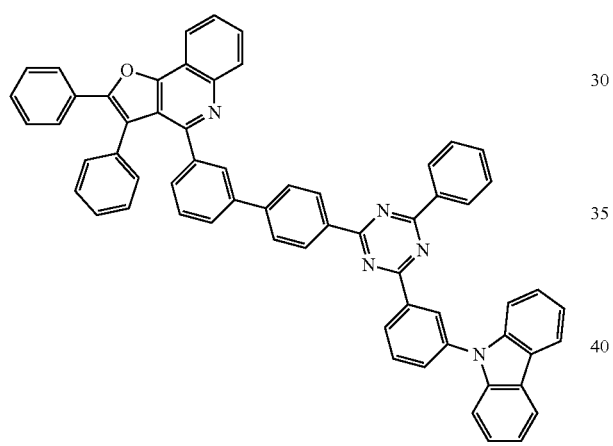
56
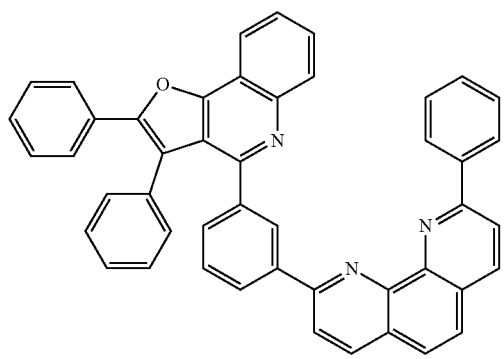
57
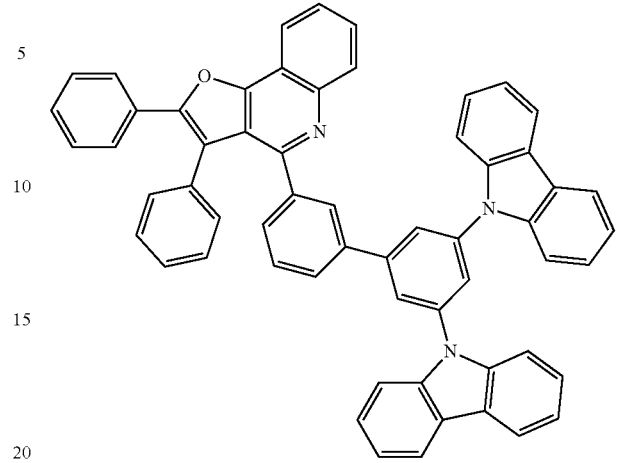
58
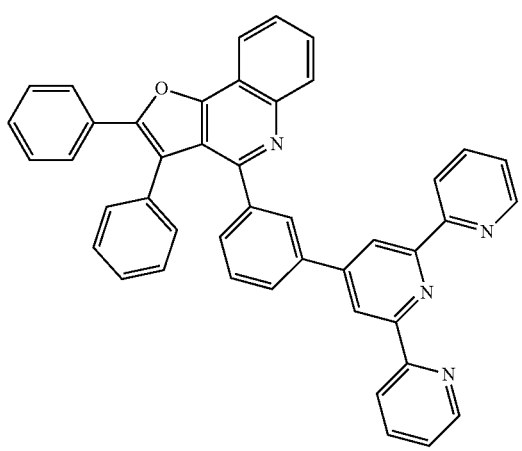
59

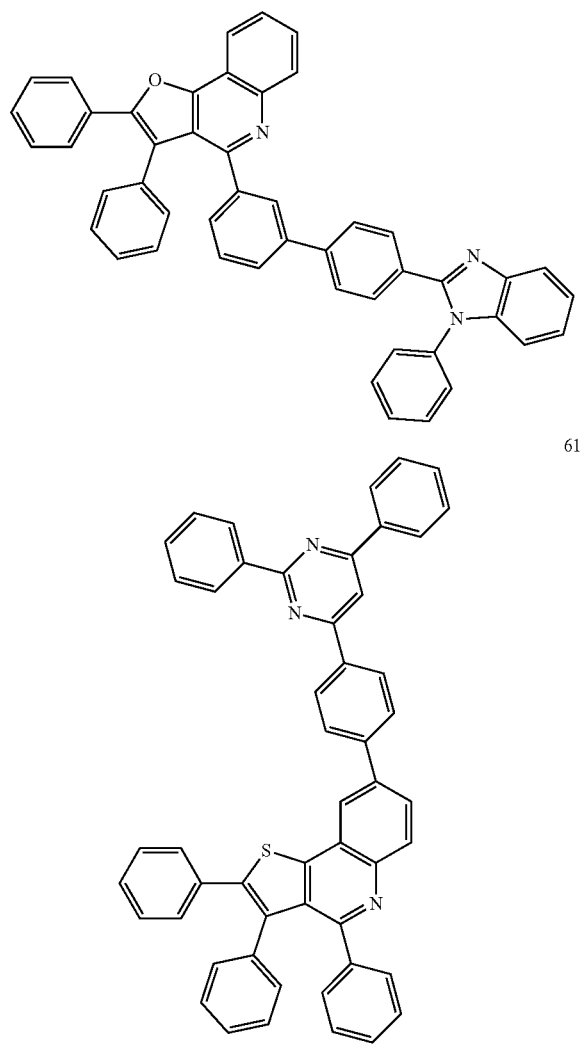
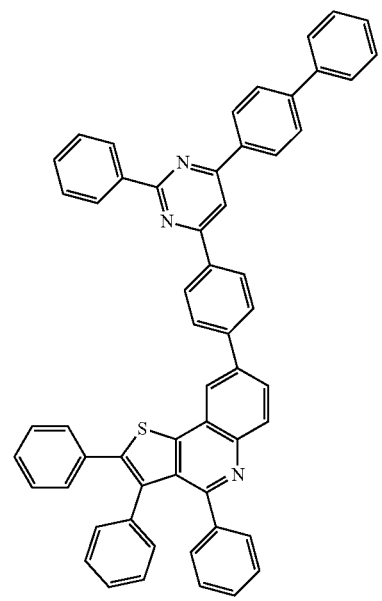
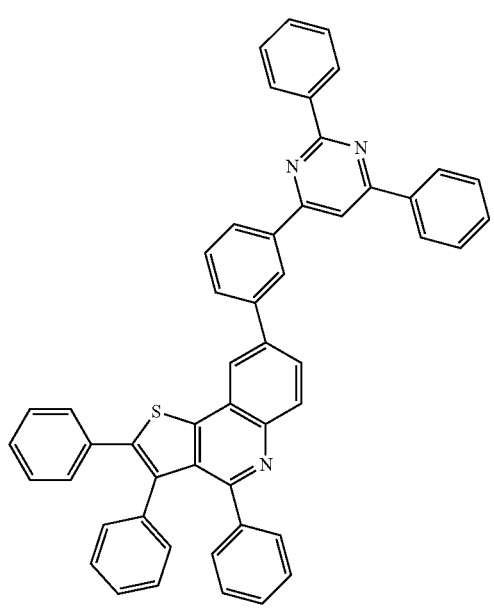

65
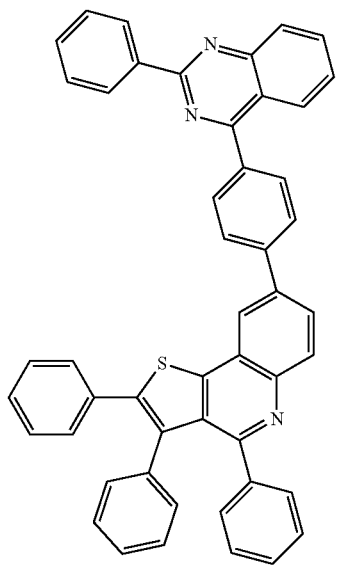
66
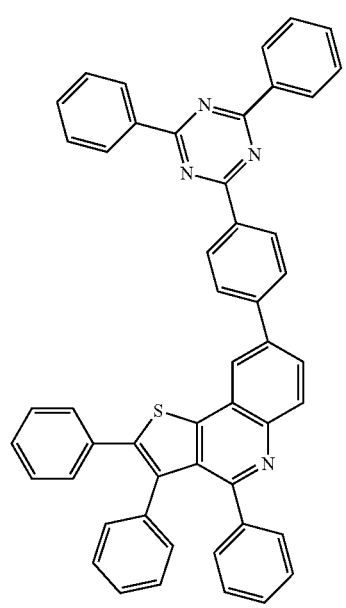
67
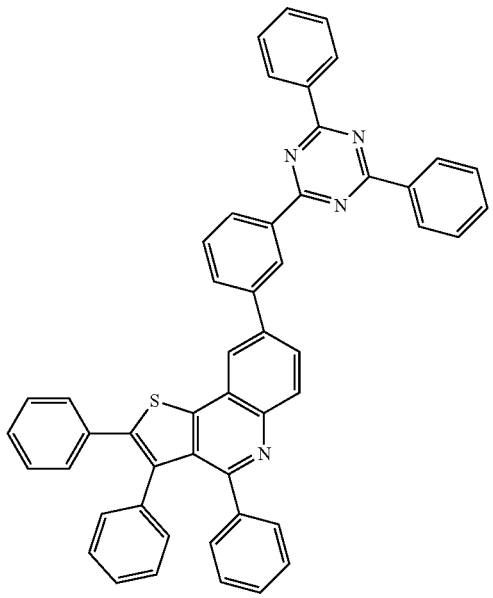
68
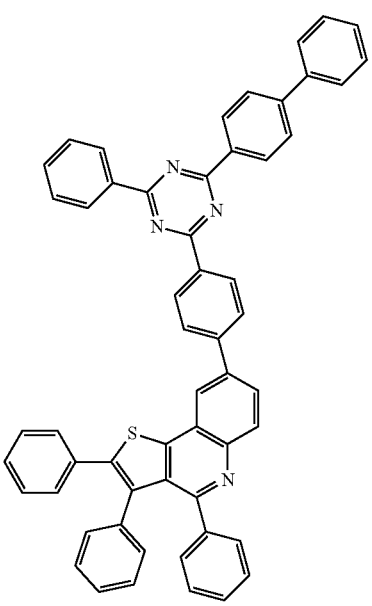

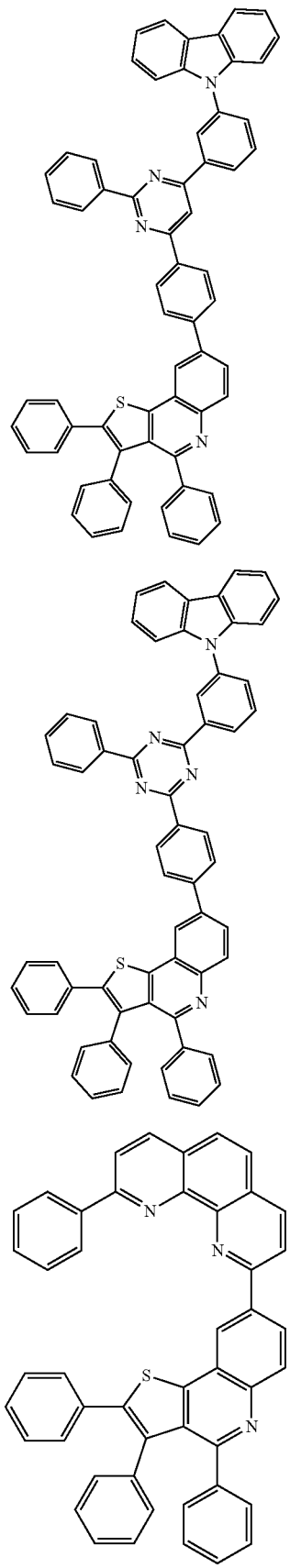
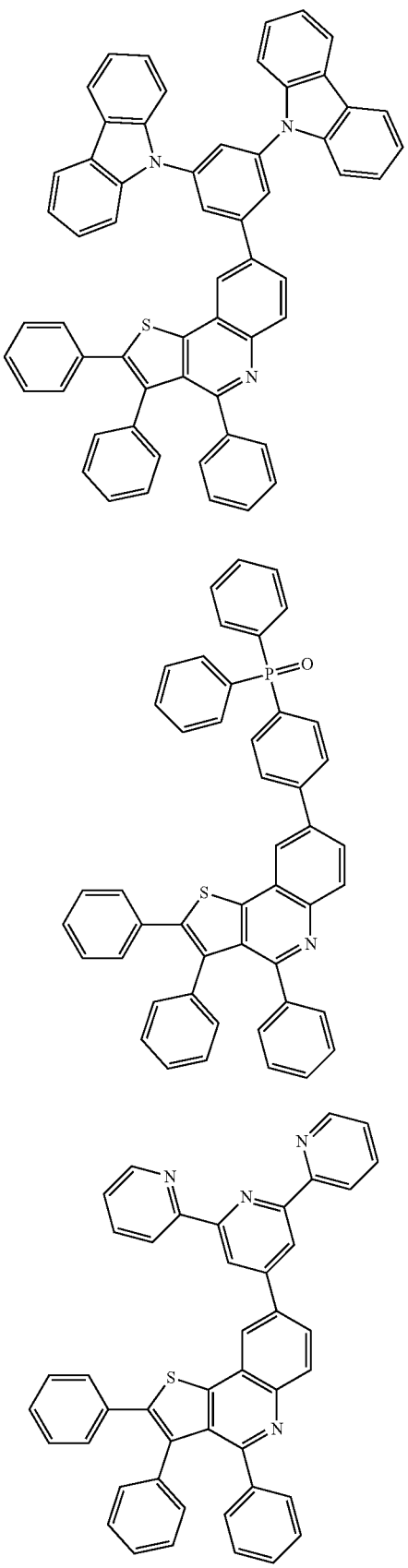

75
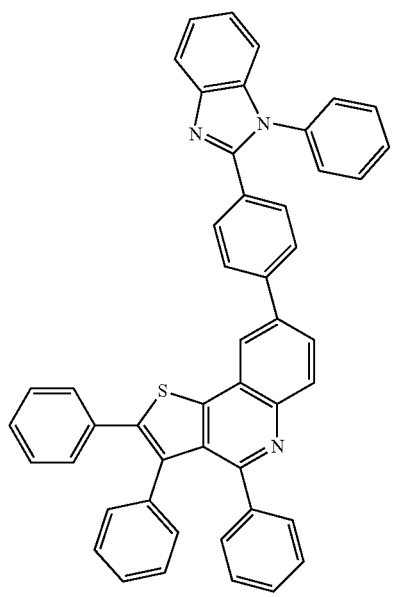
76
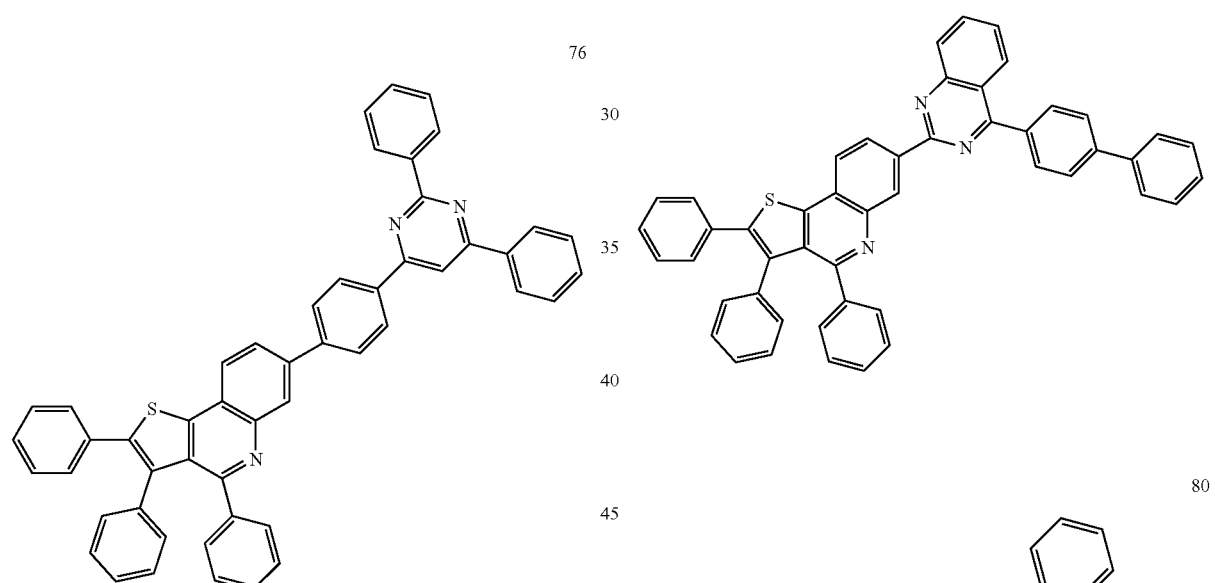
77
78
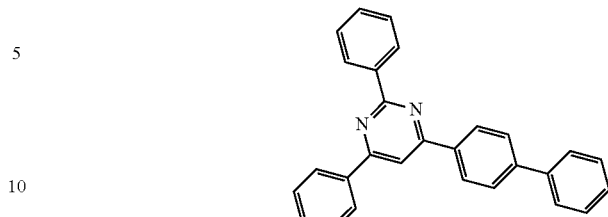
79
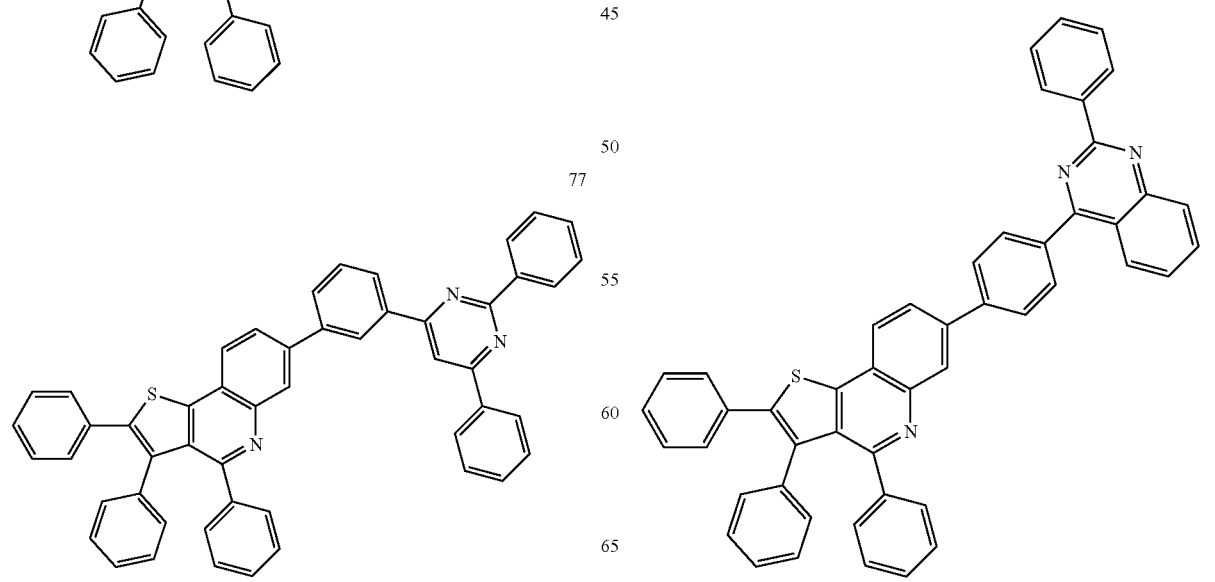
80
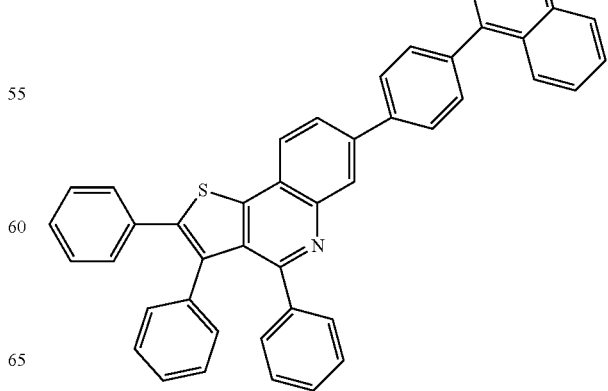

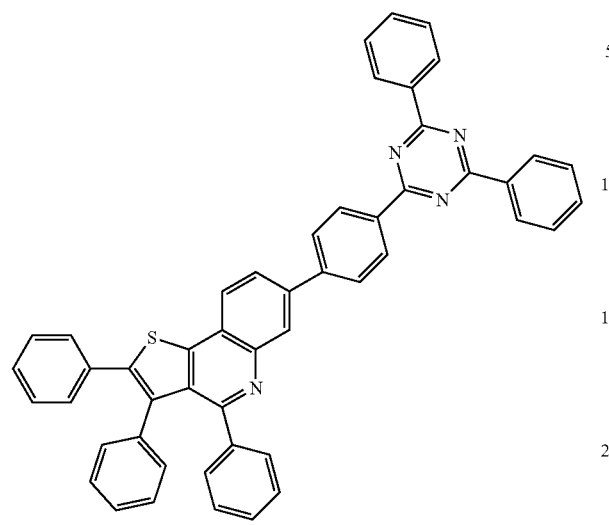
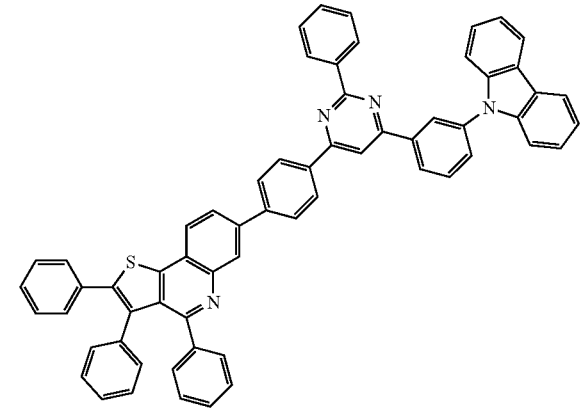
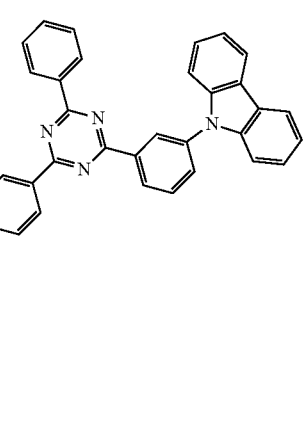
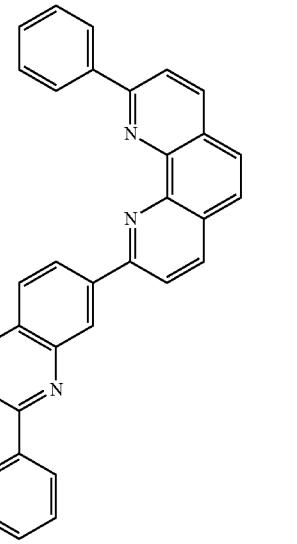

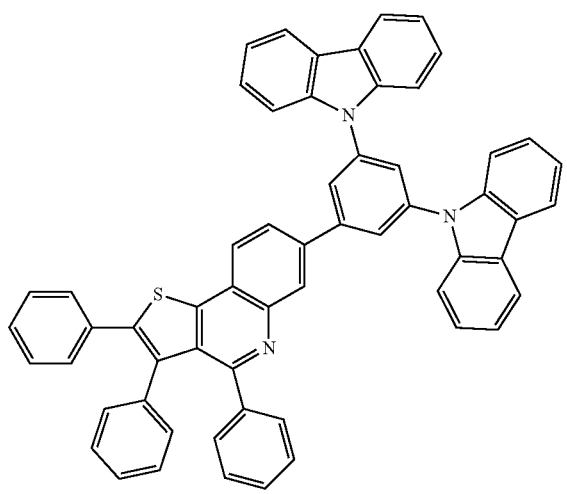
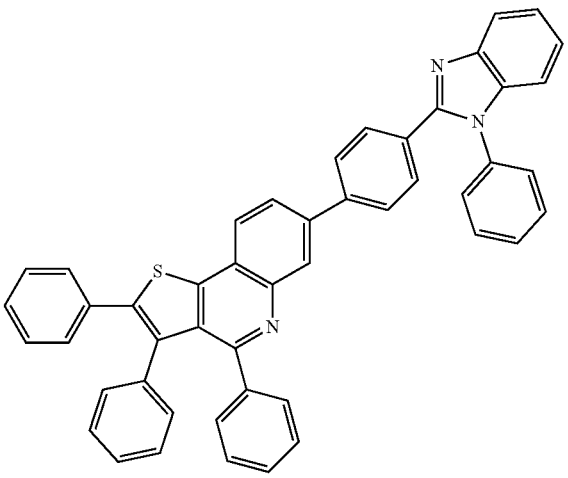
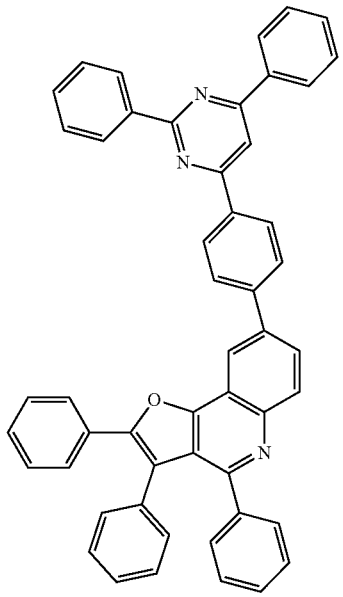

92
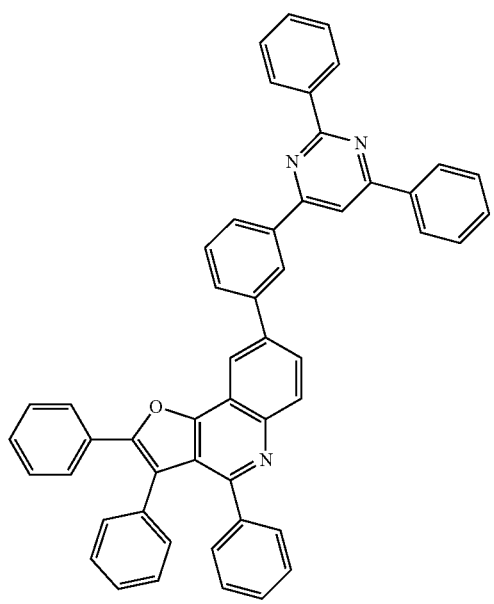
94
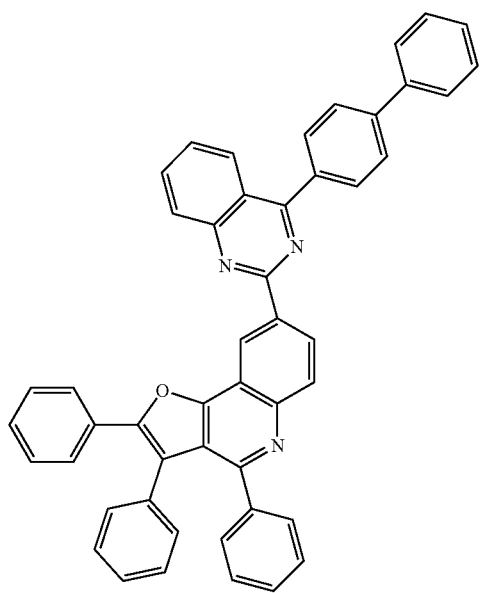
93
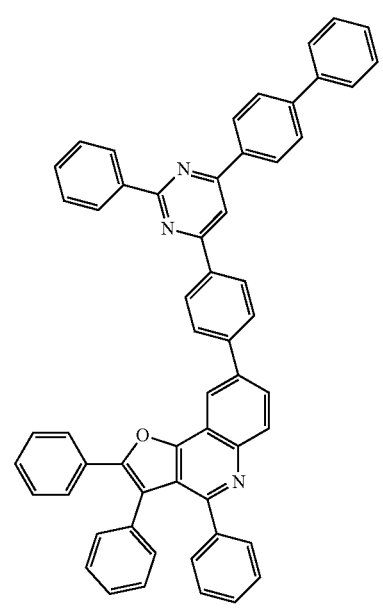
95
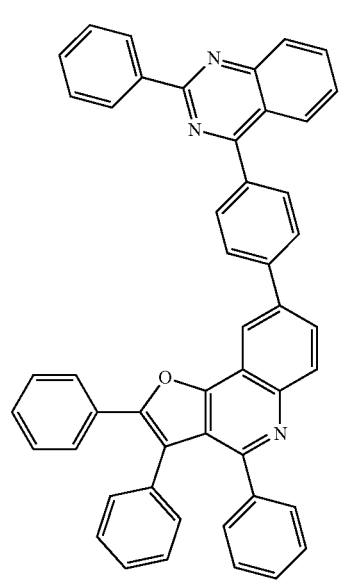

96
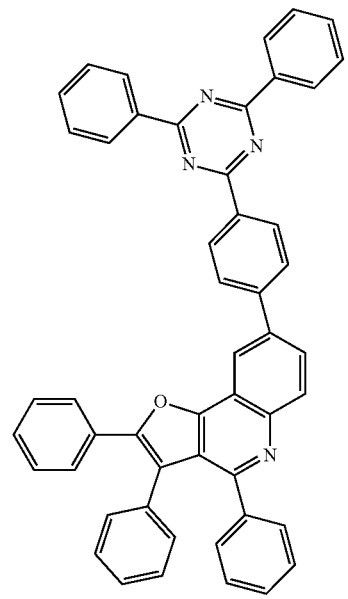
97
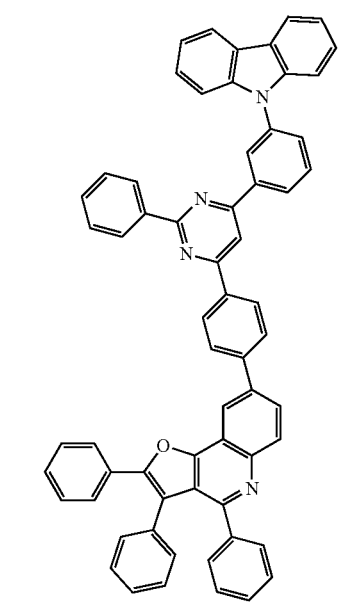
98
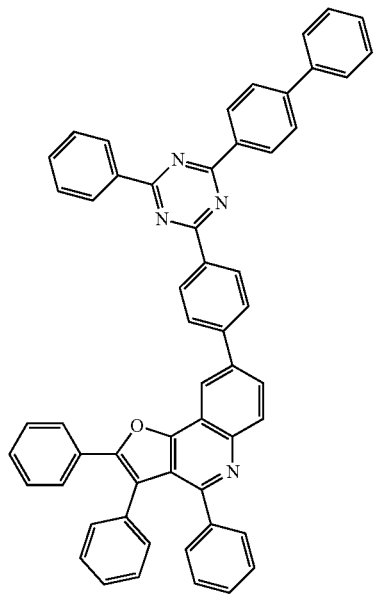
99

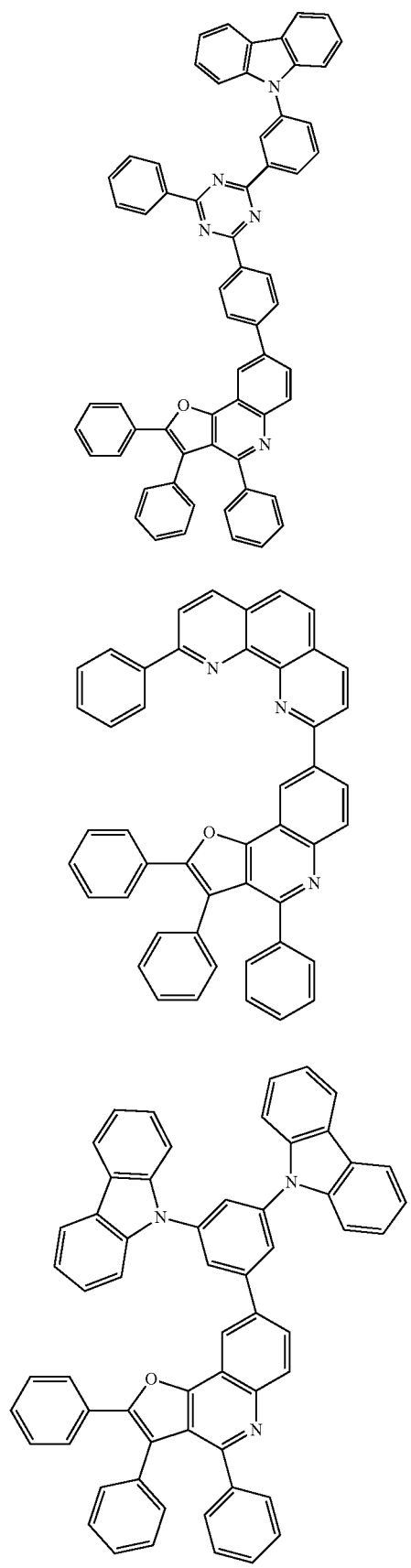
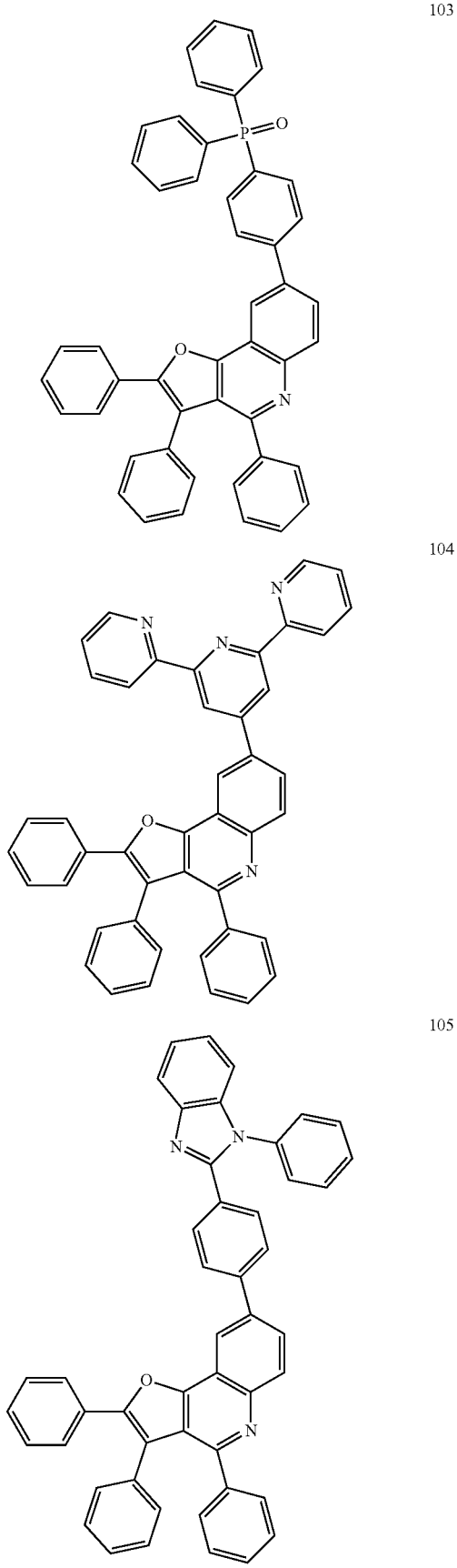

106
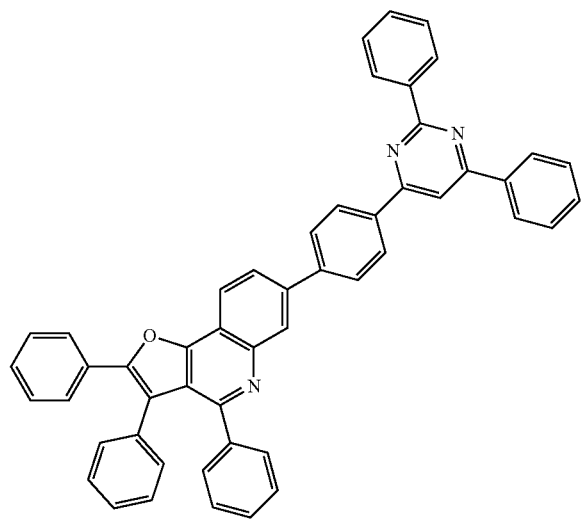
107
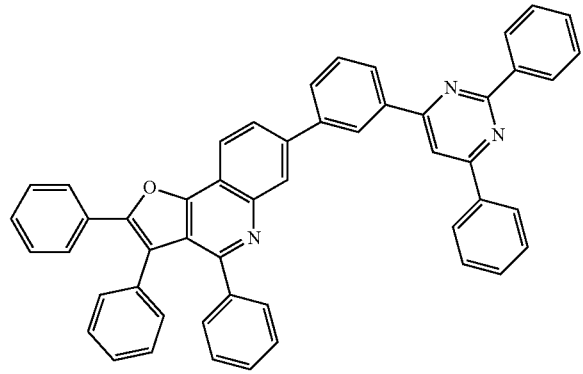
108
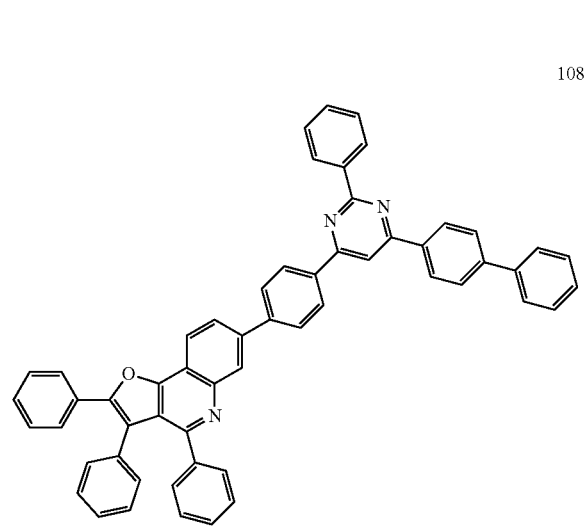
109
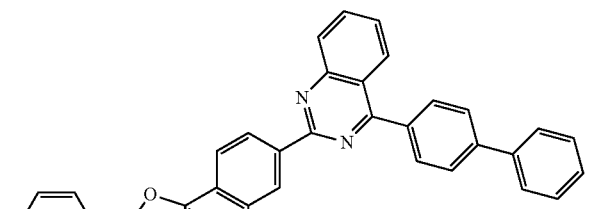
110
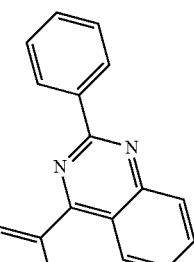
111
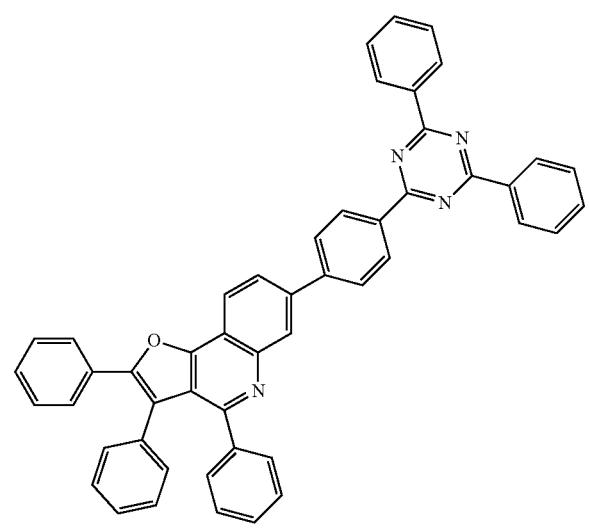

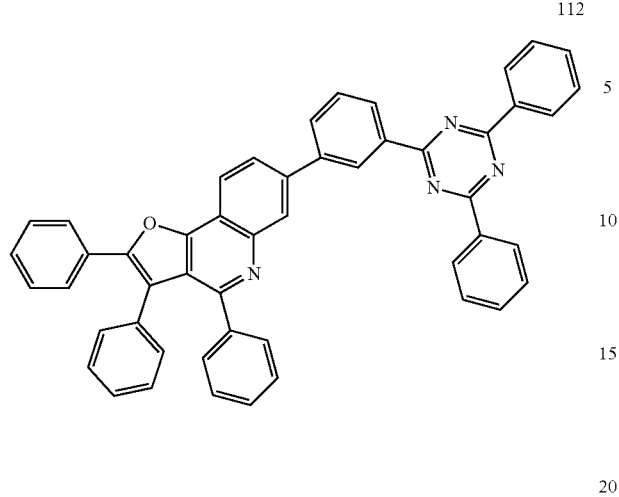
112
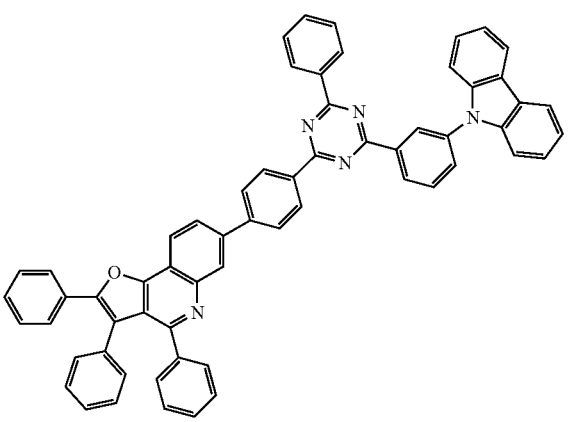
115
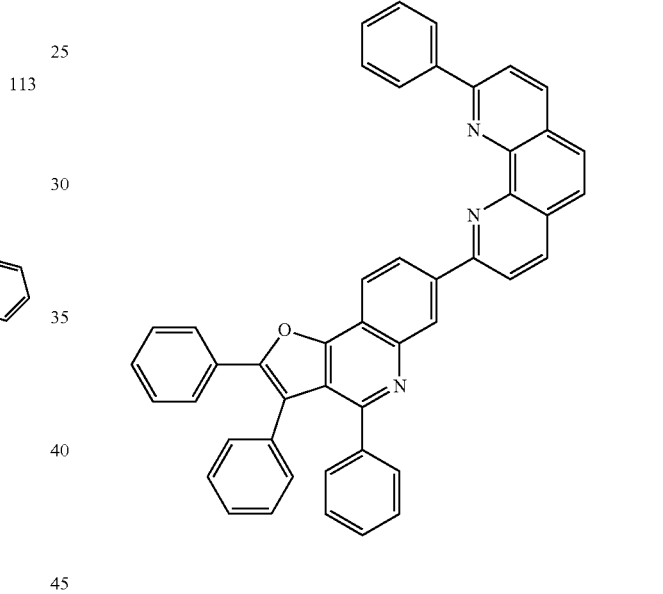
116
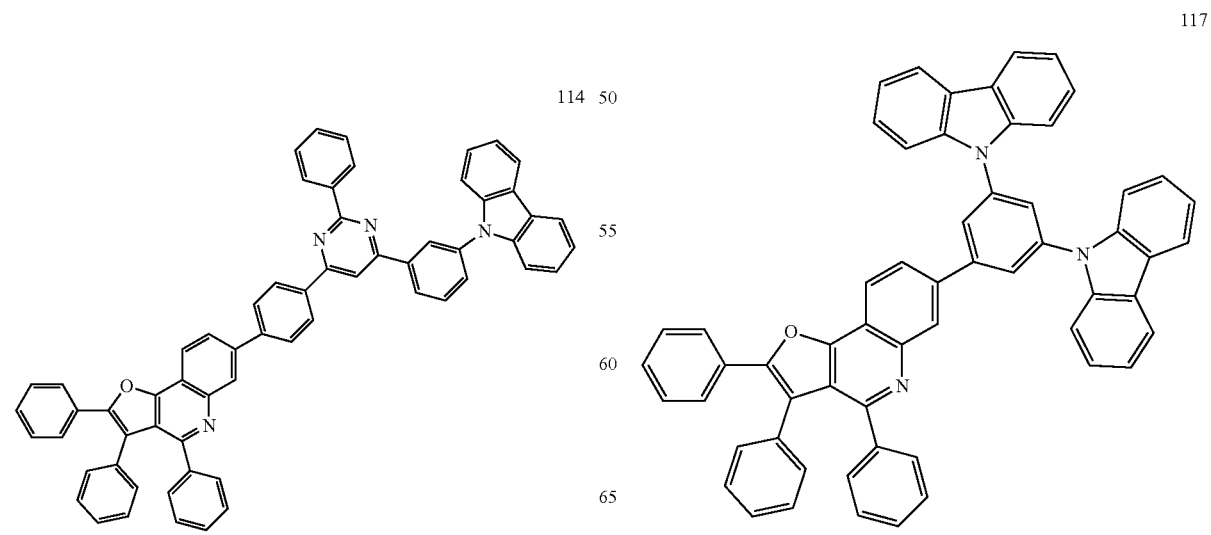

-continued
118
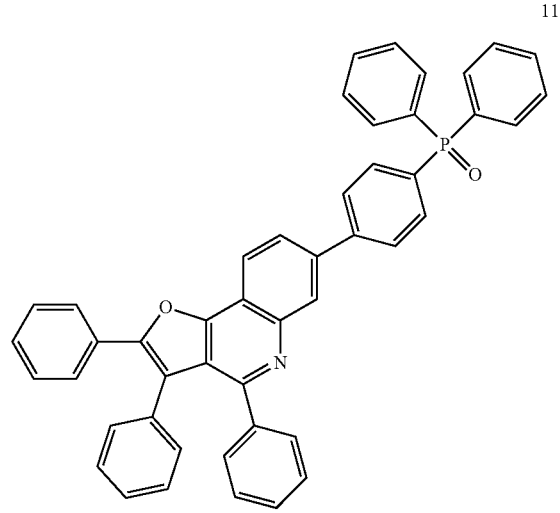
119
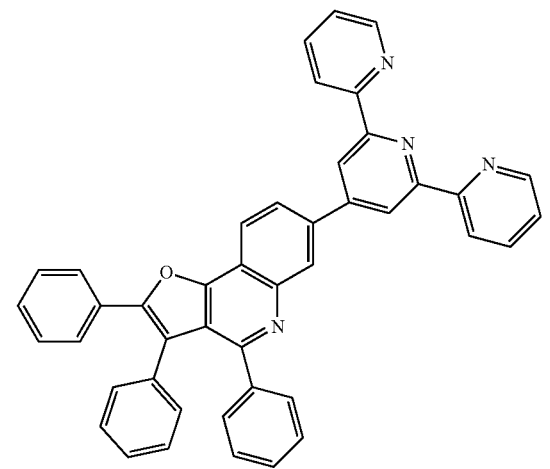
120
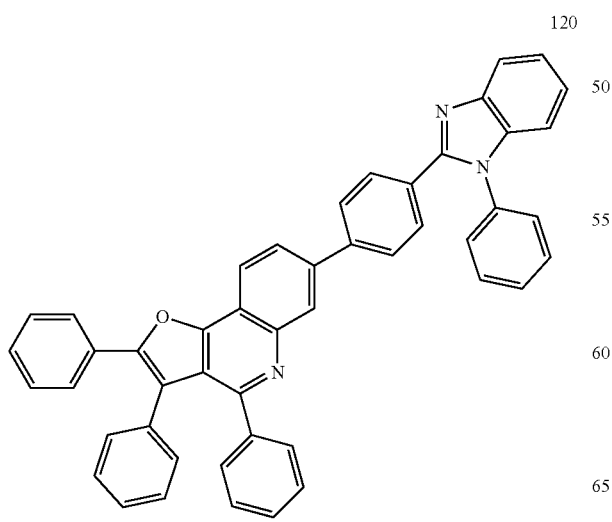
-continued
121
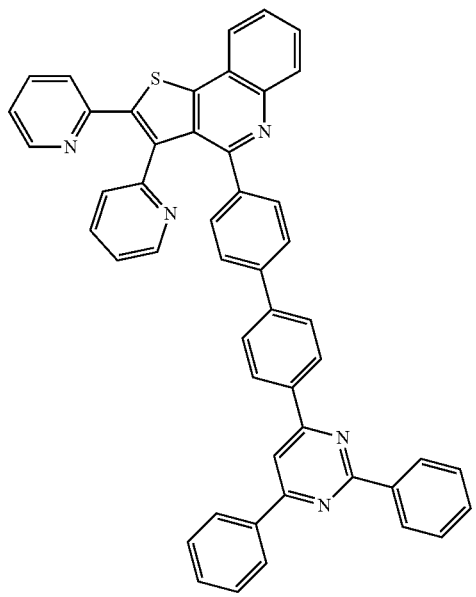
122
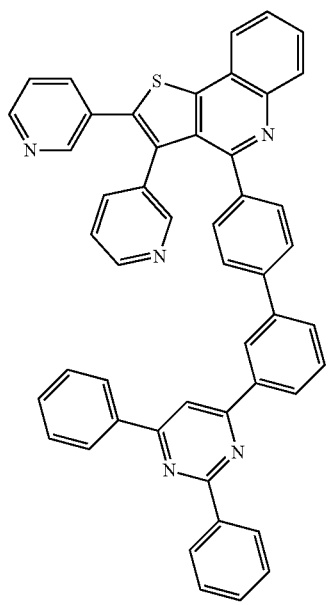

123
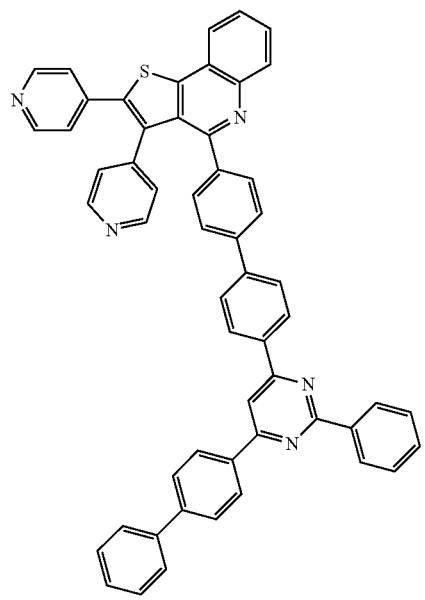
125
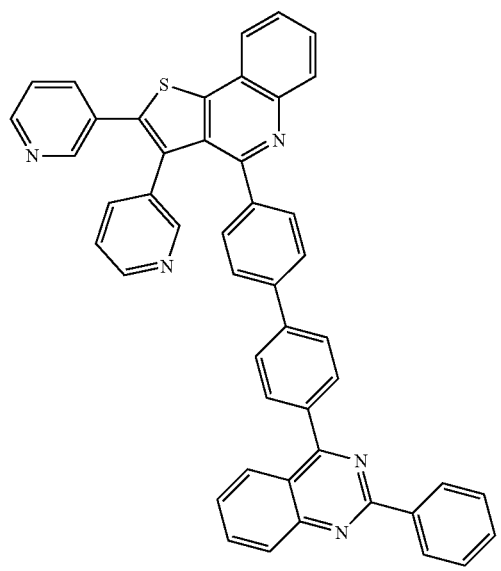
124
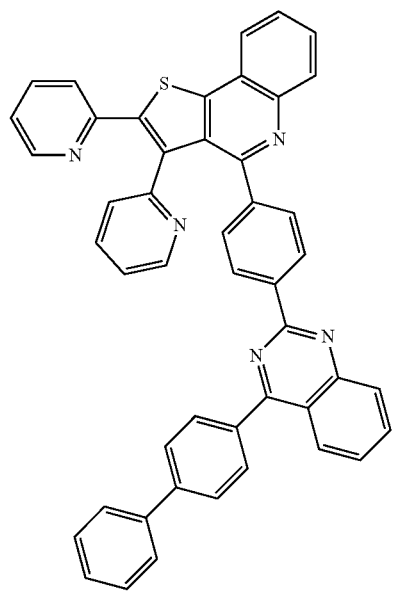
126
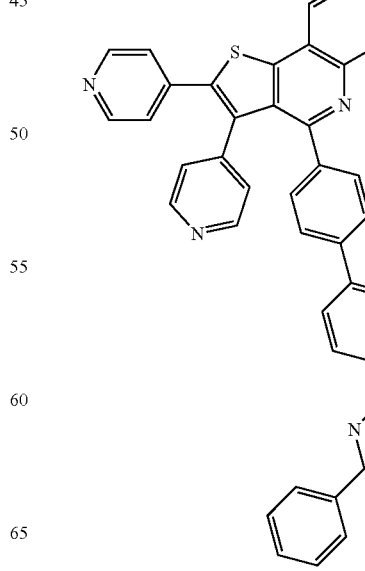

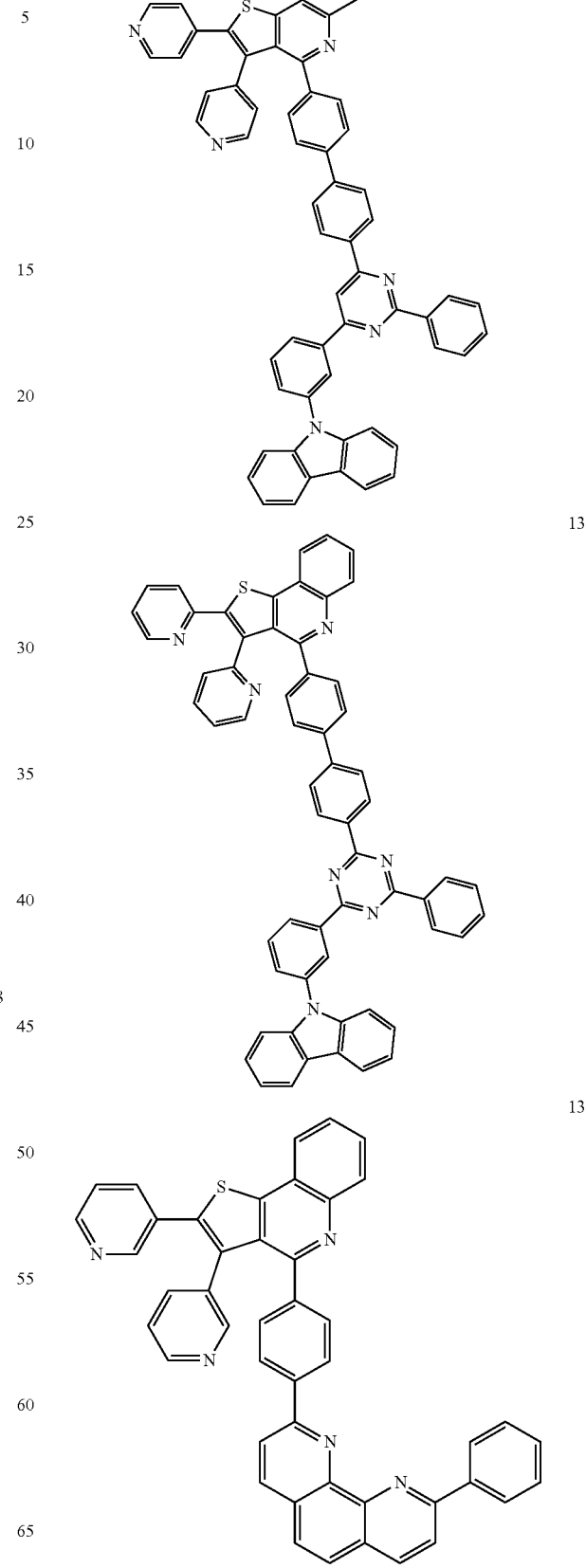

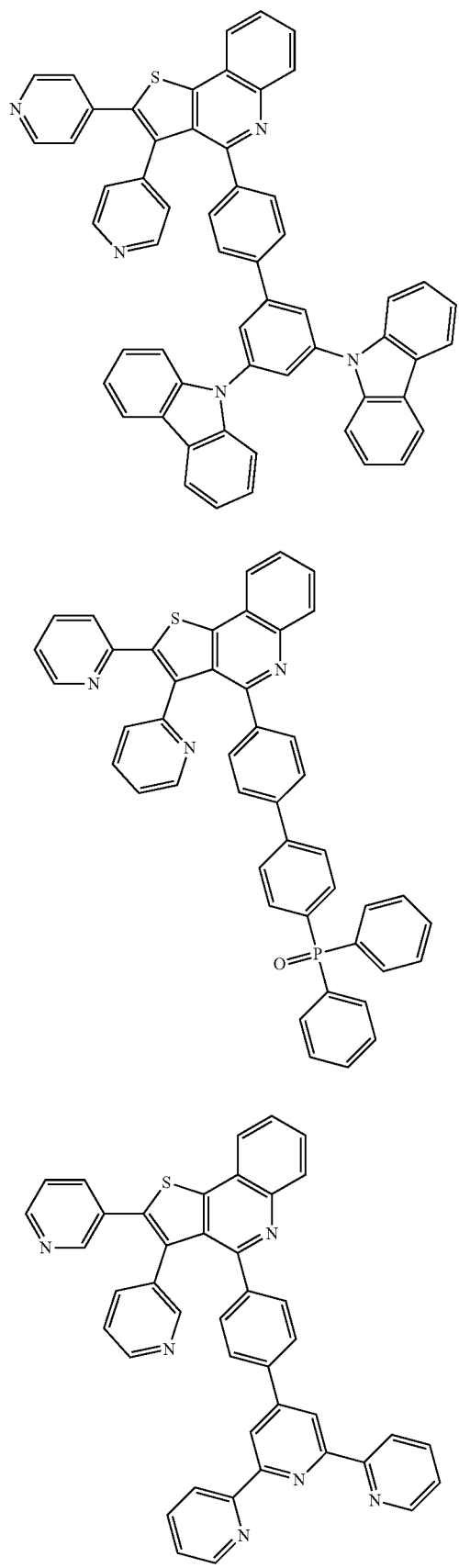
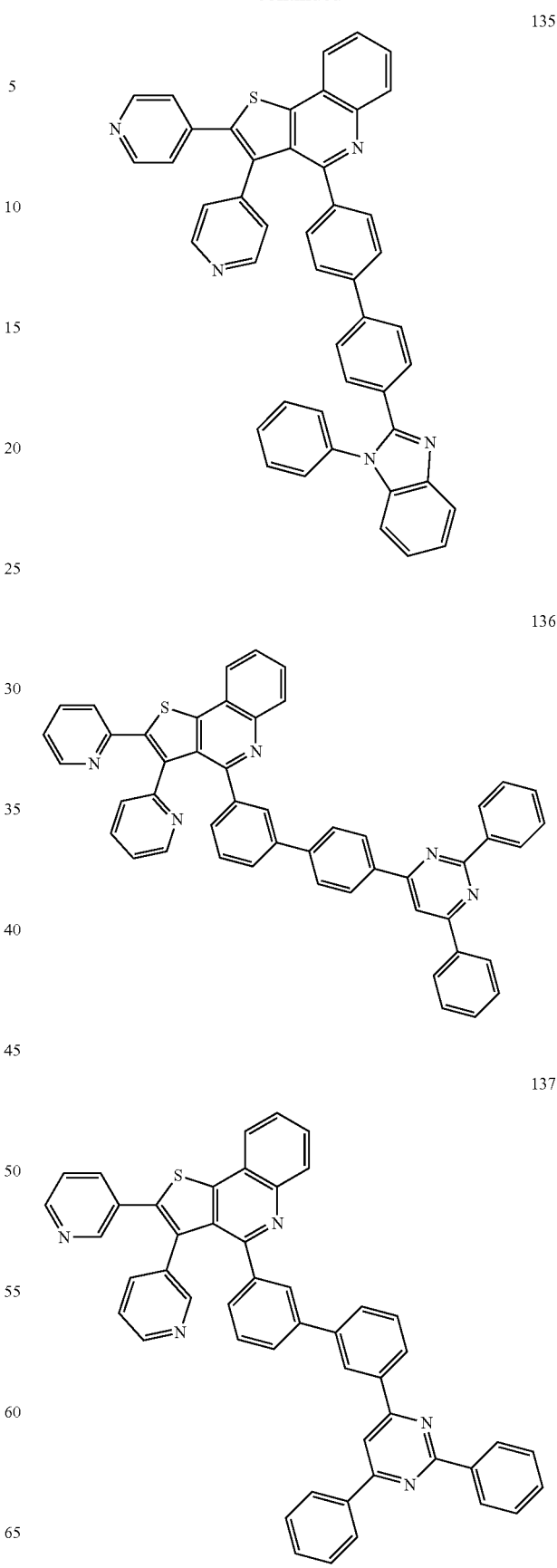

138
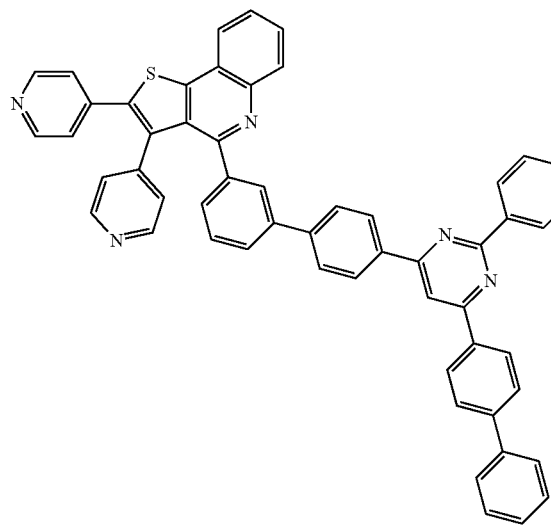
139
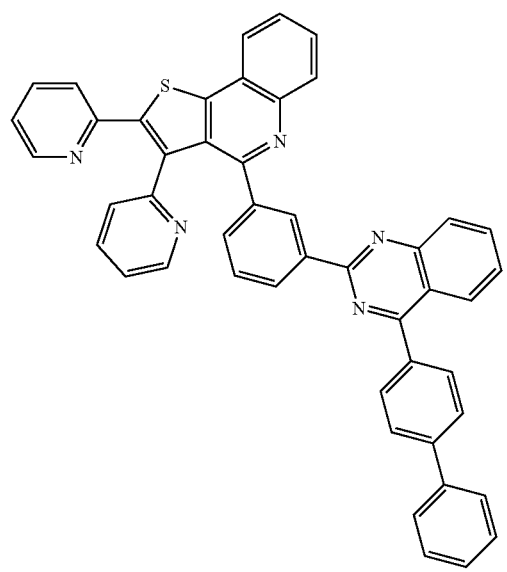
140
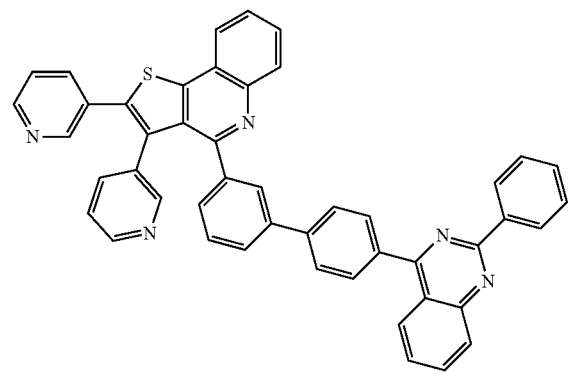
141
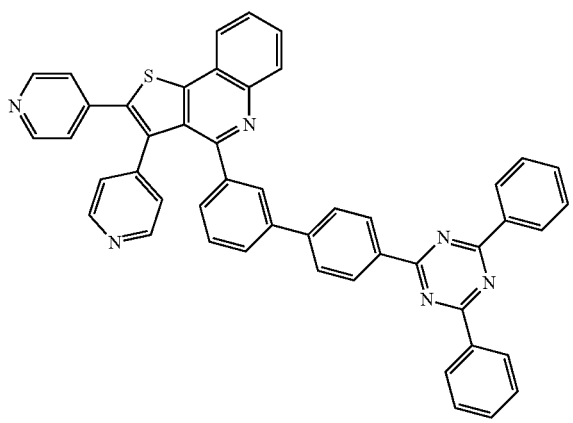
142
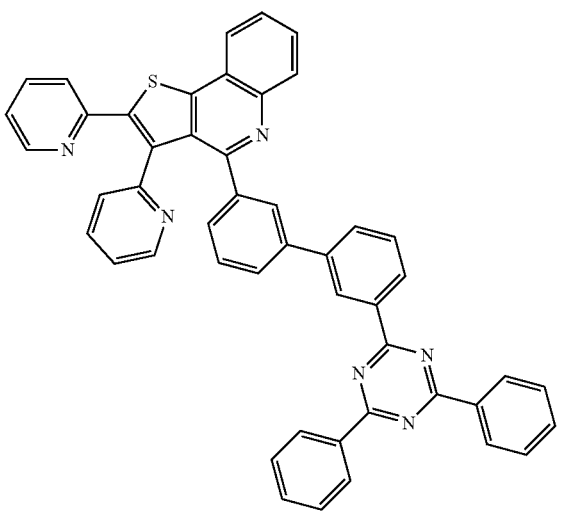
143
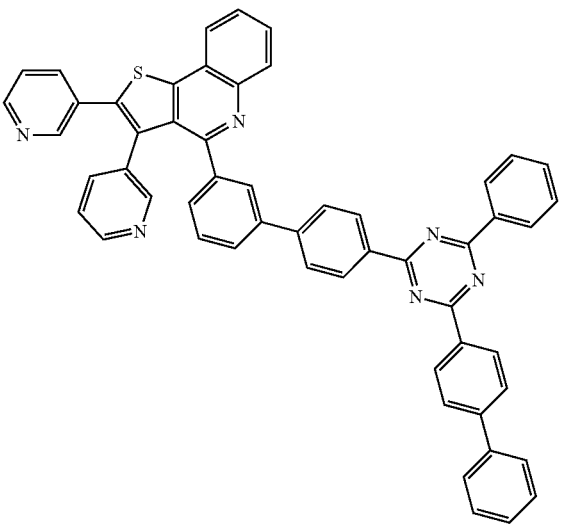

75
-continued
144
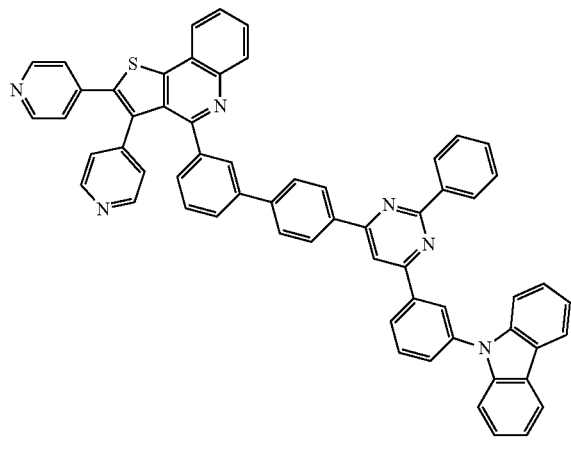
145
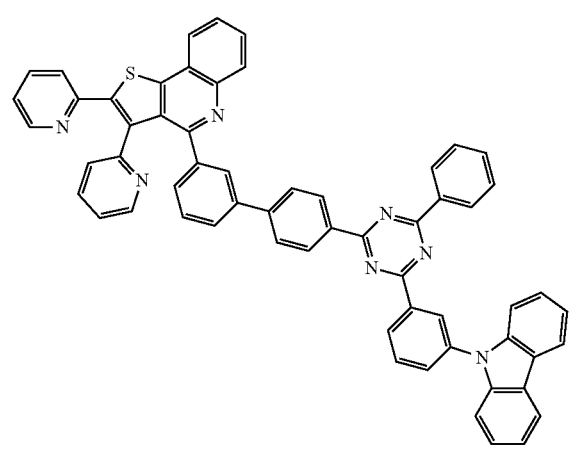
146
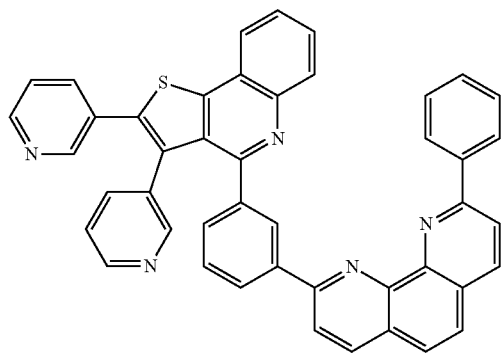
76
-continued
147
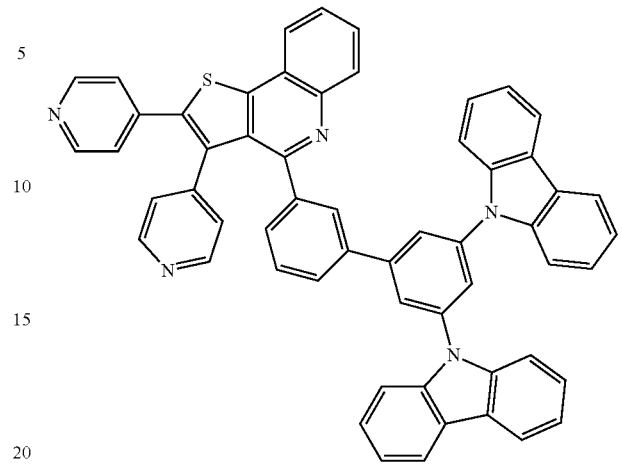
148
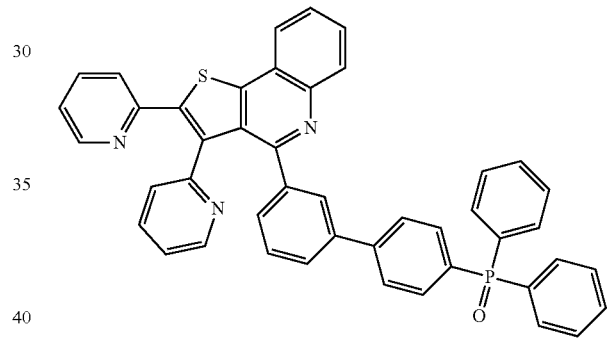
149
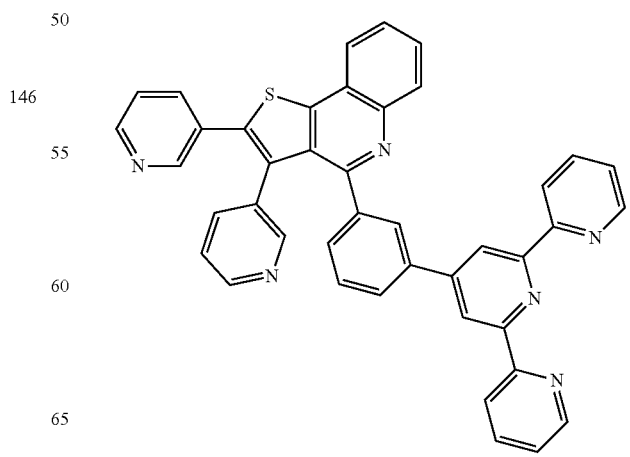

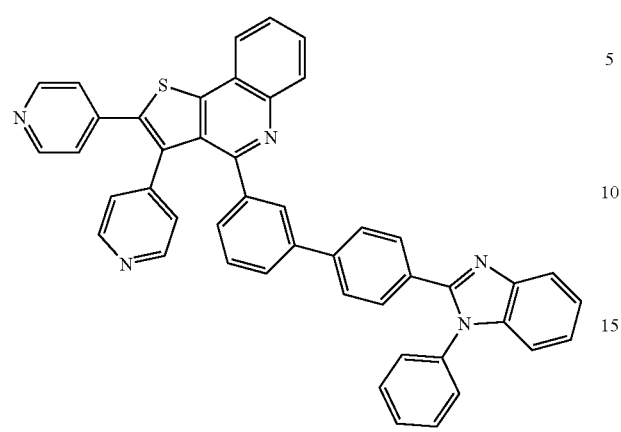
150
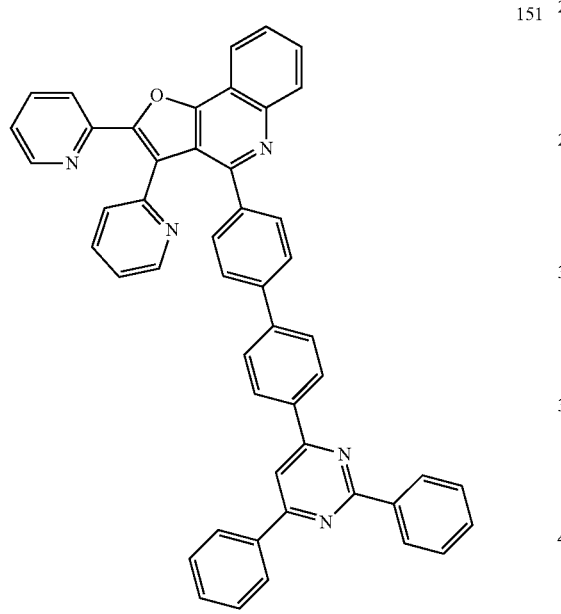
151
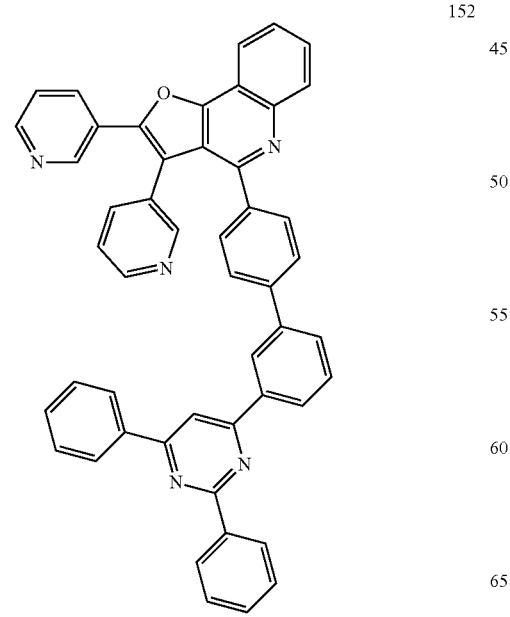
152
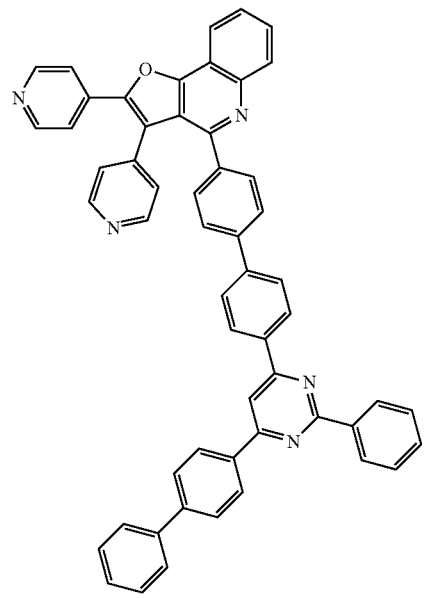
153
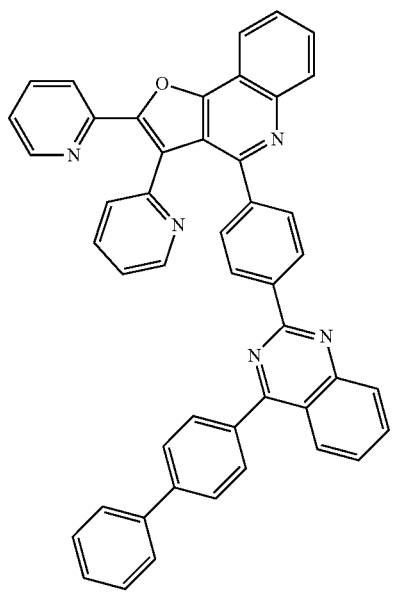
154

155
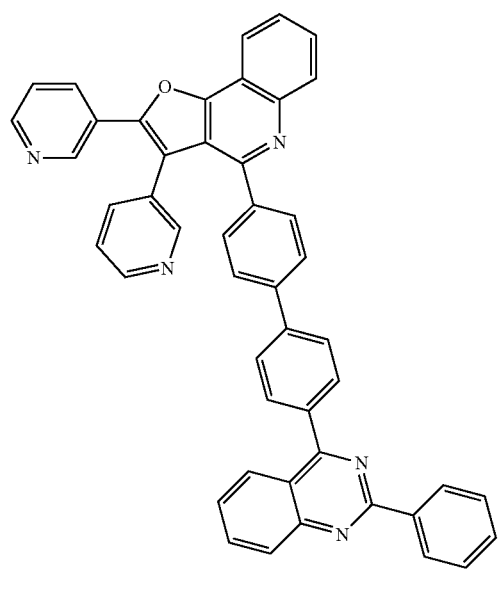
156
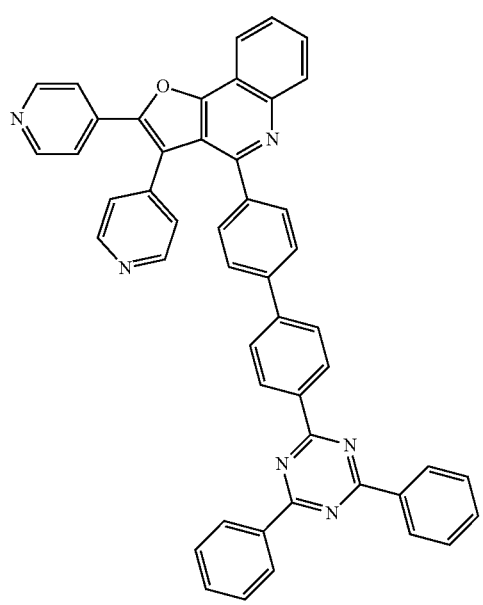
157
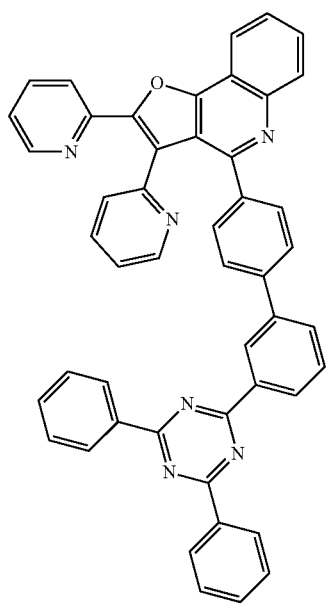
158

81
-continued
159
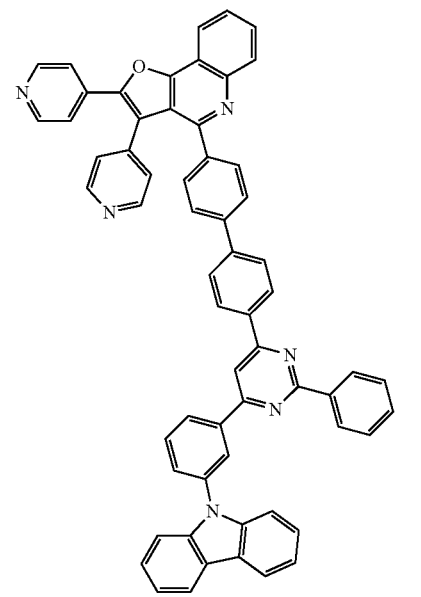
160
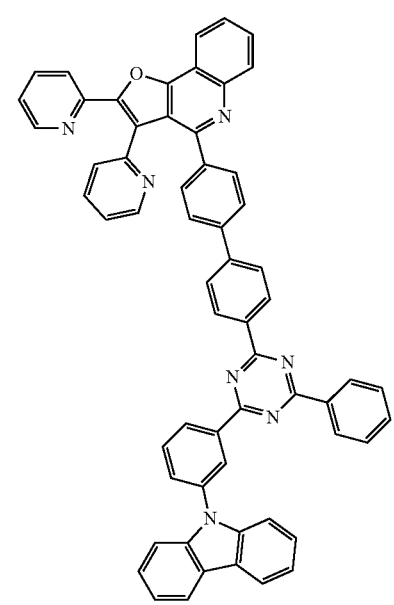
161
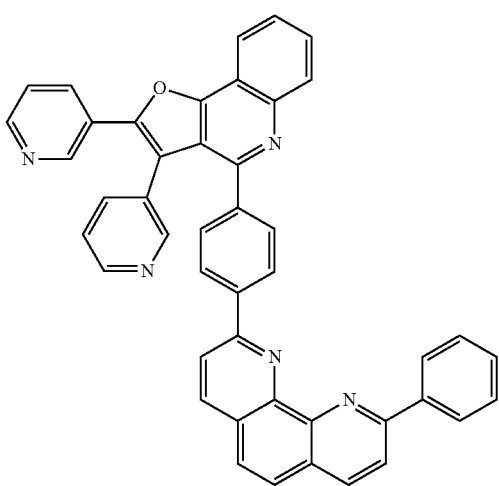
82
-continued
162
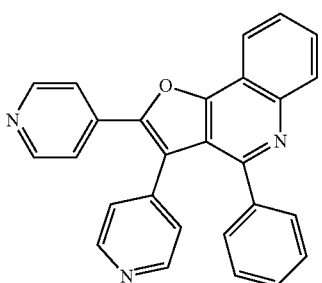
163
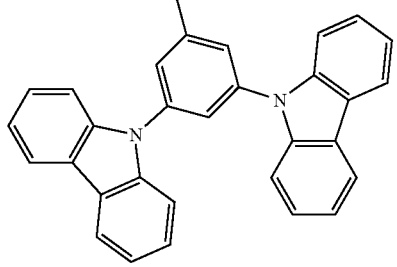
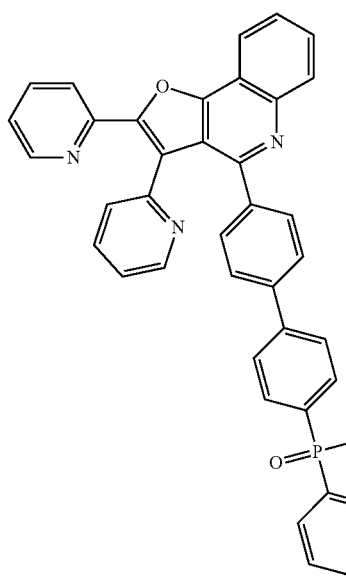
164
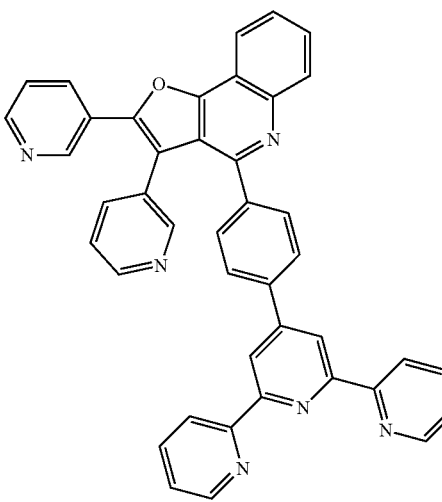

165
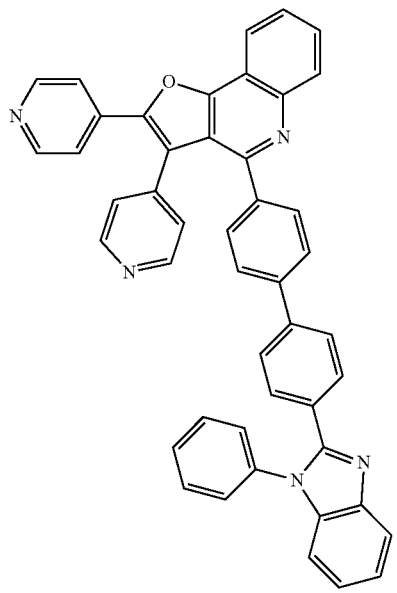
166
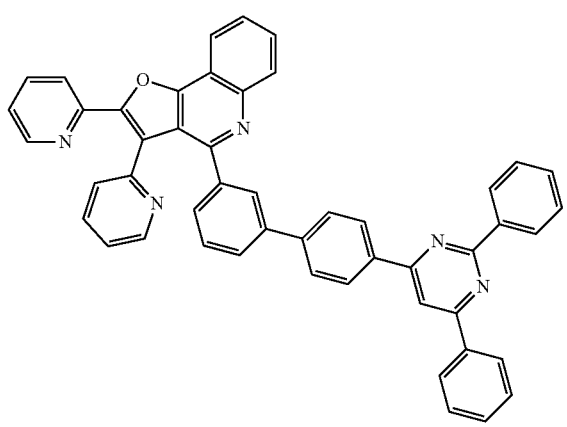
167
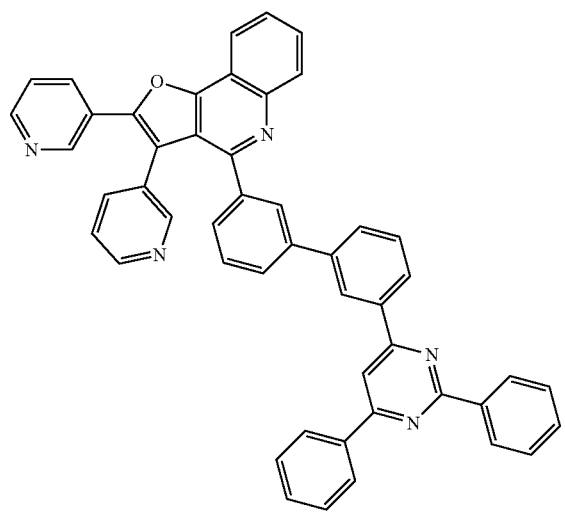
168
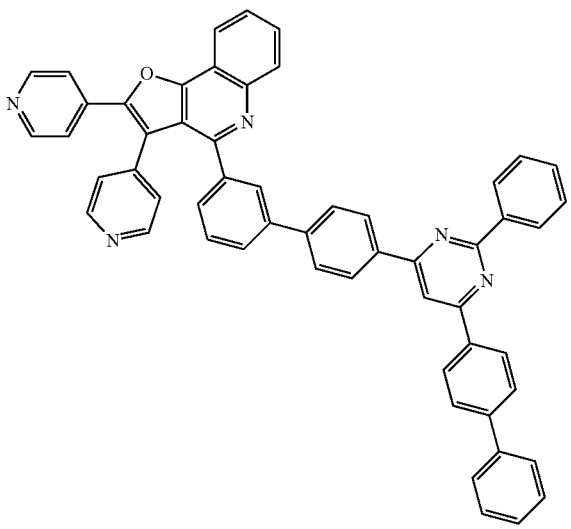
169
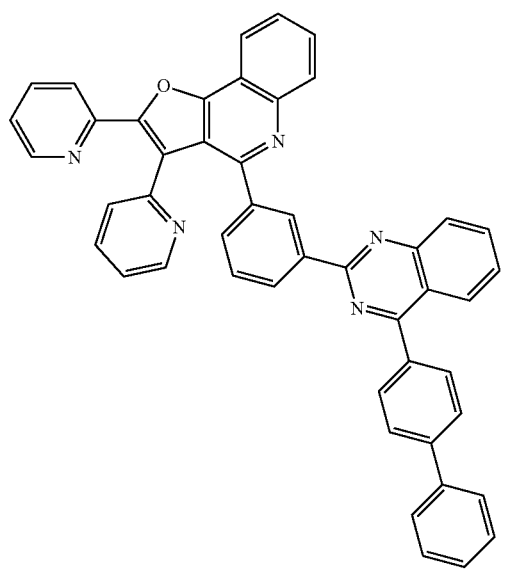
170
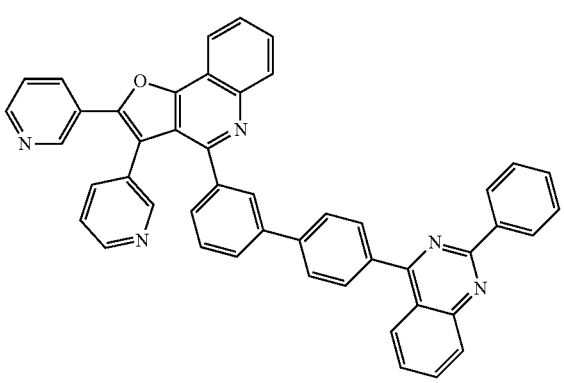

171
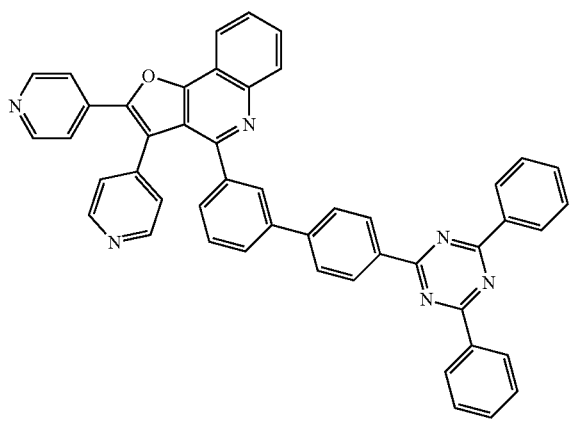
172
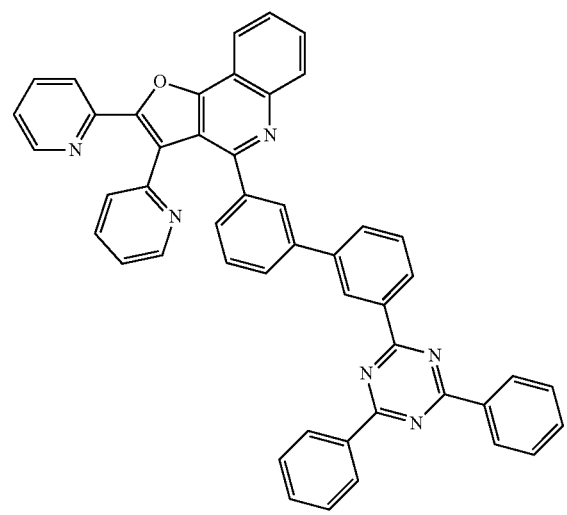
173
174
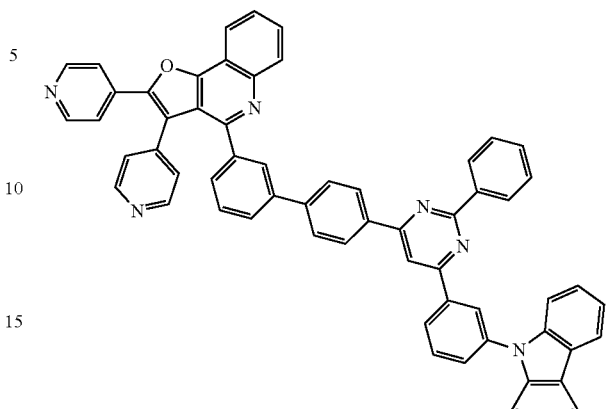
175
176
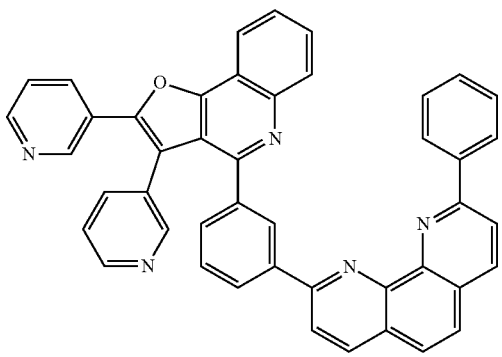

177
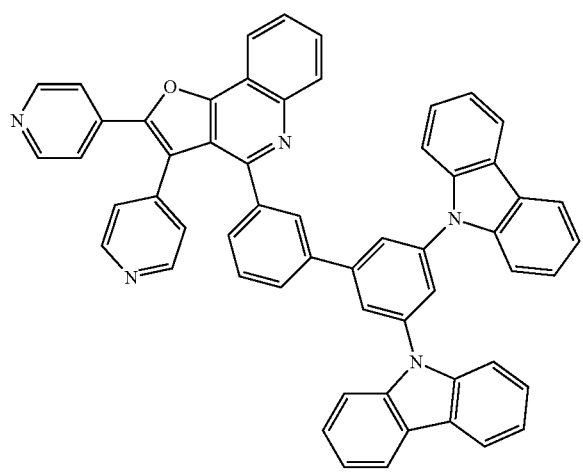
179
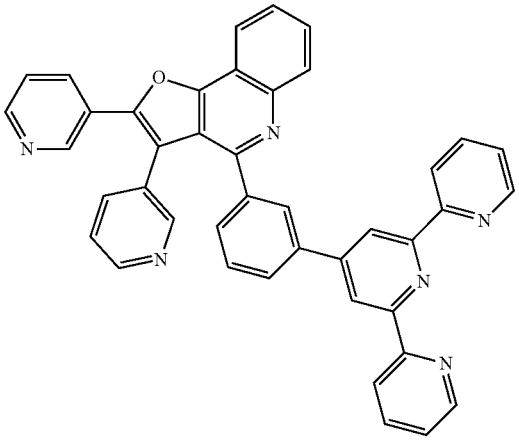
178
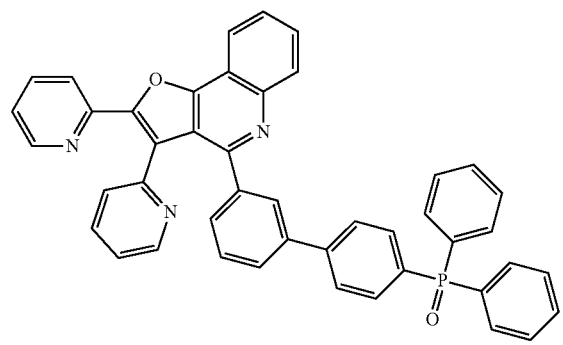
180
181
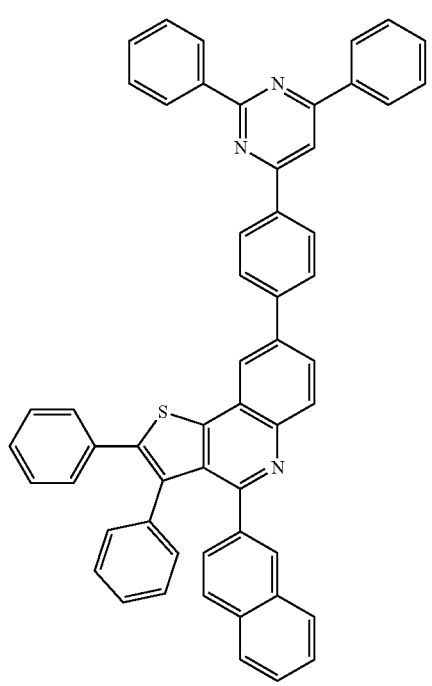
182
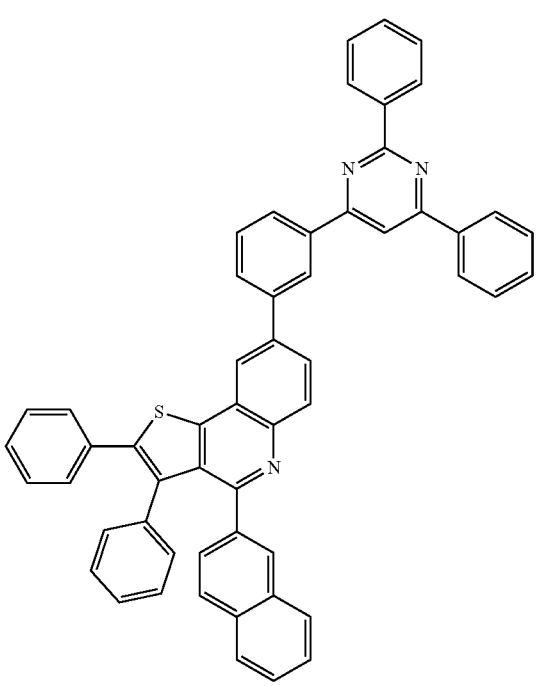

-continued
183
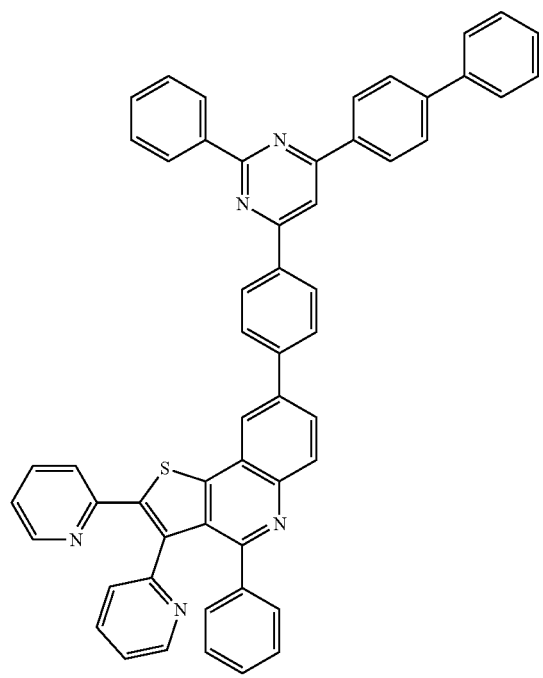
184
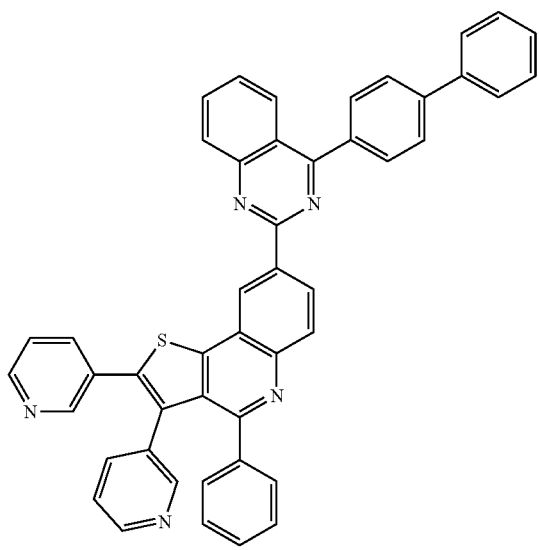
185
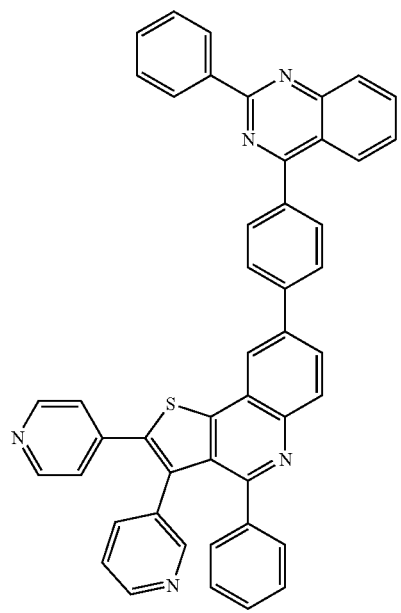
186
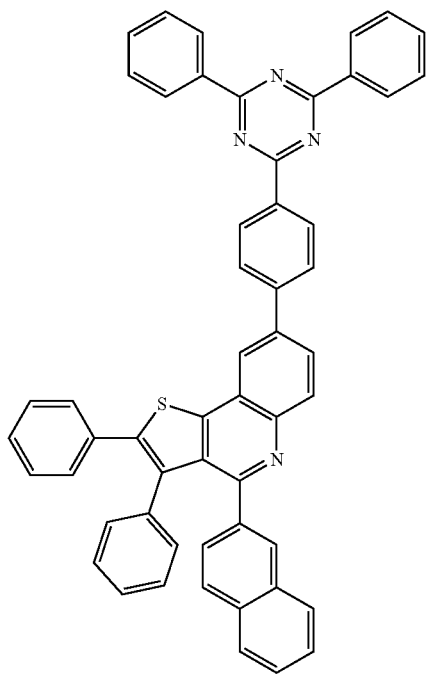

-continued
187
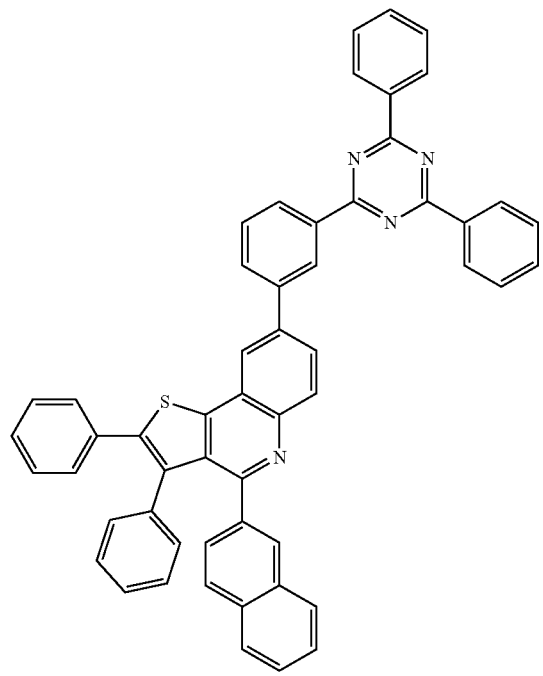
188
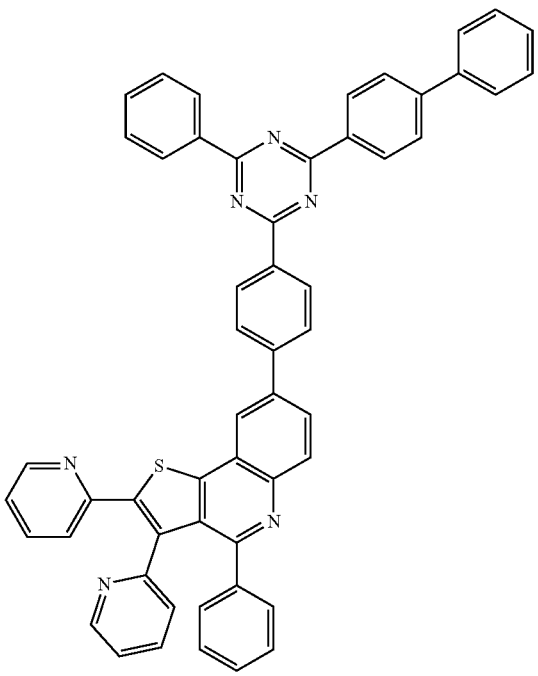
189
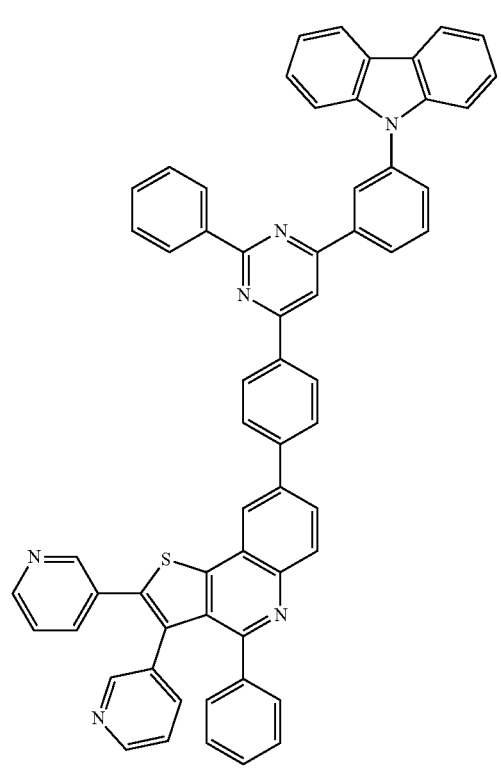
190
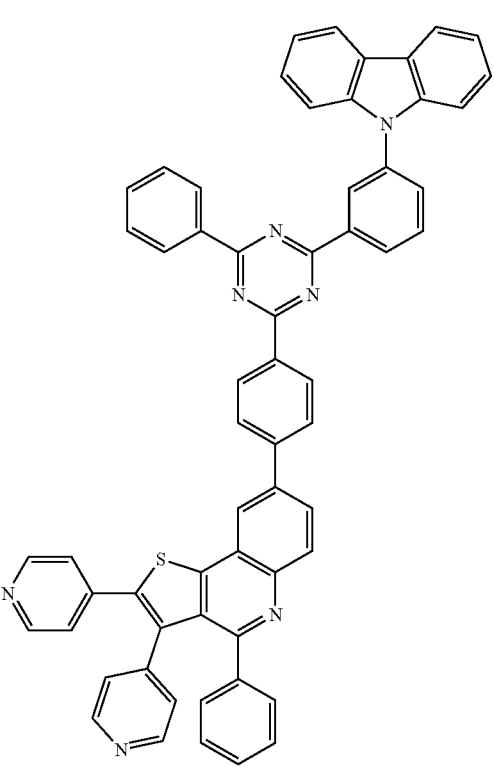

-continued
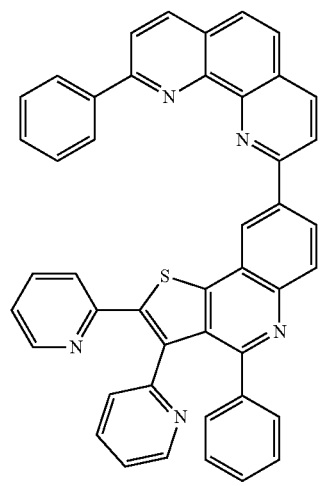
191
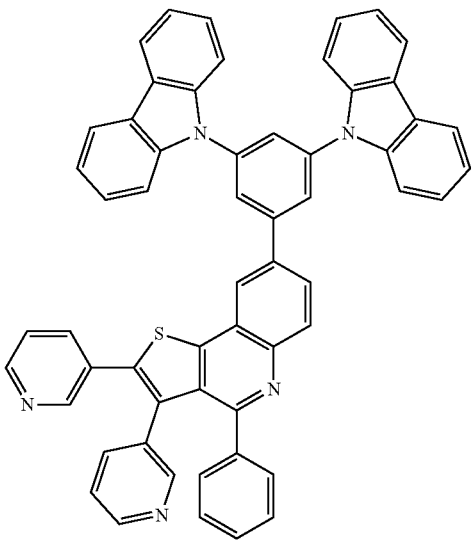
192
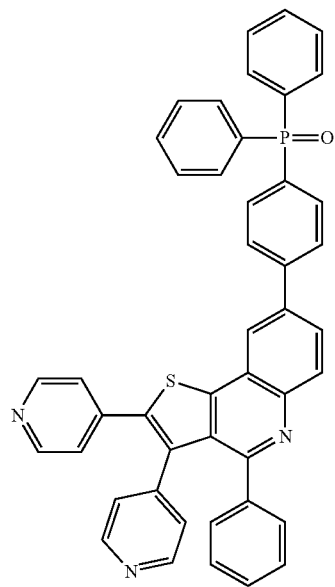
193
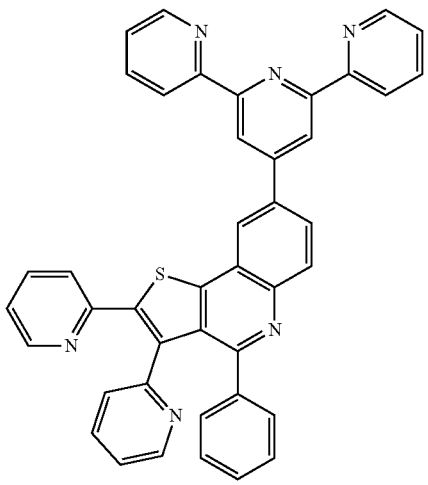
194

-continued
195
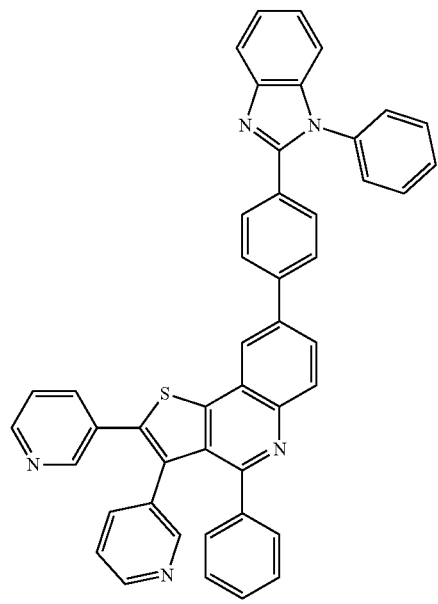
196
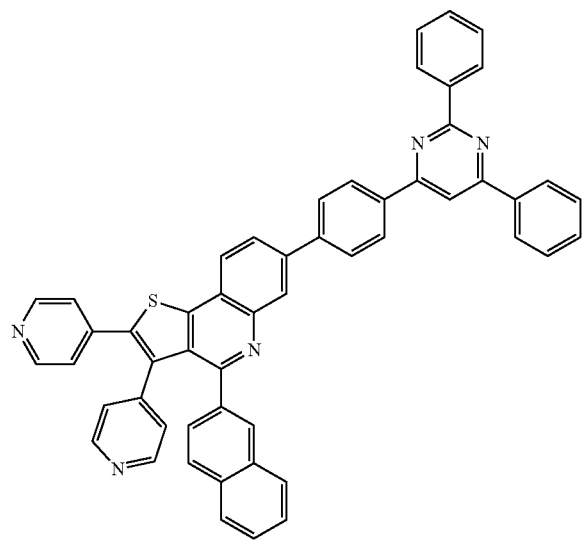
197
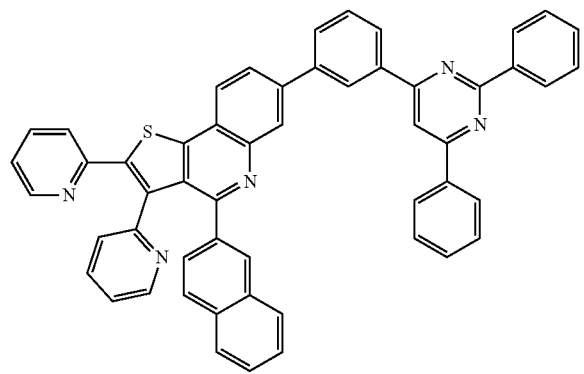
198
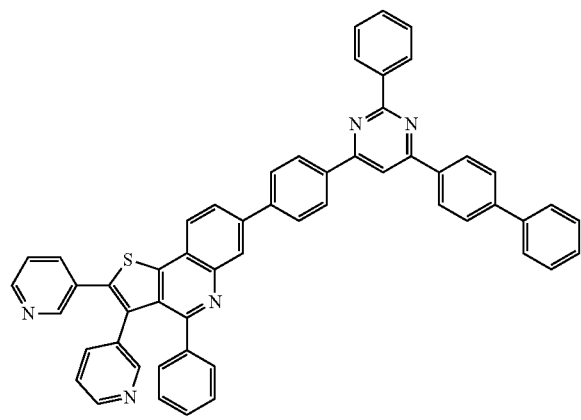
199
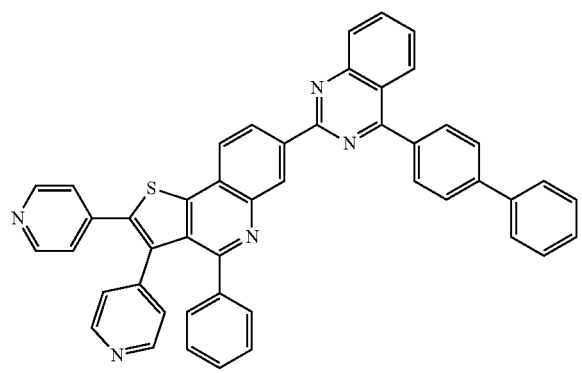
200
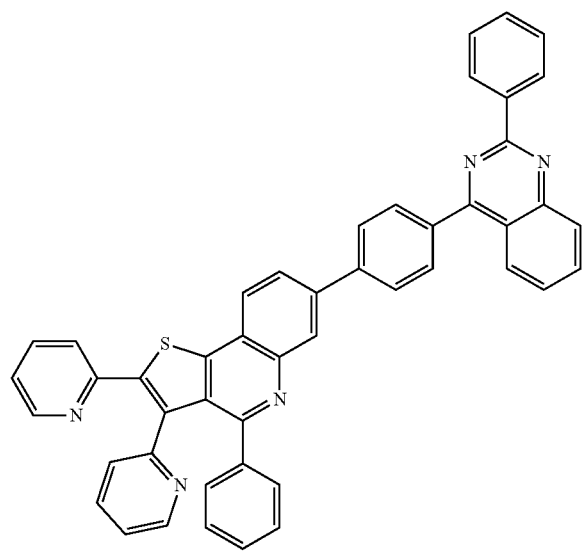

-continued
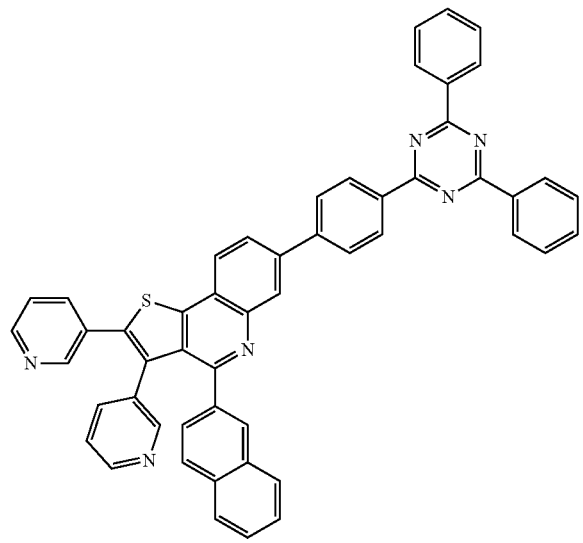
201
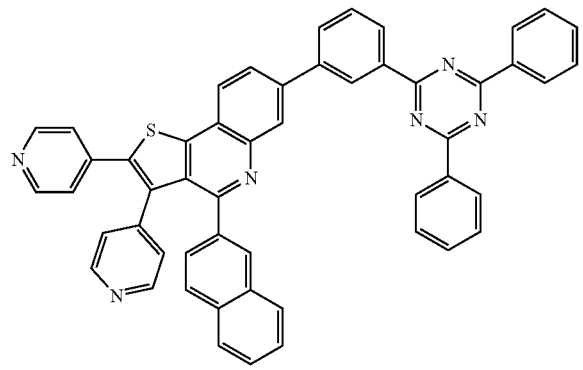
202
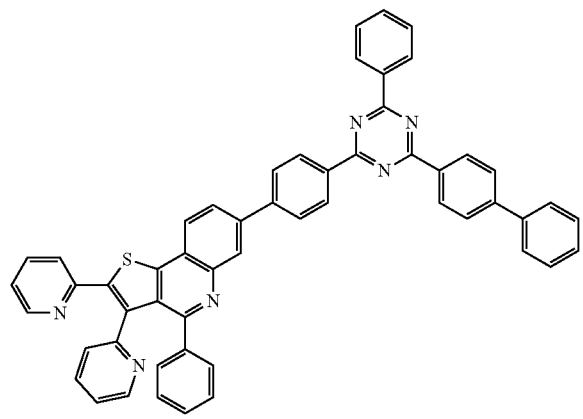
203
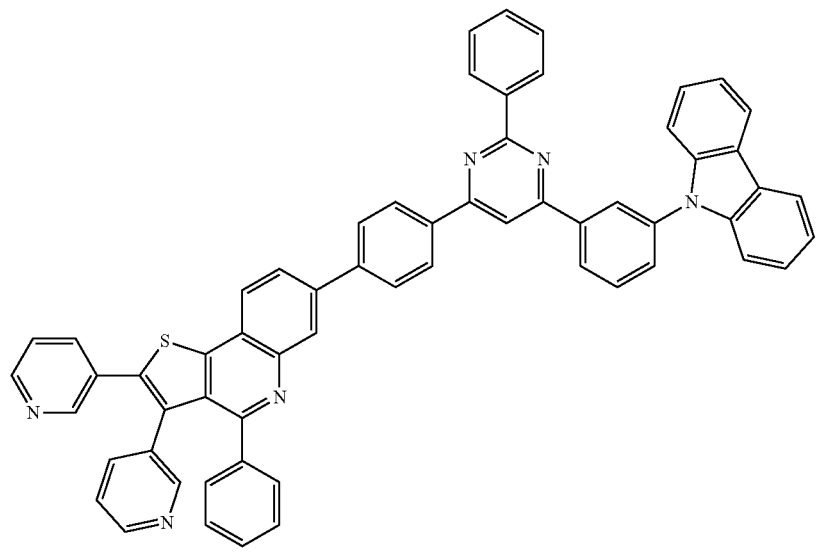
204

205
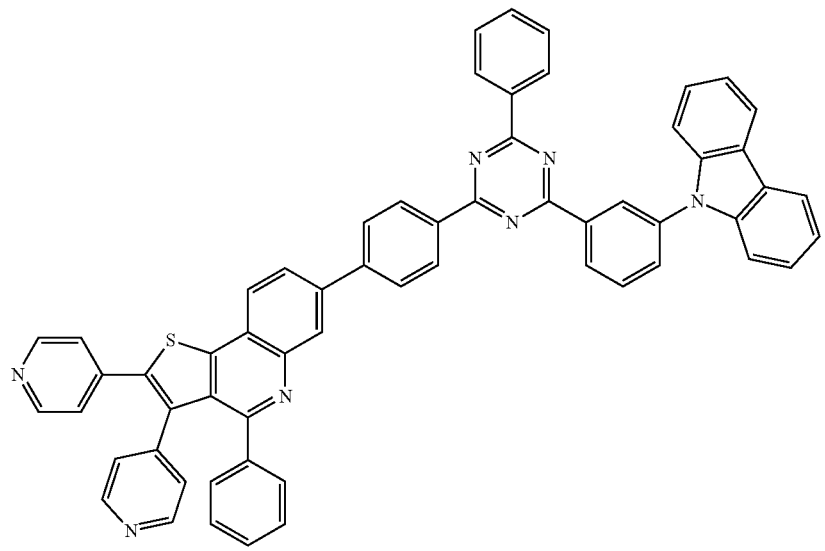
206
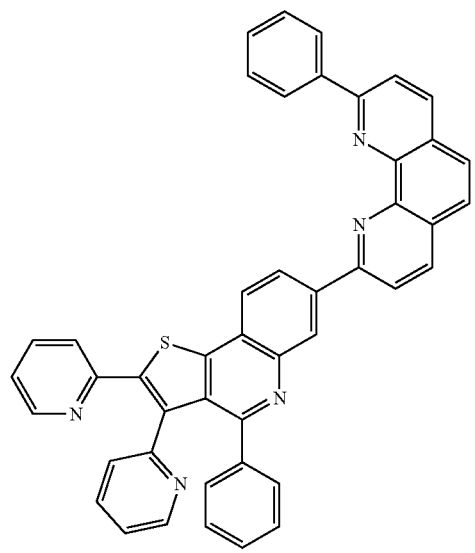
207
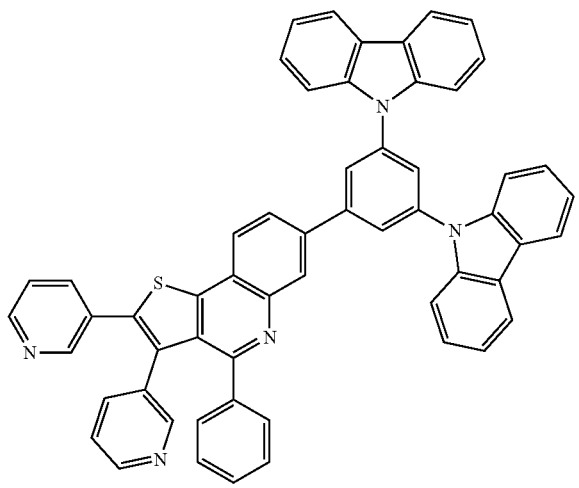
208
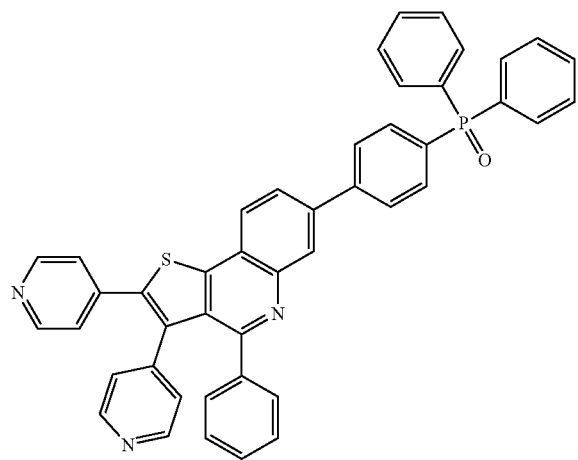
209
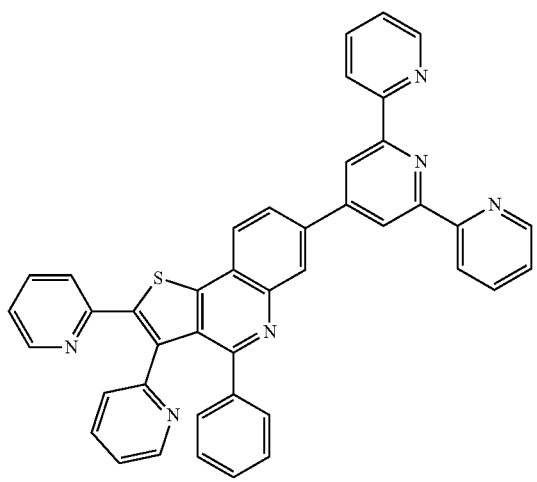

-continued
210
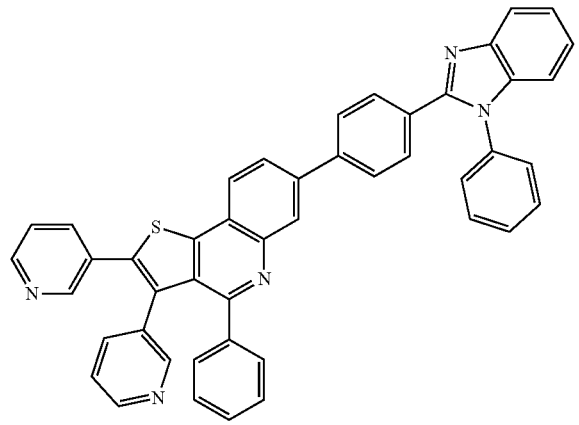
211
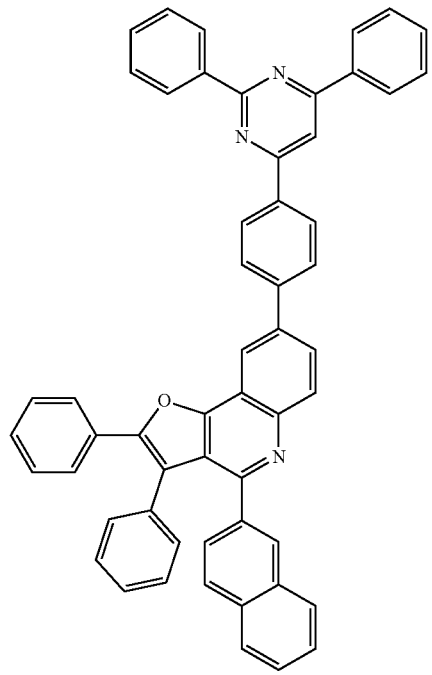
212
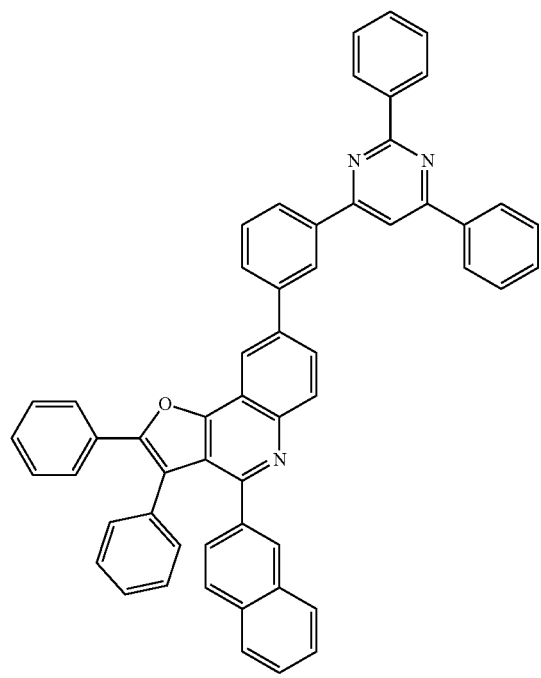
213
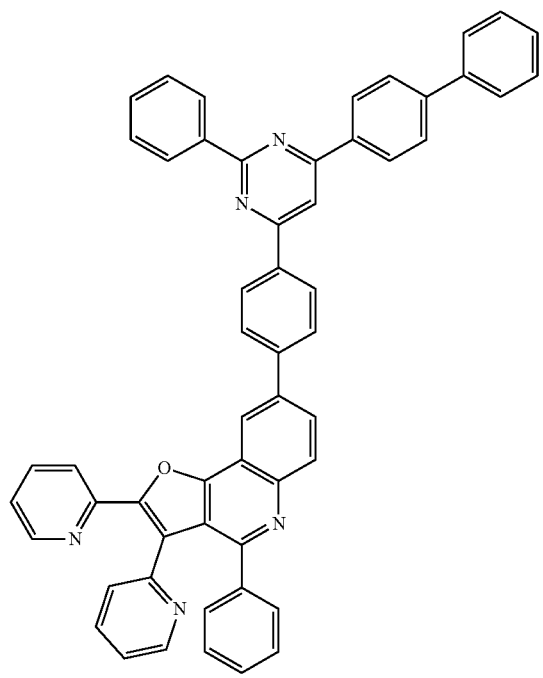

-continued
214 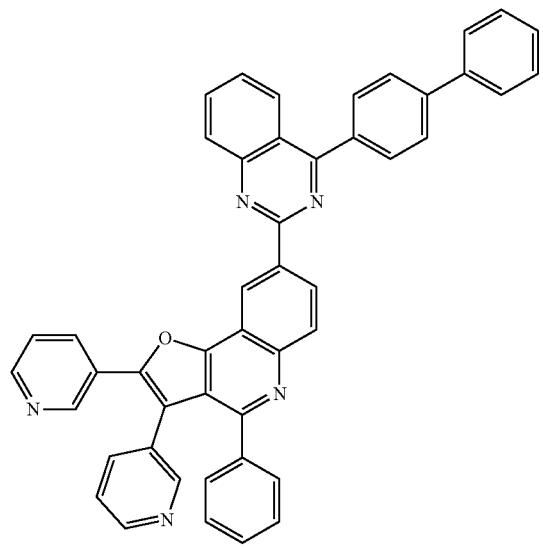
215 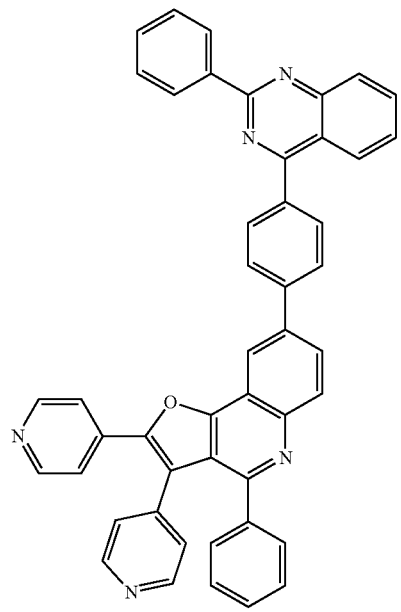
216 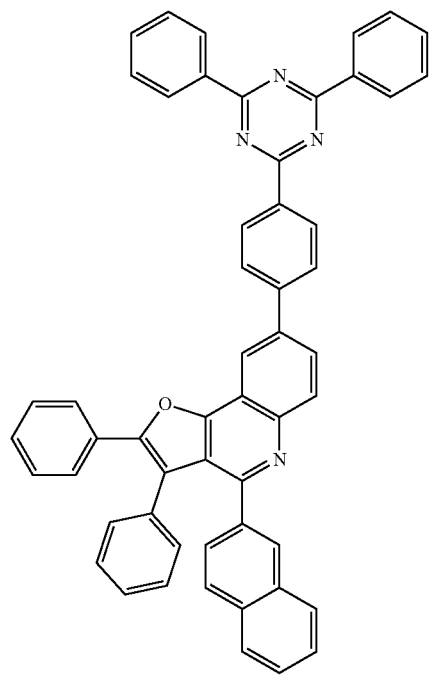
217 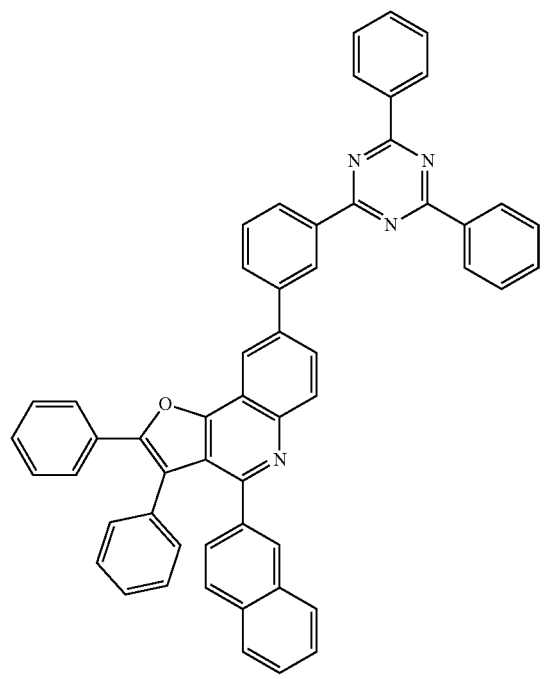

-continued
218
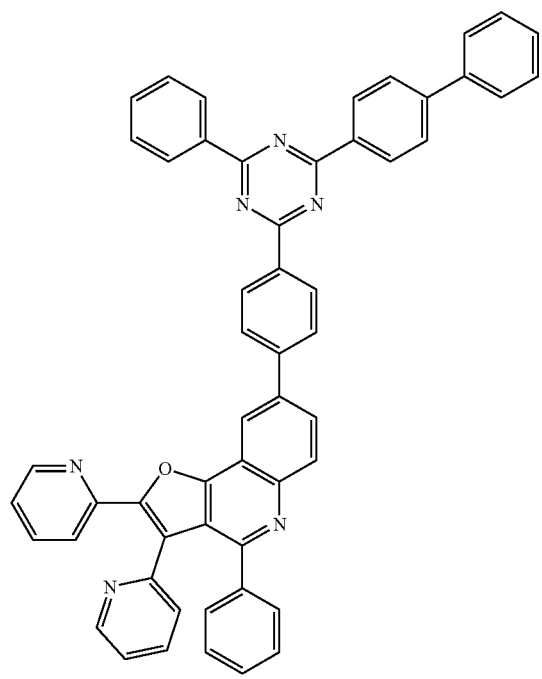
219
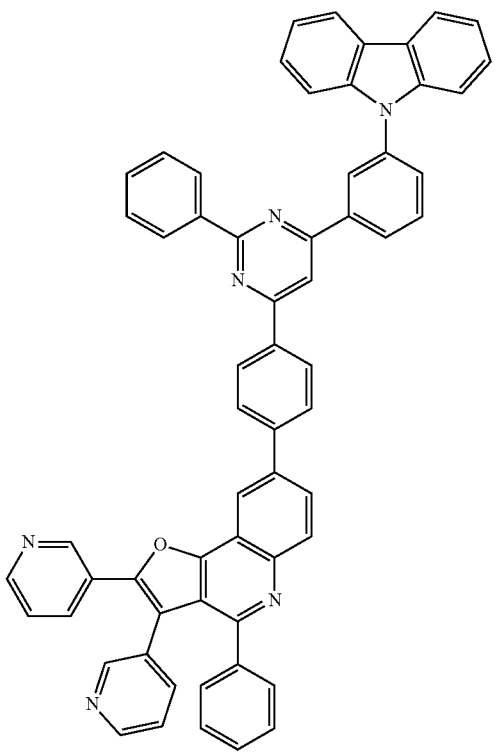
220
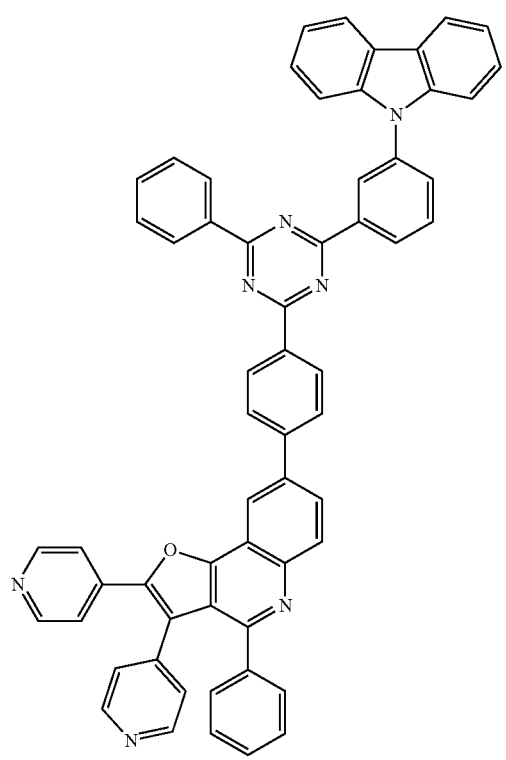
221
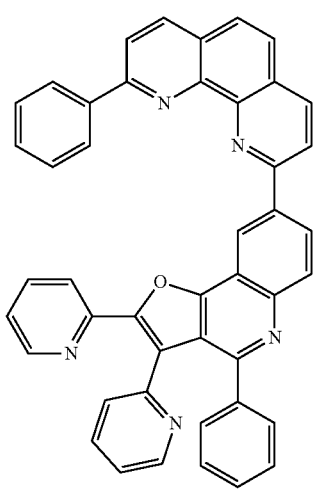

-continued
107
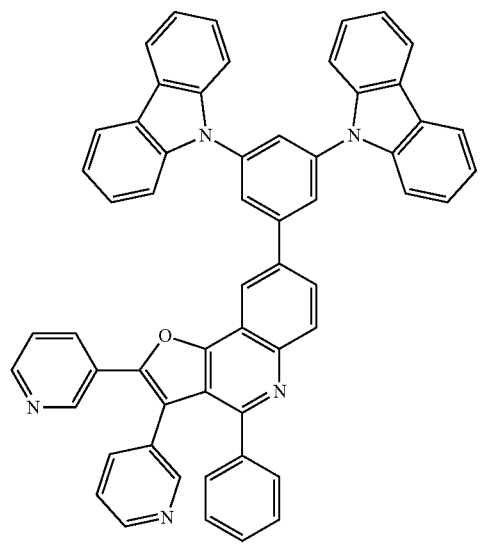
222
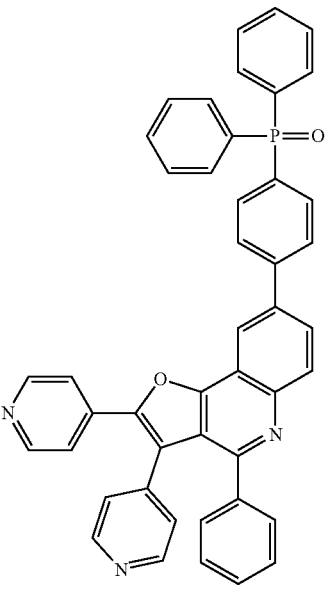
223
224
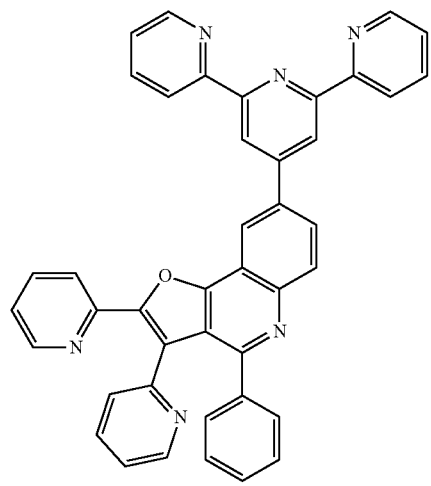
225
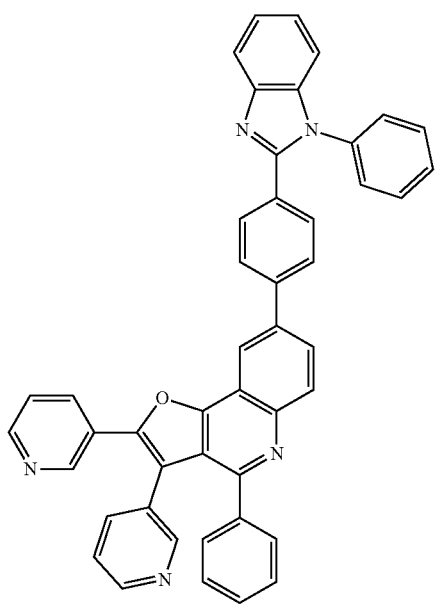

-continued
226
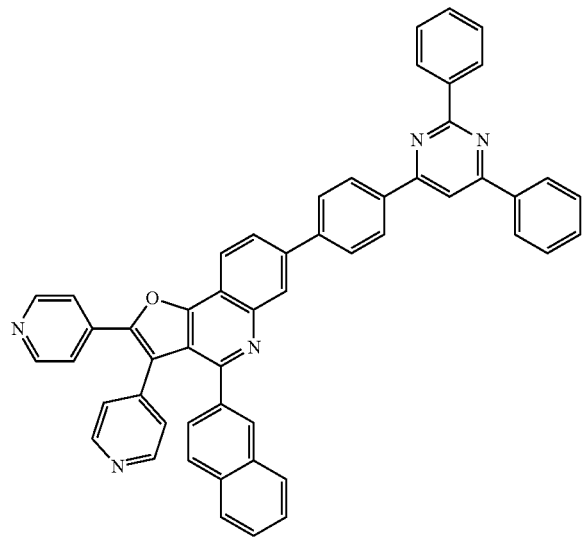
227
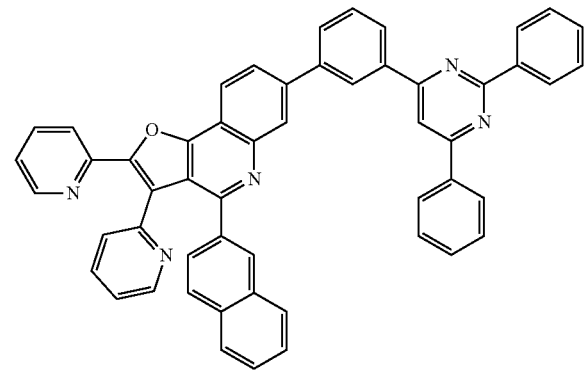
228
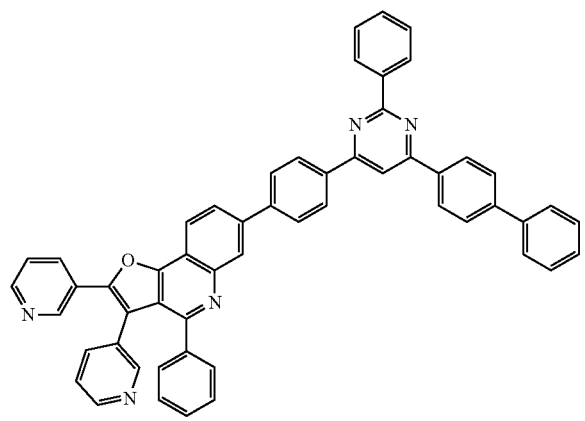
229
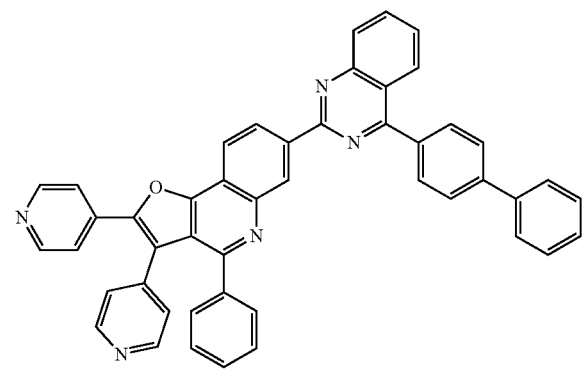
230
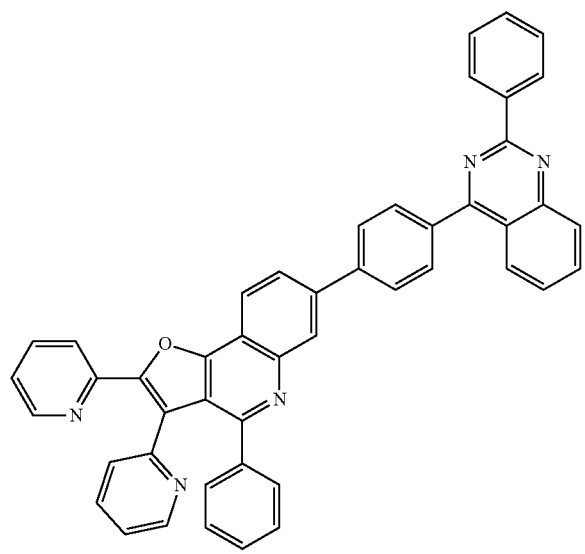
231
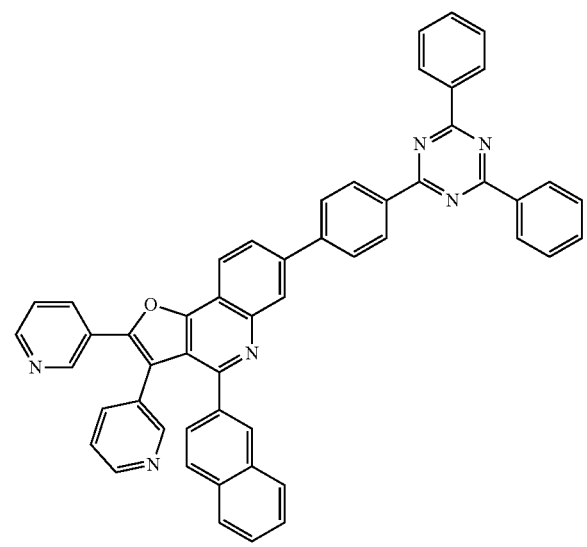

111
232
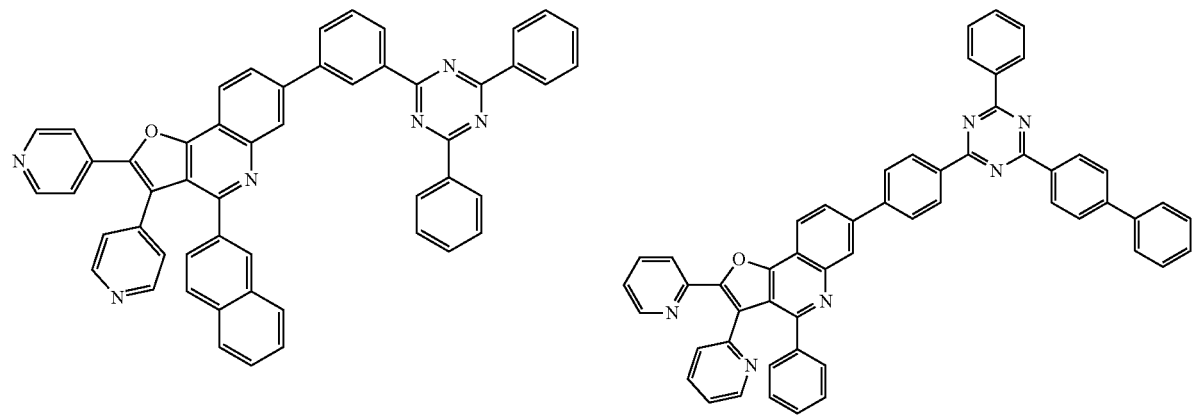
233
234
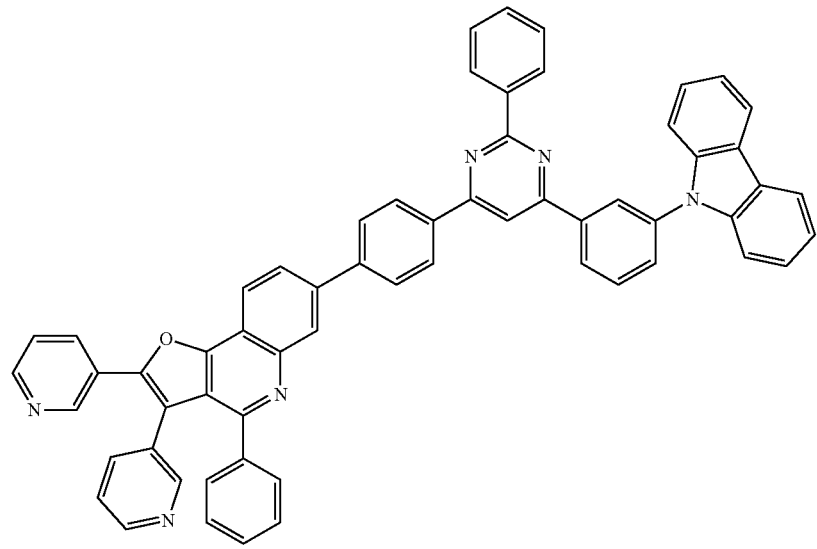
235
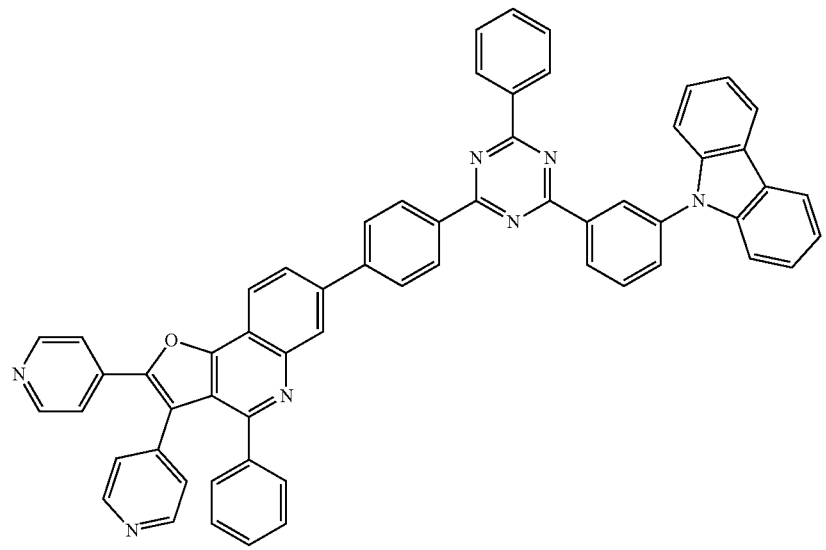

-continued
236
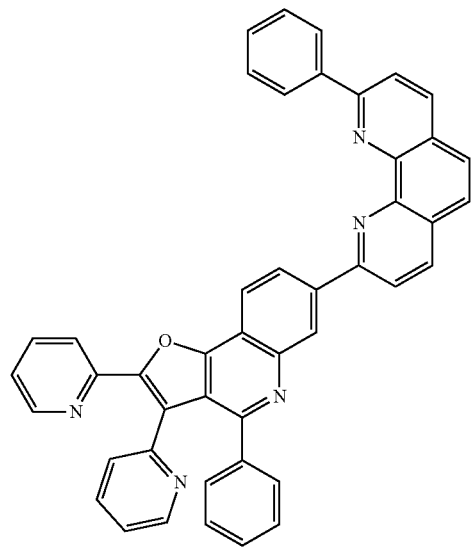
237
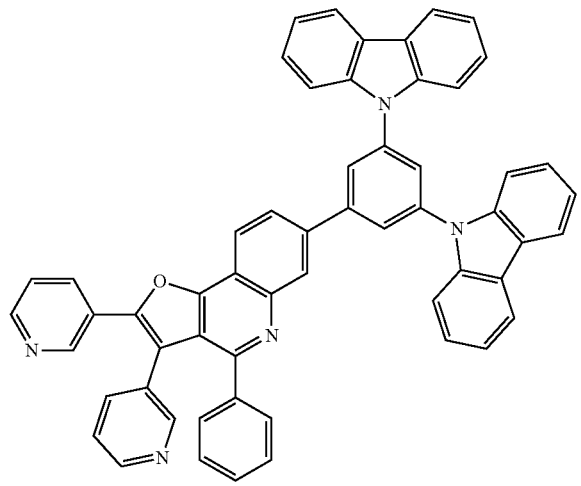
238
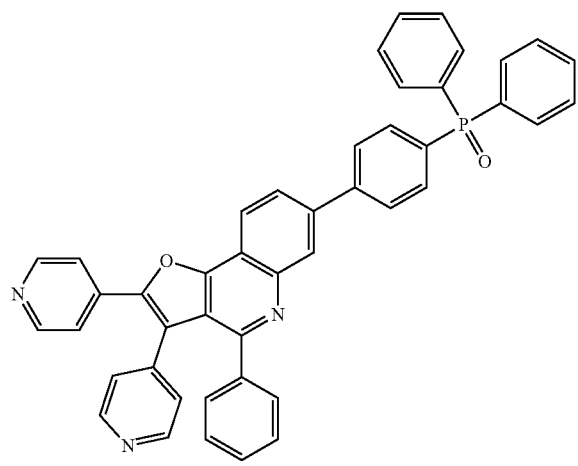
239
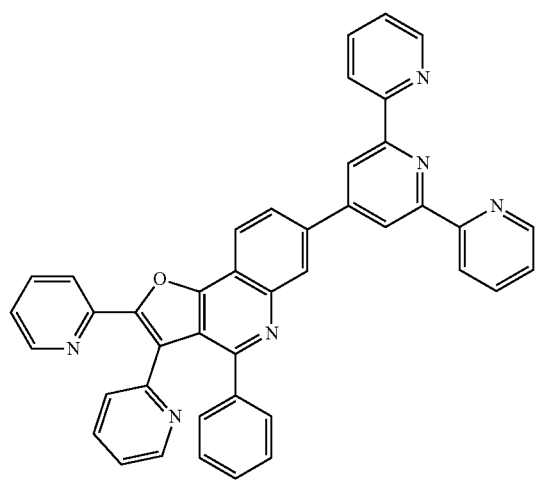

-continued
240
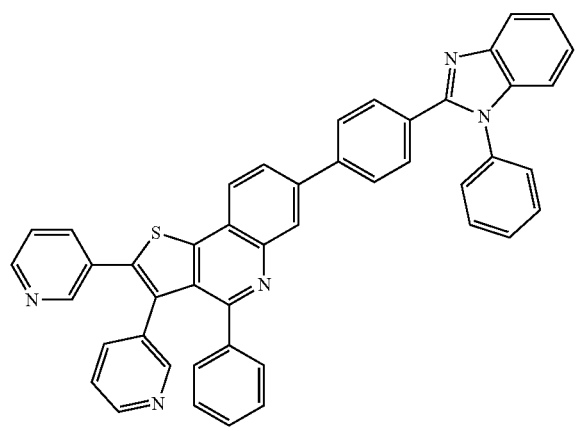
241
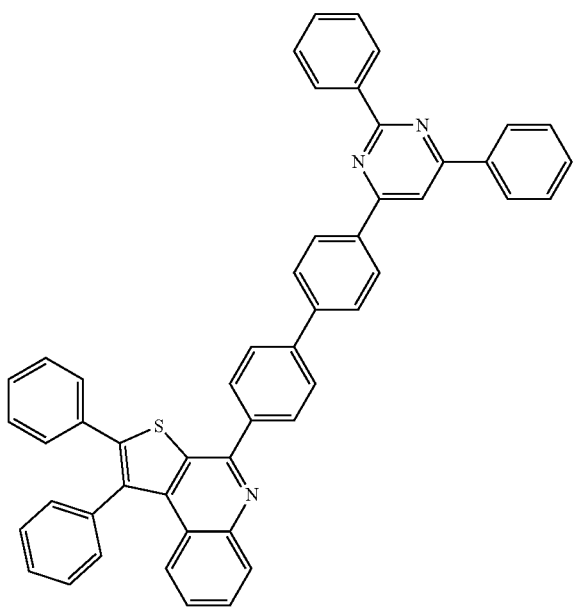
242
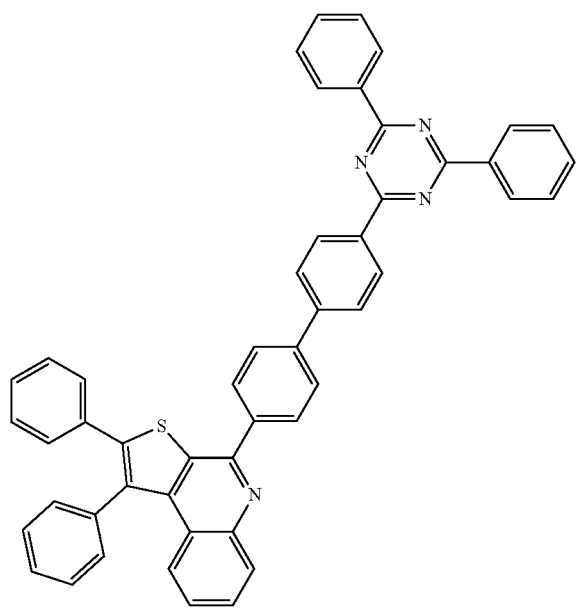
243
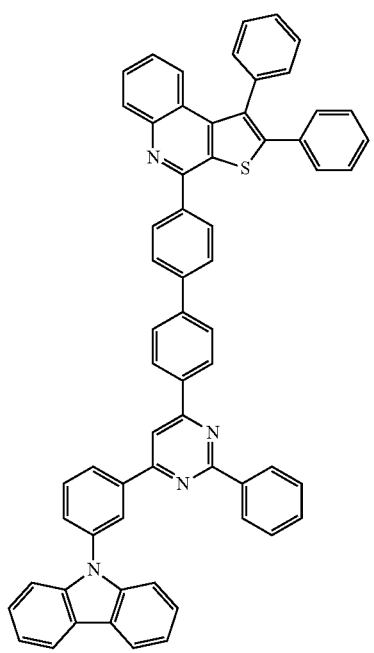

-continued
117 244 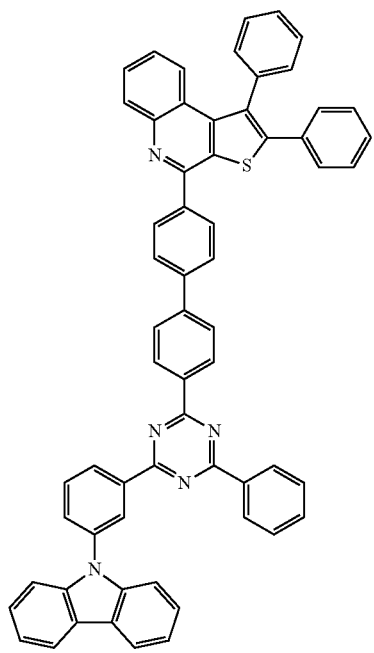
118 245 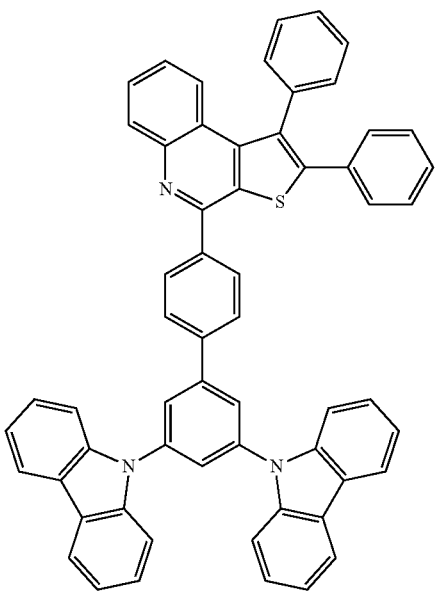
246 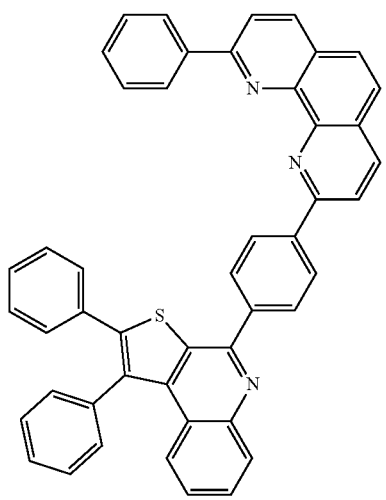
247 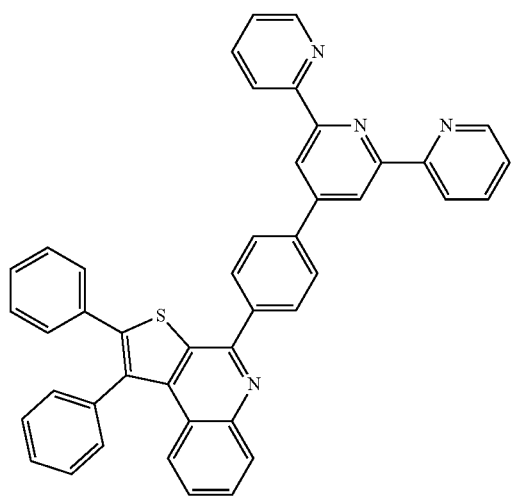
248 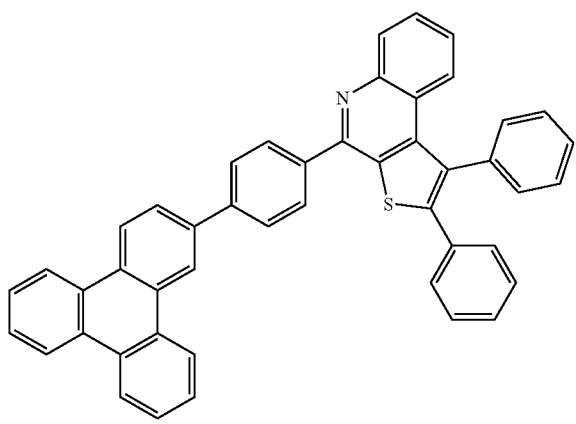
249 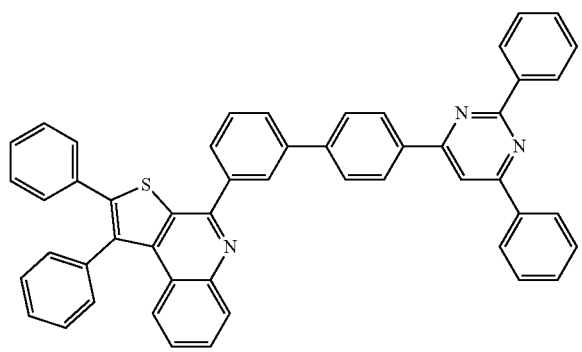

-continued
250 251
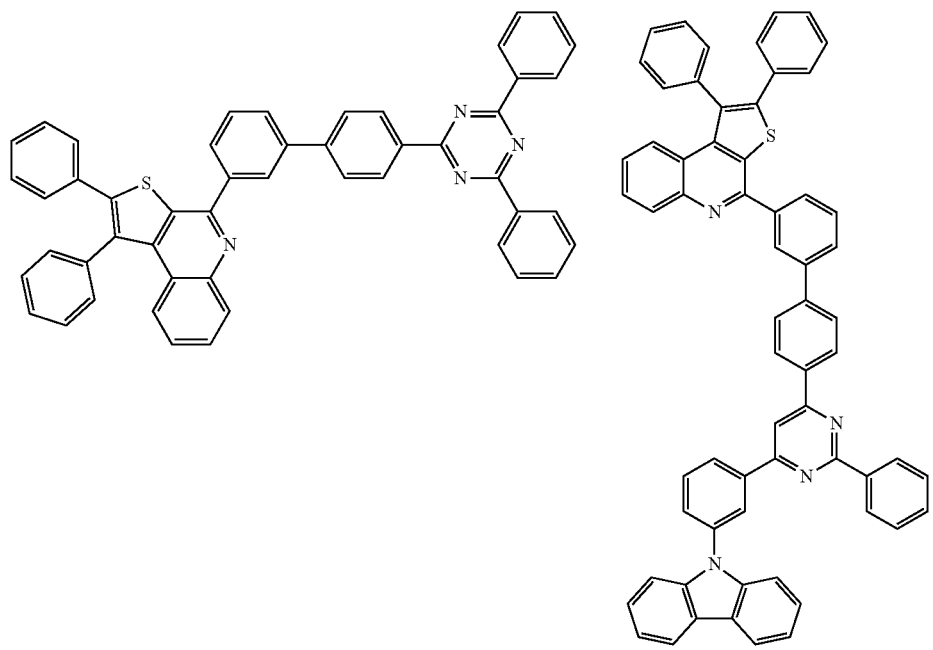
252 253
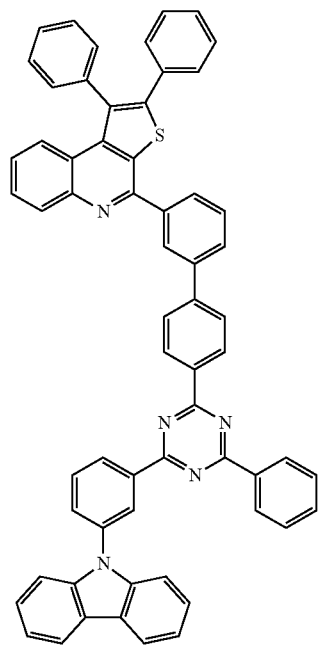 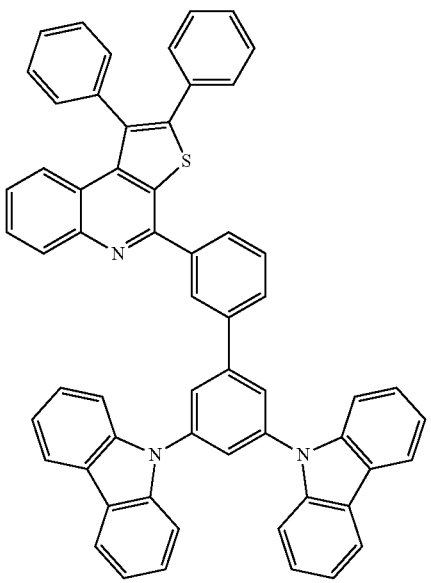

-continued
254
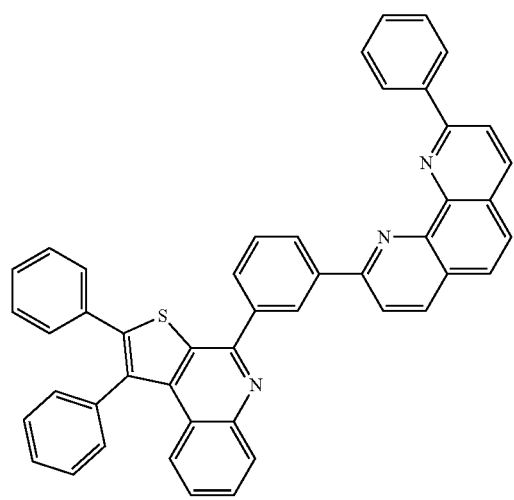
255
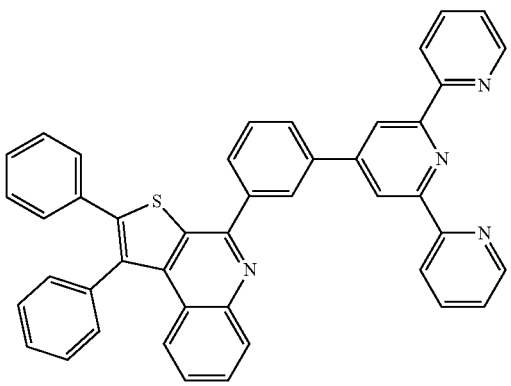
256
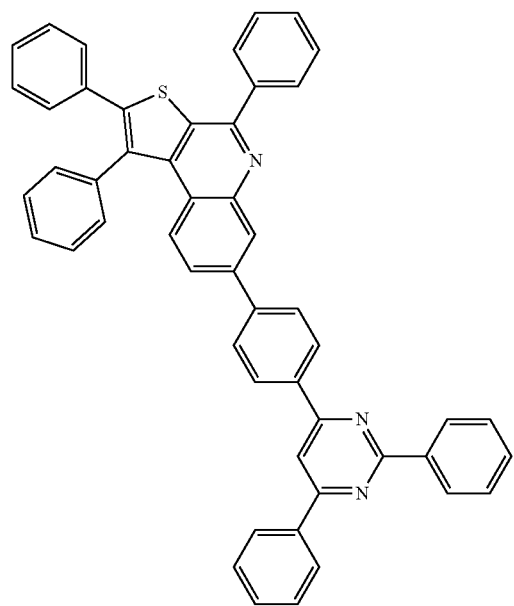
257
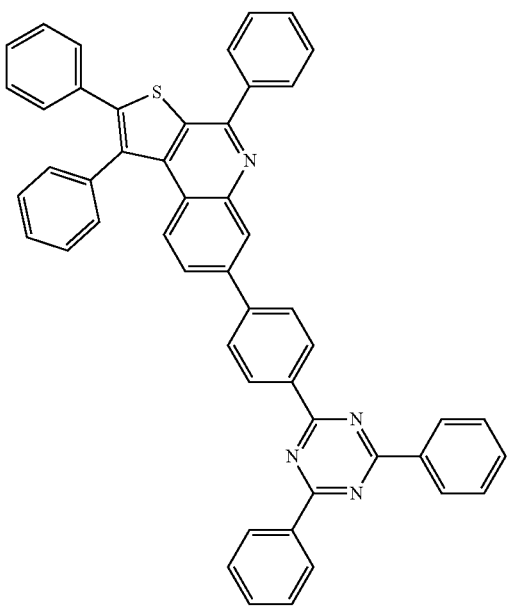

-continued
258
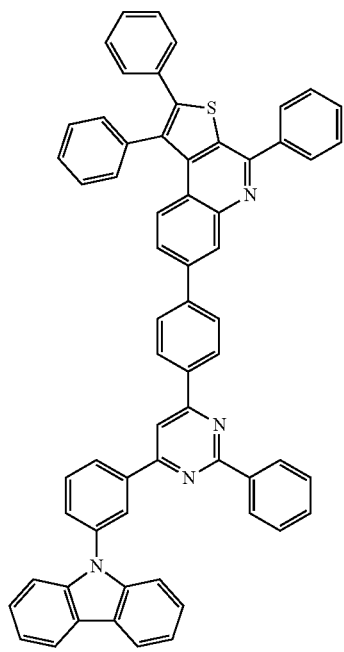
259
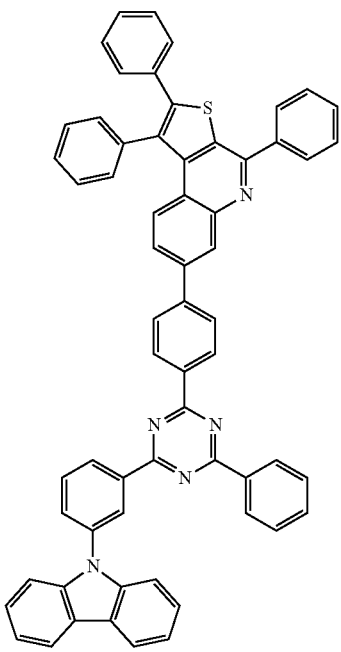
260
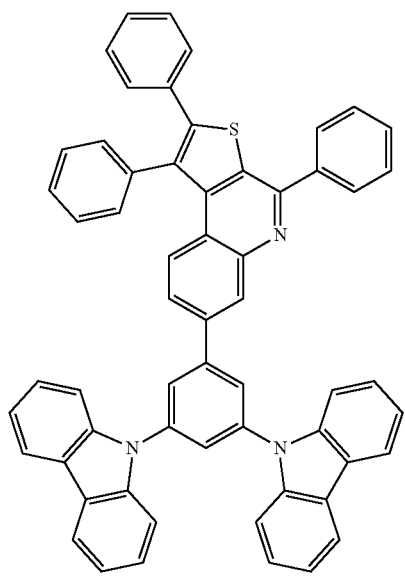
261
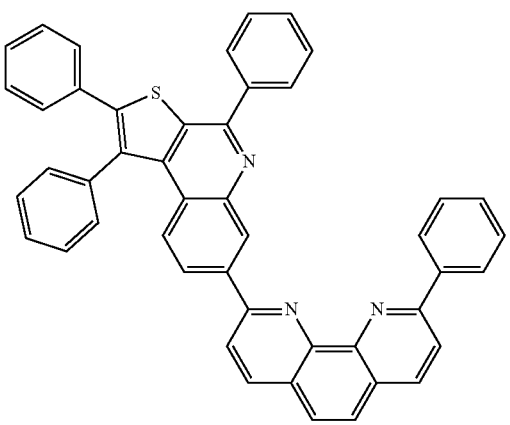

-continued
125
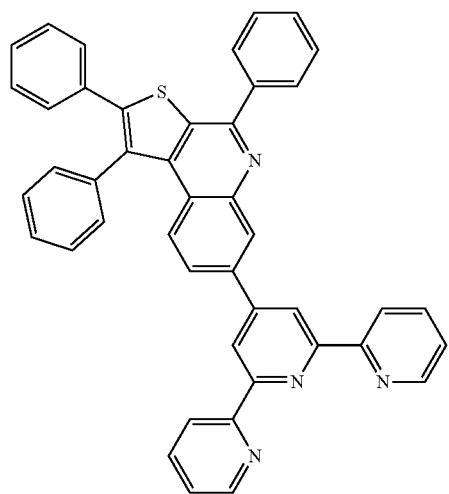
126
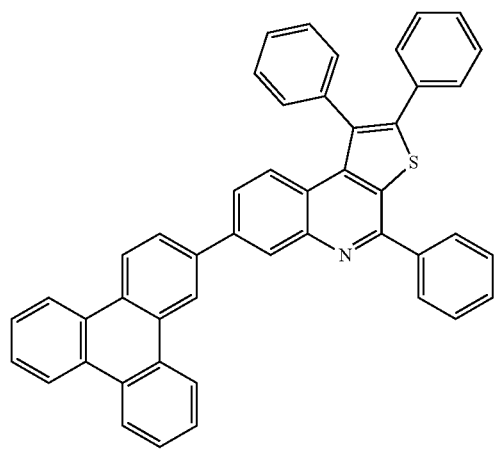
262
263
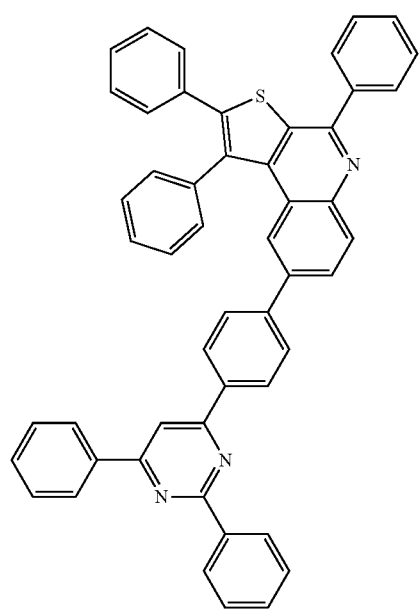
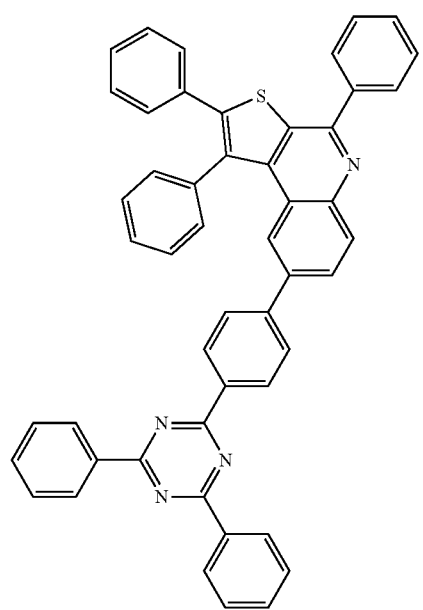
264
265

-continued
266
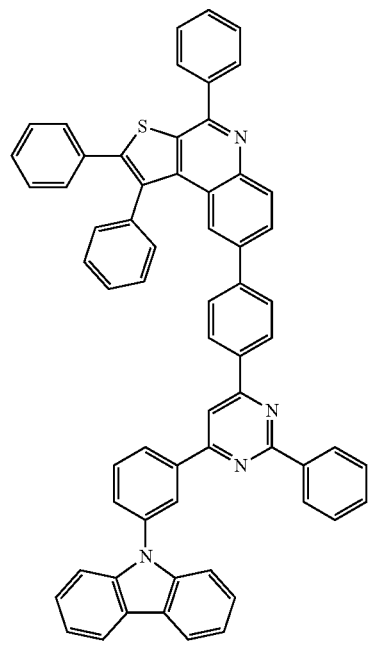
267
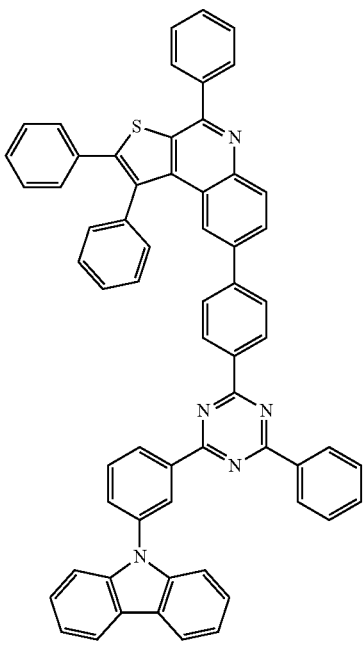
268
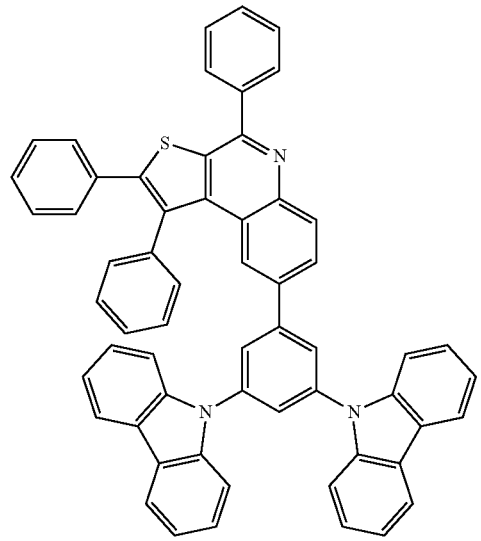
269
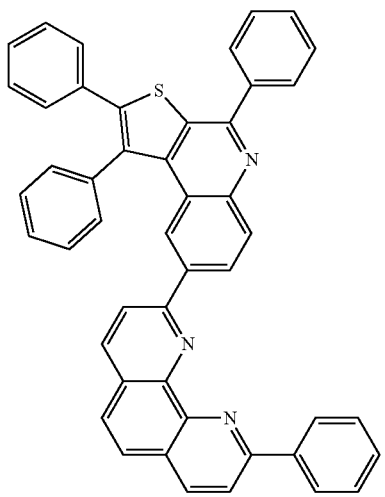

-continued
270
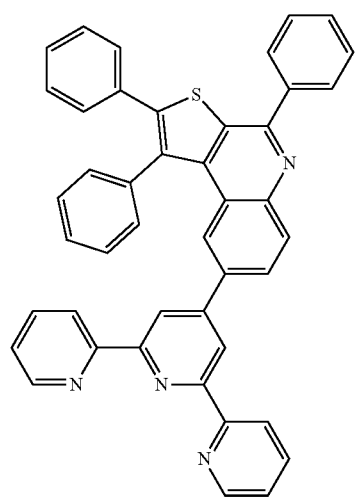
271
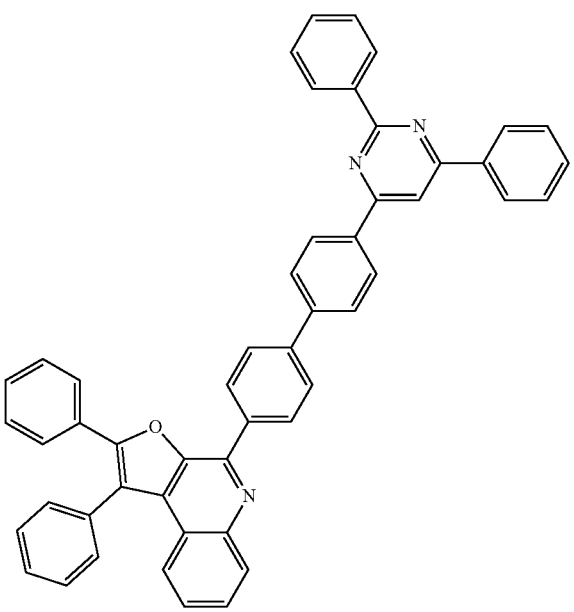
272
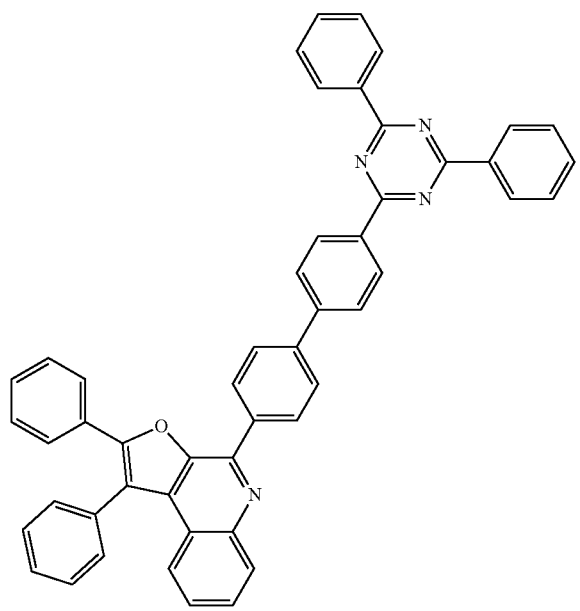
273
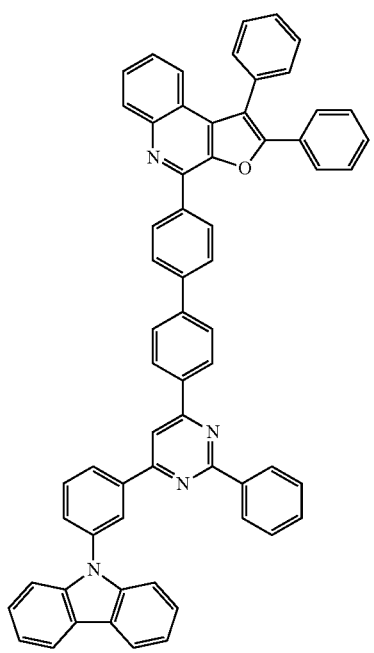

-continued
131
274
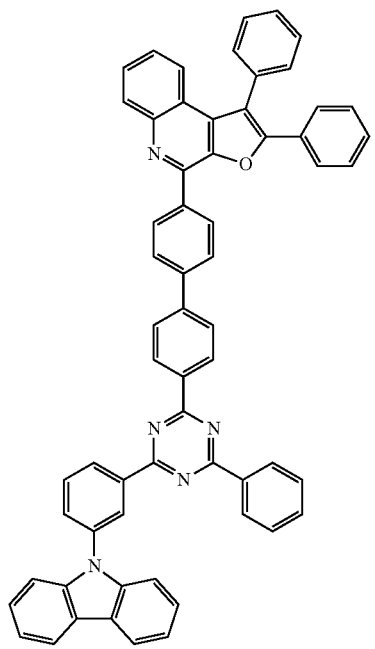
132
275
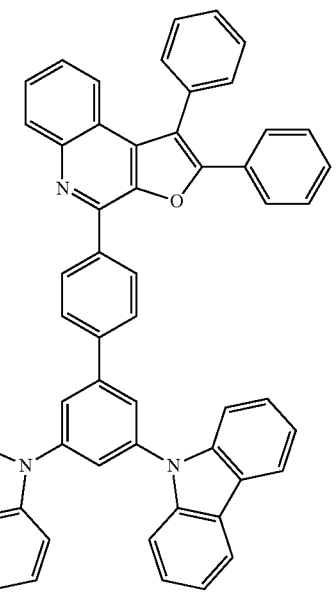
276
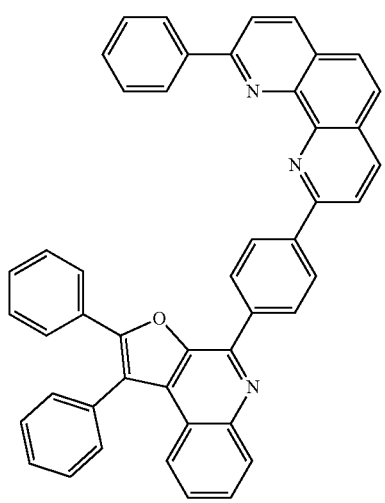
277
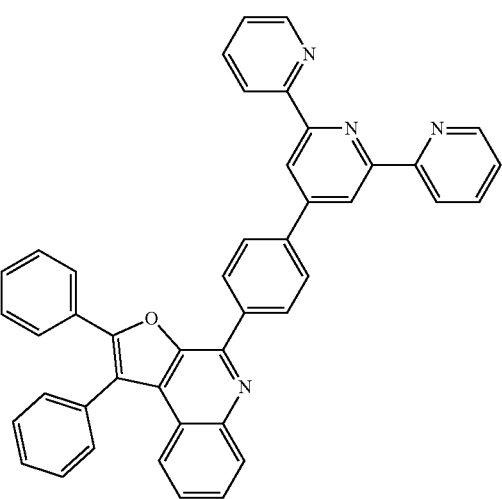
278
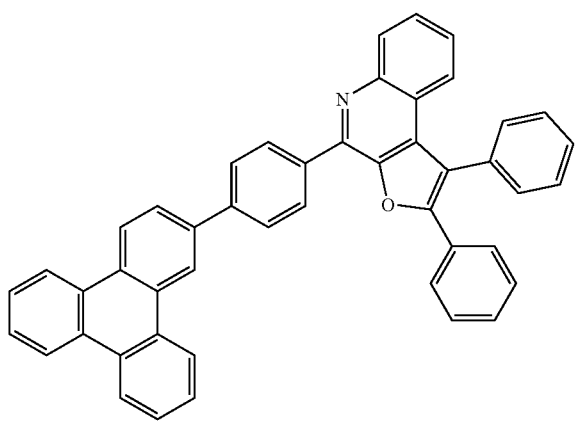
279
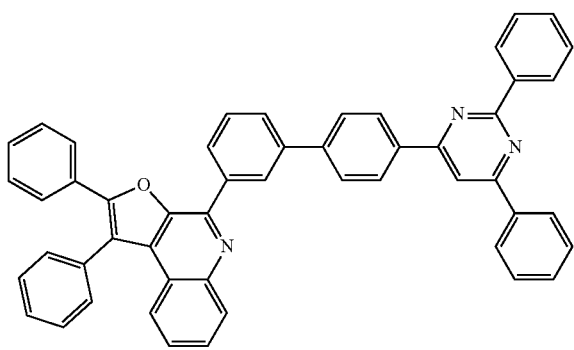

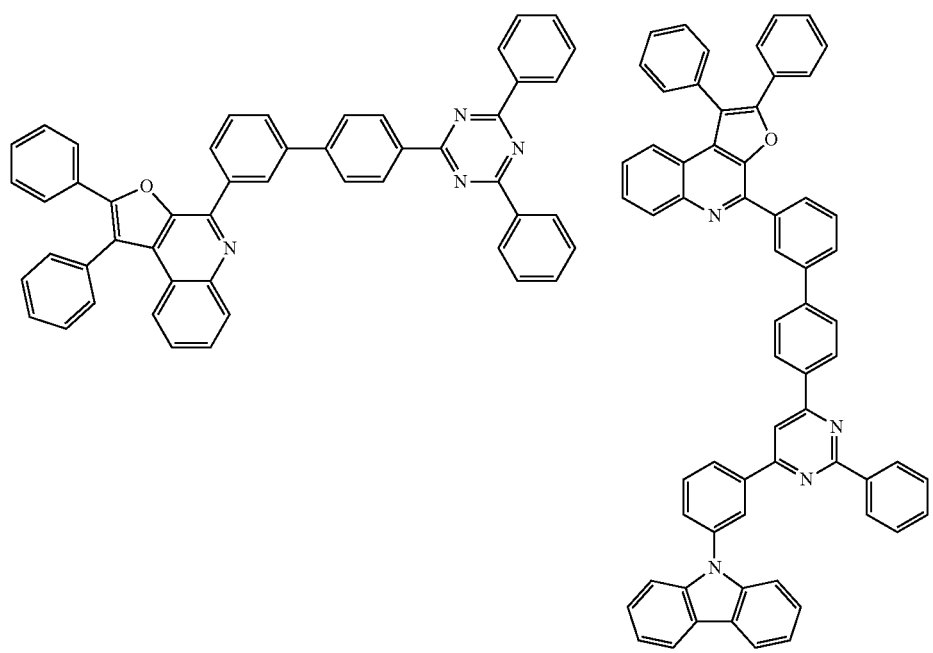
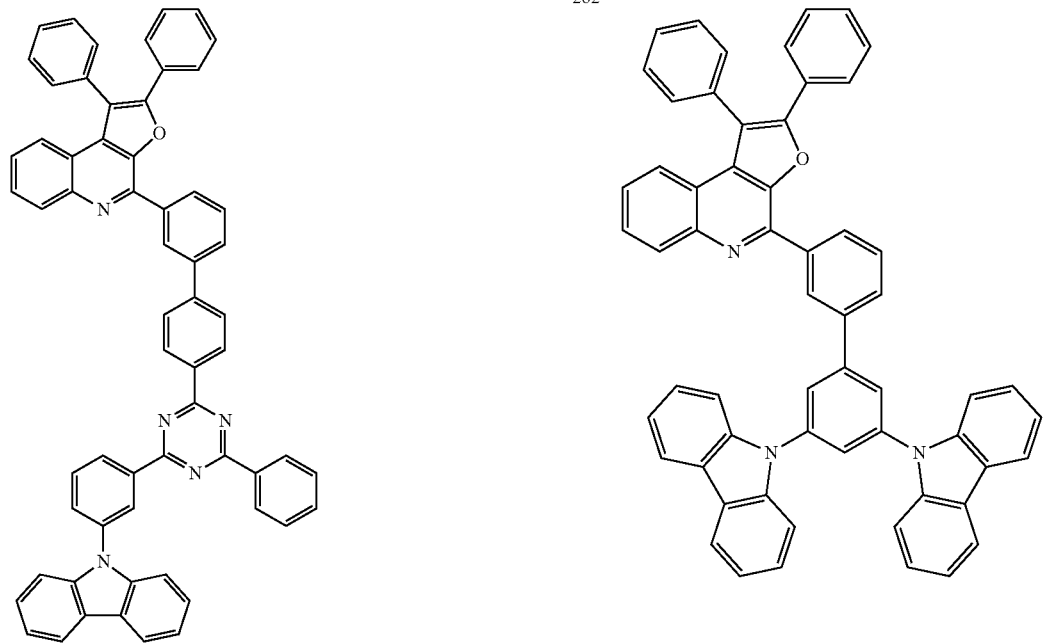

-continued
284
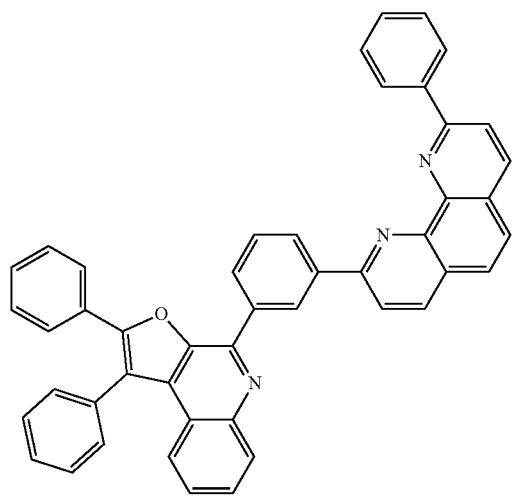
285
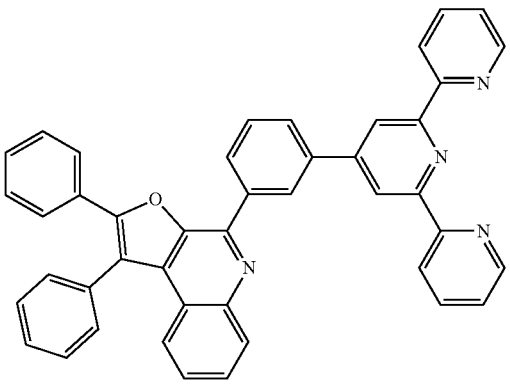
286
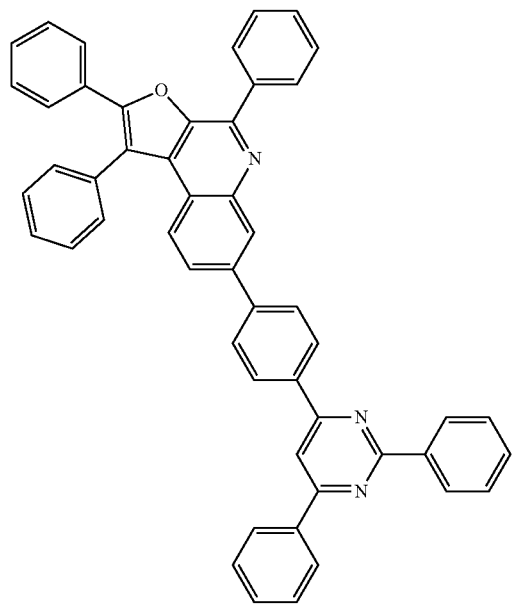
287
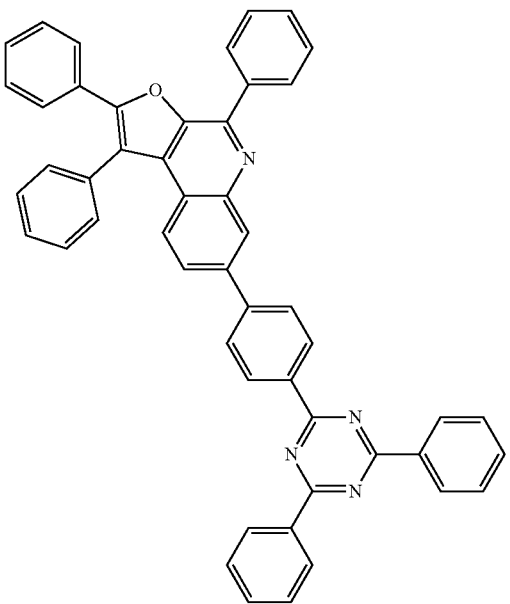

-continued
288 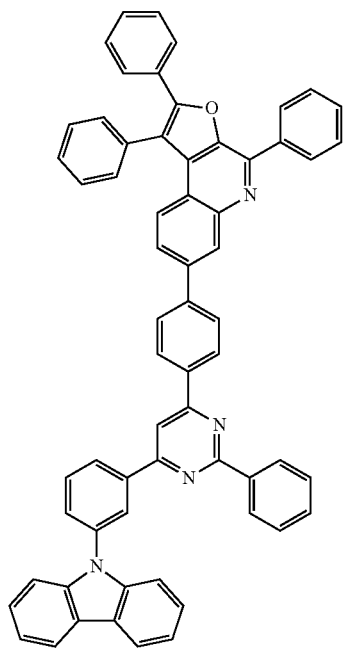
289 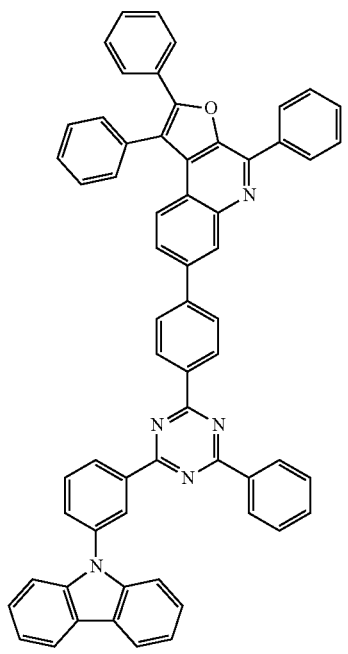
290 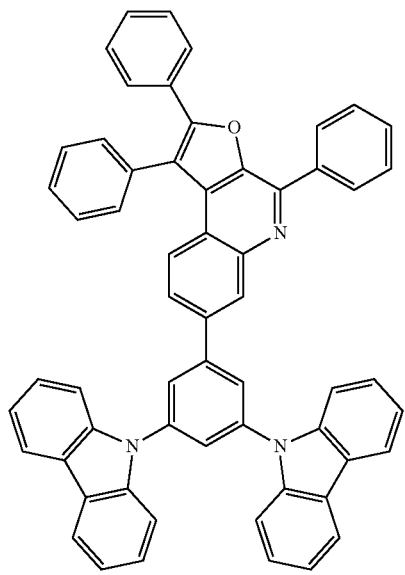
291

-continued
292
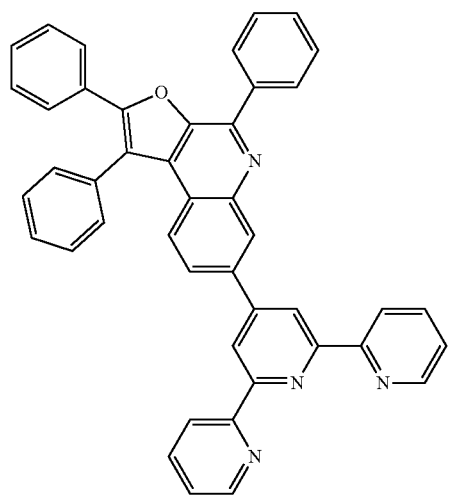
293
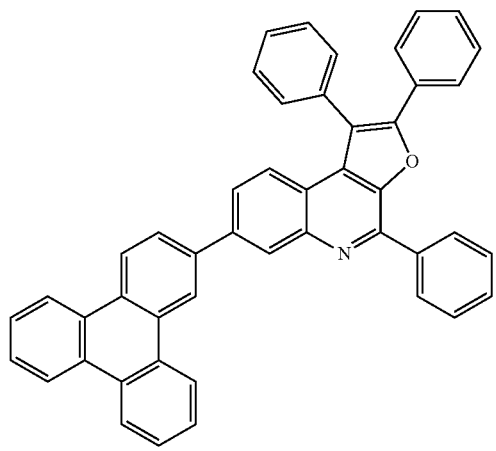
294
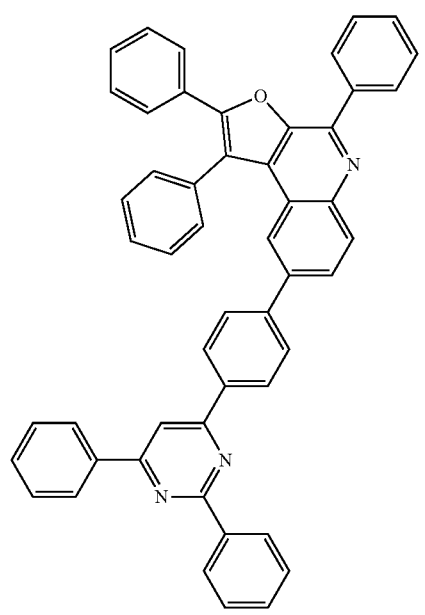
295
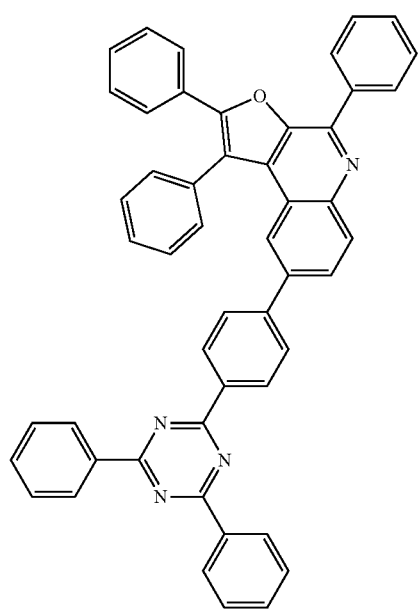

-continued
141
296
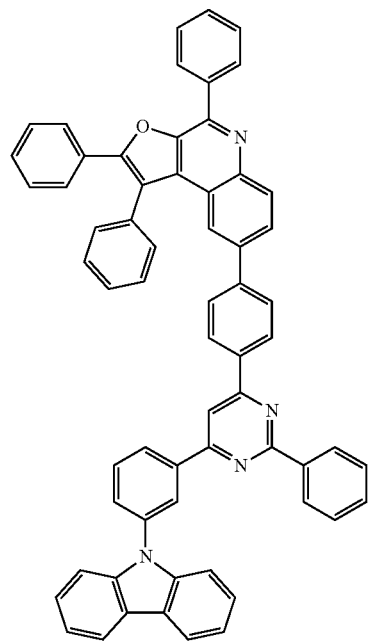
142
297
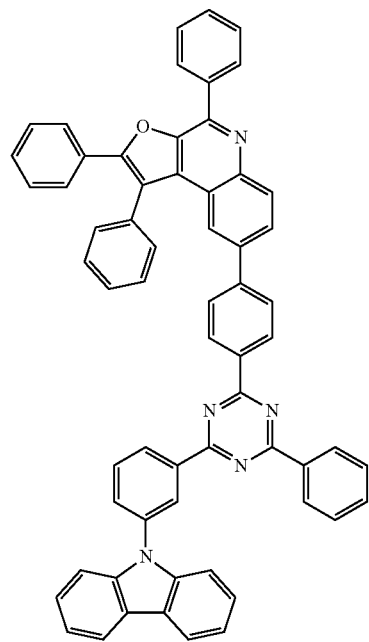
298
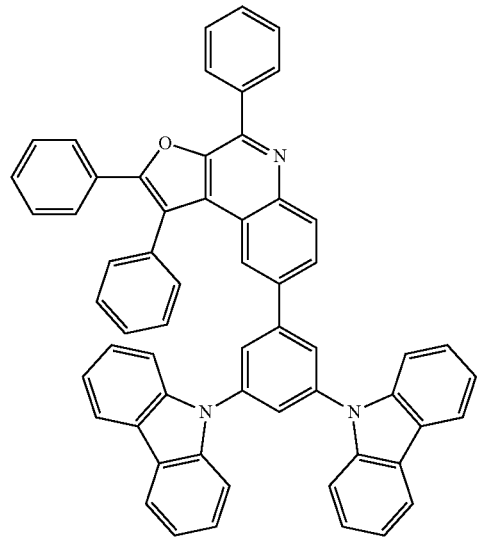
299
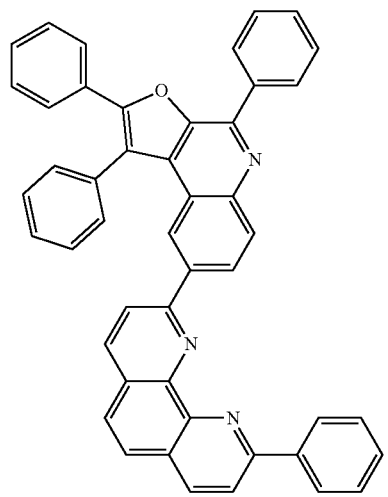

-continued
300
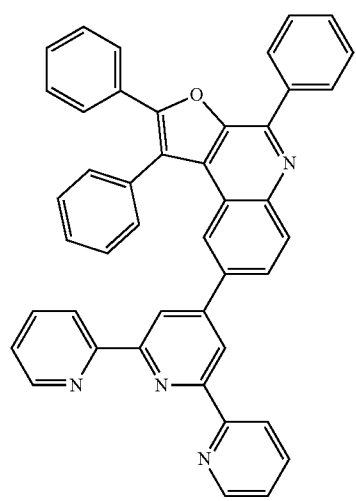
301
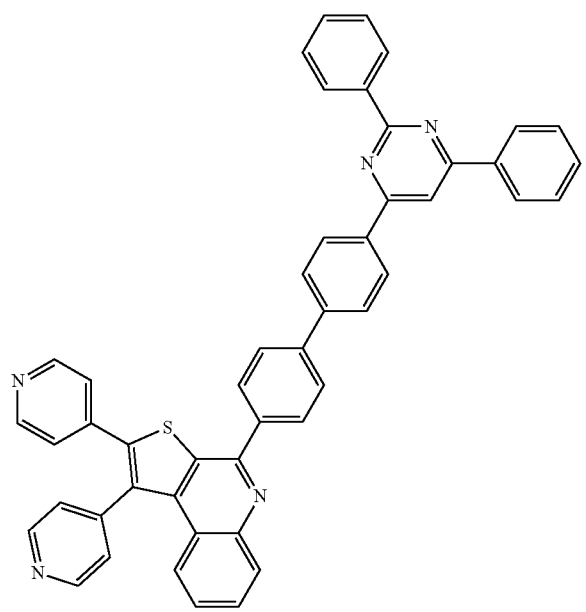
302
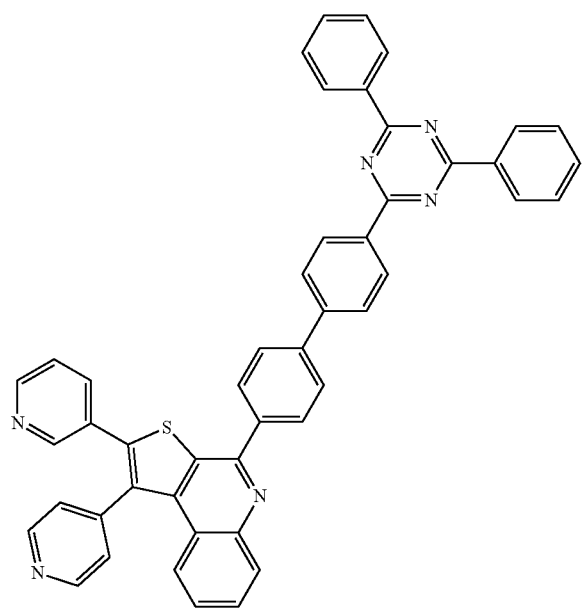
303
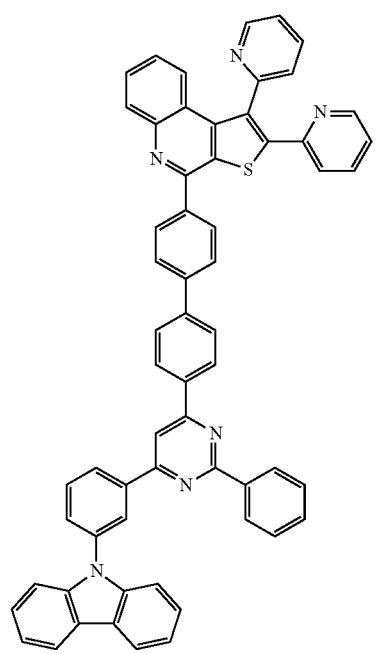

-continued
304
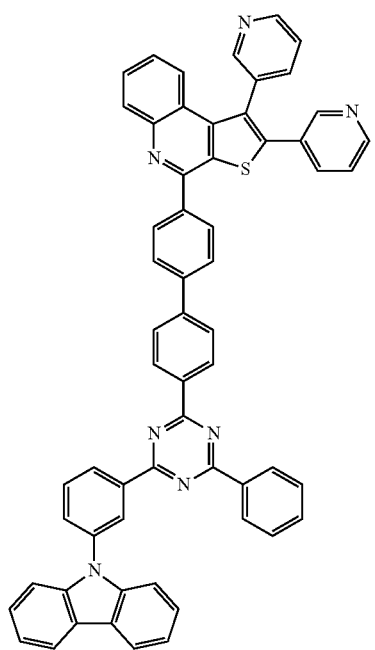
305
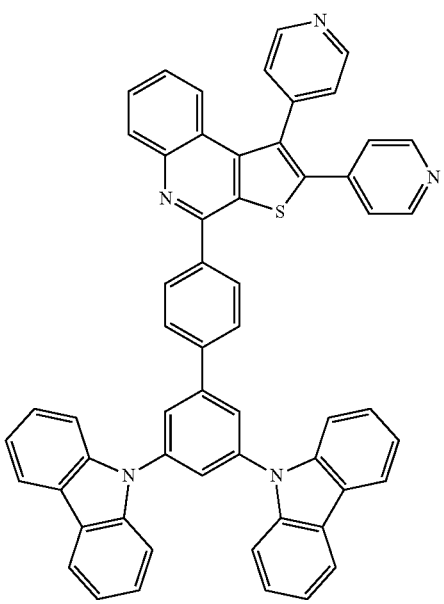
306
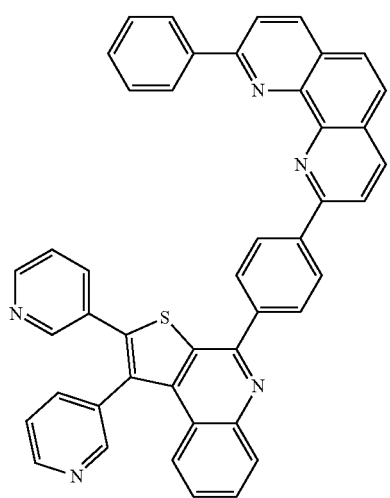
307
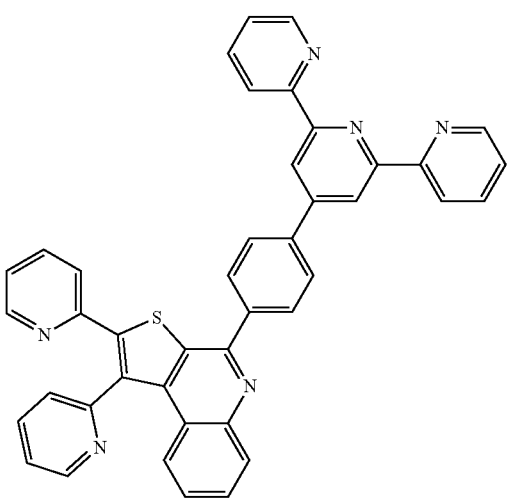

-continued
308
309
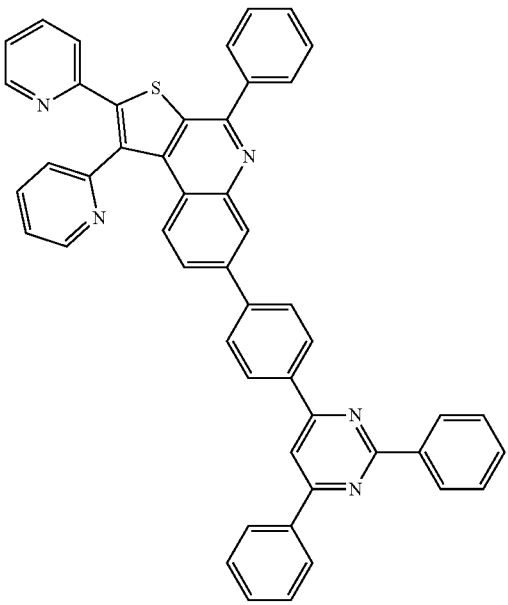
310
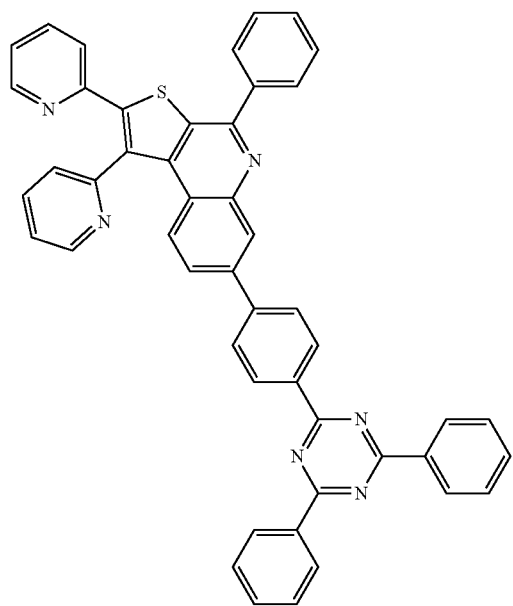
311
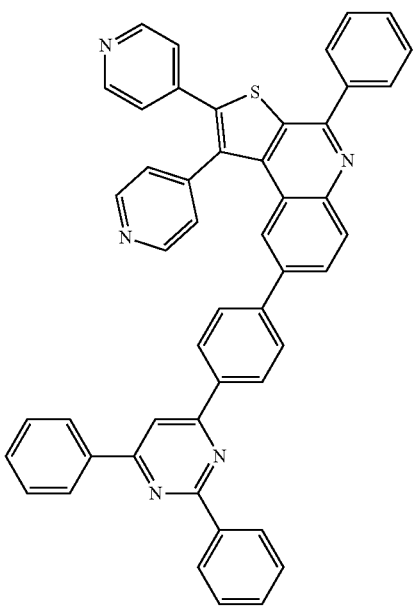

-continued
149
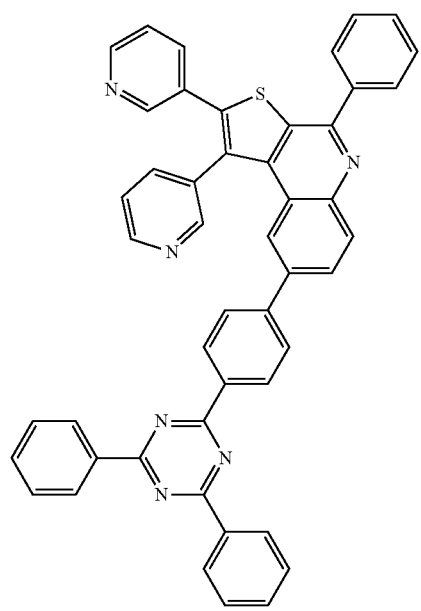
150
312
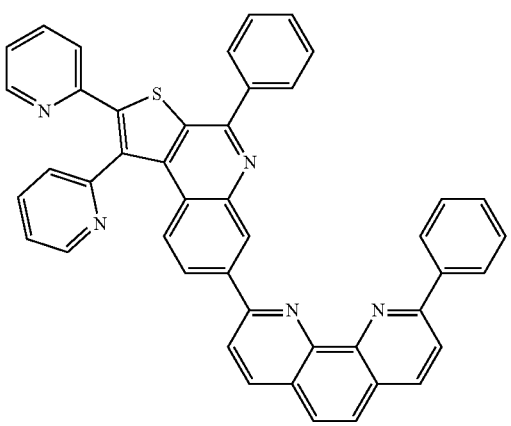
313
314
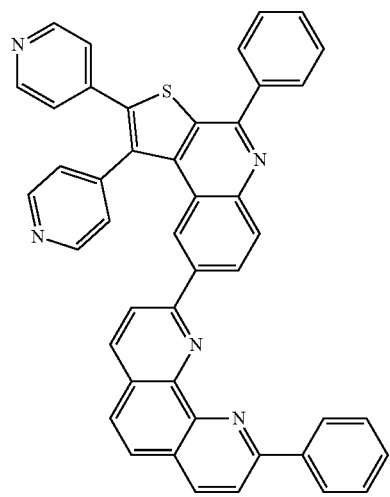
315
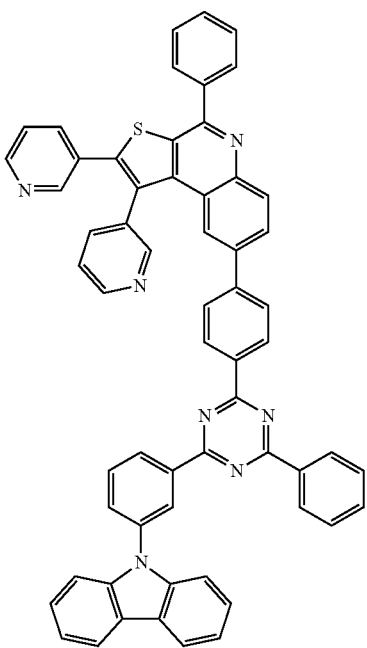

316
151
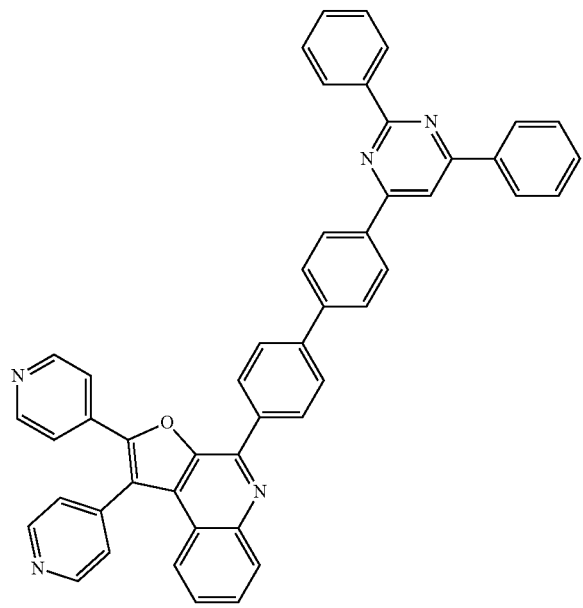
317
152
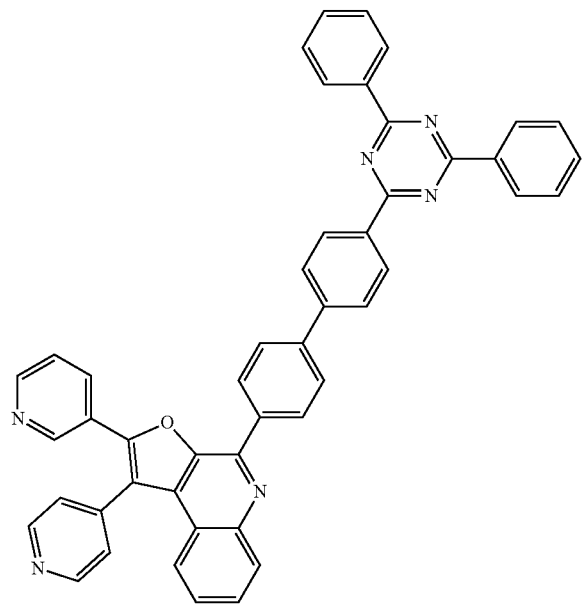
318
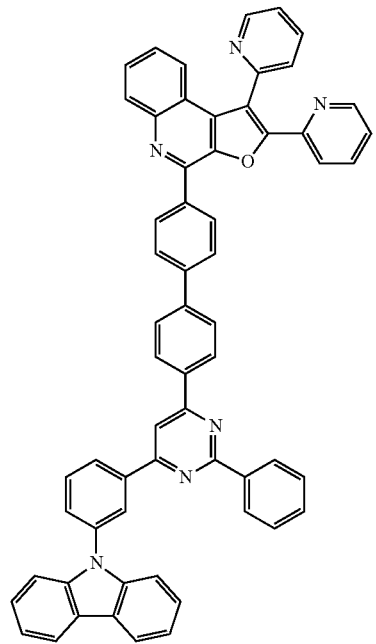
319
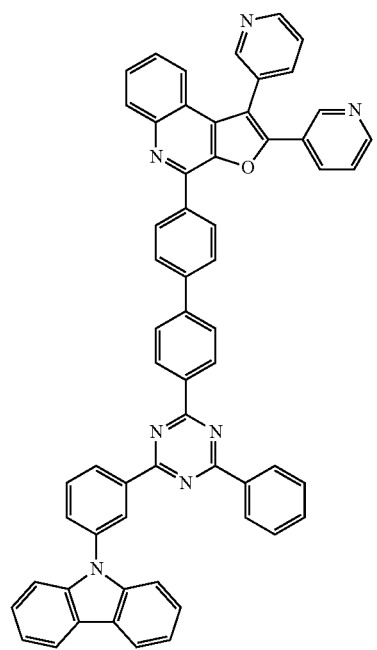

-continued
153
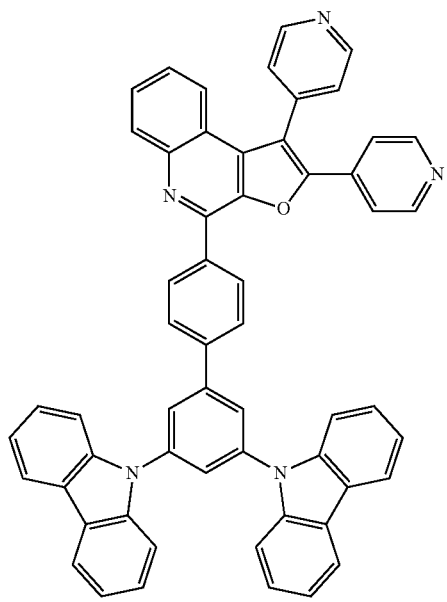
320
154
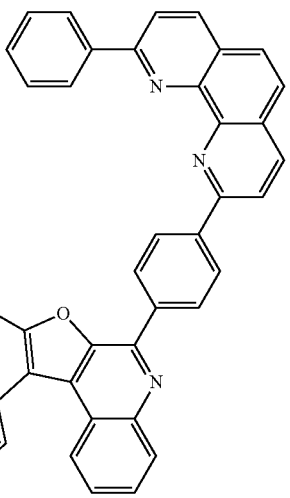
321
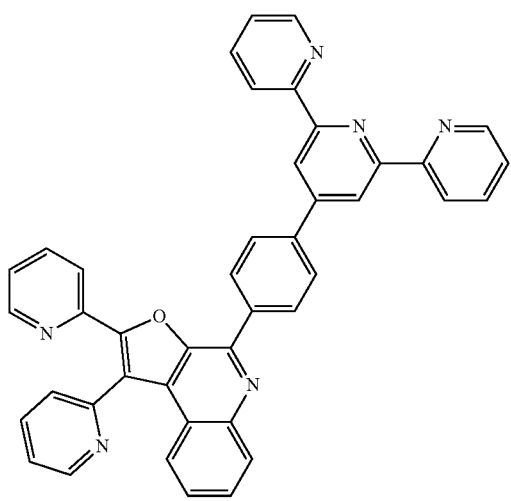
322
323

-continued
| 324 | 325 |
|---|---|
| 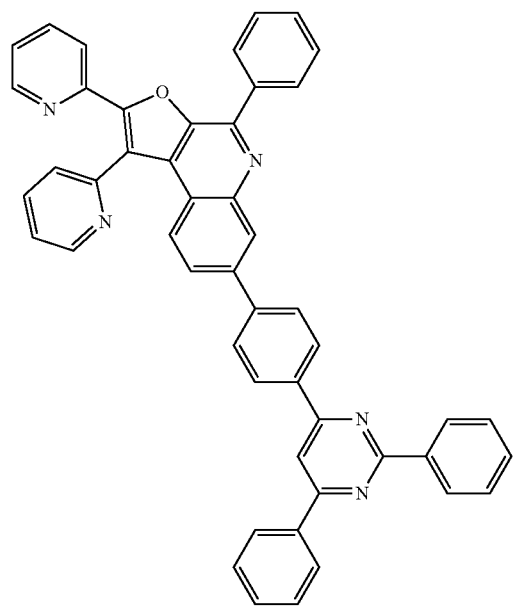 | 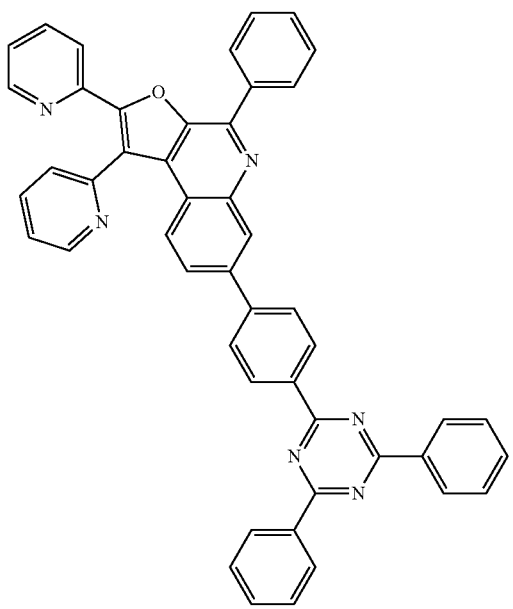 |
| 326 | 327 |
| 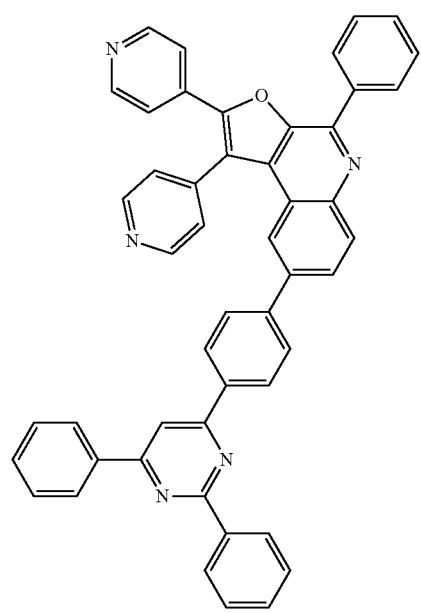 | 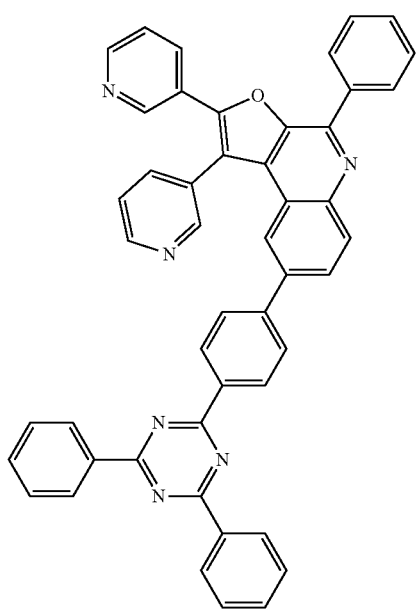 |

-continued
328 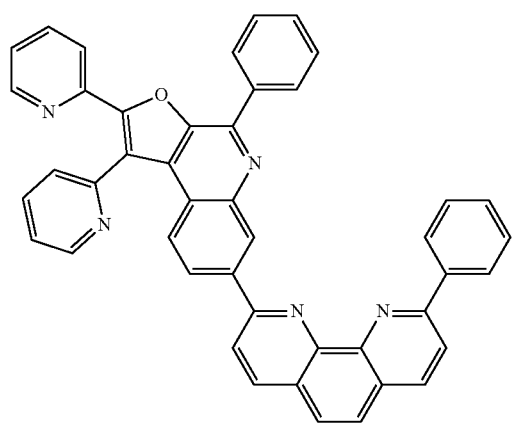 329 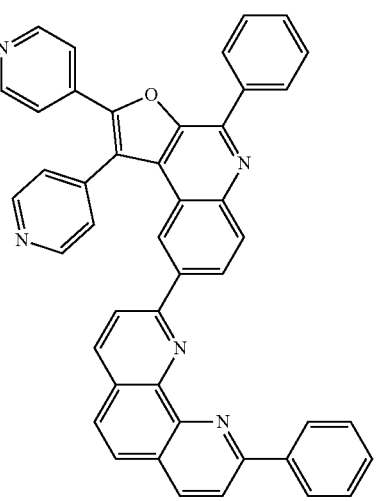
330 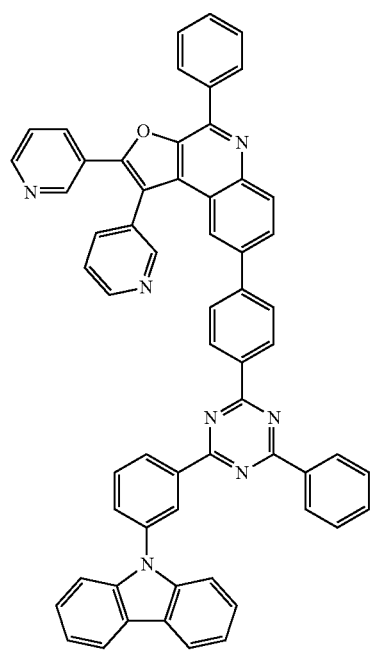 331 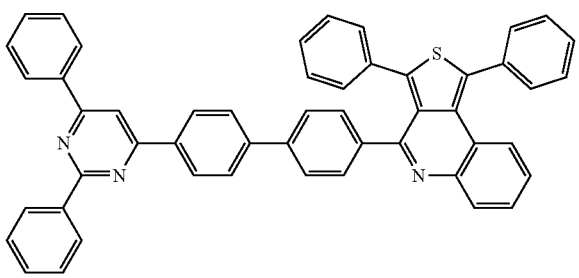

-continued
332
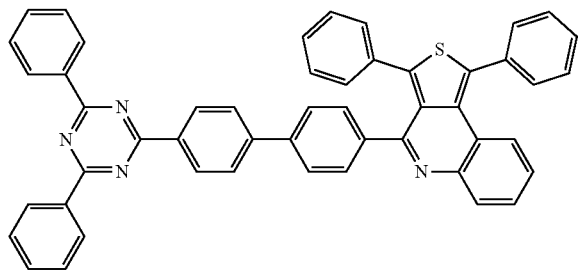
333
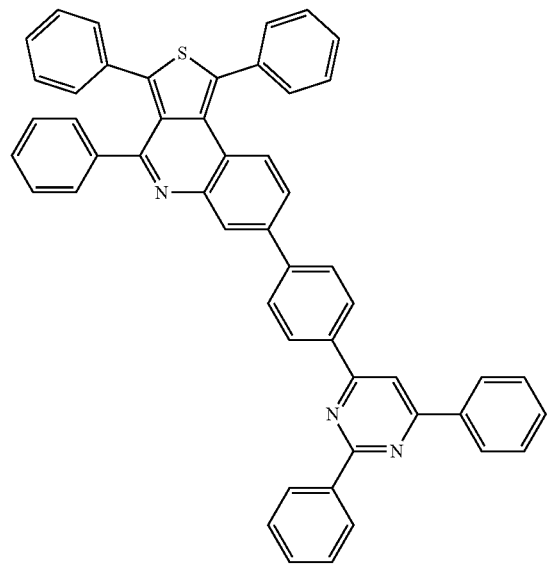
334
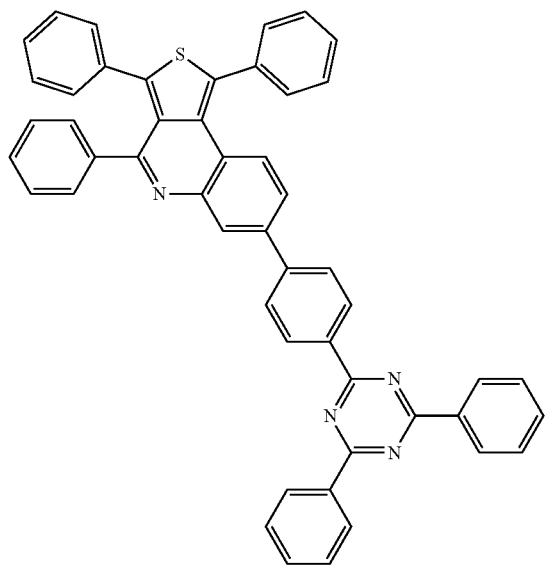
335
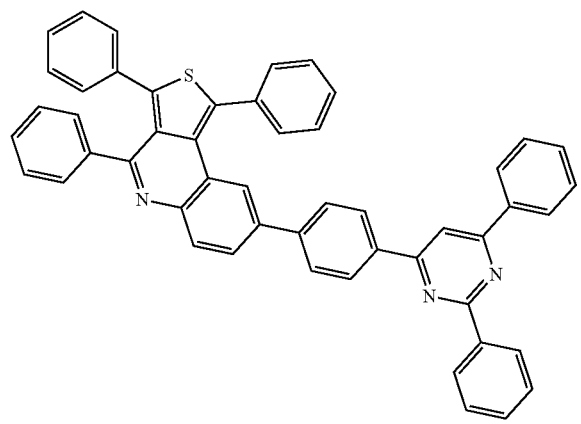
336
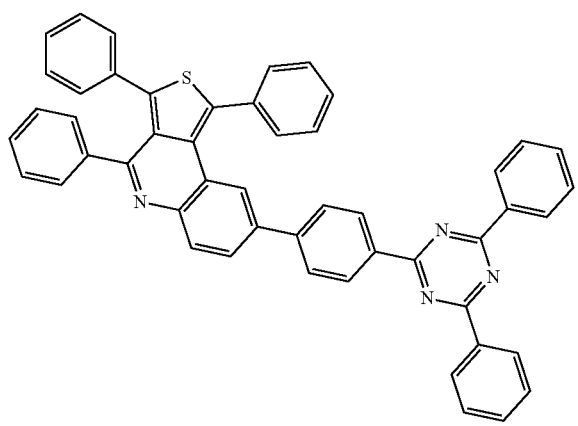
337
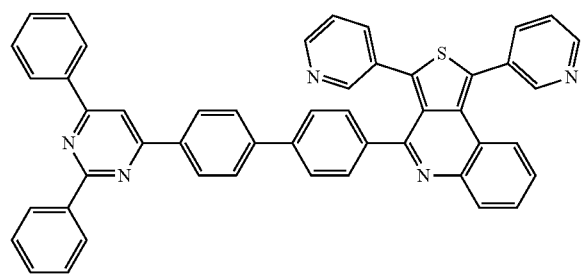

-continued
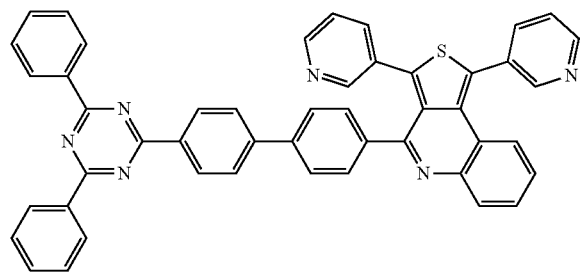
338
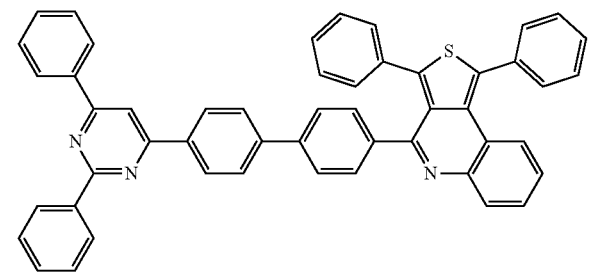
339
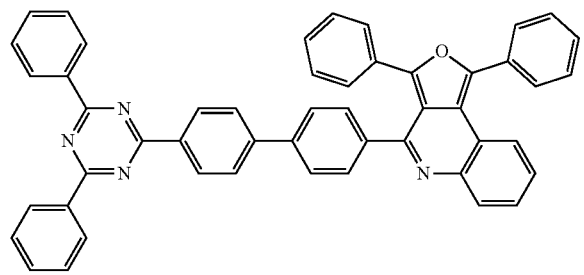
340
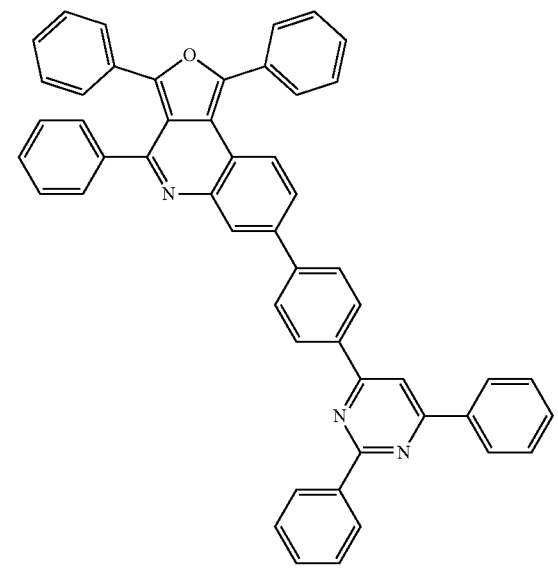
341
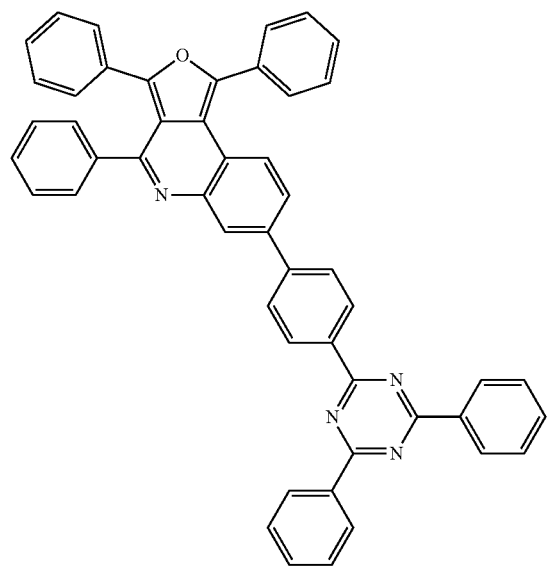
342
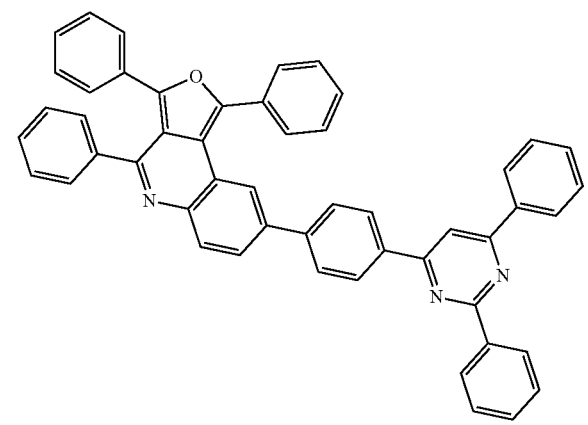
343

-continued
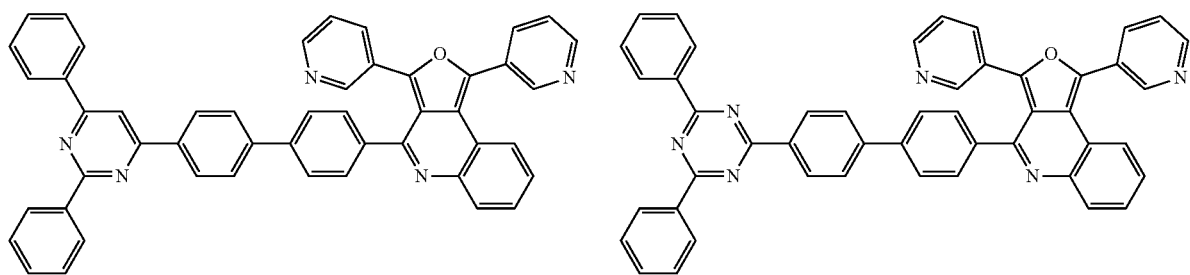
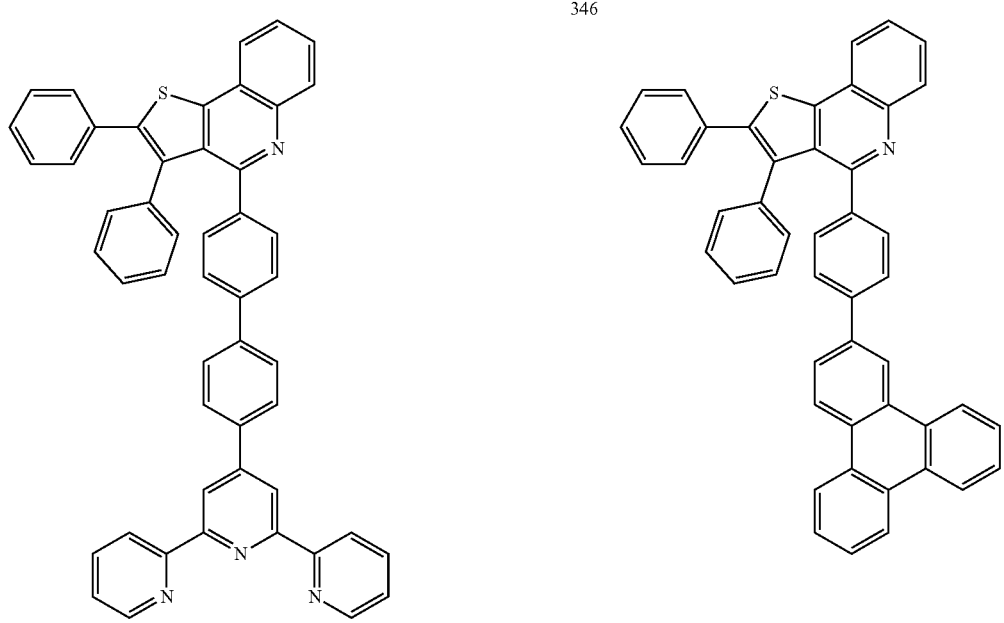
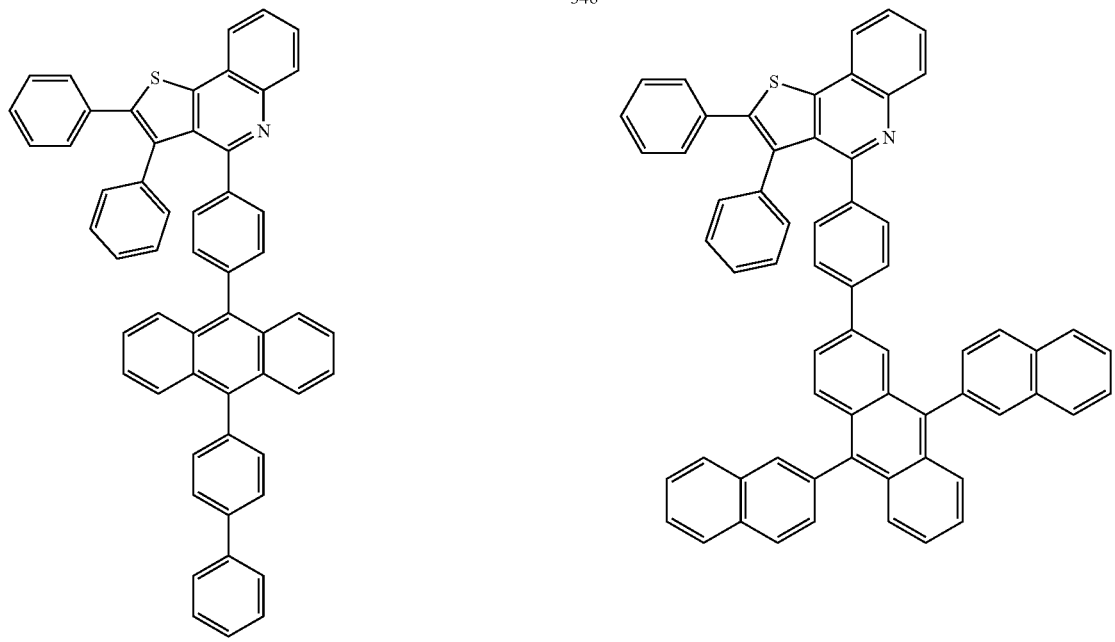

-continued
350
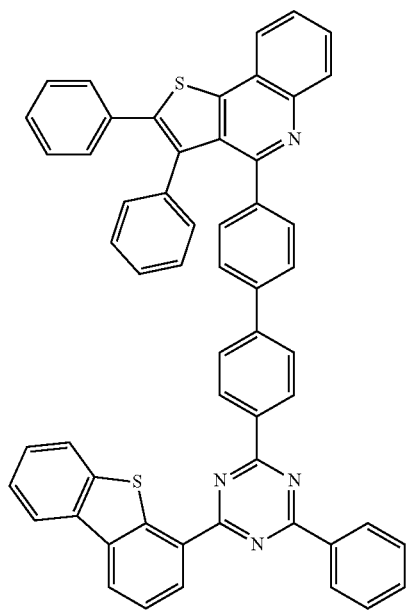
351
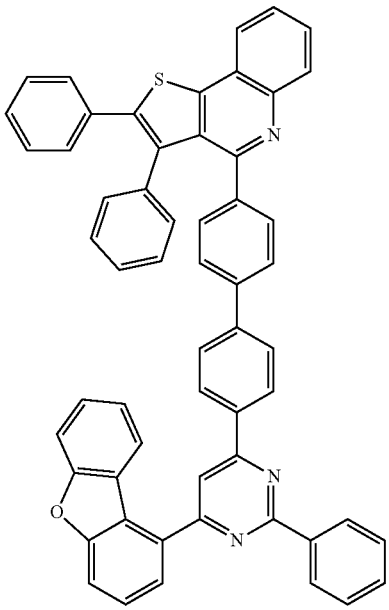
352
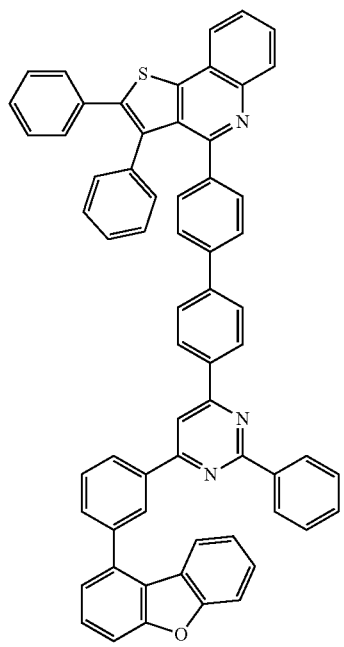
353
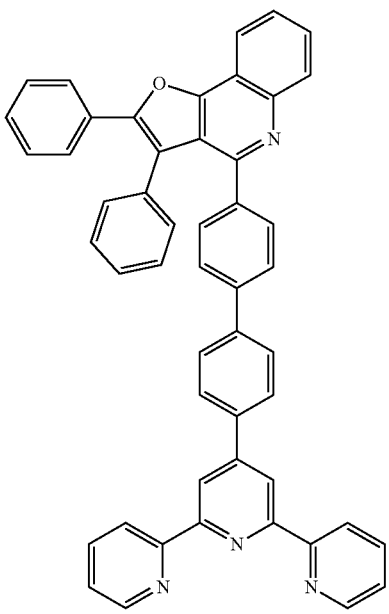

-continued
354
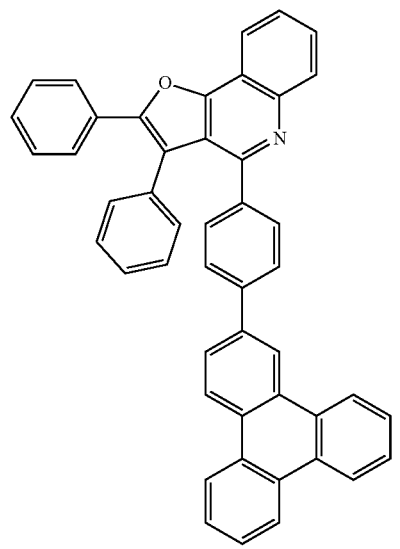
355
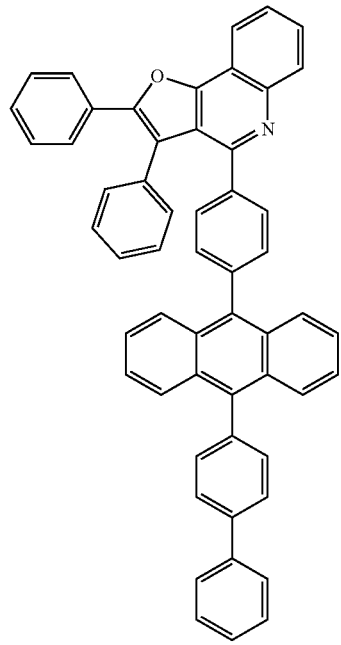
356
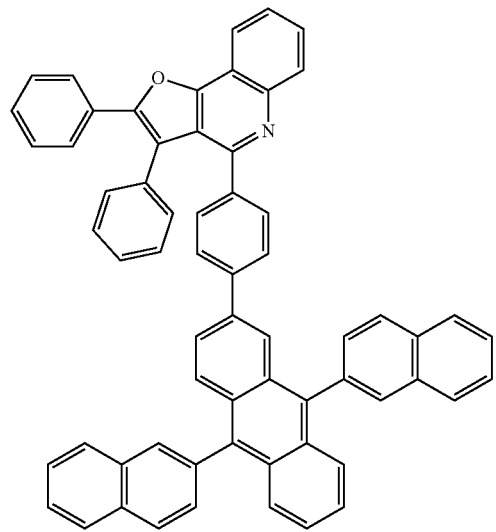
357
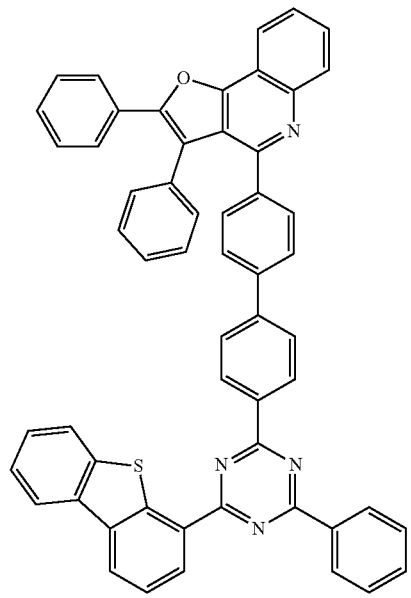

-continued
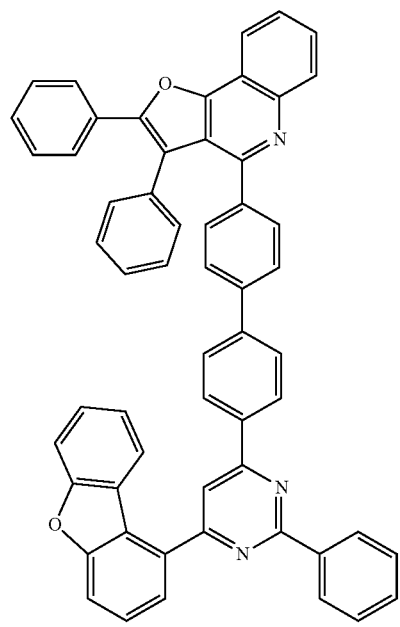
358
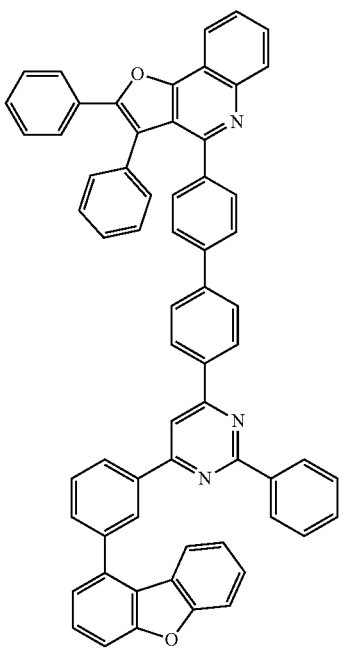
359
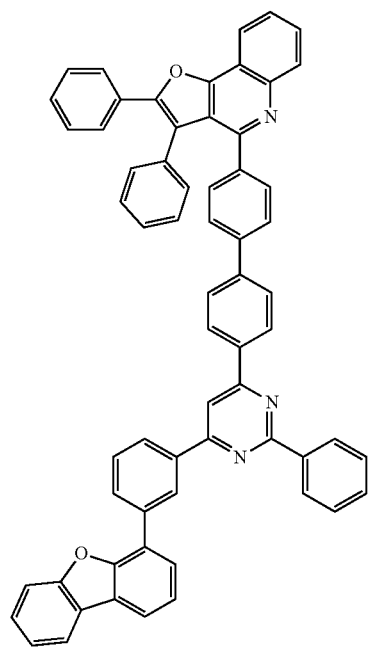
360

-continued
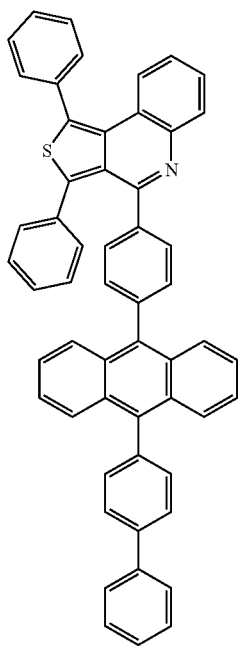
361
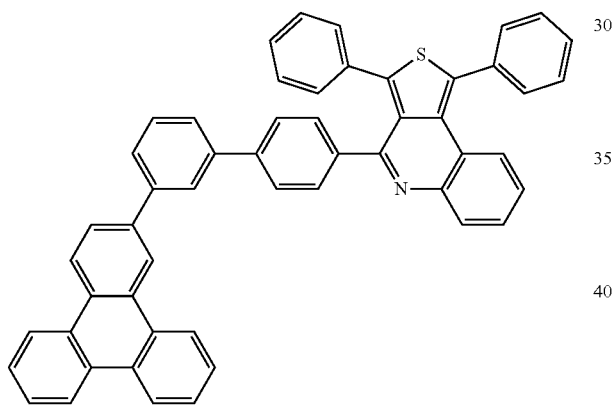
362
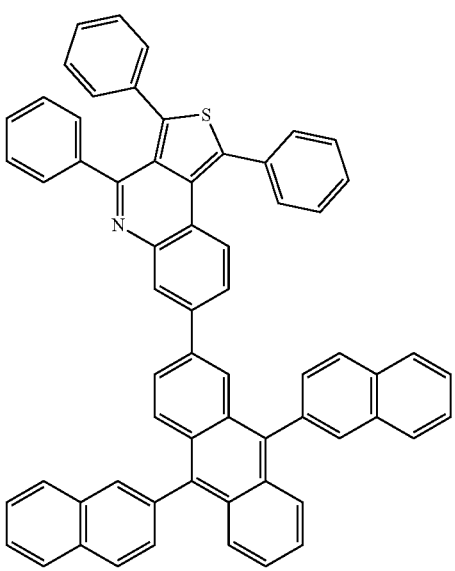
363
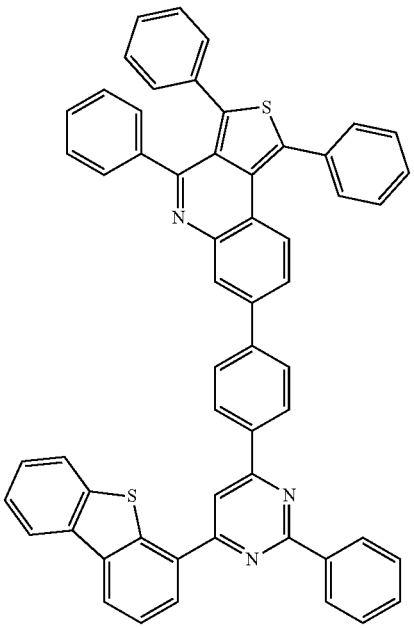
364
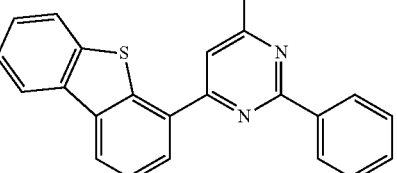
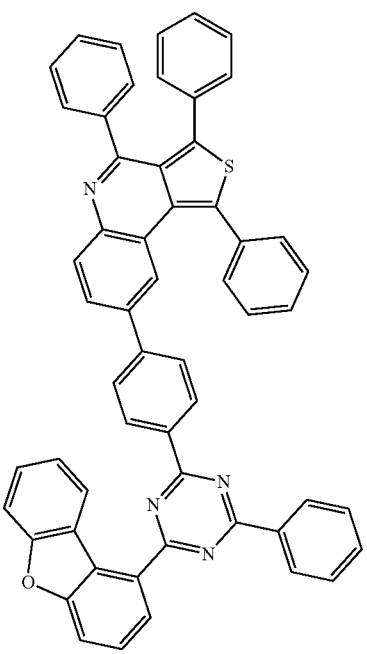
365

173
-continued
366
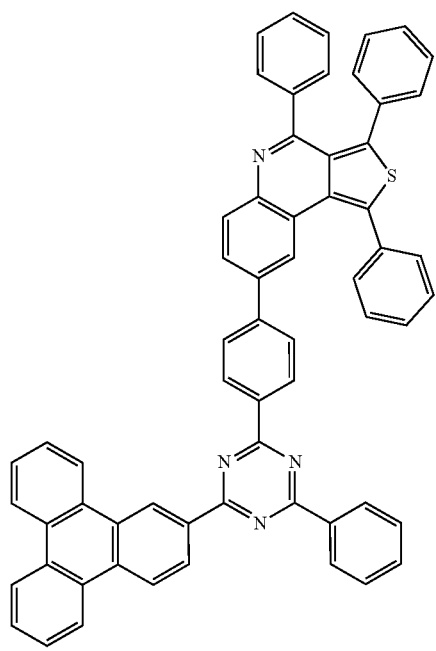
367
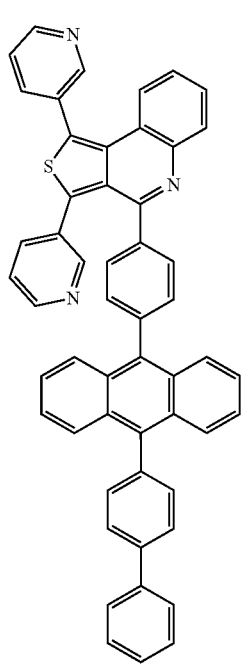
174
-continued
368
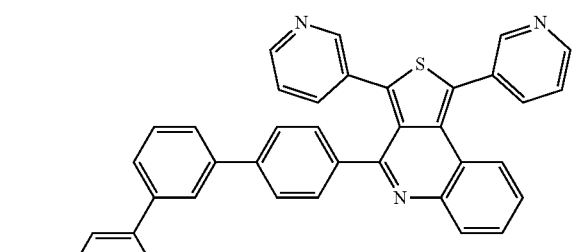
369
370
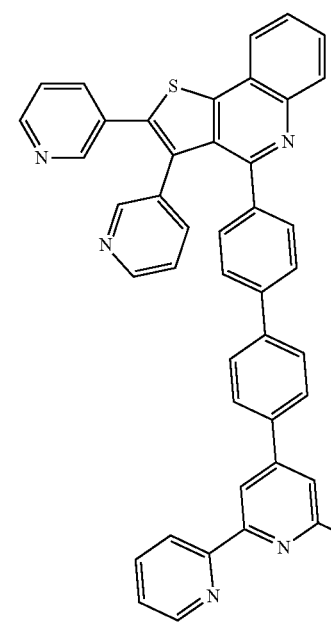

371
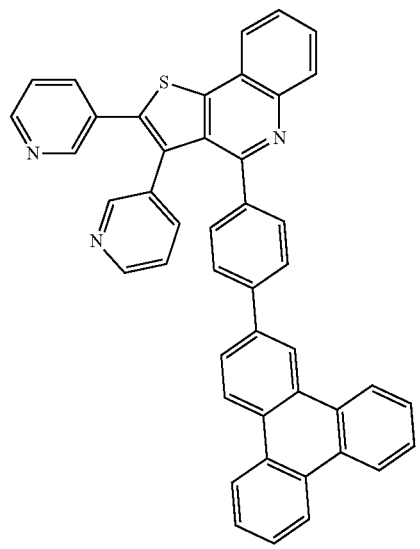
372
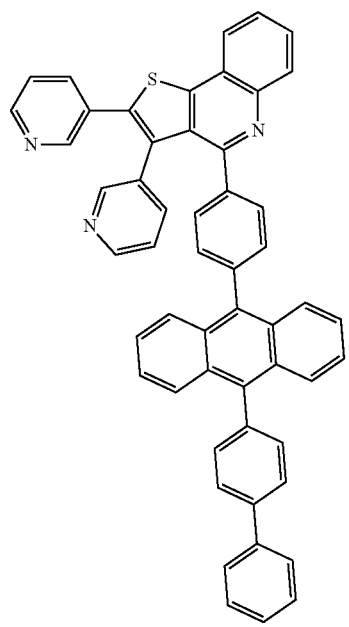
373
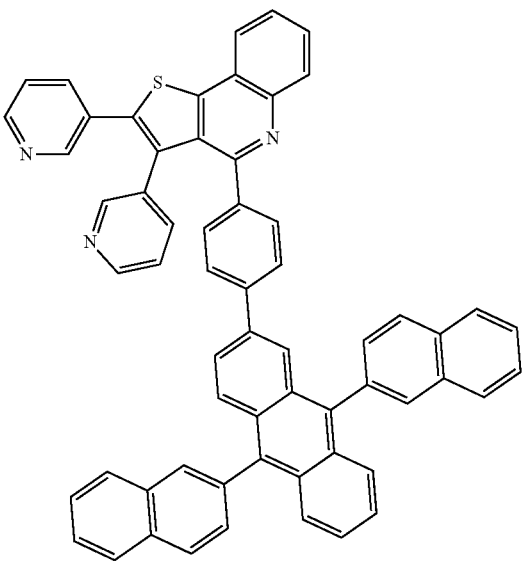
374
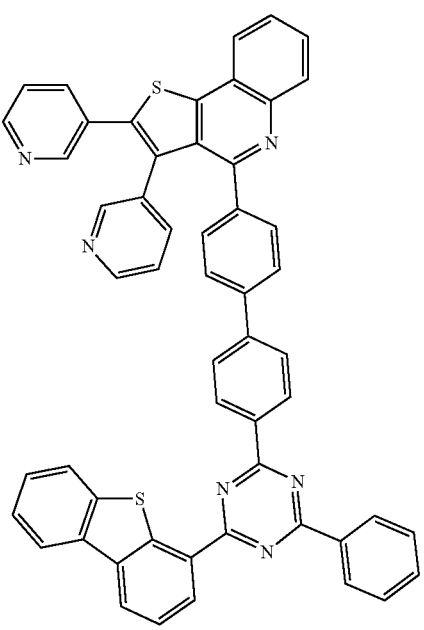

375
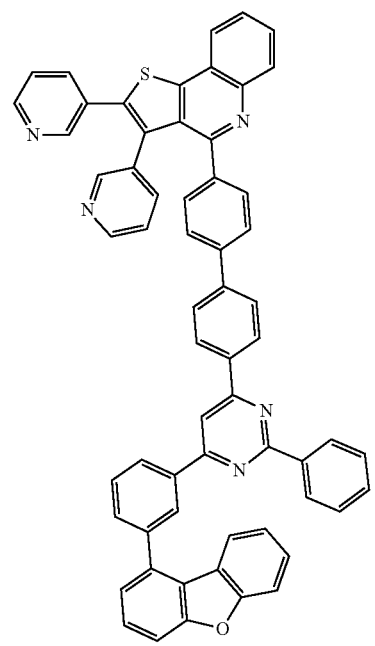
376
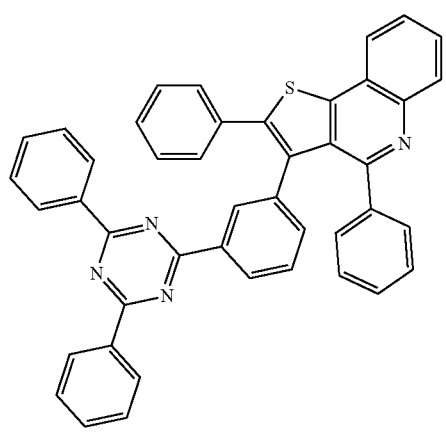
377
378
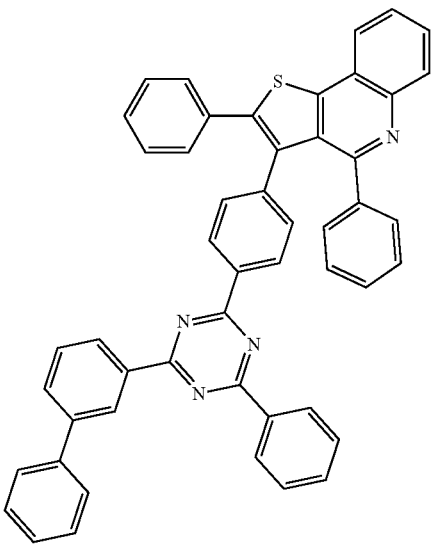
379
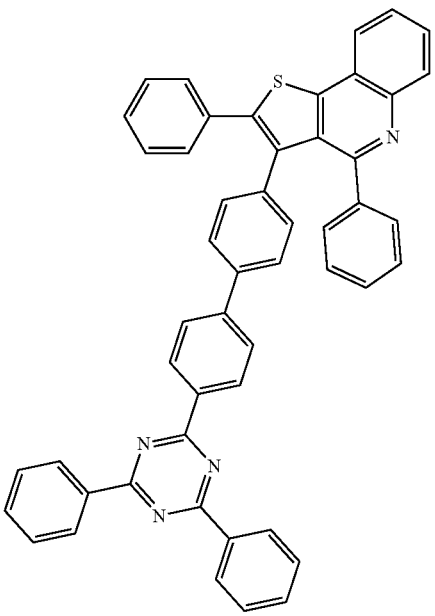

-continued
380
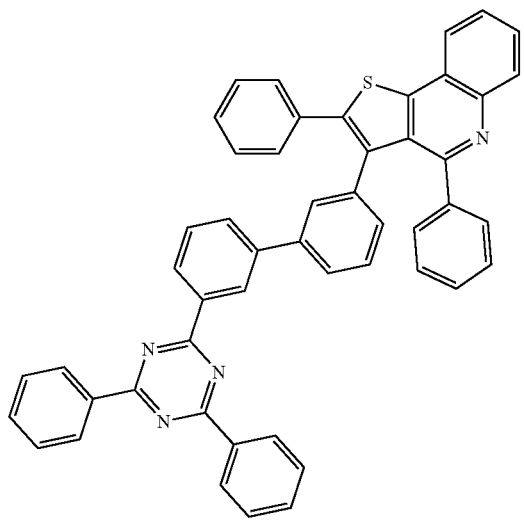
381
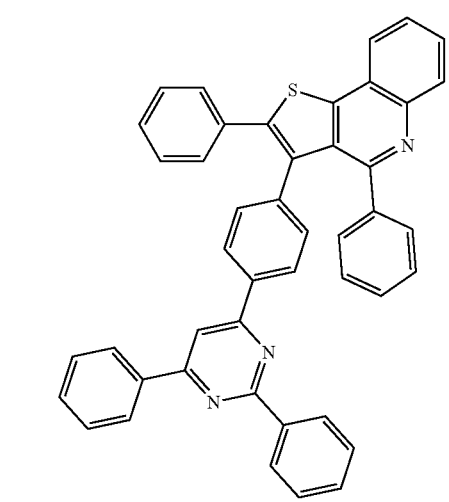
382
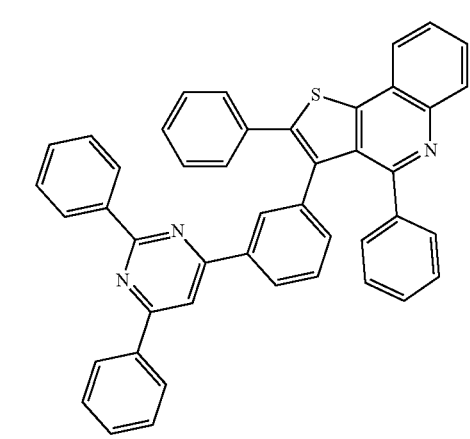
-continued
383
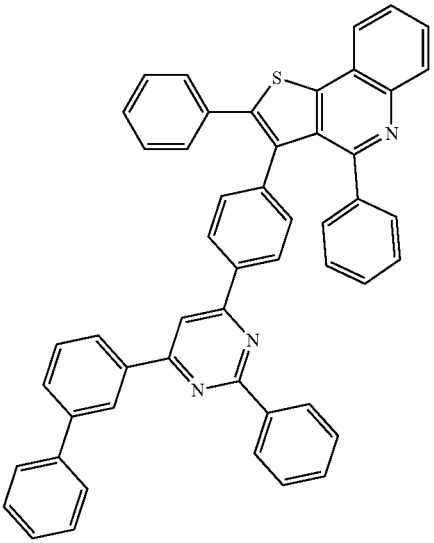
384
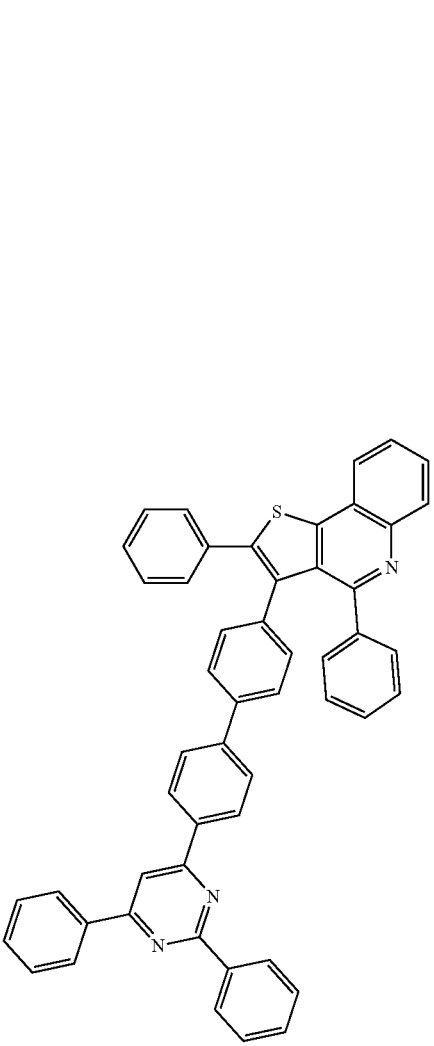

385
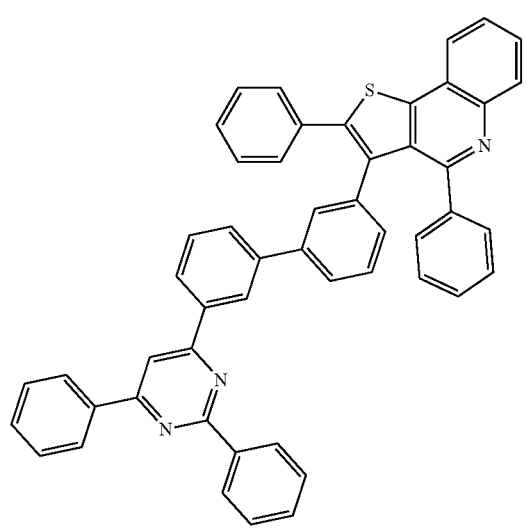
386
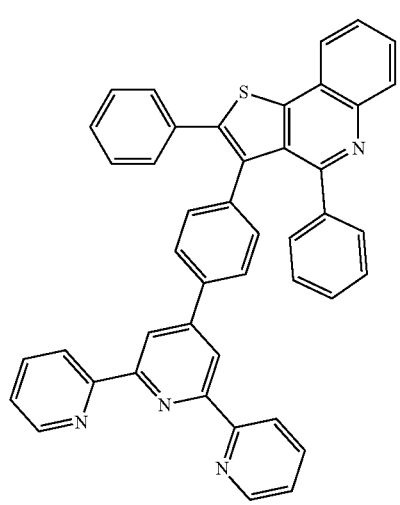
387
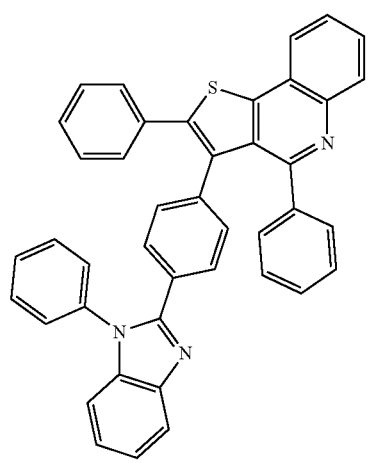
388
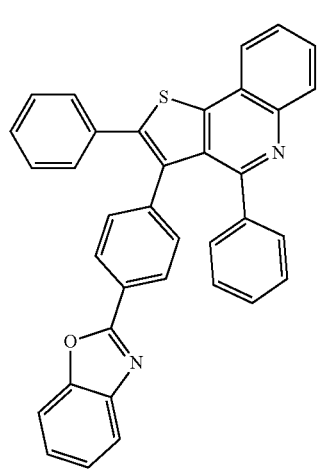
389
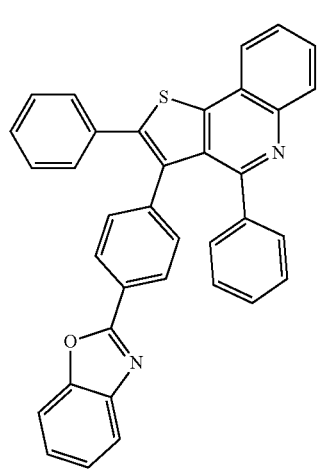
390
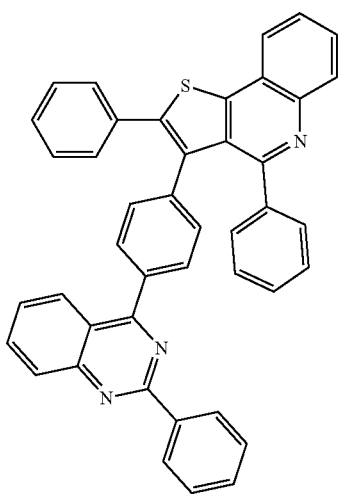

183
-continued
391
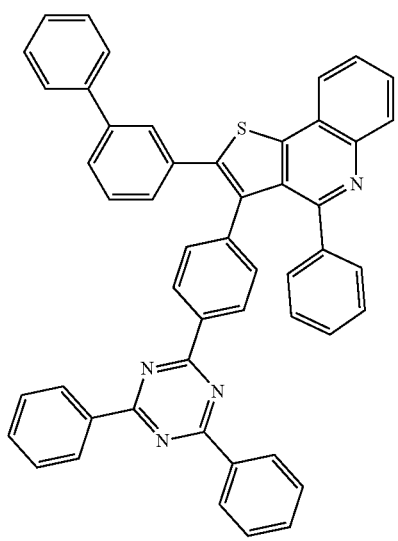
392
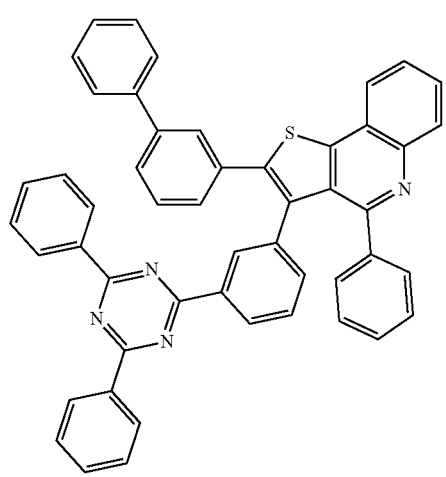
393
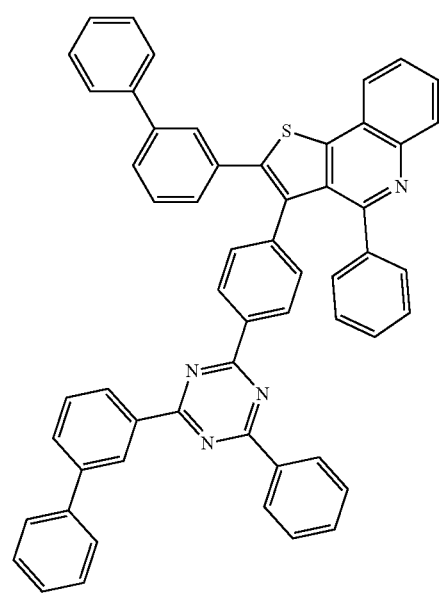
184
-continued
394
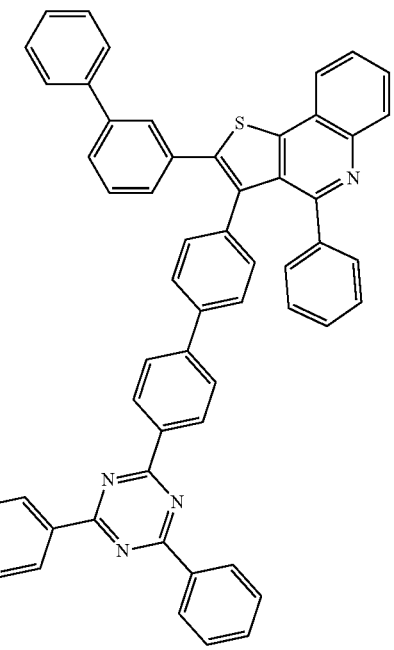
395
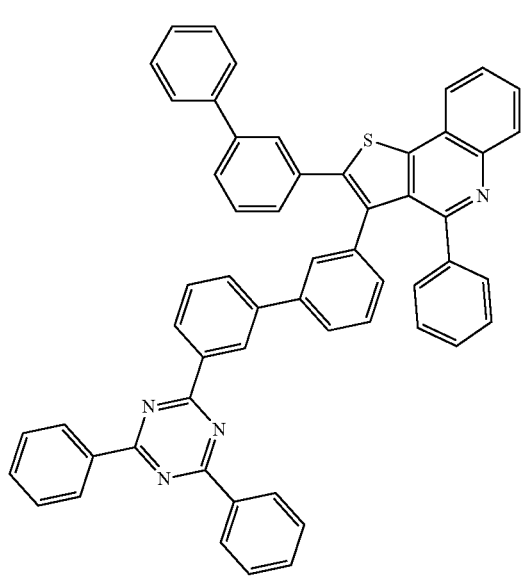

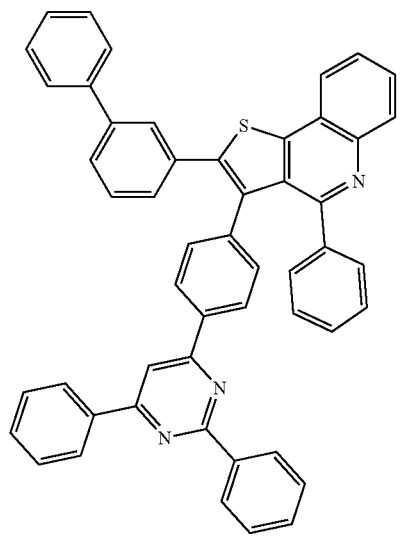
396
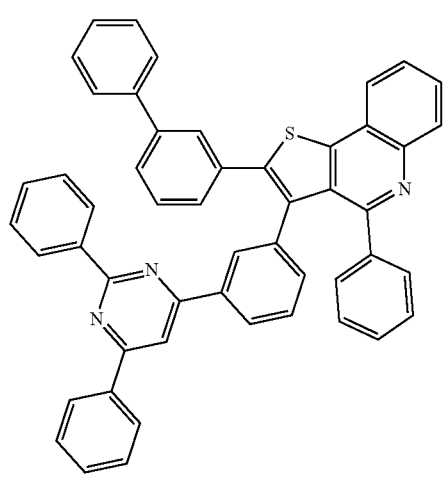
397
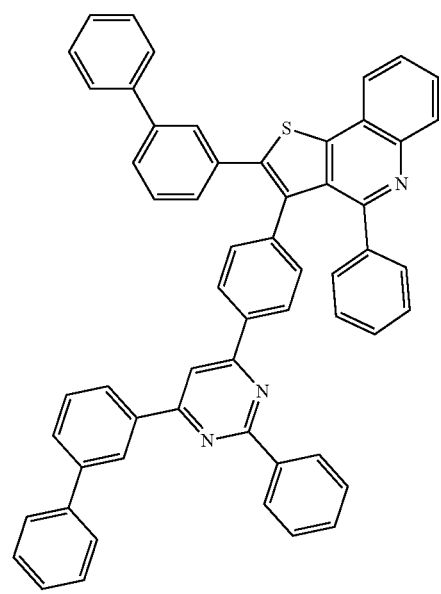
398
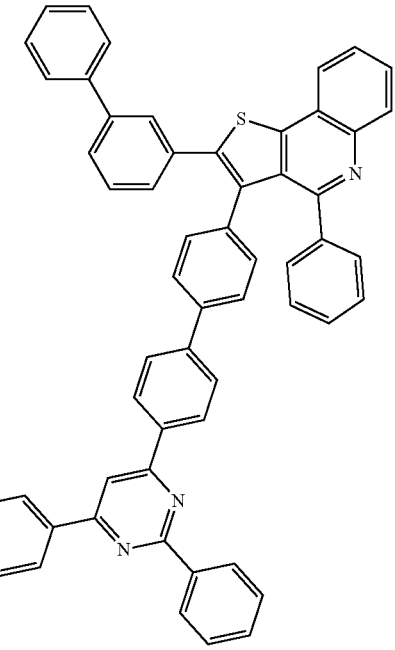
399
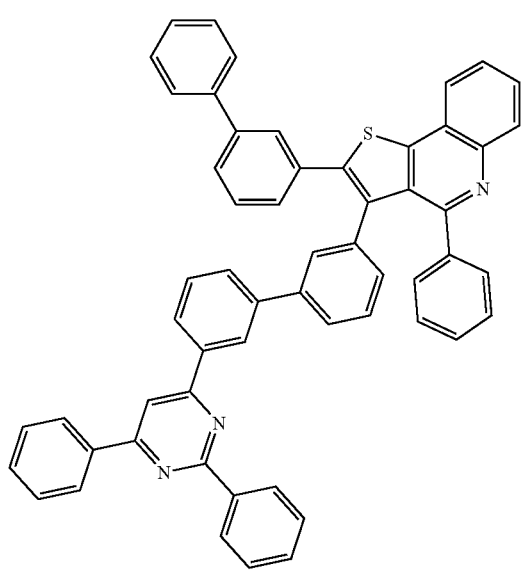
400

401
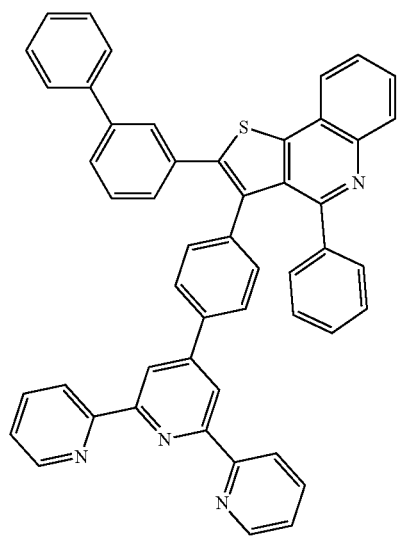
402
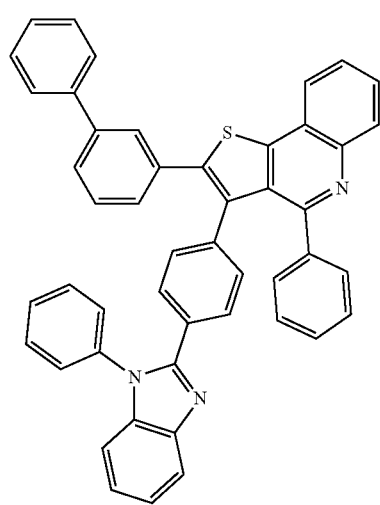
403
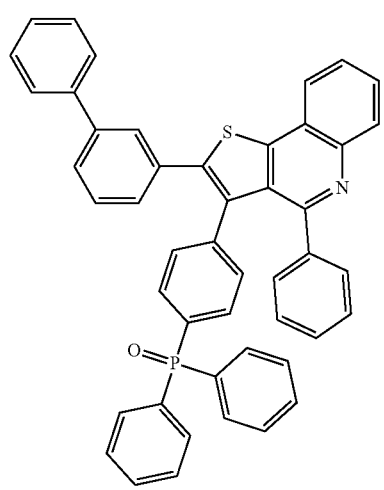
404
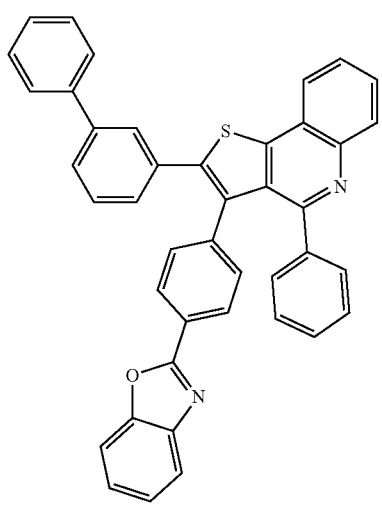
405
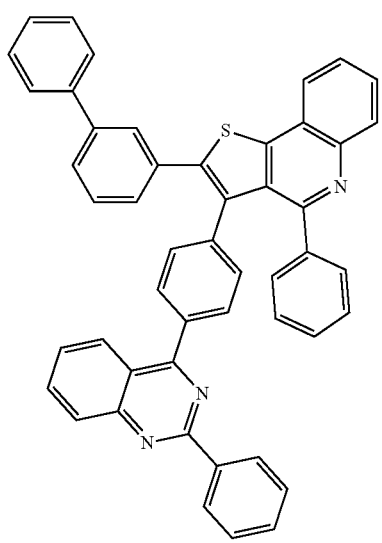
406
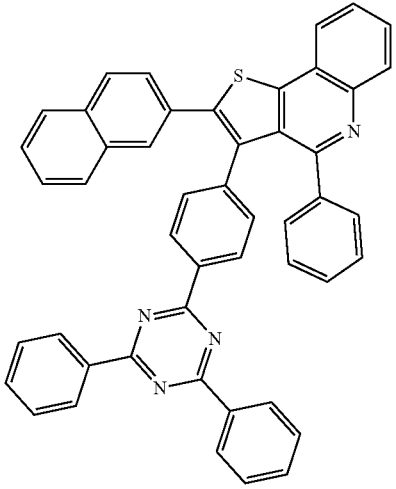

-continued
407
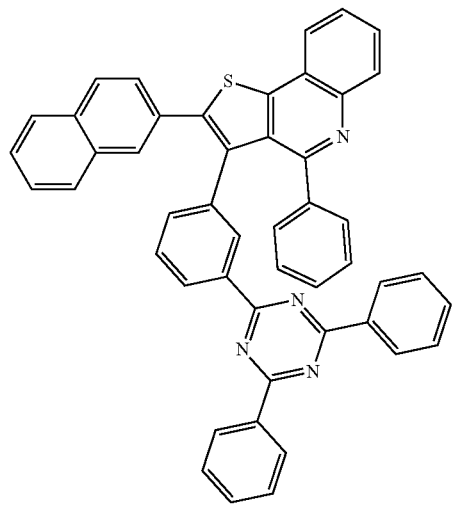
408
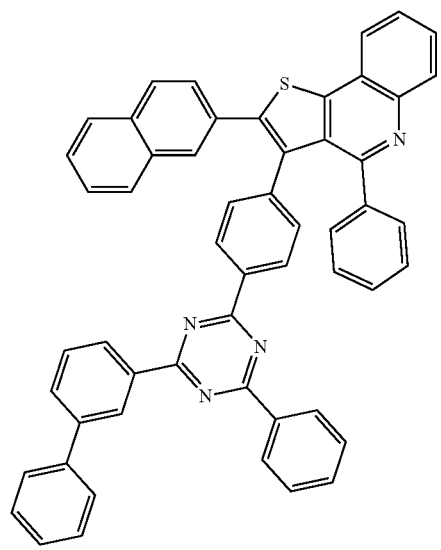
409
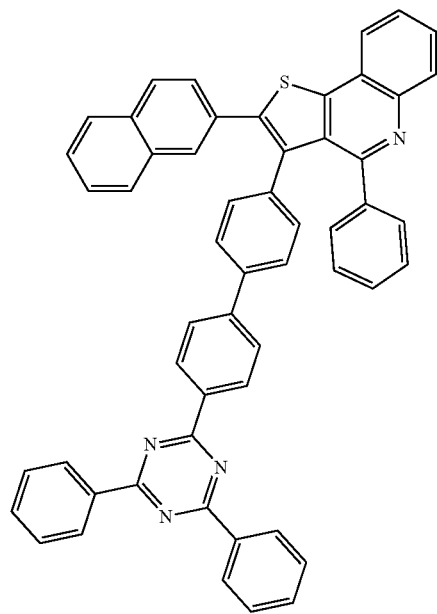
-continued
410
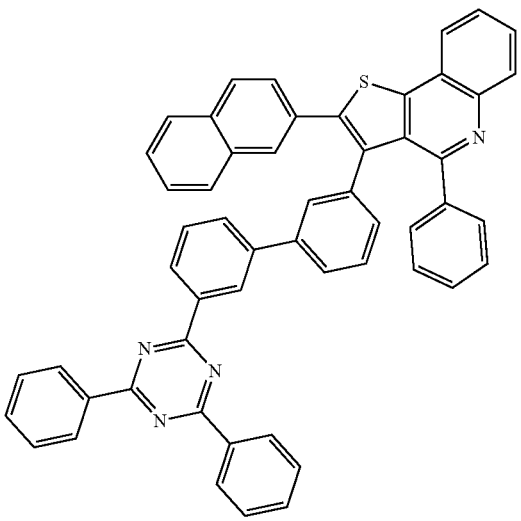
411
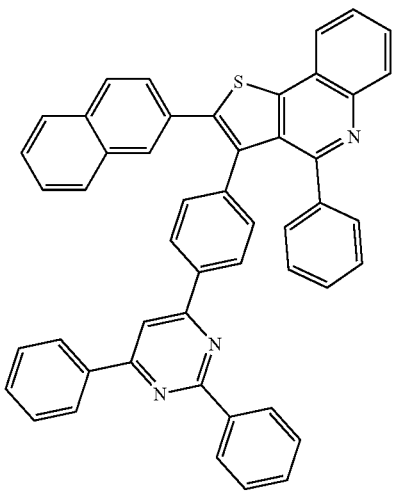
412
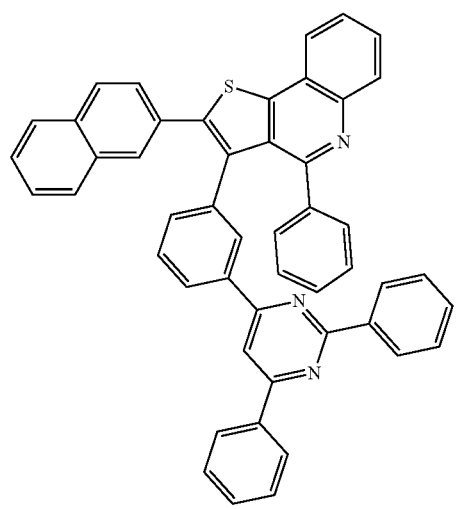

413
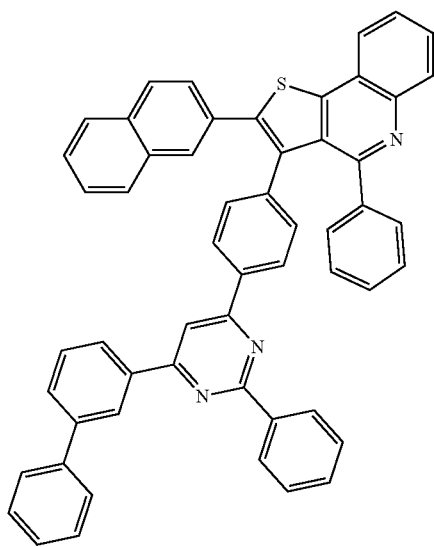
414
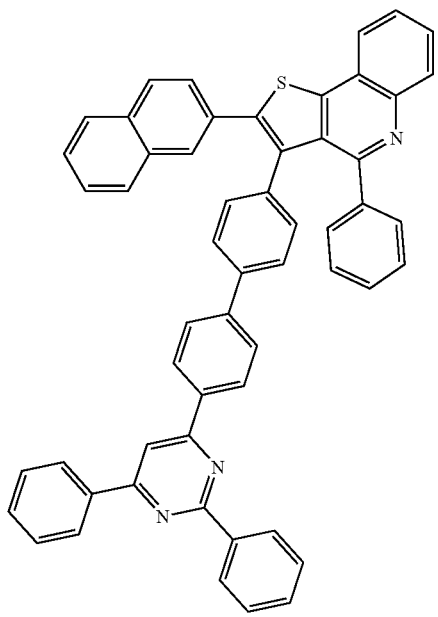
415
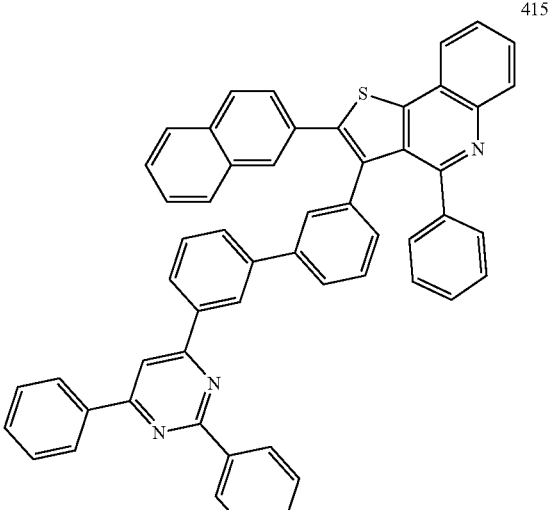
416
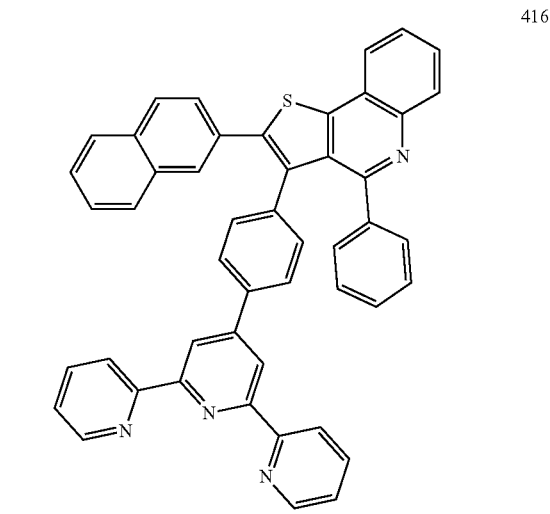
417
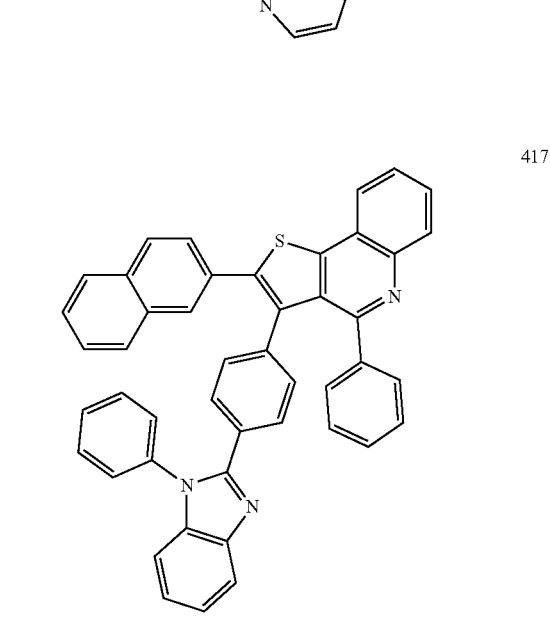

193
-continued
418
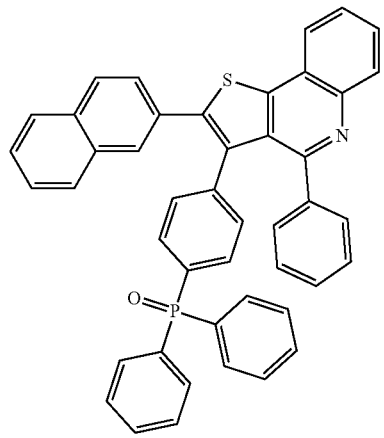
419
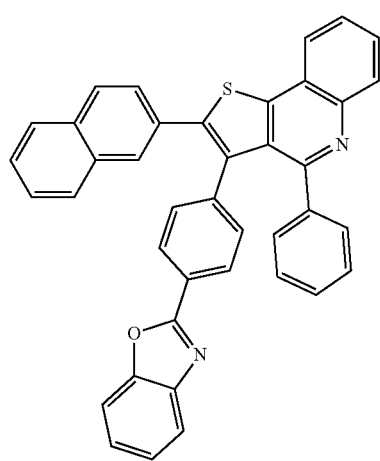
420
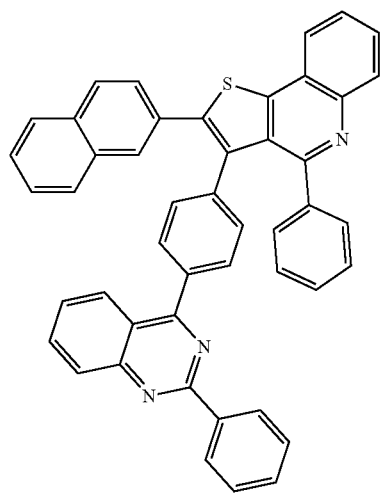
194
-continued
421
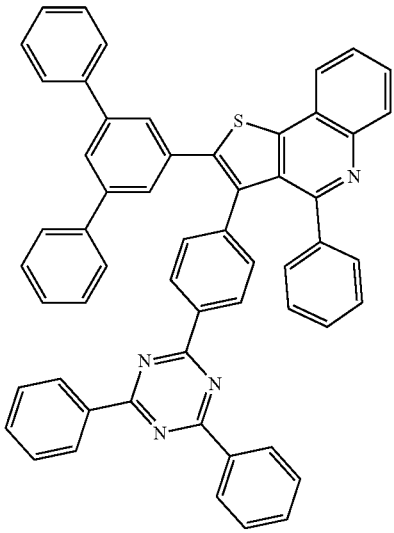
422
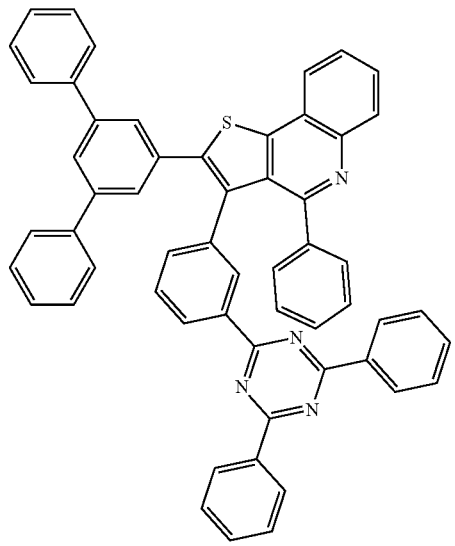

-continued

423

424

425

426

197
-continued
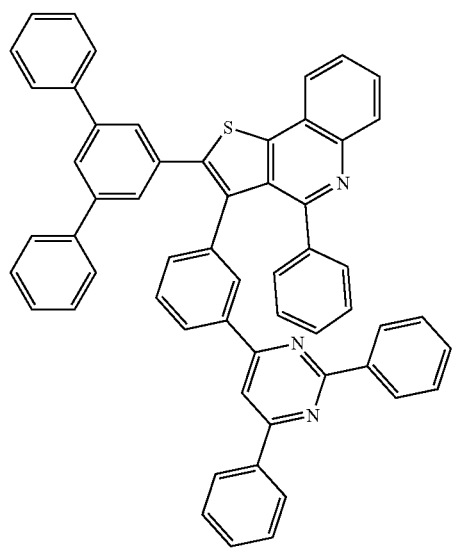
427
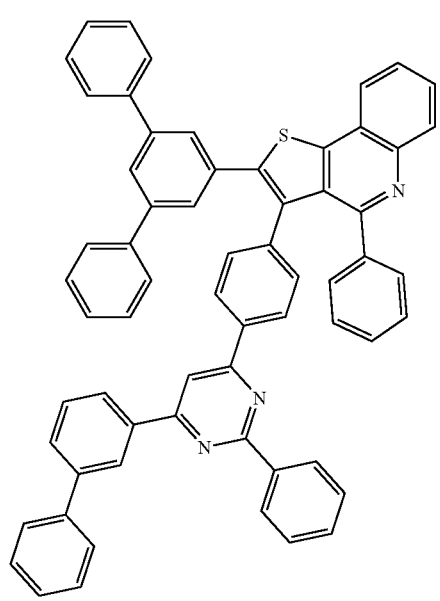
428
198
-continued
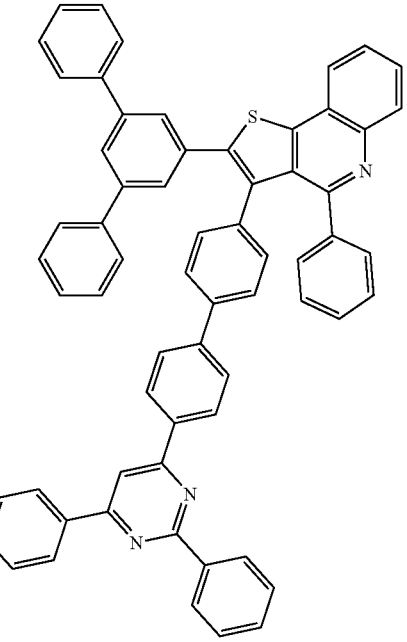
429
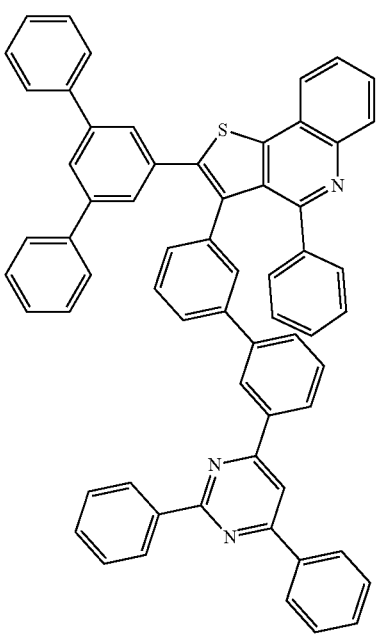
430

431
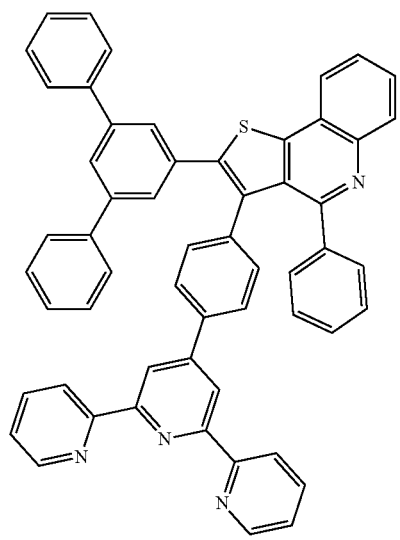
432
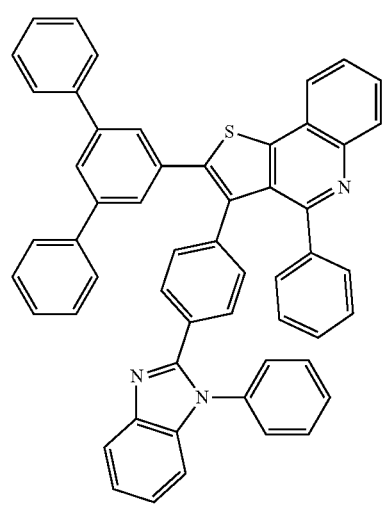
433
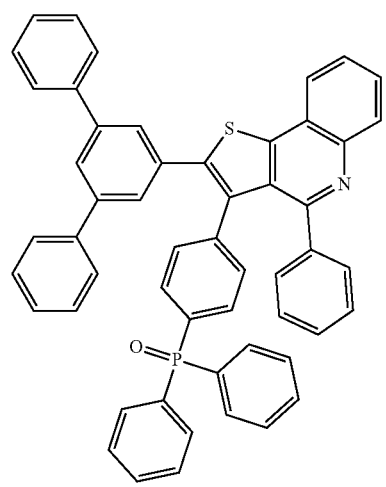
434
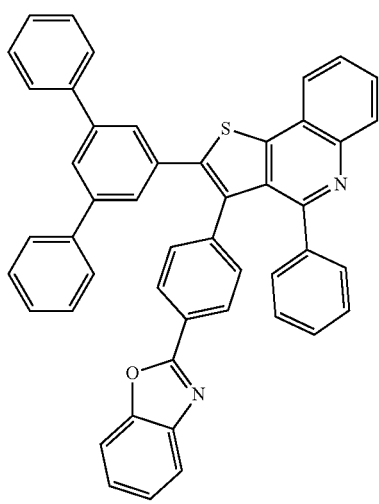
435
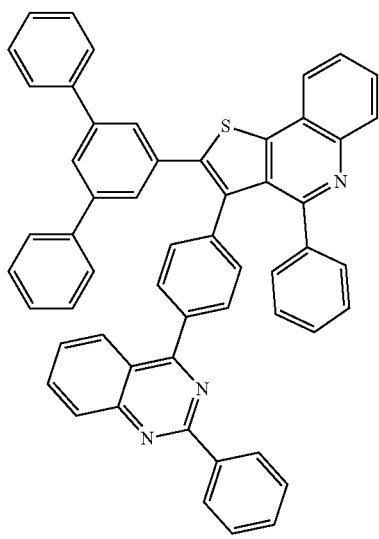
436
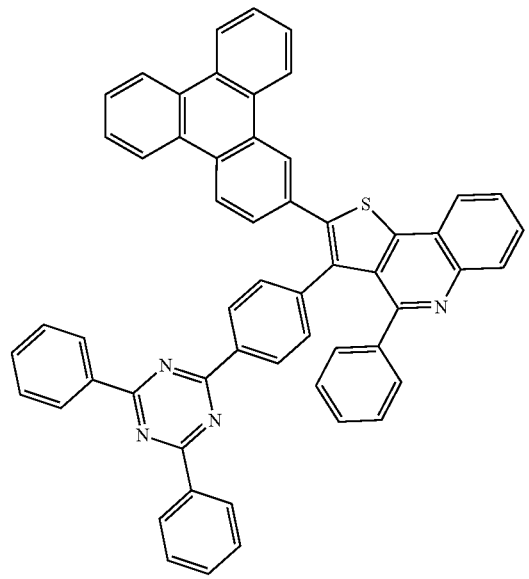

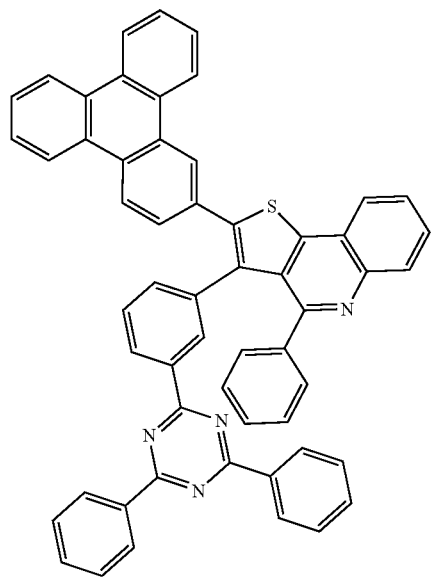
437
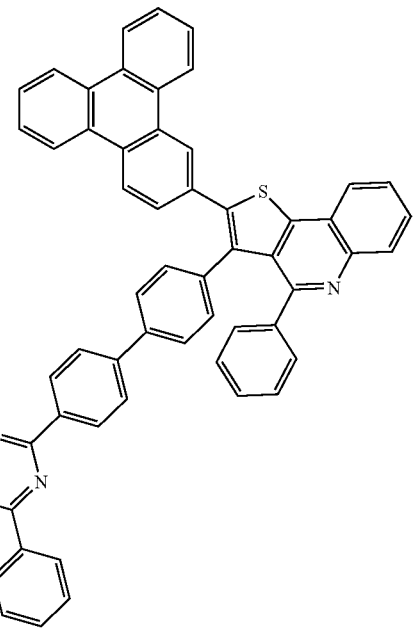
439
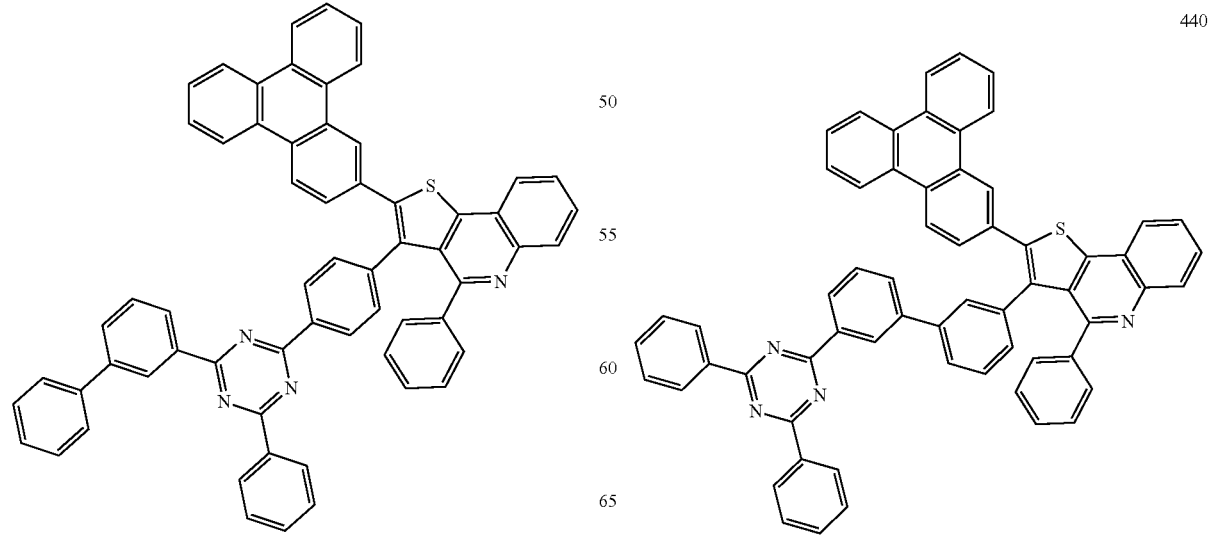
438
440

-continued
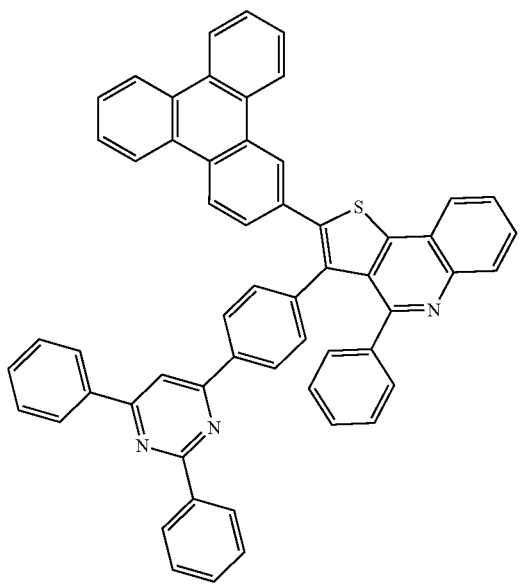
441
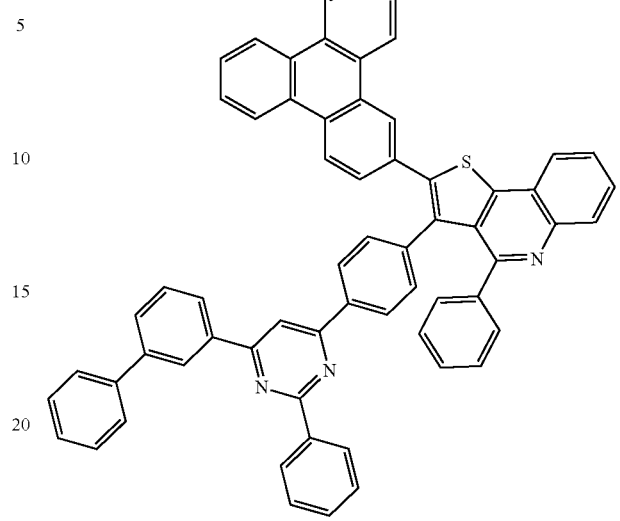
443
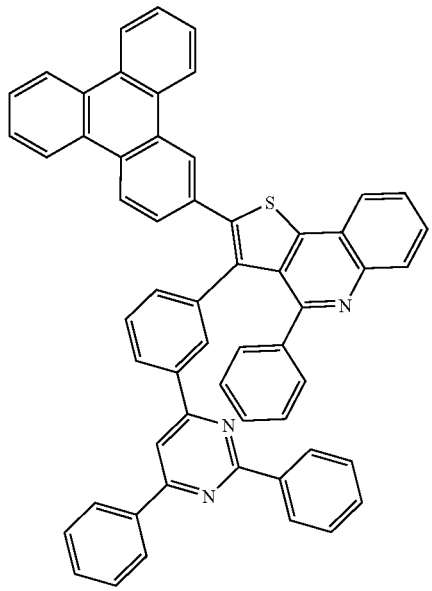
442
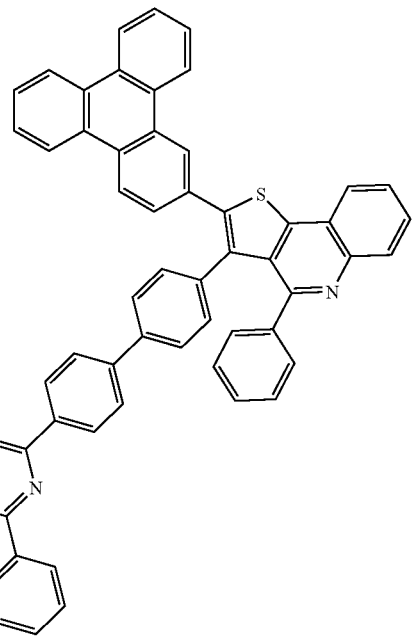
444

445
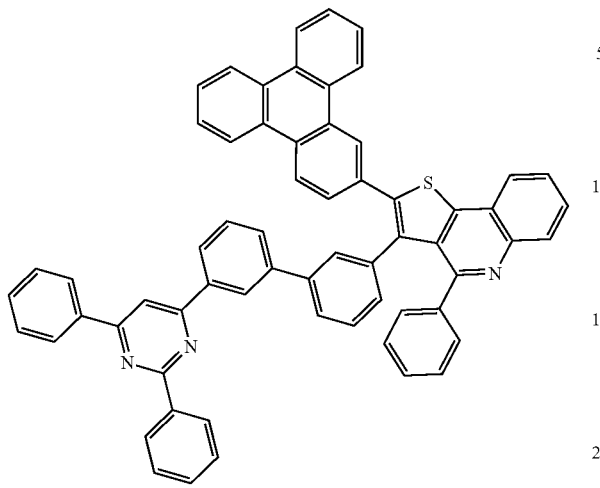
446
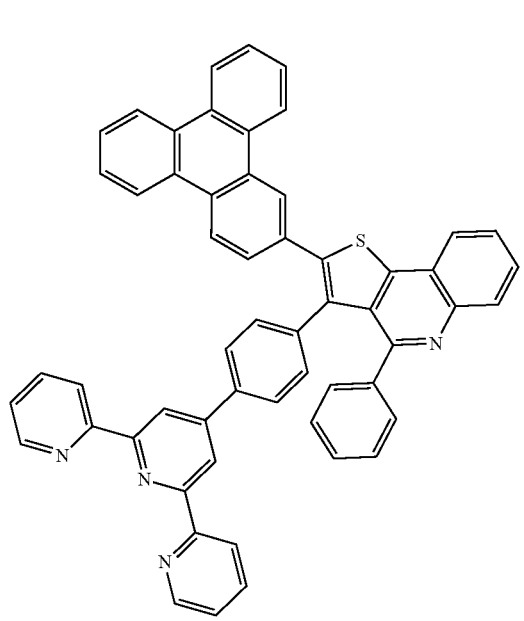
447
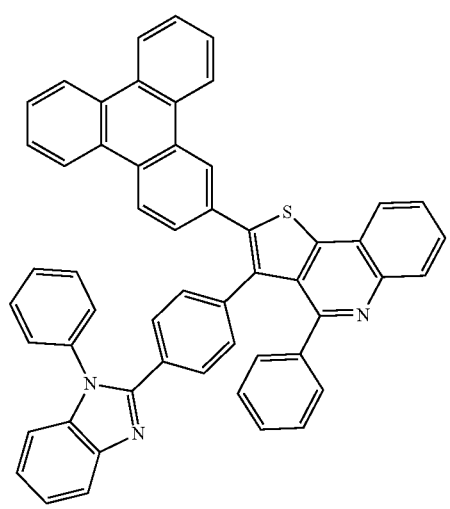
448
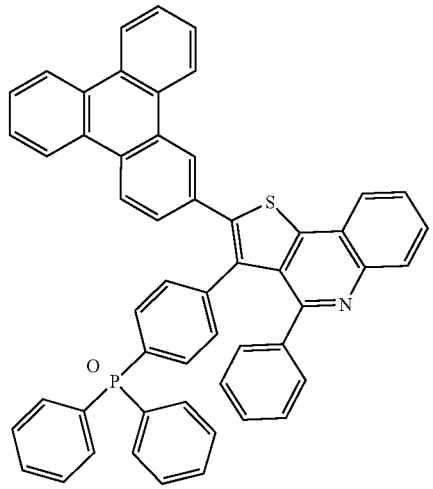
449
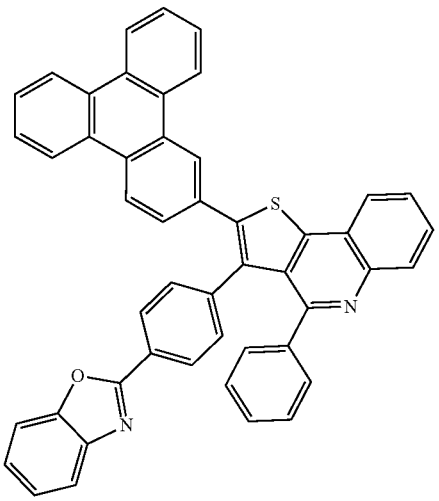
450
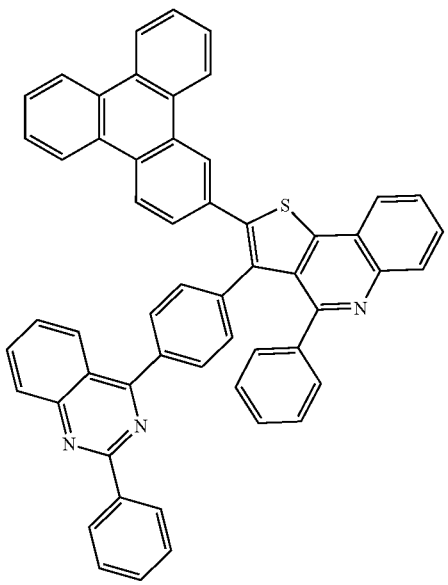

207
-continued
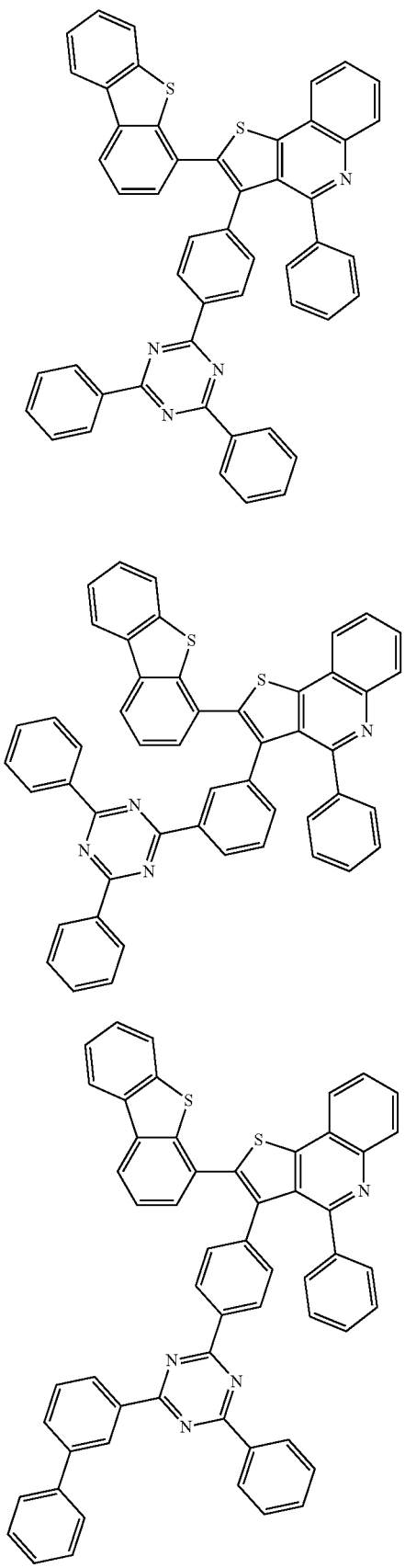
208
-continued
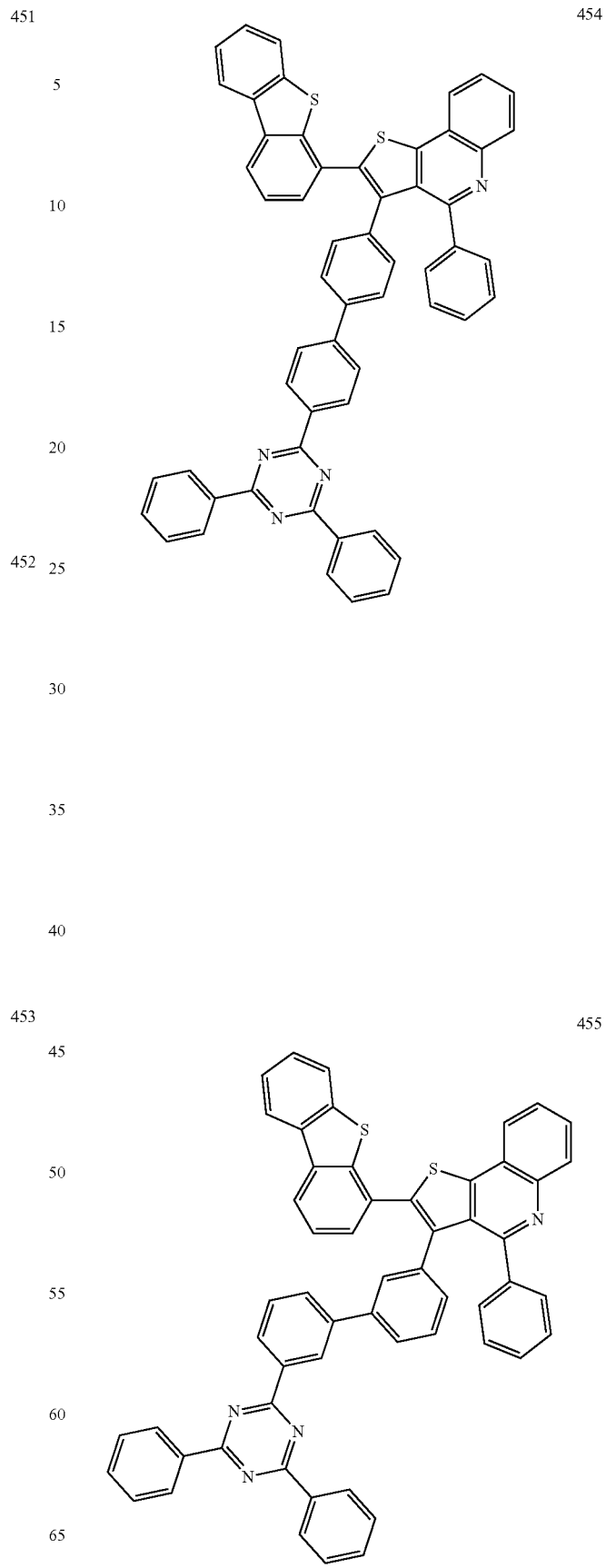

209
-continued
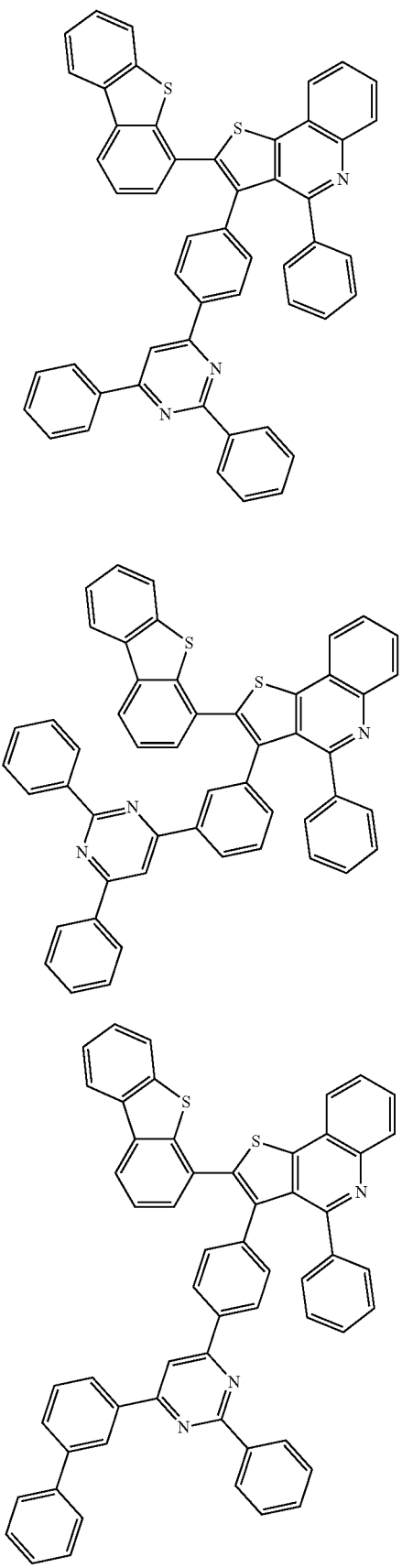
210
-continued
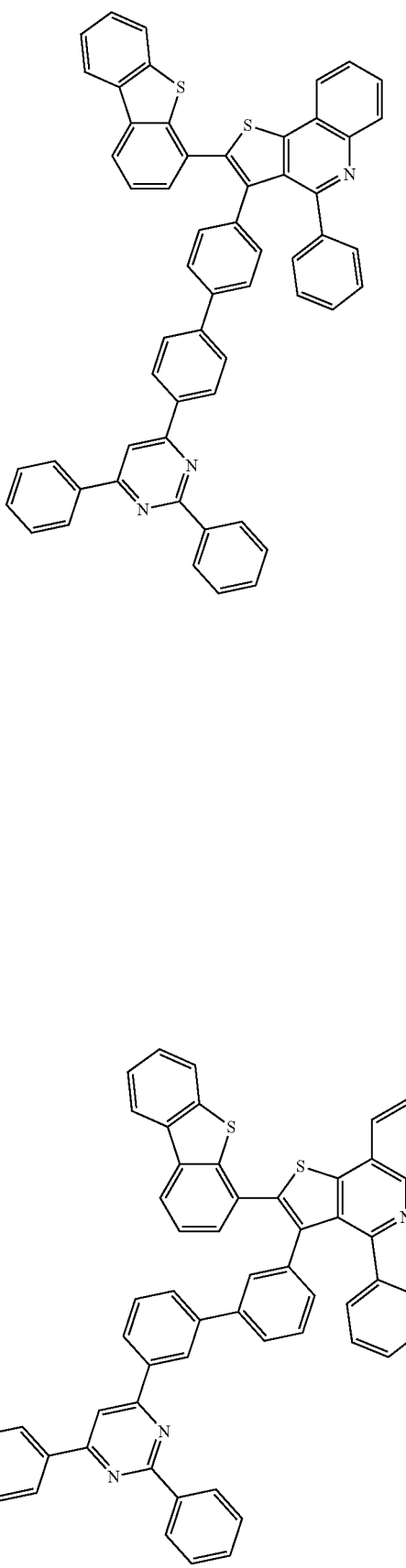

-continued
461
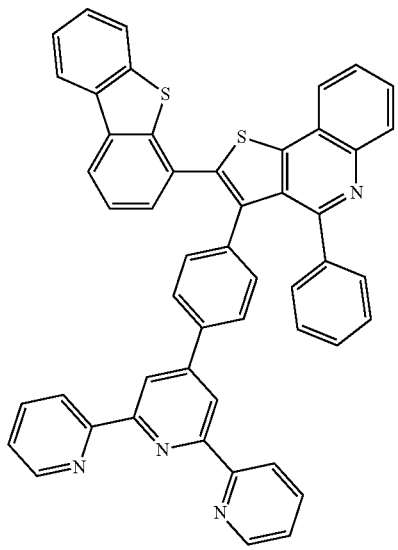
462
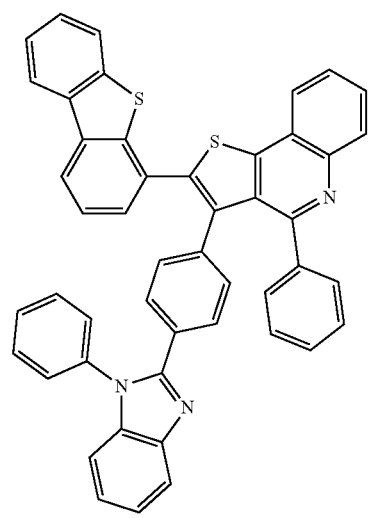
463
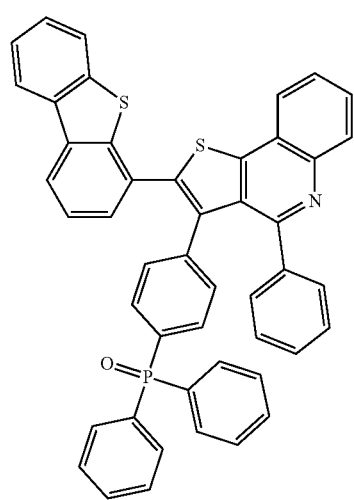
-continued
464
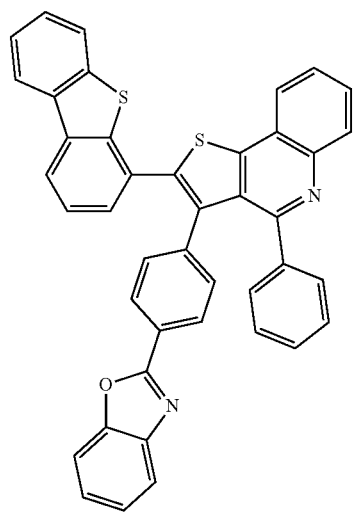
465
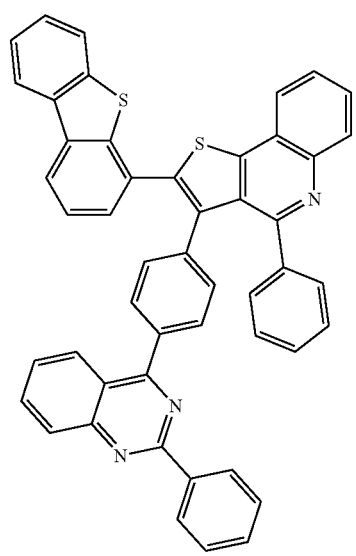
466
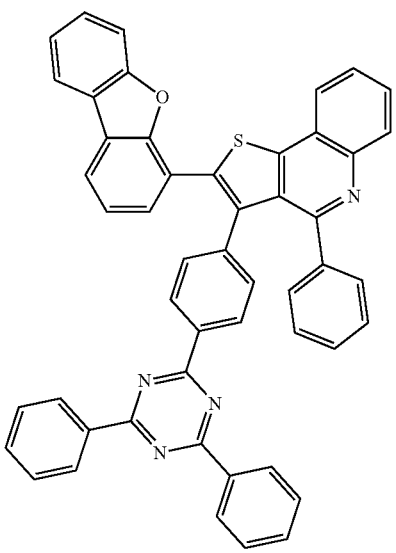

467
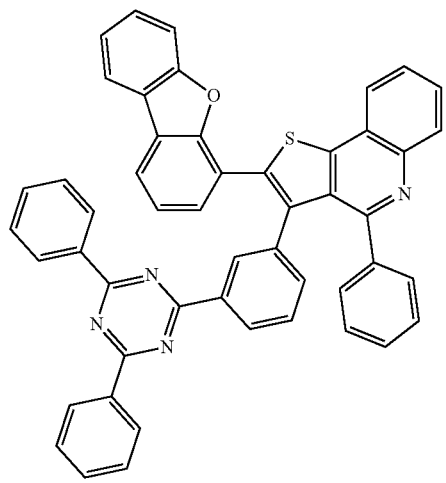
468
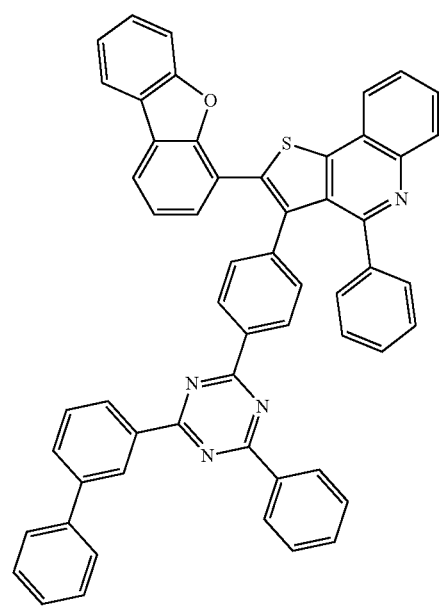
469
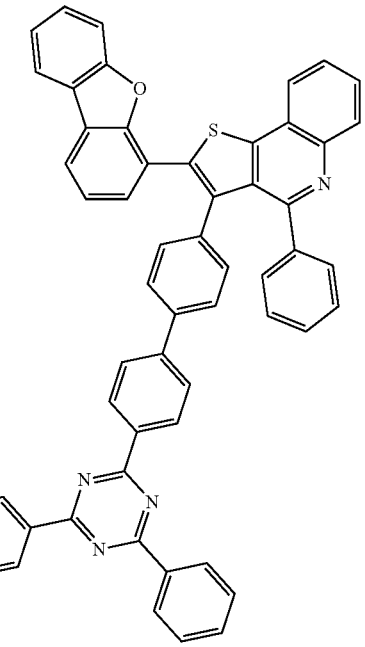
470
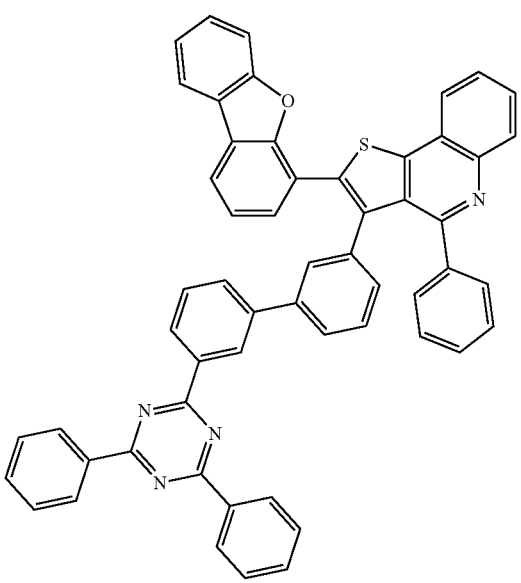

215
-continued
471
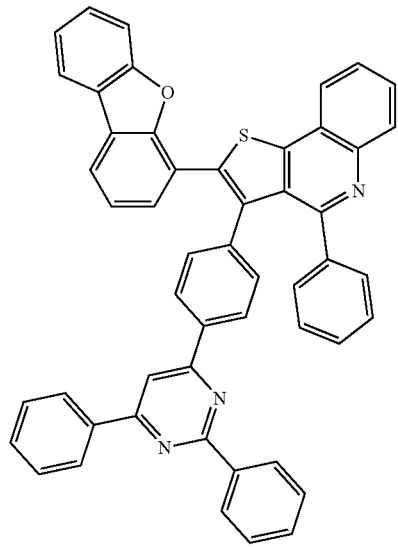
472
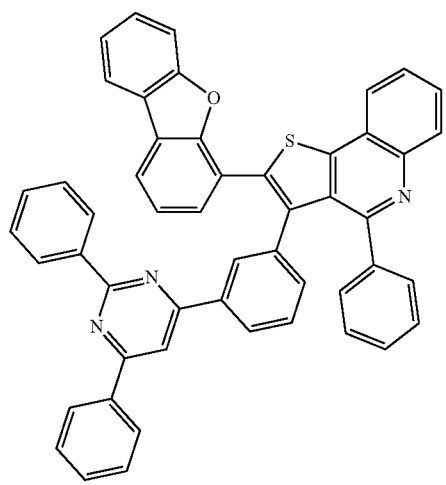
473
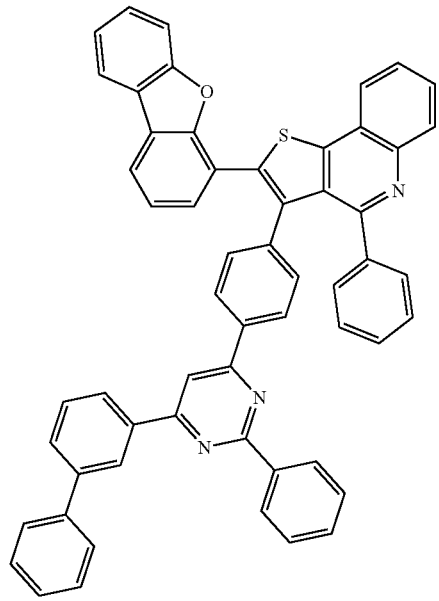
216
-continued
474
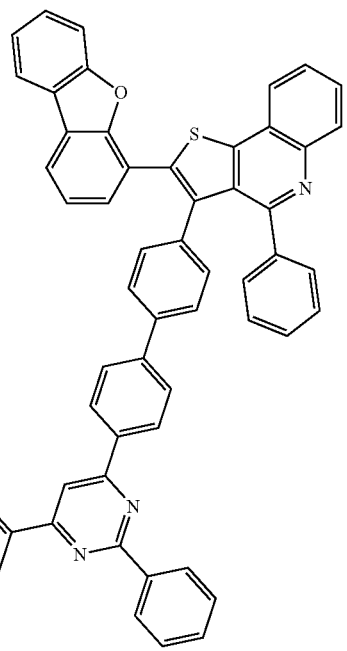
475
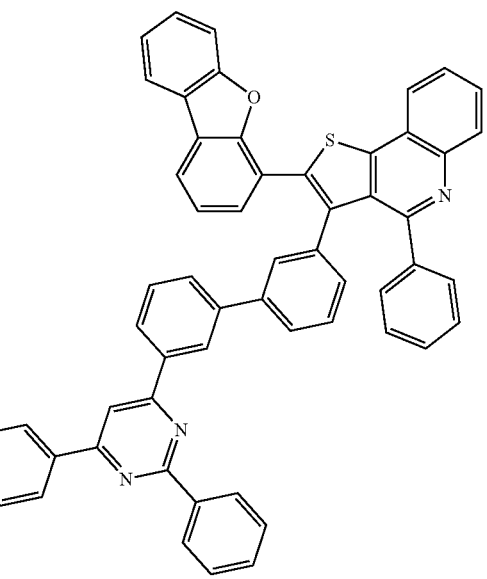

476
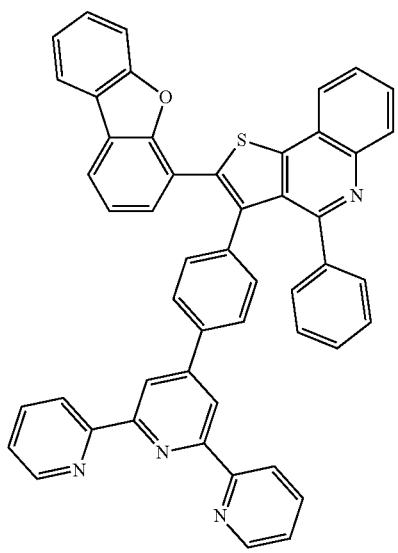
477
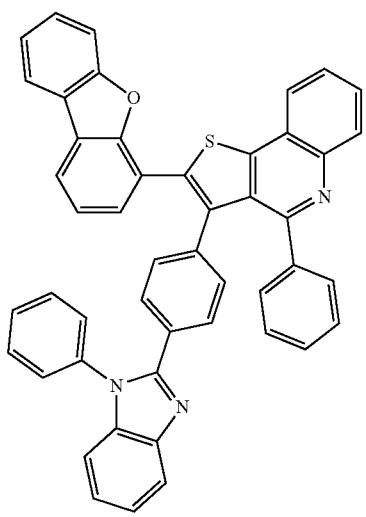
478
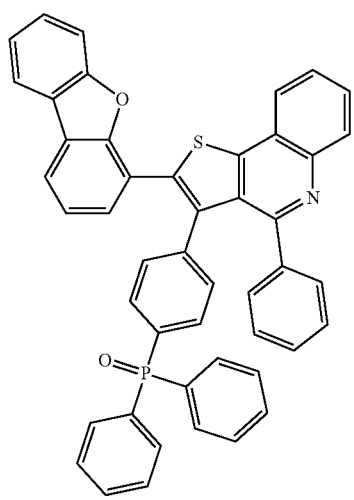
479
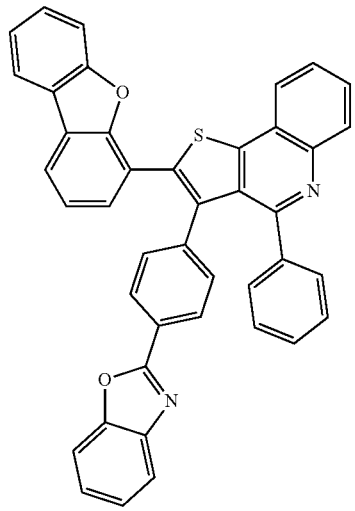
480
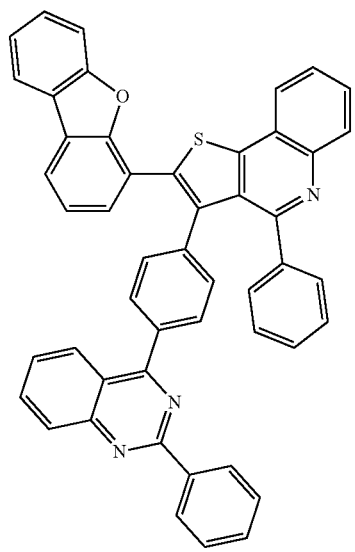
481
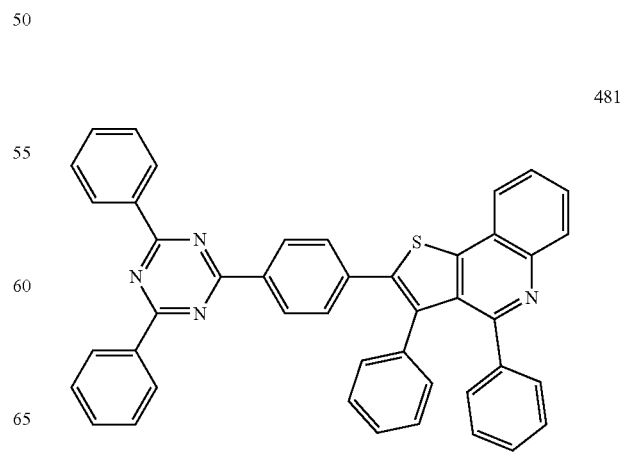

-continued
482
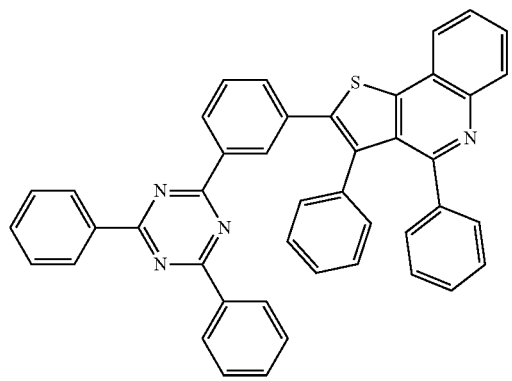
483
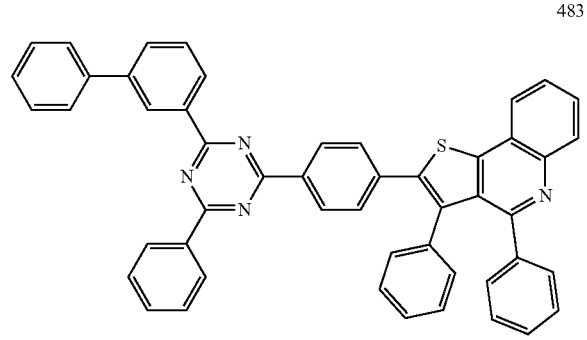
484
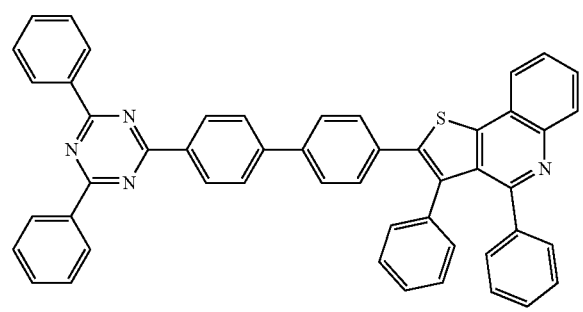
485
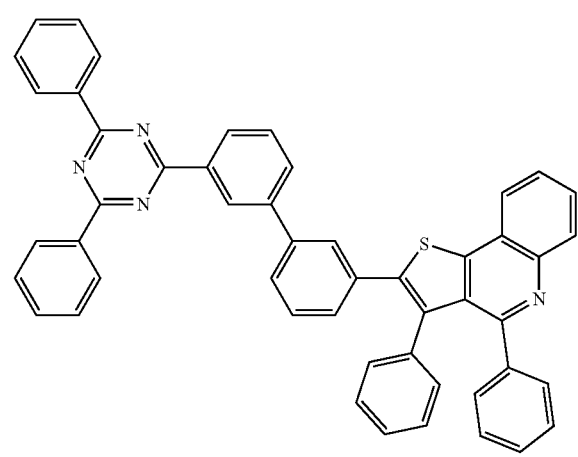
-continued
486
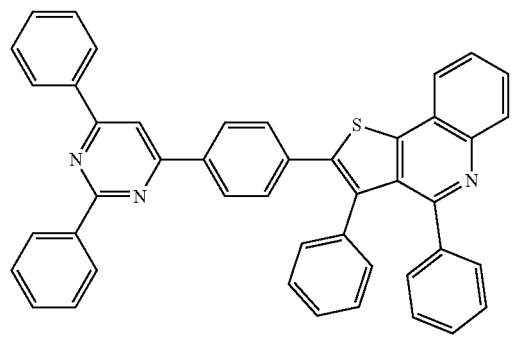
487
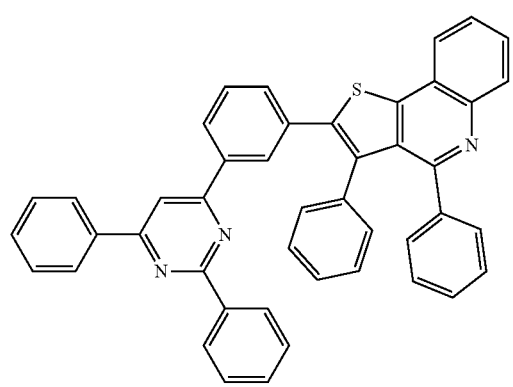
488
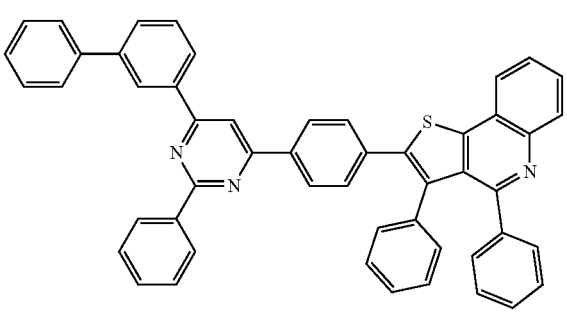
489
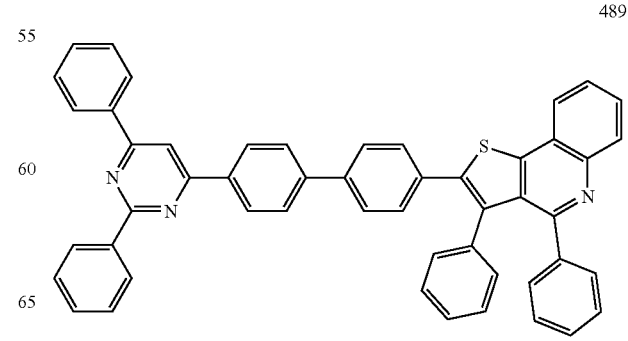

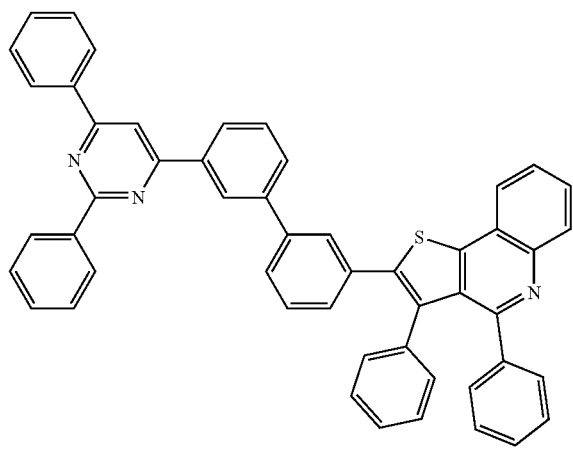
490
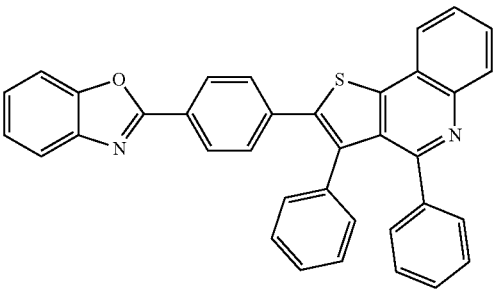
494
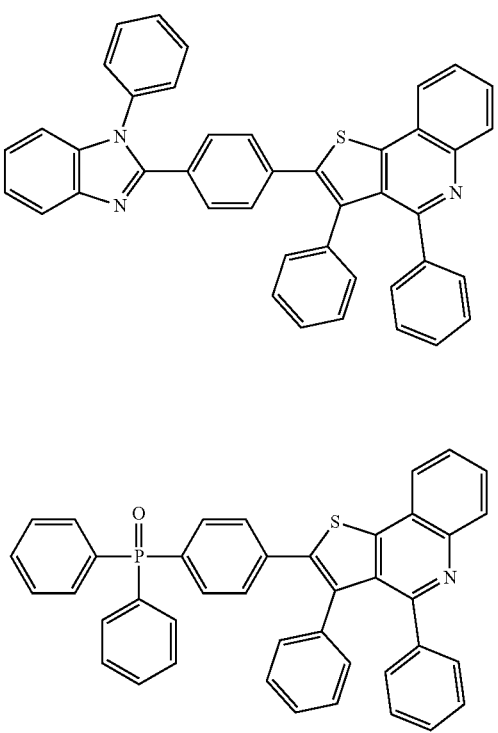
491
492
493
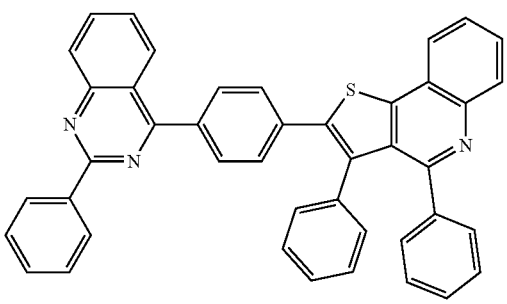
495
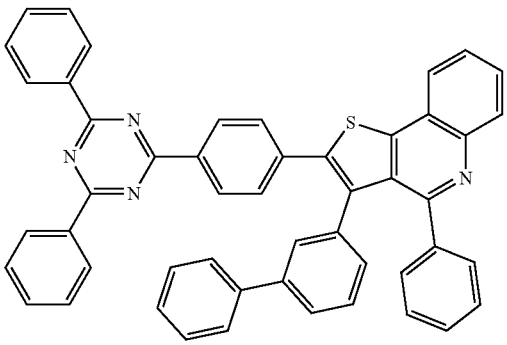
496
497

498
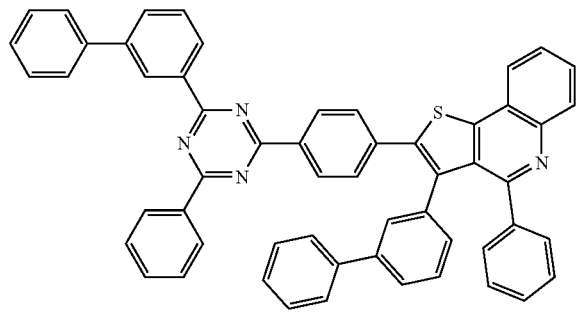
499
502
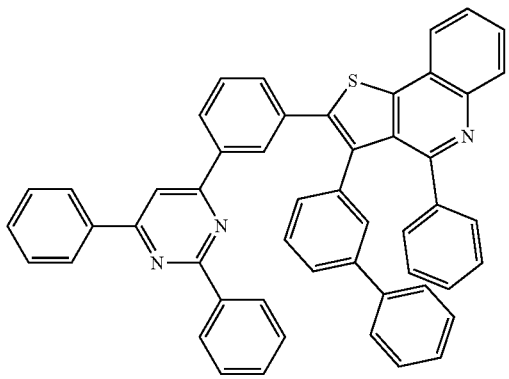
503
500
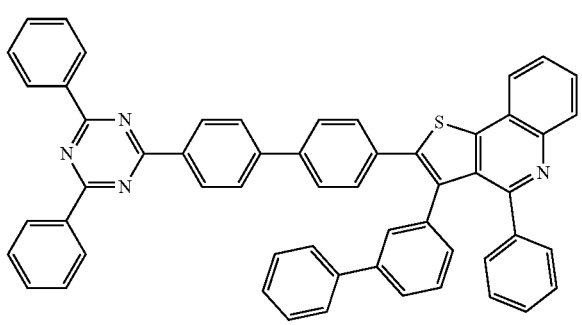
504
501
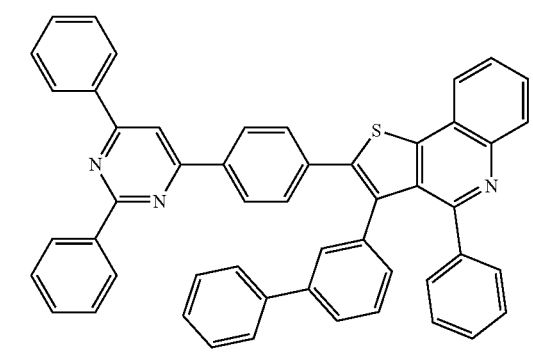
505

225
-continued
506
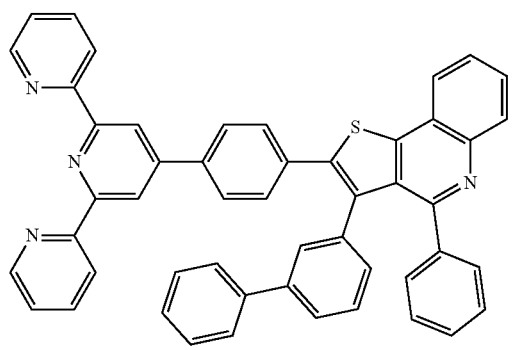
507
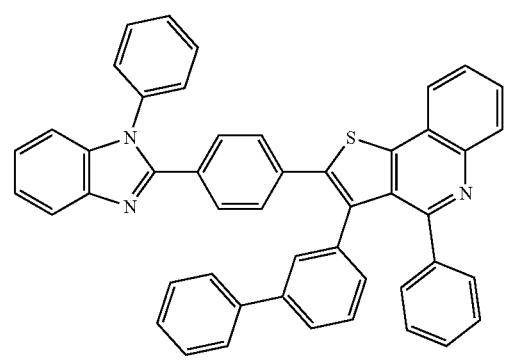
508
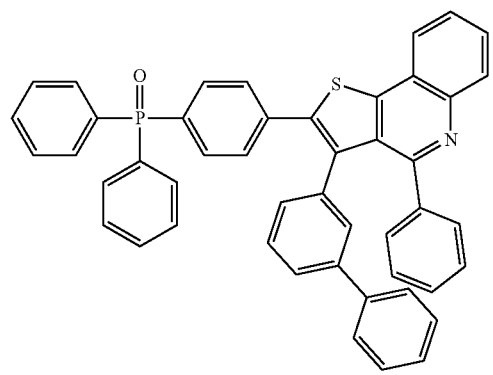
509
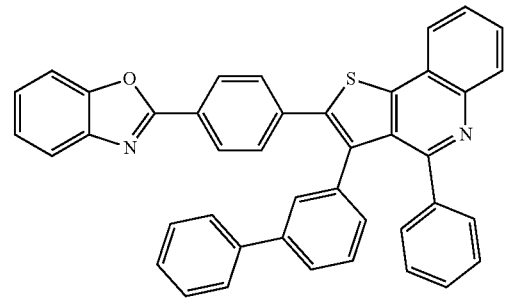
226
-continued
510
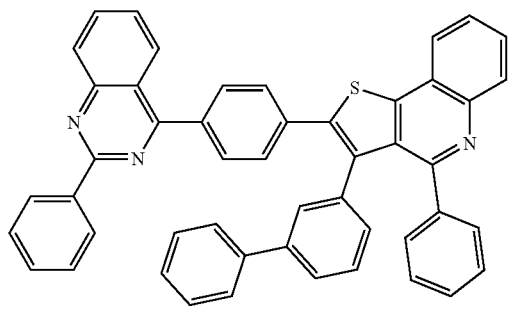
511
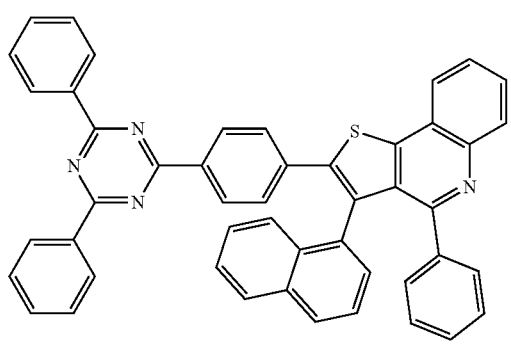
512
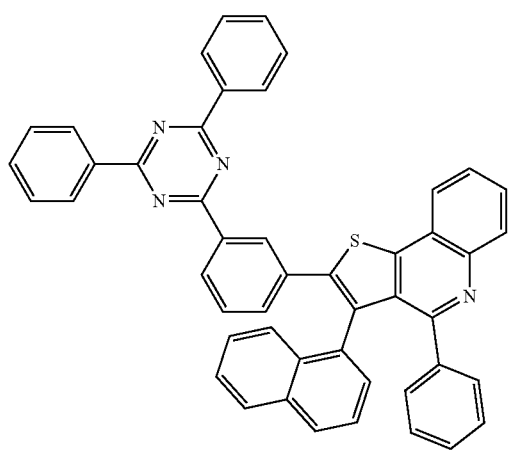
513
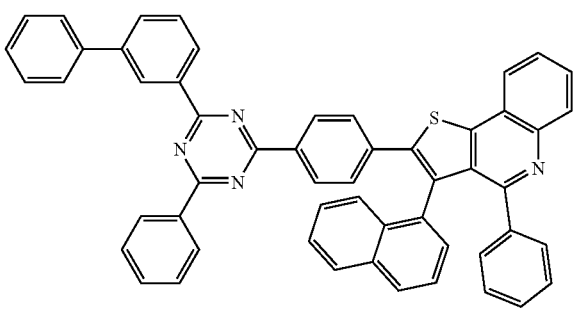

227
-continued
514
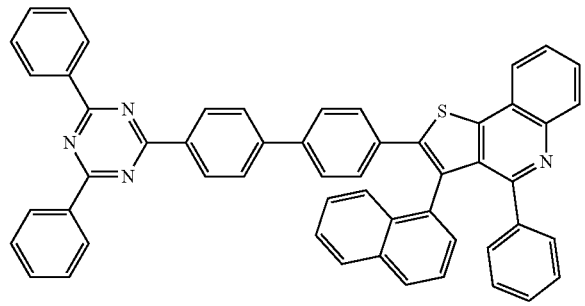
515
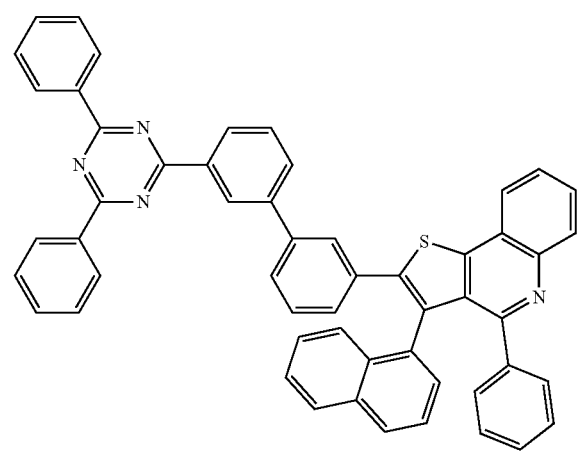
516
517
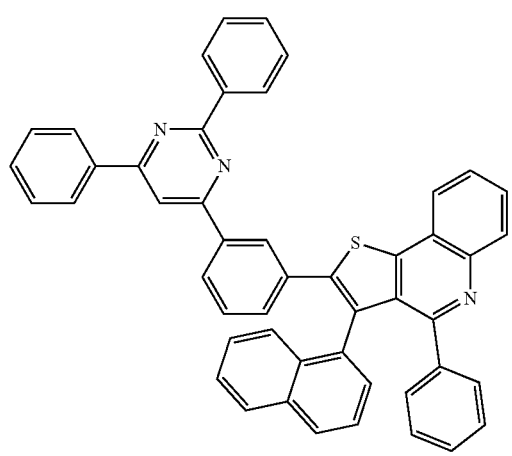
228
-continued
518
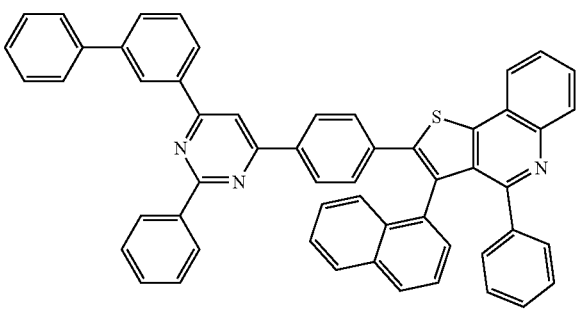
519
520
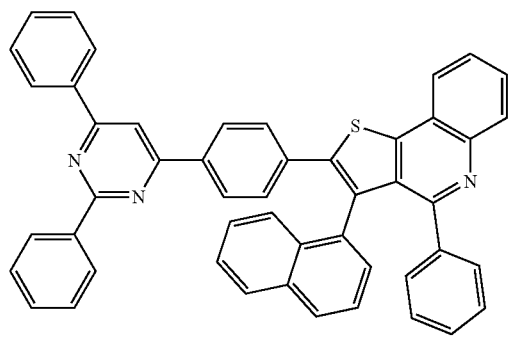
521
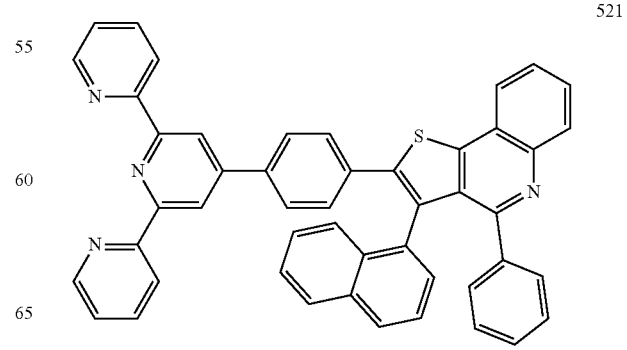

522
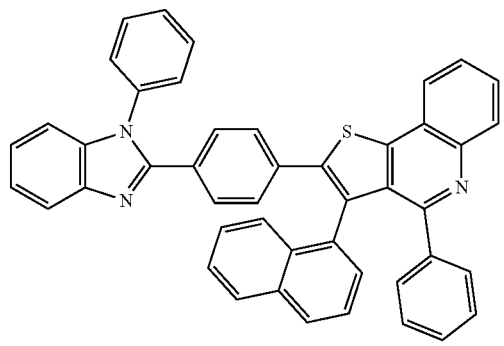
523
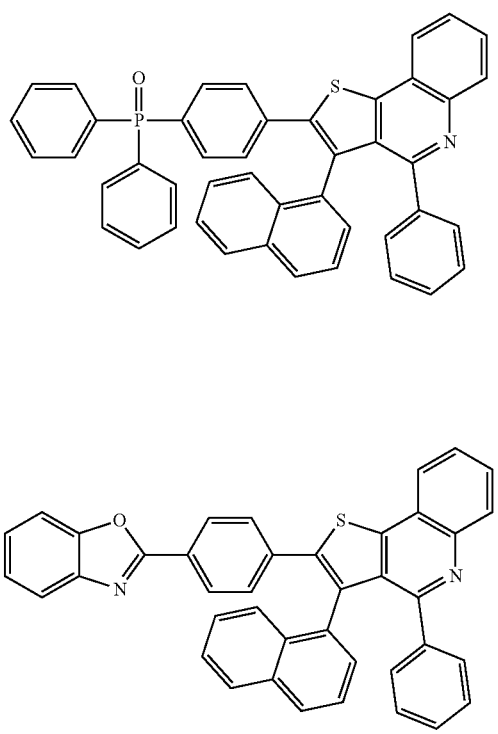
524
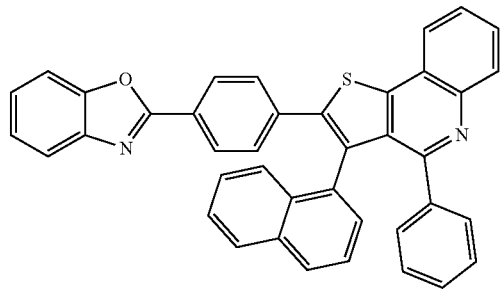
525
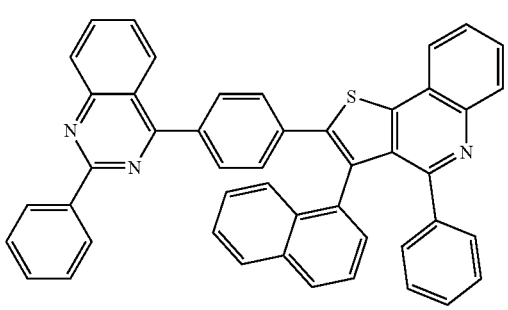
526
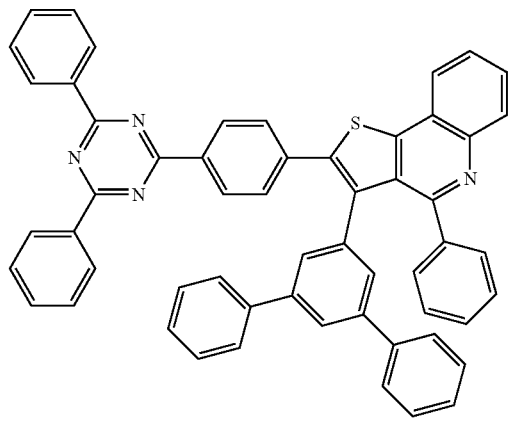
527
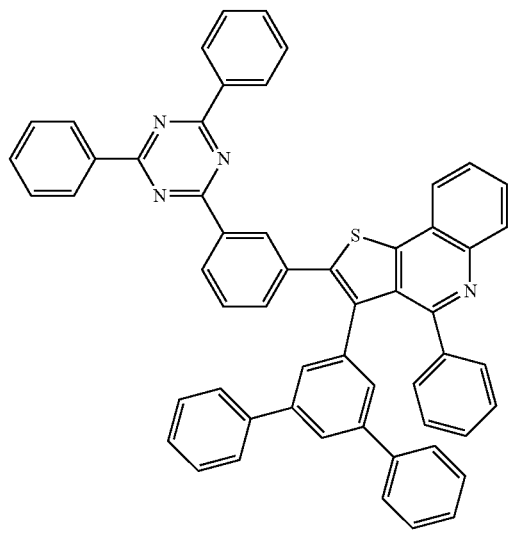
528
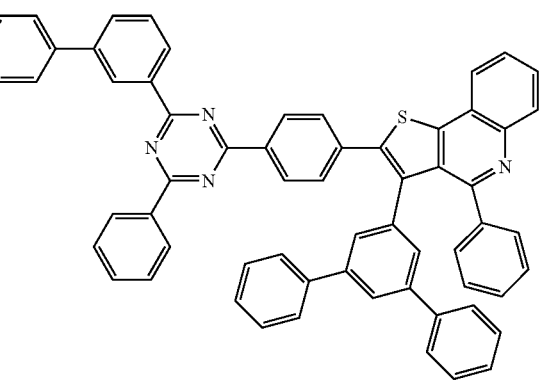

231
-continued
529
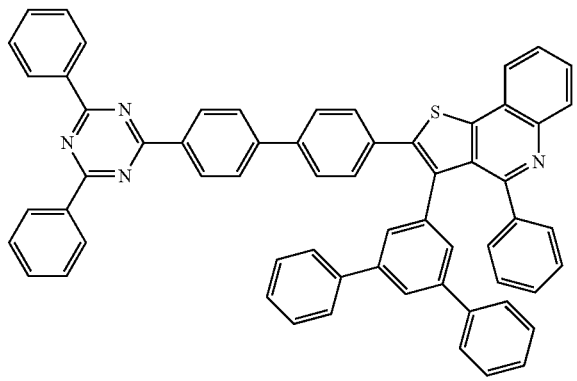
530
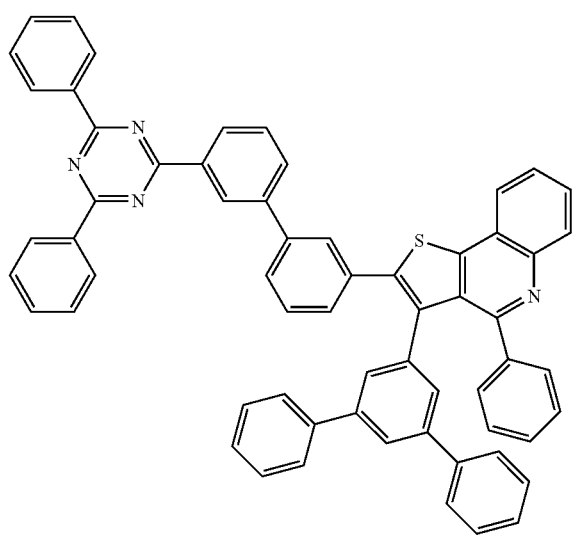
531
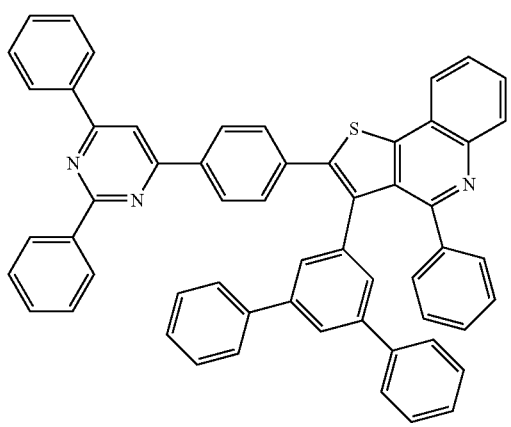
232
-continued
532
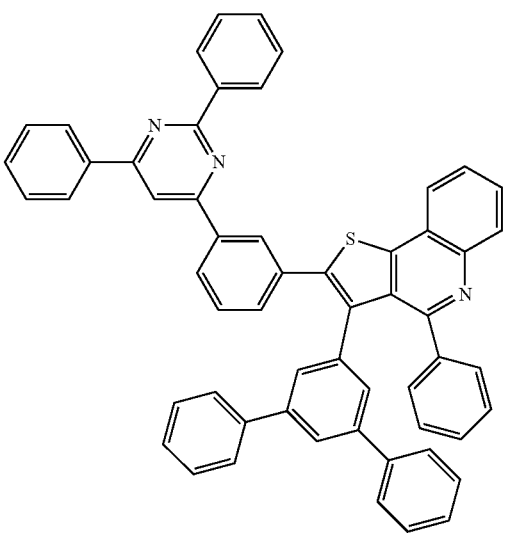
533
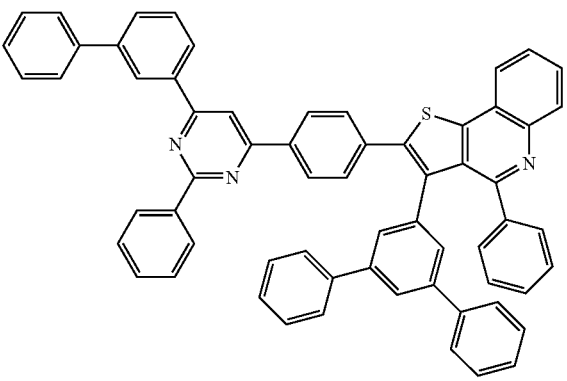
534
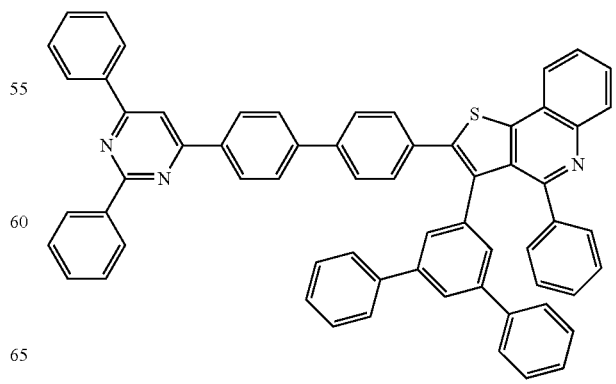

535
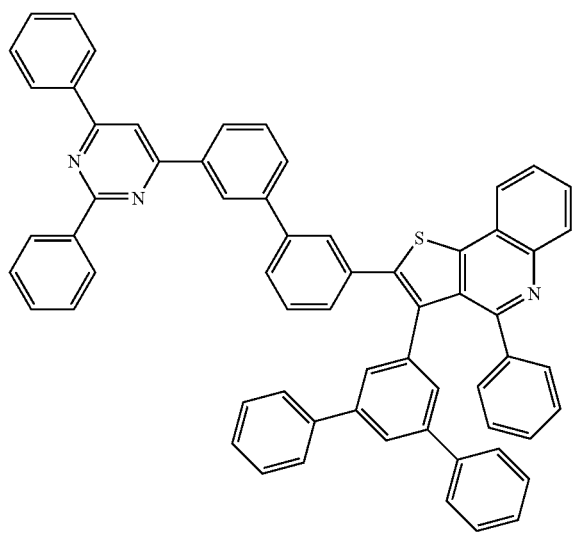
536
537
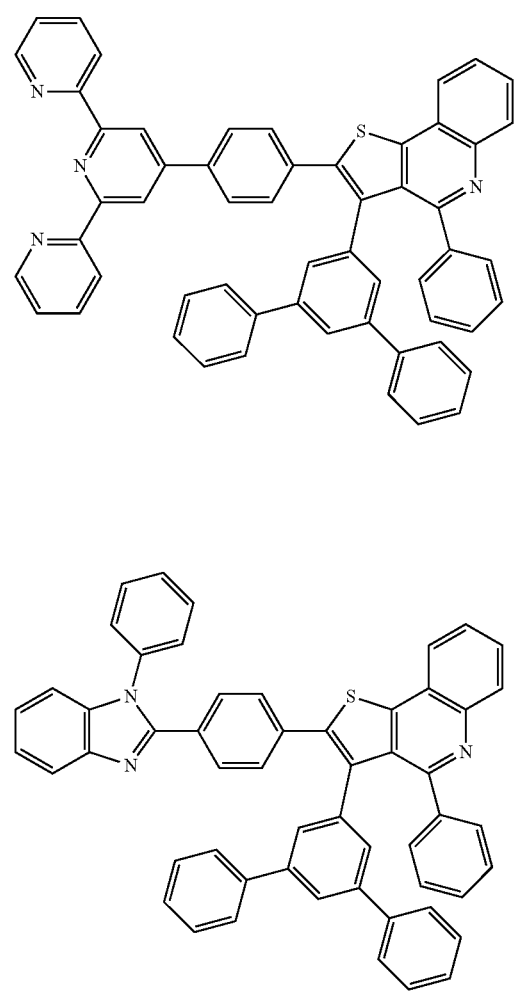
538
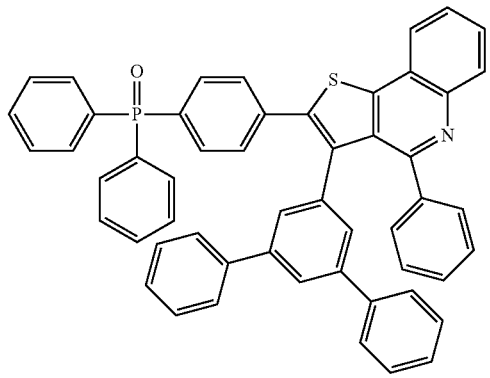
539
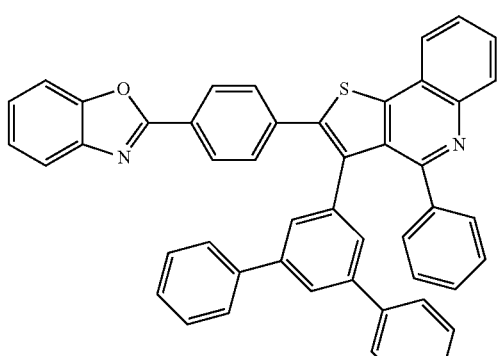
540
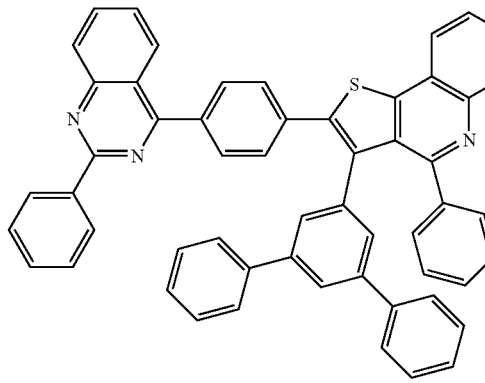
541

235
-continued
542
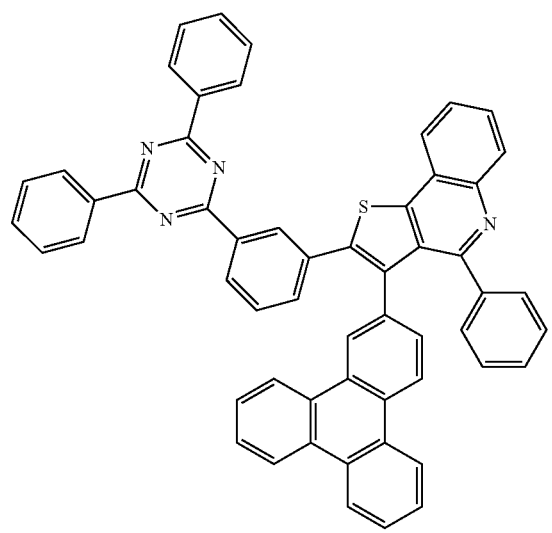
543
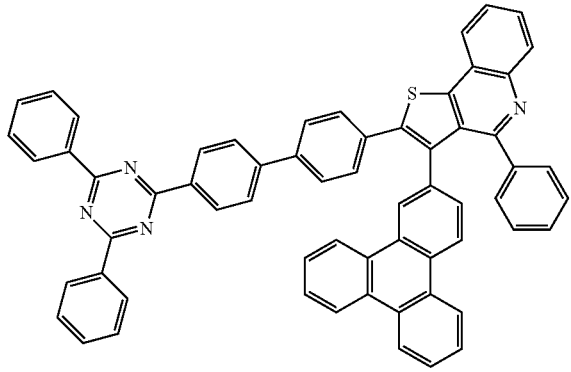
544
236
-continued
545
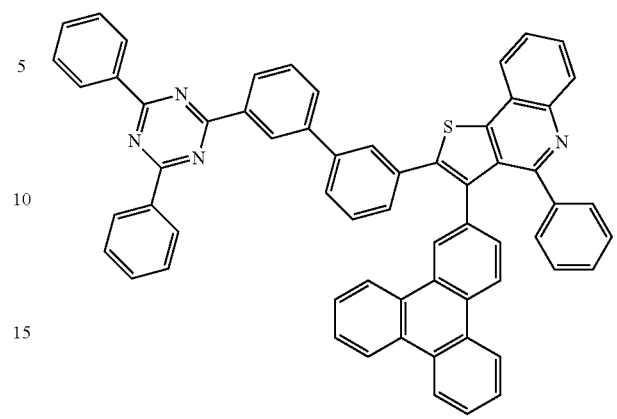
546
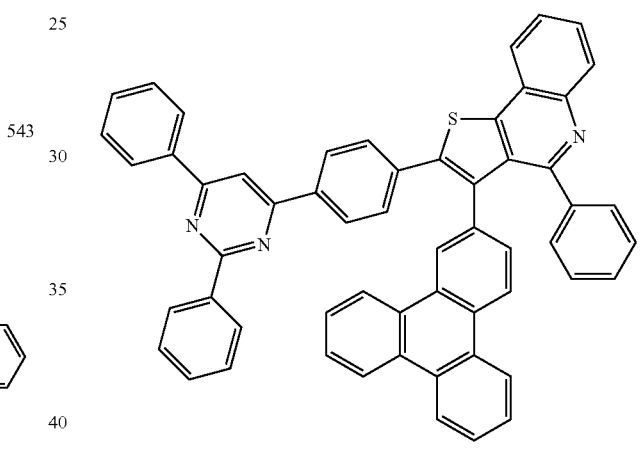
547
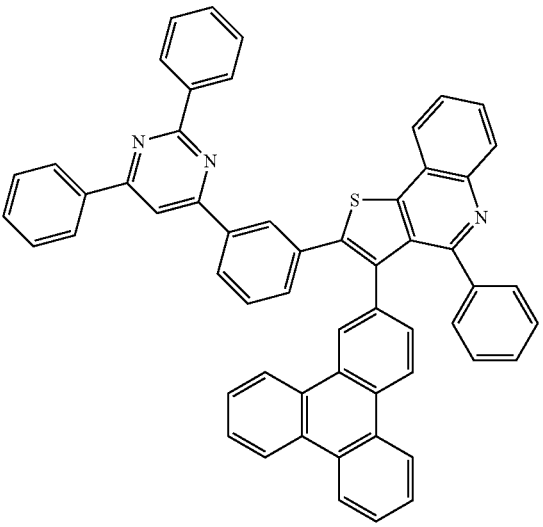

548
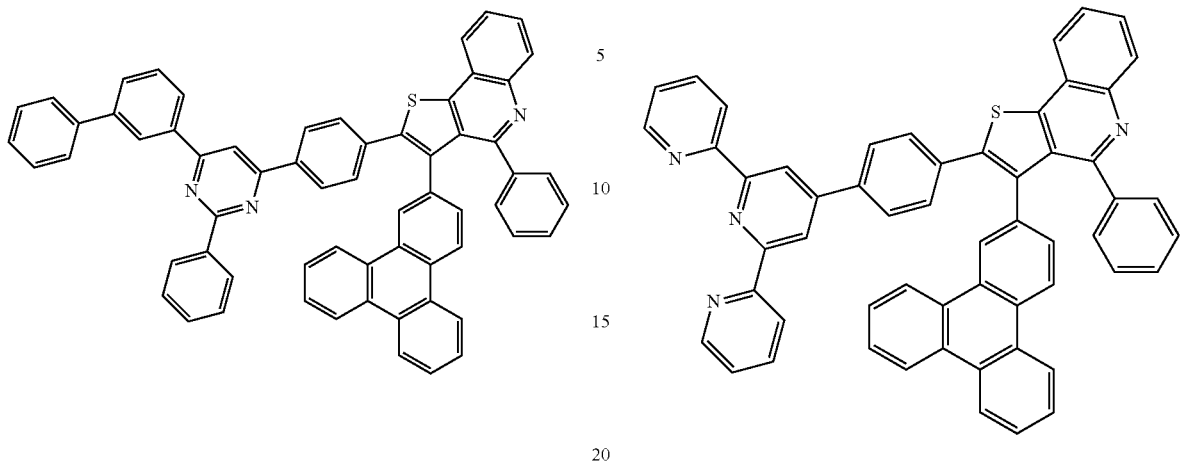
549
550
551
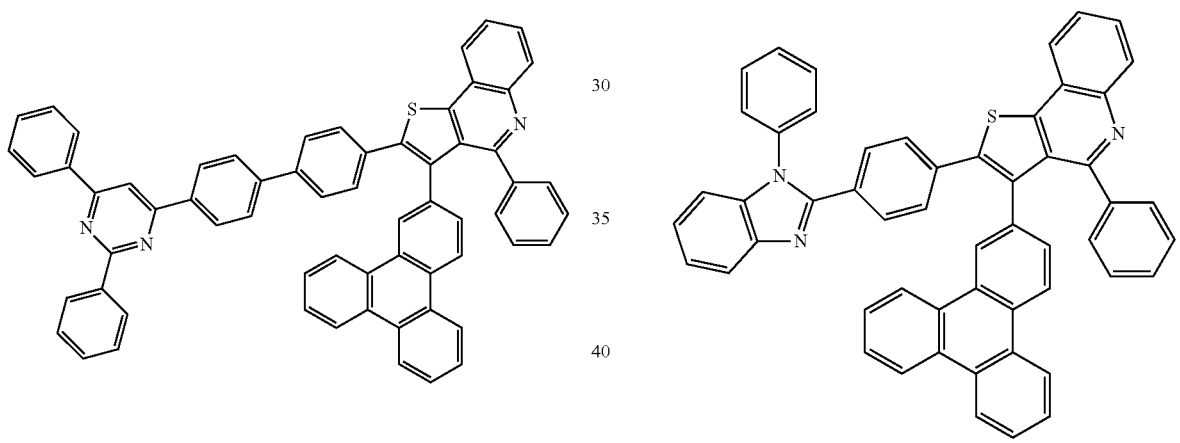
552
553
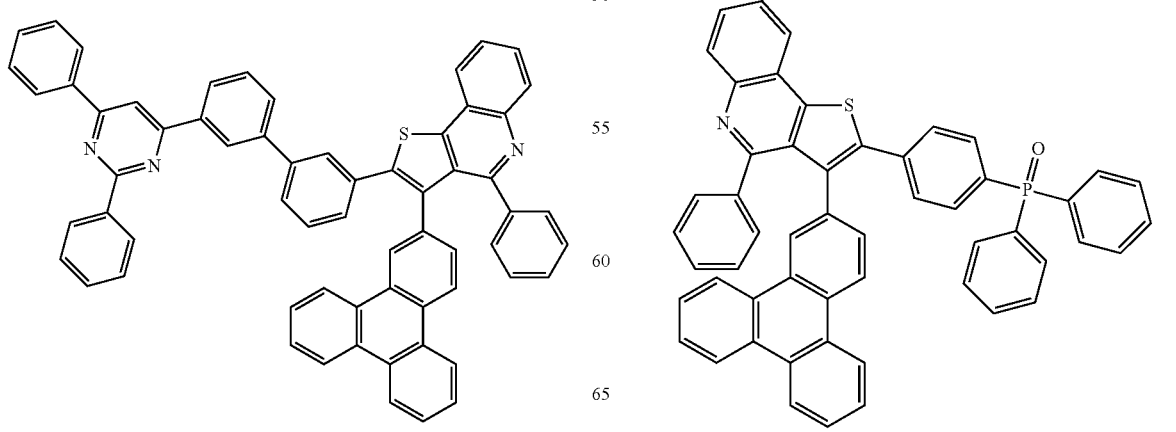

554
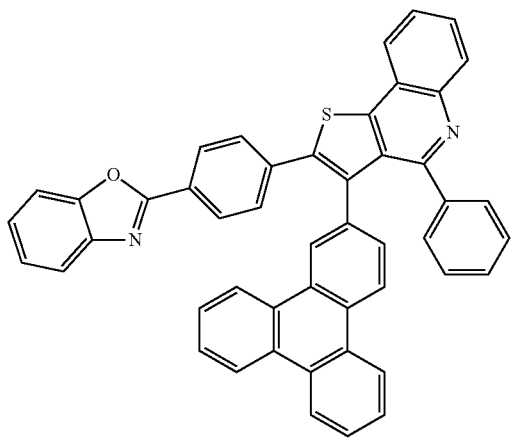
555
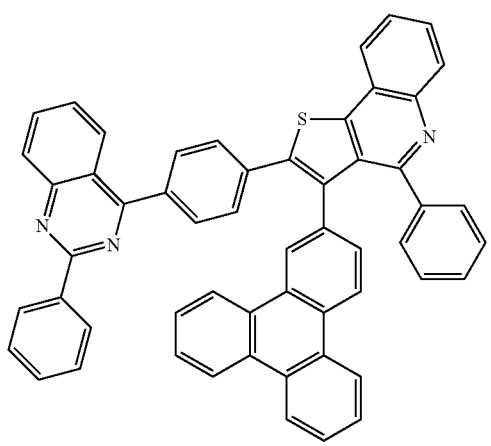
556
557
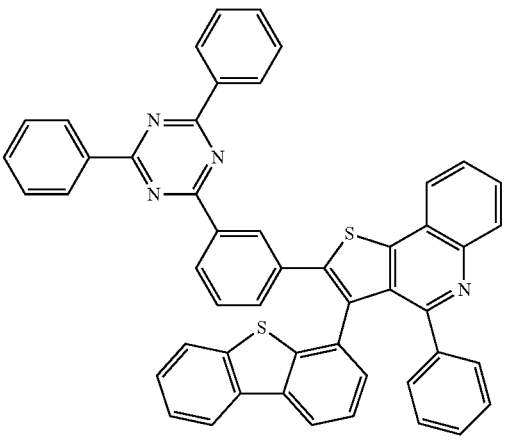
558
559
560
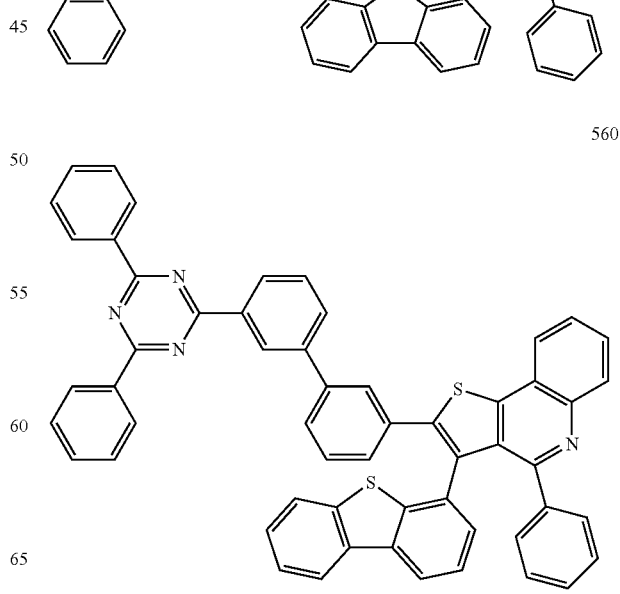

-continued
561
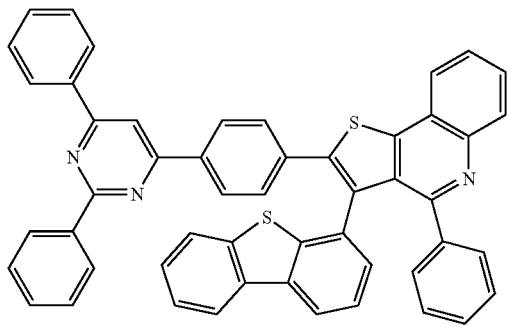
562
563
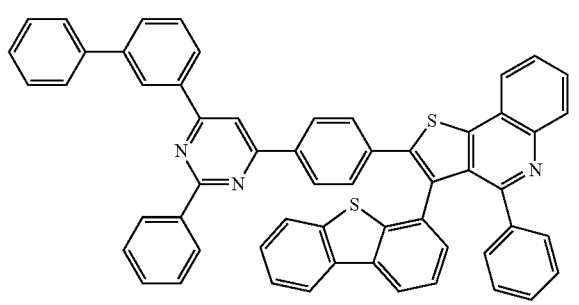
564
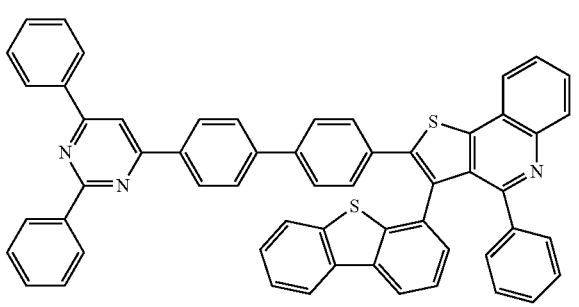
-continued
565
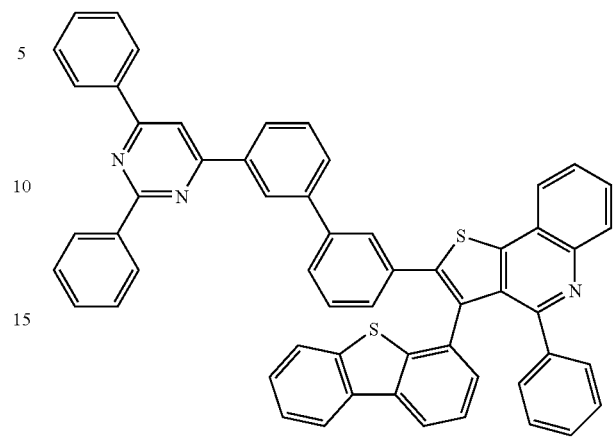
566
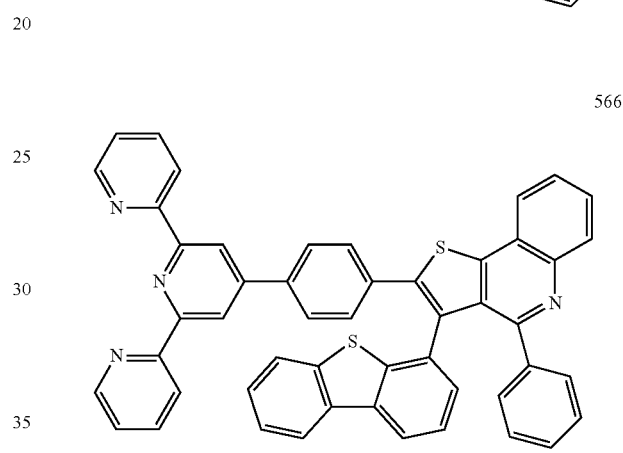
567
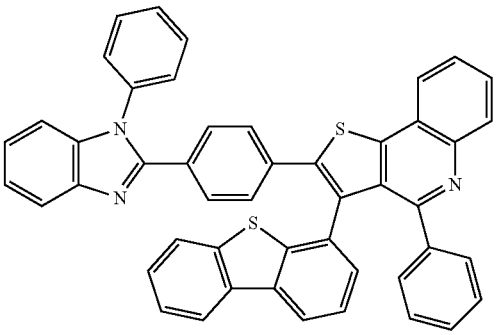
568
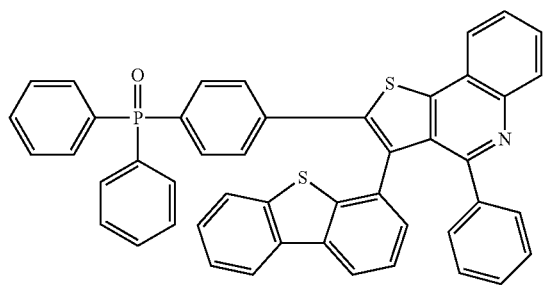

-continued
569
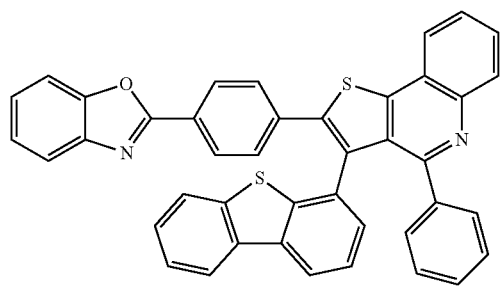
570
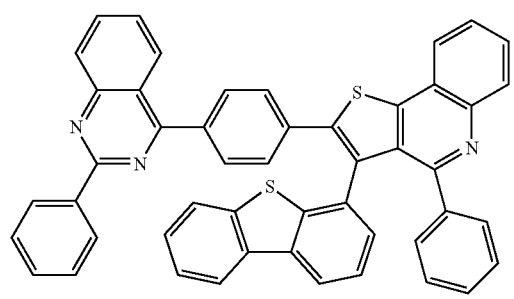
571
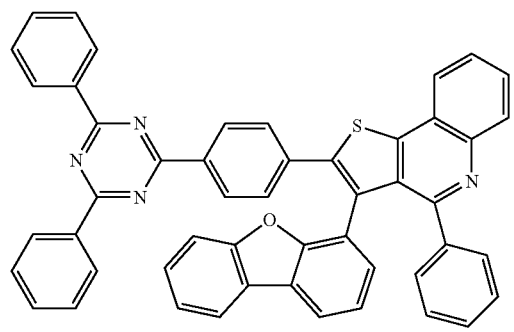
572
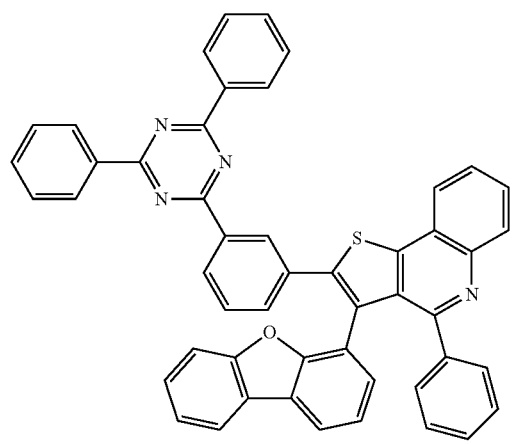
-continued
573
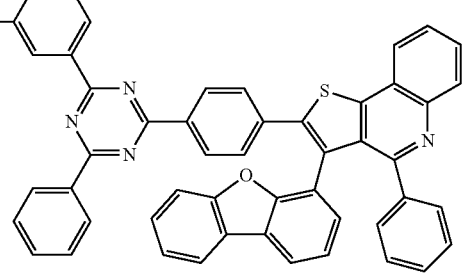
574
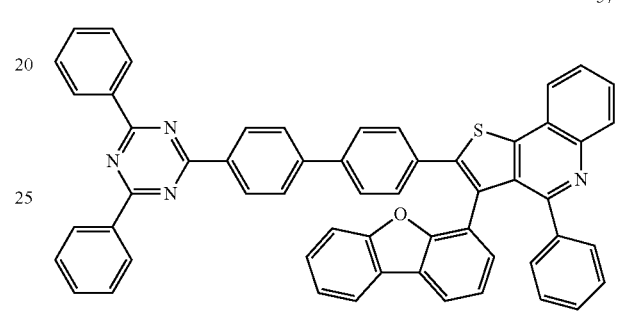
575
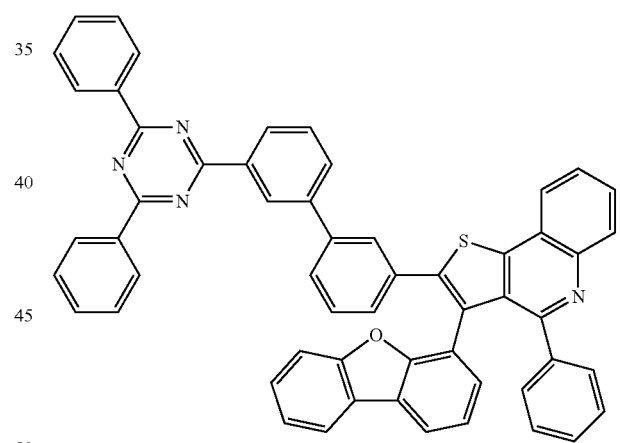
576
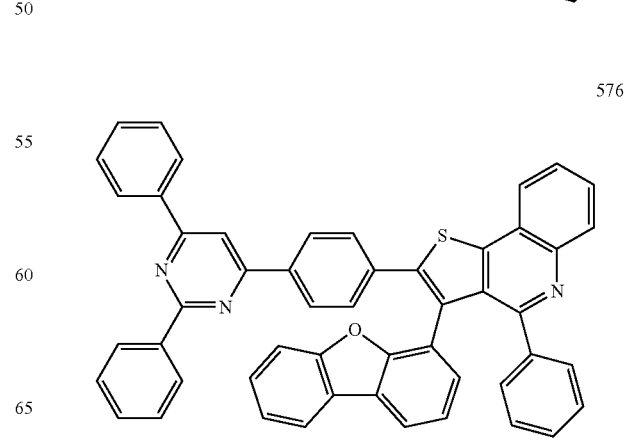

577
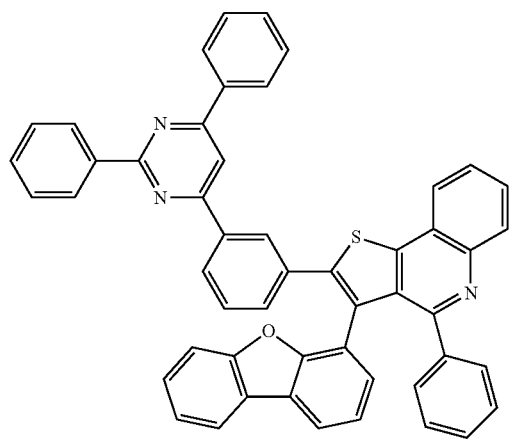
578
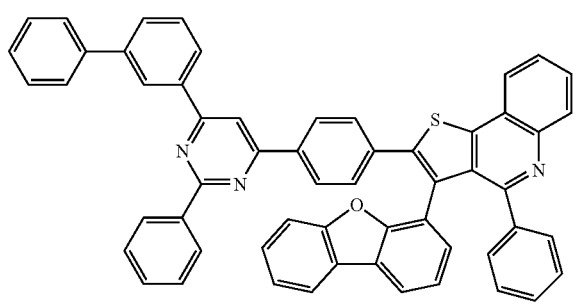
579
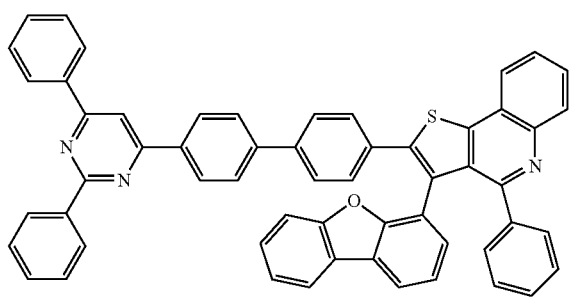
580
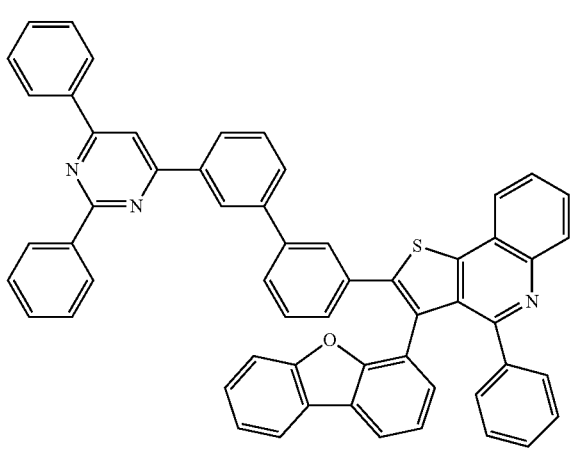
581
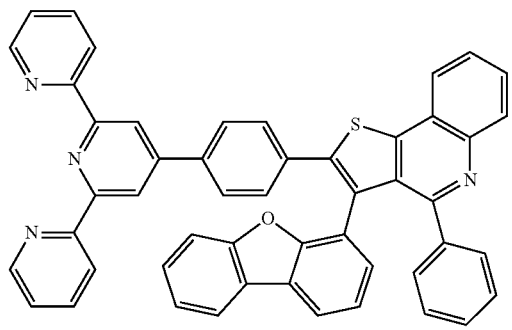
582
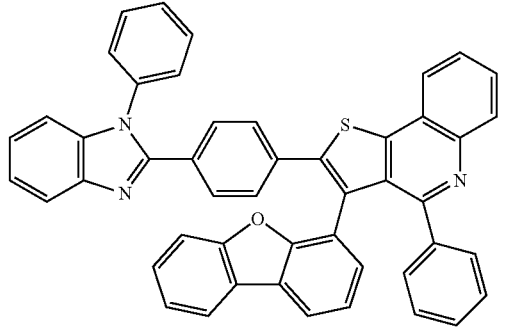
583
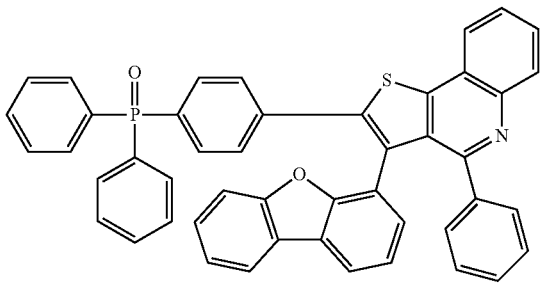
584
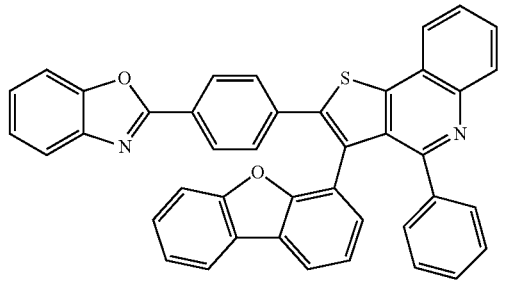
585
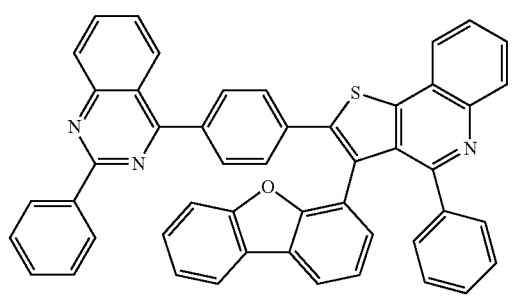

-continued
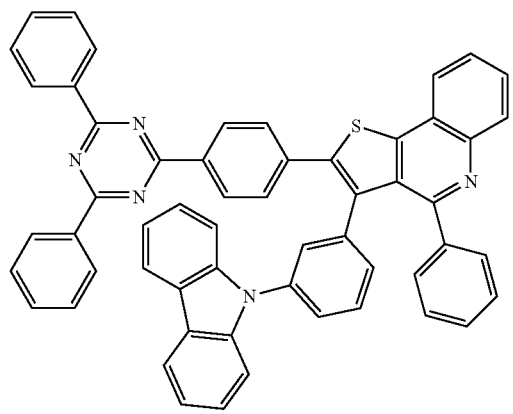
586
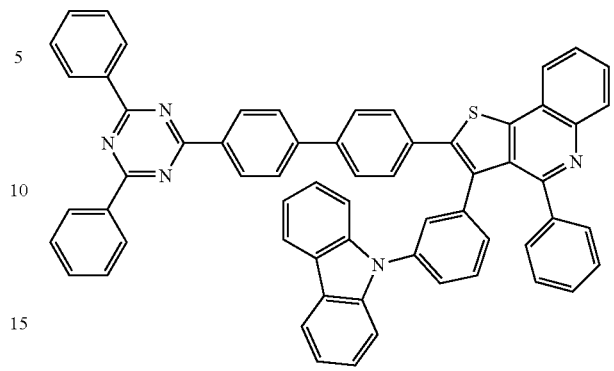
589
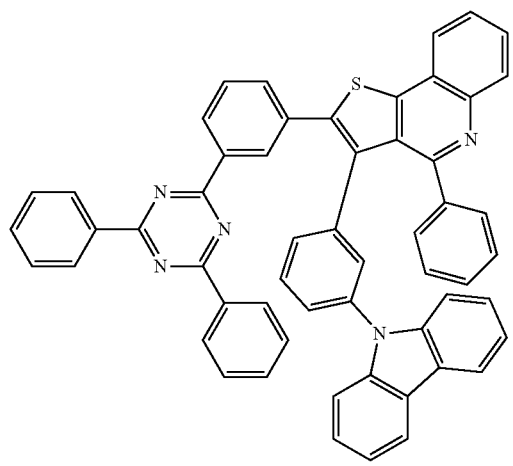
587
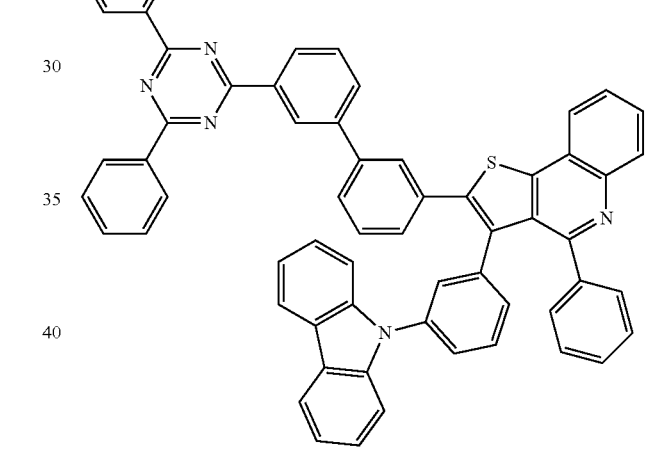
590
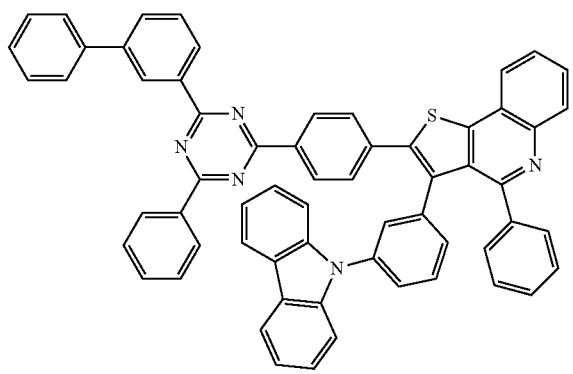
588
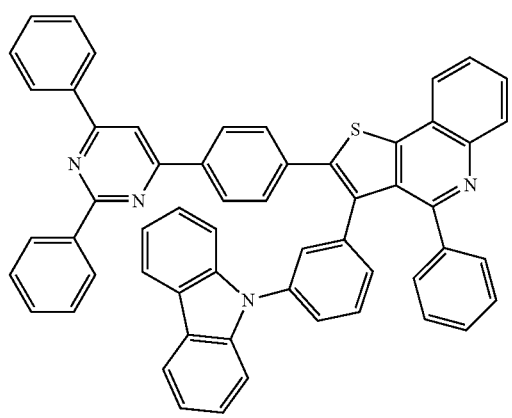
591

249
-continued
592
593
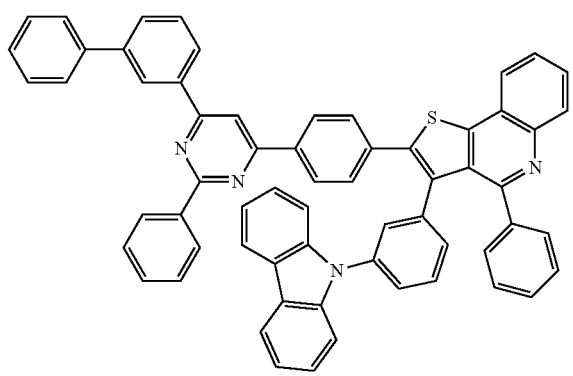
594
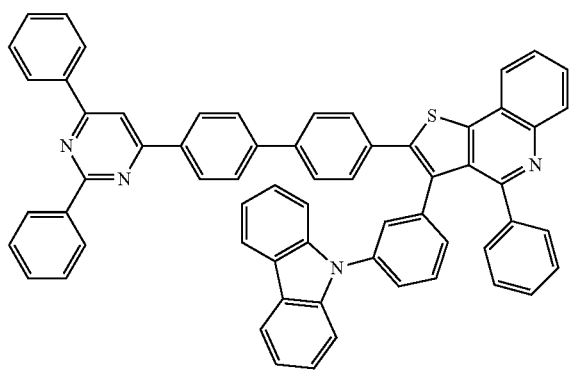
250
-continued
595
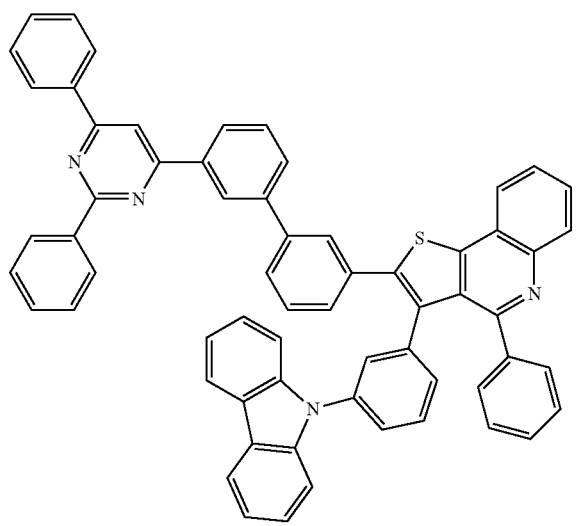
596
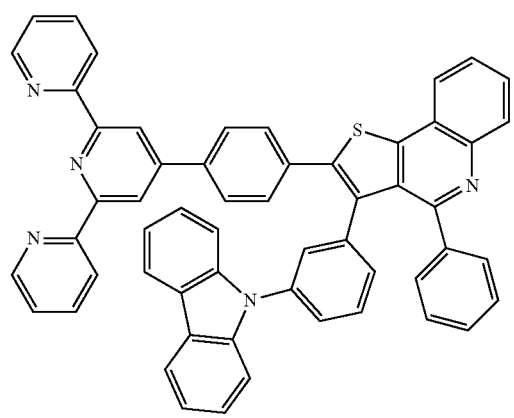
597
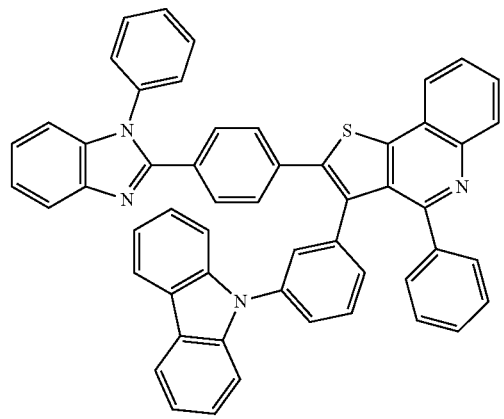

251
-continued
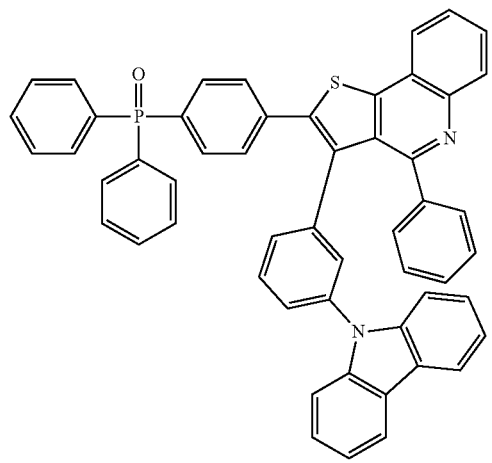
598
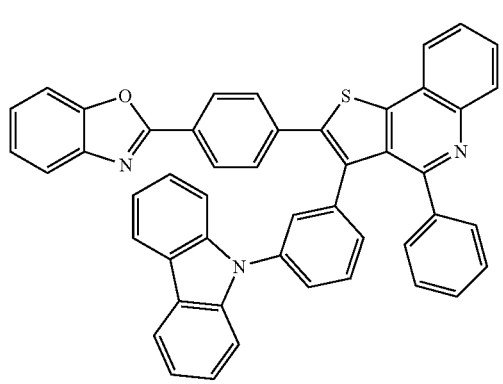
599
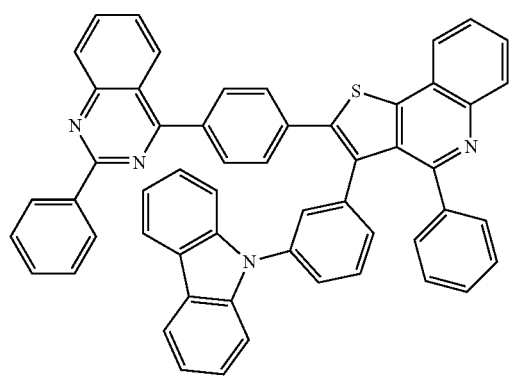
600
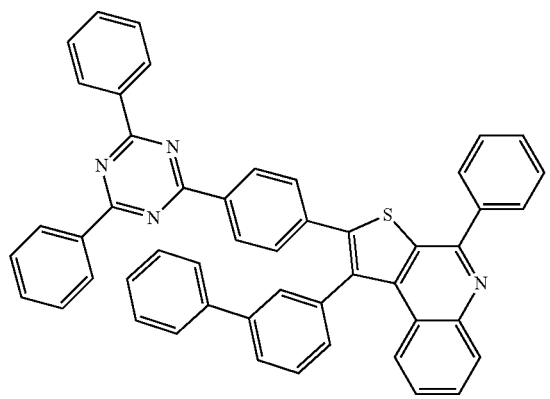
601
252
-continued
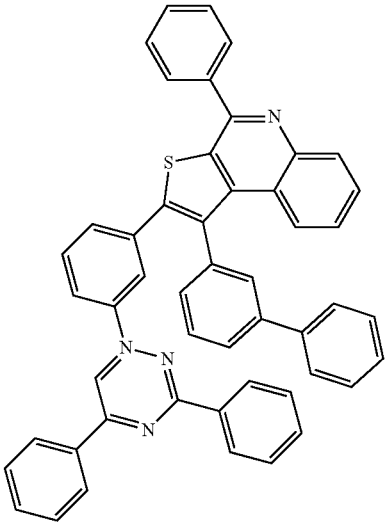
602
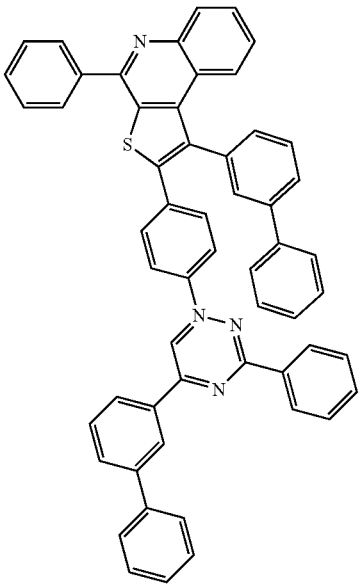
603

-continued
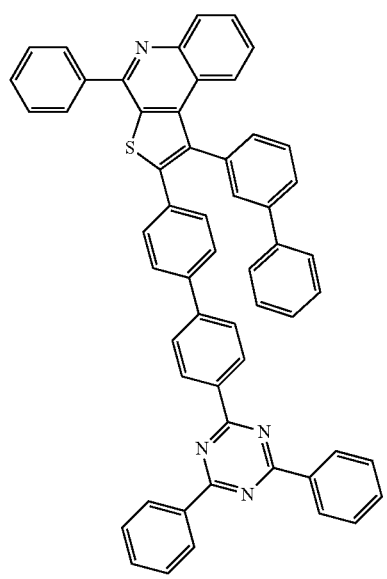
604
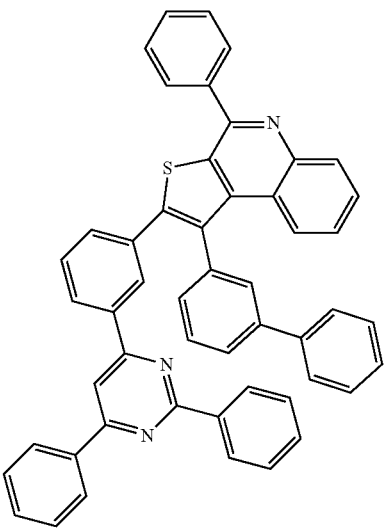
607
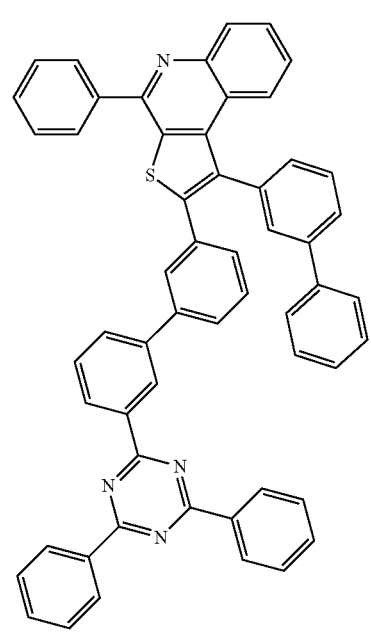
605
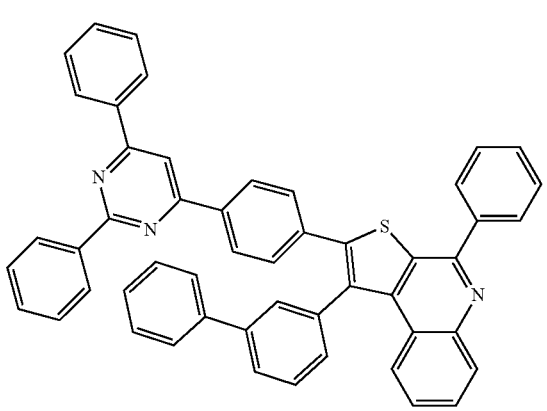
606
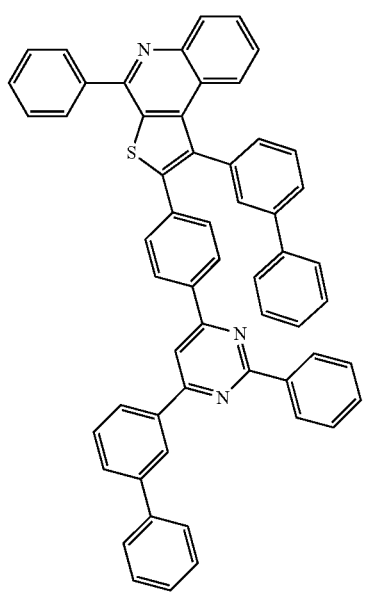
608

609
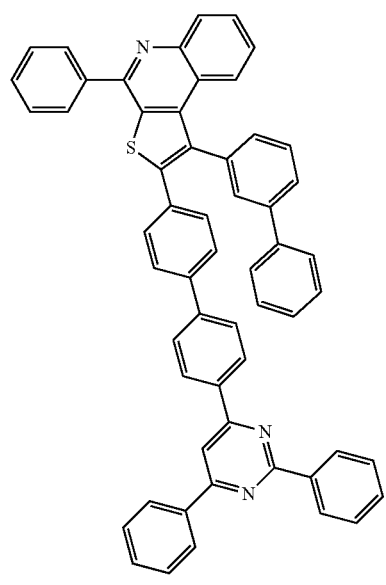
610
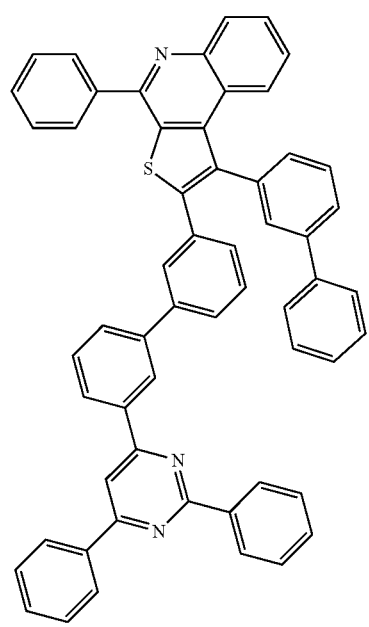
611
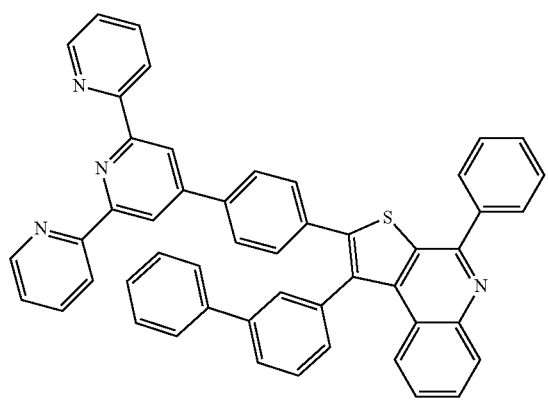
612
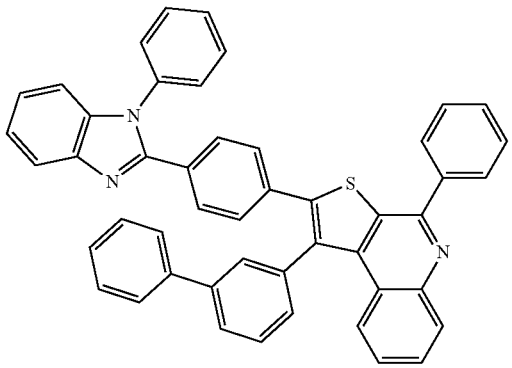
613
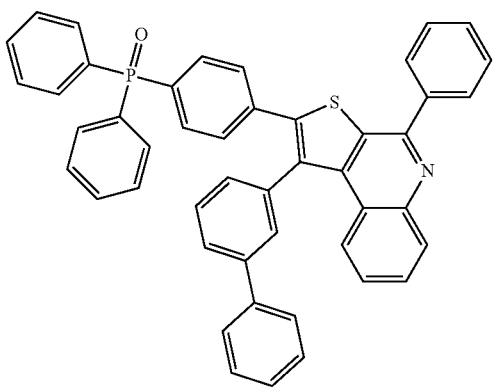
614
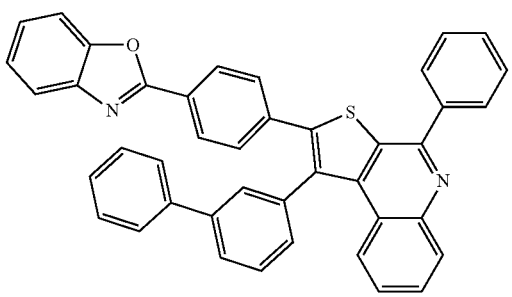
615
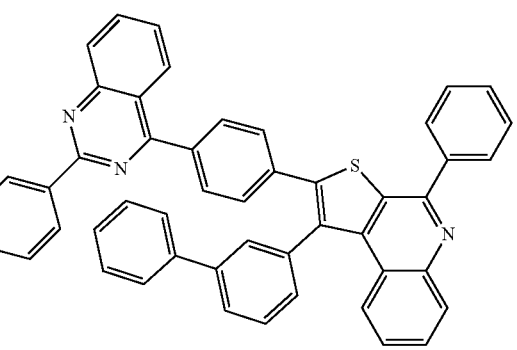

616
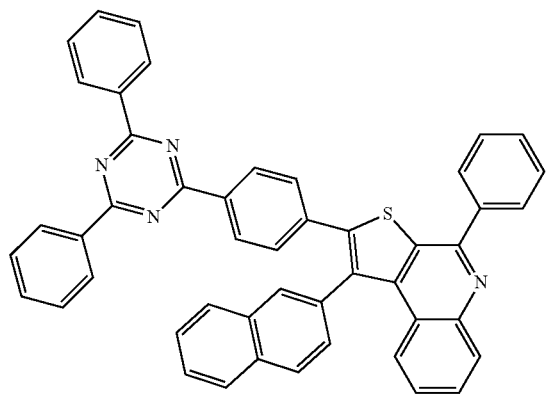
617
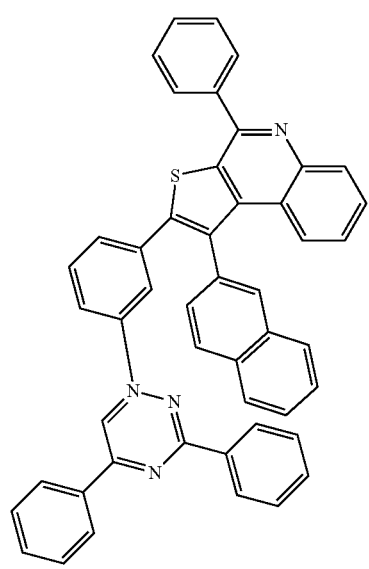
618
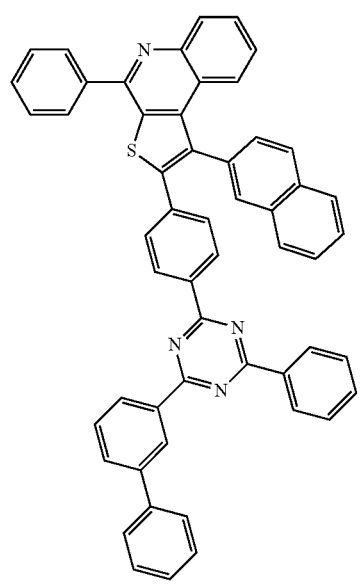
619
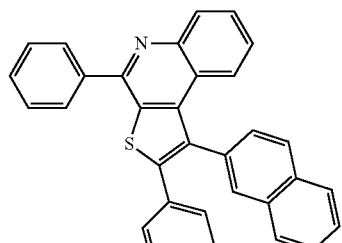
620
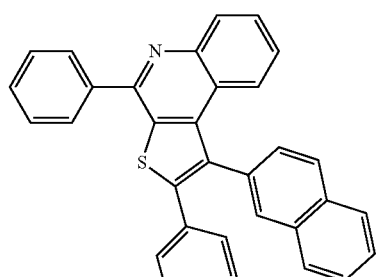
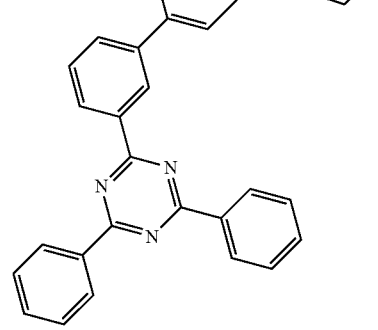
621
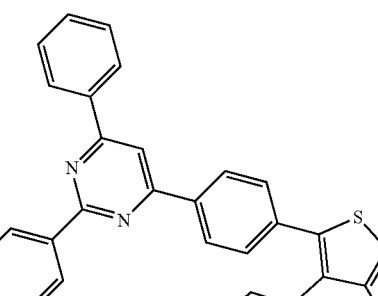
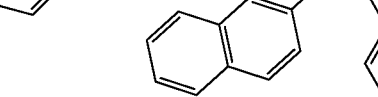

622
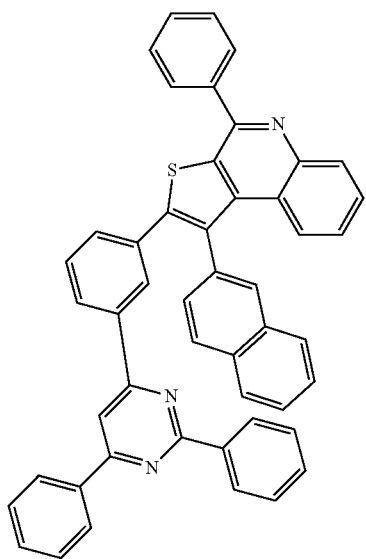
623
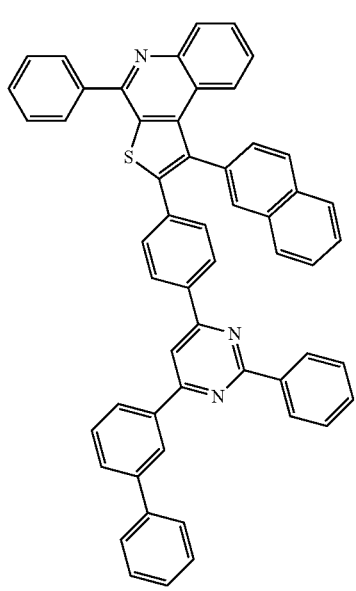
624
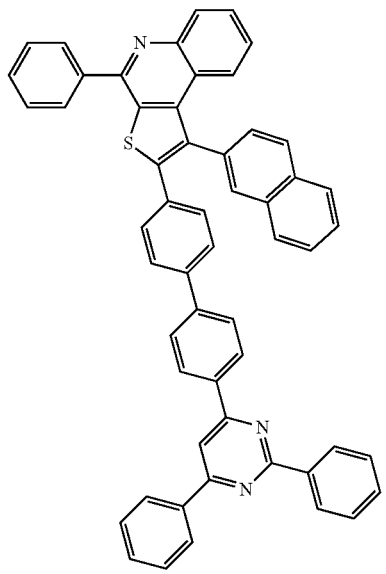
625
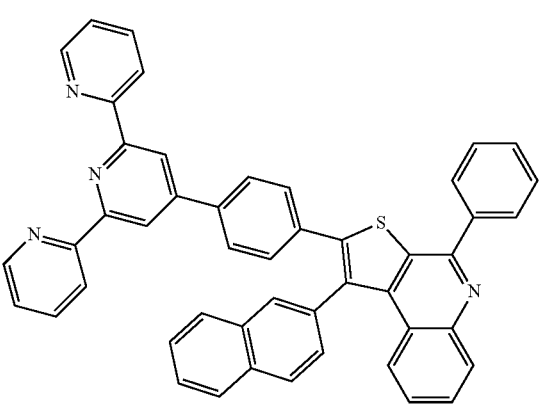
626

627
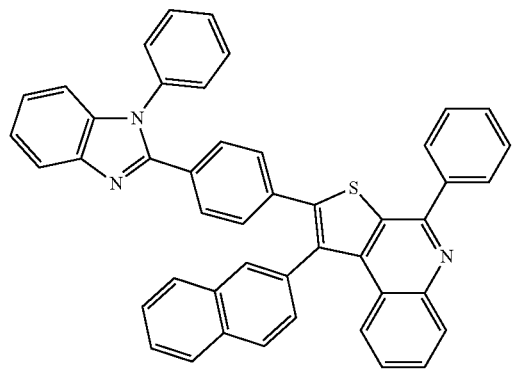
628
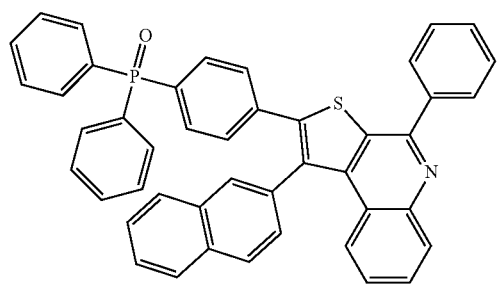
629
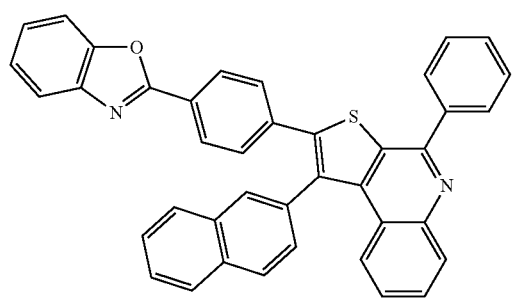
630
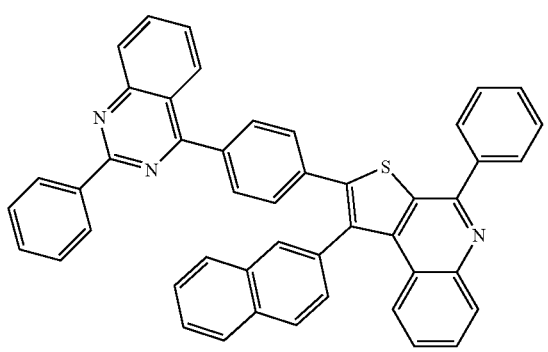
631
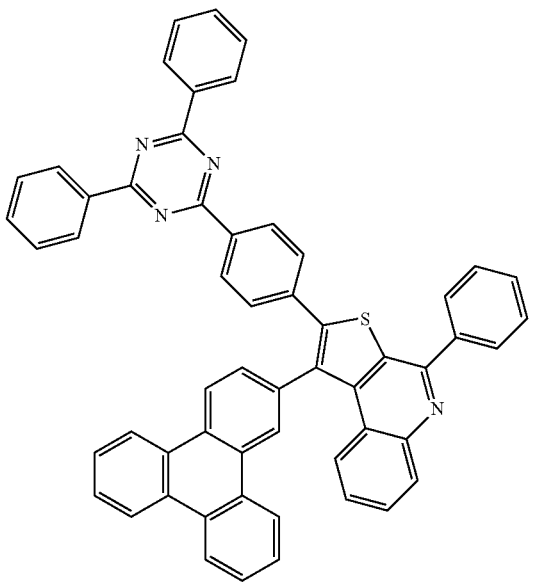
632
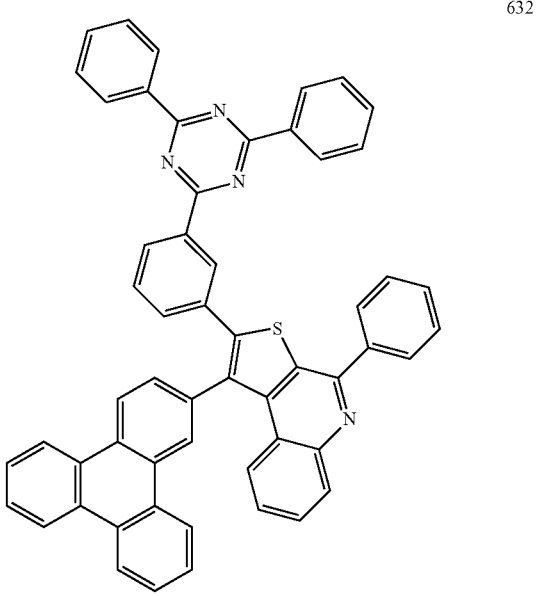

263
-continued
633
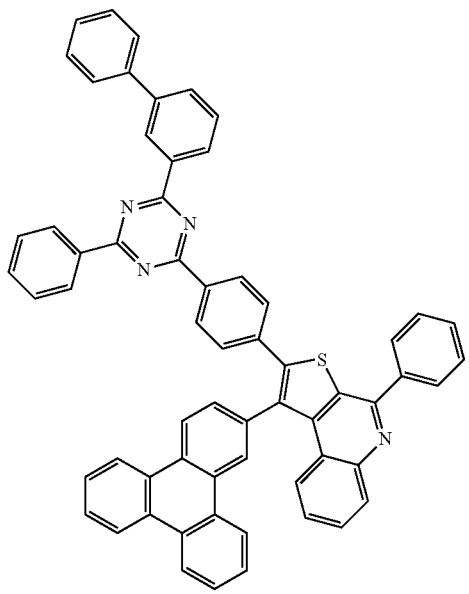
634
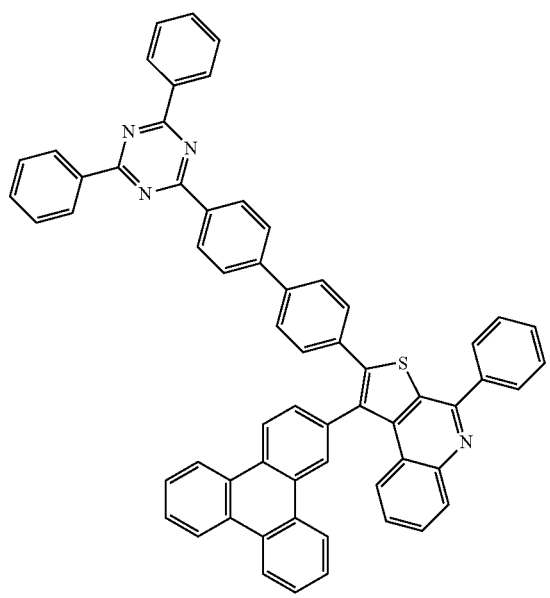
264
-continued
635
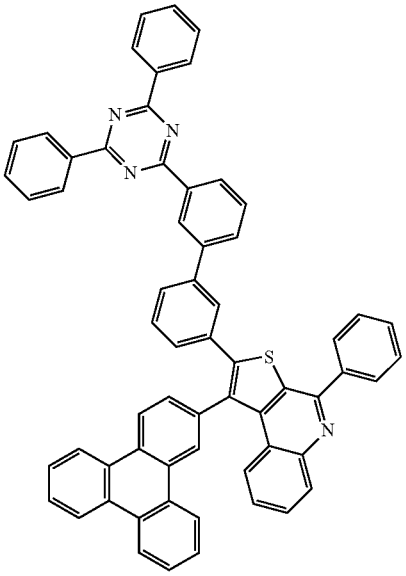
636
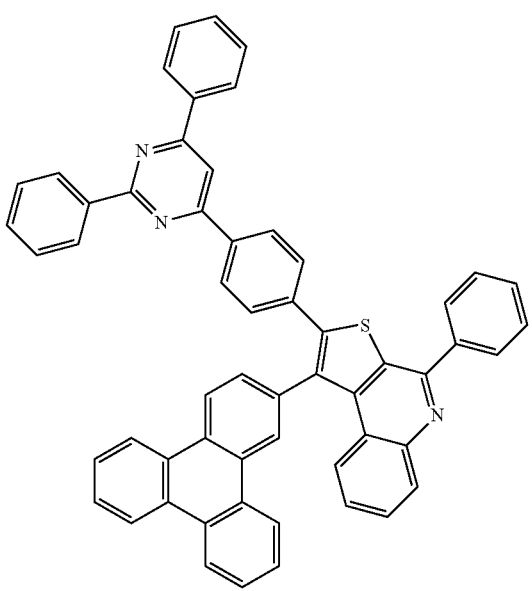

637
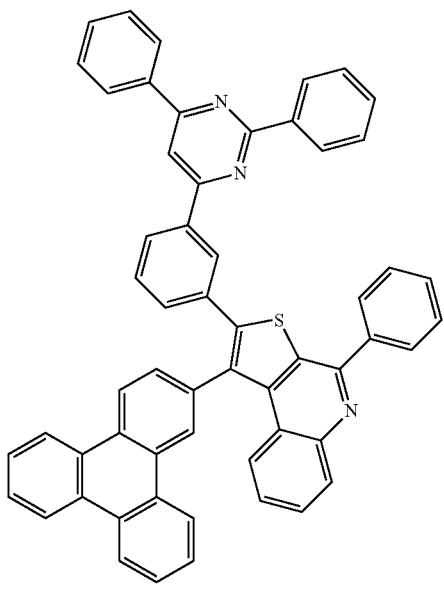
639
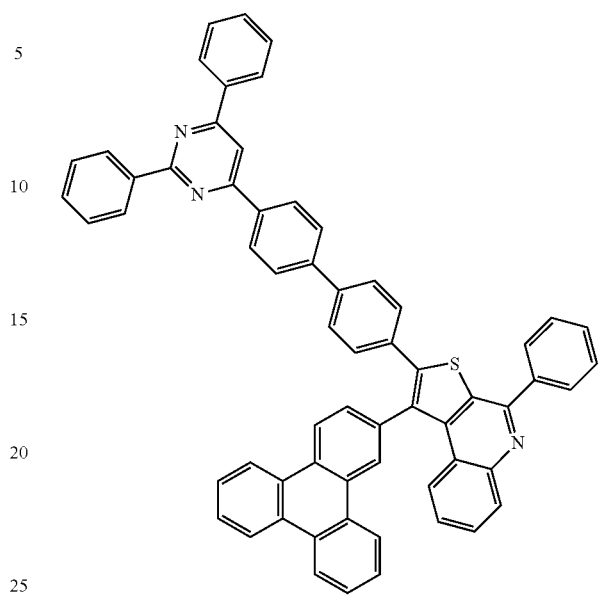
638
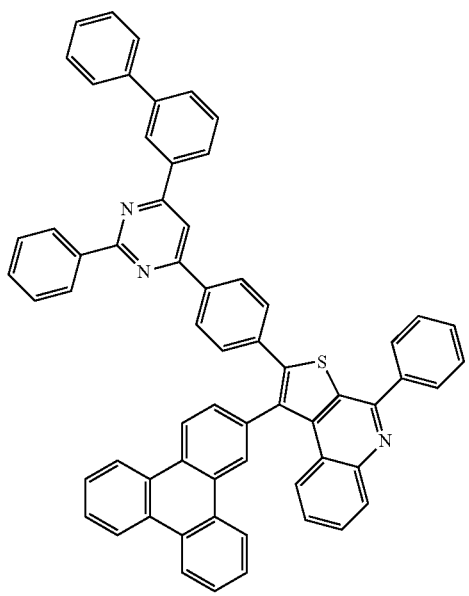
640
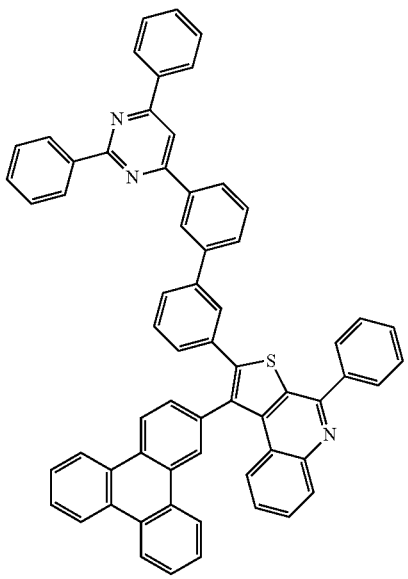

641
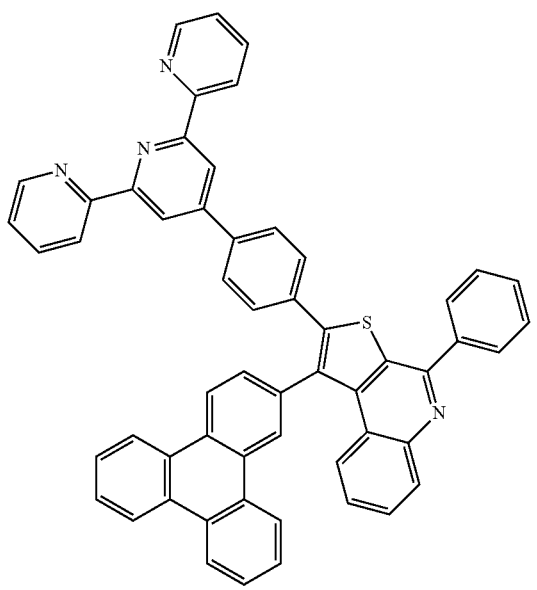
642
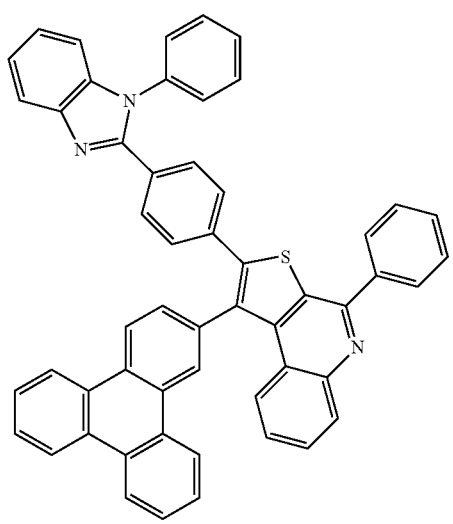
643
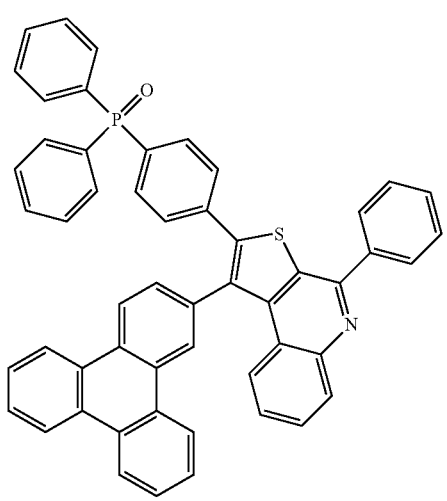
644
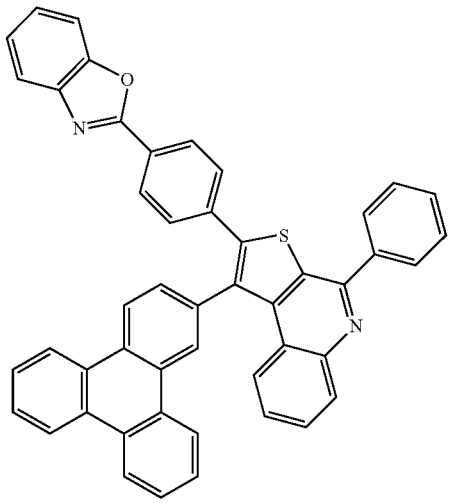
645
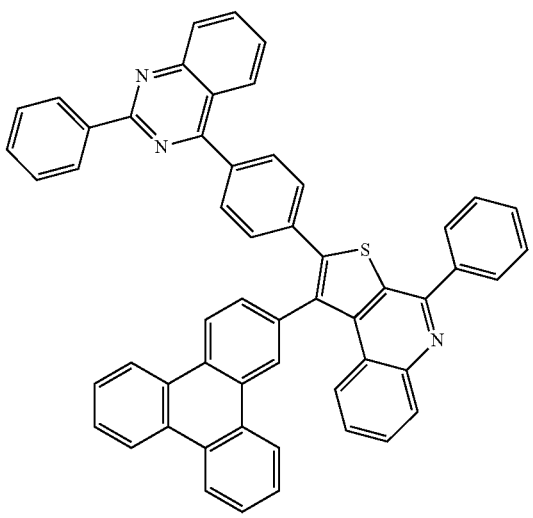
646
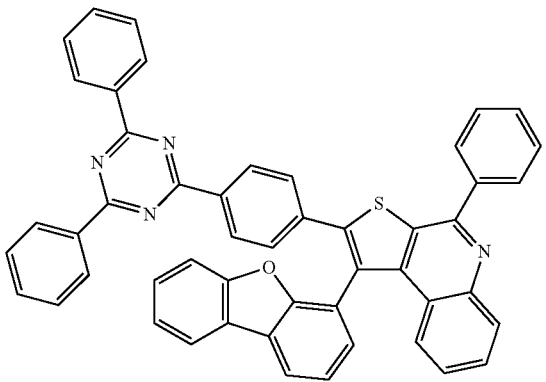

647
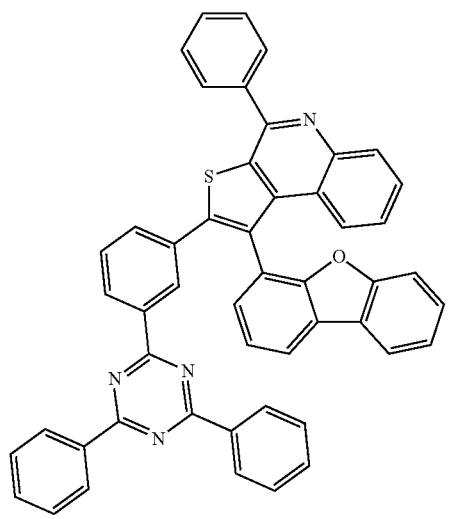
650
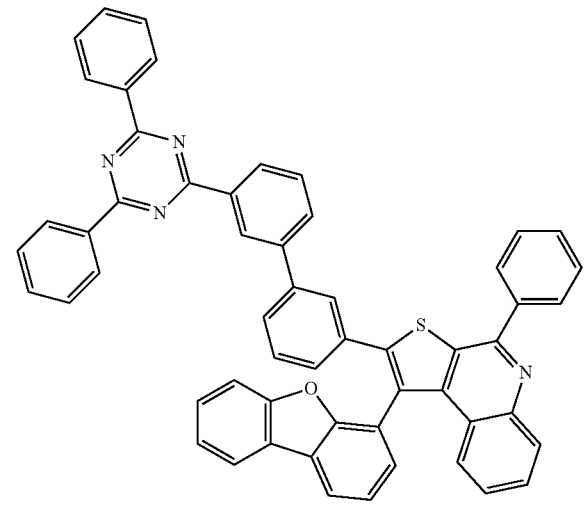
648
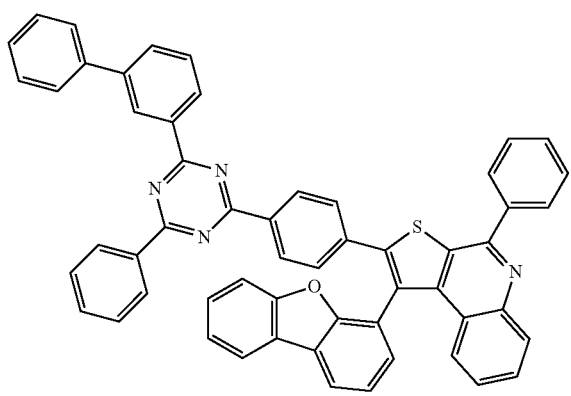
651
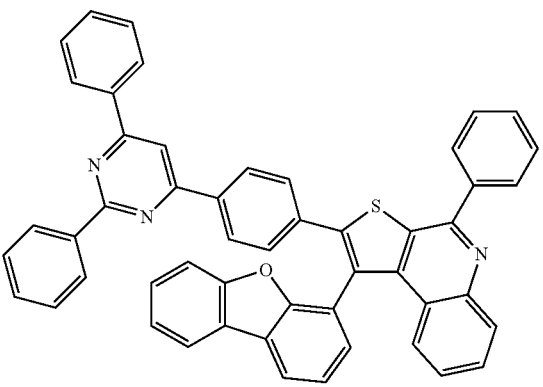
649
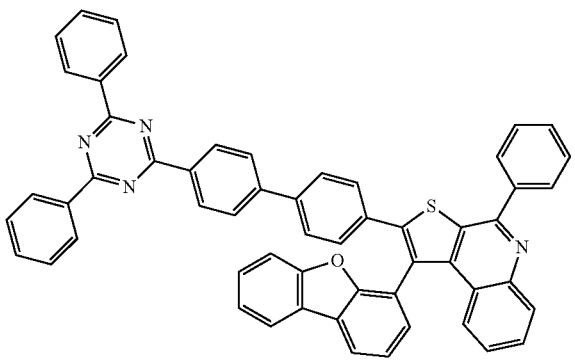
652
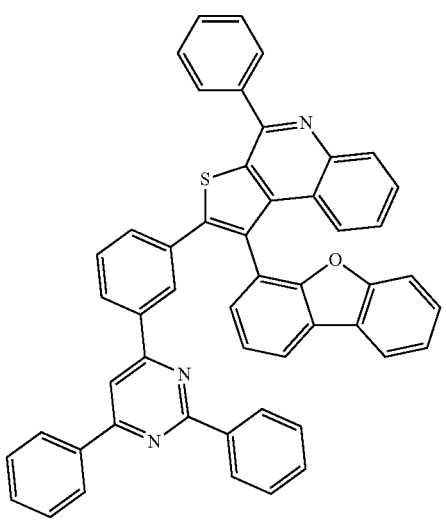

-continued
653
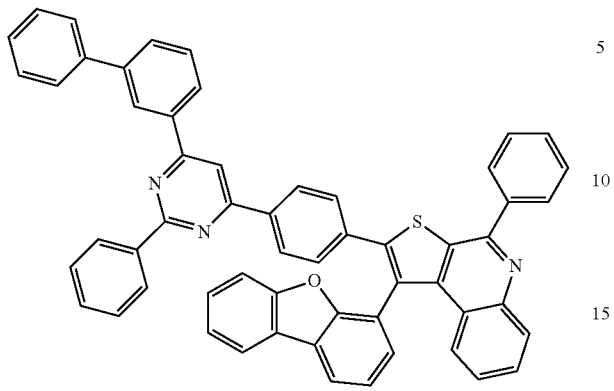
654
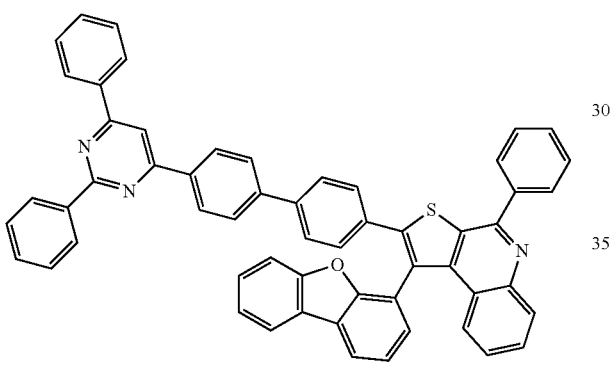
655
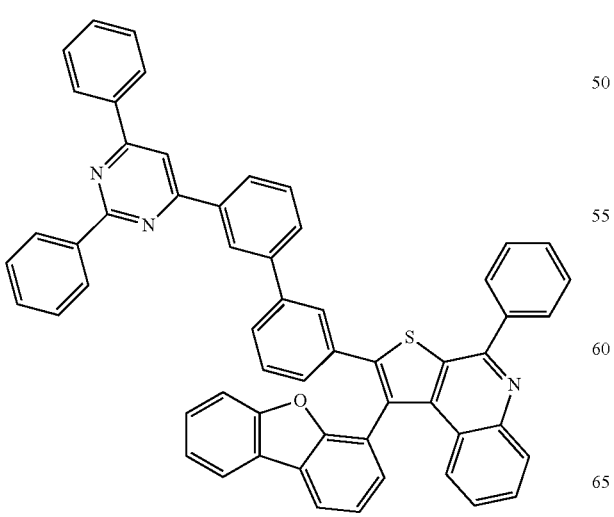
-continued
656
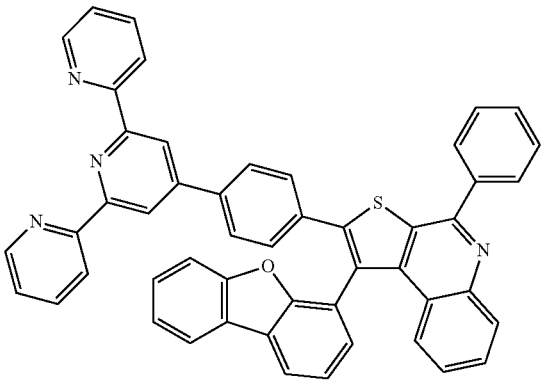
657
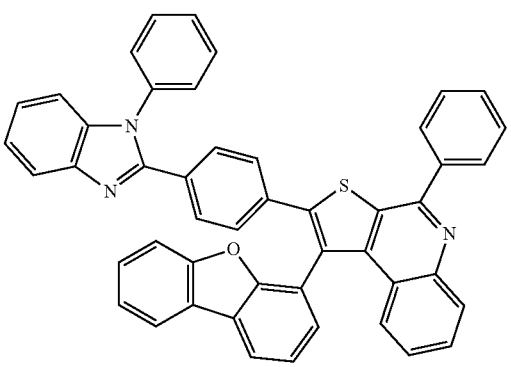
658
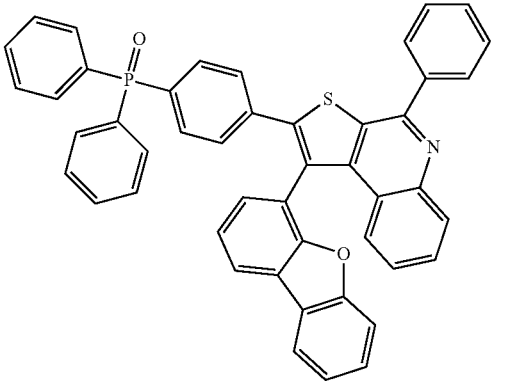
659
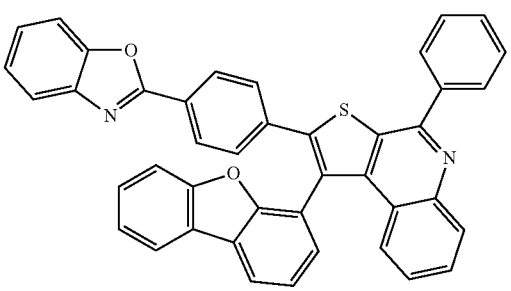

660
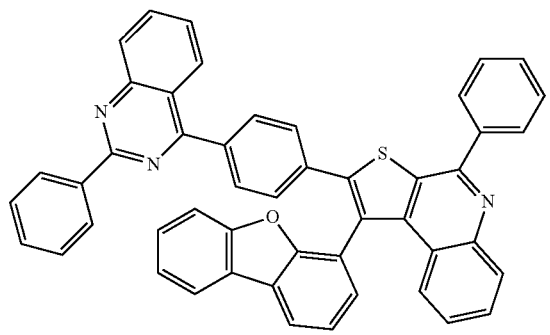
661
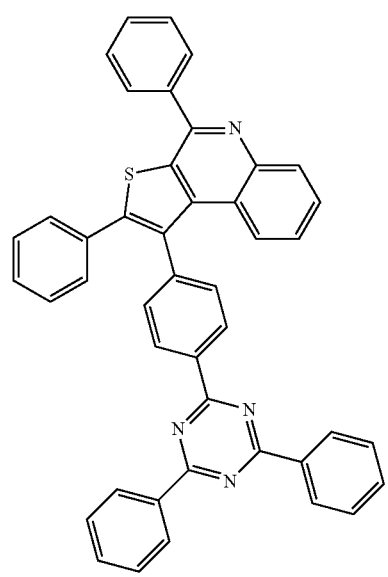
662
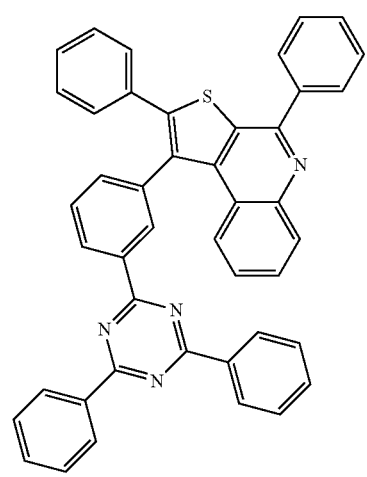
663
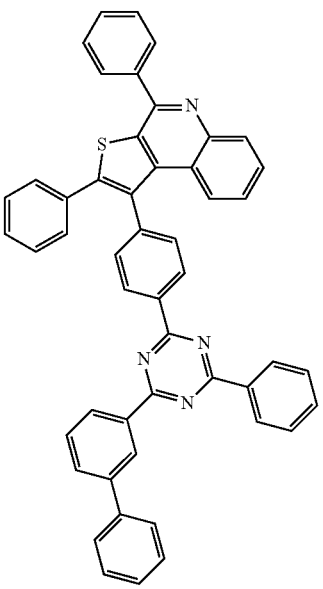
664
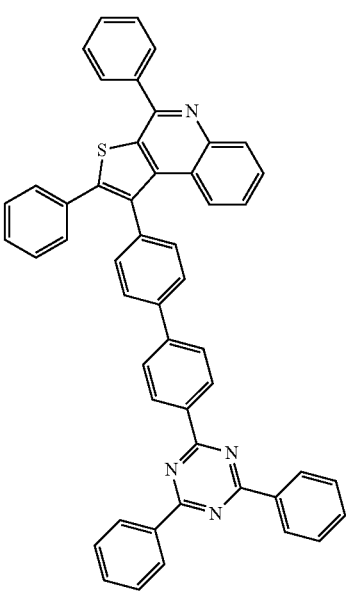

275
-continued
665
666
667
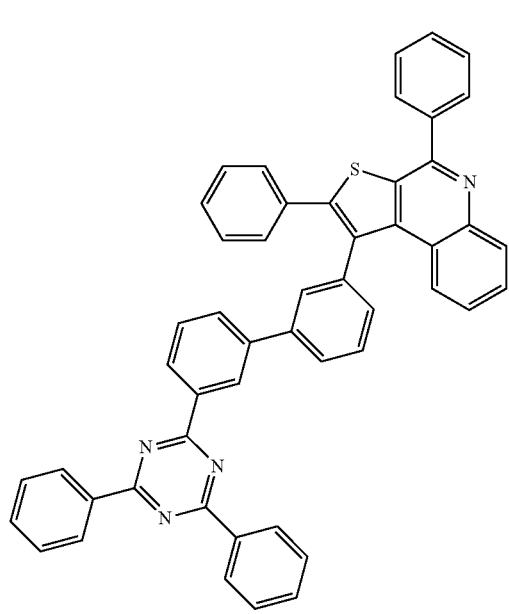
276
-continued
668
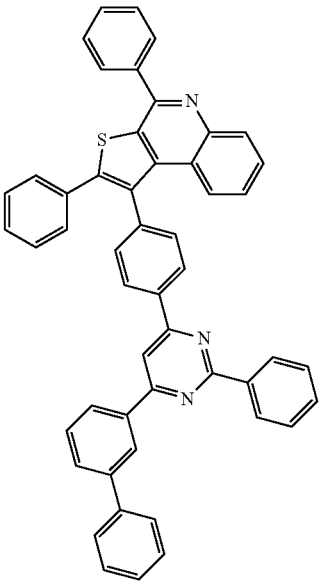
669
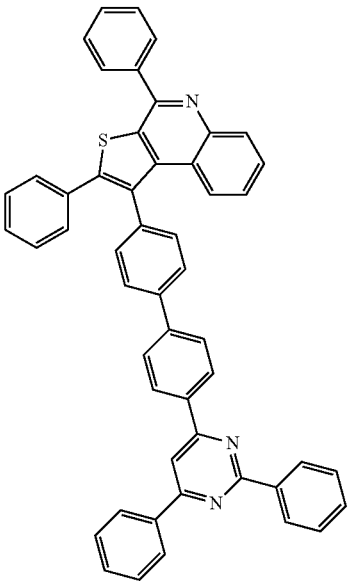

670
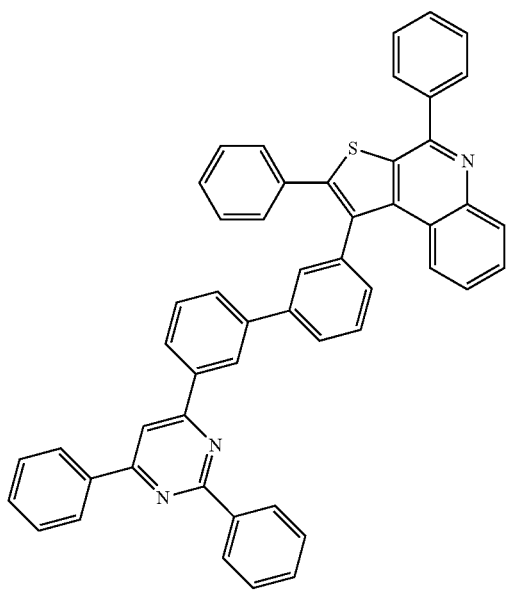
671
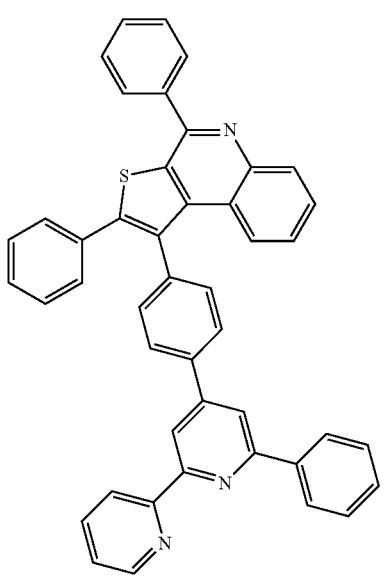
672
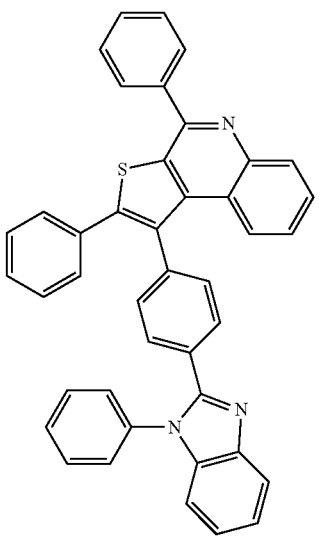
673
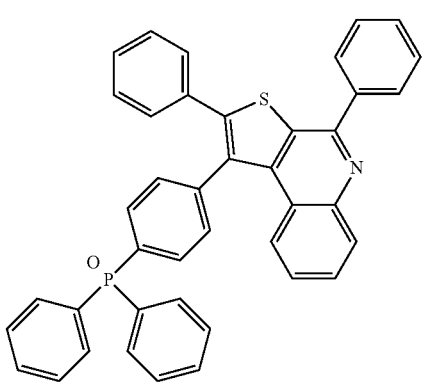
674
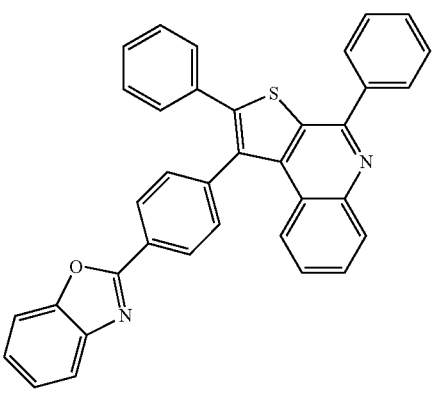

-continued
675
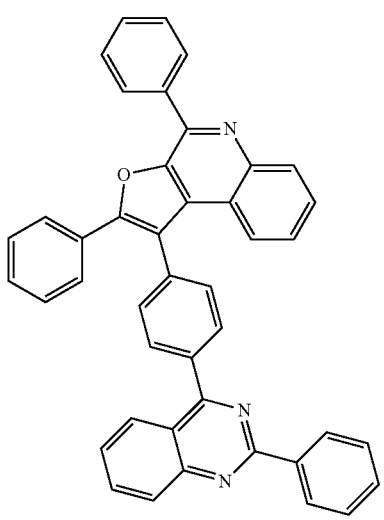
676
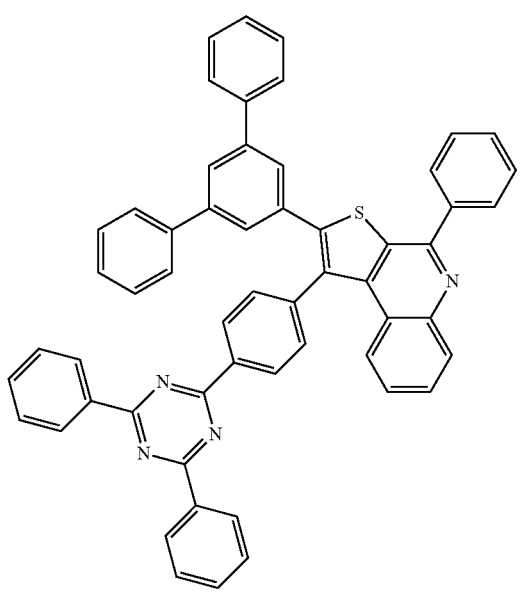
-continued
677
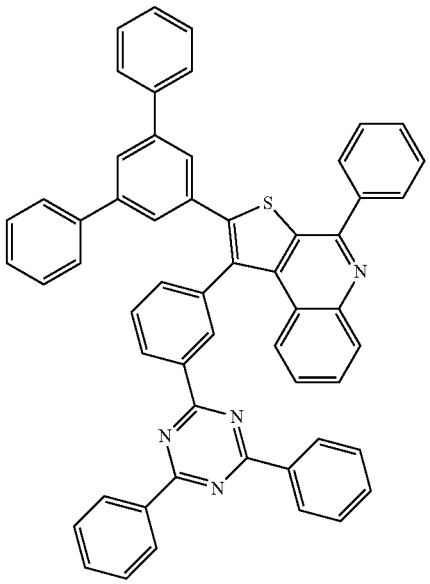
678
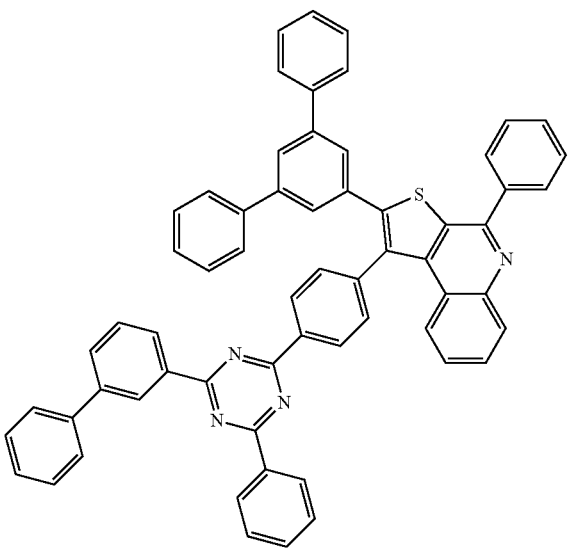

281
-continued
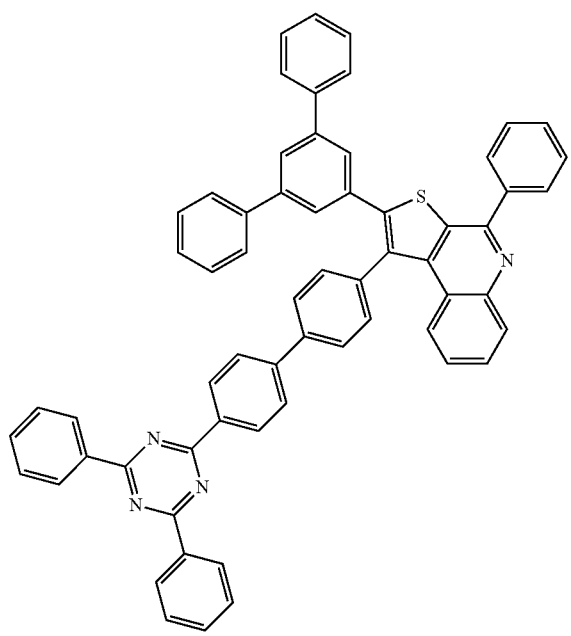
679
282
-continued
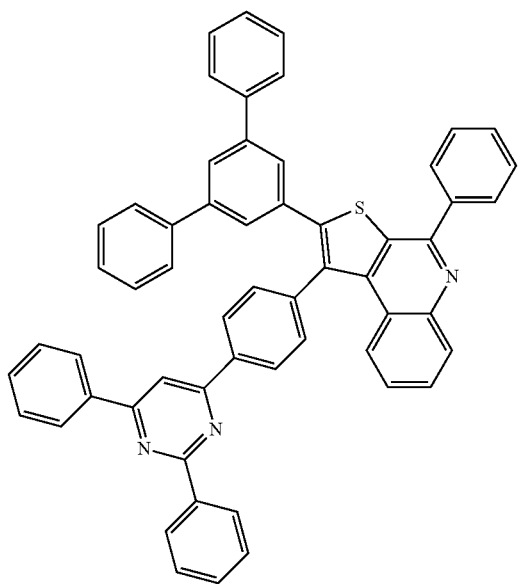
681
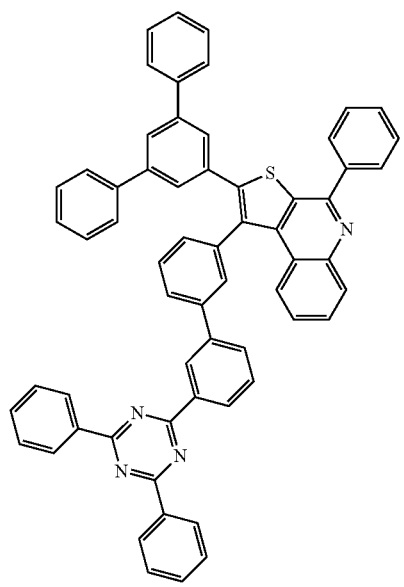
680
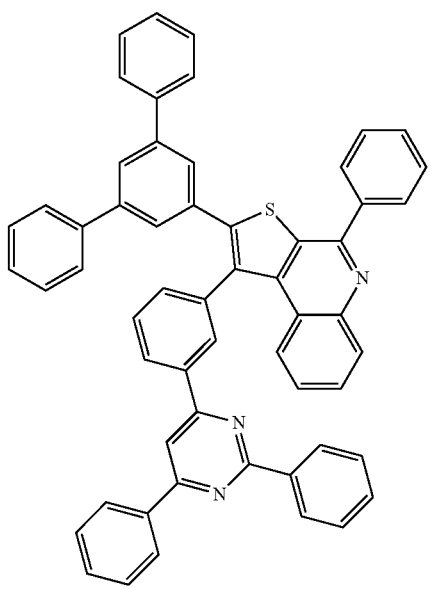
682

683
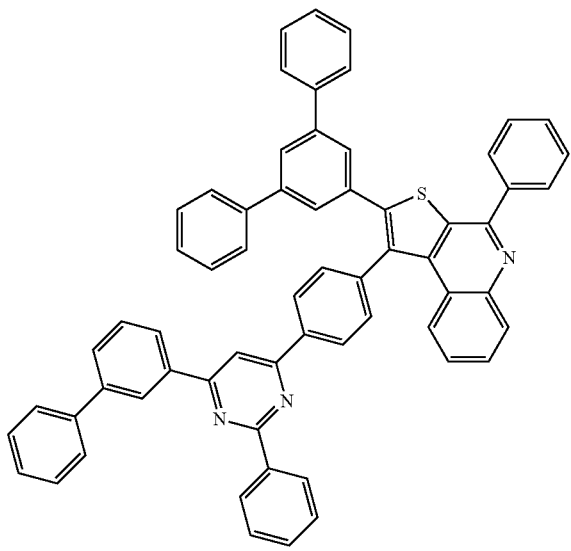
685
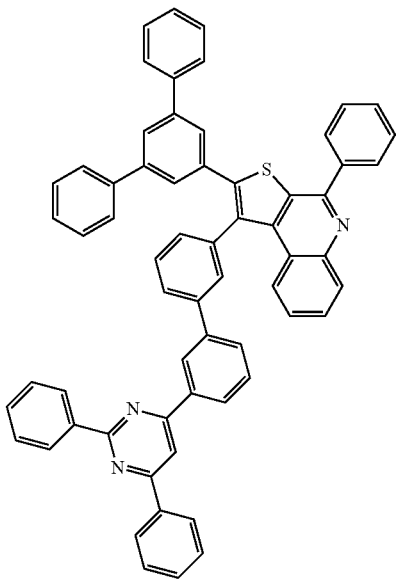
684
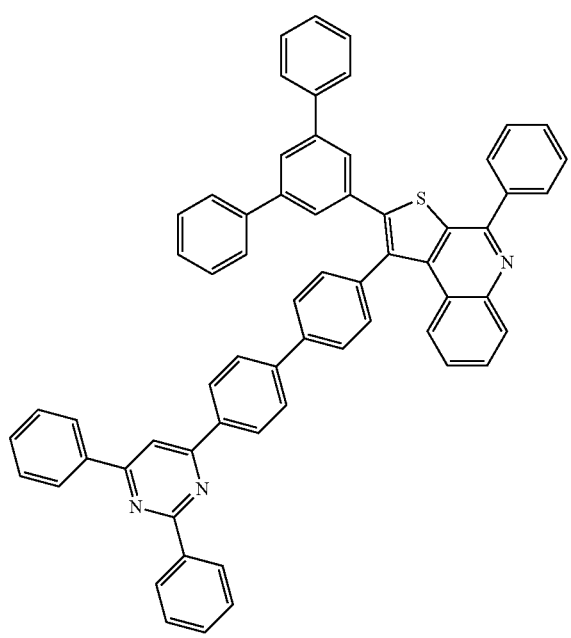
686
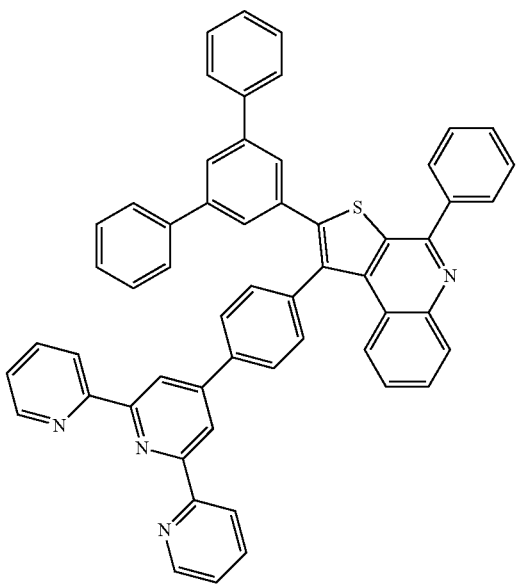

687
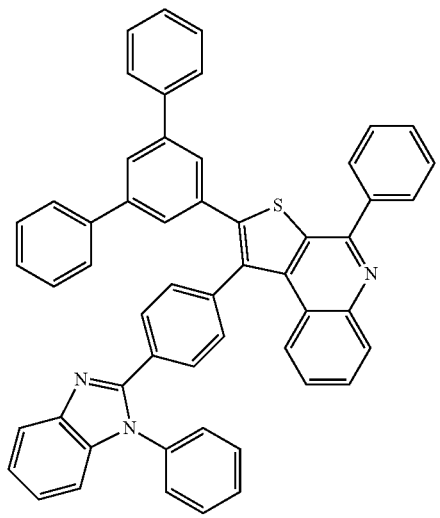
688
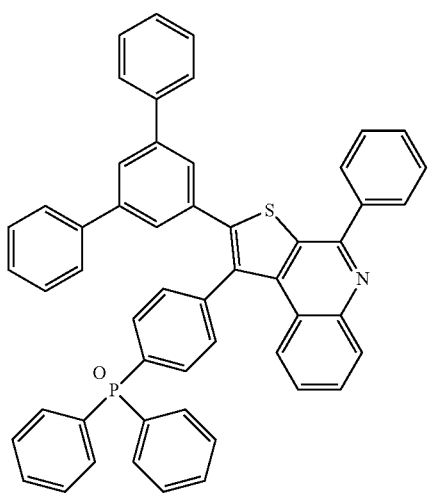
689
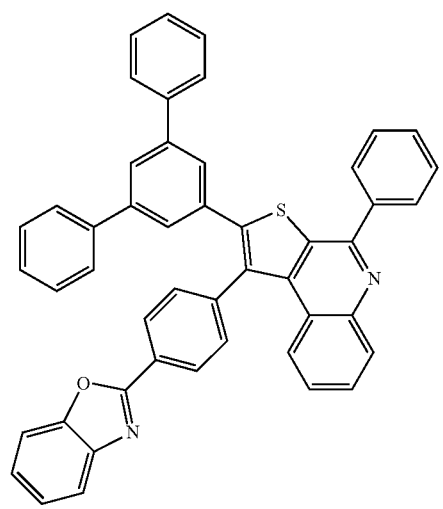
690
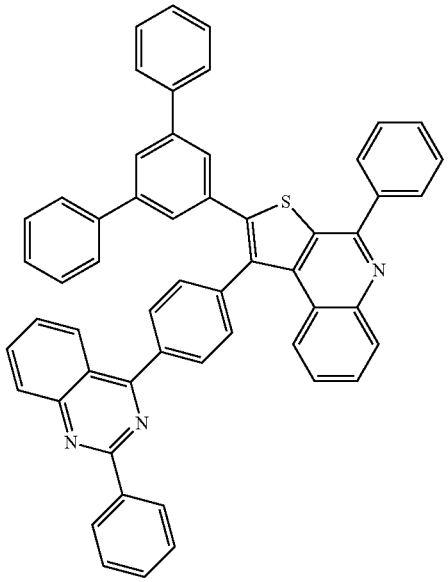
691
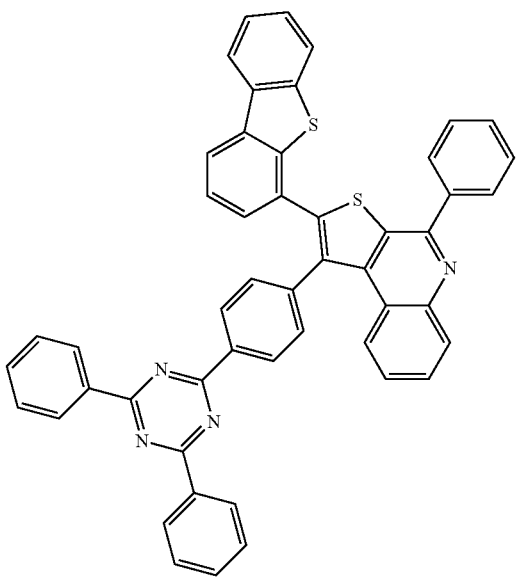

287
-continued
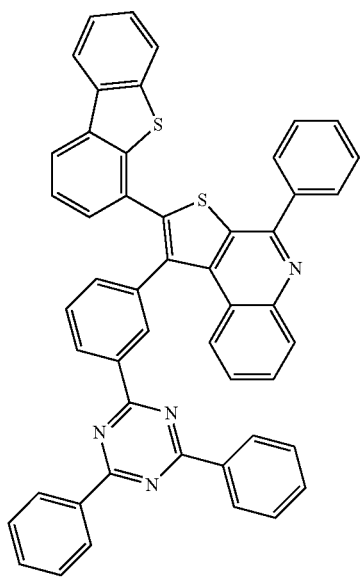
692
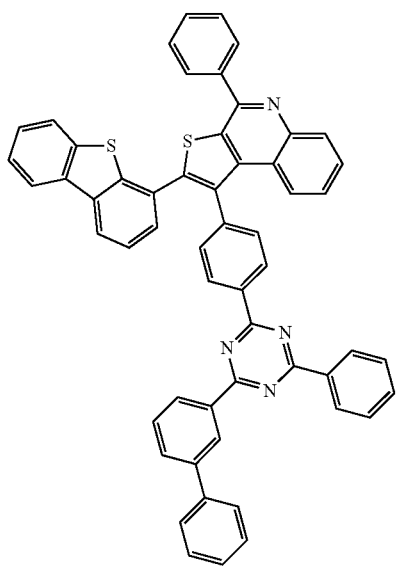
693
288
-continued
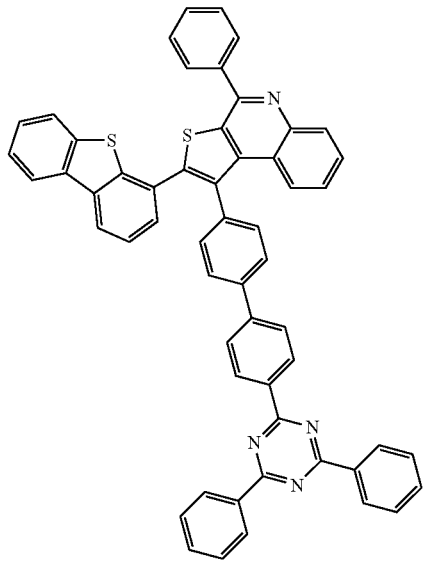
694
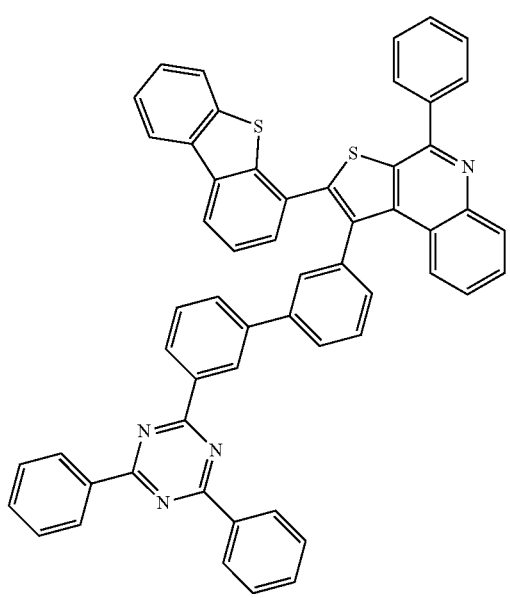
695

289
-continued
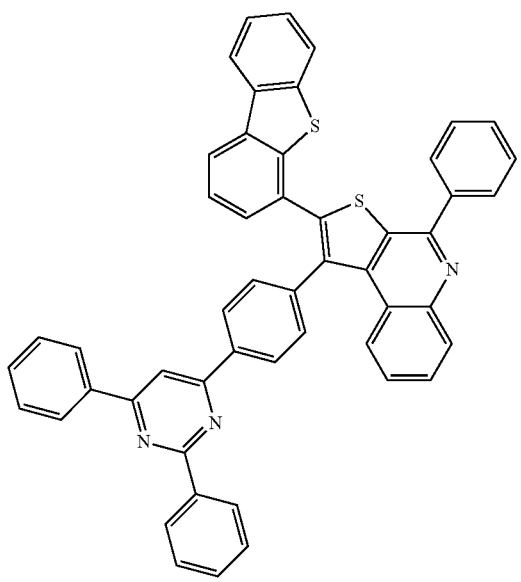
696
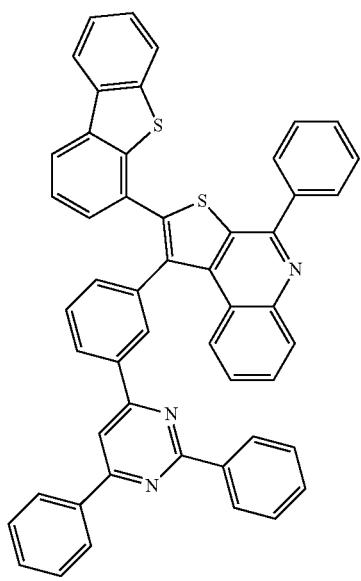
697
290
-continued
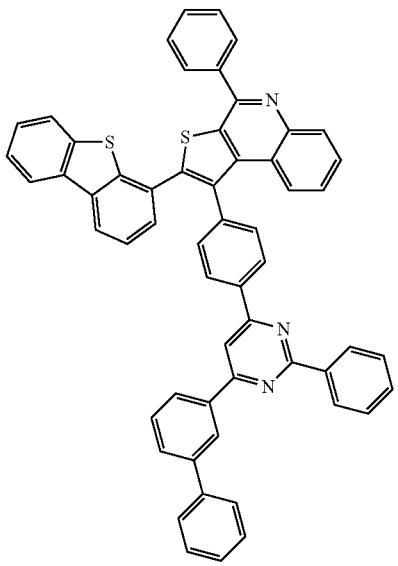
698
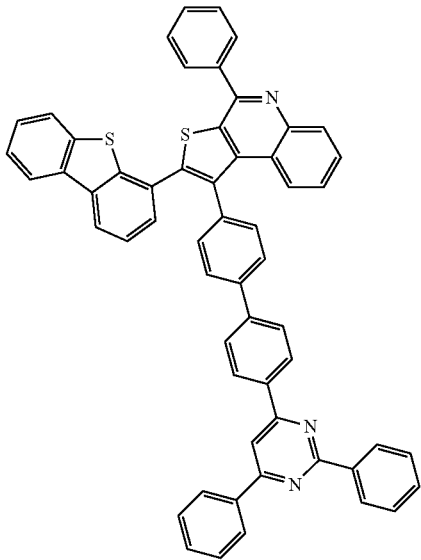
699

291
-continued
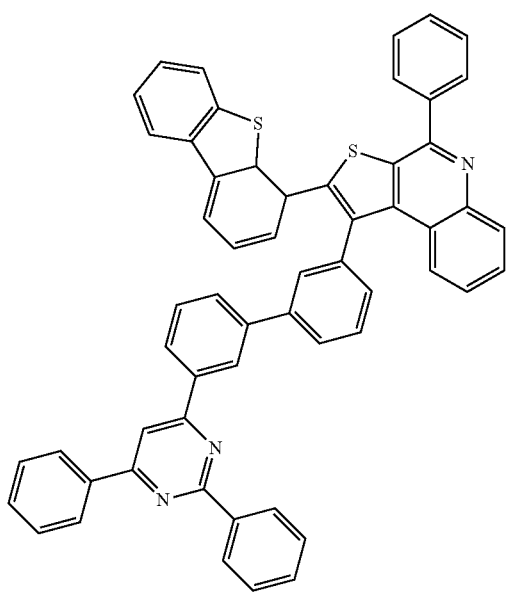
700
292
-continued
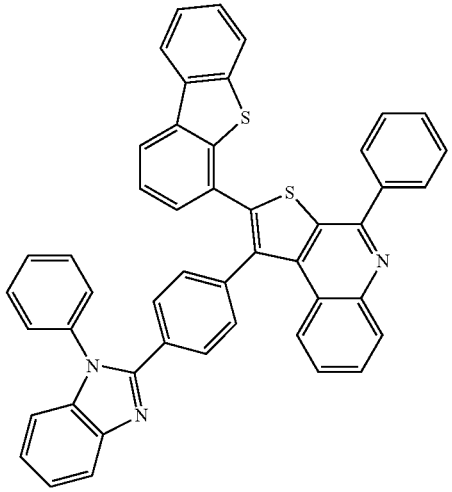
702
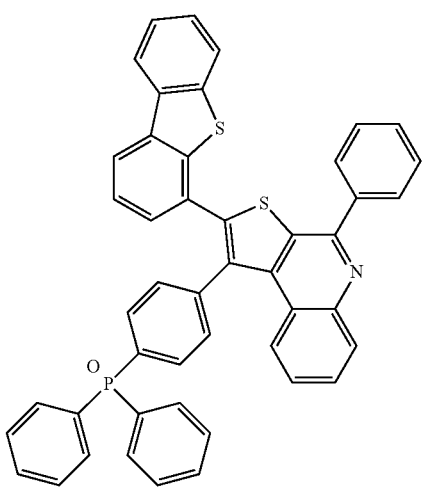
703
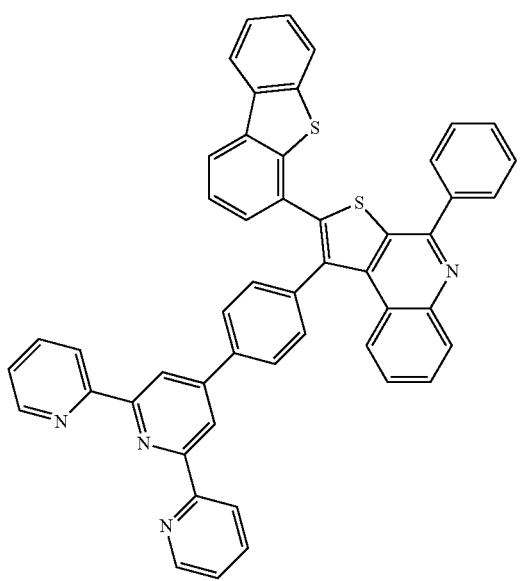
701
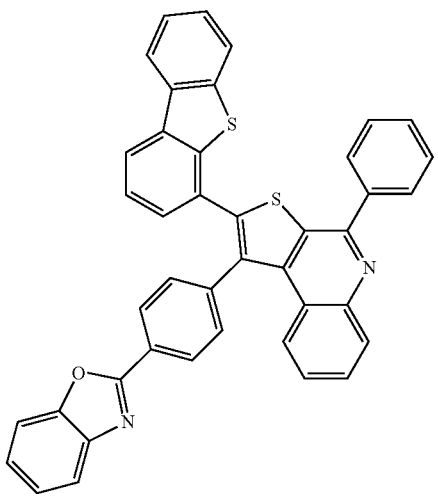
704

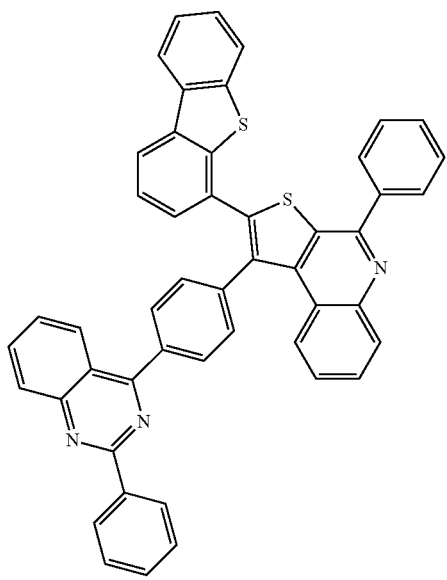
705
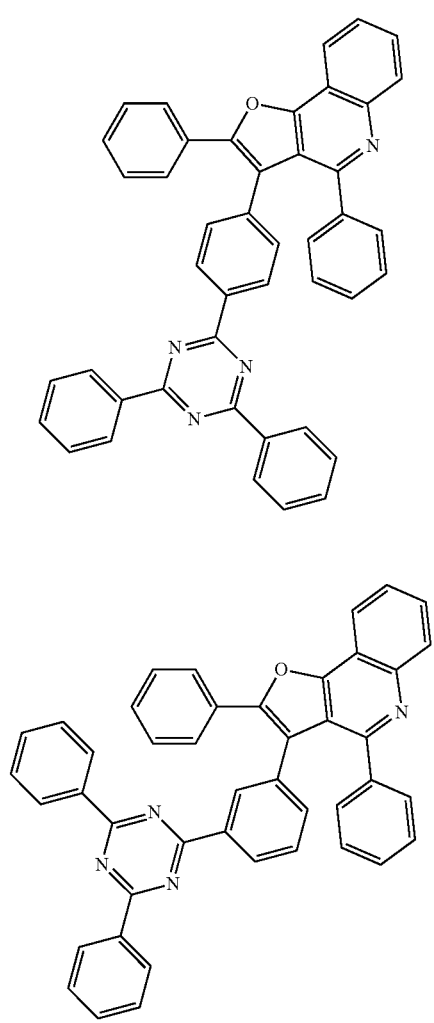
706
707
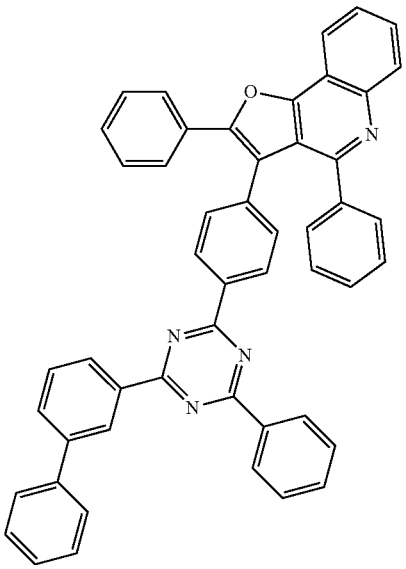
708
709

-continued
710
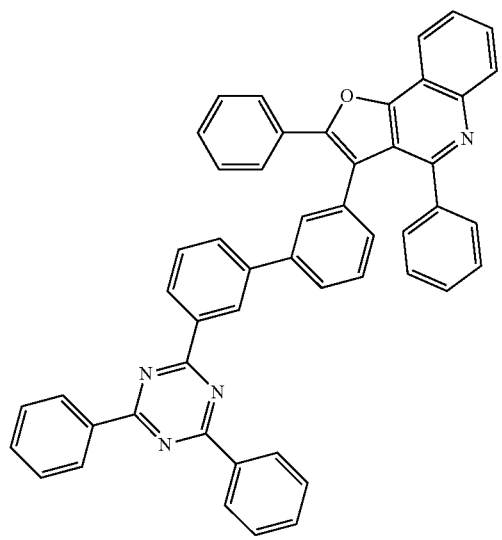
711
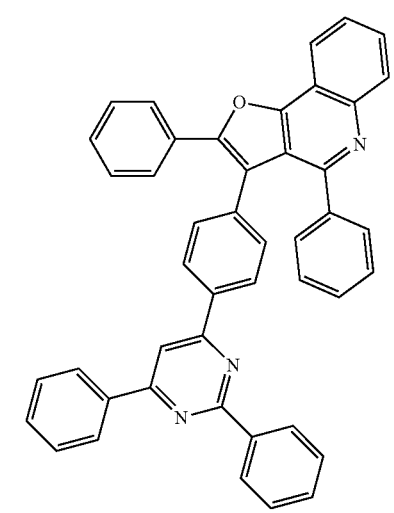
712
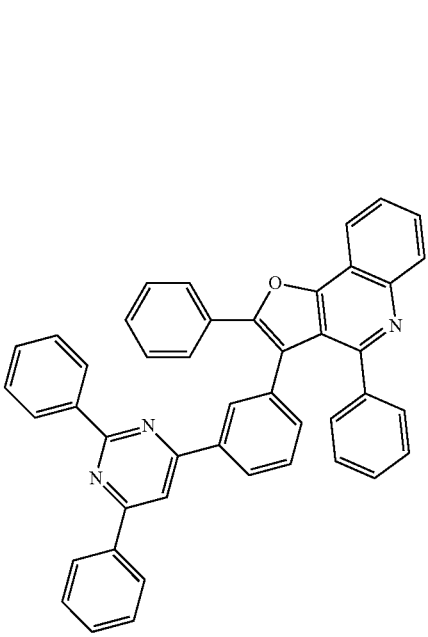
-continued
713
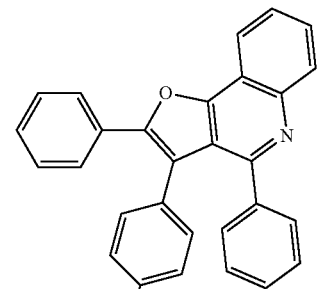
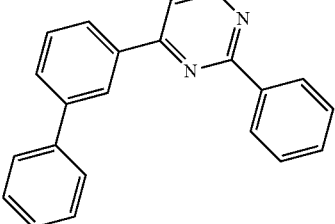
714
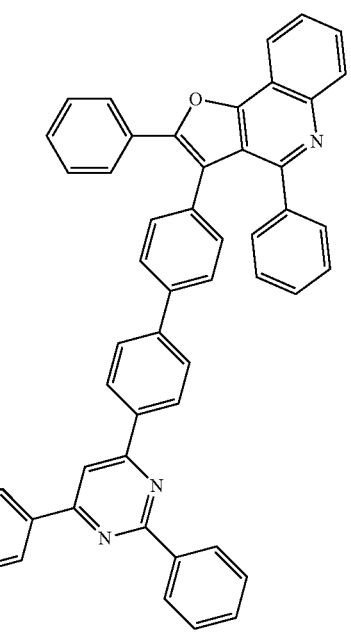

297
-continued
715
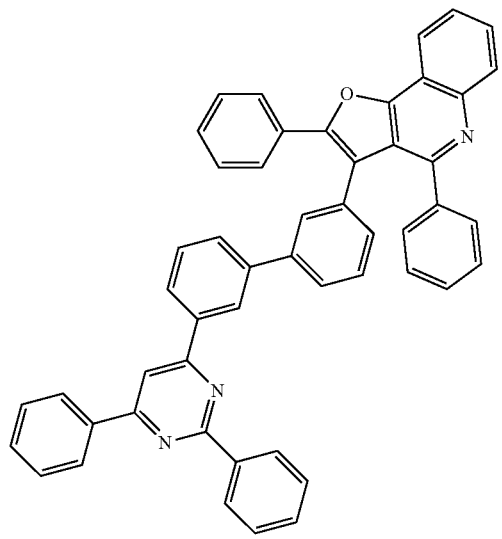
716
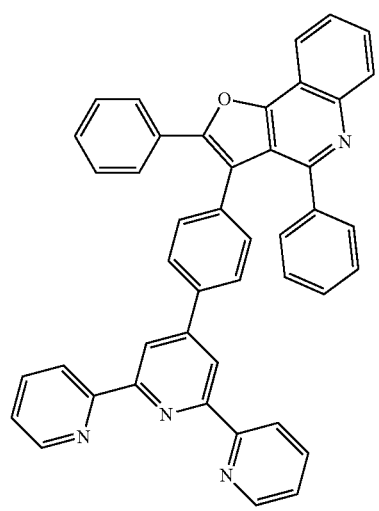
717
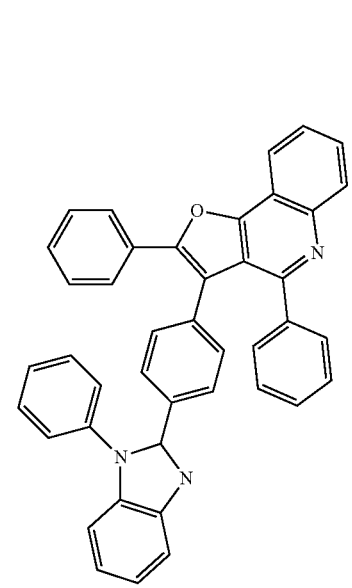
298
-continued
718
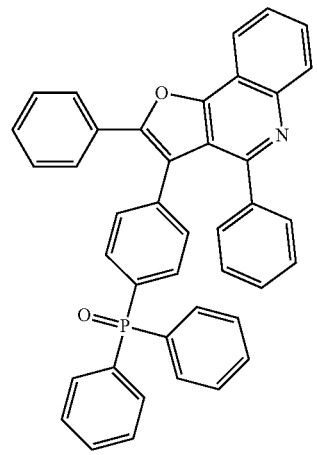
719
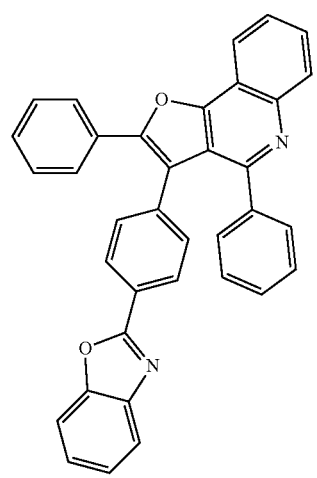
720
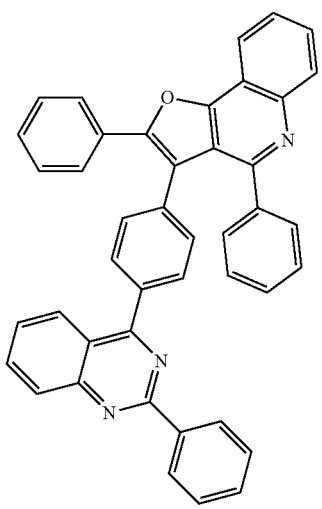

721
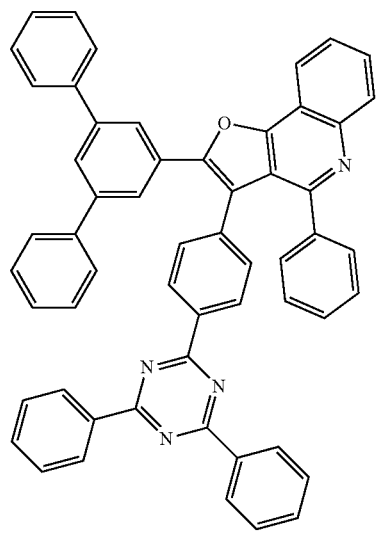
723
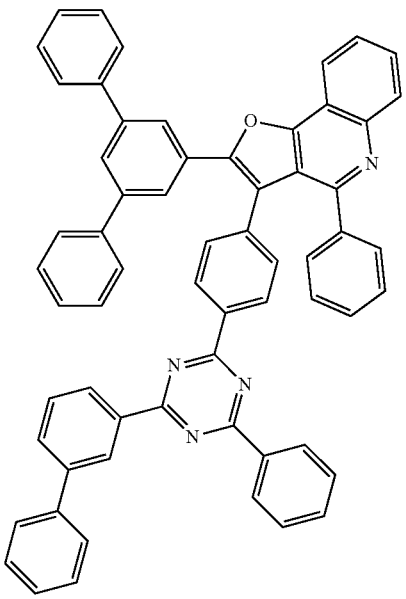
722
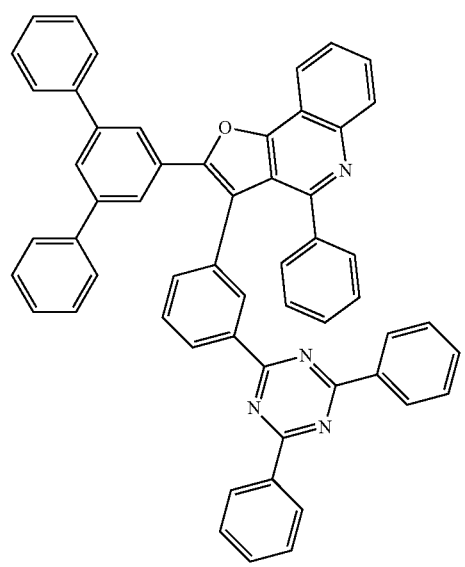
724
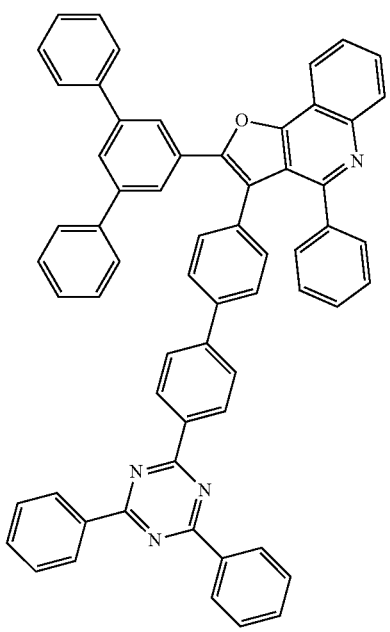

301
-continued
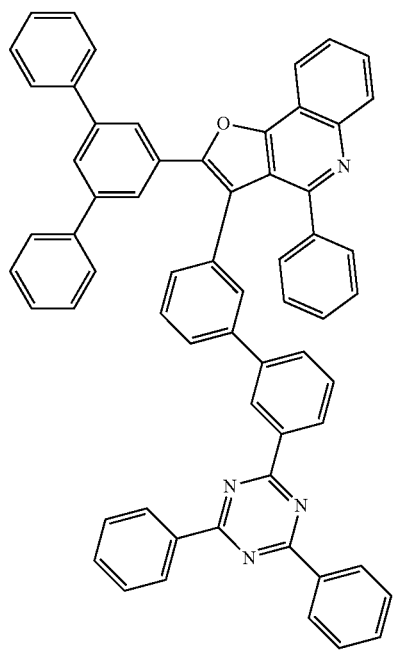
725
302
-continued
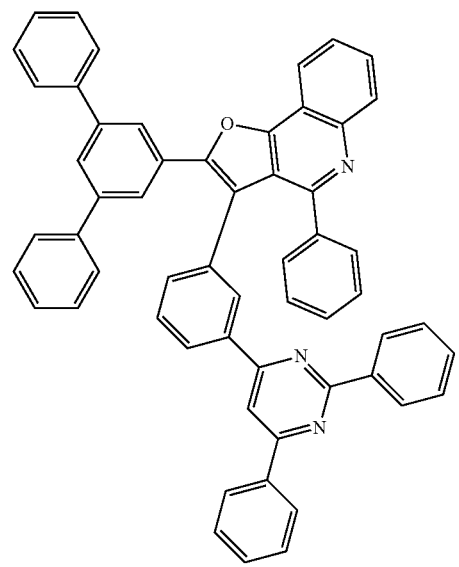
727
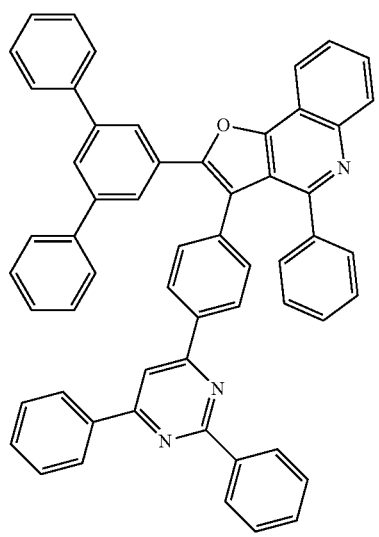
726
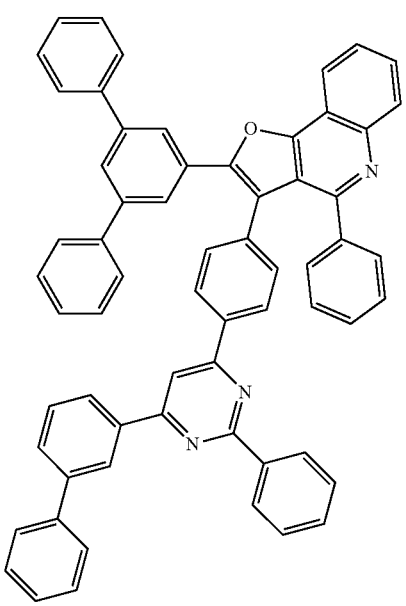
728

303
-continued
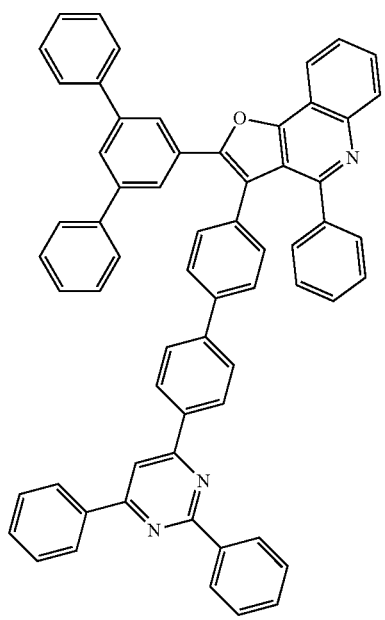
729
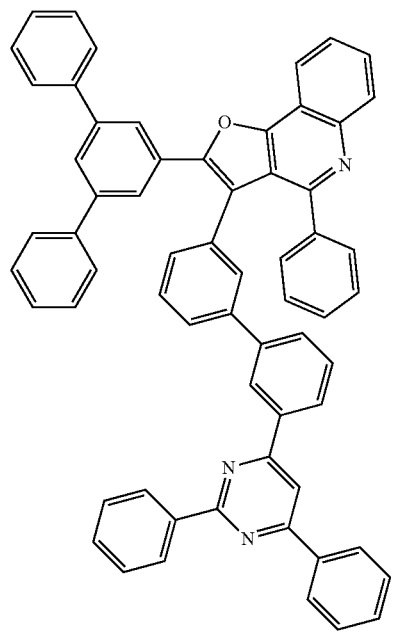
730
304
-continued
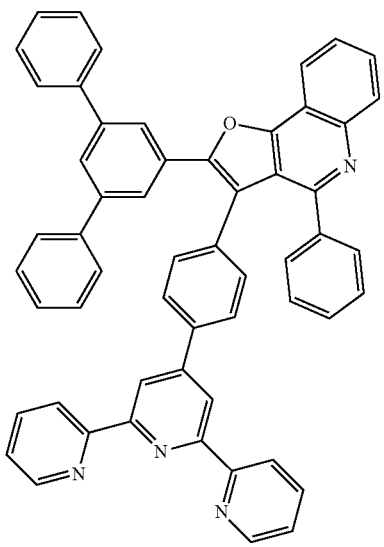
731
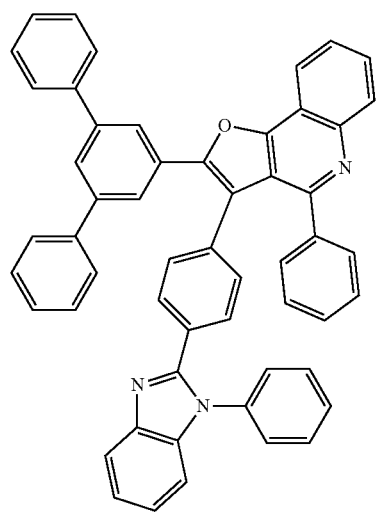
732
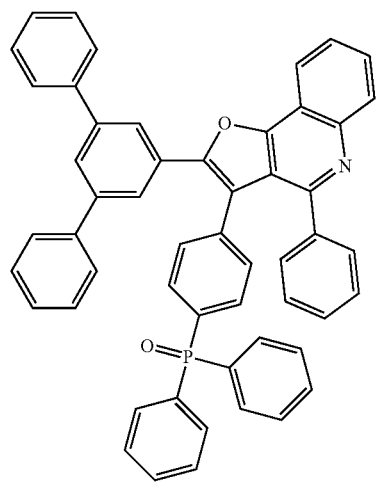
733

305
-continued
744
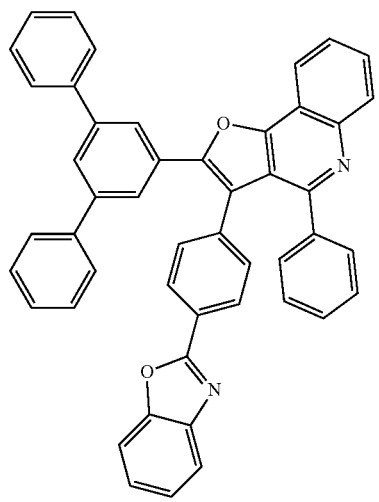
745
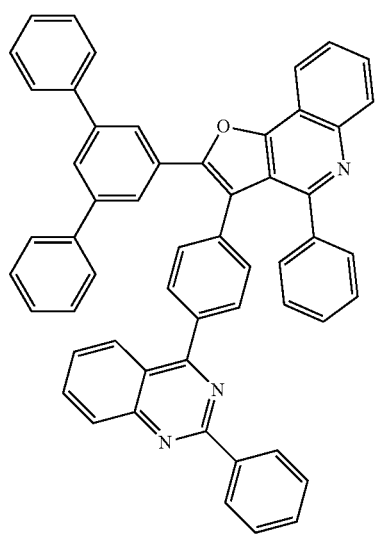
746
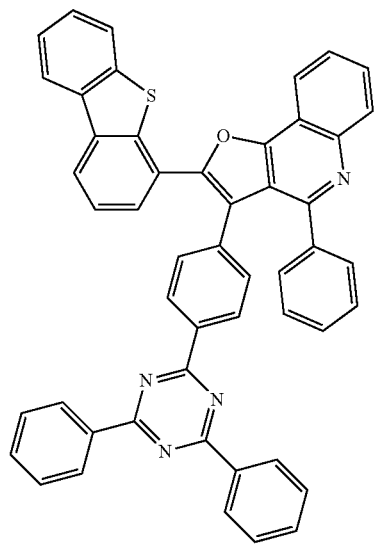
306
-continued
747
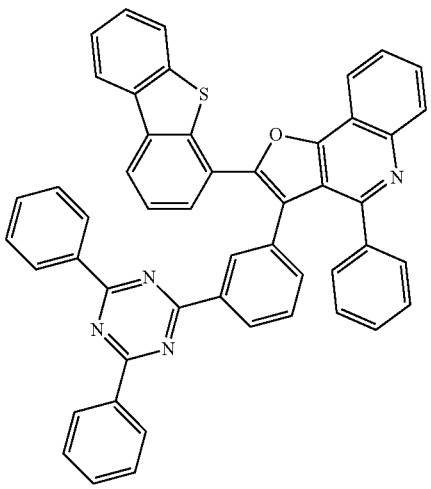
748
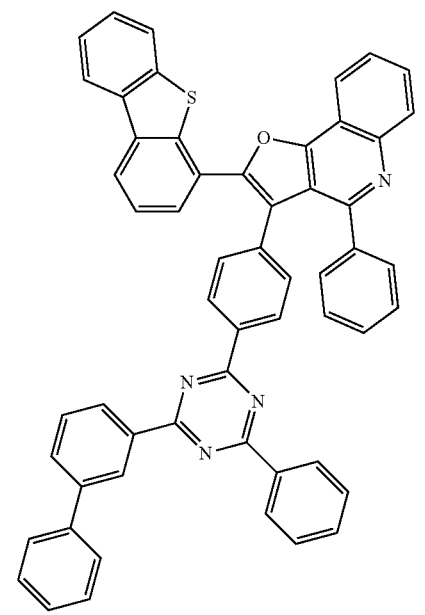

307
-continued
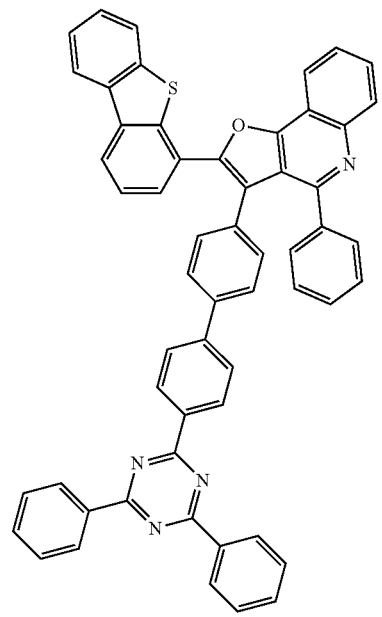
749
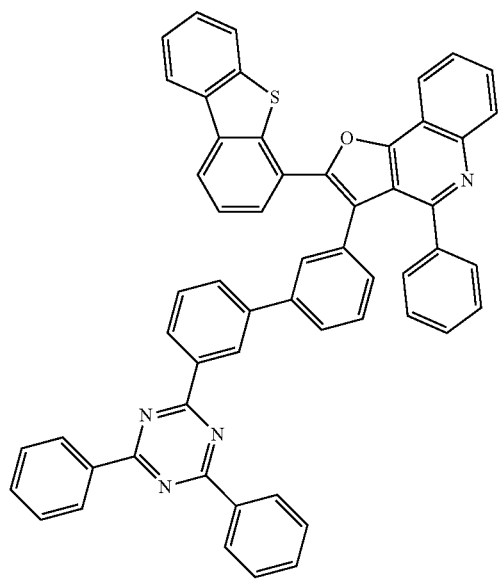
750
308
-continued
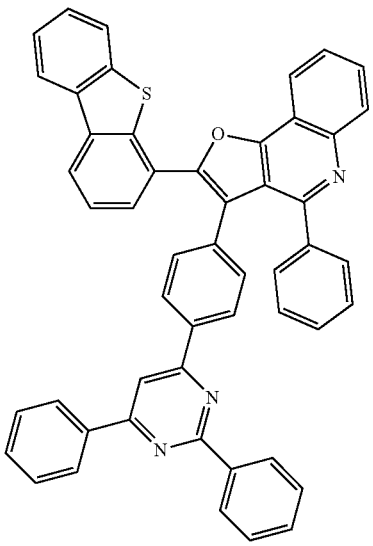
751
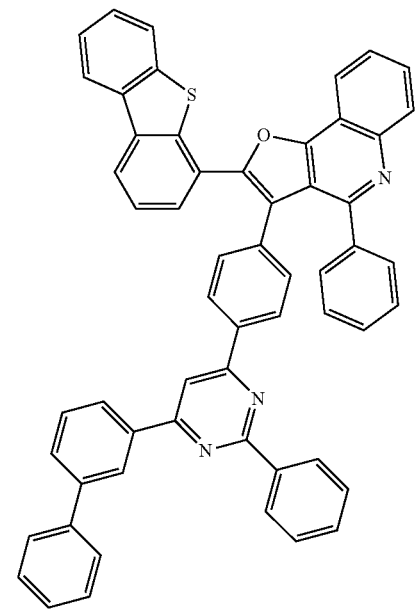
752
753

754
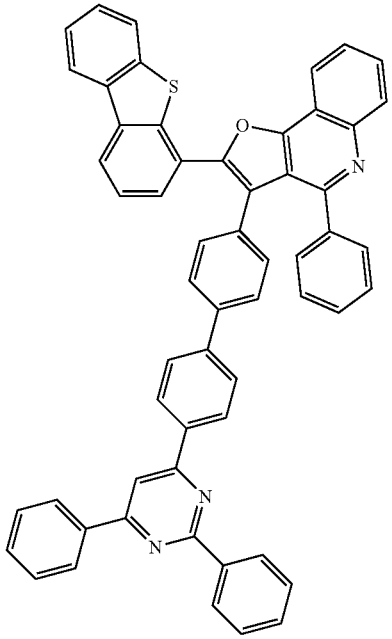
755
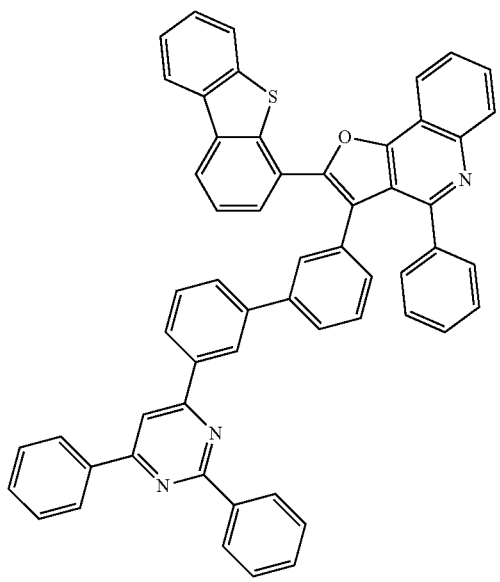
756
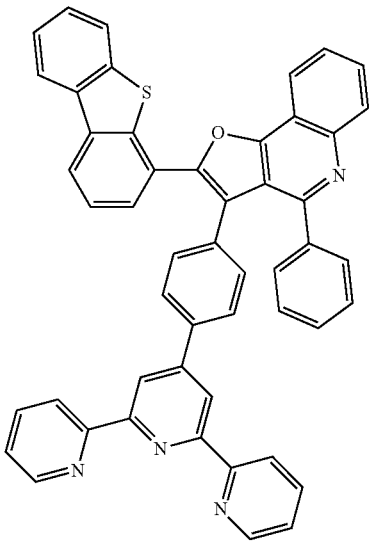
757
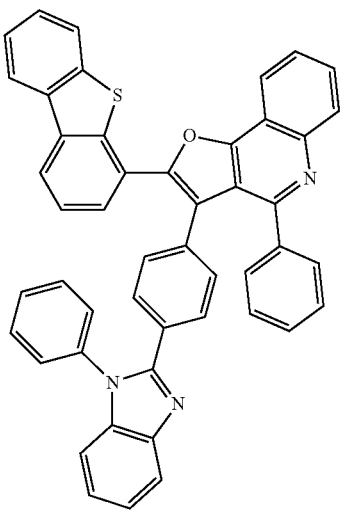
758
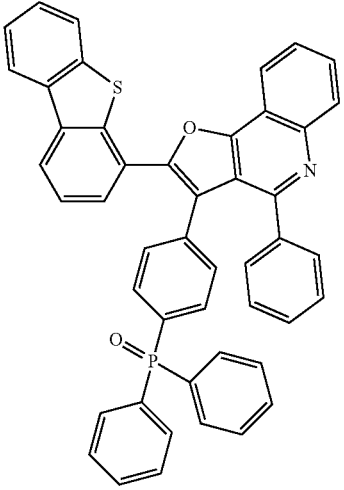

311
-continued
759
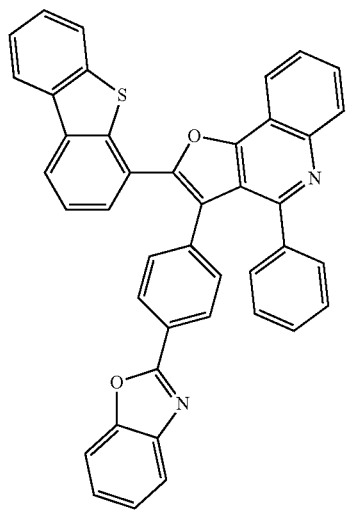
760
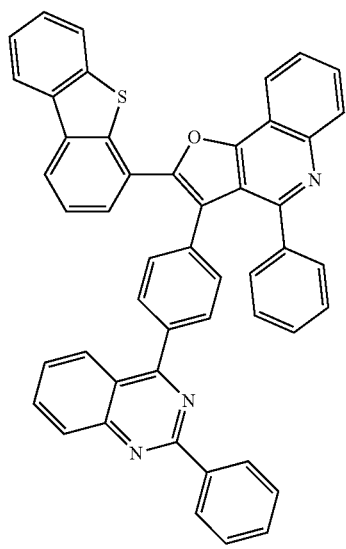
761
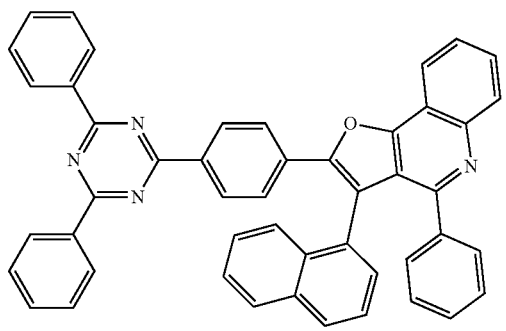
312
-continued
762
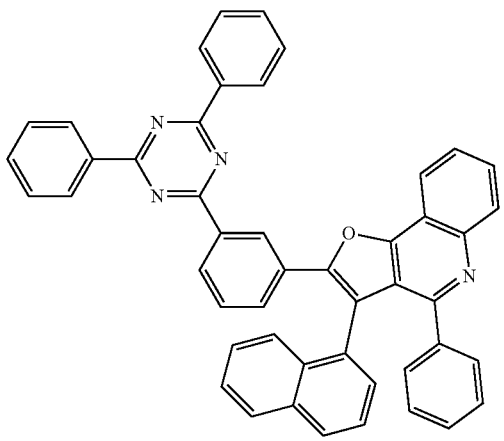
763
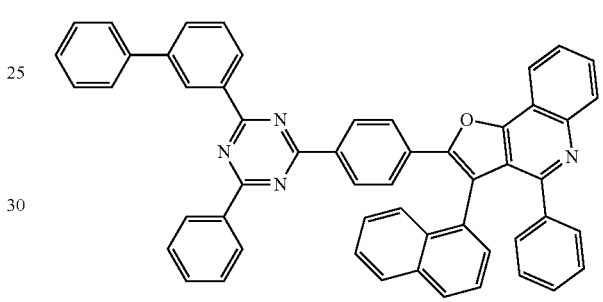
764
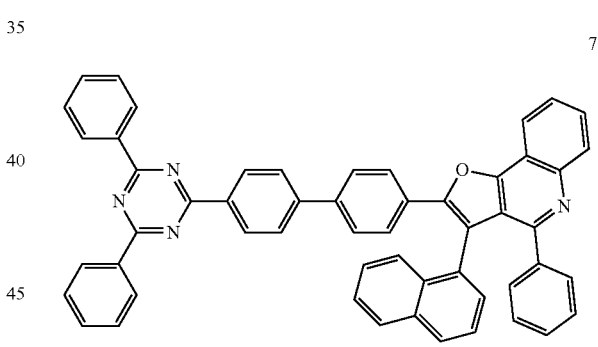
765
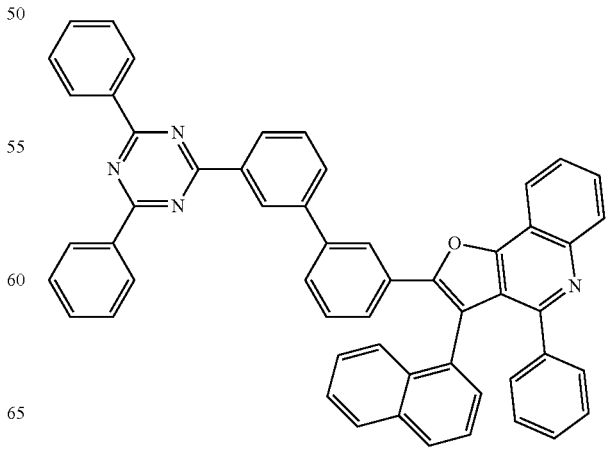

766
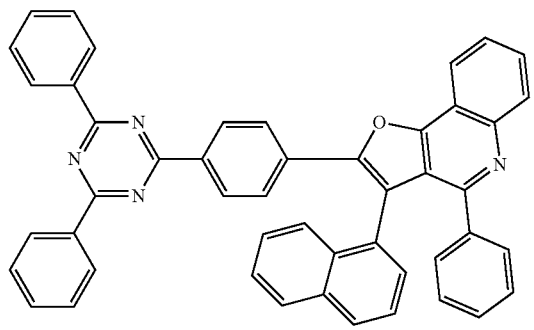
767
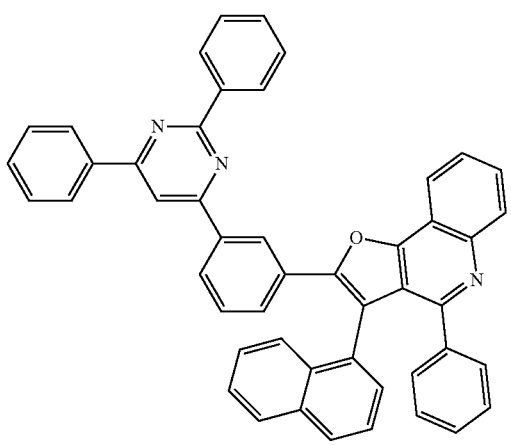
768
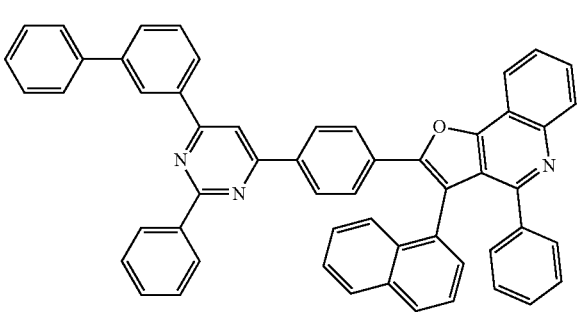
769
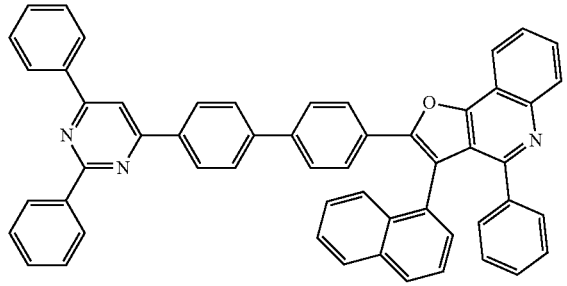
770
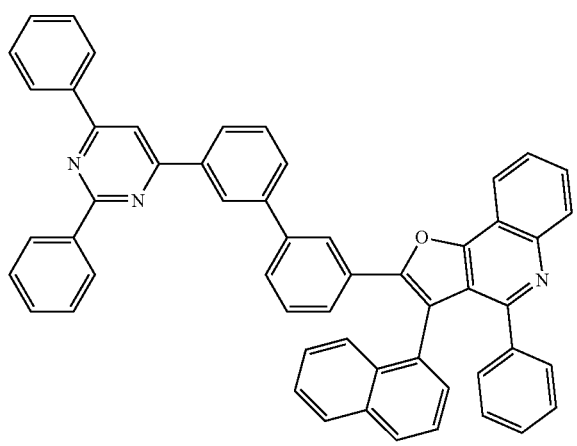
771
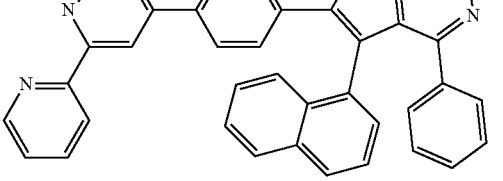
772
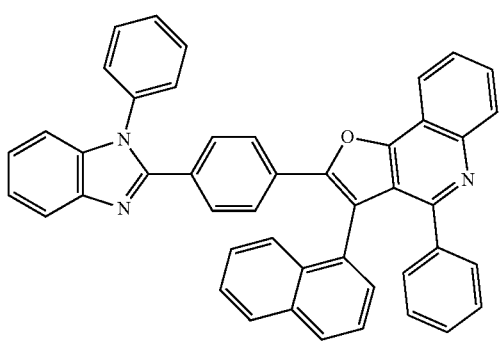
773
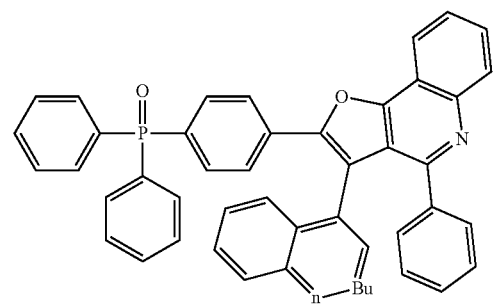

774
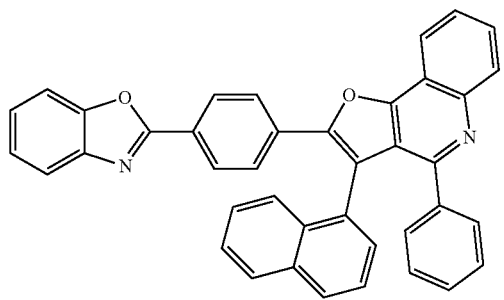
775
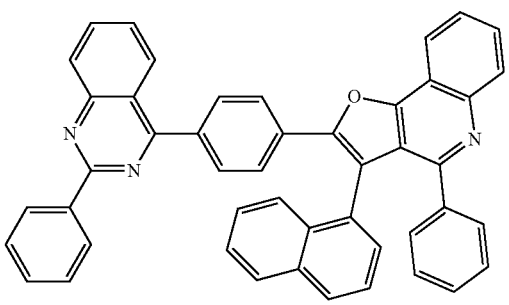
776
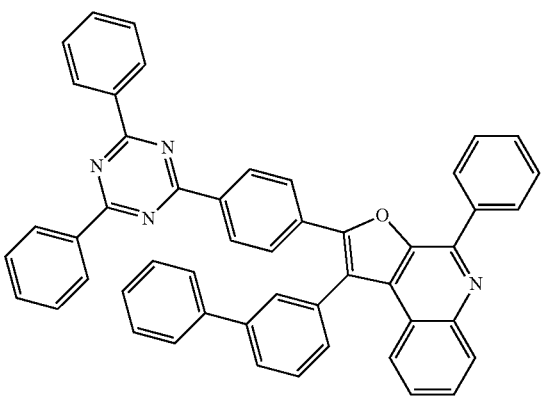
777
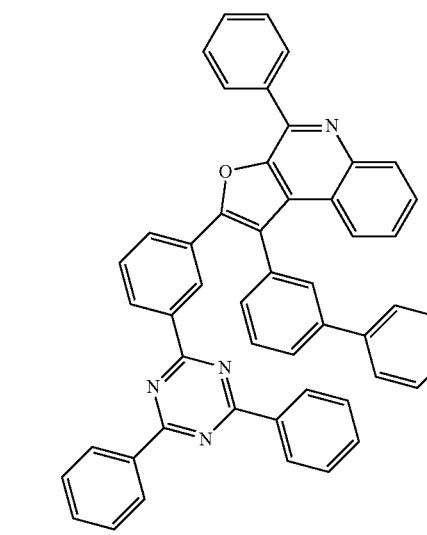
778
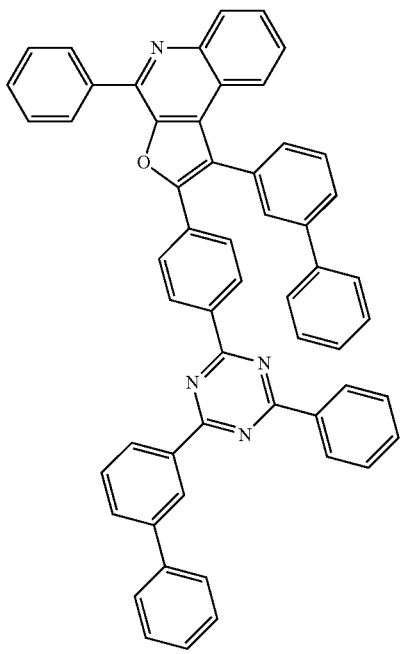
779
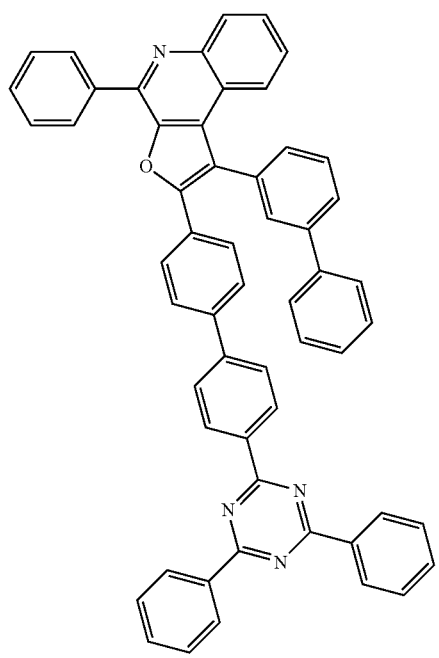

-continued
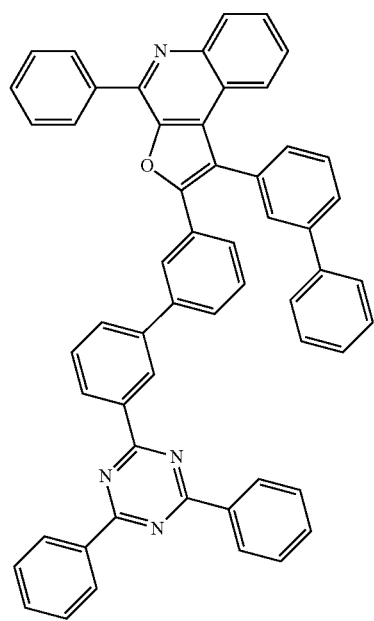
780
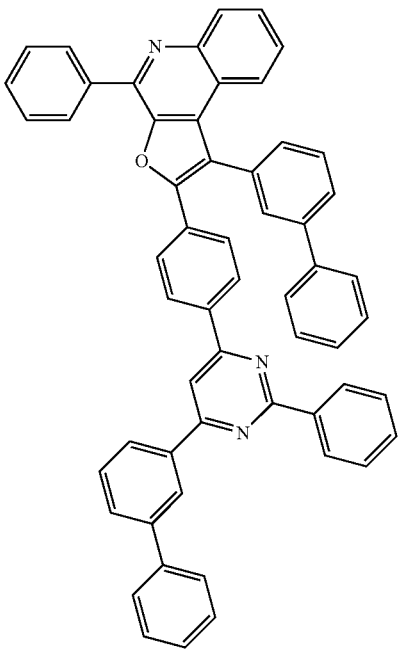
783
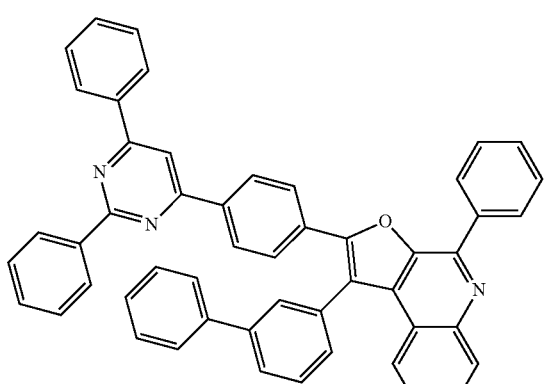
781
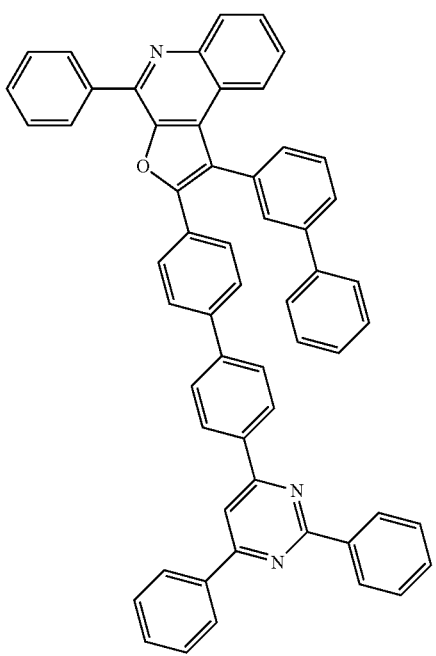
784
782

785
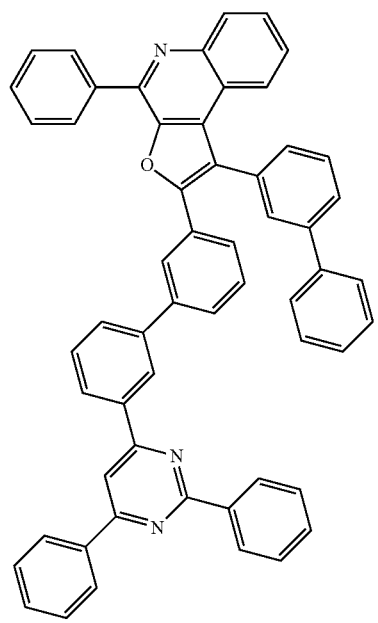
786
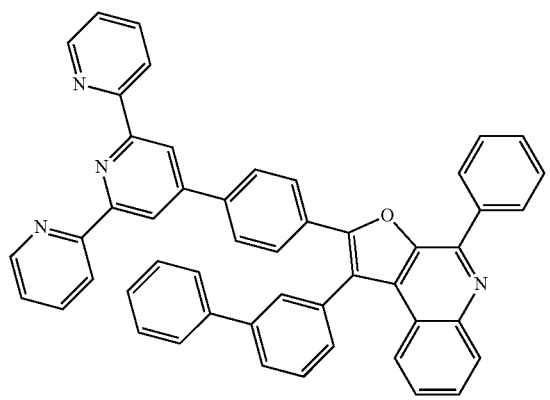
787
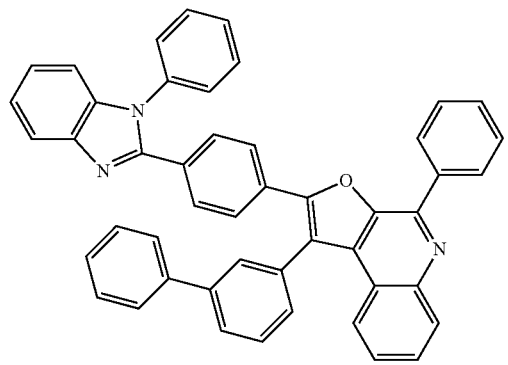
788
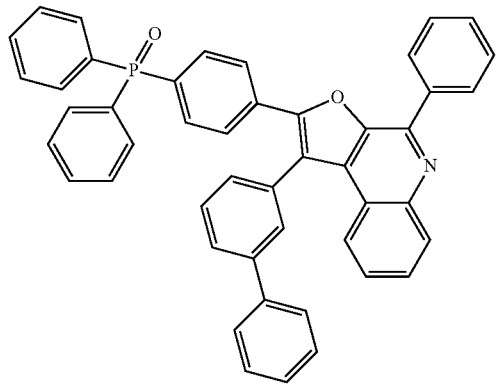
789
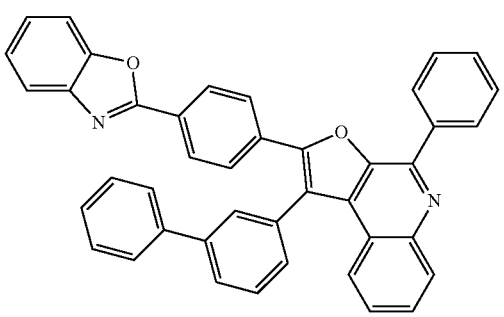
790
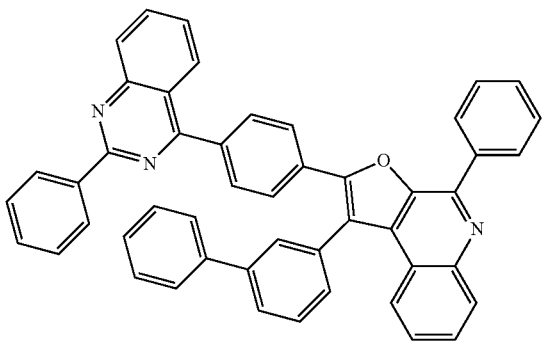
791
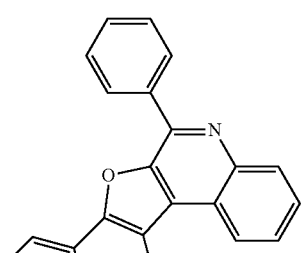
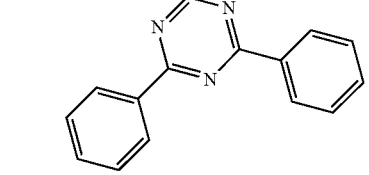

321
-continued
322
-continued
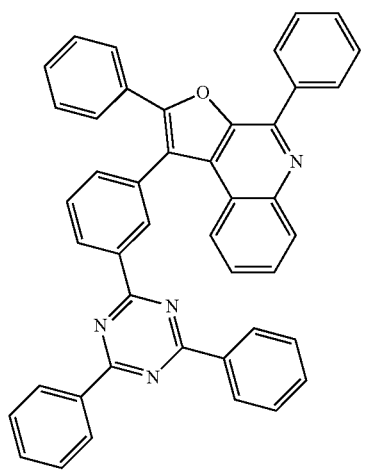
792
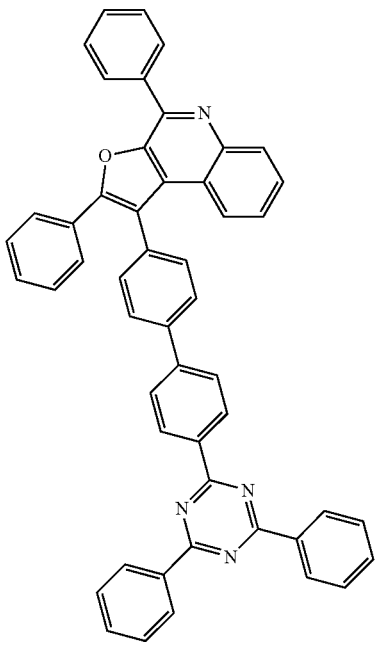
794
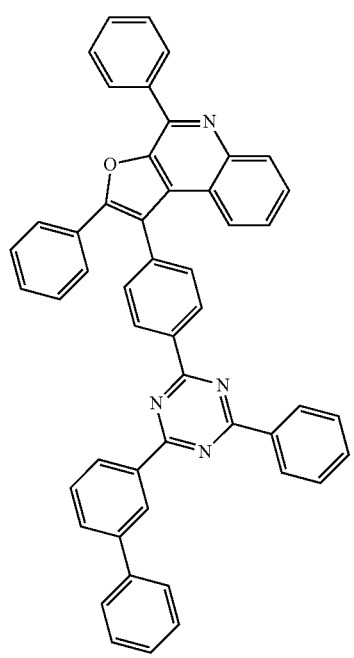
793
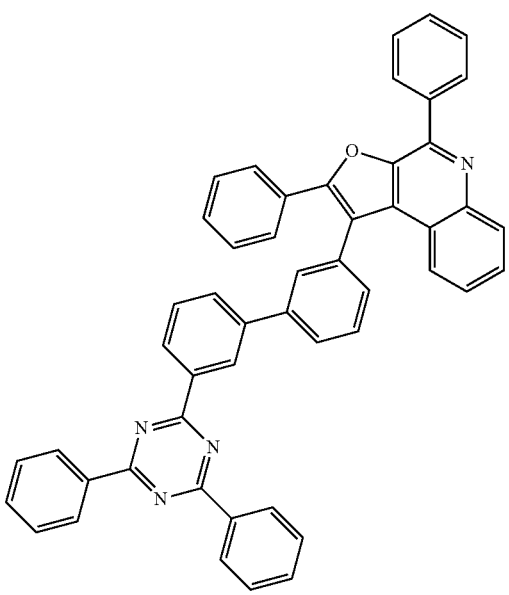
795

323
-continued
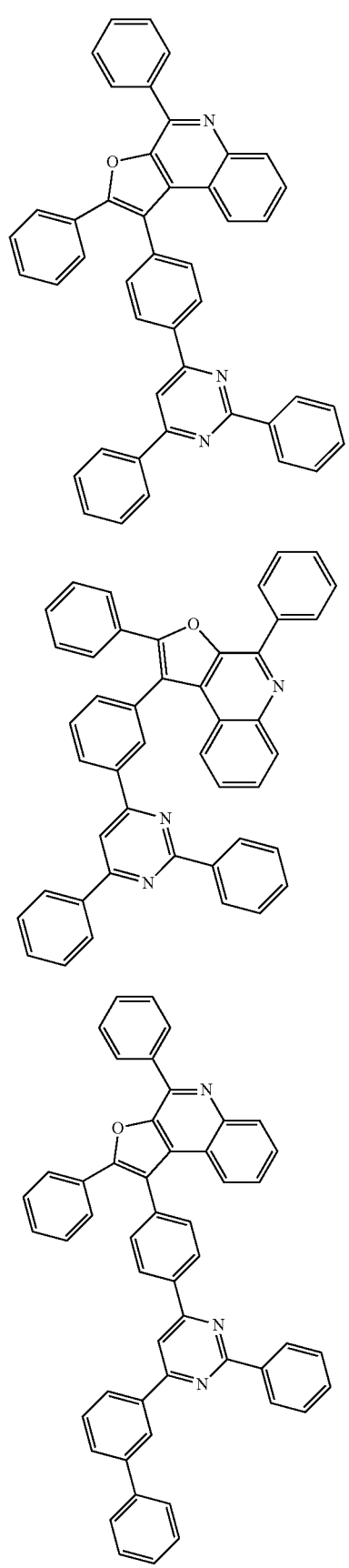
324
-continued
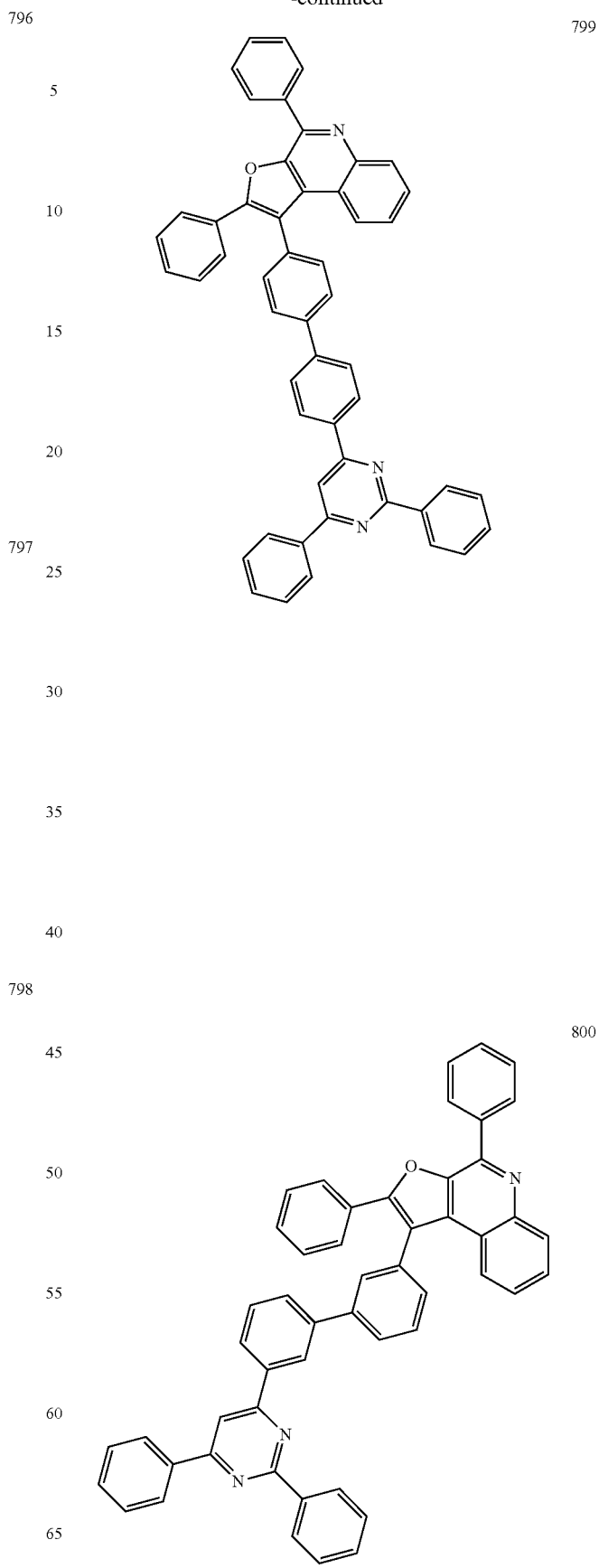

325
-continued
801
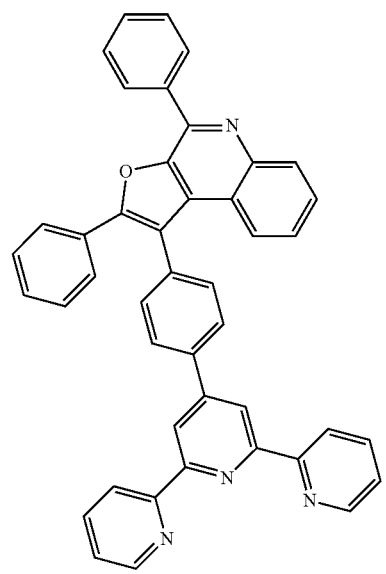
802
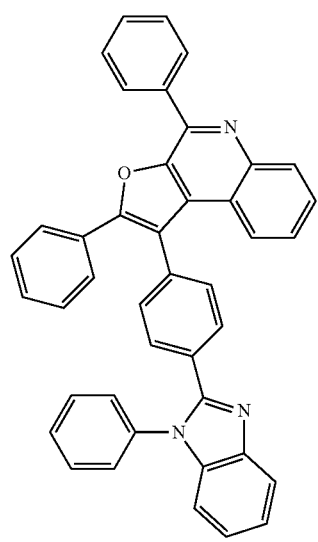
803
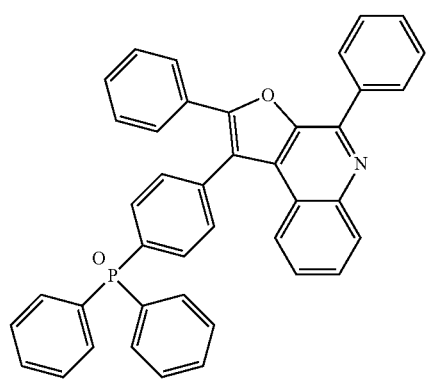
326
-continued
804
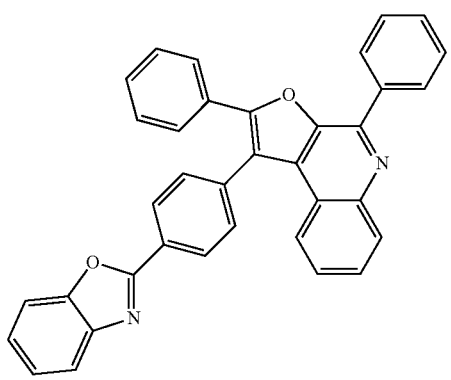
805
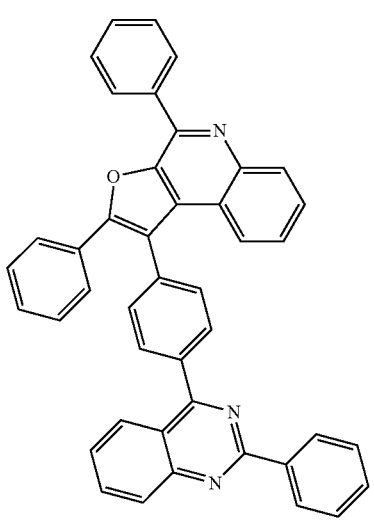
806
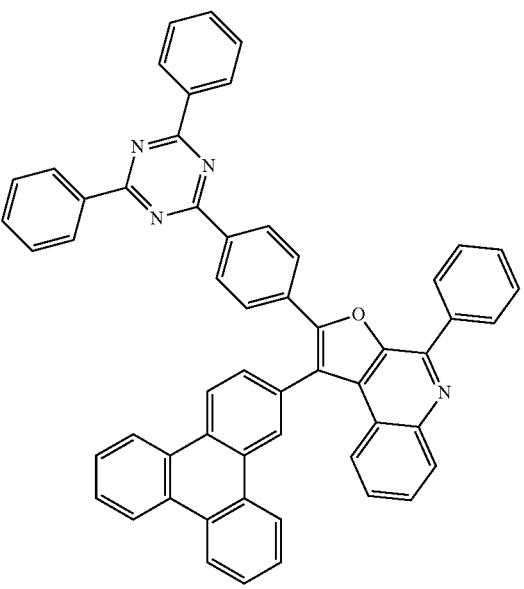

327
-continued
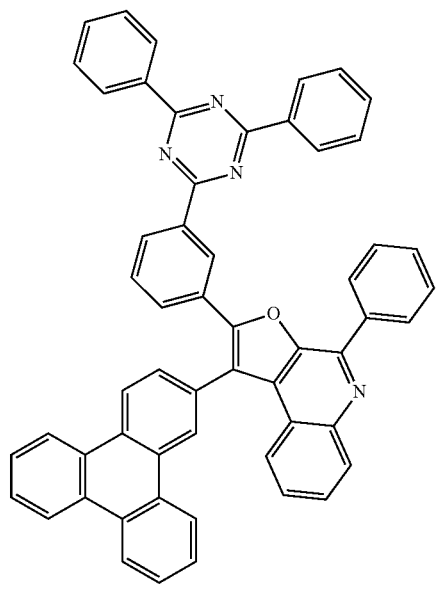
807
328
-continued
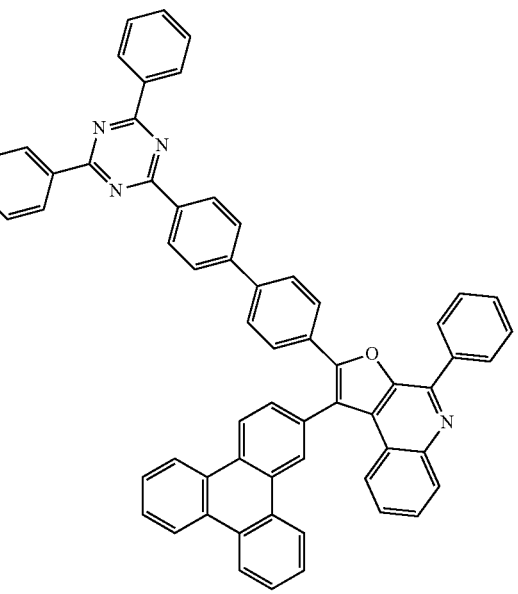
809
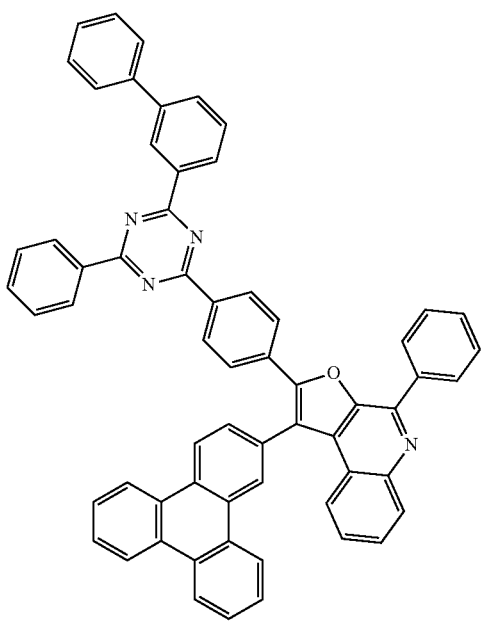
808
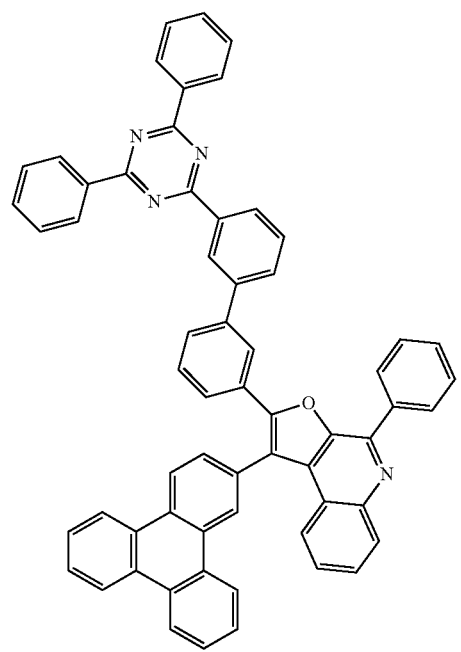
810

329
-continued
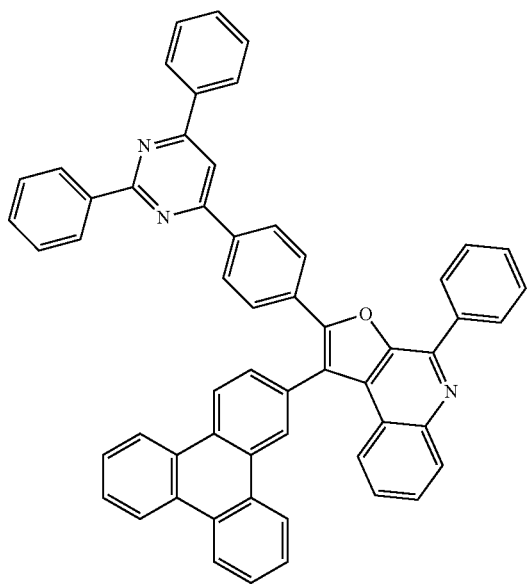
811
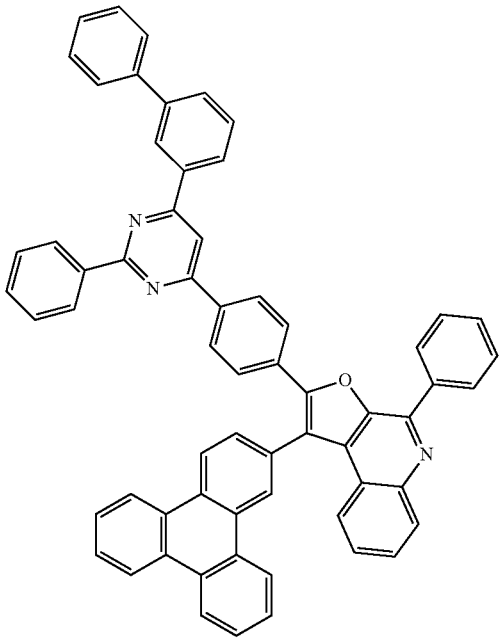
813
330
-continued
812
814
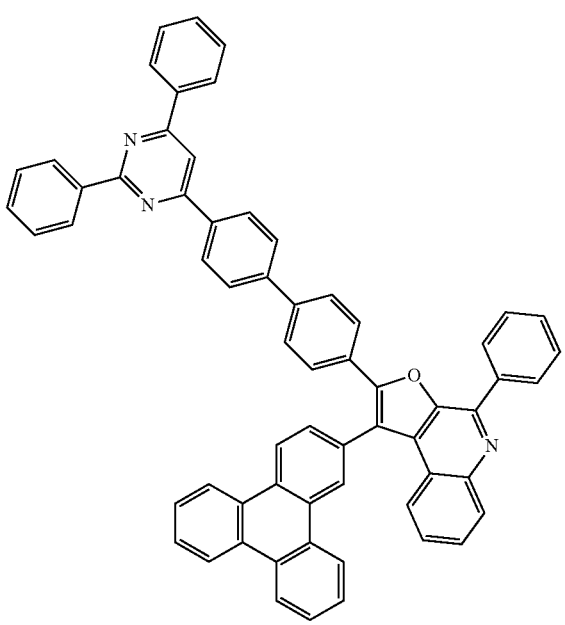

331
-continued
815
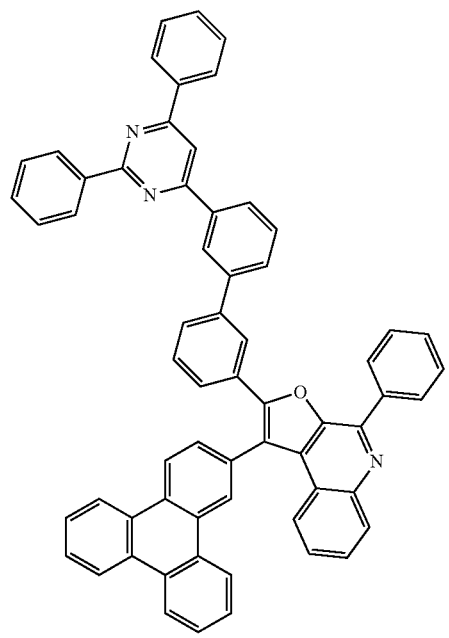
332
-continued
817
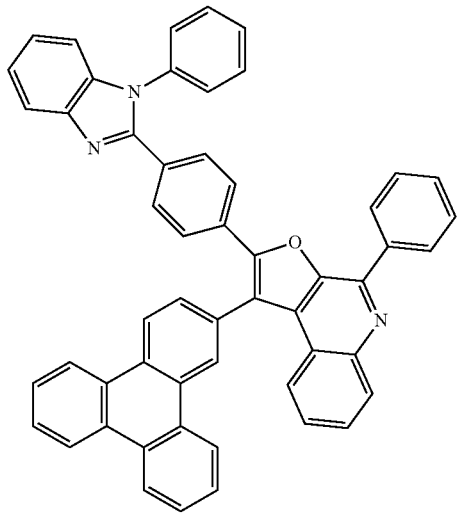
818
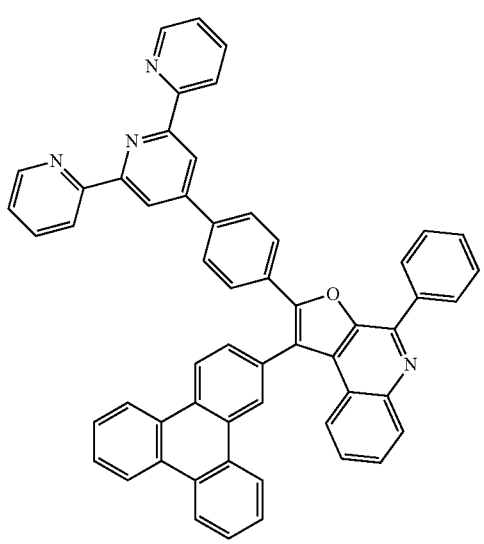
816
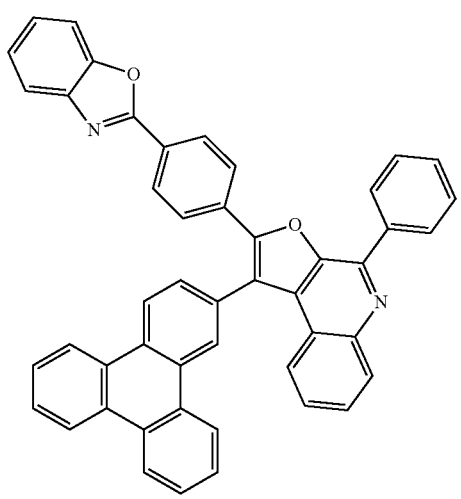
819

820
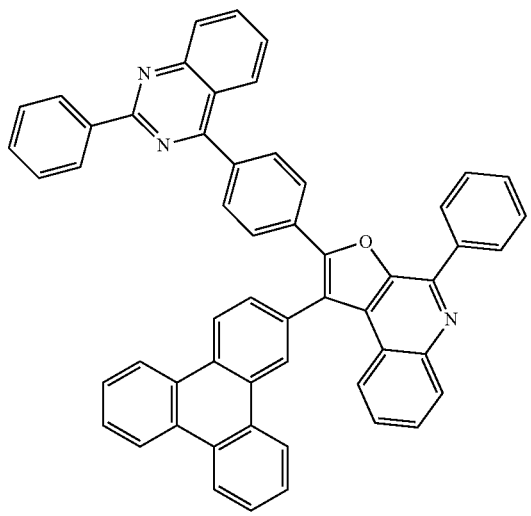
821
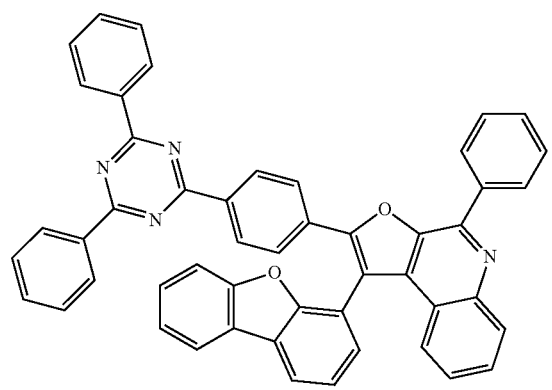
822
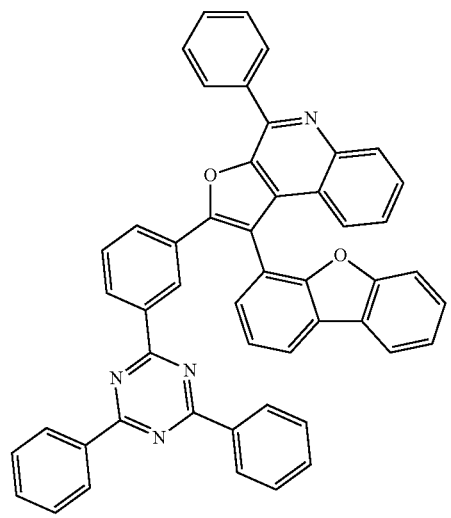
823
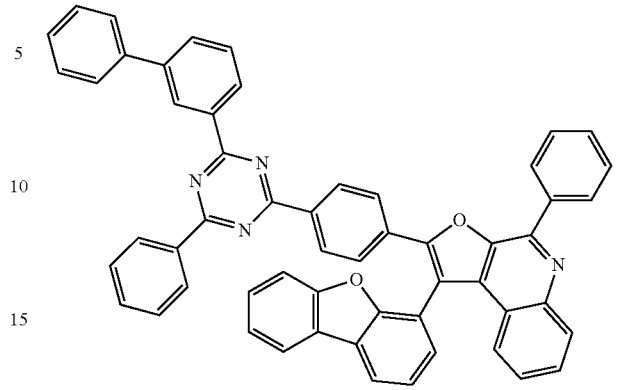
824
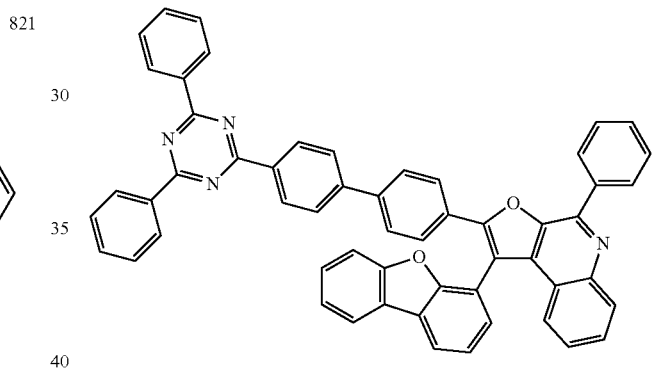
825
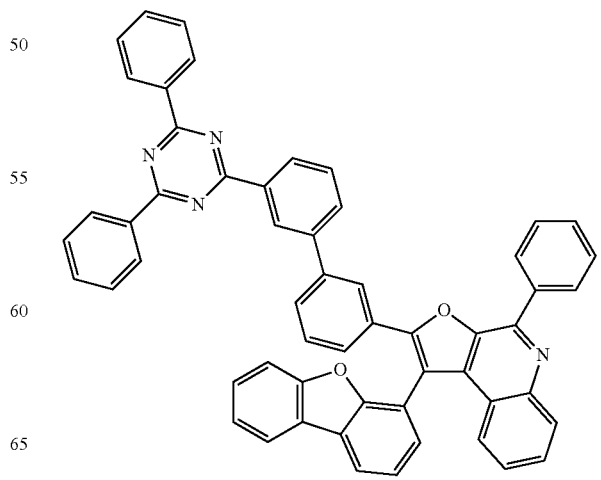

-continued
826
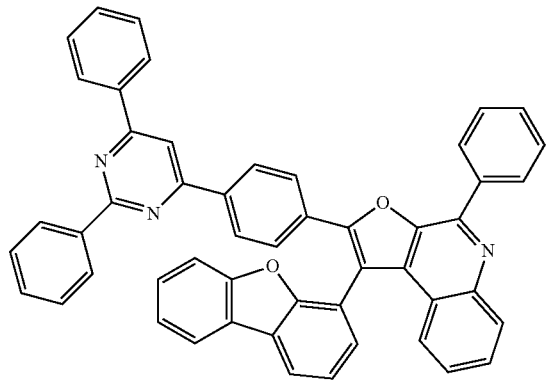
827
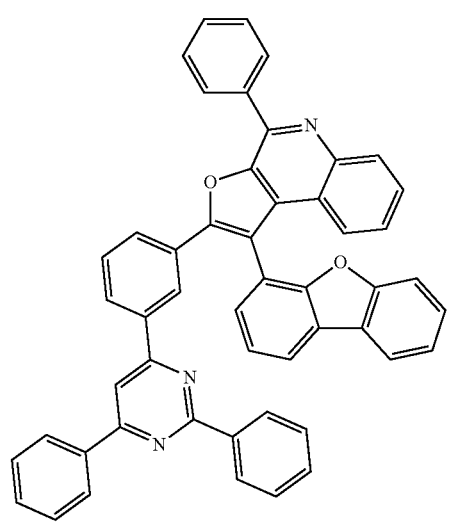
828
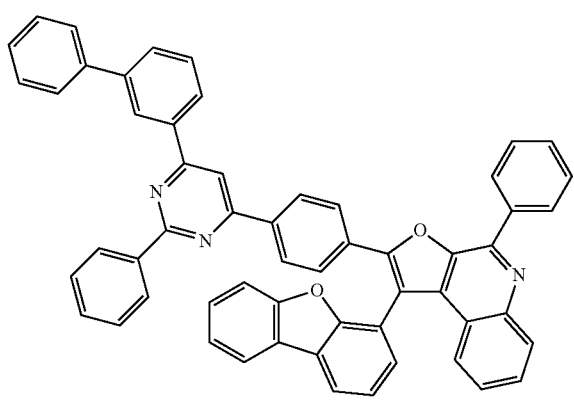
-continued
829
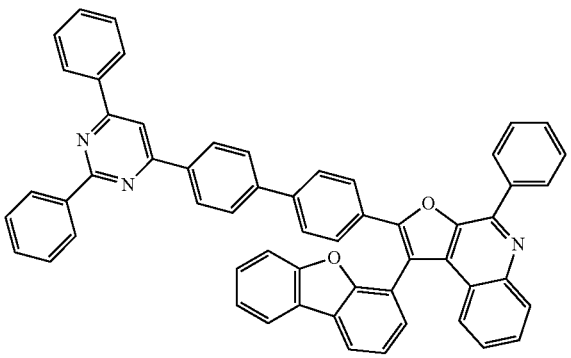
830
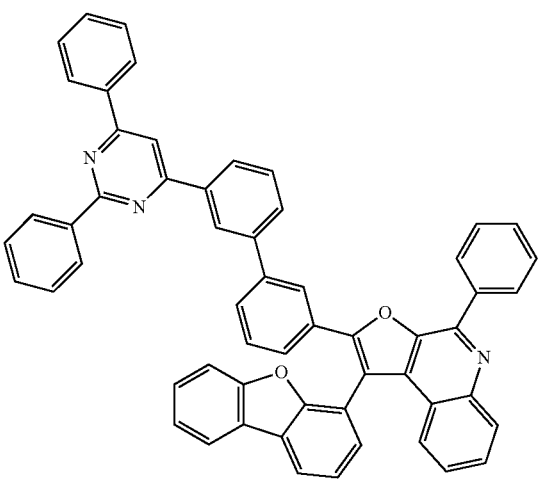
831
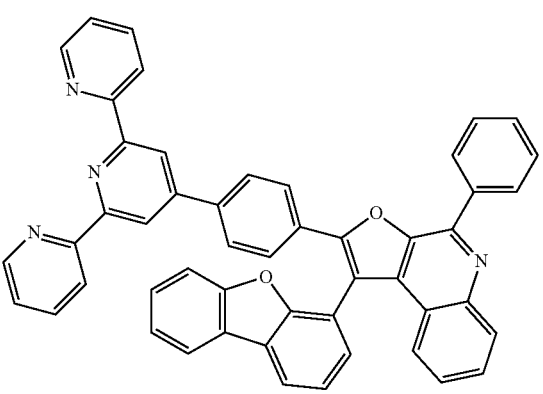
832
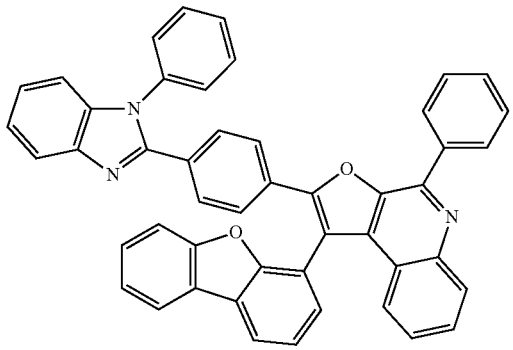

833
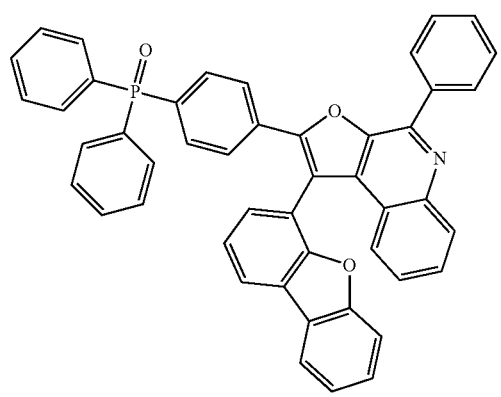
837
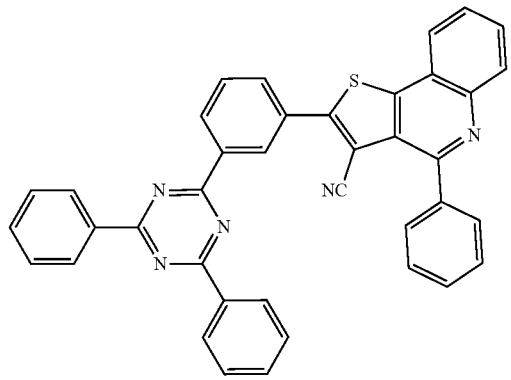
834
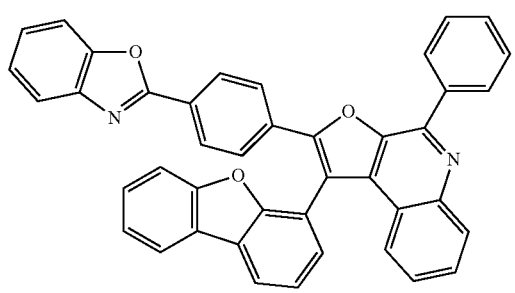
838
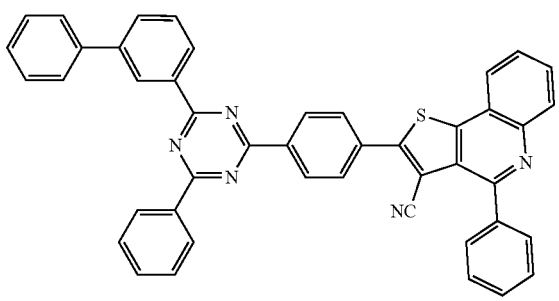
835
839
836
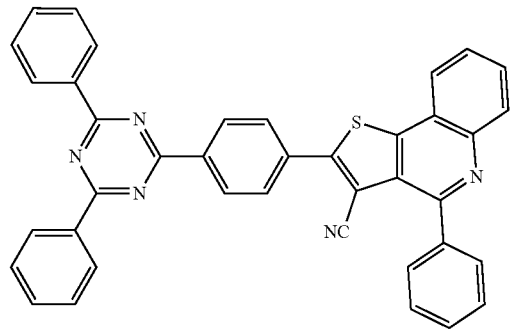
840
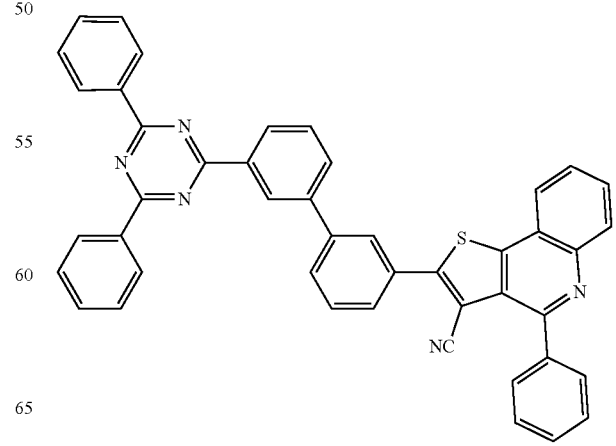

-continued
841
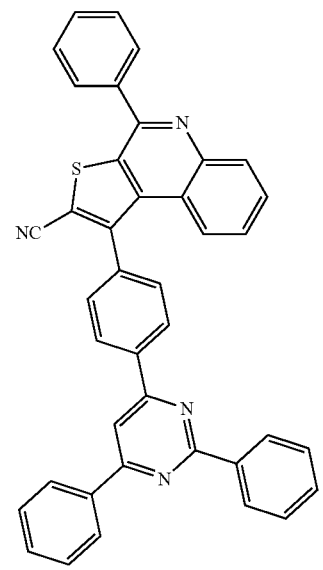
842
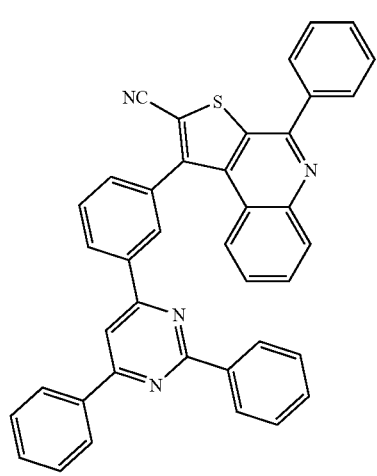
843
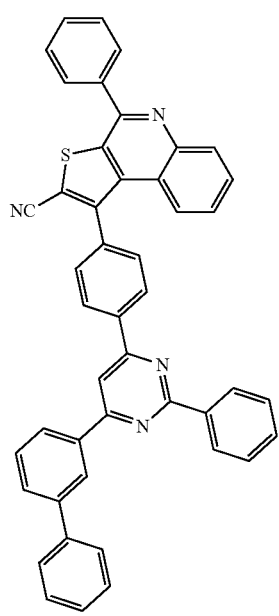
844
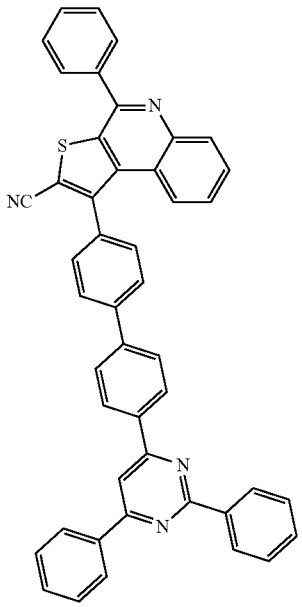
845
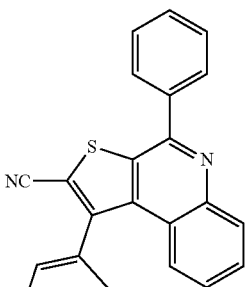
846
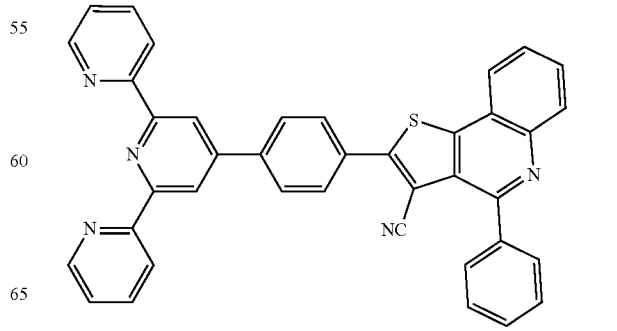

-continued
847
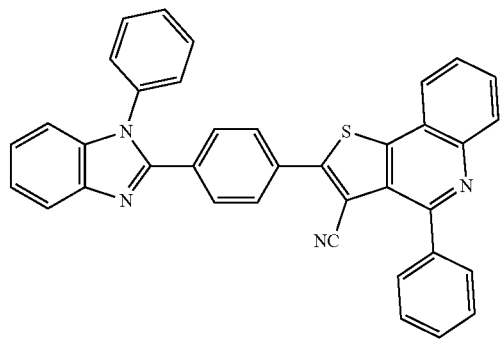
848
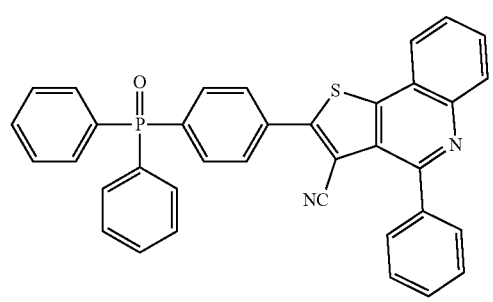
849
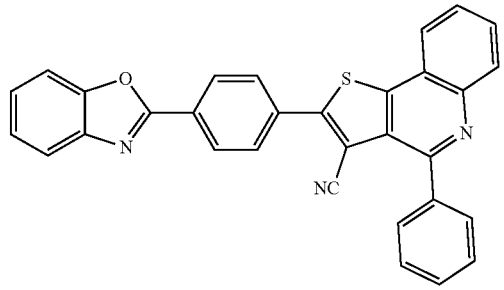
850
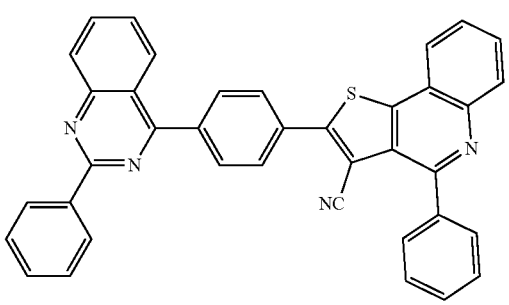
-continued
851
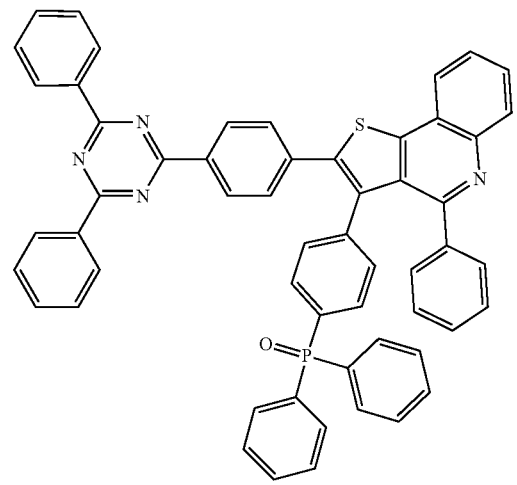
852
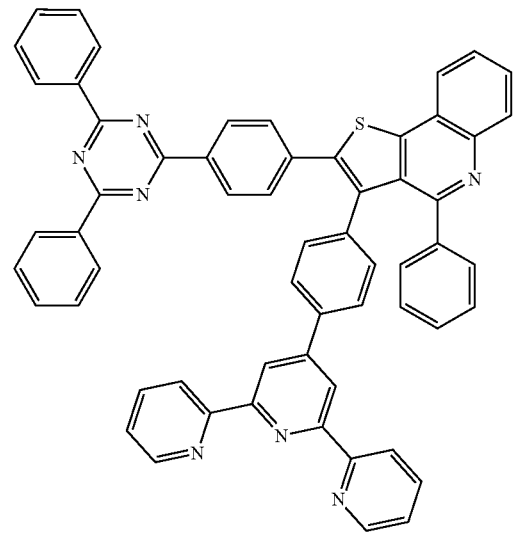
853
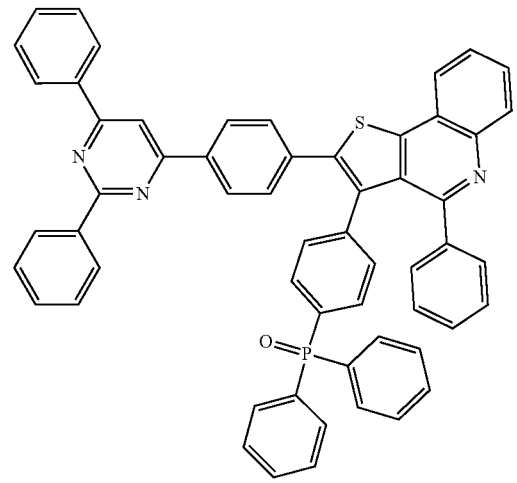

343
-continued
854
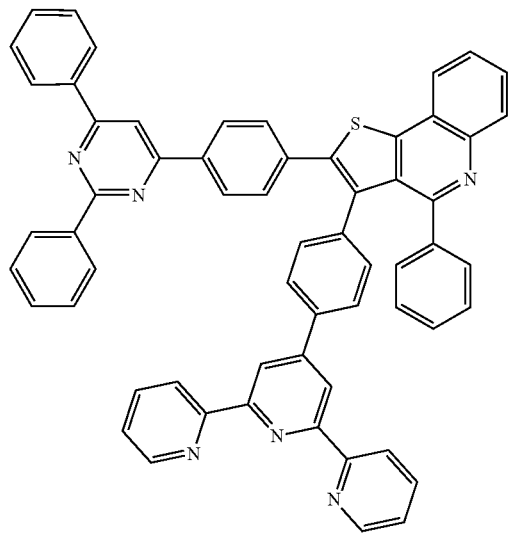
855
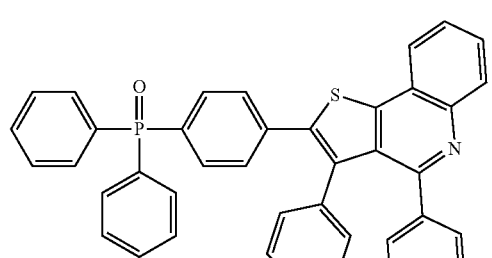
856
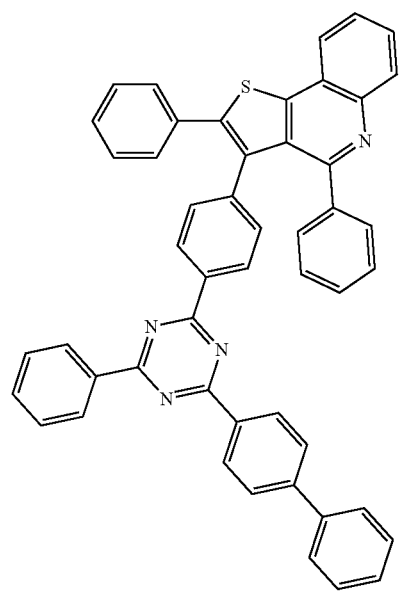
344
-continued
857
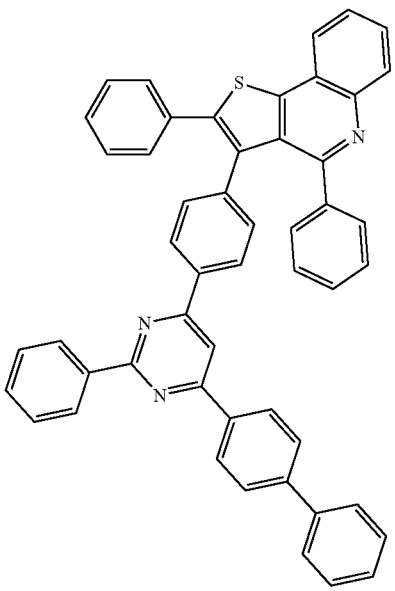
858
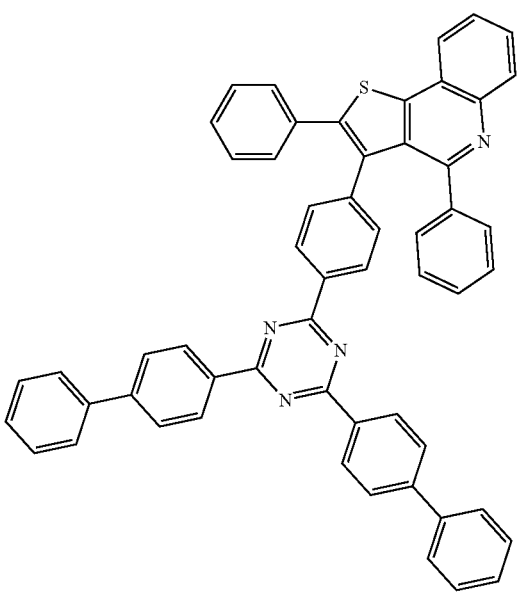

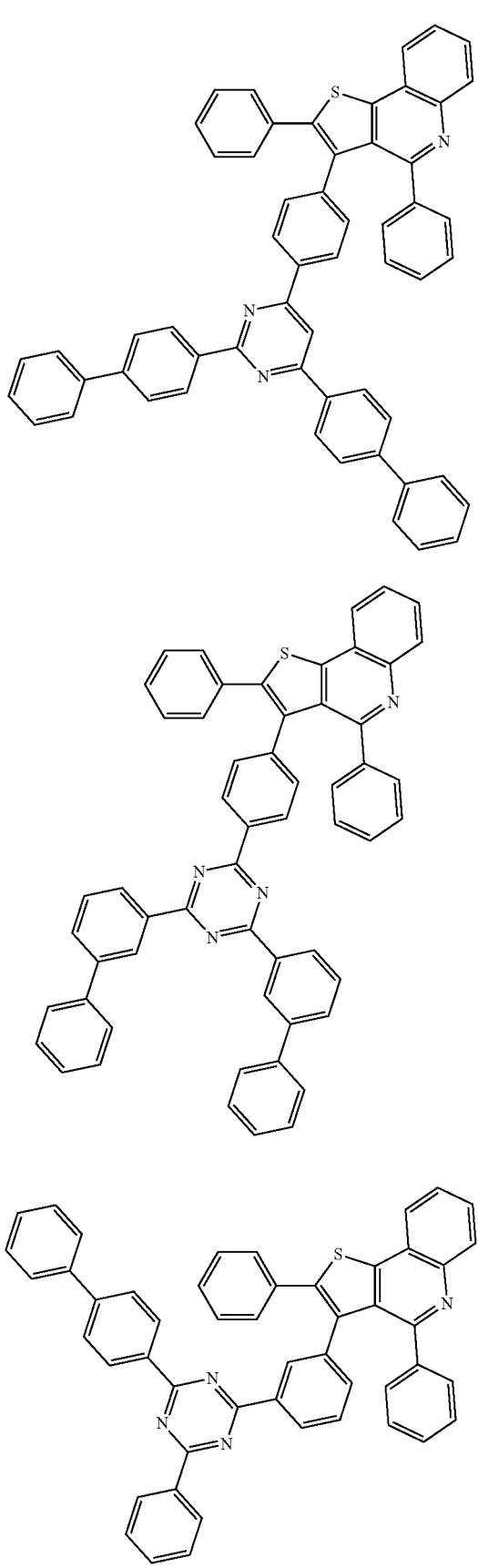
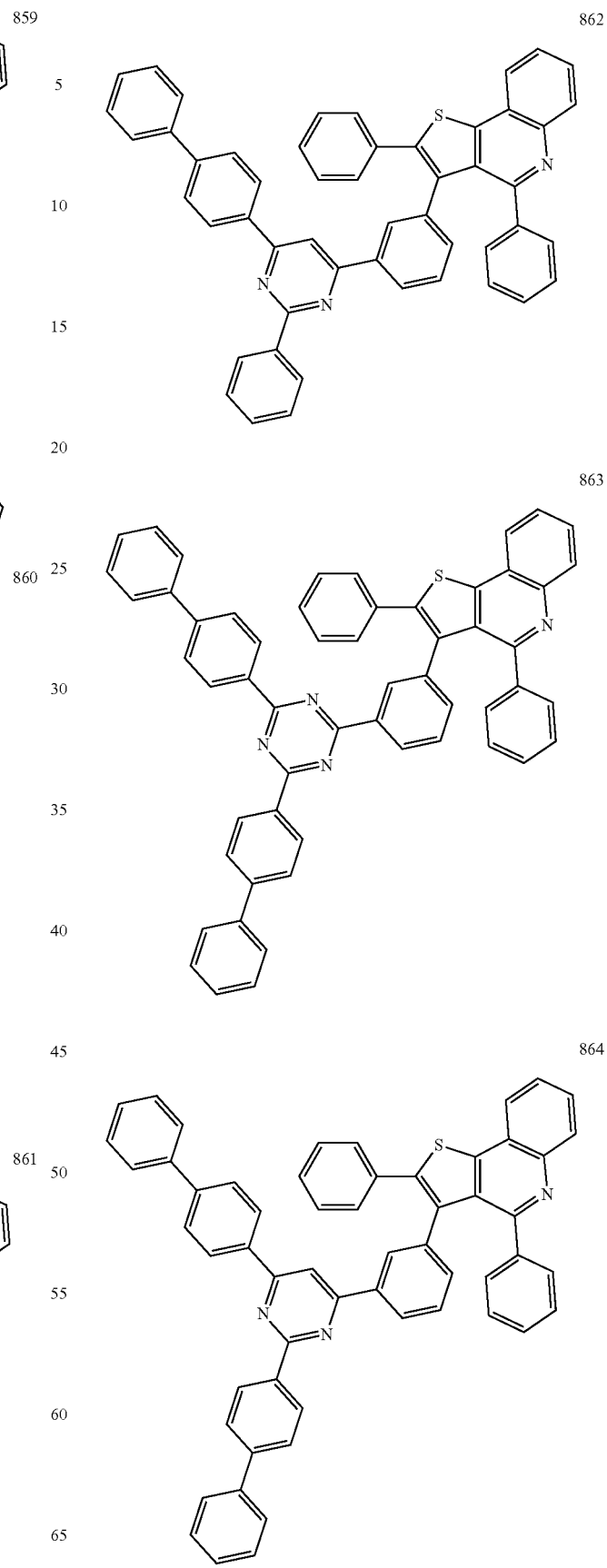

347
-continued
865
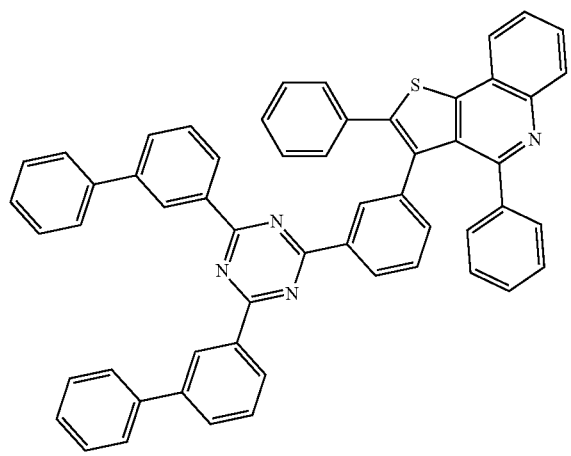
866
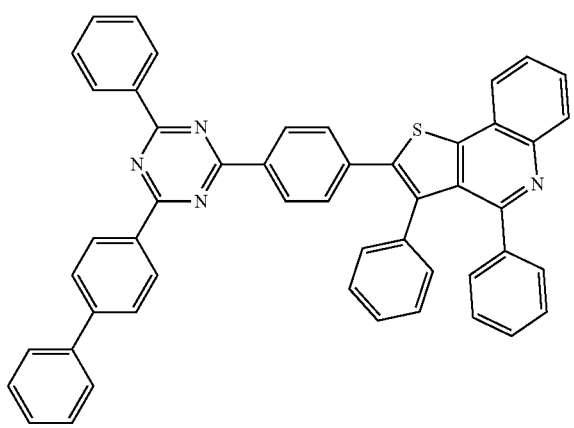
867
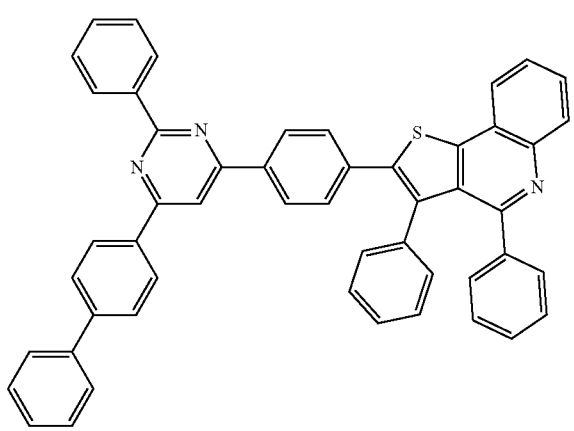
348
-continued
868
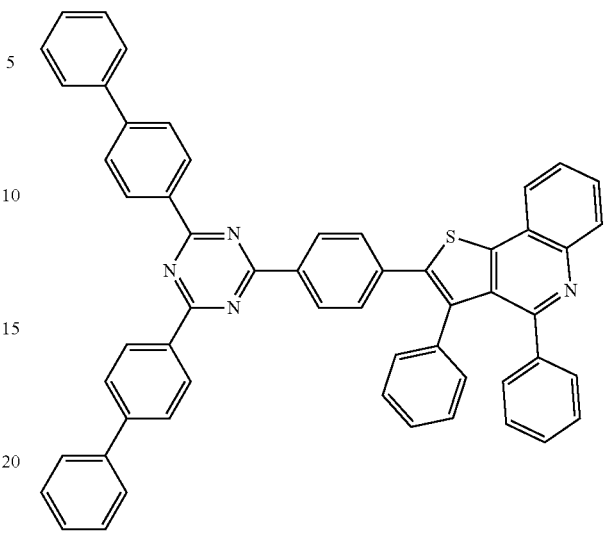
869
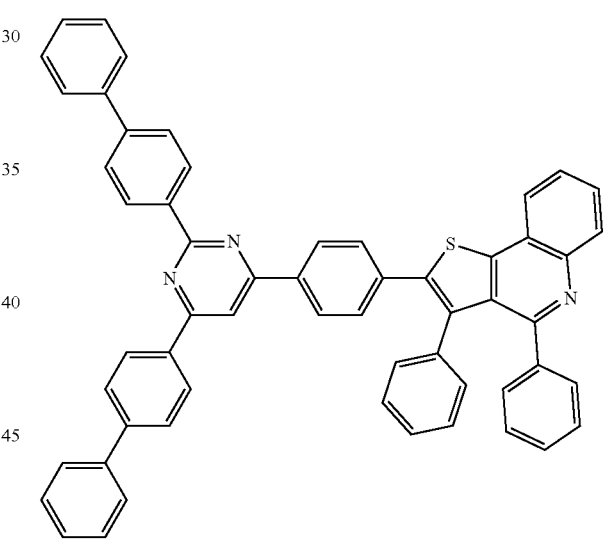
870
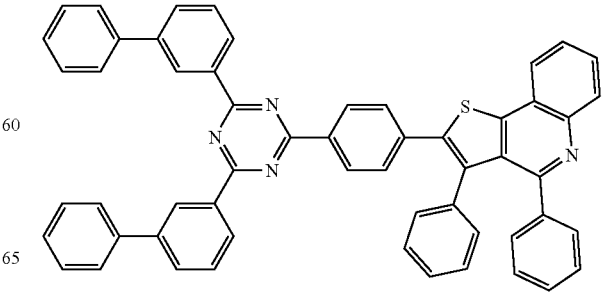

871
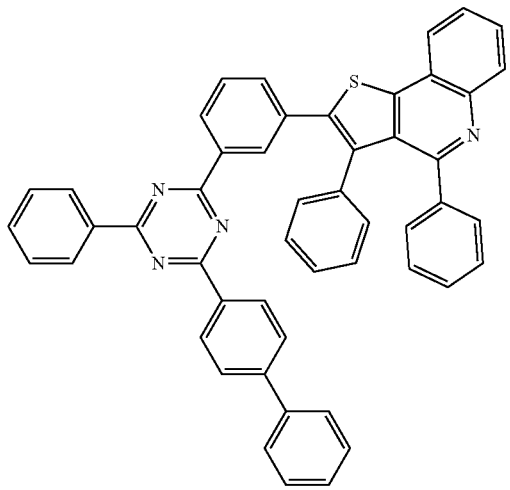
872
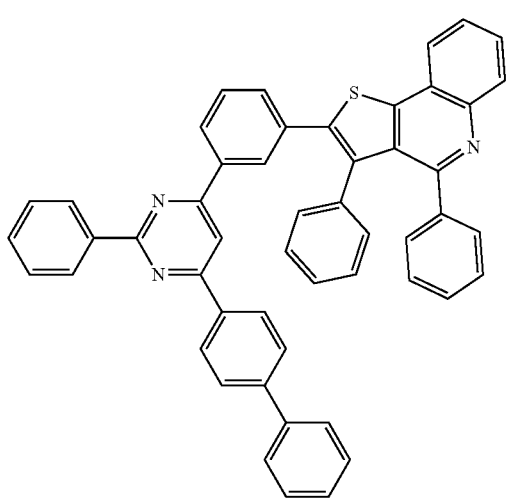
873
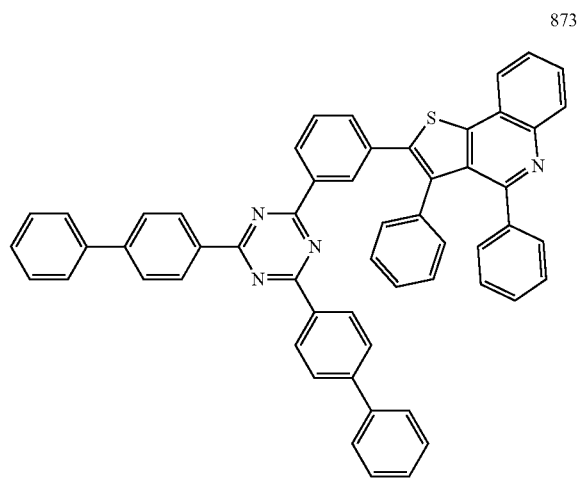
874
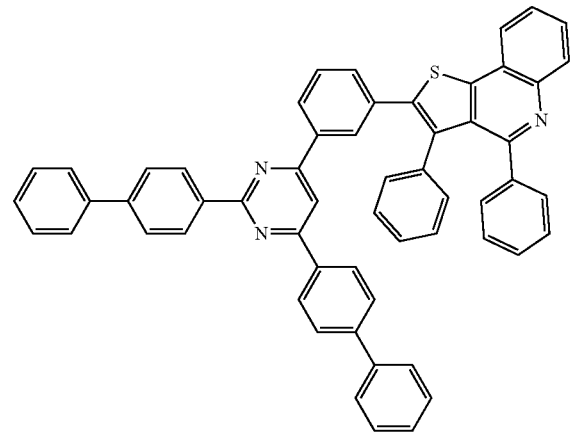
875
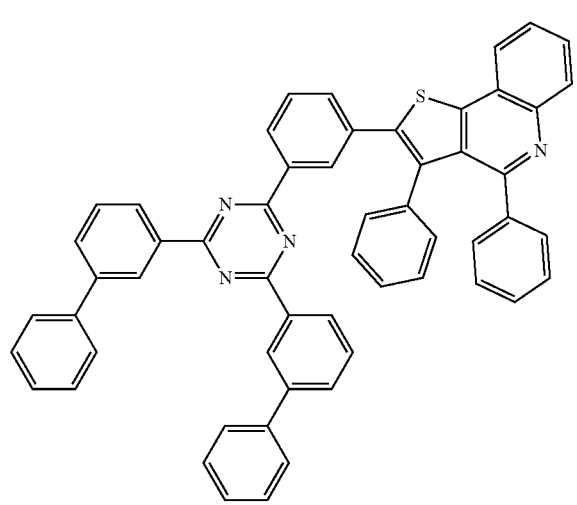
876
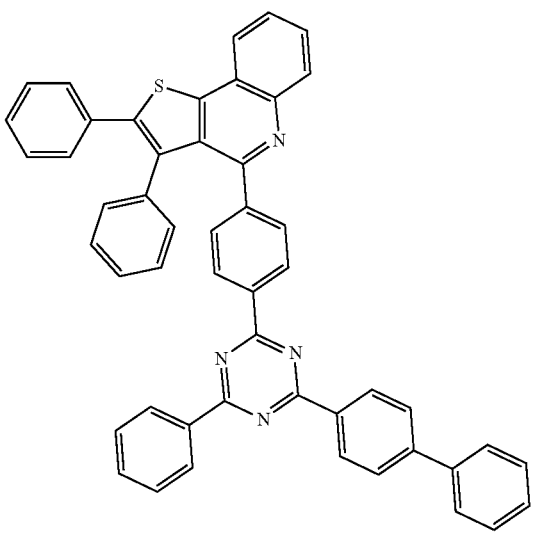

-continued
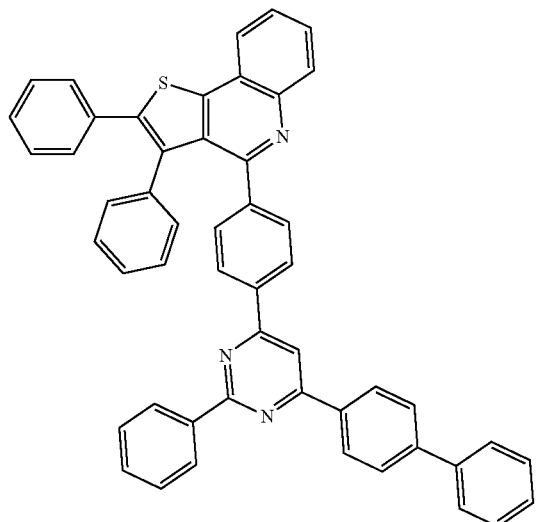
877
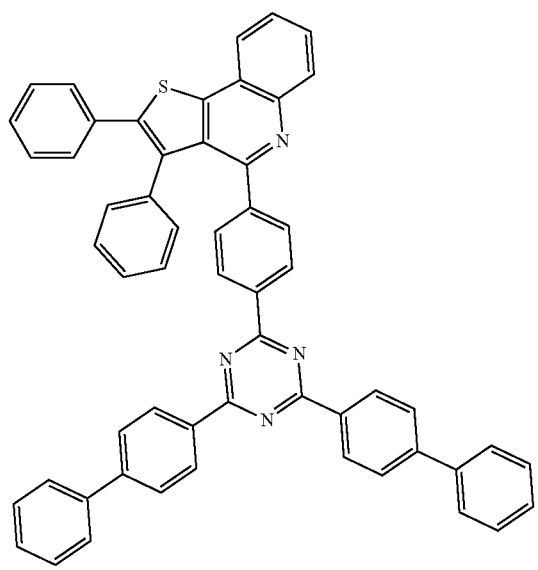
878
-continued
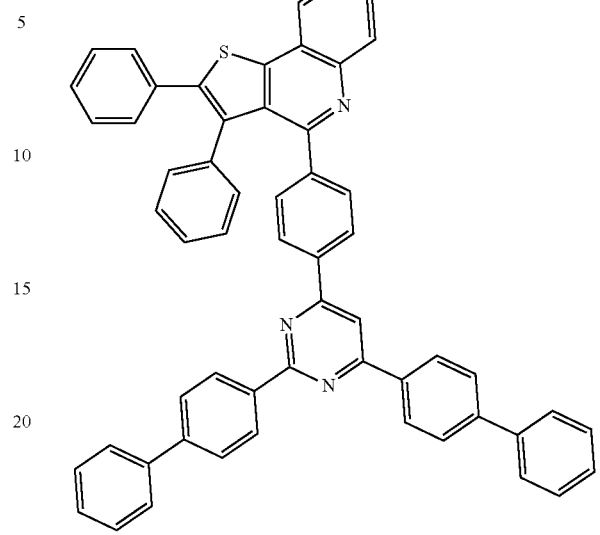
879
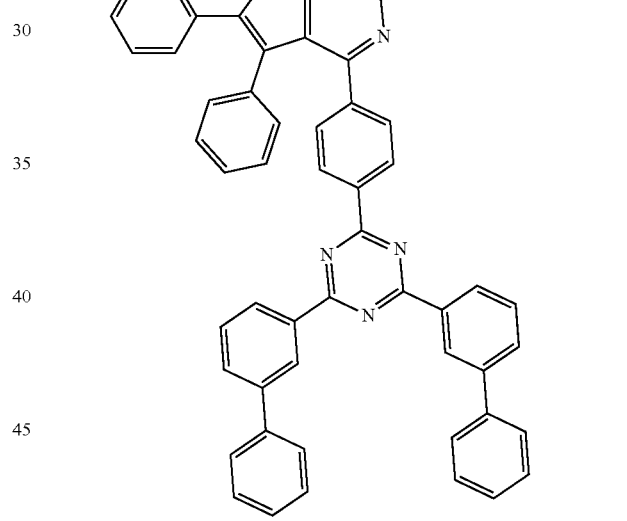
880
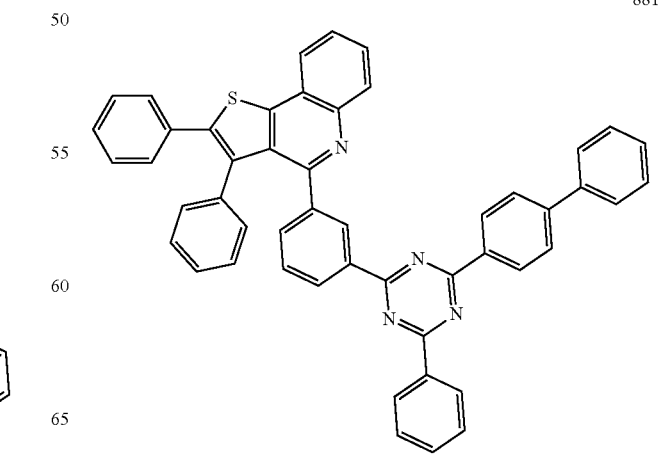
881

882
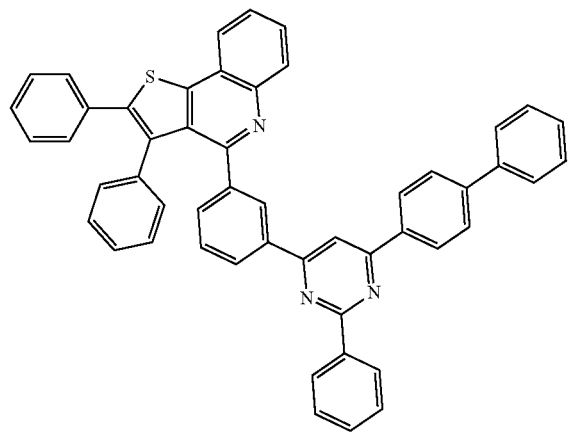
883
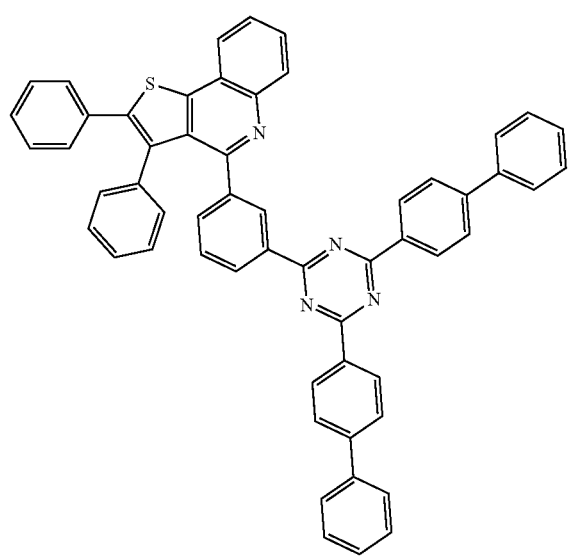
884
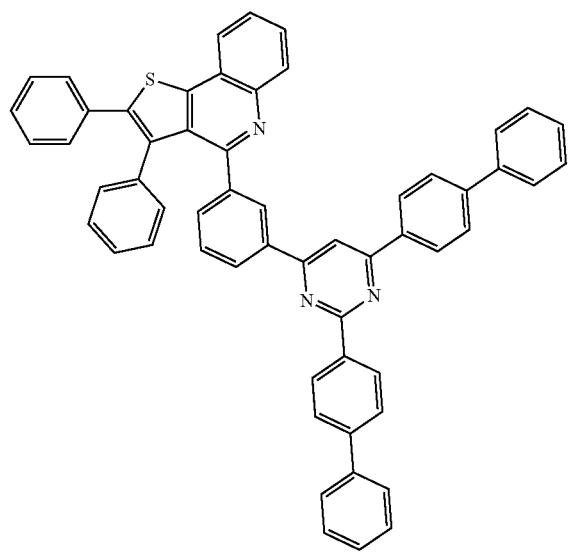
885
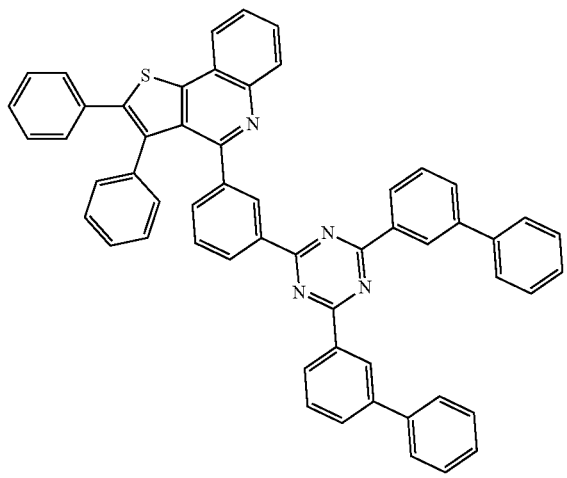
886
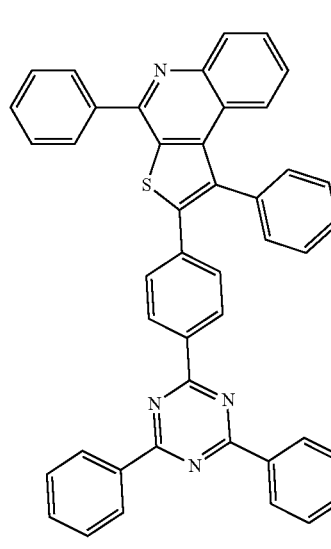
887
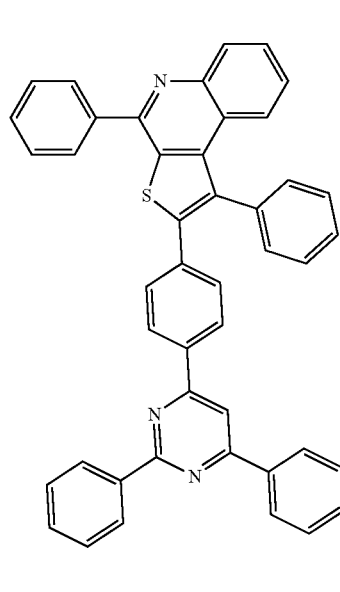

355
-continued
888
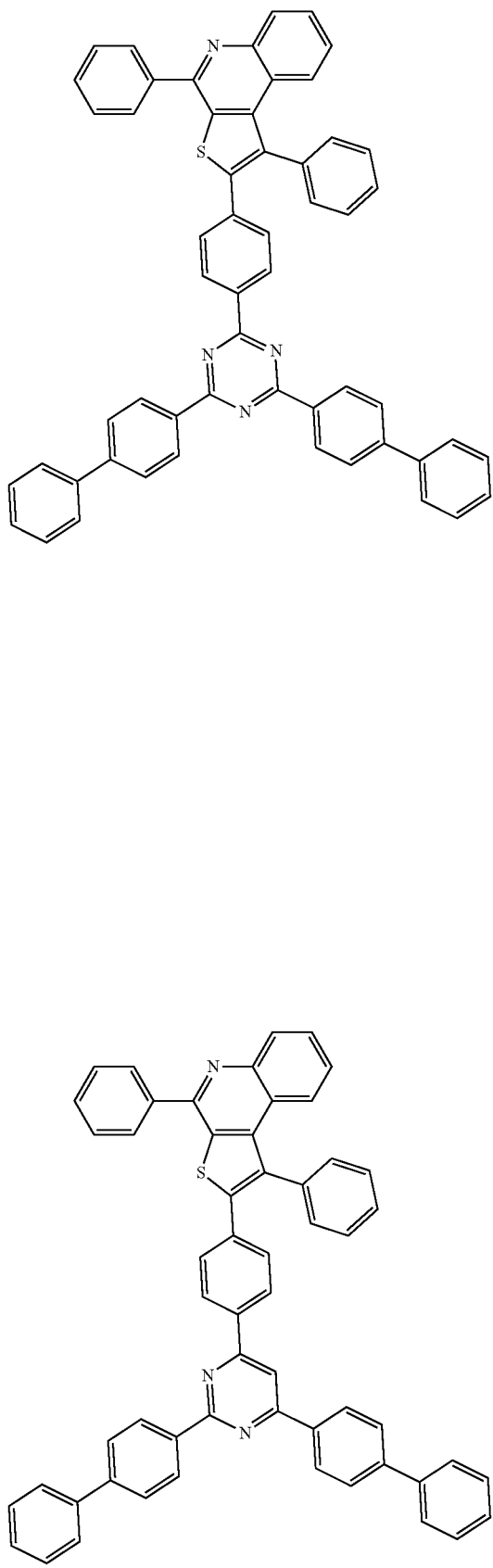
889
356
-continued
890
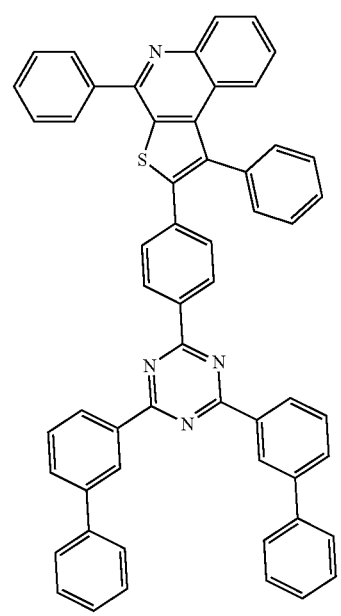
891
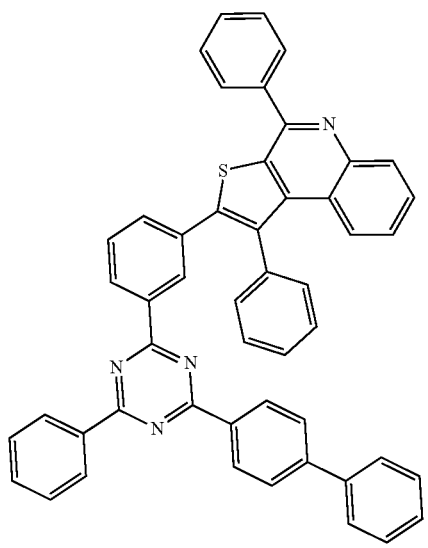

357
-continued
892
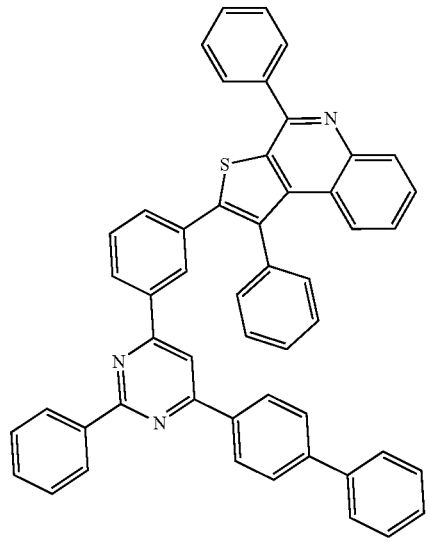
893
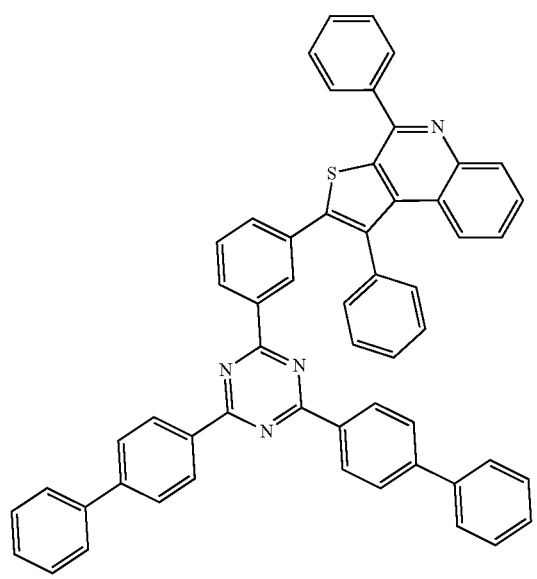
358
-continued
894
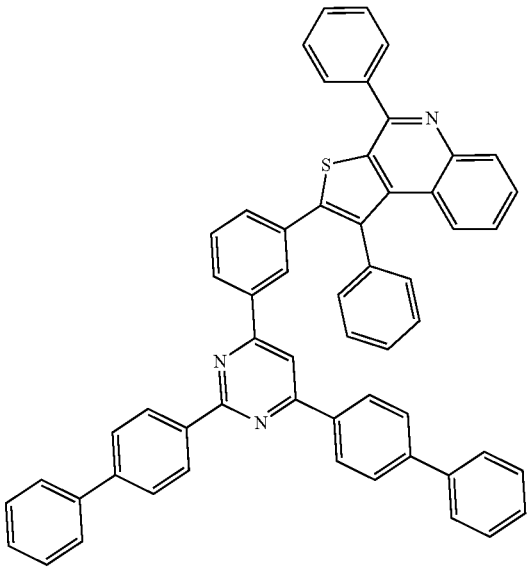
895
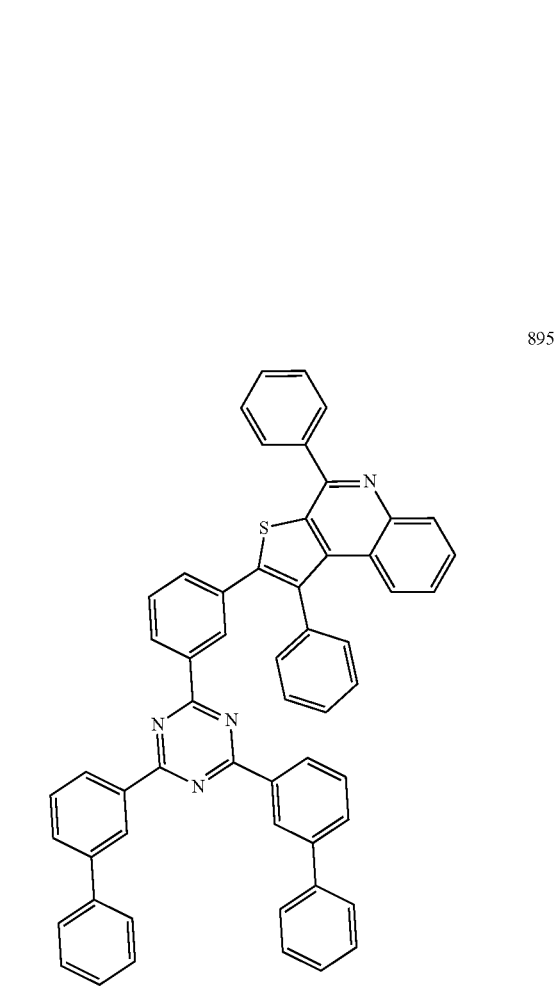

359
-continued
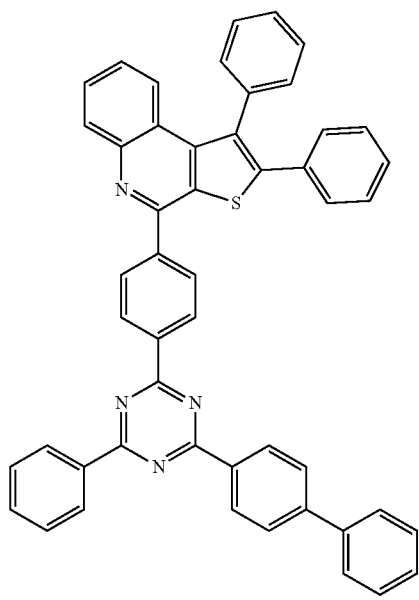
896
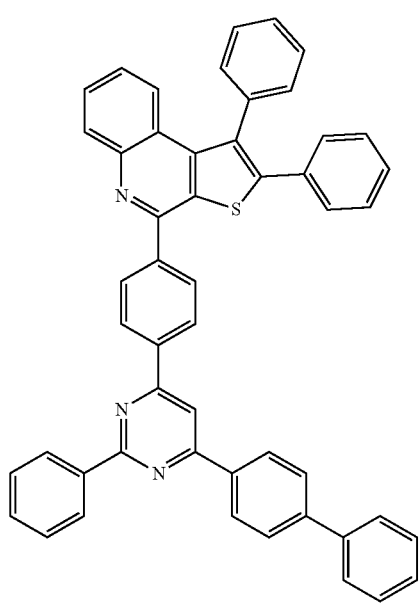
897
360
-continued
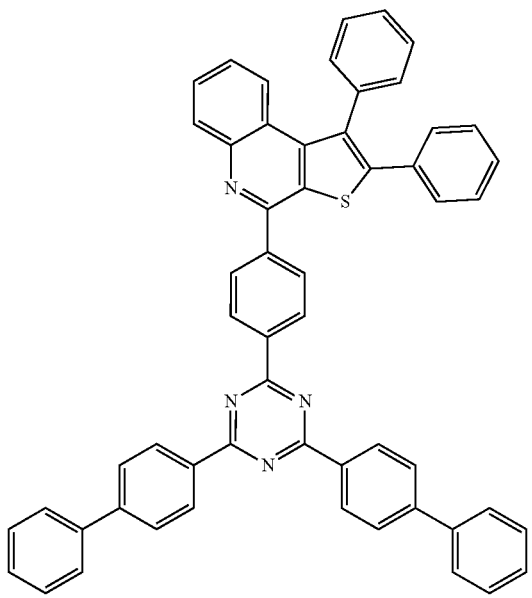
898
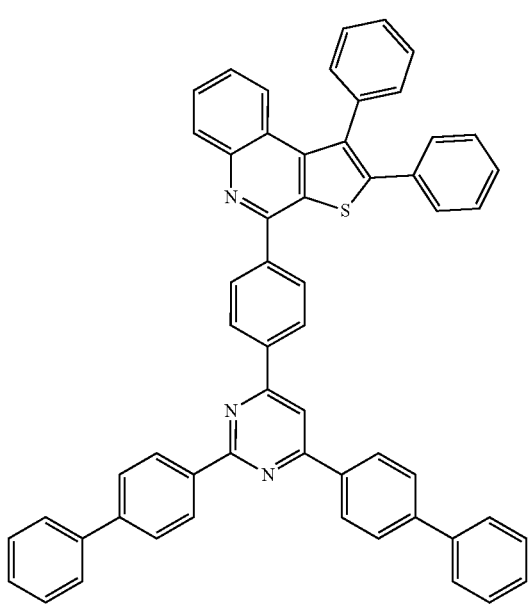
899

361
-continued
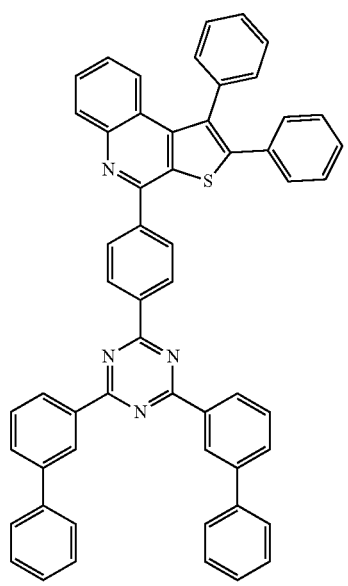
900
901
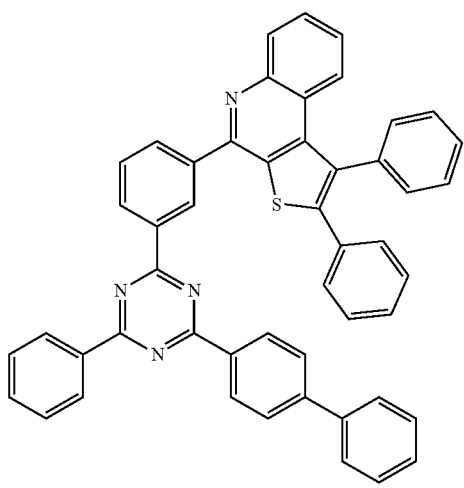
902
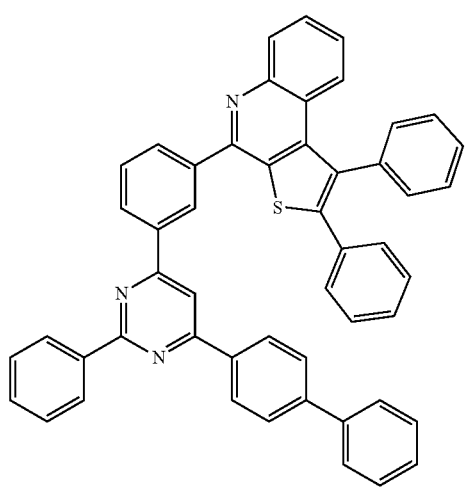
362
-continued
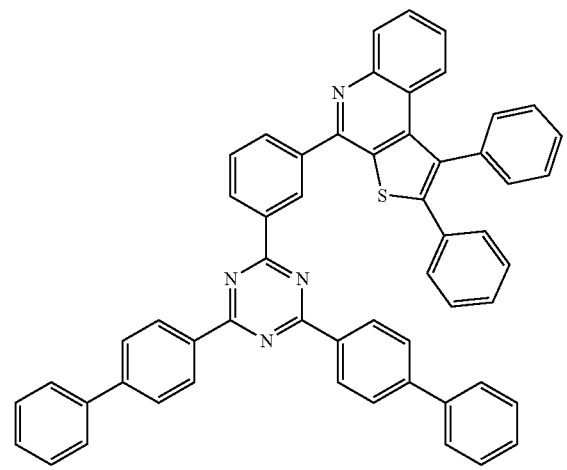
903
904
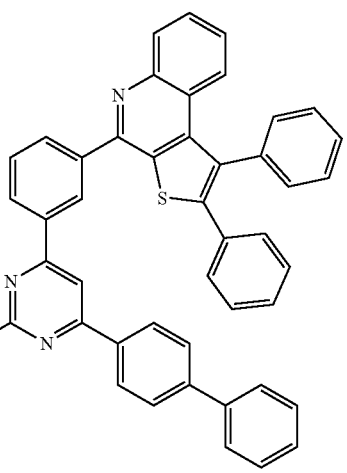
905
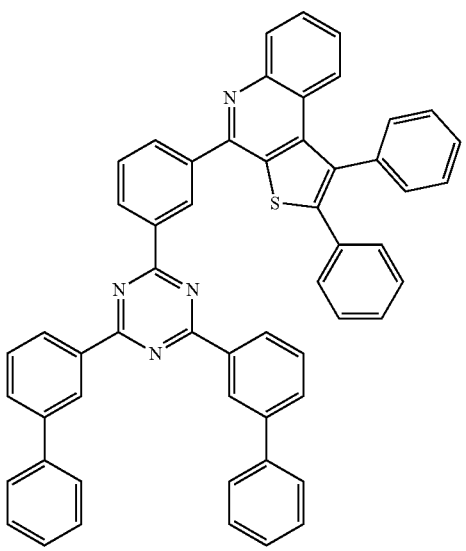

-continued
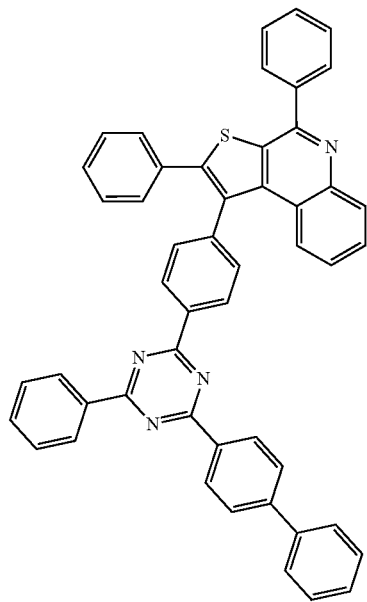
906
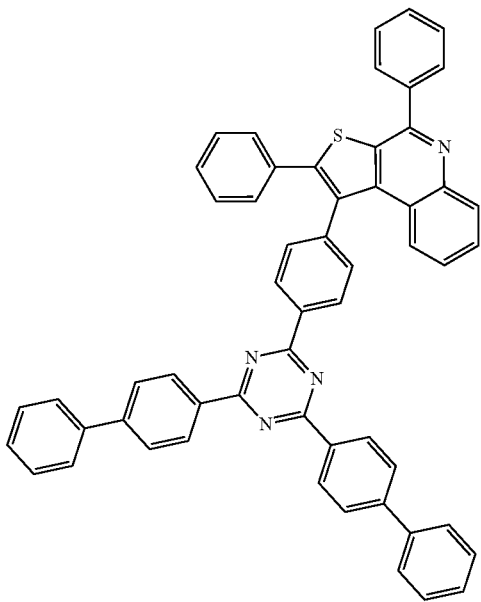
908
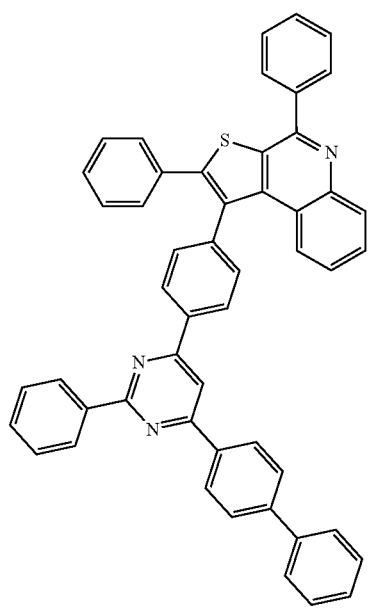
907
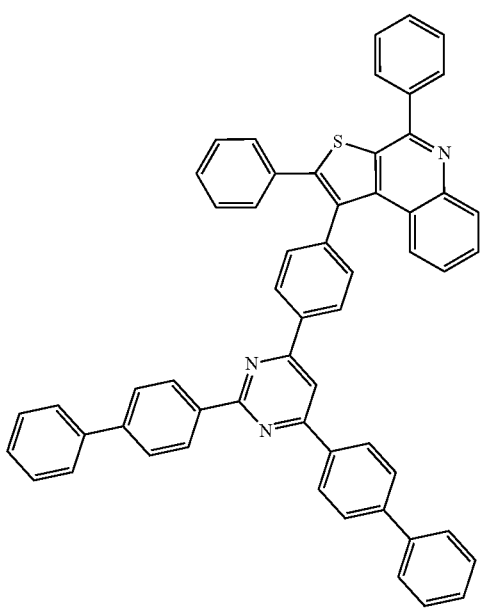
909

365
-continued
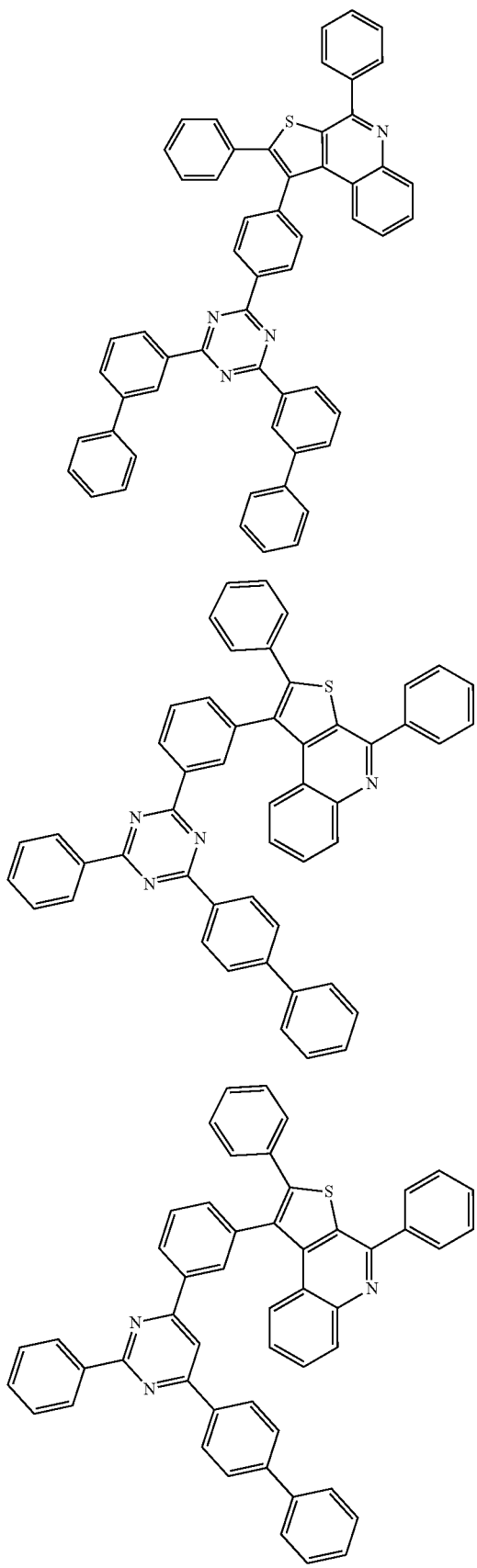
366
-continued
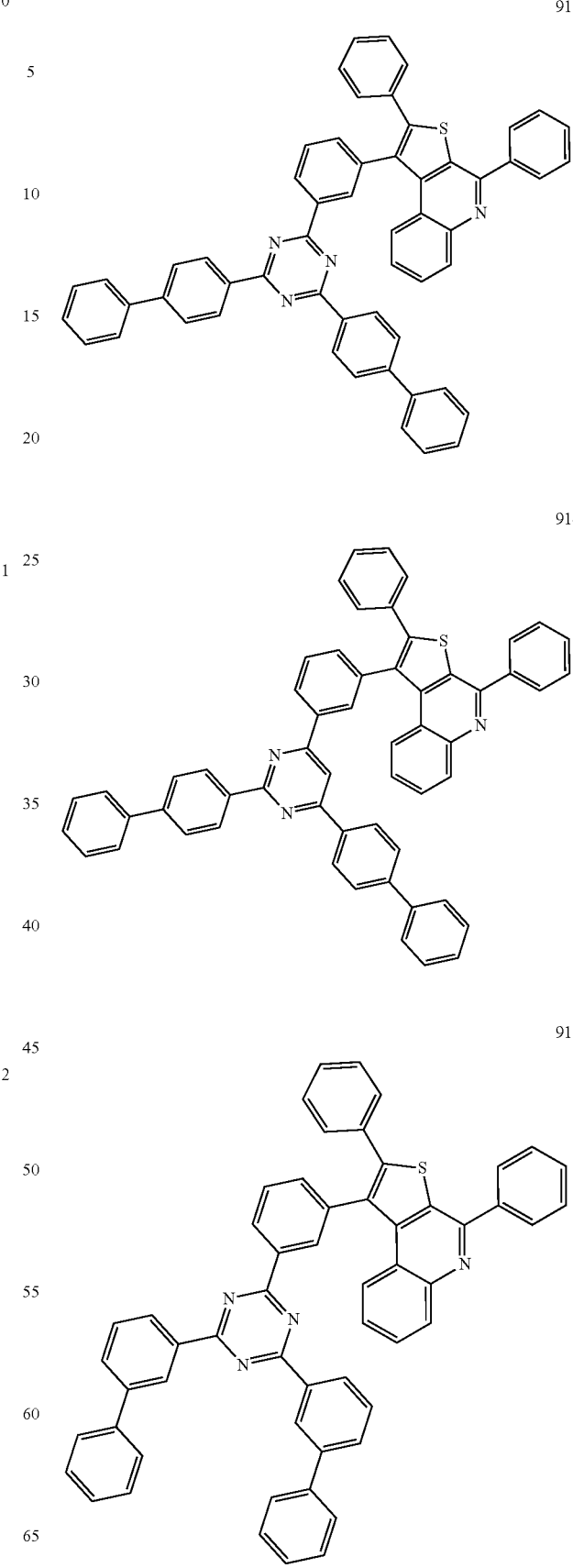

367
-continued
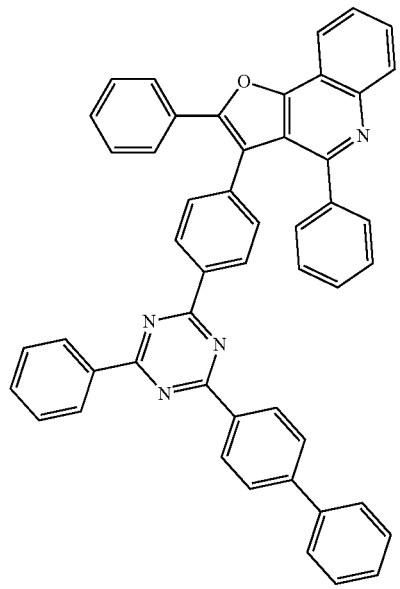
916
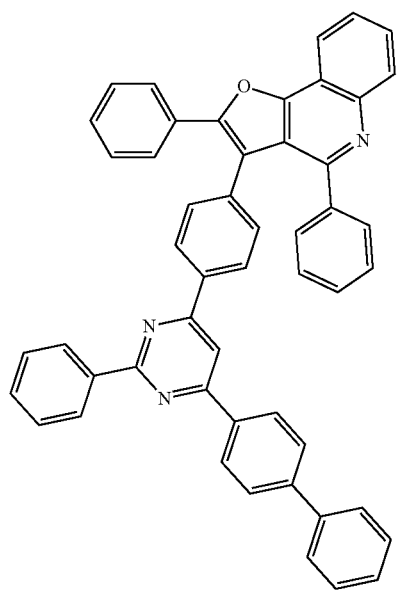
917
368
-continued
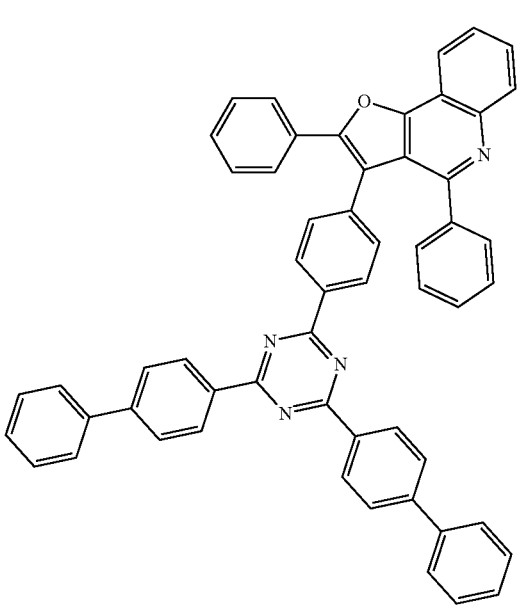
918
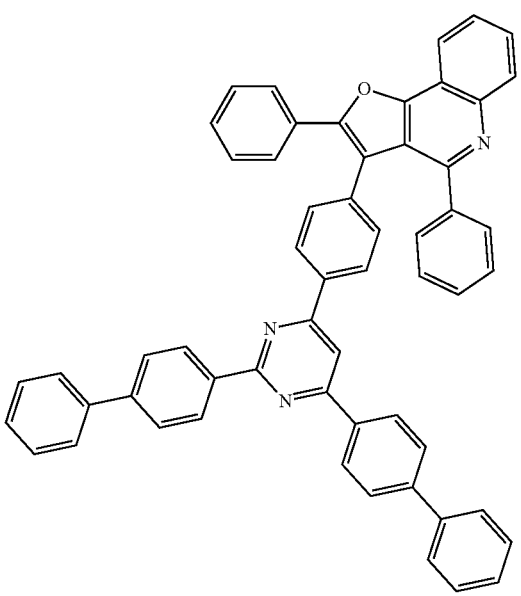
919

-continued
920
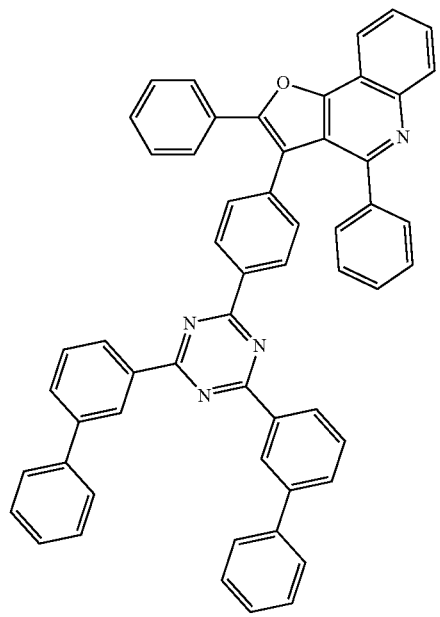
921
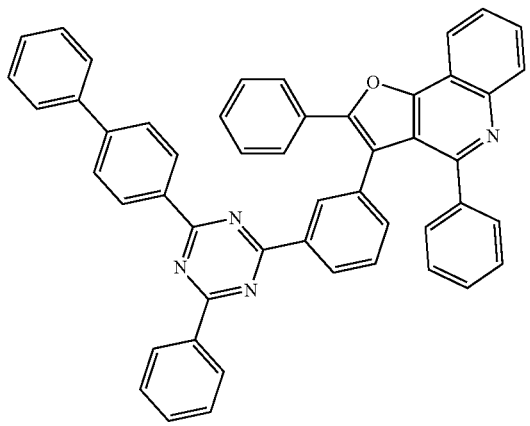
922
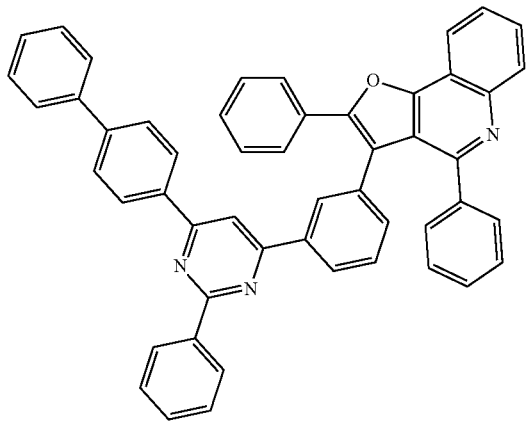
-continued
923
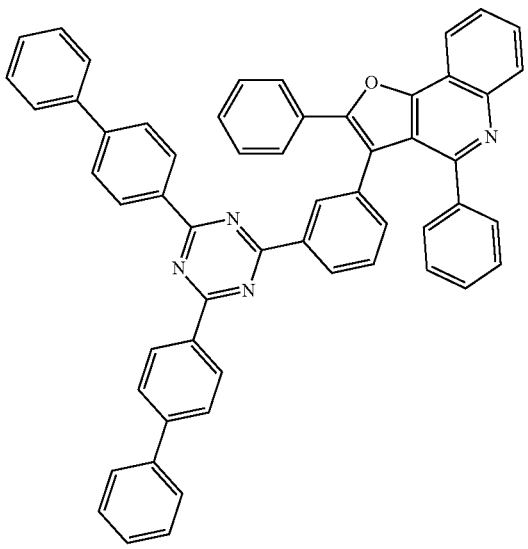
924
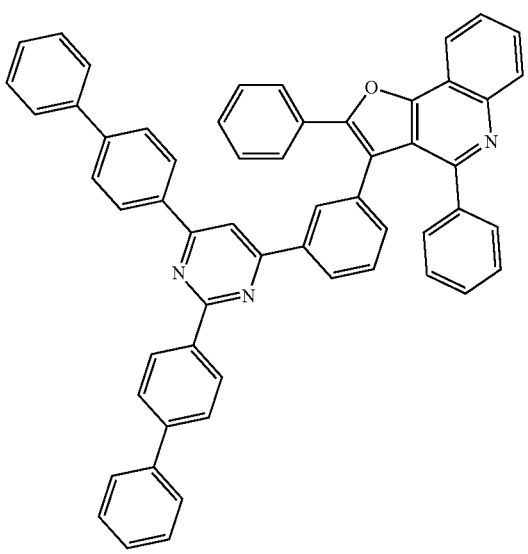
925
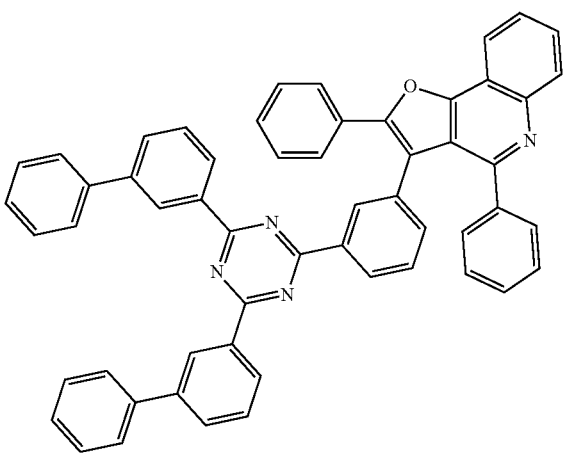

-continued
926
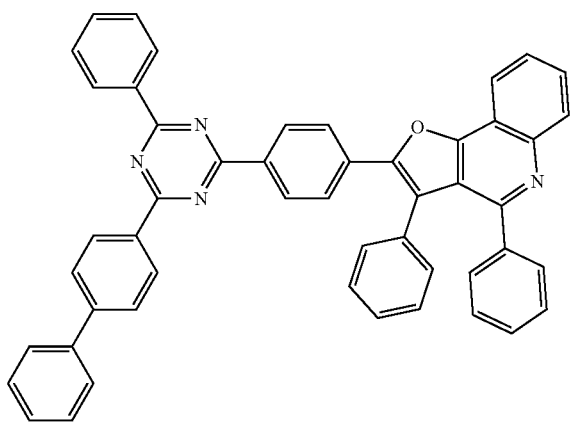
927
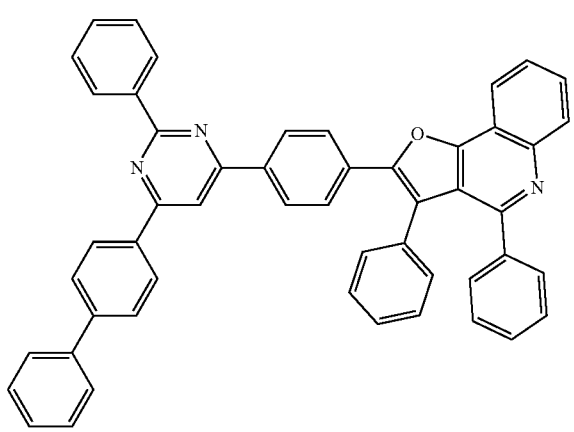
928
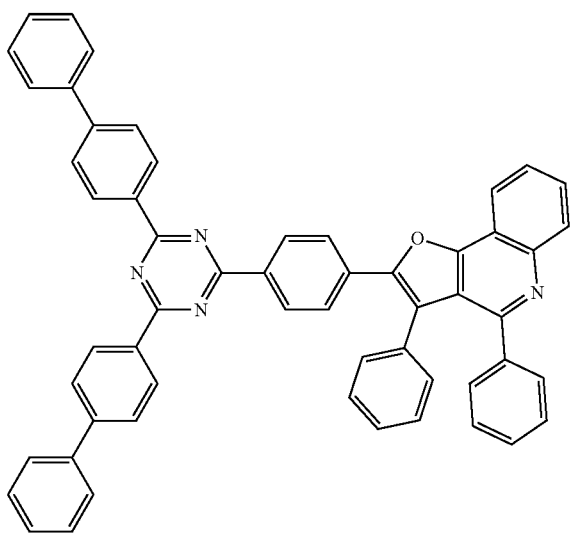
-continued
929
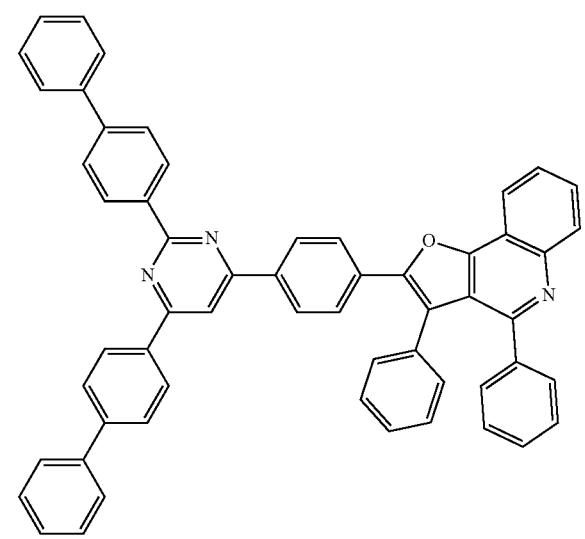
930
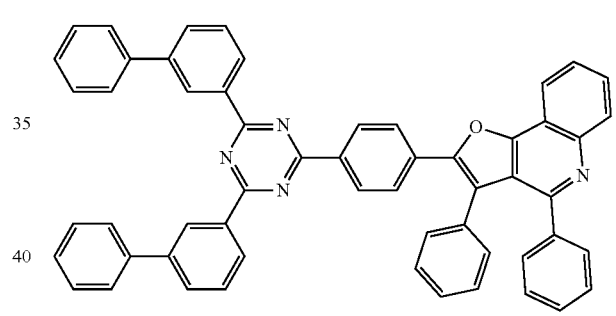
931
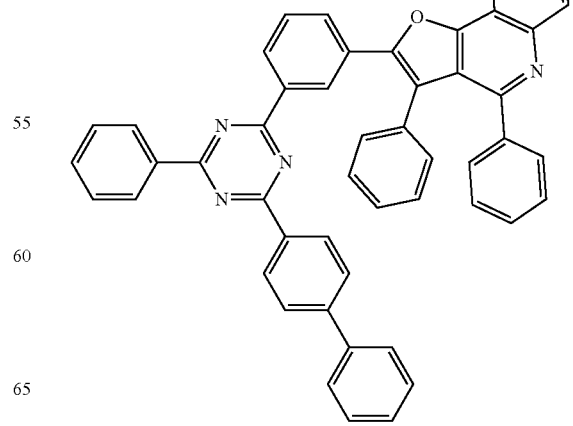

-continued
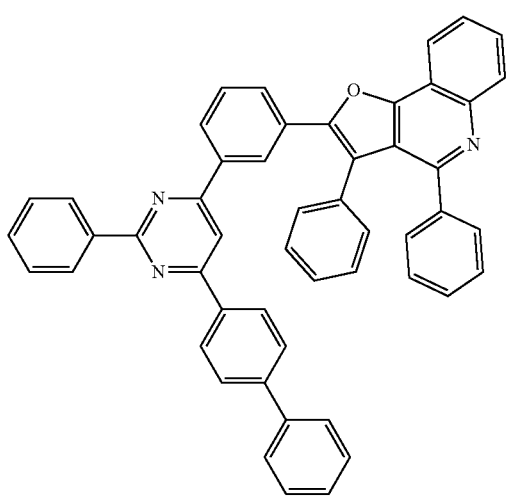
932
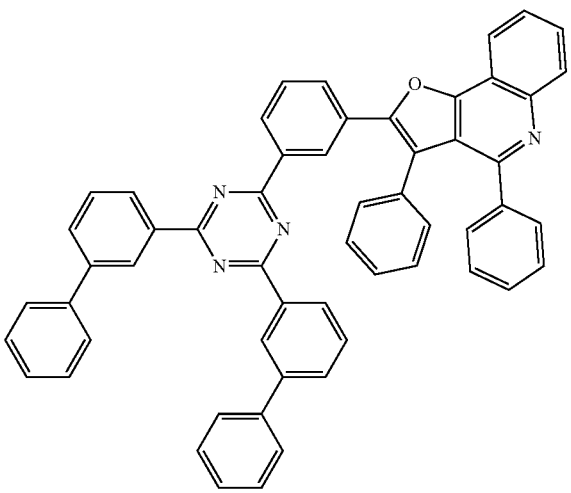
935
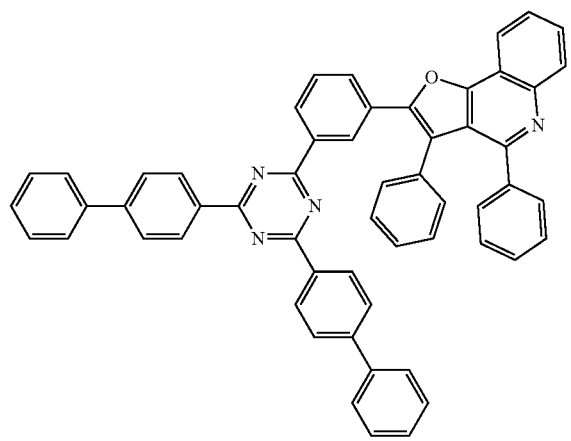
933
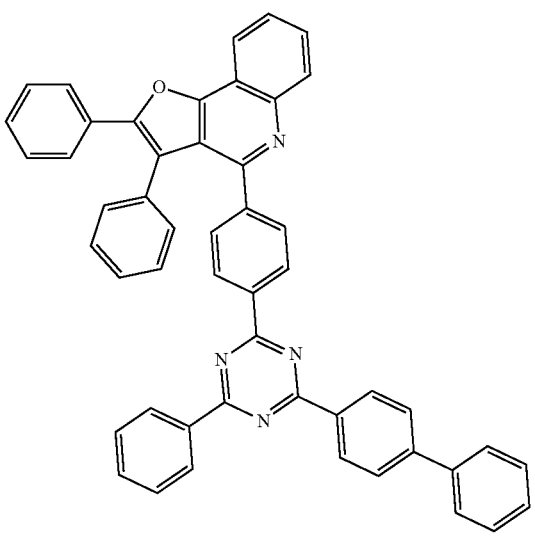
936
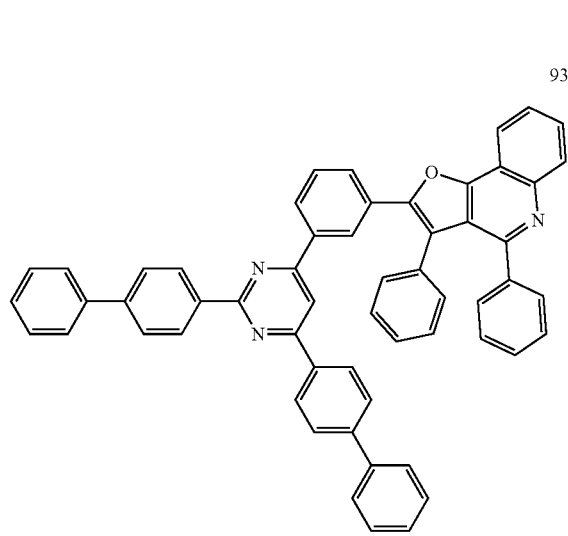
934
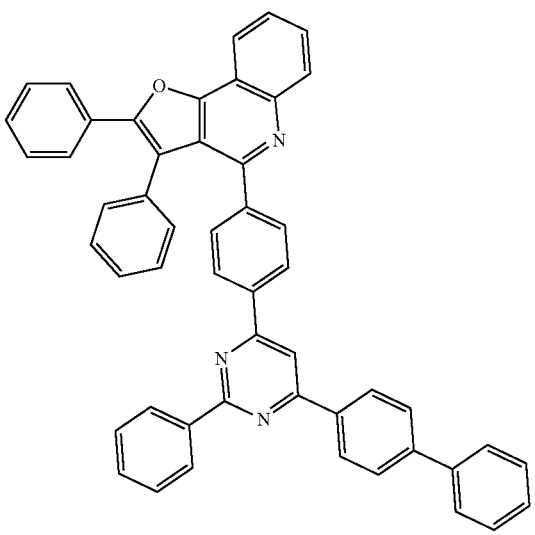
937

938
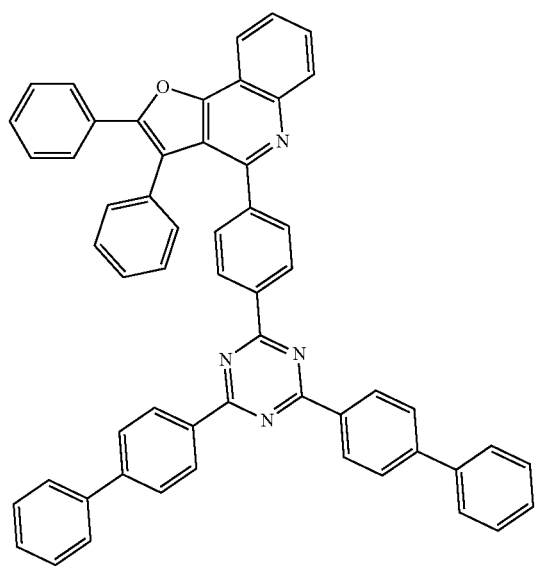
939
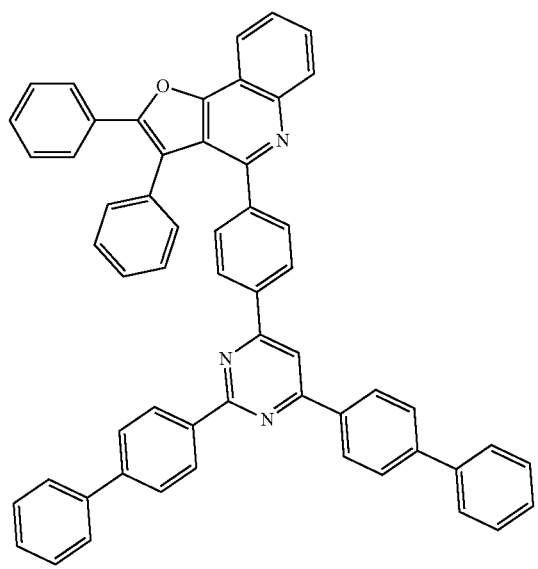
940
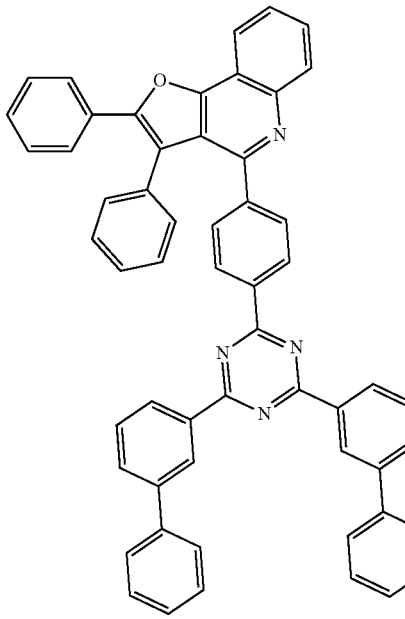
941
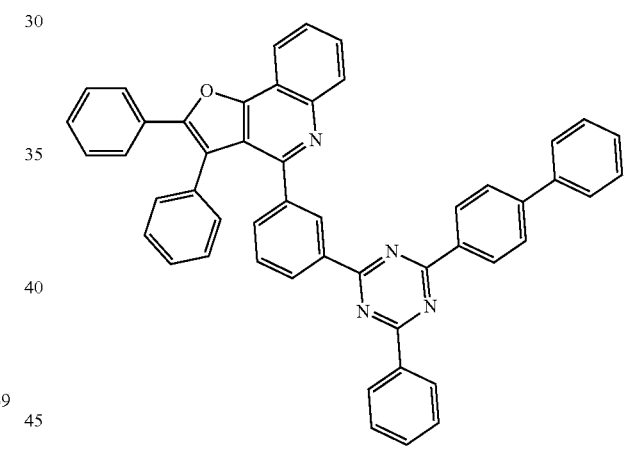
942
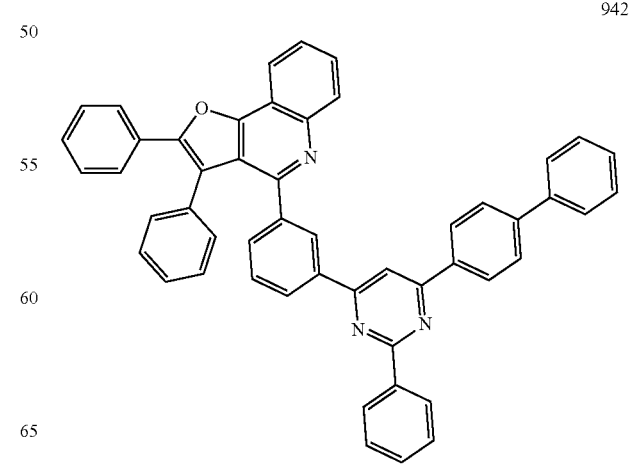

943
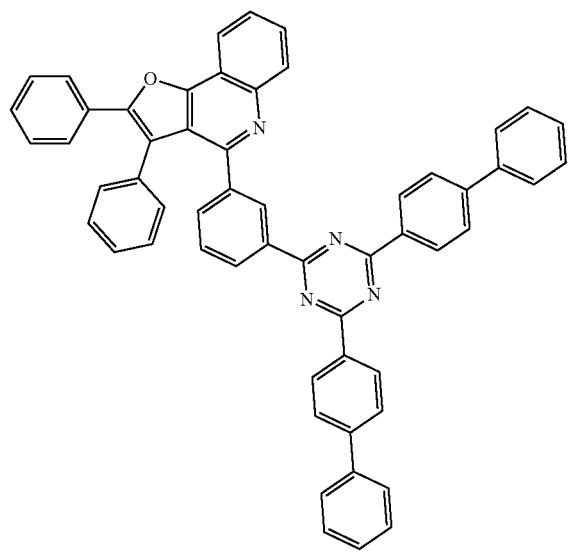
944
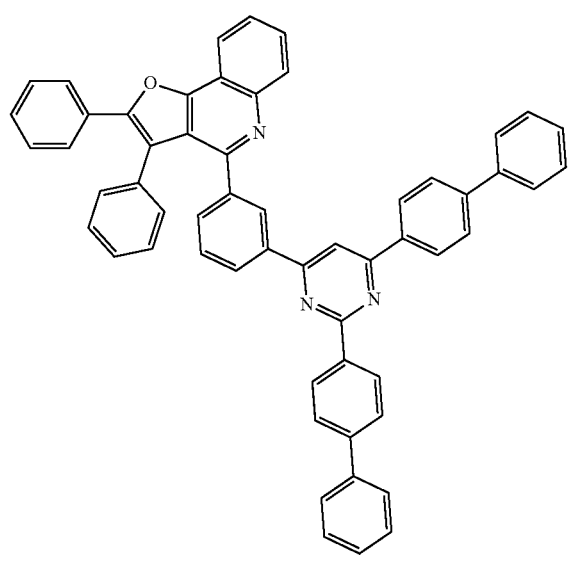
945
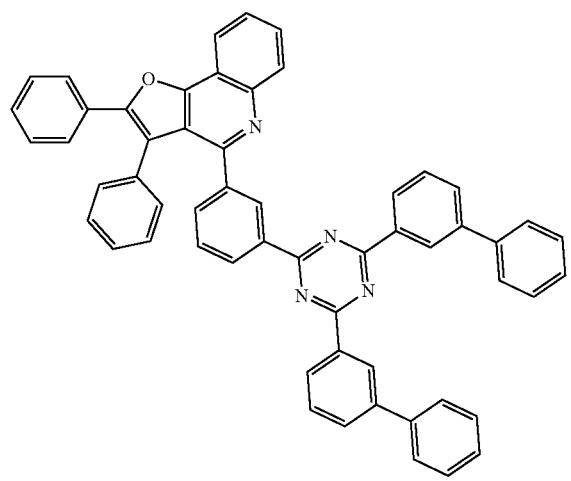
946
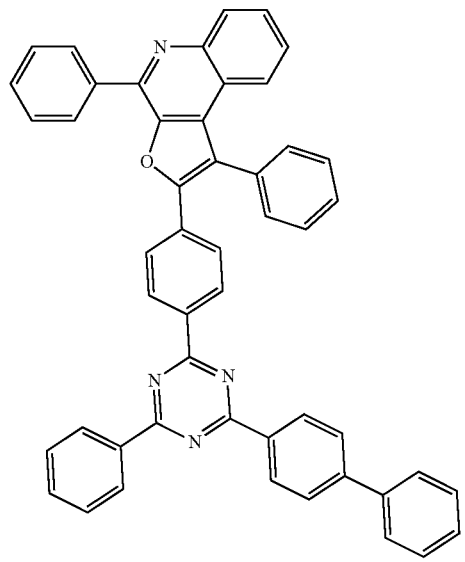
947
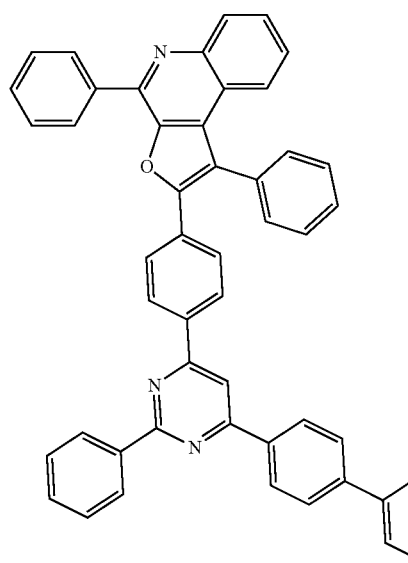

379
-continued
948
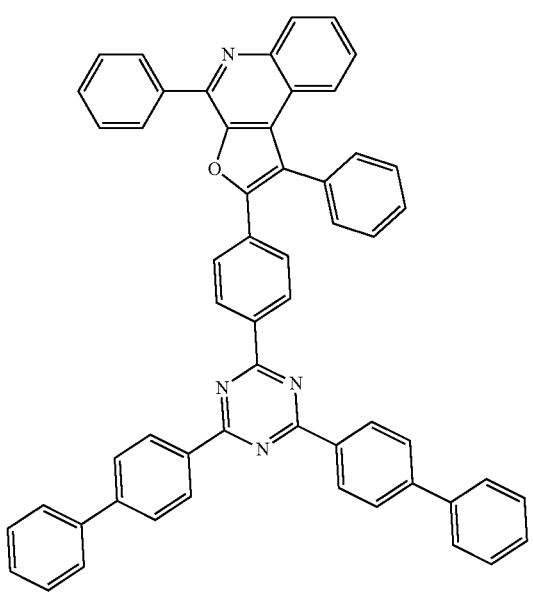
949
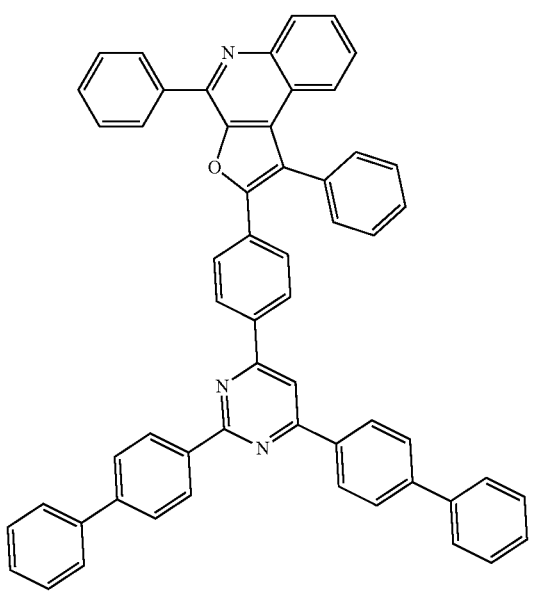
380
-continued
950
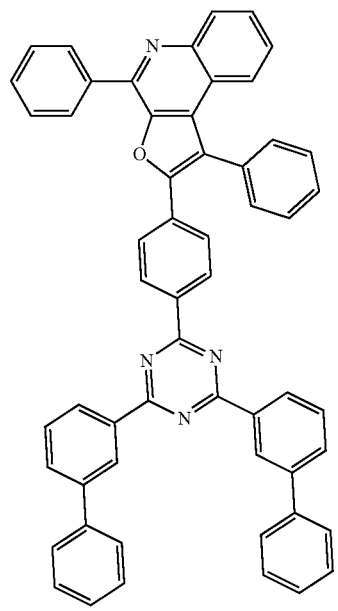
951
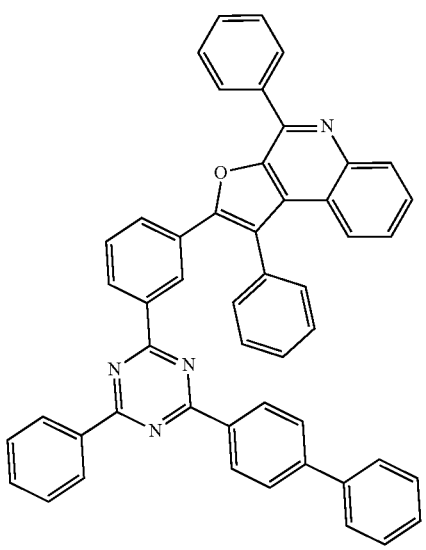

381
-continued
382
-continued
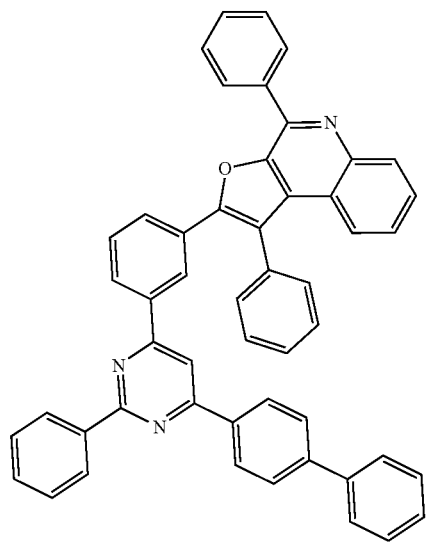
952
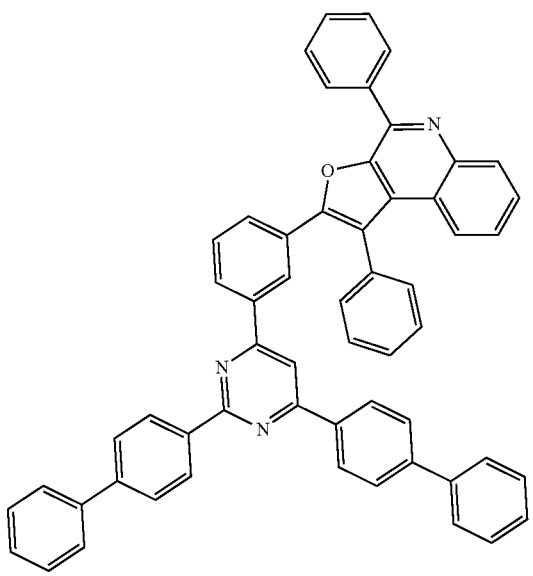
954
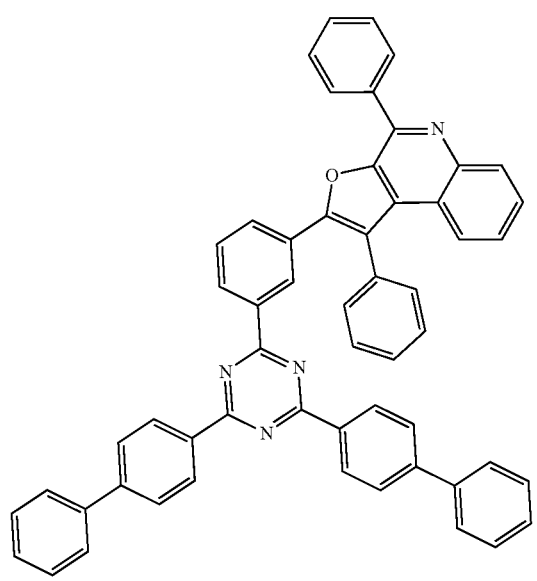
953
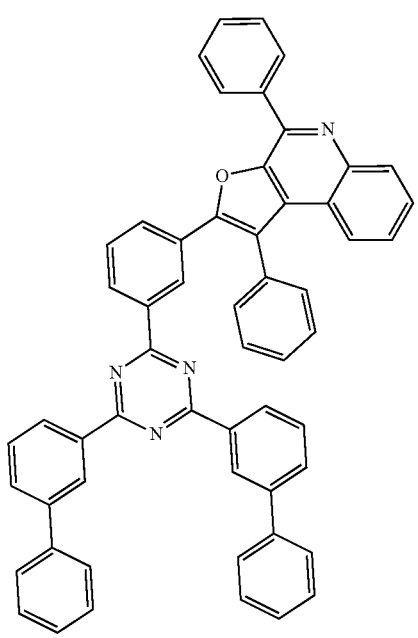
955

-continued
956
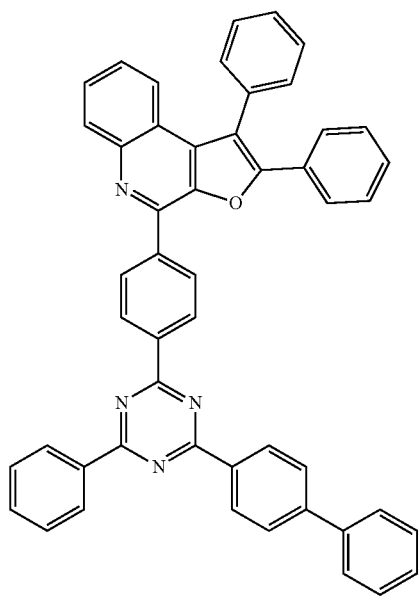
957
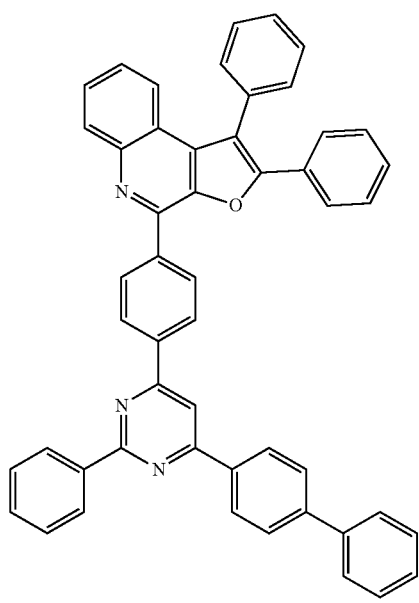
-continued
958
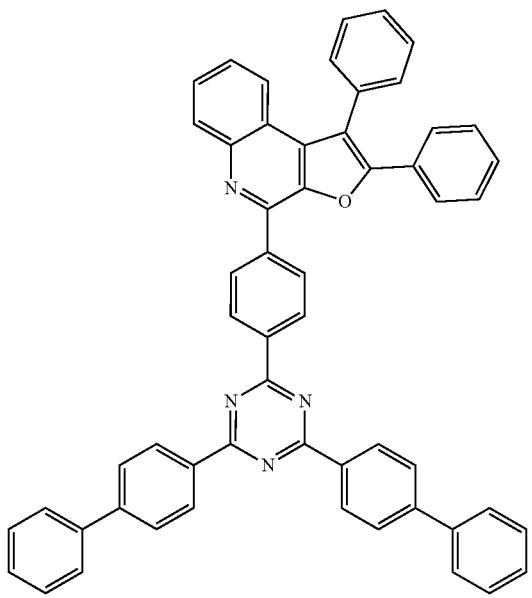
959
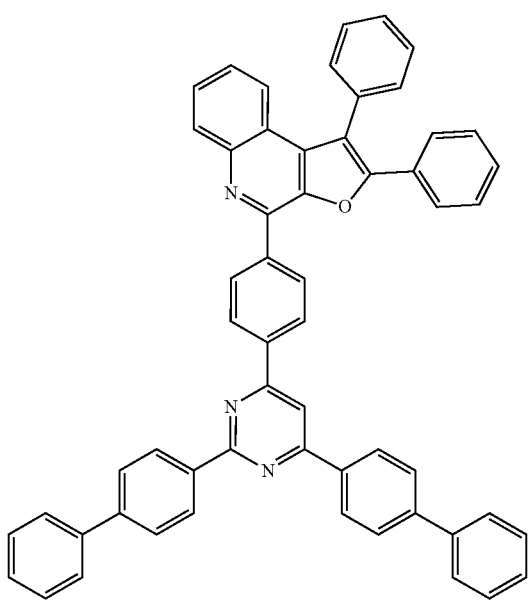

960 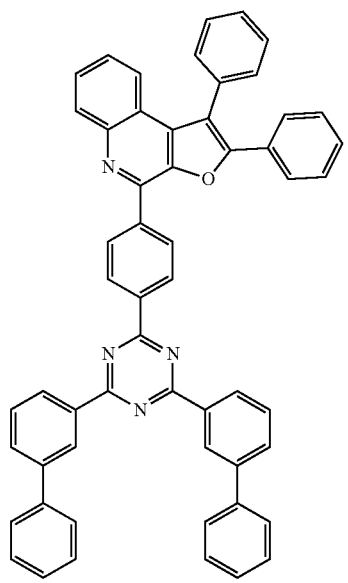
961 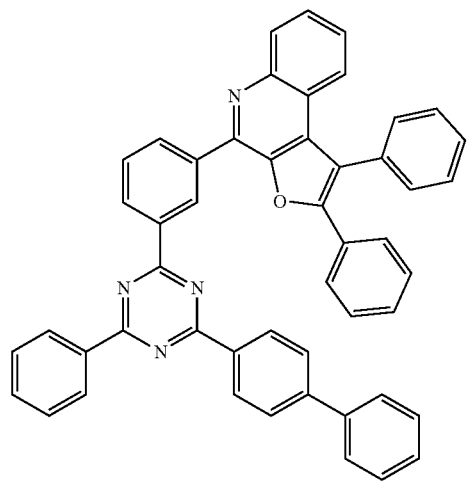
962 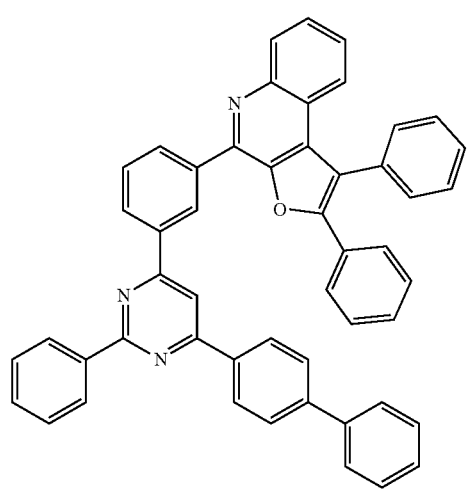
963 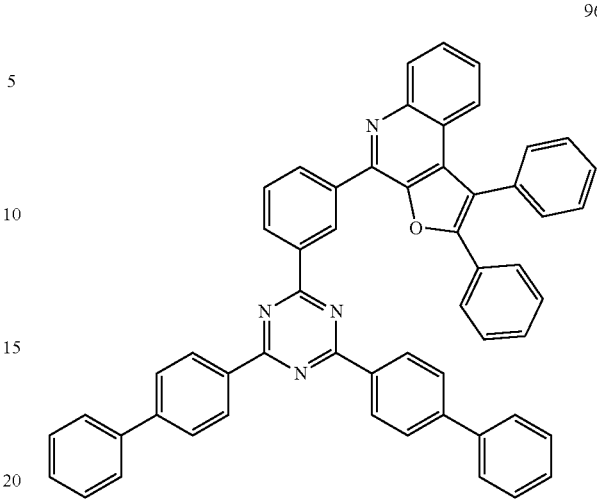
964 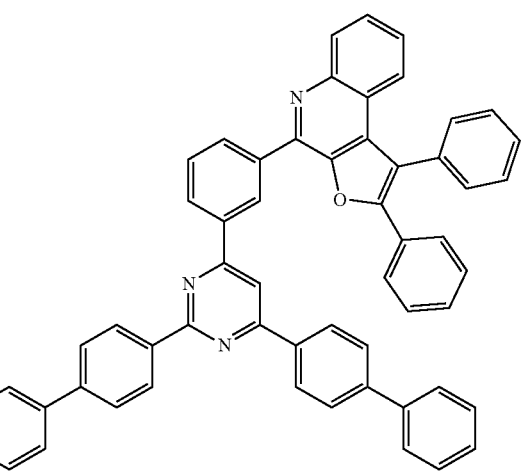
965 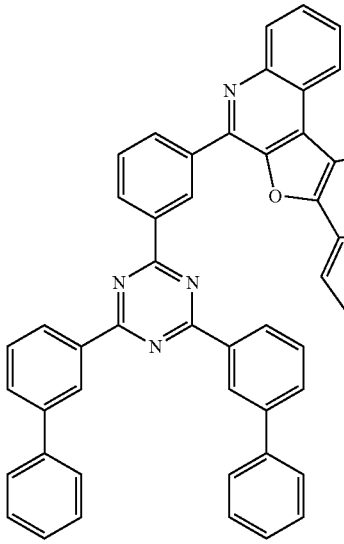

966
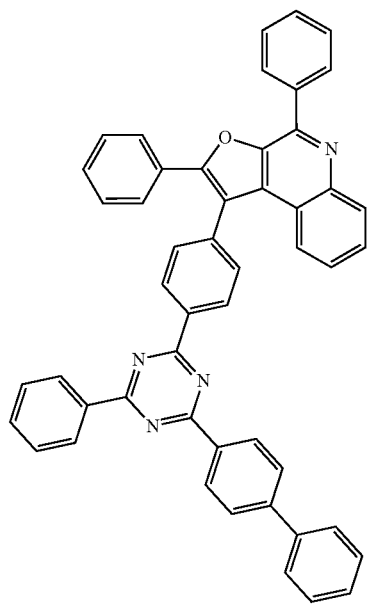
967
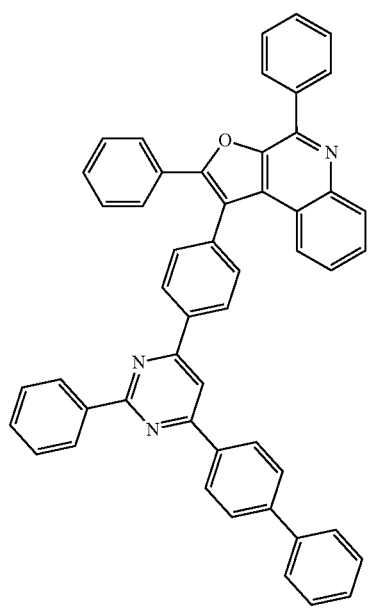
968
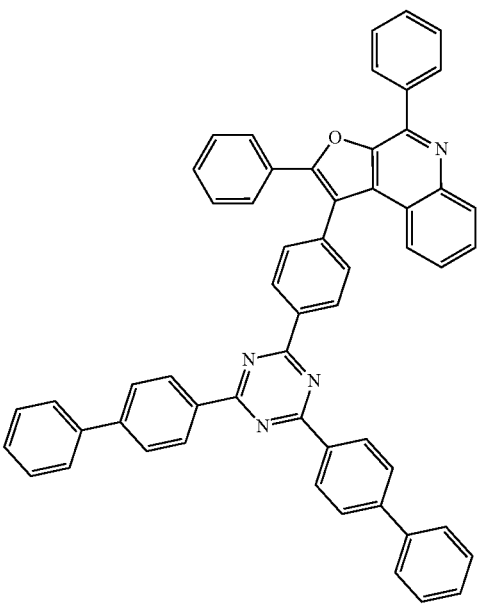
969
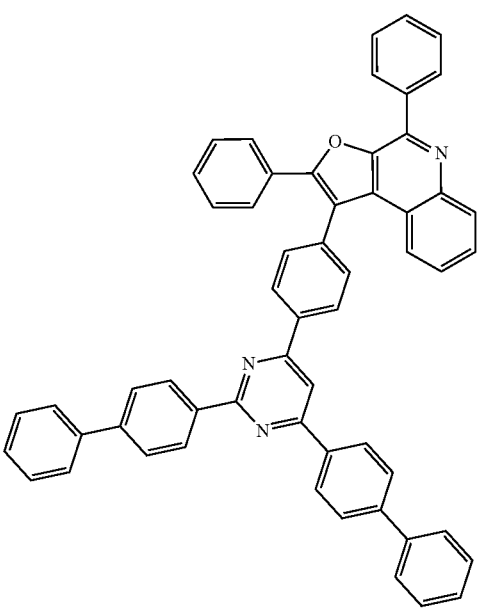

389
-continued
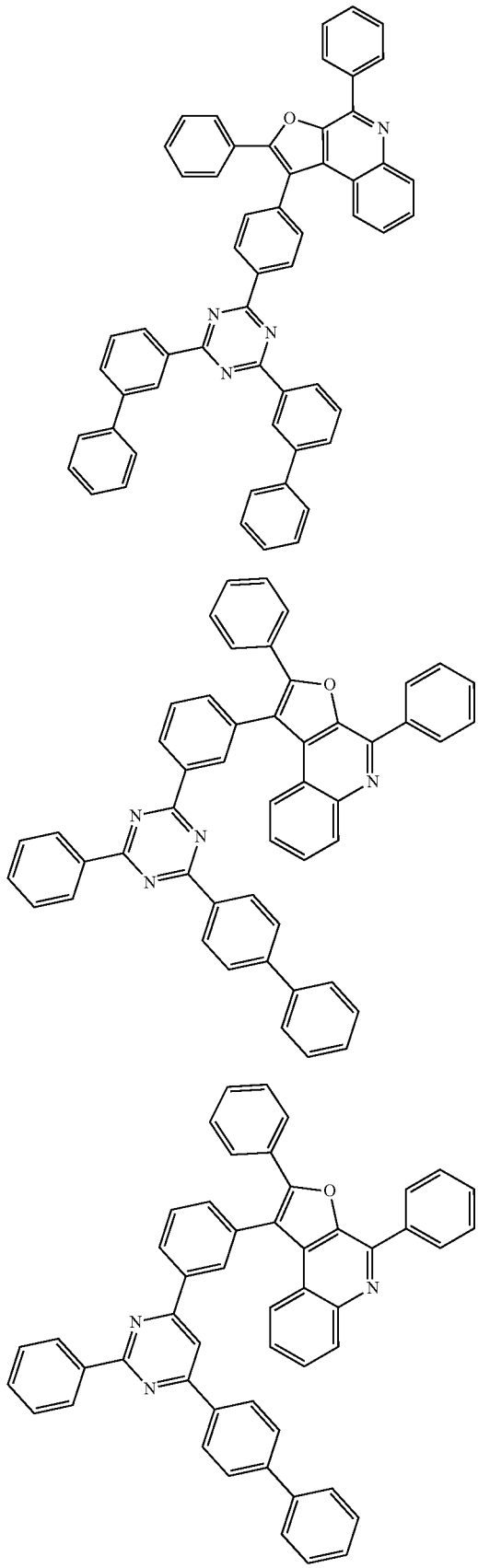
970
971
972
390
-continued
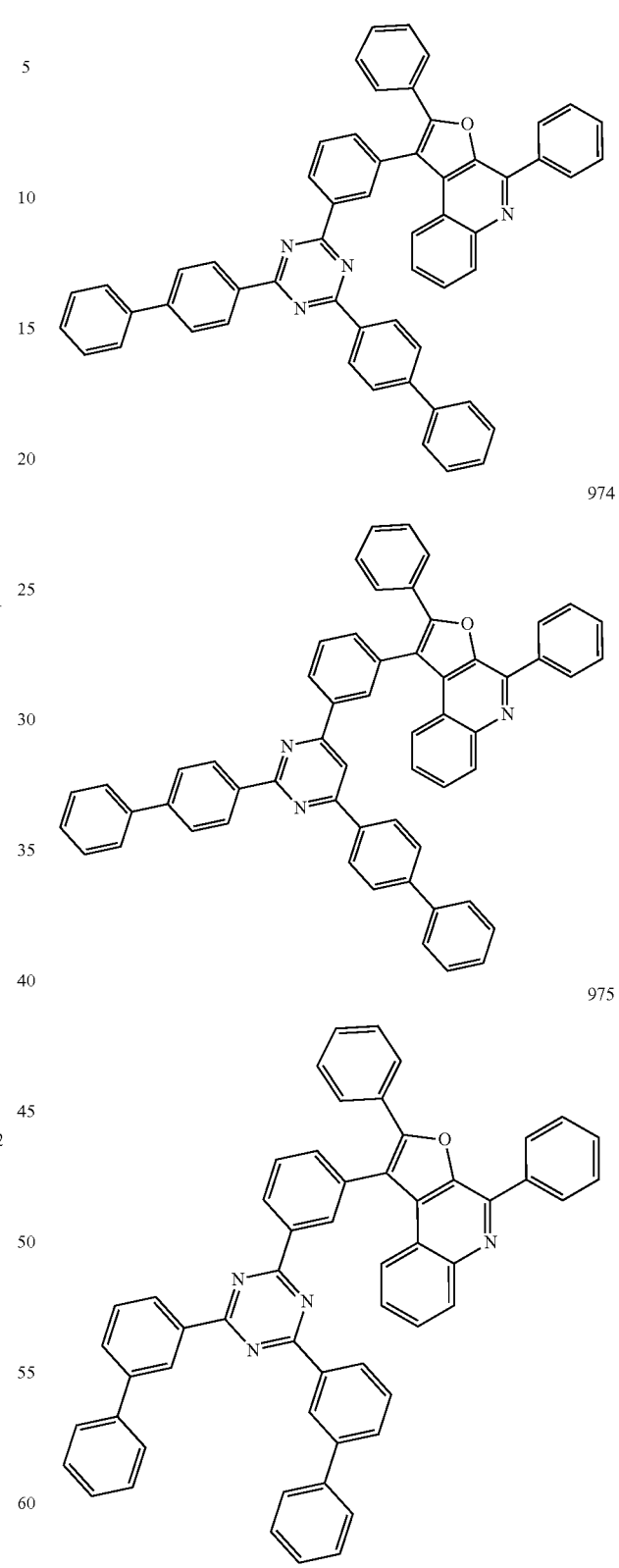
973
974
975
The compound or the composition described above may be for an organic optoelectronic diode, and the compound for an organic optoelectronic diode or the composition for an organic optoelectronic diode may be formed using a dry film-forming method such as chemical vapor deposition.

Hereinafter, an organic optoelectronic diode using the compound for an organic optoelectronic diode or the composition for an organic optoelectronic diode described above will be described.

The organic optoelectronic diode is not particularly limited as long as it is a device capable of interconverting electrical energy and light energy, and examples thereof may comprise an organic photoelectric diode, an organic light emitting diode, an organic solar cell, an organic photo conductor drum and the like.

Another embodiment of the present application provides an organic light emitting diode comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

In one embodiment of the present application, the organic light emitting diode may be a blue organic light emitting diode, and the heterocyclic compound according to Chemical Formula 1 may be used as a material of the blue organic light emitting diode.

In one embodiment of the present application, the organic light emitting diode may be a green organic light emitting diode, and the heterocyclic compound according to Chemical Formula 1 may be used as a material of the green organic light emitting diode.

In one embodiment of the present application, the organic light emitting diode may be a red organic light emitting diode, and the heterocyclic compound according to Chemical Formula 1 may be used as a material of the red organic light emitting diode.

The organic light emitting diode of the present disclosure may be manufactured using common organic light emitting diode manufacturing methods and materials except that one or more organic material layers are formed using the heterocyclic compound described above.

The heterocyclic compound may be formed into an organic material layer using a solution coating method as well as a vacuum deposition method when manufacturing the organic light emitting diode. Herein, the solution coating method means spin coating, dip coating, inkjet printing, screen printing, a spray method, roll coating and the like, but is not limited thereto.

Herein, another example of the organic light emitting diode, one example of the organic optoelectronic diode, will be described with reference to accompanying drawings.

FIGS. 1 to 3 illustrate a lamination order of electrodes and organic material layers of an organic light emitting diode according to one embodiment of the present application. However, the scope of the present application is not limited to these diagrams, and structures of organic optoelectronic diodes known in the art may also be used in the present application.

FIG. 1 illustrates an organic light emitting diode in which an anode (200), an organic material layer (300) and a cathode (400) are consecutively laminated on a substrate (100). However, the structure is not limited to such a structure, and as illustrated in FIG. 2, an organic light emitting diode in which a cathode, an organic material layer and an anode are consecutively laminated on a substrate may also be obtained.

FIG. 3 illustrates a case of the organic material layer being a multilayer. The organic light emitting diode according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further included.

In the organic light emitting diode, the compound represented by Chemical Formula 1 may be used as a material of an electron transfer layer, a hole transfer layer, a light emitting layer, or the like.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among N-type host materials or P-type host materials may be selected, and used as a host material of a light emitting layer.

The organic light emitting diode according to one embodiment of the present application may be a top-emission type, a bottom-emission type or a dual-emission type depending on the materials used.

Hereinafter, the embodiments described above will be described in more detail through examples. However, the following examples are for illustrative purposes only and do not limit the scope of a right.

Starting materials and reaction materials used in examples and synthesis examples are, unless particularly mentioned otherwise, purchased from Sigma-Aldrich, TCI, Tokyo chemical industry or P&H tech, or synthesized using known methods.

Preparation of Compound for Organic Optoelectronic Diode

[Preparation Example 1] Preparation of Intermediate A1

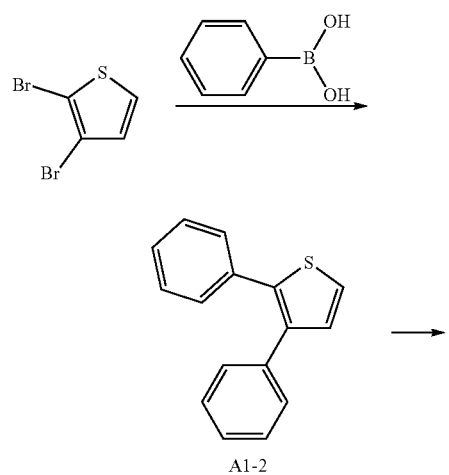

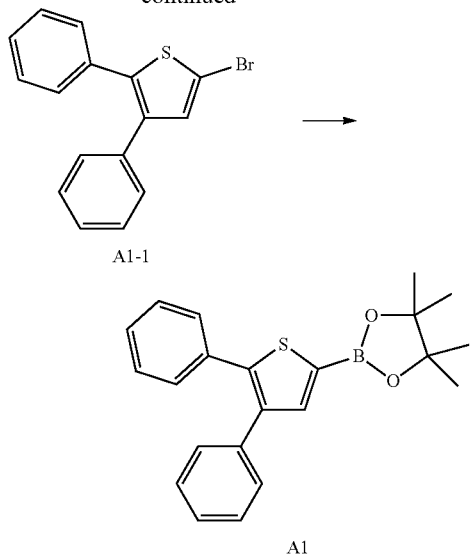

1) Preparation of Intermediate A1-2

After dissolving 2,3-dibromothiophene (40 g, 165.33 mmol) and phenylboronic acid (48.38 g, 396.79 mmol) in toluene (500 ml), EtOH (100 ml) and $H_2O$ (100 ml), $Pd(PPh_3)_4$ (3.82 g, 3.31 mmol) and $K_2CO_3$ (137.1 g, 991.98 mmol) were introduced thereto, and the result was stirred for 5 hours under reflux. After the reaction was completed, the result was extracted with MC and distilled water, and after drying the organic layer with $MgSO_4$, the solvent was removed using a rotary evaporator, and then the result was purified by column chromatography using dichloromethane and hexane as a developing solvent to obtain Intermediate A1-2 (35 g, 90%).

2) Preparation of Intermediate A1-1

After dissolving Intermediate A1-2 (40 g, 169.25 mmol) in DMF (400 ml), NBS (33.14 g, 186.18 mmol) was introduced thereto, and the result was stirred for 4 hours at room temperature. After the reaction was completed, the result was extracted with MC and distilled water, and after drying the organic layer with $MgSO_4$, the solvent was removed using a rotary evaporator, and then the result was purified by column chromatography using dichloromethane and hexane as a developing solvent to obtain Intermediate A1-1 (50 g, 93%).

3) Preparation of Intermediate A1

After dissolving Intermediate A1-1 (50 g, 158.61 mmol) and bis(pinacolato)diboron (60.42 g, 237.92 mmol) in 1,4-dioxane (500 ml), $Pd(dppf)Cl_2$ (2.32 g, 3.17 mmol) and KOAc (46.7 g, 475.84 mmol) were introduced thereto, and the result was stirred for 8 hours under reflux. After the reaction was completed, the result was extracted with MC and water, and after drying the organic layer with $MgSO_4$, the result was silica gel filtered, and precipitated with MC/MeOH. The precipitates were filtered to obtain Intermediate A1 (51 g, 89%).

Intermediate A was synthesized in the same manner as in Preparation Example 1 using S1 of the following Table 1 instead of 2,3-dibromothiophene, and using Intermediate S2 instead of phenylboronic acid.

TABLE 1
| S1 | S2 | Intermediate A | Yield |
|---|---|---|---|
| 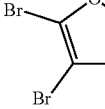 | 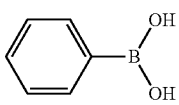 | 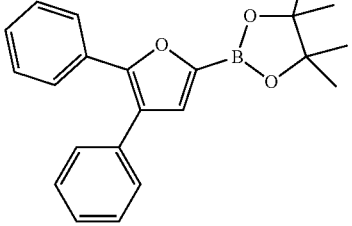 | 79% |
| 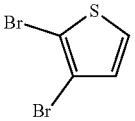 | 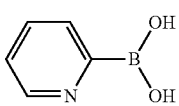 | 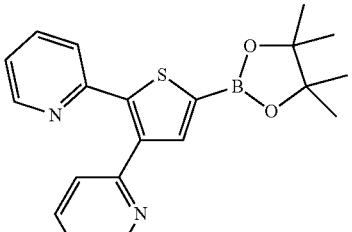 | 82% |
| 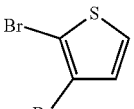 | 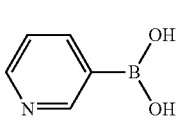 | 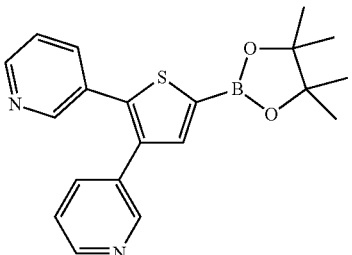 [SMILES: CC1(C)OB(c2cc(-c3ccccc3)c(-c3ccccc3)o2)OC1(C)C] | 88% |
| 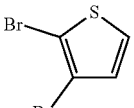 | 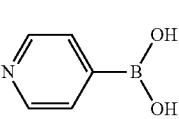 | 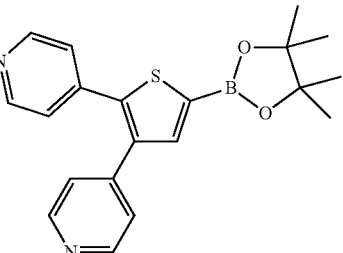 | 78% |
| 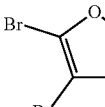 | 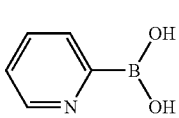 | 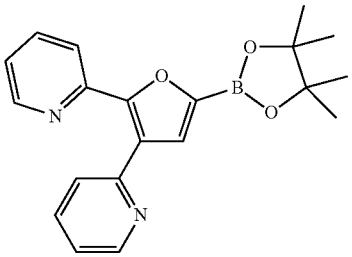 [SMILES: CC1(C)OB(c2cc(-c3ccccn3)c(-c3ccccn3)o2)OC1(C)C] | 78% |
| 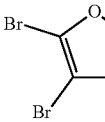 | 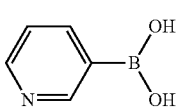 | 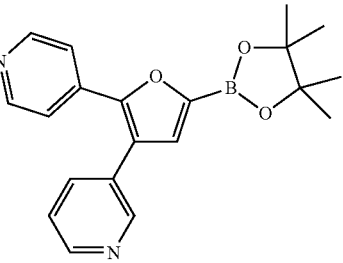 | 85% |

TABLE 1-continued

| S1 | S2 | Intermediate A | Yield |
|---|---|---|---|
| ![Br-furan-Br] | ![pyridine-B(OH)2] | ![intermediate A structure] | 87% |

[Preparation Example 2] Preparation of Intermediate B1

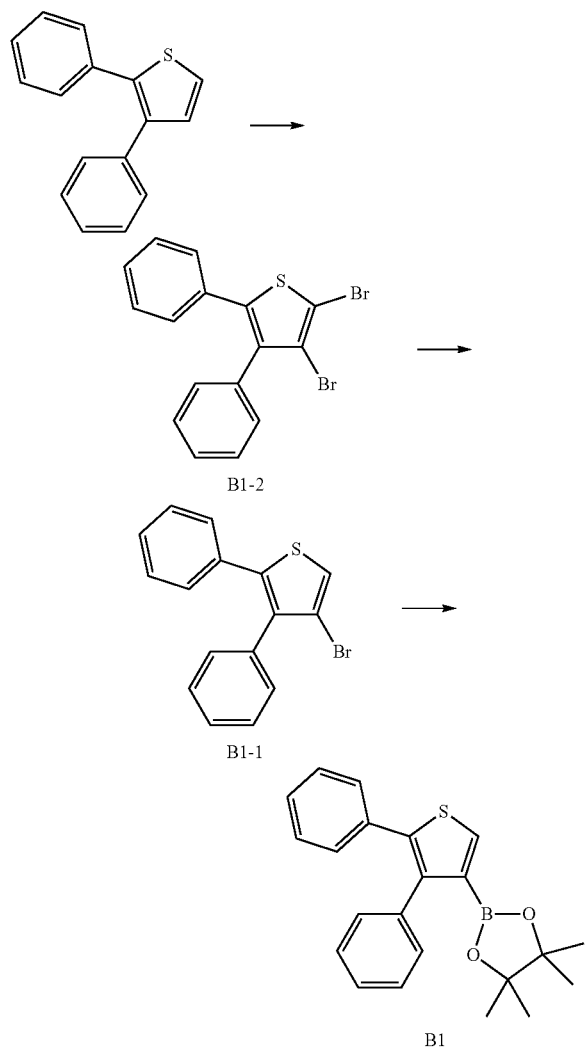

1) Preparation of Intermediate B1-2

After dissolving 2,3-diphenylthiophene (30 g, 126.94 mmol) in chloroform (300 ml), the result was cooled to 0° C., bromine (42.6 g, 266.58 mmol) was slowly introduced thereto, and the result was stirred for 3 hours. After the reaction was completed, the result was extracted with MC and distilled water, and after drying the organic layer with $MgSO_4$, the solvent was removed using a rotary evaporator, and then the result was purified by column chromatography using dichloromethane and hexane as a developing solvent to obtain Intermediate B1-2 (43 g, 86%).

2) Preparation of Intermediate B1-1

After dissolving Intermediate B1-2 (43 g, 109.1 mmol) in anhydrous diethyl ether (400 ml), the result was cooled to −78° C., n-BuLi (45.8 ml, 114.56 mmol) was slowly introduced thereto, and the result was stirred for 1 hour. After the reaction was completed, the result was extracted with EA and a dilute aqueous $NH_4Cl$ solution, and after drying the organic layer with $MgSO_4$, the solvent was removed using a rotary evaporator, and then the result was purified by column chromatography using dichloromethane and hexane as a developing solvent to obtain Intermediate B1-1 (27 g, 78%).

3) Preparation of Intermediate B1

After dissolving Intermediate B1-1 (27 g, 85.65 mmol) and bis(pinacolato)diboron (32.63 g, 128.48 mmol) in 1,4-dioxane (300 ml), Pd(dppf)Cl$_2$ (2.51 g, 3.43 mmol) and KOAc (25.22 g, 256.96 mmol) were introduced thereto, and the result was stirred for 5 hours under reflux. After the reaction was completed, the result was extracted with MC and water, and after drying the organic layer with $MgSO_4$, the result was silica gel filtered, and precipitated with MC/MeOH. The precipitates were filtered to obtain Intermediate B1 (26 g, 83%).

Intermediate B was synthesized in the same manner as in Preparation Example 2 using S3 of the following Table 2 instead of 2,3-diphenylthiophene.

TABLE 2

| S3 | Intermediate B | Yield |
|---|---|---|
| ![2,3-diphenylfuran] | ![Intermediate B with Bpin] | 76% |

TABLE 2-continued

| S3 | Intermediate B | Yield |
|---|---|---|
| | | 72% |
| | | 84% |
| | | 78% |
| | | 81% |
| | | 80% |
| | | 77% |

[Preparation Example 3] Preparation of Compound 1

-continued

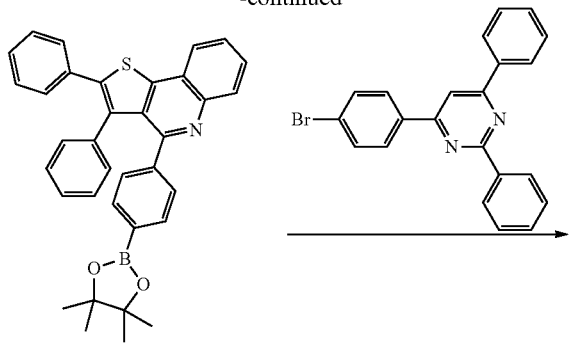

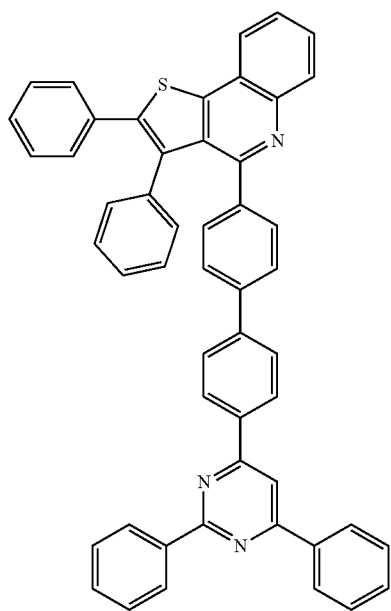

1

1) Preparation of Compound 1-4

After dissolving 5-bromo-2,3-diphenylthiophene (50 g, 158.61 mmol) and 2-(4,4,5,5-tetramethyl-1,3,2-dioxaborolan-2-yl)aniline (38.23 g, 174.48 mmol) in dioxane (500 ml) and H$_2$O (100 ml), Pd(PPh$_3$)$_4$ (9.16 g, 7.93 mmol) and NaHCO$_3$ (39.98 g, 475.84 mmol) were introduced thereto, and the result was stirred for 14 hours under reflux. After the reaction was completed, the reaction solution was dissolved by introducing MC thereto, and then extracted with distilled water. After drying the organic layer with MgSO$_4$, the solvent was removed using a rotary evaporator, and then the result was purified by column chromatography using dichloromethane and hexane as a developing solvent to obtain Compound 1-4 (41 g, 79%).

2) Preparation of Compound 1-3

After dissolving Compound 1-4 (41 g, 125.21 mmol) in MC (500 ml), TEA (38.01 g, 375.64 mmol) was introduced thereto. The temperature was lowered from room temperature to 0° C., 4-bromobenzoyl chloride (30.23 g, 137.74 mmol) dissolved in MC was slowly added dropwise thereto. After the reaction was completed, the result was extracted with MC and distilled water, and after drying the organic layer with MgSO$_4$, the solvent was removed using a rotary evaporator, and then the result was purified by column chromatography using dichloromethane and hexane as a developing solvent to obtain Compound 1-3 (55 g, 86%).

3) Preparation of Compound 1-2

After dissolving Compound 1-3 (55 g, 107.75 mmol) in nitrobenzene (500 ml), POCl$_3$ (18.17 g, 118.53 mmol) was slowly added dropwise thereto, and the result was stirred for 4 hours at 150° C. After the reaction was completed, the result was neutralized with an aqueous NaHCO$_3$ solution and then extracted with MC and distilled water. After drying the organic layer with MgSO$_4$, the solvent was removed using a rotary evaporator, and then the result was purified by column chromatography using dichloromethane and hexane as a developing solvent to obtain Compound 1-2 (48 g, 90%).

4) Preparation of Compound 1-1

After dissolving Compound 1-2 (48 g, 97.48 mmol) and bis(pinacolato)diboron (37.13 g, 146.21 mmol) in 1,4-dioxane (500 ml), Pd(dppf)Cl$_2$ (2.85 g, 3.9 mmol) and KOAc (28.7 g, 292.43 mmol) were introduced thereto, and the result was stirred for 5 hours under reflux. After the reaction was completed, the result was extracted with MC and water, and after drying the organic layer with MgSO$_4$, the result was silica gel filtered, and precipitated with MC/MeOH. The precipitates were filtered to obtain Compound 1-1 (46 g, 87%).

5) Preparation of Compound 1

After dissolving Compound 1-1 (10 g, 18.54 mmol) and 4-(4-bromophenyl)-2,6-diphenylpyrimidine (7.54 g, 19.46 mmol) in toluene (100 ml), EtOH (20 ml) and H$_2$O (20 ml), Pd(PPh$_3$)$_4$ (1.07 g, 0.93 mmol) and K$_3$PO$_4$ (11.80 g, 55.61 mmol) were introduced thereto, and the result was stirred for 5 hours under reflux. After the reaction was completed, the result was cooled to room temperature, and produced solids were filtered and then washed with EA and MeOH. After that, the solids were all dissolved in an excess amount of dichloromethane, and filtered with silica gel to obtain Compound 1 (10 g, 75%).

Target compounds were synthesized in the same manner as in Preparation Example 3 using Intermediate C of the following Table 3 instead of 5-bromo-2,3-diphenylthiophene, using Intermediate D instead of 2-(4,4,5,5-tetramethyl-1,3,2-dioxaborolan-2-yl)aniline, using Intermediate E instead of 4-bromobenzoyl chloride, and using Intermediate F instead of 4-(4-bromophenyl)-2,6-diphenylpyrimidine.

TABLE 3

| Compound | Intermediate C | Intermediate D |
|---|---|---|
| 6 | 2,3-diphenyl-5-bromothiophene | 2-aminophenylboronic acid pinacol ester |
| 9 | 2,3-diphenyl-5-bromothiophene | 2-aminophenylboronic acid pinacol ester |
| 10 | 2,3-diphenyl-5-bromothiophene | 2-aminophenylboronic acid pinacol ester |
| 11 | 2,3-diphenyl-5-bromothiophene | 2-aminophenylboronic acid pinacol ester |
| 12 | 2,3-diphenyl-5-bromothiophene | 2-aminophenylboronic acid pinacol ester |
| 26 | 2,3-diphenyl-5-bromothiophene | 2-aminophenylboronic acid pinacol ester |

TABLE 3-continued
| | | |
|---|---|---|
| 29 | 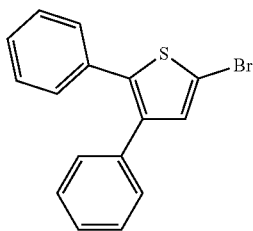 [SMILES: Brc1cc(-c2ccccc2)c(-c2ccccc2)s1] | 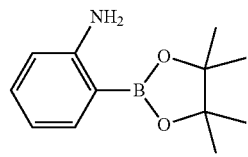 [SMILES: CC1(C)OB(c2ccccc2N)OC1(C)C] |
| 31 | 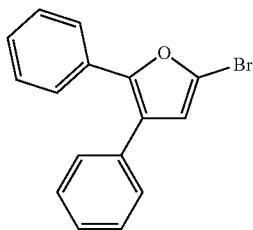 [SMILES: Brc1cc(-c2ccccc2)c(-c2ccccc2)o1] | 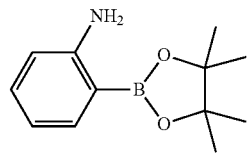 |
| 36 | 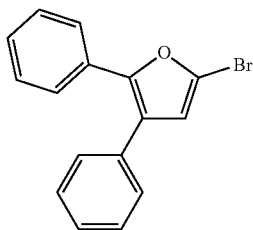 [SMILES: Brc1cc(-c2ccccc2)c(-c2ccccc2)o1] | 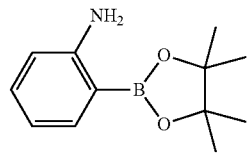 [SMILES: CC1(C)OB(c2ccccc2N)OC1(C)C] |
| 56 | 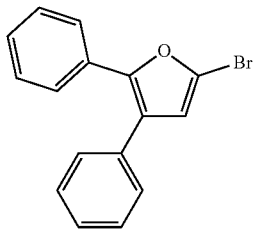 [SMILES: Brc1cc(-c2ccccc2)c(-c2ccccc2)o1] | 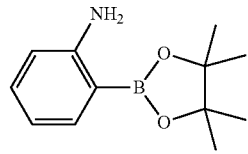 [SMILES: CC1(C)OB(c2ccccc2N)OC1(C)C] |
| 63 | 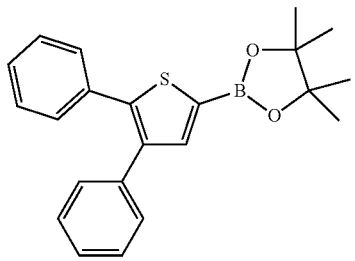 [SMILES: CC1(C)OB(c2cc(-c3ccccc3)c(-c3ccccc3)s2)OC1(C)C] | 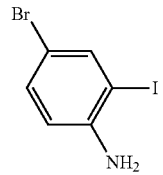 |
| 82 | 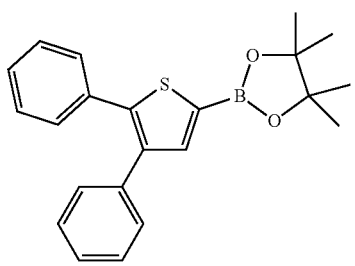 | 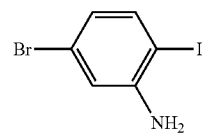 |

TABLE 3-continued
| | | |
|---|---|---|
| 104 | 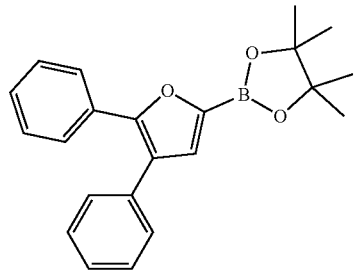 [SMILES: CC1(C)OB(c2cc(-c3ccccc3)c(-c3ccccc3)o2)OC1(C)C] | 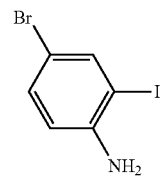 |
| 108 | 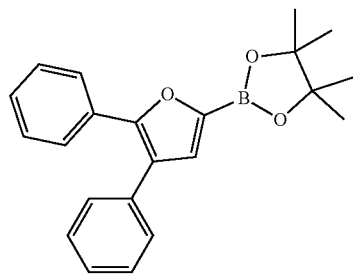 [SMILES: CC1(C)OB(c2cc(-c3ccccc3)c(-c3ccccc3)o2)OC1(C)C] | 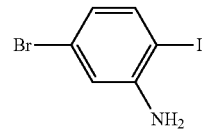 |
| 117 | 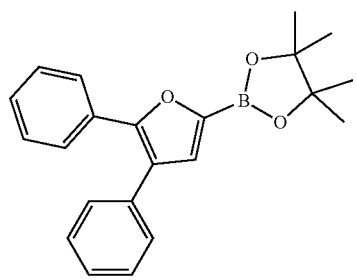 [SMILES: CC1(C)OB(c2cc(-c3ccccc3)c(-c3ccccc3)o2)OC1(C)C] | 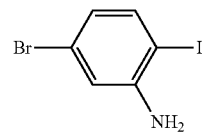 |
| 126 | 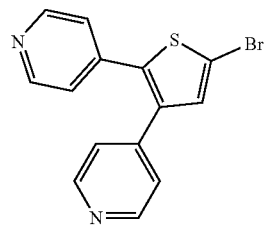 [SMILES: Brc1cc(-c2ccncc2)c(-c2ccncc2)s1] | 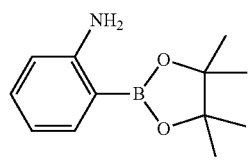 [SMILES: CC1(C)OB(c2ccccc2N)OC1(C)C] |
| 131 | 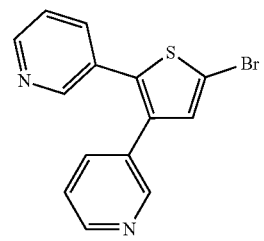 [SMILES: Brc1cc(-c2cccnc2)c(-c2cccnc2)s1] | 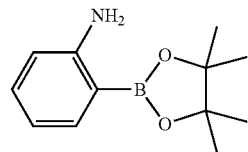 [SMILES: CC1(C)OB(c2ccccc2N)OC1(C)C] |
| 134 | 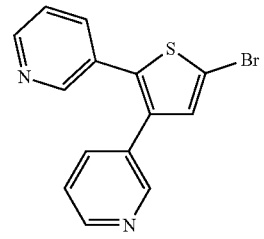 [SMILES: Brc1cc(-c2cccnc2)c(-c2cccnc2)s1] | 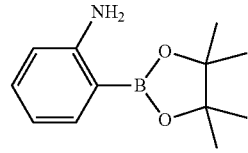 [SMILES: CC1(C)OB(c2ccccc2N)OC1(C)C] |

US 12,410,186 B2
409 410
TABLE 3-continued
| | | |
|---|---|---|
| 149 | 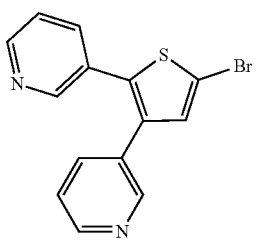 [SMILES: Brc1cc(-c2cccnc2)c(-c2cccnc2)s1] | 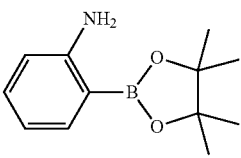 [SMILES: CC1(C)OB(c2ccccc2N)OC1(C)C] |
| 181 | 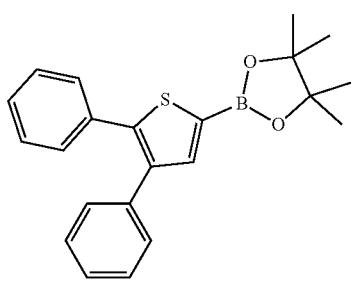 [SMILES: CC1(C)OB(c2cc(-c3ccccc3)c(-c3ccccc3)s2)OC1(C)C] | 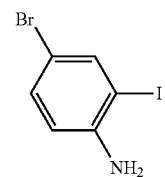 |
| 185 | 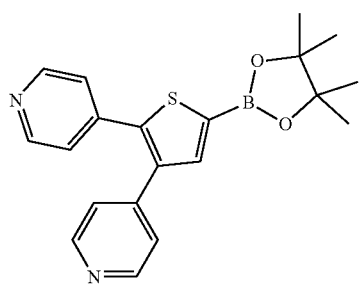 [SMILES: CC1(C)OB(c2cc(-c3ccncc3)c(-c3ccncc3)s2)OC1(C)C] | 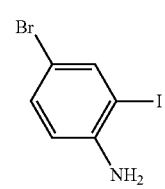 |
| 222 | 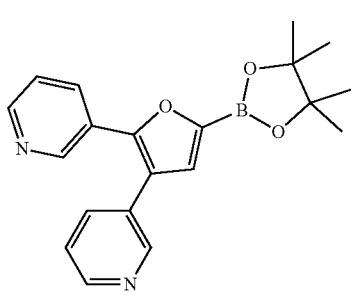 [SMILES: CC1(C)OB(c2cc(-c3cccnc3)c(-c3cccnc3)o2)OC1(C)C] | 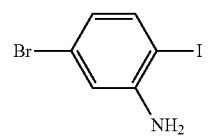 |
| 234 | 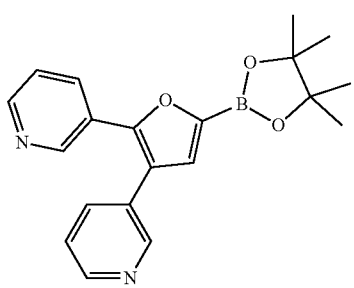 [SMILES: CC1(C)OB(c2cc(-c3cccnc3)c(-c3cccnc3)o2)OC1(C)C] | 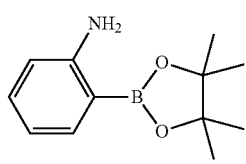 [SMILES: CC1(C)OB(c2ccccc2N)OC1(C)C] |
| 241 | 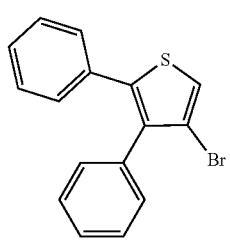 [SMILES: Brc1csc(-c2ccccc2)c1-c1ccccc1] | |

TABLE 3-continued
| | | |
|---|---|---|
| 242 | 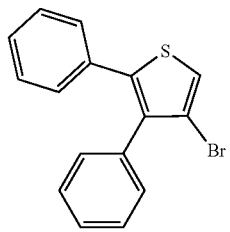 | 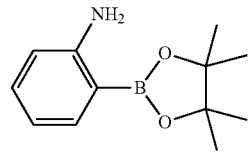 [SMILES: CC1(C)OB(c2ccccc2N)OC1(C)C] |
| 248 | 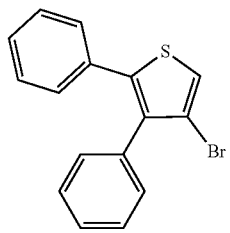 [SMILES: Brc1csc(-c2ccccc2)c1-c1ccccc1] | 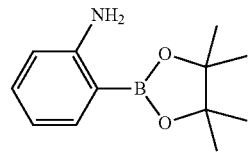 [SMILES: CC1(C)OB(c2ccccc2N)OC1(C)C] |
| 261 | 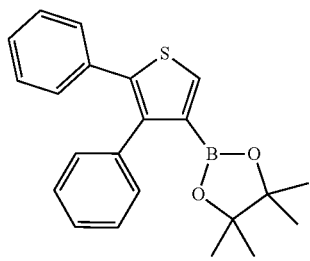 [SMILES: CC1(C)OB(c2csc(-c3ccccc3)c2-c2ccccc2)OC1(C)C] | 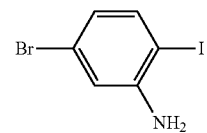 |
| 277 | 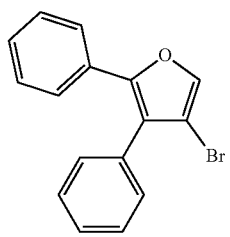 [SMILES: Brc1coc(-c2ccccc2)c1-c1ccccc1] | 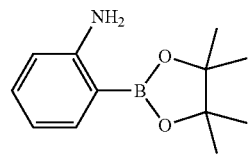 [SMILES: CC1(C)OB(c2ccccc2N)OC1(C)C] |
| 287 | 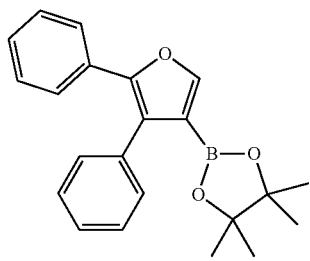 [SMILES: CC1(C)OB(c2coc(-c3ccccc3)c2-c2ccccc2)OC1(C)C] | 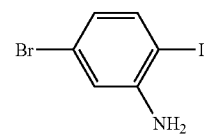 |
| 291 | 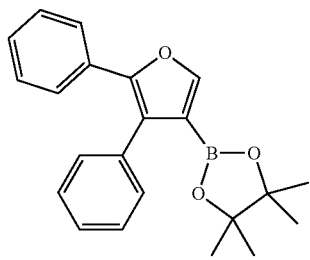 [SMILES: CC1(C)OB(c2coc(-c3ccccc3)c2-c2ccccc2)OC1(C)C] | 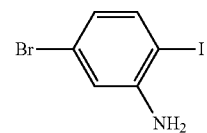 |

TABLE 3-continued
| Compound | Intermediate E | Intermediate F |
|---|---|---|
| 294 | 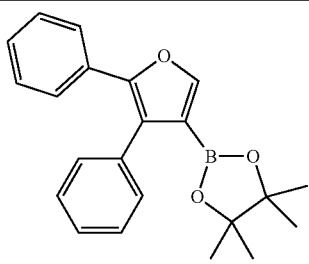 | 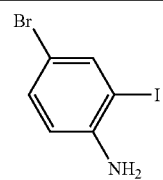 |
| 301 | 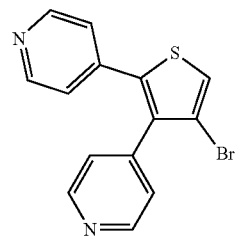 [SMILES: Brc1csc(-c2ccncc2)c1-c1ccncc1] | |
| 328 | 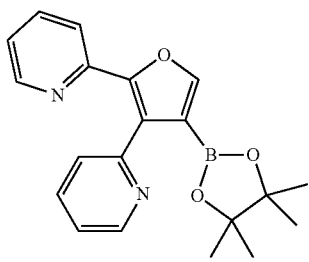 [SMILES: CC1(C)OB(c2coc(-c3ccccn3)c2-c2ccccn2)OC1(C)C] | |
| 6 | 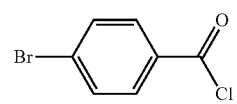 | 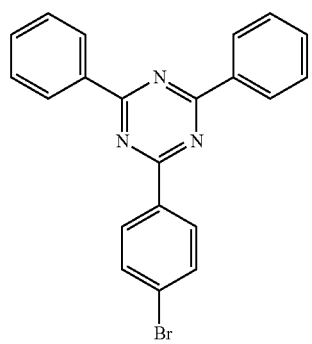 |
| 9 | 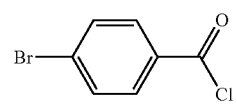 | 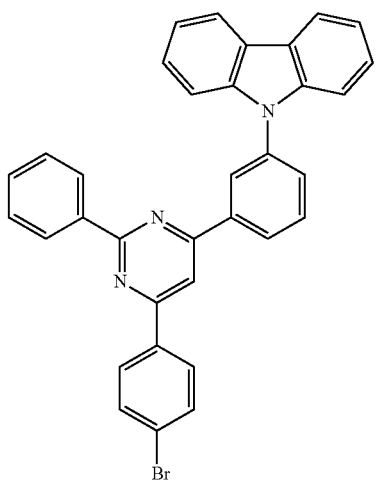 |

TABLE 3-continued
| | | |
|---|---|---|
| 10 | 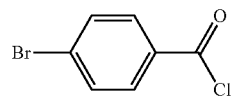 | 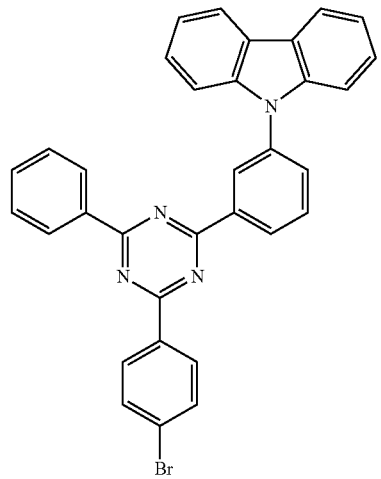 [SMILES: Brc1ccc(-c2nc(-c3ccccc3)nc(-c3cccc(-n4c5ccccc5c5ccccc54)c3)n2)cc1] |
| 11 | 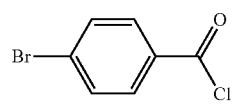 | 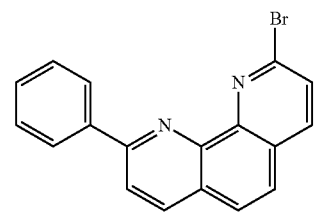 [SMILES: Brc1ccc2ccc3ccc(-c4ccccc4)nc3c2n1] |
| 12 | 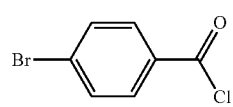 | 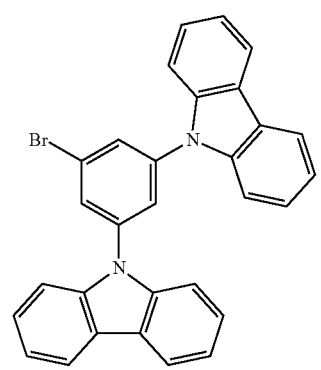 [SMILES: Brc1cc(-n2c3ccccc3c3ccccc32)cc(-n2c3ccccc3c3ccccc32)c1] |
| 26 | 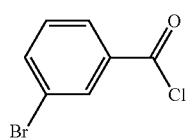 | 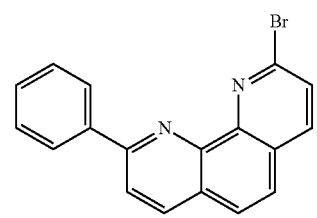 |
| 29 | 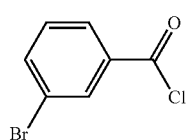 | 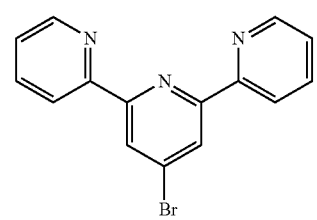 [SMILES: Brc1cc(-c2ccccn2)nc(-c2ccccn2)c1] |

TABLE 3-continued
| 31 | 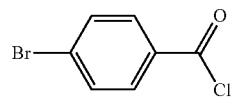 | 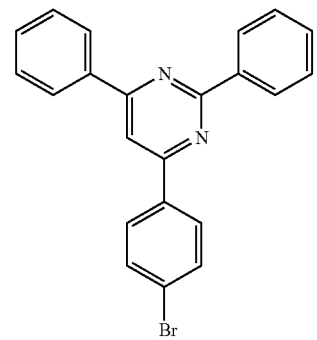 [SMILES: Brc1ccc(-c2cc(-c3ccccc3)nc(-c3ccccc3)n2)cc1] |
| --- | --- | --- |
| 36 | 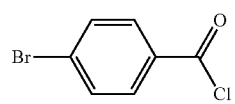 | 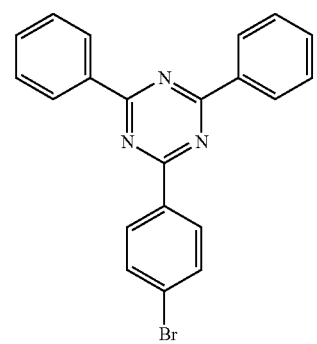 [SMILES: Brc1ccc(-c2nc(-c3ccccc3)nc(-c3ccccc3)n2)cc1] |
| 56 | 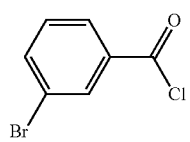 | 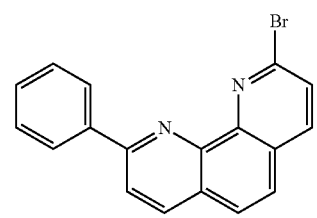 [SMILES: Brc1ccc2ccc3ccc(-c4ccccc4)nc3c2n1] |
| 63 | 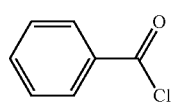 | 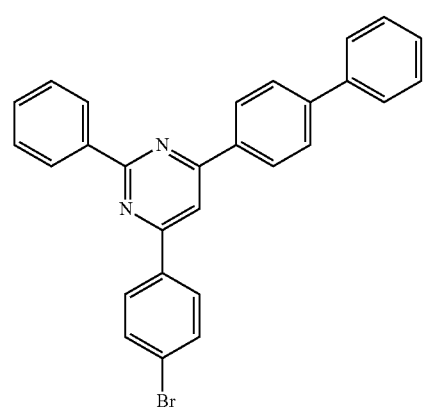 [SMILES: Brc1ccc(-c2cc(-c3ccc(-c4ccccc4)cc3)nc(-c3ccccc3)n2)cc1] |
| 82 | 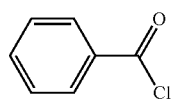 | 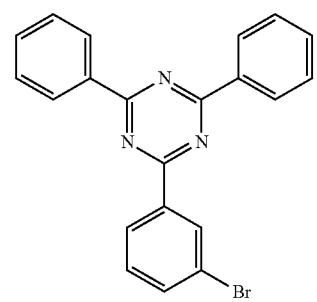 [SMILES: Brc1cccc(-c2nc(-c3ccccc3)nc(-c3ccccc3)n2)c1] |

TABLE 3-continued
| 104 | 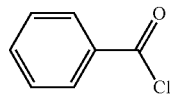 | 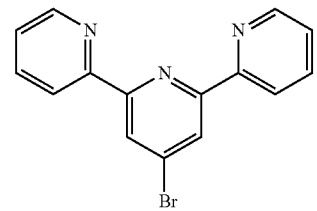 [SMILES: Brc1cc(-c2ccccn2)nc(-c2ccccn2)c1] |
| 108 | 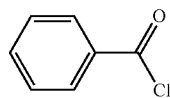 | 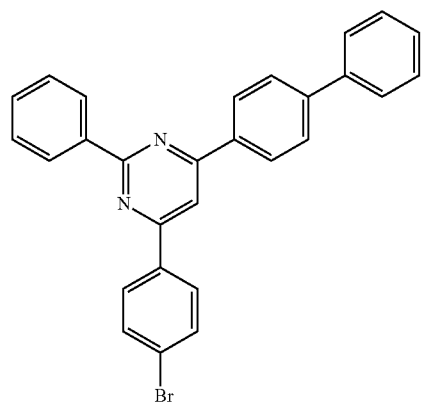 [SMILES: Brc1ccc(-c2cc(-c3ccc(-c4ccccc4)cc3)nc(-c3ccccc3)n2)cc1] |
| 117 | 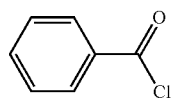 | 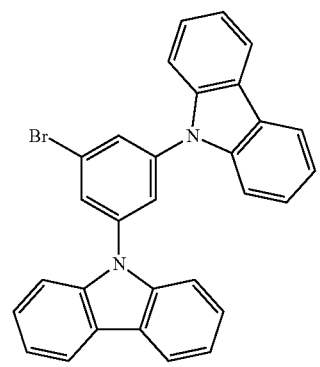 [SMILES: Brc1cc(-n2c3ccccc3c3ccccc32)cc(-n2c3ccccc3c3ccccc32)c1] |
| 126 | 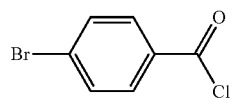 | 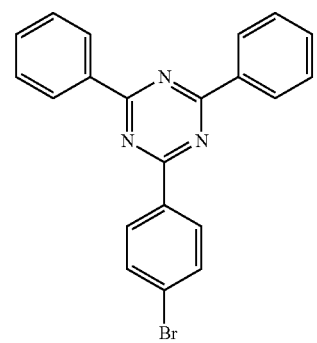 [SMILES: Brc1ccc(-c2nc(-c3ccccc3)nc(-c3ccccc3)n2)cc1] |
| 131 | 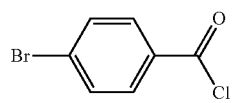 | 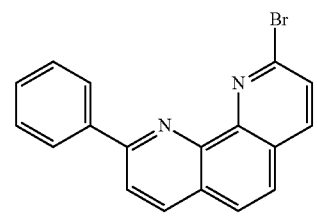 [SMILES: Brc1ccc2ccc3ccc(-c4ccccc4)nc3c2n1] |

TABLE 3-continued
| | | |
|---|---|---|
| 134 | 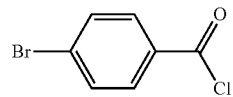 | 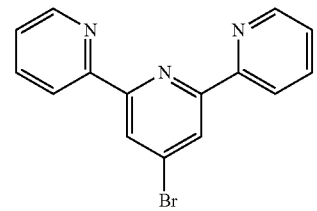 [SMILES: Brc1cc(-c2ccccn2)nc(-c2ccccn2)c1] |
| 149 | 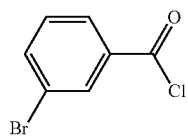 | 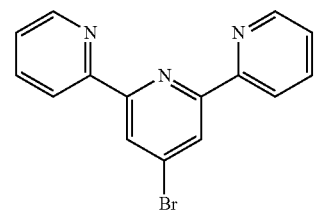 [SMILES: Brc1cc(-c2ccccn2)nc(-c2ccccn2)c1] |
| 181 | 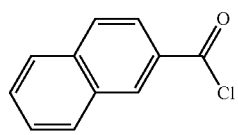 [SMILES: O=C(Cl)c1ccc2ccccc2c1] | 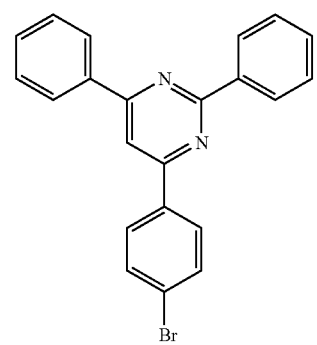 [SMILES: Brc1ccc(-c2cc(-c3ccccc3)nc(-c3ccccc3)n2)cc1] |
| 185 | 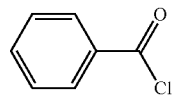 | 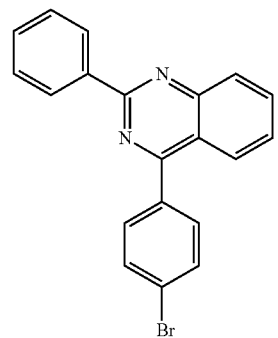 [SMILES: Brc1ccc(-c2nc(-c3ccccc3)nc3ccccc23)cc1] |
| 222 | 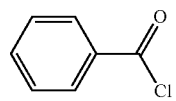 | 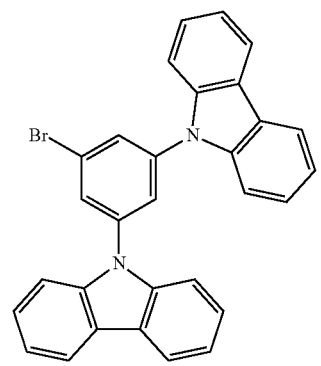 [SMILES: Brc1cc(-n2c3ccccc3c3ccccc32)cc(-n2c3ccccc3c3ccccc32)c1] |

TABLE 3-continued
| | | |
|---|---|---|
| 234 | 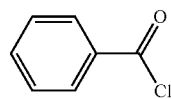 | 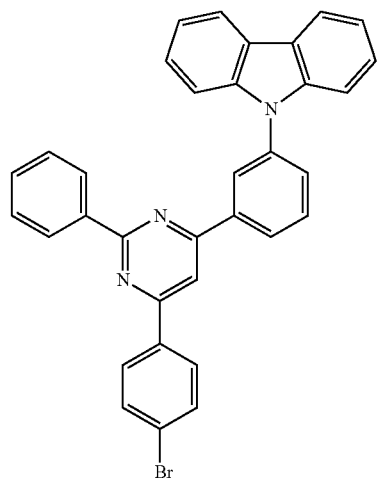 [SMILES: Brc1ccc(-c2cc(-c3cccc(-n4c5ccccc5c5ccccc54)c3)nc(-c3ccccc3)n2)cc1] |
| 241 | 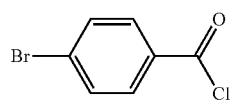 | 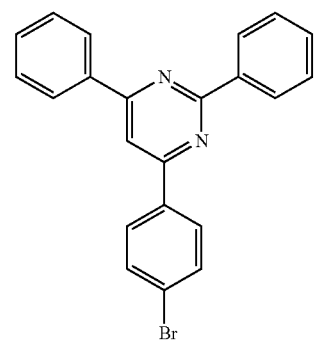 [SMILES: Brc1ccc(-c2cc(-c3ccccc3)nc(-c3ccccc3)n2)cc1] |
| 242 | 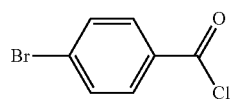 | 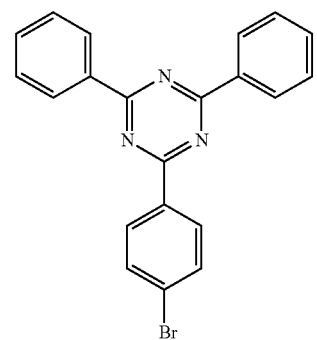 |
| 248 | 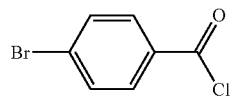 | 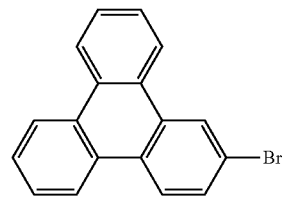 [SMILES: Brc1ccc2c3ccccc3c3ccccc3c2c1] |
| 261 | 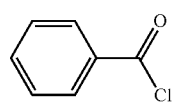 | 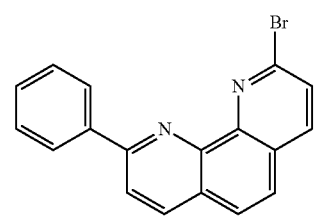 [SMILES: Brc1ccc2ccc3ccc(-c4ccccc4)nc3c2n1] |

TABLE 3-continued
| | | |
|---|---|---|
| 277 | 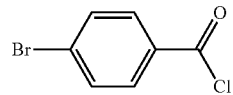 | 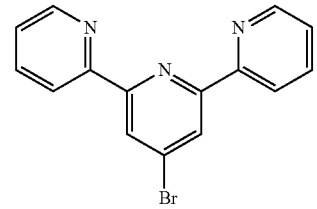 [SMILES: Brc1cc(-c2ccccn2)nc(-c2ccccn2)c1] |
| 287 | 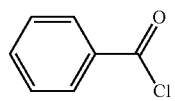 | 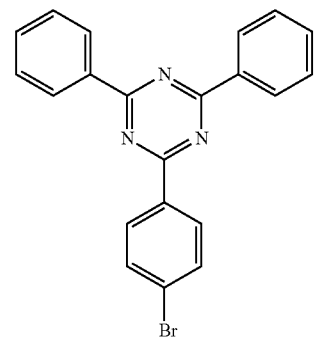 |
| 291 | 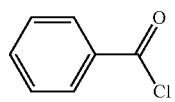 | 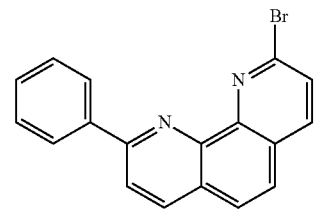 [SMILES: Brc1ccc2ccc3ccc(-c4ccccc4)nc3c2n1] |
| 294 | 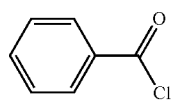 | 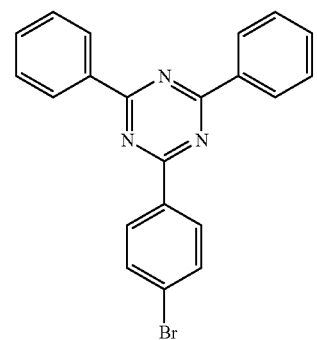 [SMILES: Brc1ccc(-c2nc(-c3ccccc3)nc(-c3ccccc3)n2)cc1] |
| 301 | 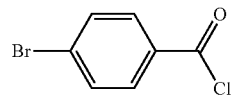 | 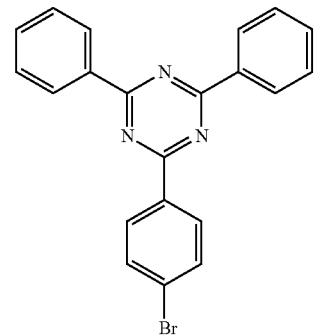 |

TABLE 3-continued
| 328 | 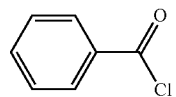 | 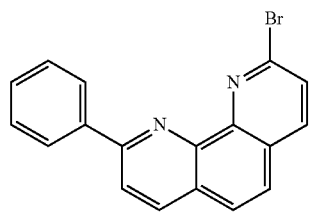 [SMILES: Brc1ccc2ccc3ccc(-c4ccccc4)nc3c2n1] |
|---|---|---|
| Compound | Target Compound | Yield |
|---|---|---|
| 6 | 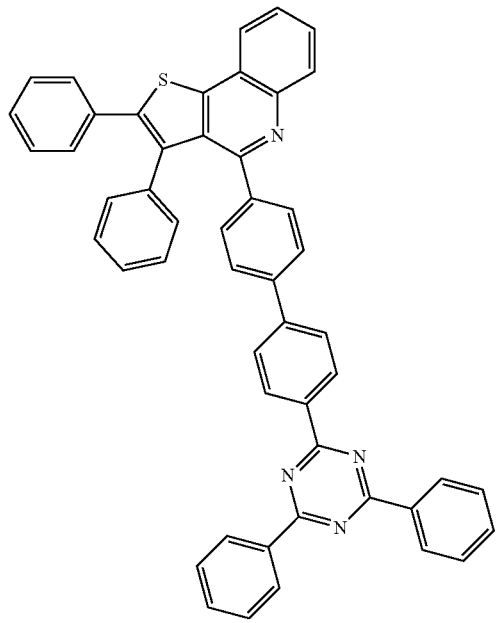 [SMILES: c1ccc(-c2nc(-c3ccccc3)nc(-c3ccc(-c4ccc(-c5nc6ccccc6c6sc(-c7ccccc7)c(-c7ccccc7)c56)cc4)cc3)n2)cc1] | 74% |
| 9 | 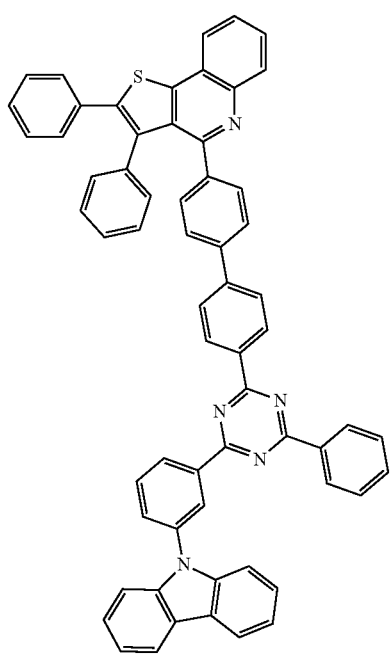 [SMILES: c1ccc(-c2nc(-c3ccc(-c4ccc(-c5nc6ccccc6c6sc(-c7ccccc7)c(-c7ccccc7)c56)cc4)cc3)nc(-c3cccc(-n4c5ccccc5c5ccccc54)c3)n2)cc1] | 72% |

TABLE 3-continued
| 10 | 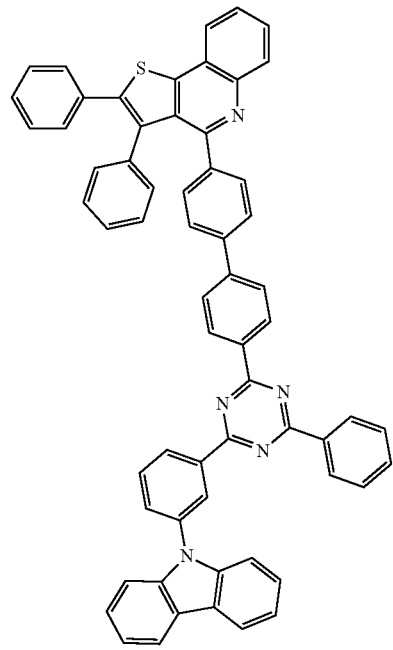 [SMILES: c1ccc(-c2nc(-c3ccc(-c4ccc(-c5nc6ccccc6c6sc(-c7ccccc7)c(-c7ccccc7)c56)cc4)cc3)nc(-c3cccc(-n4c5ccccc5c5ccccc54)c3)n2)cc1] | 81% |
| 11 | 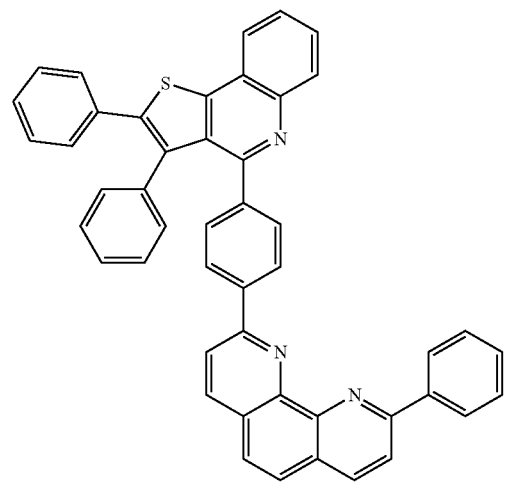 [SMILES: c1ccc(-c2ccc3ccc4ccc(-c5ccc(-c6nc7ccccc7c7sc(-c8ccccc8)c(-c8ccccc8)c67)cc5)nc4c3n2)cc1] | 77% |

TABLE 3-continued
| 12 | 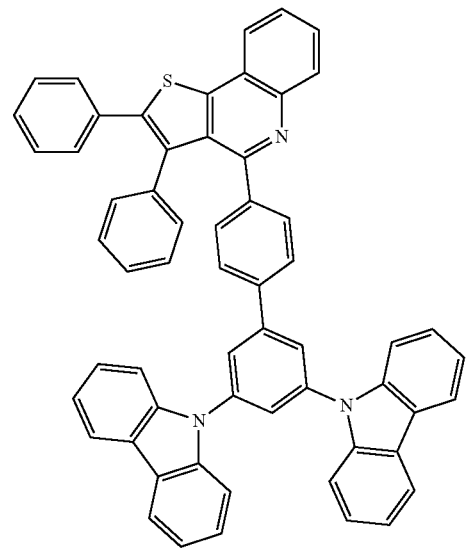 [SMILES: c1ccc(-c2sc3c(c(-c4ccc(-c5cc(-n6c7ccccc7c7ccccc76)cc(-n6c7ccccc7c7ccccc76)c5)cc4)nc4ccccc43)c2-c2ccccc2)cc1] | 72% |
| 26 | 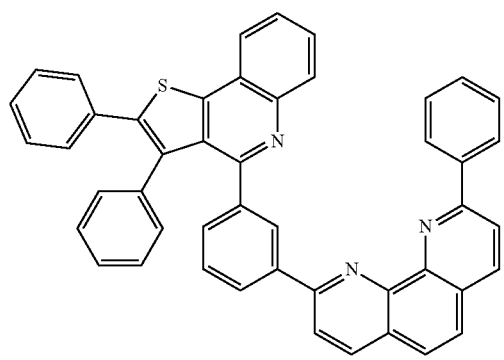 [SMILES: c1ccc(-c2ccc3ccc4ccc(-c5cccc(-c6nc7ccccc7c7sc(-c8ccccc8)c(-c8ccccc8)c67)c5)nc4c3n2)cc1] | 67% |
| 29 | 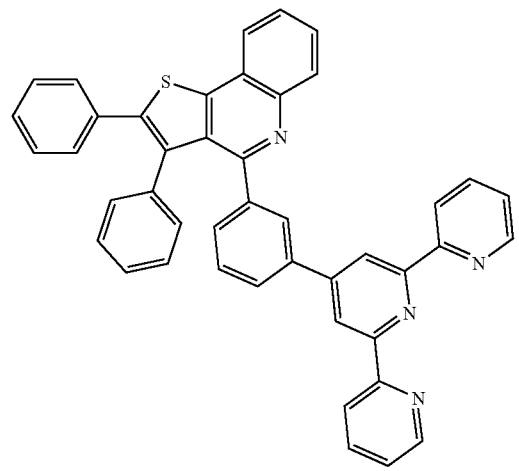 [SMILES: c1ccc(-c2sc3c(c(-c4cccc(-c5cc(-c6ccccn6)nc(-c6ccccn6)c5)c4)nc4ccccc43)c2-c2ccccc2)cc1] | 64% |

TABLE 3-continued
| | | |
|---|---|---|
| 31 | 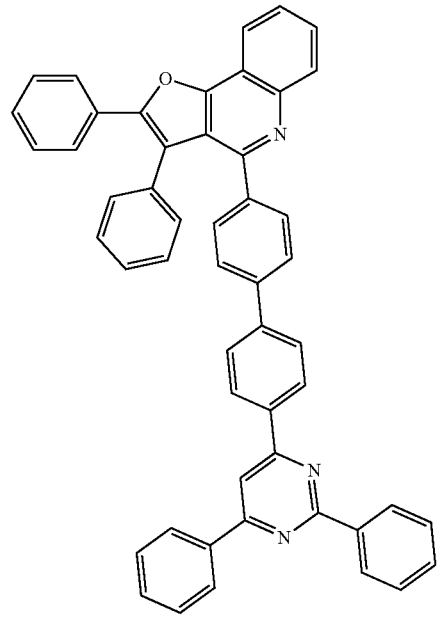 [SMILES: c1ccc(-c2cc(-c3ccc(-c4ccc(-c5nc6ccccc6c6oc(-c7ccccc7)c(-c7ccccc7)c56)cc4)cc3)nc(-c3ccccc3)n2)cc1] | 69% |
| 36 | 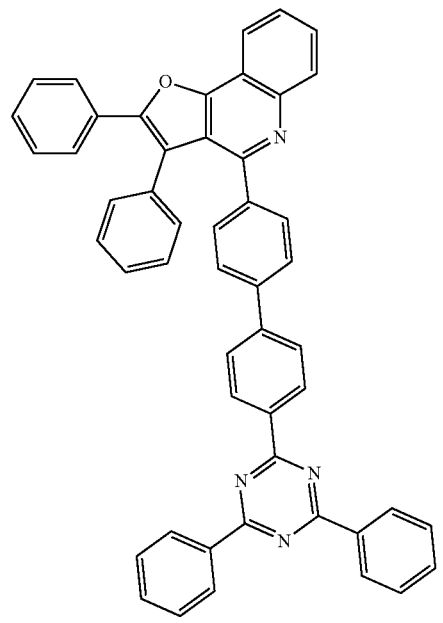 [SMILES: c1ccc(-c2nc(-c3ccccc3)nc(-c3ccc(-c4ccc(-c5nc6ccccc6c6oc(-c7ccccc7)c(-c7ccccc7)c56)cc4)cc3)n2)cc1] | 75% |
| 56 | 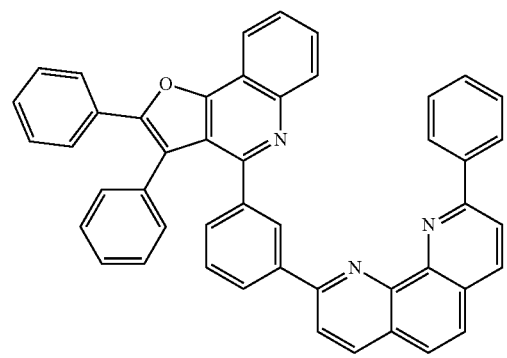 | 77% |

TABLE 3-continued
| | | |
|---|---|---|
| 63 | 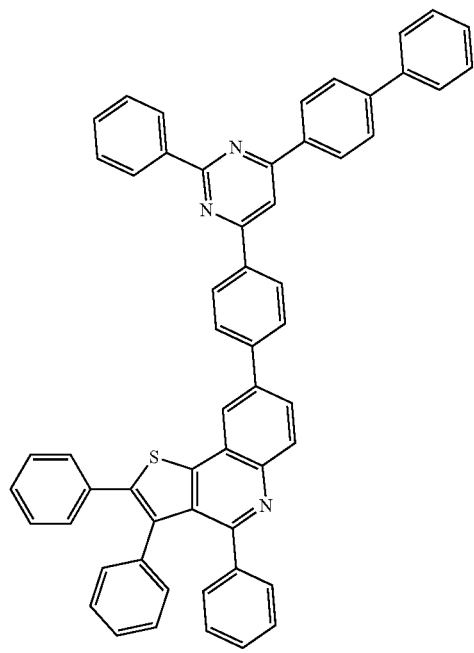 [SMILES: c1ccc(-c2ccc(-c3cc(-c4ccc(-c5ccc6nc(-c7ccccc7)c7c(-c8ccccc8)c(-c8ccccc8)sc7c6c5)cc4)nc(-c4ccccc4)n3)cc2)cc1] | 70% |
| 82 | 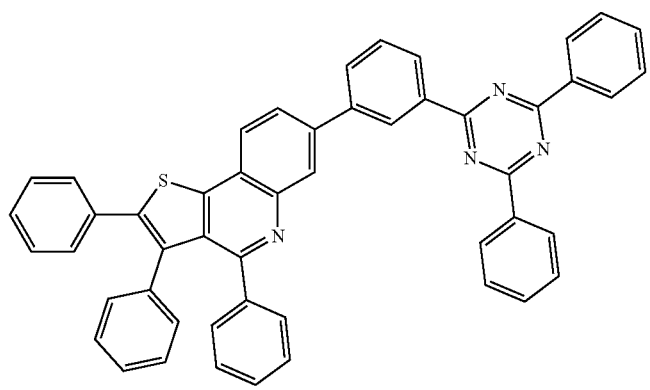 [SMILES: c1ccc(-c2nc(-c3ccccc3)nc(-c3cccc(-c4ccc5c(c4)nc(-c4ccccc4)c4c(-c6ccccc6)c(-c6ccccc6)sc45)c3)n2)cc1] | 68% |
| 104 | 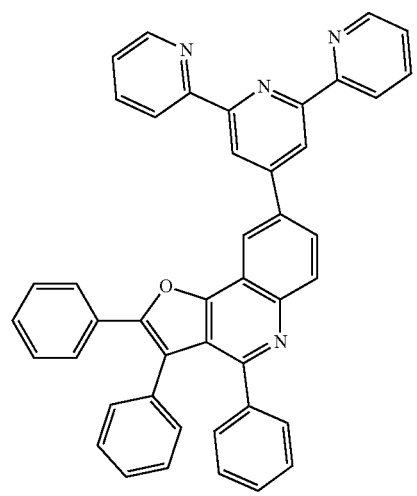 [SMILES: c1ccc(-c2oc3c(c(-c4ccccc4)nc4ccc(-c5cc(-c6ccccn6)nc(-c6ccccn6)c5)cc43)c2-c2ccccc2)cc1] | 82% |

TABLE 3-continued
| | | |
|---|---|---|
| 108 | 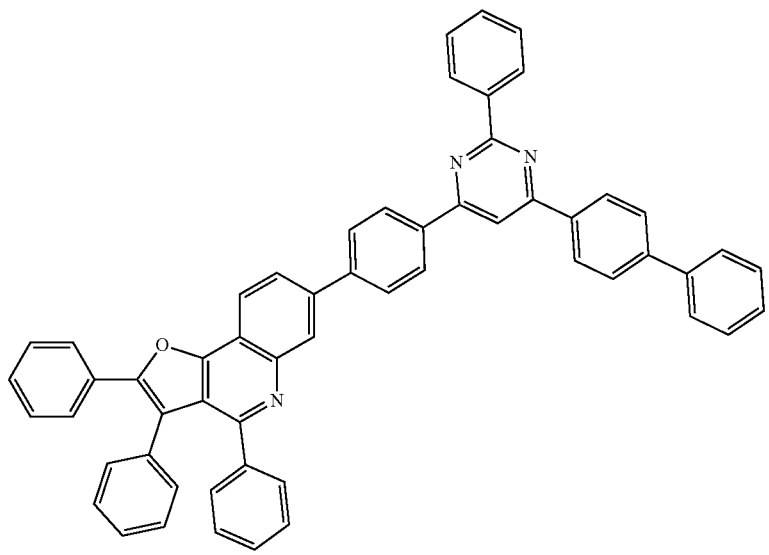 [SMILES: c1ccc(-c2ccc(-c3cc(-c4ccc(-c5ccc6c(c5)nc(-c5ccccc5)c5c(-c7ccccc7)c(-c7ccccc7)oc56)cc4)nc(-c4ccccc4)n3)cc2)cc1] | 77% |
| 117 | 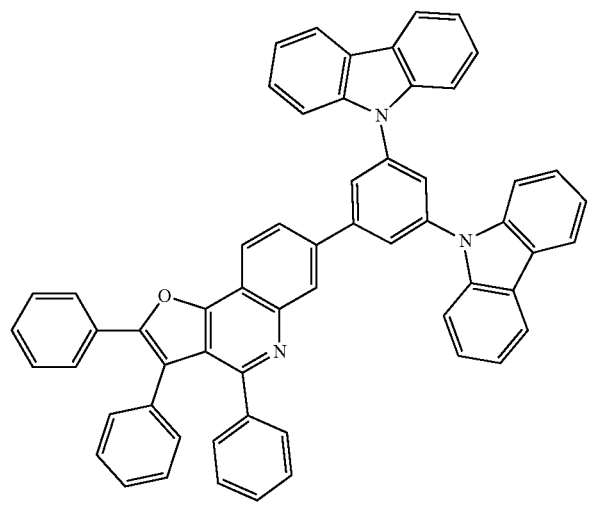 [SMILES: c1ccc(-c2oc3c(c(-c4ccccc4)nc4cc(-c5cc(-n6c7ccccc7c7ccccc76)cc(-n6c7ccccc7c7ccccc76)c5)ccc43)c2-c2ccccc2)cc1] | 62% |
| 126 | 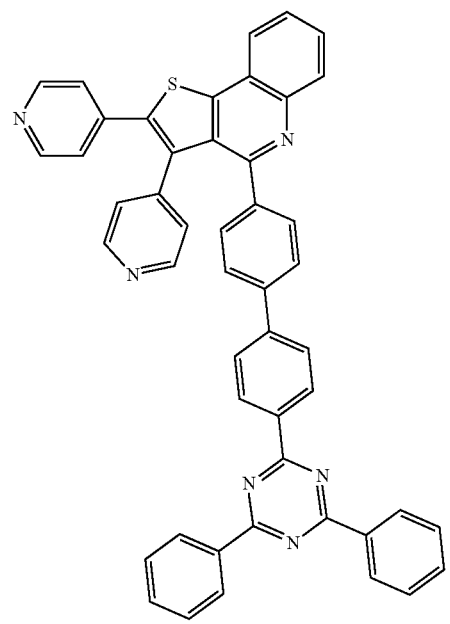 [SMILES: c1ccc(-c2nc(-c3ccccc3)nc(-c3ccc(-c4ccc(-c5nc6ccccc6c6sc(-c7ccncc7)c(-c7ccncc7)c56)cc4)cc3)n2)cc1] | 66% |

TABLE 3-continued
| 131 | 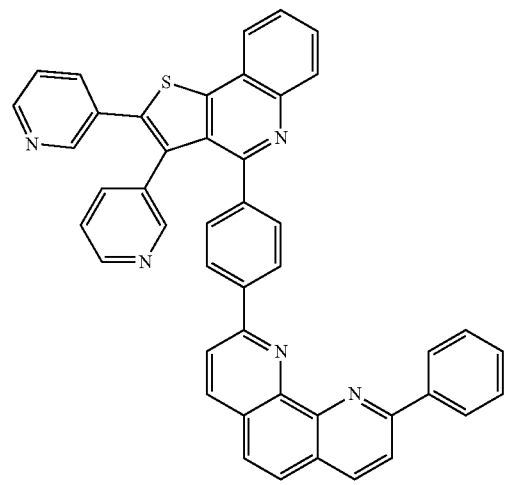 [SMILES: c1ccc(-c2ccc3ccc4ccc(-c5ccc(-c6nc7ccccc7c7sc(-c8cccnc8)c(-c8cccnc8)c67)cc5)nc4c3n2)cc1] | 72% |
| 134 | 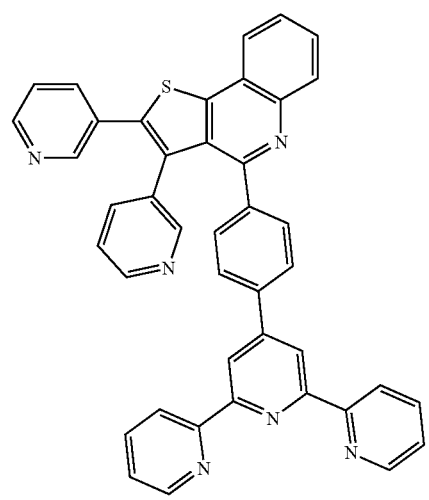 [SMILES: c1ccc(-c2cc(-c3ccc(-c4nc5ccccc5c5sc(-c6cccnc6)c(-c6cccnc6)c45)cc3)cc(-c3ccccn3)n2)nc1] | 66% |
| 149 | 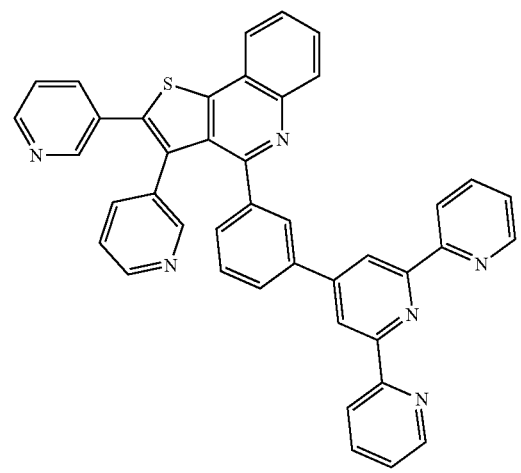 [SMILES: c1ccc(-c2cc(-c3cccc(-c4nc5ccccc5c5sc(-c6cccnc6)c(-c6cccnc6)c45)c3)cc(-c3ccccn3)n2)nc1] | 70% |

| | | |
|---|---|---|
| 181 | 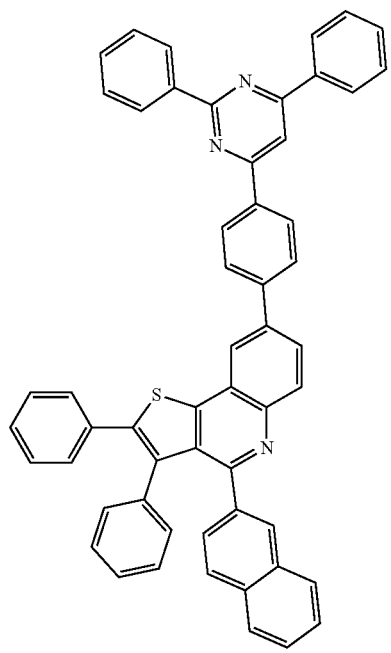 [SMILES: c1ccc(-c2cc(-c3ccc(-c4ccc5nc(-c6ccc7ccccc7c6)c6c(-c7ccccc7)c(-c7ccccc7)sc6c5c4)cc3)nc(-c3ccccc3)n2)cc1] | 59% |
| 185 | 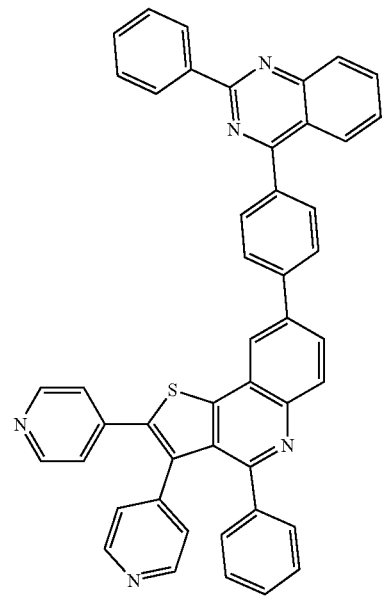 [SMILES: c1ccc(-c2nc(-c3ccc(-c4ccc5nc(-c6ccccc6)c6c(-c7ccncc7)c(-c7ccncc7)sc6c5c4)cc3)c3ccccc3n2)cc1] | 62% |

TABLE 3-continued
| 222 | 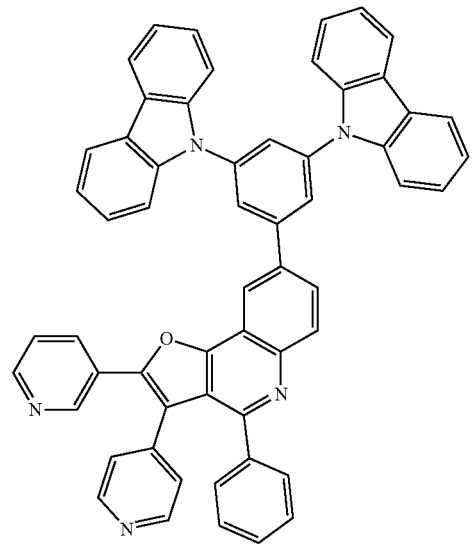 [SMILES: c1ccc(-c2nc3ccc(-c4cc(-n5c6ccccc6c6ccccc65)cc(-n5c6ccccc6c6ccccc65)c4)cc3c3oc(-c4cccnc4)c(-c4ccncc4)c23)cc1] | 64% |
| 234 | 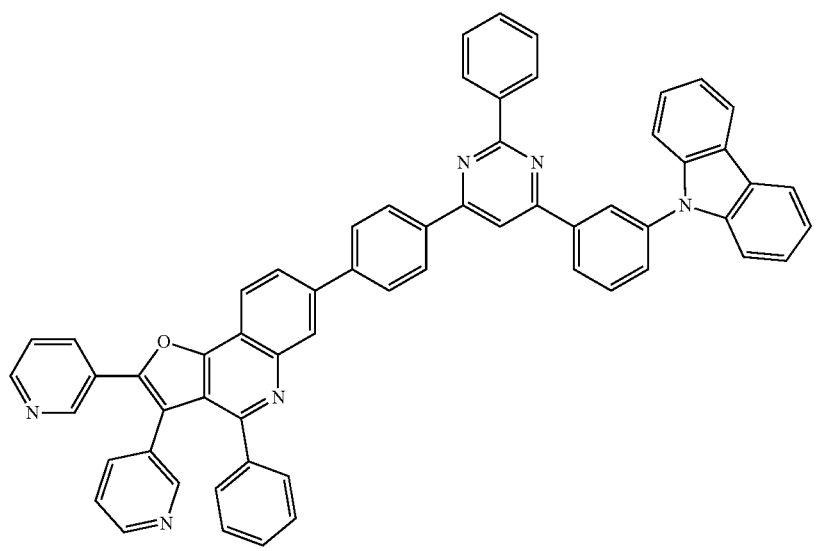 [SMILES: c1ccc(-c2nc(-c3ccc(-c4ccc5c(c4)nc(-c4ccccc4)c4c(-c6cccnc6)c(-c6cccnc6)oc45)cc3)cc(-c3cccc(-n4c5ccccc5c5ccccc54)c3)n2)cc1] | 64% |

TABLE 3-continued
| 241 | 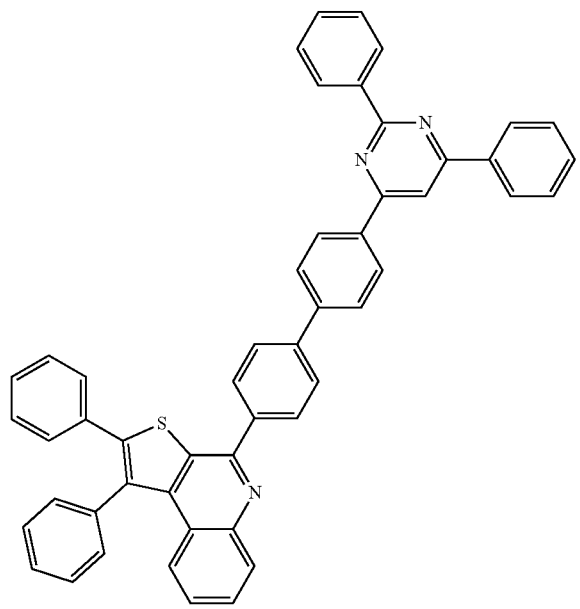 [SMILES: c1ccc(-c2cc(-c3ccc(-c4ccc(-c5nc6ccccc6c6c(-c7ccccc7)c(-c7ccccc7)sc56)cc4)cc3)nc(-c3ccccc3)n2)cc1] | 71% |
| 242 | 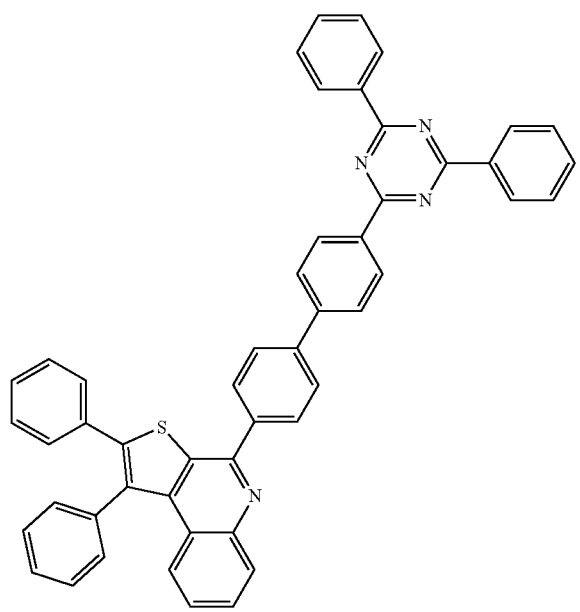 [SMILES: c1ccc(-c2nc(-c3ccccc3)nc(-c3ccc(-c4ccc(-c5nc6ccccc6c6c(-c7ccccc7)c(-c7ccccc7)sc56)cc4)cc3)n2)cc1] | 73% |
| 248 | 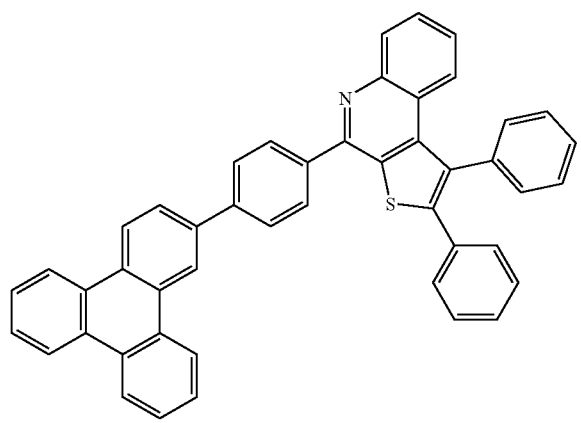 [SMILES: c1ccc(-c2sc3c(-c4ccc(-c5ccc6c7ccccc7c7ccccc7c6c5)cc4)nc4ccccc4c3c2-c2ccccc2)cc1] | 77% |

TABLE 3-continued
| | | |
|---|---|---|
| 261 | 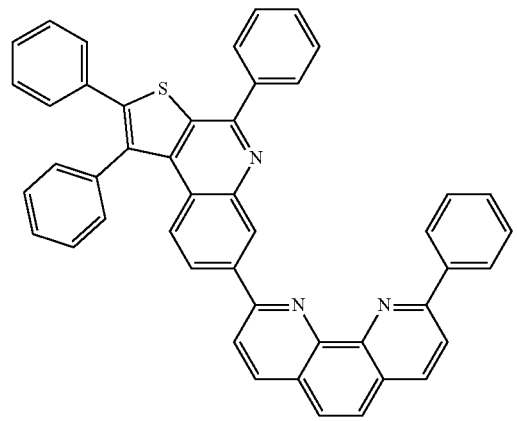 [SMILES: c1ccc(-c2ccc3ccc4ccc(-c5ccc6c(c5)nc(-c5ccccc5)c5sc(-c7ccccc7)c(-c7ccccc7)c56)nc4c3n2)cc1] | 75% |
| 277 | 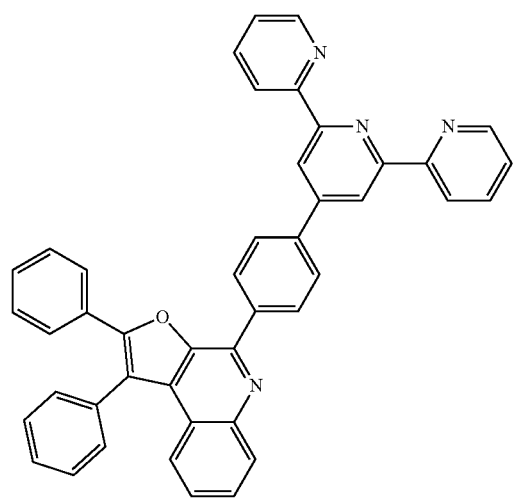 [SMILES: c1ccc(-c2oc3c(-c4ccc(-c5cc(-c6ccccn6)nc(-c6ccccn6)c5)cc4)nc4ccccc4c3c2-c2ccccc2)cc1] | 65% |
| 287 | 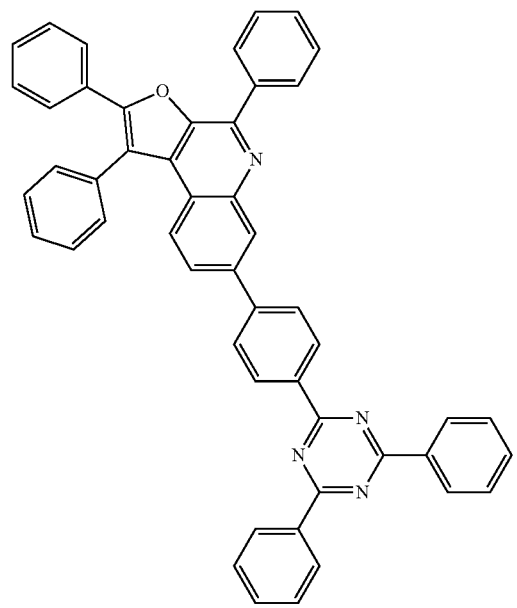 [SMILES: c1ccc(-c2nc(-c3ccccc3)nc(-c3ccc(-c4ccc5c(c4)nc(-c4ccccc4)c4oc(-c6ccccc6)c(-c6ccccc6)c45)cc3)n2)cc1] | 72% |

TABLE 3-continued
| | | |
|---|---|---|
| 291 | 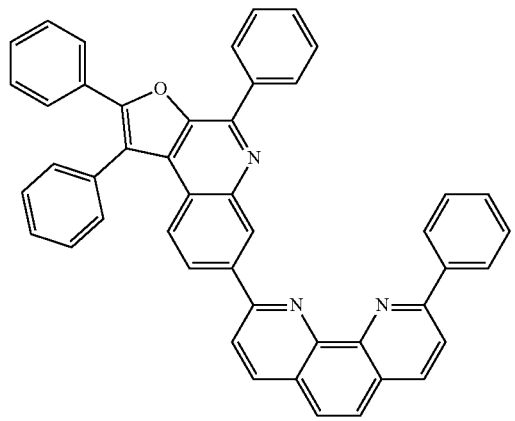 [SMILES: c1ccc(-c2ccc3ccc4ccc(-c5ccc6c(c5)nc(-c5ccccc5)c5oc(-c7ccccc7)c(-c7ccccc7)c56)nc4c3n2)cc1] | 78% |
| 294 | 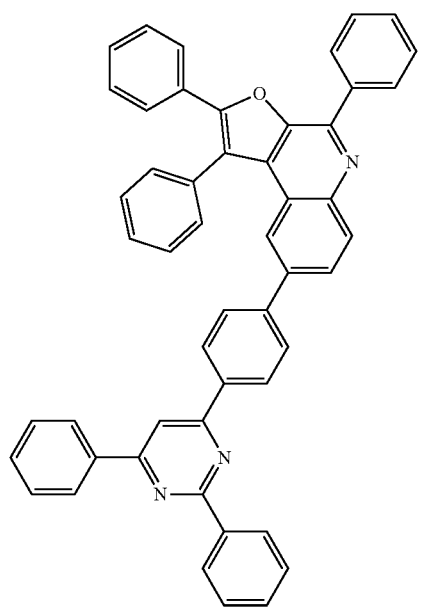 [SMILES: c1ccc(-c2cc(-c3ccc(-c4ccc5nc(-c6ccccc6)c6oc(-c7ccccc7)c(-c7ccccc7)c6c5c4)cc3)nc(-c3ccccc3)n2)cc1] | 69% |
| 301 | 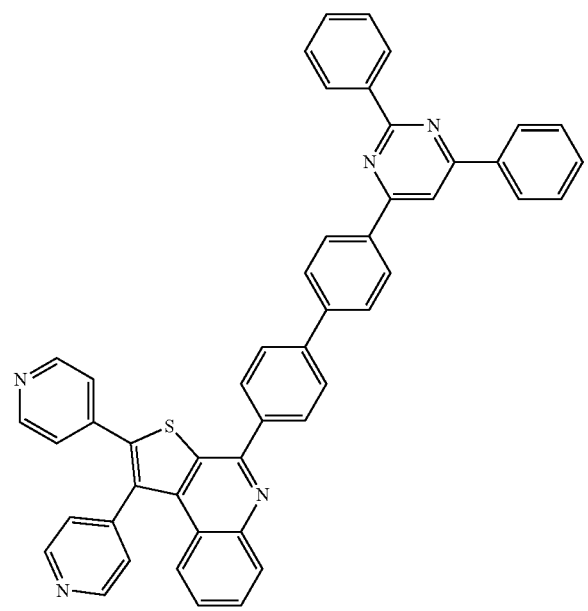 [SMILES: c1ccc(-c2cc(-c3ccc(-c4ccc(-c5nc6ccccc6c6c(-c7ccncc7)c(-c7ccncc7)sc56)cc4)cc3)nc(-c3ccccc3)n2)cc1] | 67% |

TABLE 3-continued
| 328 | 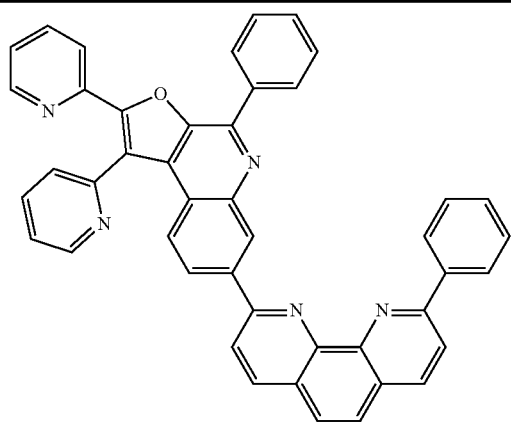 | 69% |
[Preparation Example 4] Preparation of Compound 376
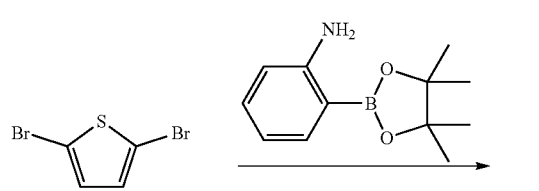
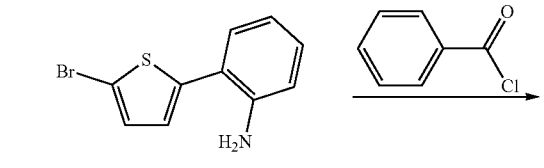
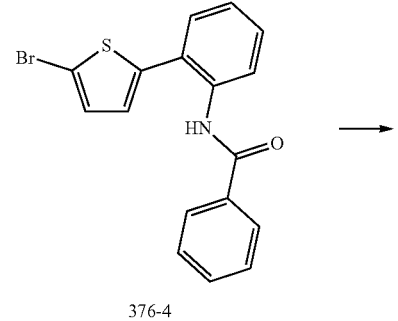
376-3
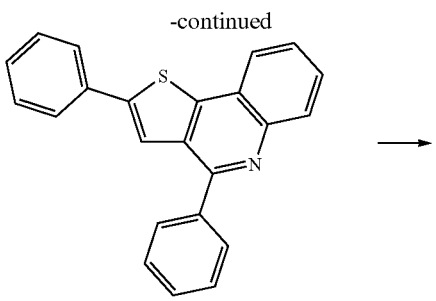
376-2
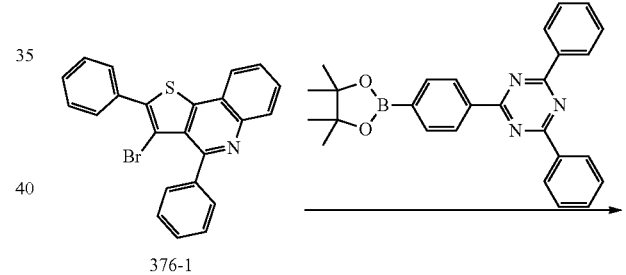
376-1
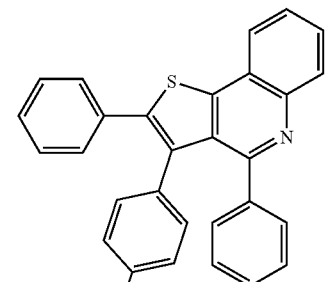
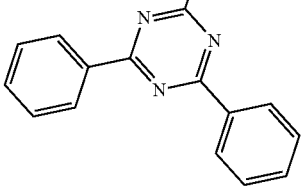
376
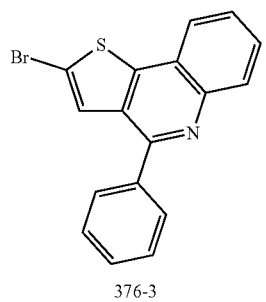
376-4

Preparation of Compound 376-5

After dissolving 2,5-dibromothiophene (82.82 g, 342.33 mmol) and 2-(4,4,5,5-tetramethyl-1,3,2-dioxaborolan-2-yl)aniline (50 g, 228.22 mmol) in 1,4-dioxane (500 ml) and $H_2O$ (100 ml), $Pd(PPh_3)_4$ (7.91 g, 6.85 mmol) and $NaHCO_3$ (57.52 g, 684.65 mmol) were introduced thereto, and the result was stirred for 8 hours under reflux. After the reaction was completed, the reaction solution was dissolved by introducing MC thereto, and then extracted with distilled water. After drying the organic layer with $MgSO_4$, the solvent was removed using a rotary evaporator, and then the result was purified by column chromatography using dichloromethane and hexane as a developing solvent to obtain Compound 376-5 (40 g, 69%).

Preparation of Compound 376-4

After dissolving Compound 376-5 (40 g, 157.39 mmol) in MC (400 ml), TEA (47.78 g, 472.16 mmol) was introduced thereto. The temperature was lowered from room temperature to 0° C., and then benzoyl chloride (24.34 g, 173.13 mmol) dissolved in MC was slowly added dropwise thereto. After the reaction was completed, the result was extracted with MC and distilled water, and after drying the organic layer with $MgSO_4$, the solvent was removed using a rotary evaporator, and then the result was purified by column chromatography using dichloromethane and hexane as a developing solvent to obtain Compound 376-4 (45 g, 80%).

Preparation of Compound 376-3

After dissolving Compound 376-4 (45 g, 125.61 mmol) in nitrobenzene (450 ml), $POCl_3$ (21.19 g, 138.17 mmol) was slowly added dropwise thereto, and the result was stirred for 4 hours at 150° C. After the reaction was completed, the result was neutralized with an aqueous $NaHCO_3$ solution and then extracted with MC and distilled water. After drying the organic layer with $MgSO_4$, the solvent was removed using a rotary evaporator, and then the result was purified by column chromatography using dichloromethane and hexane as a developing solvent to obtain Compound 376-3 (32 g, 75%).

Preparation of Compound 376-2

After dissolving Compound 376-3 (32 g, 94.05 mmol) and phenylboronic acid (12.04 g, 98.75 mmol) in toluene (300 ml), ethanol (60 ml) and $H_2O$ (60 ml), $Pd(PPh_3)_4$ (5.43 g, 4.7 mmol) and $K_2CO_3$ (39 g, 282.15 mmol) were introduced thereto, and the result was stirred for 8 hours under reflux. After the reaction was completed, the reaction solution was dissolved by introducing MC thereto, and then extracted with distilled water. After drying the organic layer with $MgSO_4$, the solvent was removed using a rotary evaporator, and then the result was purified by column chromatography using dichloromethane and hexane as a developing solvent to obtain Compound 376-2 (27 g, 85%).

Preparation of Compound 376-1

After dissolving Compound 376-2 (27 g, 80.01 mmol) in chloroform (300 ml), the temperature was lowered to 0° C., and bromine (14.07 g, 88.02 mmol) diluted in chloroform was slowly added dropwise thereto. After the reaction was completed, the result was extracted with MC and distilled water. After drying the organic layer with $MgSO_4$, the solvent was removed using a rotary evaporator, and then the result was purified by column chromatography using dichloromethane and hexane as a developing solvent to obtain Compound 376-1 (29 g, 87%).

Preparation of Compound 376

After dissolving Compound 376-1 (8 g, 19.22 mmol) and 2,4-diphenyl-6-(4-(4,4,5,5-tetramethyl-1,3,2-dioxaborolan-2-yl)phenyl)-1,3,5-triazine (8.78 g, 20.18 mmol) in toluene (100 ml), ethanol (20 ml) and $H_2O$ (20 ml), $Pd(PPh_3)_4$ (1.11 g, 0.96 mmol) and $K_2CO_3$ (7.97 g, 57.76 mmol) were introduced thereto, and the result was stirred for 5 hours under reflux. After the reaction was completed, the result was cooled to room temperature, and produced solids were filtered and then washed with EA and MeOH. After that, the solids were all dissolved in an excess amount of dichloromethane, and filtered with silica gel to obtain Compound 376 (9.3 g, 75%).

Target compounds were synthesized in the same manner as in Preparation Example 4 using Intermediate G of the following Table 4 instead of 2,5-dibromothiophene, using Intermediate H instead of phenylboronic acid, and using Intermediate I instead of 2,4-diphenyl-6-(4-(4,4,5,5-tetramethyl-1,3,2-dioxaborolan-2-yl)phenyl)-1,3,5-triazine.

TABLE 4

| Compound | Intermediate G | Intermediate H | Intermediate I |
|---|---|---|---|
| 380 | Br-thiophene-Br (2,5-dibromothiophene) | phenylboronic acid (PhB(OH)₂) | [structure: 2,4-diphenyl-1,3,5-triazine linked to biphenyl with pinacol boronate] |

TABLE 4-continued
| 382 | 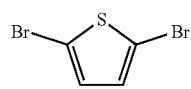 | 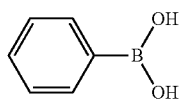 | 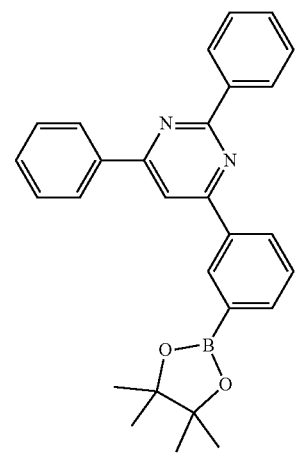 [SMILES: CC1(C)OB(c2cccc(-c3cc(-c4ccccc4)nc(-c4ccccc4)n3)c2)OC1(C)C] |
| 390 | 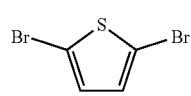 | 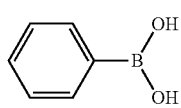 | 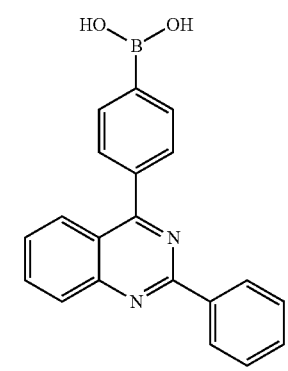 [SMILES: OB(O)c1ccc(-c2nc(-c3ccccc3)nc3ccccc23)cc1] |
| 406 | 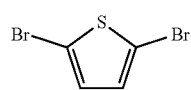 | 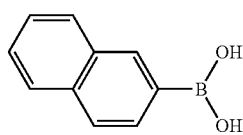 [SMILES: OB(O)c1ccc2ccccc2c1] | 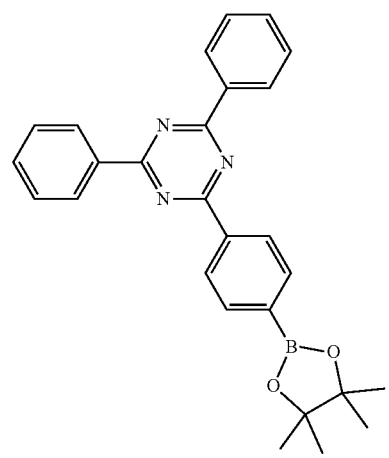 |
| 419 | 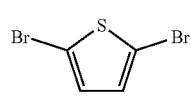 | 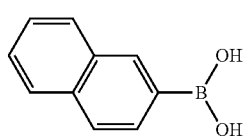 | 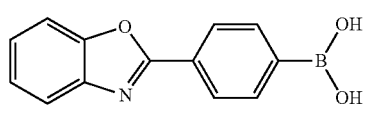 [SMILES: OB(O)c1ccc(-c2nc3ccccc3o2)cc1] |

TABLE 4-continued
| 421 | 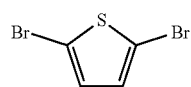 | 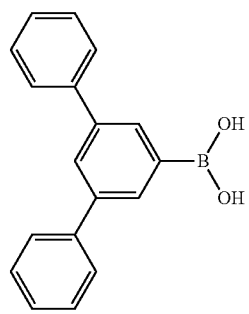 [SMILES: OB(O)c1cc(-c2ccccc2)cc(-c2ccccc2)c1] | 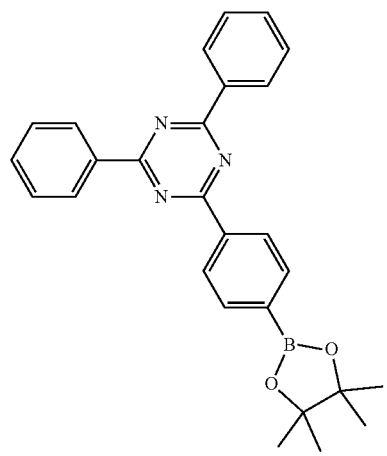 [SMILES: CC1(C)OB(c2ccc(-c3nc(-c4ccccc4)nc(-c4ccccc4)n3)cc2)OC1(C)C] |
| 429 | 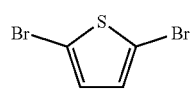 | 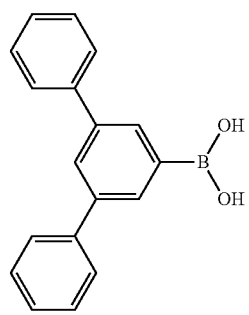 [SMILES: OB(O)c1cc(-c2ccccc2)cc(-c2ccccc2)c1] | 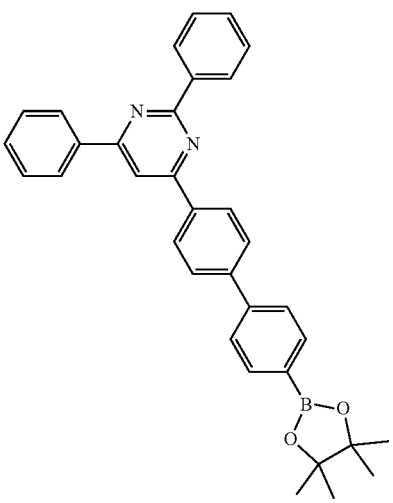 [SMILES: CC1(C)OB(c2ccc(-c3ccc(-c4cc(-c5ccccc5)nc(-c5ccccc5)n4)cc3)cc2)OC1(C)C] |
| 437 | 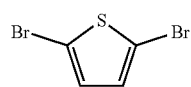 | 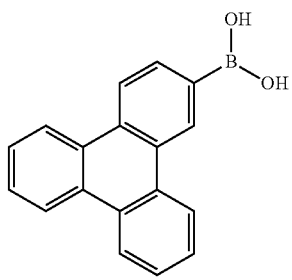 [SMILES: OB(O)c1ccc2c3ccccc3c3ccccc3c2c1] | 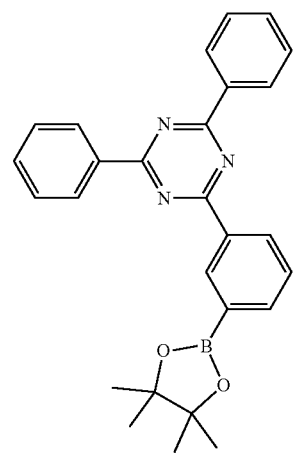 [SMILES: CC1(C)OB(c2cccc(-c3nc(-c4ccccc4)nc(-c4ccccc4)n3)c2)OC1(C)C] |
| 463 | 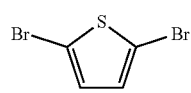 | 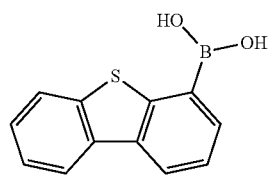 [SMILES: OB(O)c1cccc2c1sc1ccccc12] | 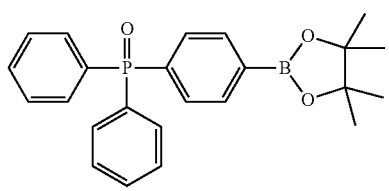 [SMILES: CC1(C)OB(c2ccc(P(=O)(c3ccccc3)c3ccccc3)cc2)OC1(C)C] |

TABLE 4-continued
| 481 | 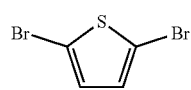 |  | 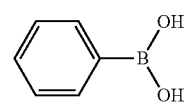 |
| 487 | 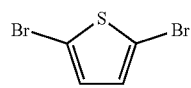 | 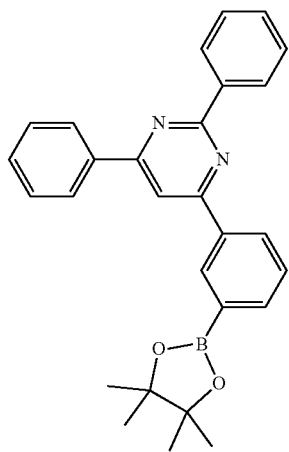 [SMILES: CC1(C)OB(c2cccc(-c3cc(-c4ccccc4)nc(-c4ccccc4)n3)c2)OC1(C)C] | 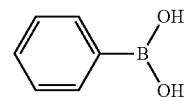 |
| 495 | 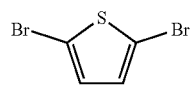 | 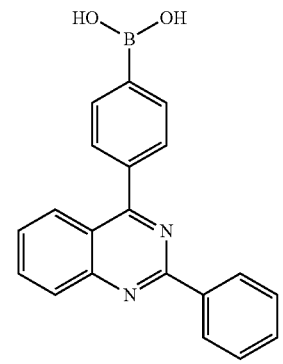 [SMILES: OB(O)c1ccc(-c2nc(-c3ccccc3)nc3ccccc23)cc1] | 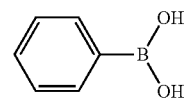 |

US 12,410,186 B2
TABLE 4-continued
| | | | |
|---|---|---|---|
| 516 | 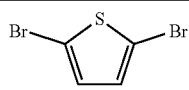 | 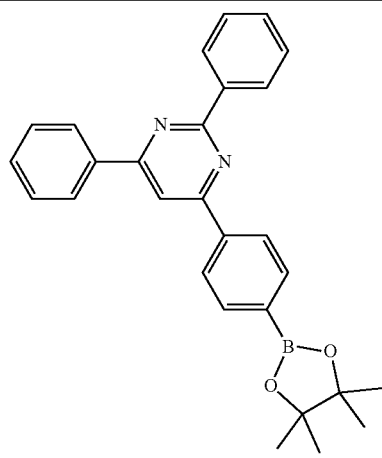 | 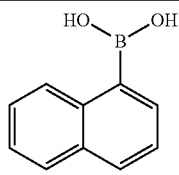 |
| 526 | 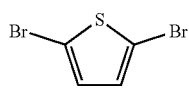 | 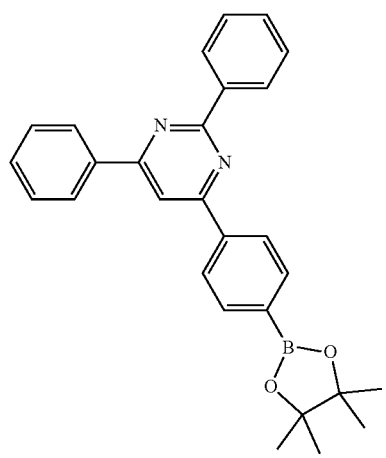 | 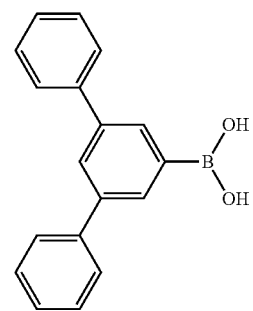 [SMILES: OB(O)c1cc(-c2ccccc2)cc(-c2ccccc2)c1] |
| 541 | 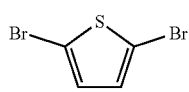 | 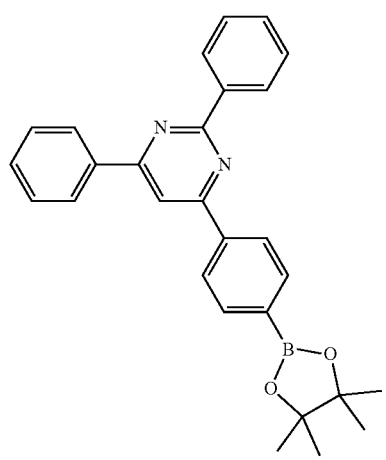 | 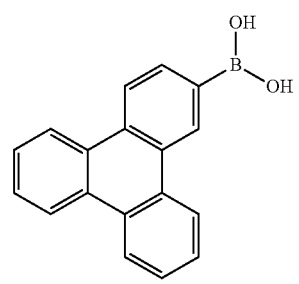 [SMILES: OB(O)c1ccc2c3ccccc3c3ccccc3c2c1] |
| 552 | 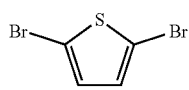 | 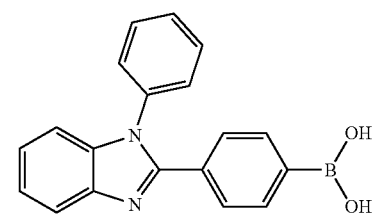 [SMILES: OB(O)c1ccc(-c2nc3ccccc3n2-c2ccccc2)cc1] | 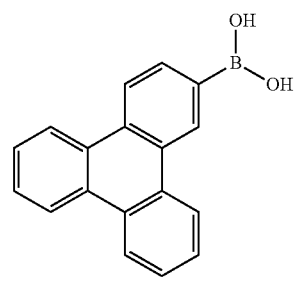 [SMILES: OB(O)c1ccc2c3ccccc3c3ccccc3c2c1] |

TABLE 4-continued
| 561 | 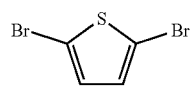 | 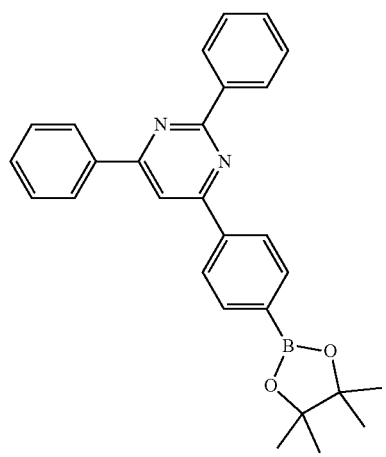 [SMILES: CC1(C)OB(c2ccc(-c3cc(-c4ccccc4)nc(-c4ccccc4)n3)cc2)OC1(C)C] | 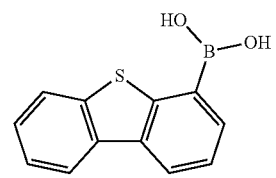 [SMILES: OB(O)c1cccc2c1sc1ccccc12] |
| 571 | 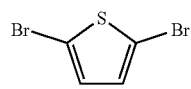 | 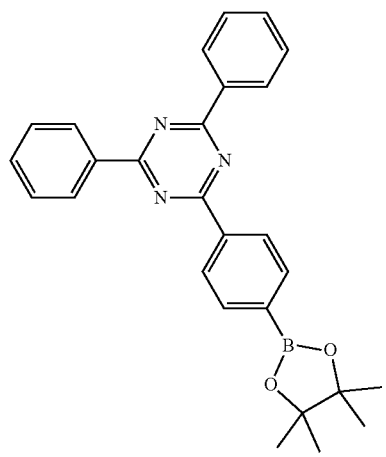 [SMILES: CC1(C)OB(c2ccc(-c3nc(-c4ccccc4)nc(-c4ccccc4)n3)cc2)OC1(C)C] | 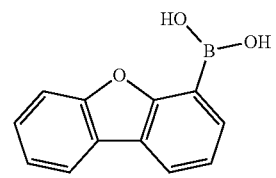 |
| 592 | 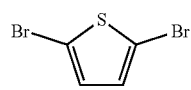 | 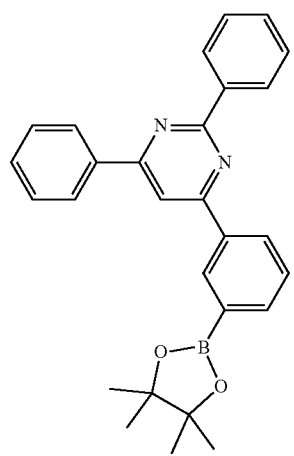 [SMILES: CC1(C)OB(c2cccc(-c3cc(-c4ccccc4)nc(-c4ccccc4)n3)c2)OC1(C)C] | 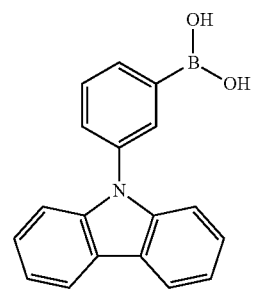 [SMILES: OB(O)c1cccc(-n2c3ccccc3c3ccccc32)c1] |

TABLE 4-continued
| | | | |
|---|---|---|---|
| 605 | 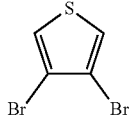 | 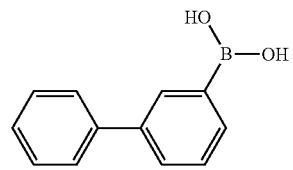 [SMILES: OB(O)c1cccc(-c2ccccc2)c1] | 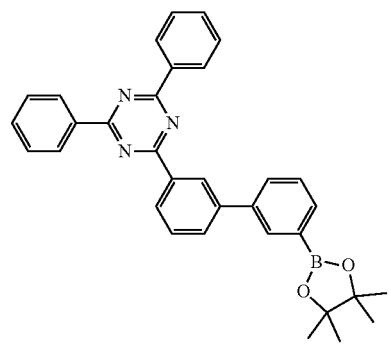 [SMILES: CC1(C)OB(c2cccc(-c3cccc(-c4nc(-c5ccccc5)nc(-c5ccccc5)n4)c3)c2)OC1(C)C] |
| 628 | 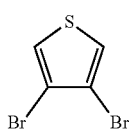 | 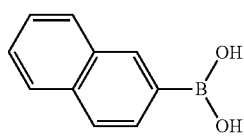 [SMILES: OB(O)c1ccc2ccccc2c1] | 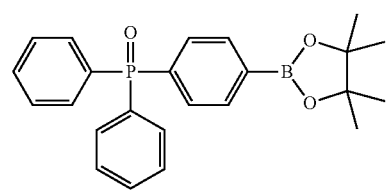 [SMILES: CC1(C)OB(c2ccc(P(=O)(c3ccccc3)c3ccccc3)cc2)OC1(C)C] |
| 632 | 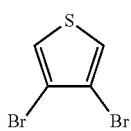 | 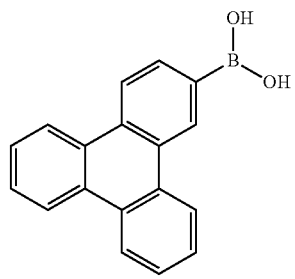 [SMILES: OB(O)c1ccc2c3ccccc3c3ccccc3c2c1] | 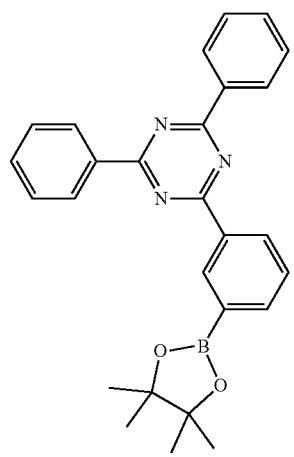 [SMILES: CC1(C)OB(c2cccc(-c3nc(-c4ccccc4)nc(-c4ccccc4)n3)c2)OC1(C)C] |
| 646 | 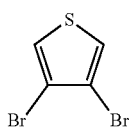 | 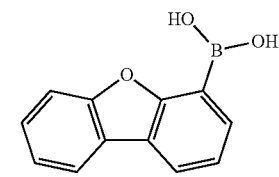 [SMILES: OB(O)c1cccc2c1oc1ccccc12] | 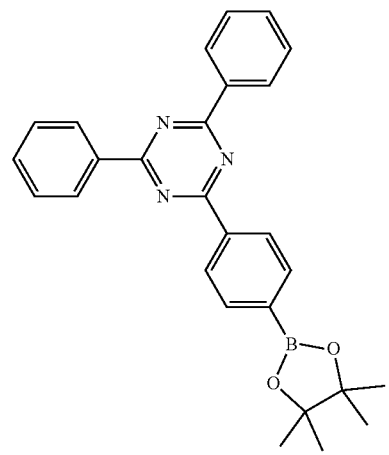 |

TABLE 4-continued
| | | | |
|---|---|---|---|
| 665 | 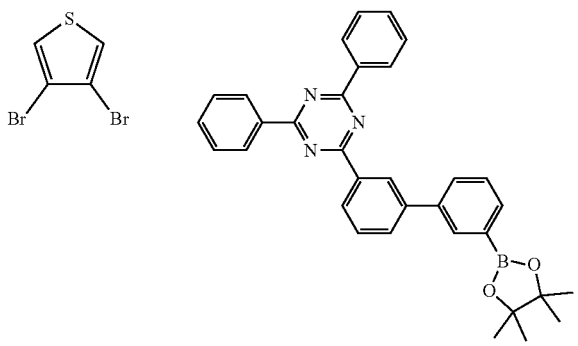 | | |
| 706 | | 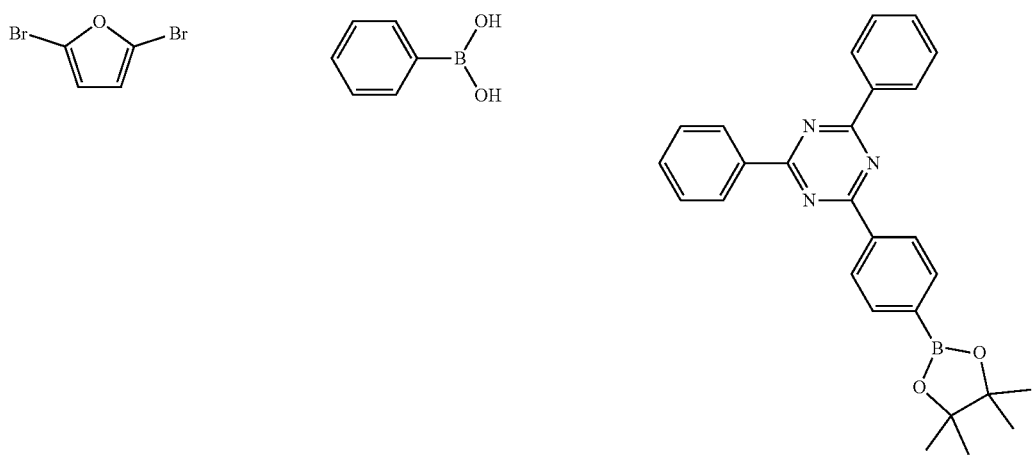 | |
| 725 | | 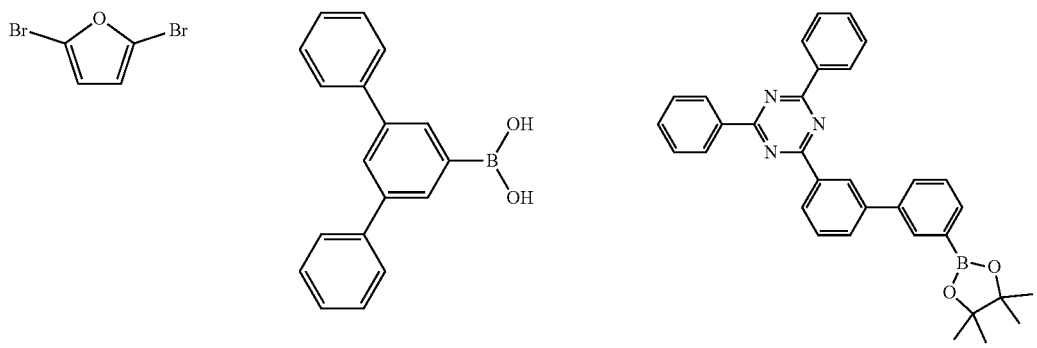 | |
| 792 | 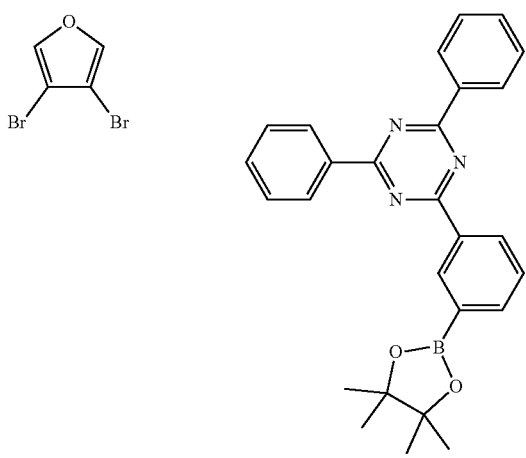 | | 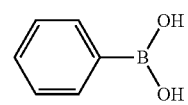 |

TABLE 4-continued

| | | | |
|---|---|---|---|
| 816 | 3,4-dibromofuran | triphenylene-2-boronic acid | 4-(2,6-di(pyridin-2-yl)pyridin-4-yl)phenyl boronic acid pinacol ester |
| 856 | 2,5-dibromothiophene | phenylboronic acid | 4-(4-([1,1'-biphenyl]-4-yl)-6-phenyl-1,3,5-triazin-2-yl)phenyl boronic acid pinacol ester |

| Compound | Target Compound | Yield |
|---|---|---|
| 380 | | 74% |
| 382 | | 72% |

TABLE 4-continued
| 390 | 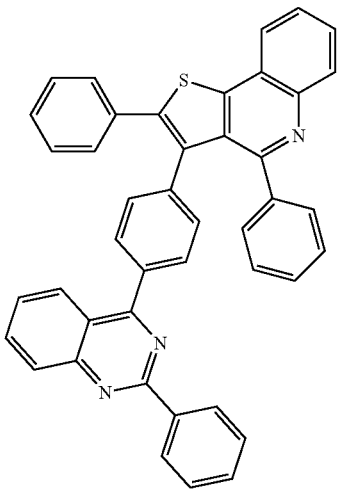 [SMILES: c1ccc(-c2nc(-c3ccc(-c4c(-c5ccccc5)sc5c4c(-c4ccccc4)nc4ccccc45)cc3)c3ccccc3n2)cc1] | 81% |
| 406 | 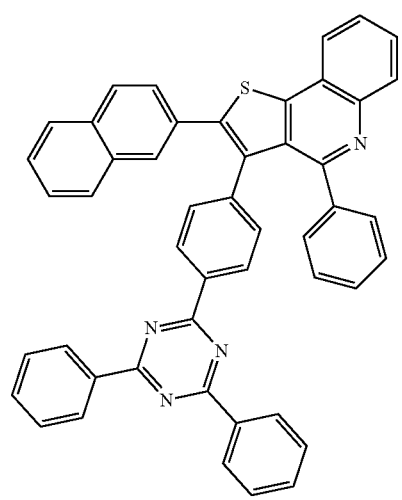 [SMILES: c1ccc(-c2nc(-c3ccccc3)nc(-c3ccc(-c4c(-c5ccc6ccccc6c5)sc5c4c(-c4ccccc4)nc4ccccc45)cc3)n2)cc1] | 77% |
| 419 | 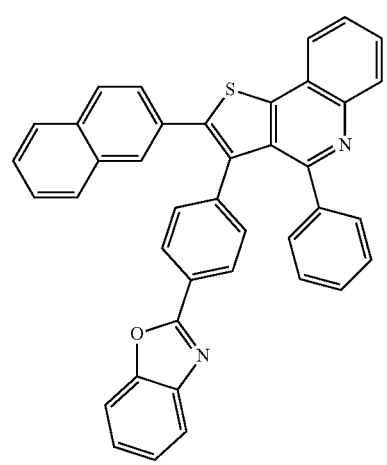 [SMILES: c1ccc(-c2nc3ccccc3c3sc(-c4ccc5ccccc5c4)c(-c4ccc(-c5nc6ccccc6o5)cc4)c23)cc1] | 72% |

TABLE 4-continued
| 421 | 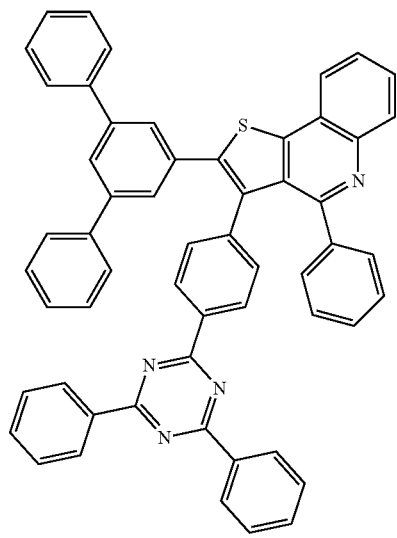 [SMILES: c1ccc(-c2cc(-c3ccccc3)cc(-c3sc4c(c(-c5ccccc5)nc5ccccc54)c3-c3ccc(-c4nc(-c5ccccc5)nc(-c5ccccc5)n4)cc3)c2)cc1] | 67% |
| 429 | 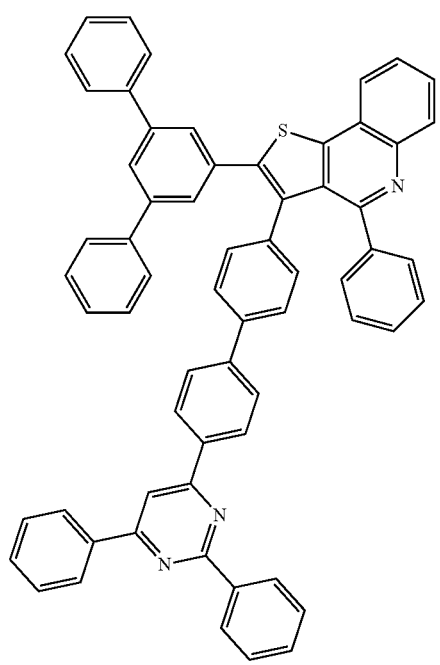 [SMILES: c1ccc(-c2cc(-c3ccccc3)cc(-c3sc4c(c(-c5ccccc5)nc5ccccc54)c3-c3ccc(-c4ccc(-c5cc(-c6ccccc6)nc(-c6ccccc6)n5)cc4)cc3)c2)cc1] | 64% |

TABLE 4-continued
437 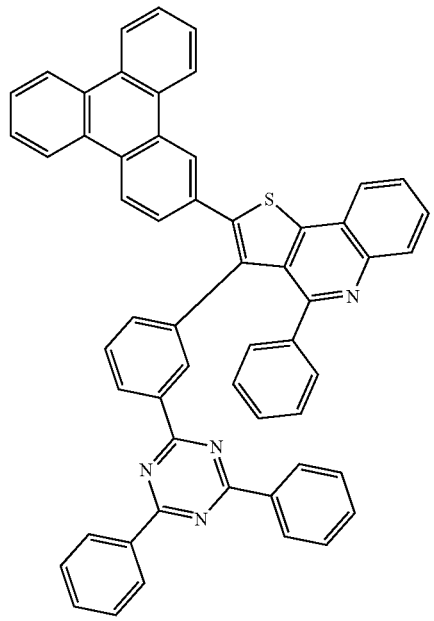 [SMILES: c1ccc(-c2nc(-c3ccccc3)nc(-c3cccc(-c4c(-c5ccc6c7ccccc7c7ccccc7c6c5)sc5c4c(-c4ccccc4)nc4ccccc45)c3)n2)cc1] 69%
463 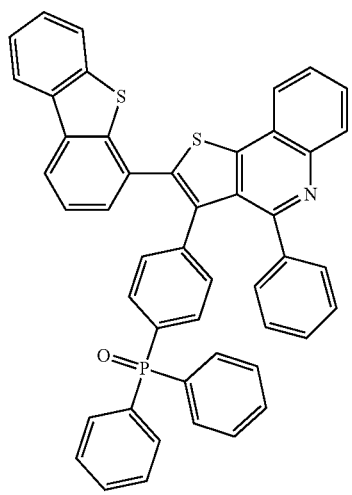 [SMILES: O=P(c1ccccc1)(c1ccccc1)c1ccc(-c2c(-c3cccc4c3sc3ccccc34)sc3c2c(-c2ccccc2)nc2ccccc23)cc1] 75%
481 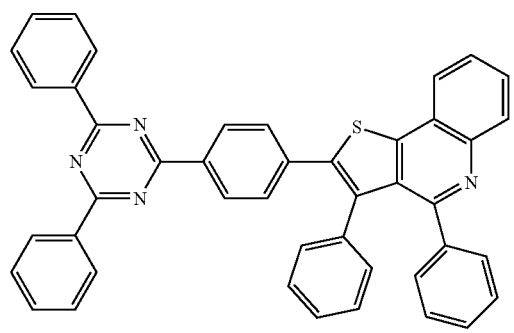 [SMILES: c1ccc(-c2nc(-c3ccccc3)nc(-c3ccc(-c4sc5c(c(-c6ccccc6)nc6ccccc65)c4-c4ccccc4)cc3)n2)cc1] 77%

TABLE 4-continued
| 487 | 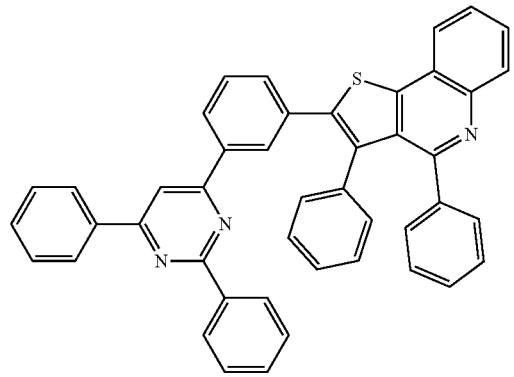 [SMILES: c1ccc(-c2cc(-c3cccc(-c4sc5c(c(-c6ccccc6)nc6ccccc65)c4-c4ccccc4)c3)nc(-c3ccccc3)n2)cc1] | 70% |
| 495 | 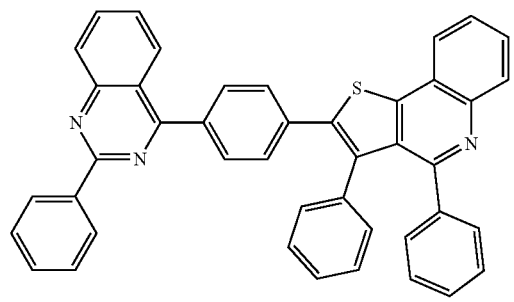 [SMILES: c1ccc(-c2nc(-c3ccc(-c4sc5c(c(-c6ccccc6)nc6ccccc65)c4-c4ccccc4)cc3)c3ccccc3n2)cc1] | 68% |
| 516 | 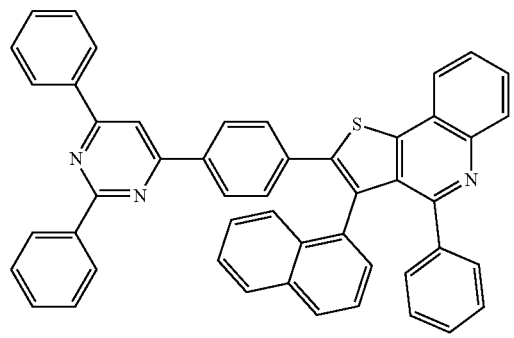 [SMILES: c1ccc(-c2cc(-c3ccc(-c4sc5c(c(-c6ccccc6)nc6ccccc65)c4-c4cccc5ccccc45)cc3)nc(-c3ccccc3)n2)cc1] | 82% |
| 526 | 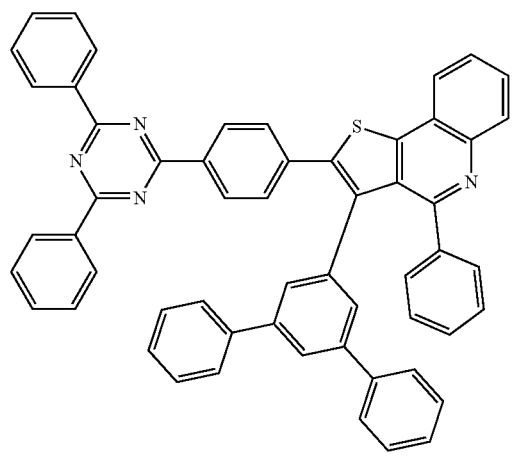 [SMILES: c1ccc(-c2cc(-c3ccccc3)cc(-c3c(-c4ccc(-c5nc(-c6ccccc6)nc(-c6ccccc6)n5)cc4)sc4c3c(-c3ccccc3)nc3ccccc34)c2)cc1] | 77% |

TABLE 4-continued
| 541 | 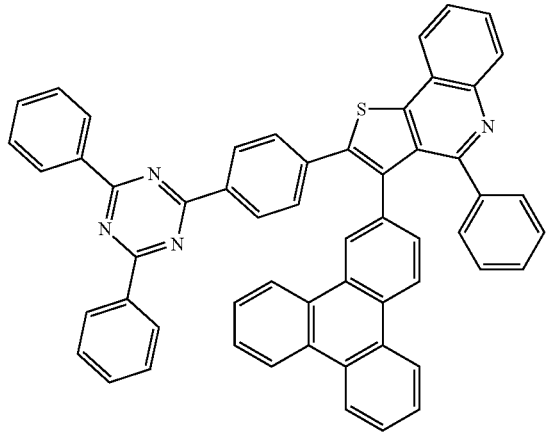 [SMILES: c1ccc(-c2nc(-c3ccccc3)nc(-c3ccc(-c4sc5c(c(-c6ccccc6)nc6ccccc65)c4-c4ccc5c6ccccc6c6ccccc6c5c4)cc3)n2)cc1] | 62% |
| 552 | 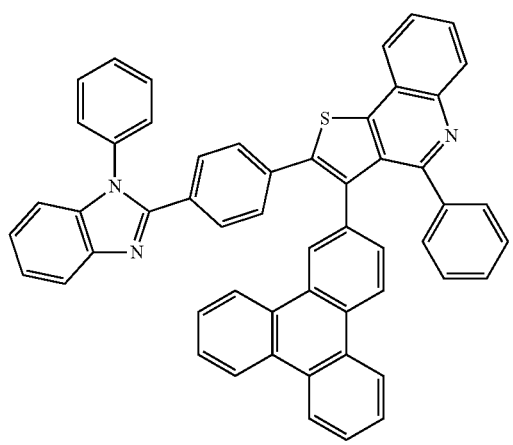 [SMILES: c1ccc(-c2nc3ccccc3c3sc(-c4ccc(-c5nc6ccccc6n5-c5ccccc5)cc4)c(-c4ccc5c6ccccc6c6ccccc6c5c4)c23)cc1] | 66% |
| 561 | 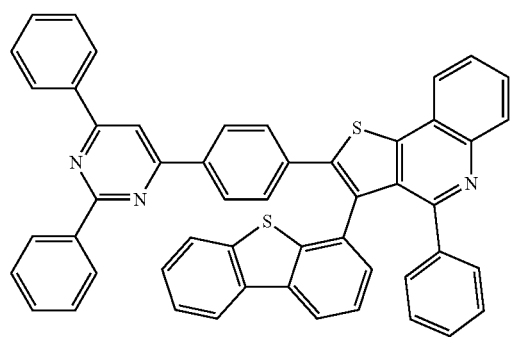 [SMILES: c1ccc(-c2cc(-c3ccc(-c4sc5c(c(-c6ccccc6)nc6ccccc65)c4-c4cccc5c4sc4ccccc45)cc3)nc(-c3ccccc3)n2)cc1] | 72% |
| 571 | 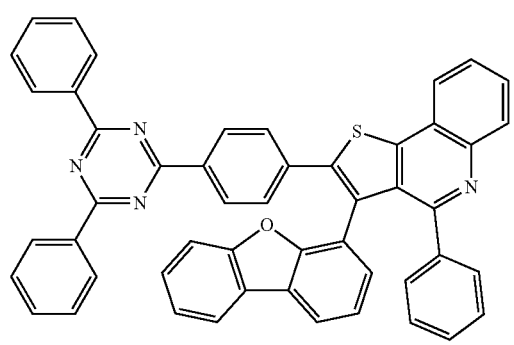 [SMILES: c1ccc(-c2nc(-c3ccccc3)nc(-c3ccc(-c4sc5c(c(-c6ccccc6)nc6ccccc65)c4-c4cccc5c4oc4ccccc45)cc3)n2)cc1] | 66% |

TABLE 4-continued
592 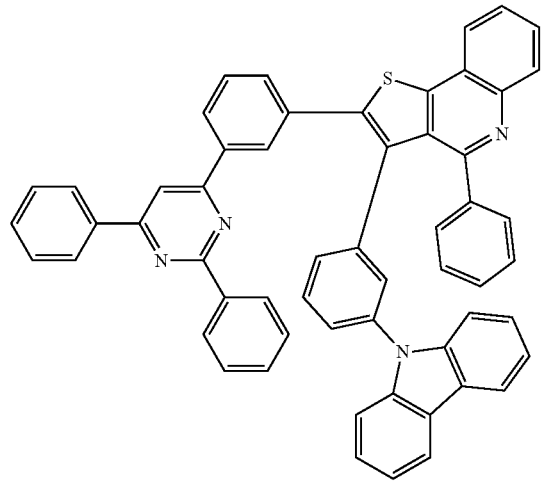 [SMILES: c1ccc(-c2cc(-c3cccc(-c4sc5c(c(-c6ccccc6)nc6ccccc65)c4-c4cccc(-n5c6ccccc6c6ccccc65)c4)c3)nc(-c3ccccc3)n2)cc1] 66%
605 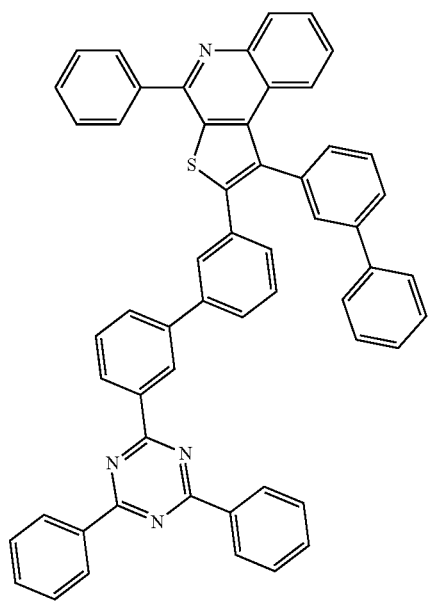 [SMILES: c1ccc(-c2cccc(-c3c(-c4cccc(-c5cccc(-c6nc(-c7ccccc7)nc(-c7ccccc7)n6)c5)c4)sc4c(-c5ccccc5)nc5ccccc5c34)c2)cc1] 59%
628 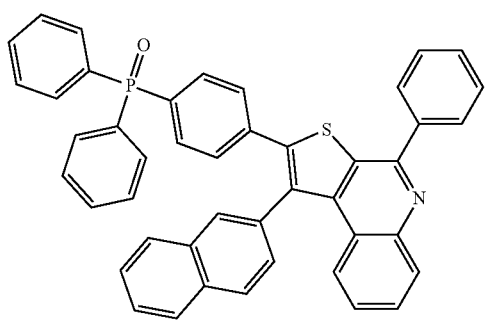 [SMILES: O=P(c1ccccc1)(c1ccccc1)c1ccc(-c2sc3c(-c4ccccc4)nc4ccccc4c3c2-c2ccc3ccccc3c2)cc1] 62%

TABLE 4-continued
| 632 | 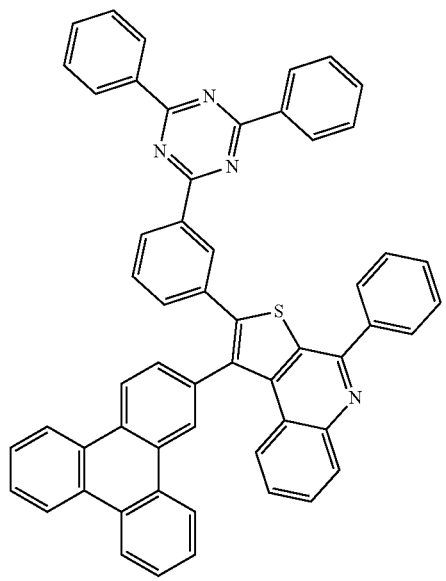 [SMILES: c1ccc(-c2nc(-c3ccccc3)nc(-c3cccc(-c4sc5c(-c6ccccc6)nc6ccccc6c5c4-c4ccc5c6ccccc6c6ccccc6c5c4)c3)n2)cc1] | 64% |
| 646 | 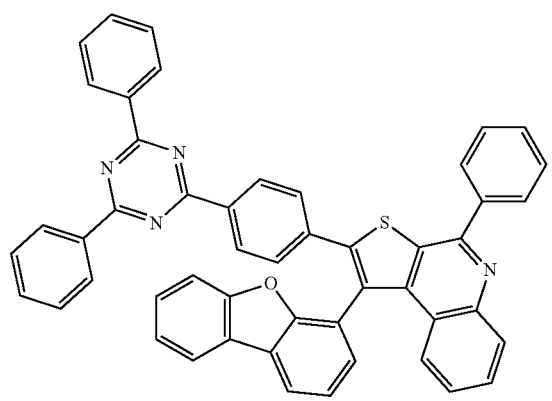 [SMILES: c1ccc(-c2nc(-c3ccccc3)nc(-c3ccc(-c4sc5c(-c6ccccc6)nc6ccccc6c5c4-c4cccc5c4oc4ccccc45)cc3)n2)cc1] | 64% |
| 665 | 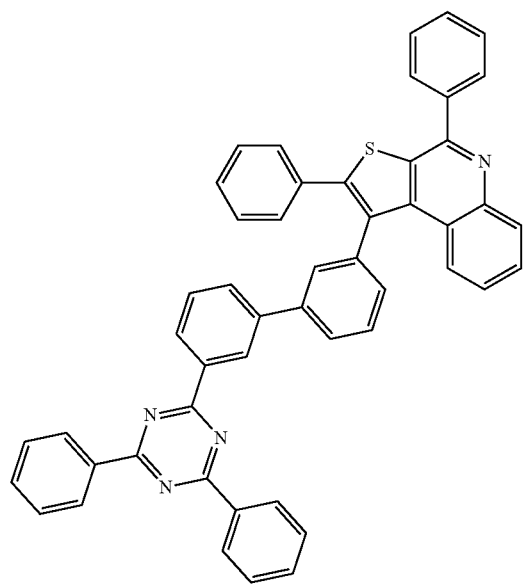 [SMILES: c1ccc(-c2nc(-c3ccccc3)nc(-c3cccc(-c4cccc(-c5c(-c6ccccc6)sc6c(-c7ccccc7)nc7ccccc7c56)c4)c3)n2)cc1] | 72% |

TABLE 4-continued
| 706 | 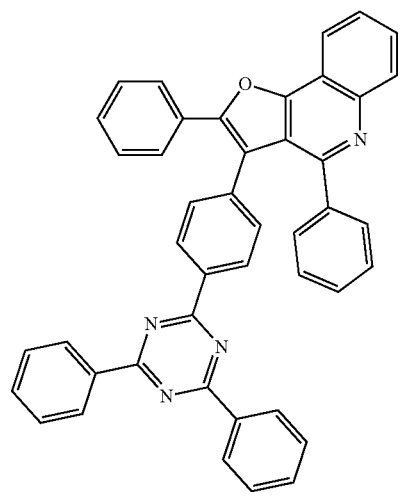 [SMILES: c1ccc(-c2nc(-c3ccccc3)nc(-c3ccc(-c4c(-c5ccccc5)oc5c4c(-c4ccccc4)nc4ccccc45)cc3)n2)cc1] | 66% |
| 725 | 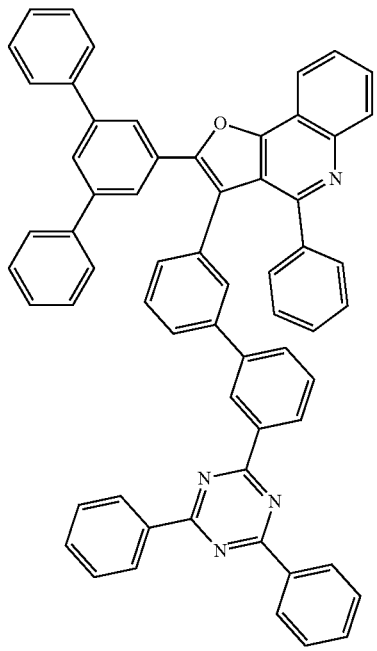 [SMILES: c1ccc(-c2cc(-c3ccccc3)cc(-c3oc4c(c(-c5ccccc5)nc5ccccc54)c3-c3cccc(-c4cccc(-c5nc(-c6ccccc6)nc(-c6ccccc6)n5)c4)c3)c2)cc1] | 70% |
| 792 | 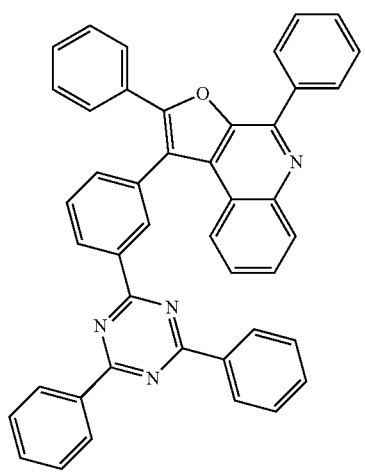 [SMILES: c1ccc(-c2nc(-c3ccccc3)nc(-c3cccc(-c4c(-c5ccccc5)oc5c(-c6ccccc6)nc6ccccc6c45)c3)n2)cc1] | 59% |

TABLE 4-continued

816 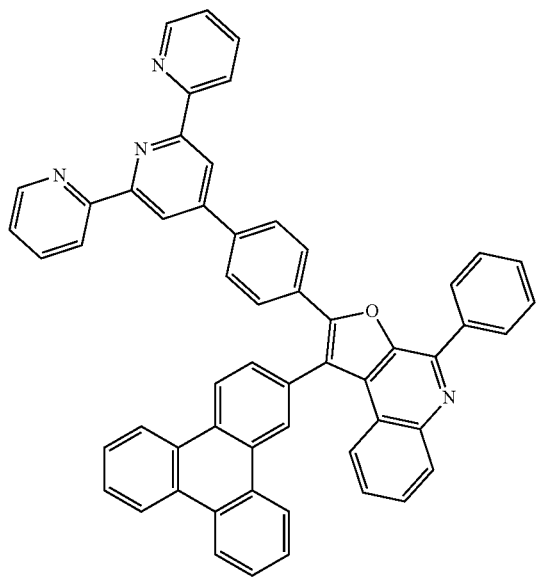 [SMILES: c1ccc(-c2nc3ccccc3c3c(-c4ccc5c6ccccc6c6ccccc6c5c4)c(-c4ccc(-c5cc(-c6ccccn6)nc(-c6ccccn6)c5)cc4)oc23)cc1] 62%

856 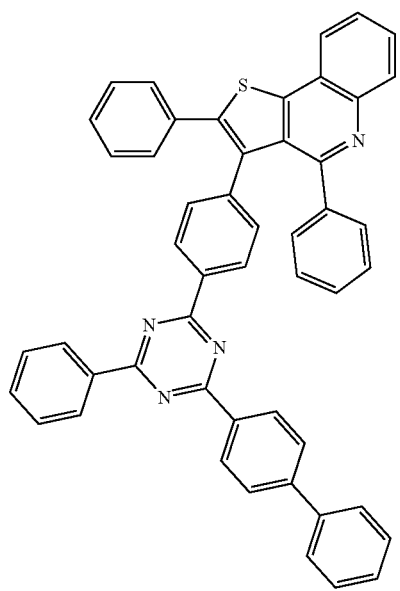 [SMILES: c1ccc(-c2ccc(-c3nc(-c4ccccc4)nc(-c4ccc(-c5c(-c6ccccc6)sc6c5c(-c5ccccc5)nc5ccccc56)cc4)n3)cc2)cc1] 68%

Compounds were prepared in the same manner as in the preparation examples described above, and the synthesis identification results are shown in the following Table 5 and Table 6.

TABLE 5

| NO | 1H NMR (CDCl$_3$, 300 Mz) |
|---|---|
| 1 | 8.69 (2H, d), 8.36-8.29 (4H, m), 8.23 (1H, s), 8.14 (1H, d), 7.95-7.74 (10H, m), 7.58-7.33 (15H, m) |
| 6 | 8.69 (2H, d), 8.39-8.30 (4H, m), 8.25 (2H, d), 8.14 (1H, d), 7.86-7.74 (6H, m), 7.59-7.32 (15H, m), 7.34-7.25 (3H, m) |
| 9 | 8.69 (2H, d), 8.55 (2H, dd), 8.36-8.29 (4H, m), 8.23-8.19 (4H, m), 7.86-7.33 (25H, m), 7.20-7.11 (4H, m) |
| 10 | 8.69 (2H, d), 8.55 (1H, dd), 8.39-8.32 (2H, m), 8.25-8.14 (5H, m), 7.87-7.10 (28H, m) |
| 11 | 8.69 (4H, s), 8.38-8.32 (4H, m), 8.14 (1H, d), 7.86-7.75 (5H, m), 7.58-7.39 (15H, m) |

TABLE 5-continued

| NO | 1H NMR (CDCl$_3$, 300 Mz) |
|---|---|
| 12 | 8.69 (2H, d), 8.55 (2H, dd), 8.20-8.13 (5H, m), 7.87-7.74 (6H, m), 7.60-7.33 (14H, m), 7.21-7.10 (8H, m) |
| 26 | 8.72 (1H, dd), 8.38-8.32 (6H, m), 8.14 (1H, dd), 7.87-7.75 (6H, m), 7.59-7.33 (15H, m) |
| 29 | 9.18-9.14 (4H, m), 8.55 (2H, dd), 8.35-8.31 (2H, m), 8.14 (1H, dd), 7.86-7.71 (7H, m), 7.61-7.23 (12H, m) |
| 31 | 8.69 (1H, dd), 8.35-8.29 (4H, m), 8.23 (s, 1H), 8.15-8.06 (3H, m), 7.95-7.83 (7H, m), 7.75 (1H, ddd), 7.60-7.41 (15H, m) |
| 36 | 8.69 (2H, d), 8.36 (4H, dd), 8.25 (2H, d), 8.15-8.06 (3H, m), 7.87-8.84 (3H, m), 7.75 (1H, ddd), 7.61-7.40 (15H, m) |
| 56 | 8.72 (1H, dd), 8.38-8.31 (6H, m), 8.15-8.06 (3H, m), 7.88-7.84 (2H, m) |
| 63 | 8.42-8.28 (7H, m), 8.24-8.18 (3H, m), 7.94 (1H, s), 7.86-7.74 (9H, m), 7.65 (2H, dd), 7.51-7.32 (15H, m) |
| 82 | 8.39-8.35 (5H, m), 8.24-8.18 (3H, m), 8.11 (1H, s), 7.94 (1H, dd), 7.85-7.80 (2H, m), 7.72-7.33 (20H, m) |

TABLE 5-continued

| NO | 1H NMR (CDCl3, 300 Mz) |
|---|---|
| 104 | 9.20-9.12 (4H, m), 8.55 (2H, dd), 8.35 (1H, d), 8.19 (2H, dd), 8.10-8.06 (4H, m), 7.75-7.40 (13H, m), 7.23 (2H, ddd) |
| 108 | 8.36-8.18 (10H, m), 8.12-8.06 (3H, m), 7.86-7.84 (4H, m), 7.75 (2H, dd), 7.67-7.39 (18H, m) |
| 117 | 8.55 (2H, dd), 8.25-8.05 (10H, m), 7.66-7.39 (17H, m), 7.22-7.09 (8H, m) |
| 126 | 8.77-8.62 (6H, m), 8.39-8.33 (4H, m), 8.25 (2H, d), 8.14 (1H, dd), 7.91-7.83 (7H, m), 7.75 (1H, ddd), 7.60-7.48 (7H, m), 7.25 (2H, d) |
| 131 | 9.25-9.21 (2H, m), 8.72-8.60 (6H, m), 8.38-8.30 (6H, m), 8.14 (1H, dd), 7.88-7.85 (2H, m), 7.75 (1H, ddd), 7.60-7.37 (7H, m) |
| 134 | 9.26-9.12 (6H, m), 8.72-8.55 (6H, m), 8.34-8.30 (2H, m), 8.14 (1H, dd), 7.88-7.72 (6H, m), 7.58 (1H, ddd), 7.48-7.39 (2H, m), 7.23 (2H, ddd) |
| 149 | 9.26-9.12 (6H, m), 8.72-8.53 (4H, m), 8.29-8.35 (4H, m), 8.14 (1H, dd), 7.86 (1H, dd), 7.76-7.69 (4H, m), 7.62-7.57 (2H, m), 7.49-7.39 (2H, m), 7.23 (1H, ddd) |
| 181 | 8.85 (1H, dd), 8.43-8.28 (6H, m), 8.08-7.93 (6H, m), 7.87-7.73 (5H, m), 7.63-7.31 (16H, m) |
| 185 | 8.75 (2H, d), 8.64 (2H, d), 8.43-8.33 (5H, m), 8.21-8.11 (3H, m), 7.96-7.72 (10H, m), 7.67-7.48 (7H, m) |
| 222 | 9.26-9.22 (2H, m), 8.72-8.68 (2H, m), 8.55 (2H, dd), 8.41 (1H, d), 8.35-8.31 (2H, m), 8.21-8.15 (6H, m), 7.94 (1H, dd), 7.75 (1H, ddd), 7.67-7.58 (3H, m), 7.54-7.38 (7H, m), 7.22-7.09 (8H, m) |
| 234 | 9.26-9.22 (2H, m), 8.72-8.68 (2H, m), 8.55 (1H, dd), 8.37-8.17 (13H, m), 7.87-7.78 (3H, m), 7.68-7.38 (13H, m), 7.22-7.08 (4H, m) |
| 241 | 8.69 (2H, d), 8.37-8.28 (4H, m), 8.23 (1H, s), 8.14 (1H, dd), 7.97-7.72 (10H, m), 7.60-7.31 (15H, m) |
| 242 | 8.69 (2H, d), 8.39-8.31 (4H, m), 8.25 (2H, d), 8.14 (1H, dd), 7.87-7.72 (6H, m), 7.59-7.31 (15H, m), 7.35-7.23 (3H, m) |
| 248 | 9.27 (1H, s), 8.79 (1H, dd), 8.69 (2H, d), 8.39-8.28 (4H, m), 8.14 (1H, dd), 7.89-7.30 (18H, m) |
| 261 | 8.76 (1H, d), 8.39-8.21 (6H, m), 8.06 (1H, d), 7.88-7.80 (3H, m), 7.58-7.30 (17H, m) |
| 277 | 9.20-9.12 (4H, m), 8.69 (2H, d), 8.55 (2H, dd), 8.16-8.05 (3H, m), 7.88-7.71 (6H, m), 7.62-7.39 (9H, m), 7.23 (2H, ddd) |
| 287 | 8.39-8.33 (4H, m), 8.27-8.21 (5H, m), 8.11-8.05 (3H, m), 7.62-7.39 (18H, m), 7.25 (2H, d) |
| 291 | 8.76 (1H, s), 8.39-8.21 (7H, m), 8.09-8.04 (3H, m), 7.86 (1H, dd), 7.62-36 (17H, m) |
| 294 | 8.43-8.20 (8H, m), 8.09-8.05 (2H, m), 7.96-7.92 (3H, m), 7.85 (2H, d), 7.75 (1H, m), 7.62-7.38 (17H, m) |
| 301 | 8.77-8.61 (6H, m), 8.37-8.28 (4H, m), 8.23 (1H, s), 8.14 (1H, dd), 7.96-7.83 (11H, m), 7.75 (1H, ddd), 7.60-7.47 (7H, m) |
| 328 | 8.76 (1H, d), 8.60-8.56 (2H, m), 8.39-8.21 (7H, m), 8.07-7.98 (2H, m), 7.88-7.83 (3H, m), 7.58-7.30 (12H, m) |
| 376 | 8.30-8.28 (6H, m), 8.06 (1H, d), 7.98 (1H, d), 7.85-7.78 (5H, m), 7.60-7.41 (13H, m), 7.25 (2H, d) |
| 380 | 8.30-8.24 (7H, m), 8.06 (1H, d), 7.98 (1H, d), 7.79-7.78 (3H, m), 7.70 (2H, s), 7.60-7.41 (18H, m) |
| 382 | 8.30-8.23 (5H, m), 8.06 (1H, d), 7.98 (1H, d), 7.79-7.75 (7H, m), 7.60-7.41 (15H, m) |
| 390 | 8.30-8.28 (6H, m), 8.16 (1H, d), 8.06 (1H, d), 7.98 (1H, d), 7.84-7.78 (5H, m), 7.60-7.41 (11H, m), 7.25 (2H, d) |
| 406 | 8.30-8.24 (7H, m), 8.00-7.78 (9H, m), 7.60-7.41 (12H, m), 7.25 (2H, d) |
| 419 | 8.30-8.24 (3H, m), 8.06-7.74 (11H, m), 7.60-7.39 (8H, m), 7.25 (2H, d) |
| 421 | 8.30-8.28 (6H, m), 8.06 (1H, d), 7.98 (1H, d), 7.85-7.78 (3H, m), 7.66-7.41 (23H, m), 7.25 (2H, d) |
| 429 | 8.30-8.23 (7H, m), 8.06 (1H, d), 7.98 (1H, d), 7.85-7.78 (5H, m), 7.60-7.41 (23H, m), 7.25 (4H, d) |
| 437 | 9.15 (1H, s), 8.93 (2H, d), 8.30-7.98 (13H, m), 7.88-7.78 (5H, m), 7.70 (1H, s), 7.60-7.41 (12H, m) |
| 463 | 8.45-8.41 (2H, m), 8.30 (2H, d), 8.06 (1H, d), 7.98 (2H, m), 7.83-7.77 (10H, m), 7.60-7.45 (13H, m) |
| 481 | 8.30-8.28 (6H, m), 8.06 (1H, d), 7.98 (1H, d), 7.85-7.78 (5H, m), 7.60-7.41 (15H, m) |
| 487 | 8.30-8.23 (5H, m), 8.06 (1H, d), 7.98 (1H, d), 7.79-7.75 (6H, m), 7.60-7.41 (16H, m) |
| 495 | 8.30-8.28 (6H, m), 8.16 (1H, d), 8.06 (1H, d), 7.98 (1H, d), 7.85-7.78 (5H, m), 7.60-7.41 (13H, m) |
| 516 | 8.55 (1H, d), 8.42 (1H, d), 8.30-8.23 (7H, m), 8.08-7.98 (4H, m), 7.85-7.78 (5H, m), 7.61-7.41 (13H, m) |
| 526 | 8.30-8.28 (6H, m), 8.06 (1H, d), 7.98 (1H, d), 7.85-7.78 (5H, m), 7.66-7.41 (23H, m) |
| 541 | 9.15 (1H, s), 8.93 (2H, d), 8.30-8.28 (6H, m), 8.18-7.98 (6H, m), 7.88-7.78 (9H, m), 7.60-7.41 (10H, m) |
| 552 | 9.15 (1H, s), 8.93 (2H, d), 8.56 (1H, d), 8.30 (2H, d), 8.18-7.98 (6H, m), 7.88-7.78 (9H, m), 7.59-7.45 (10H, m), 7.22 (2H, m) |
| 561 | 8.45-8.41 (2H, m), 8.30-8.23 (8H, m), 8.06 (1H, d), 7.98 (1H, d), 7.85-7.78 (5H, m), 7.60-7.41 (13H, m) |
| 571 | 8.30-8.28 (6H, m), 8.06 (1H, d), 7.98 (1H, d), 7.89-7.78 (8H, m), 7.60-7.32 (14H, m) |
| 592 | 8.55 (1H, d), 8.30-8.23 (5H, m), 8.12-8.06 (3H, m), 7.98-7.94 (2H, m), 7.79-7.70 (6H, m), 7.60-7.25 (19H, m) |
| 605 | 8.30-8.24 (7H, m), 8.06 (1H, d), 7.98 (1H, d), 7.78-7.70 (5H, d), 7.60-7.41 (22H, m) |
| 628 | 8.30 (2H, d), 8.06-7.92 (5H, m), 7.83-7.78 (10H, m), 7.60-7.45 (13H, m) |
| 632 | 9.15 (1H, s), 8.93 (2H, d), 8.30-7.98 (13H, m), 7.88-7.70 (7H, m), 7.57-7.41 (11H, m) |
| 646 | 8.30-8.28 (6H, m), 8.06 (1H, d), 7.98 (1H, d), 7.89-7.78 (8H, m), 7.66-7.34 (14H, m) |
| 665 | 8.30-8.24 (7H, m), 8.06 (1H, d), 7.98 (1H, d), 7.79-7.78 (3H, m), 7.70 (2H, s), 7.60-7.41 (18H, m) |
| 706 | 8.30-8.28 (6H, m), 8.10-8.06 (3H, m), 7.98 (1H, d), 7.85-7.78 (3H, m), 7.60-7.41 (13H, m), 7.25 (2H, d) |
| 725 | 8.30-8.24 (7H, m), 8.06 (1H, d), 798 (1H, d), 7.78 (1H, t), 7.70-7.41 (30H, m) |
| 792 | 8.30-8.24 (7H, m), 8.10-8.06 (3H, m), 7.98 (1H, d), 7.78 (1H, t), 7.70 (1H, s), 7.60-7.41 (15H, m) |
| 816 | 9.30 (2H, d), 9.15 (3H, s), 8.93 (2H, d), 8.53 (2H, d), 8.30 (2H, d), 812-7.98 (6H, m), 7.88-7.47 (13H, m), 7.25 (2H, d), 7.14 (2H, t) |
| 856 | 8.30-8.28 (4H, m), 8.06 (1H, d), 7.98 (1H, d), 7.85-7.78 (7H, m), 7.60-7.41 (15H, m), 7.25 (4H, d) |

TABLE 6

| Compound | FD-MS | Compound | FD-MS |
|---|---|---|---|
| 1 | m/z = 719.91 (C51H33N3S = 719.24) | 6 | m/z = 720.89 (C50H32N4S = 720.23) |
| 9 | m/z = 885.10 (C63H40N4S = 884.30) | 10 | m/z = 886.09 (C62H39N5S = 885.29) |
| 11 | m/z = 667.83 (C47H29N3S = 667.21) | 12 | m/z = 820.03 (C59H37N3S = 819.27) |
| 26 | m/z = 667.83 (C47H29N3S = 667.21) | 29 | m/z = 644.80 (C44H28N4S = 644.20) |
| 31 | m/z = 703.85 (C51H33N3O = 703.26) | 36 | m/z = 704.83 (C50H32N4O = 704.26) |
| 56 | m/z = 651.77 (C47H29N3O = 651.23) | 63 | m/z = 796.00 (C57H37N3S = 795.27) |
| 82 | m/z = 720.89 (C50H32N4S = 720.23) | 104 | m/z = 628.74 (C44H28N4O = 628.23) |
| 108 | m/z = 779.94 (C57H37N3O = 779.29) | 117 | m/z = 803.97 (C59H37N3O = 803.29) |
| 126 | m/z = 722.87 (C48H30N6S = 722.23) | 131 | m/z = 669.81 (C45H27N5S = 669.20) |
| 134 | m/z = 646.77 (C42H26N6S = 646.19) | 149 | m/z = 646.77 (C42H26N6S = 646.19) |
| 181 | m/z = 769.97 (C55H35N3S = 769.26) | 185 | m/z = 695.84 (C47H29N5S = 695.21) |
| 222 | m/z = 805.94 (C57H35N5O = 805.28) | 234 | m/z = 871.02 (C61H38N6O = 870.31) |
| 241 | m/z = 719.91 (C51H33N3S = 719.24) | 242 | m/z = 720.89 (C50H32N4S = 720.23) |
| 248 | m/z = 639.82 (C47H29NS = 639.20) | 261 | m/z = 667.83 (C47H29N3S = 667.21) |
| 277 | m/z = 628.74 (C44H28N4O = 628.23) | 287 | m/z = 704.83 (C60H32N4O = 704.26) |

TABLE 6-continued

| Compound | FD-MS | Compound | FD-MS |
|---|---|---|---|
| 291 | m/z = 651.77 (C47H29N3O = 651.23) | 294 | m/z = 703.85 (C51H33N3O = 703.26) |
| 301 | m/z = 721.88 (C49H31N5S = 721.23) | 328 | m/z = 653.75 (C45H27N5O = 653.22) |
| 376 | m/z = 644.78 (C44H28N4S = 644.20) | 380 | m/z = 720.88 (C50H32N4S = 720.23) |
| 382 | m/z = 643.80 (C45H29N3S = 643.21) | 390 | m/z = 617.76 (C43H27N3S = 617.19) |
| 406 | m/z = 694.84 (C48H30N4S = 694.22) | 419 | m/z = 580.70 (C40H24N2OS = 580.16) |
| 421 | m/z = 796.98 (C56H36N4S = 796.27) | 429 | m/z = 872.08 (C63H41N3S = 871.30) |
| 437 | m/z = 794.96 (C56H34N4S = 794.25) | 463 | m/z = 719.85 (C47H30NOPS2 = 719.15) |
| 481 | m/z = 644.78 (C44H28N4S = 644.20) | 487 | m/z = 643.80 (C45H29N3S = 643.21) |
| 495 | m/z = 617.76 (C43H27N3S = 617.19) | 516 | m/z = 693.86 (C49H31N3S = 693.22) |
| 526 | m/z = 796.98 (C56H36N4S = 796.27) | 541 | m/z = 794.96 (C56H34N4S = 794.25) |
| 552 | m/z = 755.92 (C54H33N3S = 755.24) | 561 | m/z = 749.94 (C51H31N3S2 = 749.20) |
| 571 | m/z = 734.86 (C50H30N4OS = 734.21) | 592 | m/z = 808.99 (C57H36N4S = 808.27) |
| 605 | m/z = 796.98 (C56H36N4S = 796.27) | 628 | m/z = 663.76 (C45H30NOPS = 663.18) |
| 632 | m/z = 794.96 (C56H34N4S = 794.25) | 646 | m/z = 734.86 (C50H30N4OS = 734.21) |
| 665 | m/z = 720.88 (C50H32N4S = 720.23) | 706 | m/z = 628.72 (C44H28N4O = 628.23) |
| 725 | m/z = 857.01 (C62H40N4O = 856.32) | 792 | m/z = 628.72 (C44H28N4O = 628.23) |
| 816 | m/z = 778.90 (C56H34N4O = 778.27) | 856 | m/z = 720.88 (C50H32N4S = 720.23) |

<Experimental Example 1> Manufacture of Organic Light Emitting Diode

Comparative Examples 1-1 to 1-3 and Examples 1 to 53

1) Manufacture of Organic Light Emitting Diode

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

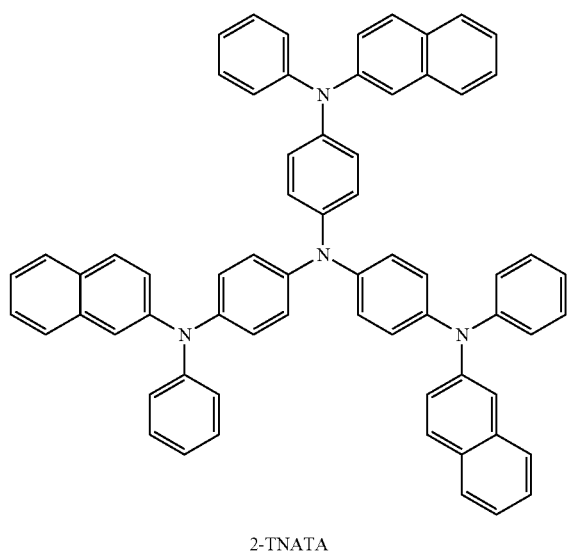 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

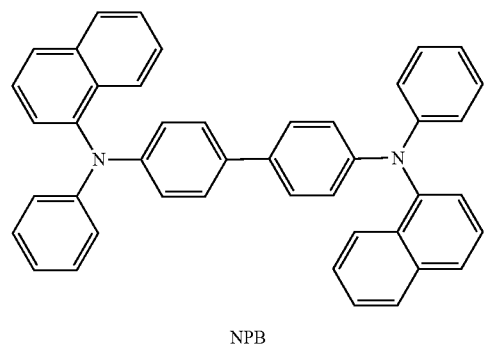 [SMILES: c1ccc(N(c2ccc(-c3ccc(N(c4ccccc4)c4cccc5ccccc45)cc3)cc2)c2cccc3ccccc23)cc1 ; "NPB"]

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

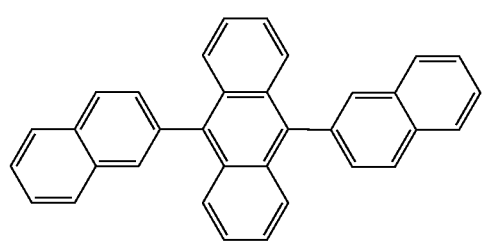

H1

-continued

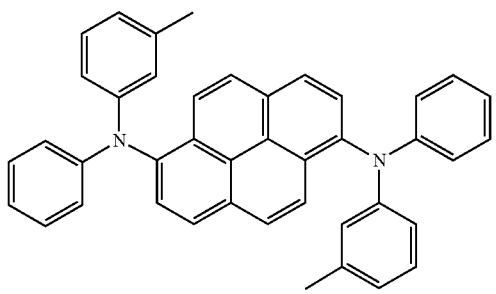

D1

Subsequently, as an electron transfer layer, a compound shown in Table 6 was deposited to a thickness of 300 Å.

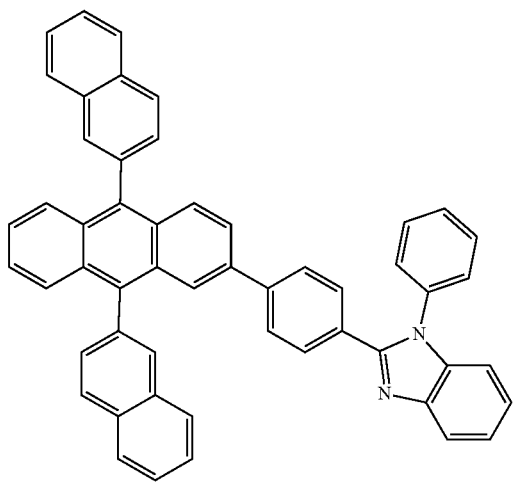

E1

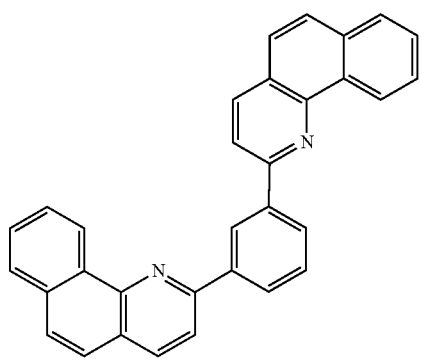

BBQB

-continued

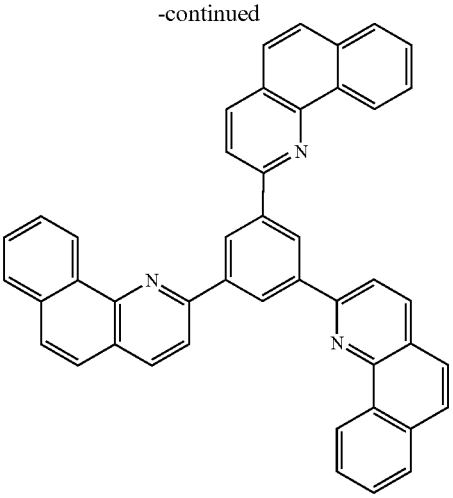

TBQB

As an electron injection layer, lithium fluoride (LiF) was deposited to a thickness of 10 Å, and an Al cathode was deposited to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

2) Driving Voltage and Light Emission Efficiency of Organic Light Emitting Diode For the organic light emitting diodes manufactured as above, electroluminescent (EL) properties were measured using M7000 manufactured by McScience Inc., and with the measurement results, 195 was measured when standard luminance was 700 cd/m² using a lifetime measurement system (M6000) manufactured by McScience Inc. Results of measuring driving voltage, light emission efficiency, external quantum efficiency and color coordinate (CIE) of the blue organic light emitting diode are as shown in Table 7.

TABLE 7

| | Compound | Driving Voltage (V) | Light Emission Efficiency (cd/A) | CIE (x, y) | Lifetime (T95) |
|---|---|---|---|---|---|
| Comparative Example 1-1 | E1 | 5.56 | 5.91 | (0.134, 0.100) | 28 |
| Comparative Example 1-2 | BBQB | 5.50 | 6.10 | (0.134, 0.101) | 30 |
| Comparative Example 1-3 | TBQB | 5.51 | 6.15 | (0.134, 0.102) | 29 |
| Example 1 | 1 | 5.11 | 6.95 | (0.134, 0.101) | 32 |
| Example 2 | 6 | 4.96 | 6.84 | (0.134, 0.102) | 47 |
| Example 3 | 9 | 5.14 | 6.79 | (0.134, 0.101) | 33 |
| Example 4 | 10 | 4.99 | 6.88 | (0.134, 0.103) | 49 |
| Example 5 | 29 | 5.45 | 6.12 | (0.134, 0.102) | 34 |
| Example 6 | 31 | 5.03 | 7.09 | (0.134, 0.101) | 30 |
| Example 7 | 36 | 4.72 | 7.12 | (0.134, 0.102) | 52 |
| Example 8 | 63 | 5.32 | 6.33 | (0.134, 0.101) | 29 |
| Example 9 | 82 | 5.40 | 6.13 | (0.134, 0.101) | 31 |
| Example 10 | 104 | 5.30 | 6.72 | (0.134, 0.100) | 33 |
| Example 11 | 108 | 5.37 | 6.35 | (0.134, 0.101) | 32 |
| Example 12 | 126 | 5.38 | 6.41 | (0.134, 0.100) | 30 |
| Example 13 | 134 | 5.27 | 6.42 | (0.134, 0.100) | 31 |
| Example 14 | 149 | 5.48 | 6.21 | (0.134, 0.100) | 32 |
| Example 15 | 181 | 4.72 | 7.39 | (0.134, 0.100) | 49 |

TABLE 7-continued

| Com-pound | Driving Voltage (V) | Light Emission Efficiency (cd/A) | CIE (x, y) | Lifetime (T95) |
|---|---|---|---|---|
| Example 16 | 185 | 5.45 | 6.68 | (0.134, 0.100) | 34 |
| Example 17 | 234 | 5.22 | 6.28 | (0.134, 0.102) | 37 |
| Example 18 | 241 | 5.12 | 6.20 | (0.134, 0.101) | 32 |
| Example 19 | 242 | 5.09 | 6.97 | (0.134, 0.102) | 56 |
| Example 20 | 277 | 5.42 | 6.88 | (0.134, 0.100) | 25 |
| Example 21 | 287 | 5.21 | 5.45 | (0.134, 0.103) | 37 |
| Example 22 | 294 | 5.38 | 6.66 | (0.134, 0.100) | 35 |
| Example 23 | 301 | 5.40 | 6.36 | (0.134, 0.102) | 32 |
| Example 24 | 376 | 4.72 | 7.11 | (0.134, 0.102) | 45 |
| Example 25 | 380 | 5.19 | 6.13 | (0.134, 0.100) | 33 |
| Example 26 | 382 | 5.22 | 6.21 | (0.134, 0.102) | 32 |
| Example 27 | 390 | 5.21 | 6.21 | (0.134, 0.101) | 35 |
| Example 28 | 406 | 5.31 | 6.13 | (0.134, 0.102) | 36 |
| Example 29 | 419 | 5.21 | 6.19 | (0.134, 0.100) | 33 |
| Example 30 | 421 | 4.67 | 6.49 | (0.134, 0.102) | 41 |
| Example 31 | 429 | 5.11 | 6.03 | (0.134, 0.101) | 34 |
| Example 32 | 437 | 5.09 | 6.32 | (0.134, 0.102) | 35 |
| Example 33 | 463 | 5.77 | 5.73 | (0.134, 0.102) | 58 |
| Example 34 | 481 | 4.62 | 6.44 | (0.134, 0.101) | 44 |
| Example 35 | 487 | 4.55 | 7.30 | (0.134, 0.102) | 21 |
| Example 36 | 495 | 5.22 | 6.11 | (0.134, 0.101) | 36 |
| Example 37 | 516 | 5.65 | 5.69 | (0.134, 0.103) | 61 |
| Example 38 | 526 | 5.12 | 5.99 | (0.134, 0.102) | 35 |
| Example 39 | 541 | 4.83 | 6.87 | (0.134, 0.102) | 46 |
| Example 40 | 552 | 5.20 | 6.17 | (0.134, 0.101) | 33 |
| Example 41 | 561 | 5.32 | 6.16 | (0.134, 0.102) | 36 |
| Example 42 | 571 | 5.15 | 5.89 | (0.134, 0.101) | 35 |
| Example 43 | 592 | 5.26 | 6.08 | (0.134, 0.102) | 37 |
| Example 44 | 605 | 5.21 | 6.10 | (0.134, 0.101) | 36 |
| Example 45 | 628 | 5.74 | 5.79 | (0.134, 0.102) | 60 |
| Example 46 | 632 | 5.23 | 6.12 | (0.134, 0.101) | 31 |
| Example 47 | 646 | 5.32 | 6.23 | (0.134, 0.102) | 36 |
| Example 48 | 665 | 5.12 | 6.53 | (0.134, 0.101) | 35 |
| Example 49 | 706 | 5.18 | 6.05 | (0.134, 0.102) | 33 |
| Example 50 | 725 | 5.11 | 5.96 | (0.134, 0.101) | 34 |
| Example 51 | 792 | 5.27 | 5.99 | (0.134, 0.103) | 37 |
| Example 52 | 816 | 5.23 | 6.03 | (0.134, 0.101) | 36 |
| Example 53 | 856 | 4.81 | 7.13 | (0.134, 0.102) | 47 |

As seen from the results of Table 7, the organic light emitting diode using the electron transfer layer material of the blue organic light emitting diode of the present disclosure had lower driving voltage and significantly improved light emission efficiency and lifetime compared to Comparative Example 1. Particularly, it was identified that Compounds 6, 10, 36, 181, 242, 376, 421, 481, 541 and 856 were superior in all aspects of driving, efficiency and lifetime.

Such a result is considered to be due to the fact that, when using the disclosed compound having proper length and strength, and flatness as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

<Experimental Example 2> Manufacture of Organic Light Emitting Diode

Comparative Example 2

1) Manufacture of Organic Light Emitting Diode

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was deposited to a cell in the vacuum deposition apparatus.

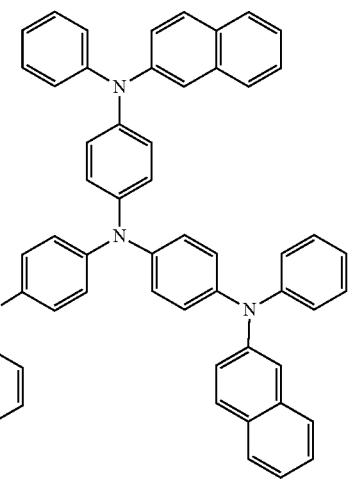

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

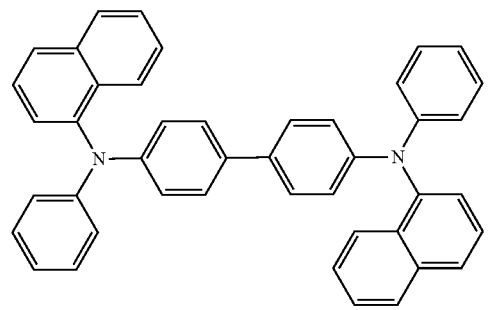

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

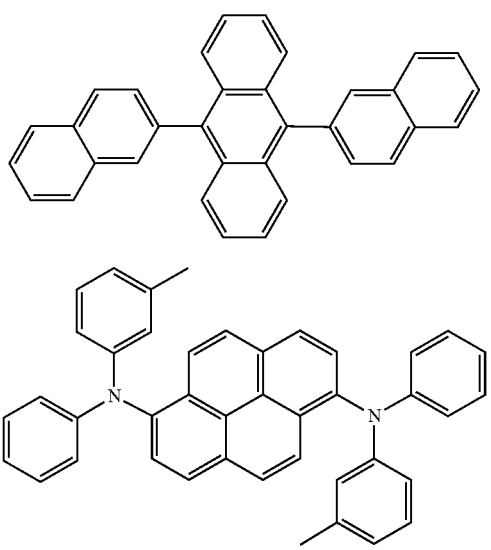

Then, as an electron transfer layer, a compound having the following structural formula E1 was deposited to a thickness of 300 Å.

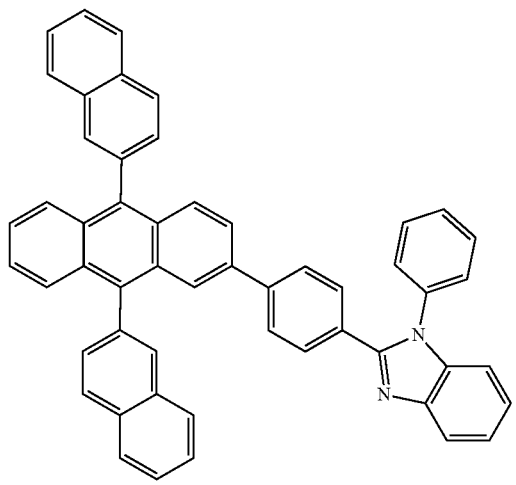

As an electron injection layer, lithium fluoride (LiF) was deposited to a thickness of 10 Å, and an Al cathode was deposited to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Examples 54 to 63

Organic electroluminescent diodes were manufactured in the same manner as in Comparative Example 2 except that E1 was formed to a thickness of 250 Å as the electron transfer layer, and on the electron transfer layer, a hole blocking layer having a thickness of 50 Å was formed using a compound presented in Table 8.

Results of measuring driving voltage, light emission efficiency, color coordinate (CIE) and lifetime of the blue organic light emitting diode manufactured according to the present disclosure are as shown in Table 8.

TABLE 8

| Compound | Driving Voltage (V) | Light Emission Efficiency (cd/A) | CIE (x, y) | Lifetime (T95) |
|---|---|---|---|---|
| Comparative Example 2 | — | 5.50 | 5.57 | (0.134, 0.100) | 31 |
| Example 54 | 12 | 4.87 | 6.17 | (0.134, 0.101) | 51 |
| Example 55 | 117 | 4.73 | 6.59 | (0.134, 0.102) | 56 |
| Example 56 | 222 | 5.11 | 6.65 | (0.134, 0.101) | 55 |
| Example 57 | 248 | 4.87 | 6.54 | (0.134, 0.103) | 61 |
| Example 58 | 406 | 4.82 | 6.44 | (0.134, 0.103) | 54 |
| Example 59 | 421 | 4.95 | 6.59 | (0.134, 0.103) | 56 |
| Example 60 | 437 | 5.11 | 6.45 | (0.134, 0.103) | 57 |
| Example 61 | 463 | 4.85 | 6.31 | (0.134, 0.103) | 55 |
| Example 62 | 541 | 4.92 | 6.67 | (0.134, 0.103) | 58 |
| Example 63 | 571 | 4.87 | 6.55 | (0.134, 0.103) | 49 |

As seen from the results of Table 8, the organic electroluminescent diode using the hole blocking layer material of the blue organic electroluminescent diode of the present disclosure had lower driving voltage and significantly improved light emission efficiency and lifetime compared to Comparative Example 2.

<Experimental Example 3> Manufacture of Organic Light Emitting Diode

Comparative Example 3

1) Manufacture of Organic Light Emitting Diode

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

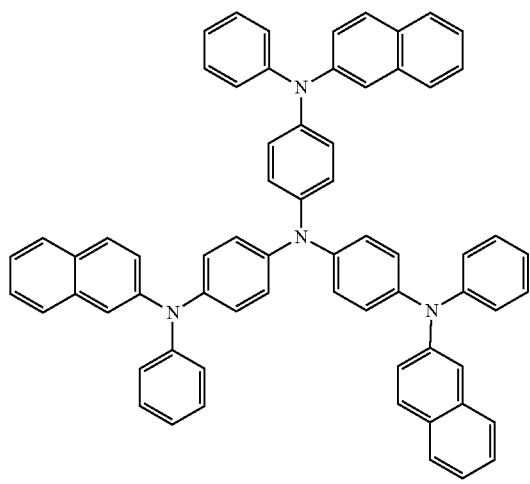

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

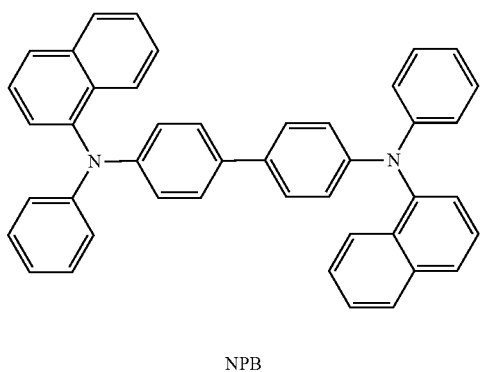 [SMILES: c1ccc(N(c2ccc(-c3ccc(N(c4ccccc4)c4cccc5ccccc45)cc3)cc2)c2cccc3ccccc23)cc1 ; "NPB"]

NPB

The hole injection layer and the hole transfer layer were formed as above.

As a light emitting layer, H2, a host, and Ir(ppy)$_3$, a green phosphorescent dopant, by 7% doping were deposited to 400 Å thereon.

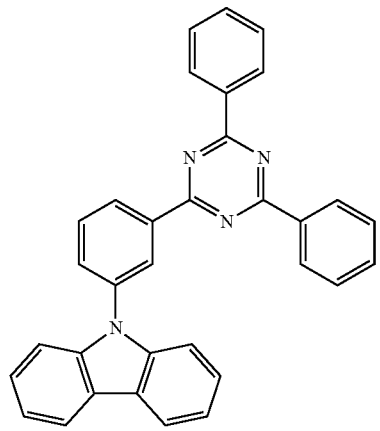

H2

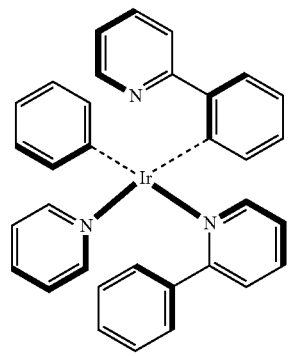

Ir(ppy)$_3$

After that, BCP was deposited to 60 Å as a hole blocking layer, and Alq$_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent diode was manufactured.

Meanwhile, all the organic compounds required to manufacture the OLED were vacuum sublimation purified under $10^{-6}$ torr to $10^{-8}$ torr for each material to be used in the OLED manufacture.

Examples 64 to 69

Organic electroluminescent diodes were manufactured in the same manner as in Comparative Example 3 except that, when forming the host, a compound presented in Table 9 was used instead of H2.

Results of measuring driving voltage, light emission efficiency, color coordinate (CIE) and lifetime of the green organic light emitting diode manufactured according to the present disclosure are as shown in Table 9.

TABLE 9

| Com-pound | Driving Voltage (V) | Light Emission Efficiency (cd/A) | CIE (x, y) | Lifetime (T95) |
|---|---|---|---|---|
| Comparative Example 3 | H2 | 5.24 | 35.83 | (0.266, 0.711) | 63 |
| Example 64 | 421 | 5.11 | 41.23 | (0.266, 0.712) | 92 |
| Example 65 | 437 | 4.96 | 43.88 | (0.265, 0.711) | 79 |
| Example 66 | 571 | 4.74 | 46.02 | (0.265, 0.712) | 89 |
| Example 67 | 592 | 5.12 | 38.82 | (0.266, 0.713) | 92 |
| Example 68 | 632 | 4.89 | 39.44 | (0.266, 0.711) | 93 |
| Example 69 | 646 | 4.72 | 41.36 | (0.267, 0.711) | 77 |

<Experimental Example 4> Manufacture of Organic Light Emitting Diode

Comparative Example 4 and Examples 70 to 79

1) Manufacture of Organic Light Emitting Diode

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

On the transparent ITO electrode (anode), an organic material was formed in a 2-stack white organic light emitting diode (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping FIrpic to TCz1, a host, by 8% as a blue phosphorescent dopant. After forming an electron transfer layer to 400 Å using TmPyPB, a charge generation layer was formed to 100 Å by doping $Cs_2CO_3$ to a compound described in the following Table 10 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and then depositing TAPC to 300 Å. A light emitting layer was deposited thereon to 300 Å by doping $Ir(ppy)_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting diode was manufactured.

Meanwhile, all the organic compounds required to manufacture the OLED were vacuum sublimation purified under $10^{-6}$ torr to $10^{-8}$ torr by each material to be used in the OLED manufacture.

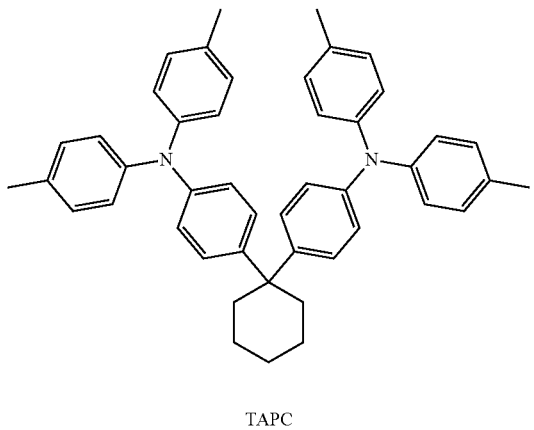

TAPC

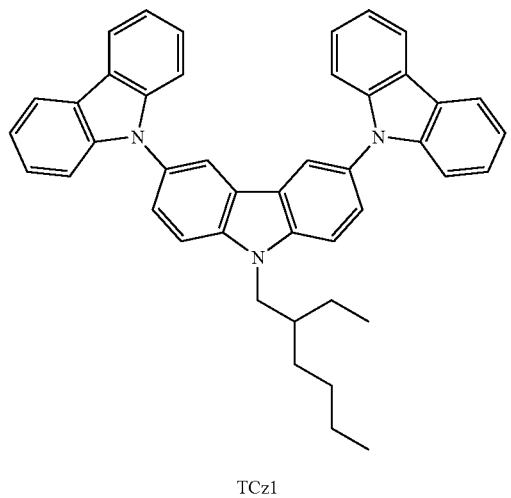

TCz1

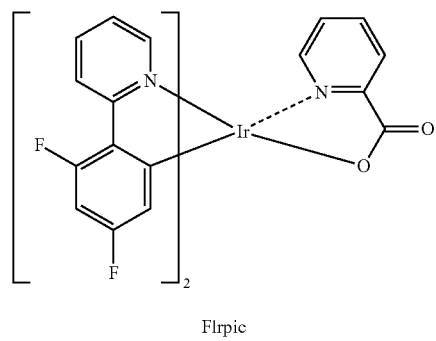

FIrpic

-continued

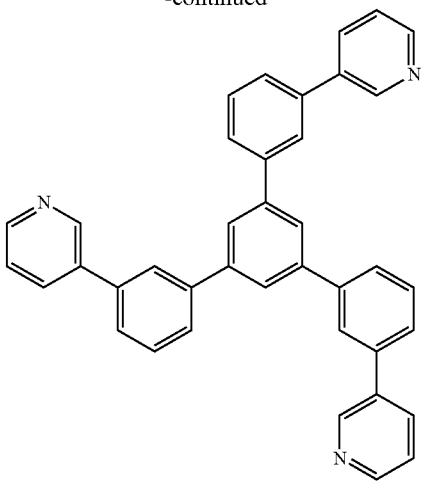

TmPyPB

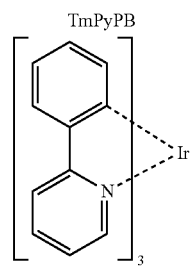

Ir(ppy)3

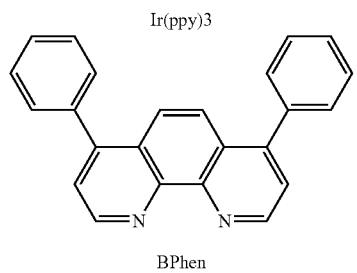

BPhen

Results of measuring driving voltage, light emission efficiency, color coordinate (CIE) and lifetime of the white organic light emitting diodes manufactured according to the present disclosure are as shown in Table 10.

TABLE 10

| | Compound | Driving Voltage (V) | Light Emission Efficiency (cd/A) | CIE (x, y) | Lifetime (T95) |
|---|---|---|---|---|---|
| Comparative Example 4 | BPhen | 7.54 | 54.23 | (0.213, 0.430) | 25 |
| Example 70 | 11 | 6.84 | 60.44 | (0.212, 0.421) | 35 |
| Example 71 | 26 | 6.44 | 66.32 | (0.211, 0.433) | 40 |
| Example 72 | 29 | 6.92 | 59.68 | (0.214, 0.439) | 31 |
| Example 73 | 56 | 6.27 | 67.99 | (0.212, 0.424) | 53 |
| Example 74 | 104 | 6.82 | 59.18 | (0.214, 0.437) | 34 |
| Example 75 | 131 | 6.73 | 62.44 | (0.212, 0.426) | 37 |
| Example 76 | 134 | 6.82 | 57.18 | (0.214, 0.437) | 34 |
| Example 77 | 261 | 6.29 | 68.49 | (0.213, 0.424) | 51 |
| Example 78 | 291 | 6.37 | 67.41 | (0.213, 0.423) | 46 |
| Example 79 | 328 | 6.41 | 66.31 | (0.212, 0.421) | 45 |

As seen from the results of Table 10, the organic electroluminescent diode using the charge generation layer material of the 2-stack white organic electroluminescent diode of the present disclosure had lower driving voltage and improved light emission efficiency compared to Comparative Example 3. Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting diode.

Hereinbefore, preferred examples of the present disclosure have been described in detail, however, the scope of a right of the present disclosure is not limited thereto, and various modifications and improvements made by those skilled in the art using the basic concept of the present disclosure defined in the attached claims also fall within the scope of a right of the present disclosure.

The invention claimed is:

1. A compound represented by one of the following Chemical Formulae 2 to 4:

[Chemical Formula 2]

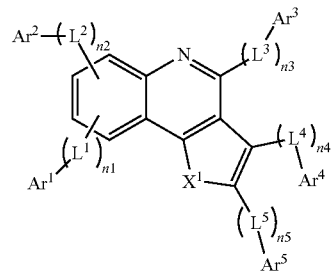

[Chemical Formula 3]

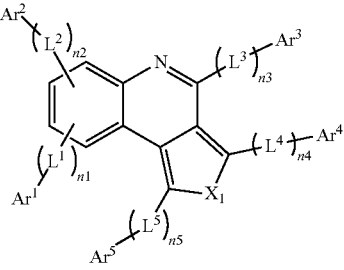

[Chemical Formula 4]

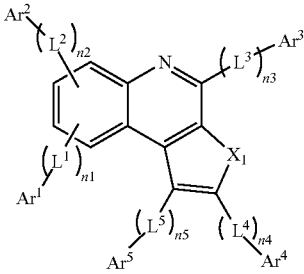

wherein, in Chemical Formulae 2 to 4,

X¹ is —O—; or —S—;

Ar¹ to Ar⁵ are each independently hydrogen; deuterium; a cyano group; —P(=O) RR'; a substituted or unsubstituted C1 to C60 alkyl group; a substituted or unsubstituted C6 to C60 aryl group; or a substituted or unsubstituted C2 to C60 heteroaryl group;

in chemical formulae 2 to 4, L¹ to L³ are each independently a single bond; a substituted or unsubstituted C6 to C60 arylene group; or a substituted or unsubstituted C2 to C60 heteroarylene group;

in chemical formulae 2 to 4, L⁴ and L⁵ are each independently a substituted or unsubstituted C6 to C60 arylene group; or a substituted or unsubstituted C2 to C60 heteroarylene group;

R and R' are each independently hydrogen; a substituted or unsubstituted C1 to C60 alkyl group; a substituted or unsubstituted C6 to C60 aryl group; or a substituted or unsubstituted C2 to C60 heteroaryl group;

n1 to n5 are each independently one of integers of 1 to 4; and at least one of Ar¹ to Ar⁵ is a substituent having electron properties; or a substituent having hole properties, wherein the substituent having hole properties is a substituted or unsubstituted C6 to C60 aryl group having hole properties, a substituted or unsubstituted C2 to C60 heteroaryl group having hole properties, a substituted or unsubstituted arylamine group, or a substituted or unsubstituted heteroarylamine group, wherein the substituent having electron properties is a substituted or unsubstituted C2 to C60 heteroaryl group having electron properties; and the substituted or unsubstituted C2 to C60 heteroaryl group having electron properties is a substituted or unsubstituted imidazolyl group, a substituted or unsubstituted tetrazolyl group, a substituted or unsubstituted quinolinylene group, a substituted or unsubstituted isoquinolinylene group, a substituted or unsubstituted pyridinylene group, a substituted or unsubstituted pyrimidinylene group, a substituted or unsubstituted triazinylene group, a substituted or unsubstituted furanyl group, a substituted or unsubstituted benzofuranyl group, a substituted or unsubstituted isofuranyl group, a substituted or unsubstituted benzoisofuranyl group, a substituted or unsubstituted oxazoline group, a substituted or unsubstituted benzoxazoline group, a substituted or unsubstituted oxadiazoline group, a substituted or unsubstituted benzoxadiazoline group, a substituted or unsubstituted oxatriazolyl group, a substituted or unsubstituted thiophenyl group, a substituted or unsubstituted benzothiophenyl group, a substituted or unsubstituted isothiazoline group, a substituted or unsubstituted benzoisothiazoline group, a substituted or unsubstituted thiazoline group, a substituted or unsubstituted benzothiazoline group, a substituted or unsubstituted pyridazinyl group, a substituted or unsubstituted benzopyridazinyl group, a substituted or unsubstituted pyrazinyl group, a substituted or unsubstituted benzopyrazinyl group, a substituted or unsubstituted phthalazinyl group, a substituted or unsubstituted benzoquinolinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof, wherein "substituted or unsubstituted" means being substituted with one or more substituents selected from the group consisting of deuterium, —CN, —P(=O) RR', a C1 to C20 linear or branched alkyl group, a C6 to C60 monocyclic or polycyclic aryl group and a C2 to C60 monocyclic or polycyclic heteroaryl group, or being unsubstituted.

2. The compound of claim 1, wherein the compound represented by one of Chemical Formulae 2 to 4 is one of compounds of the following Group I:

[Group I]

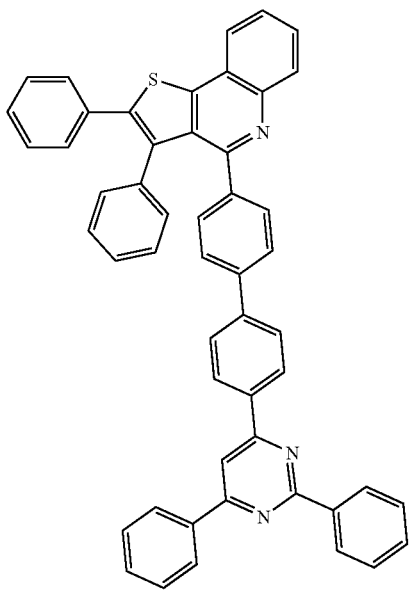

1

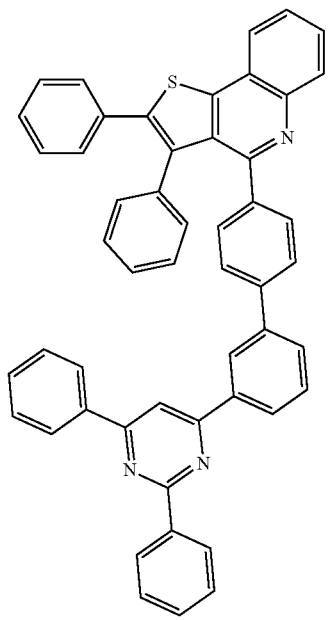

2

507-continued
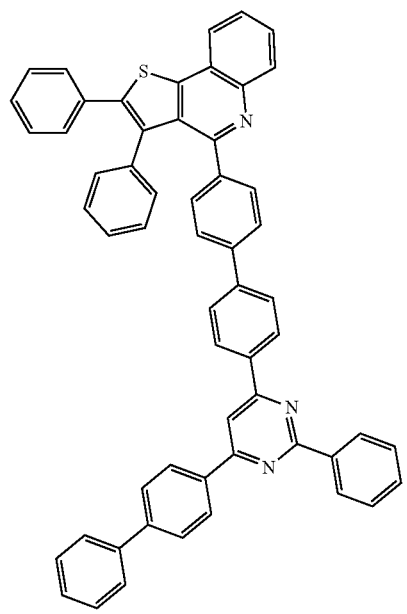
3
508-continued
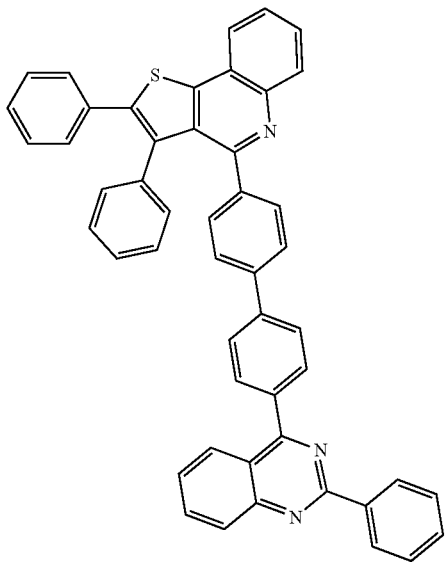
5
4
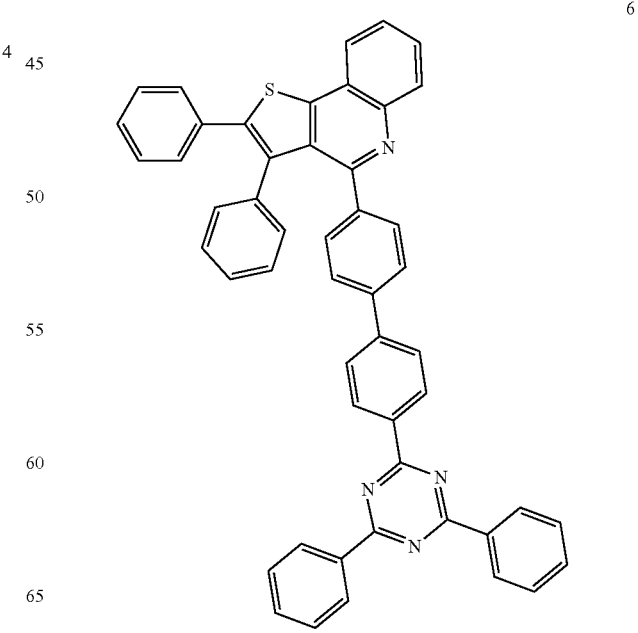
6

509
-continued
7
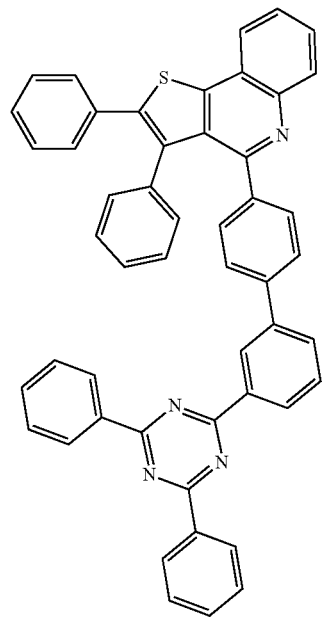
8
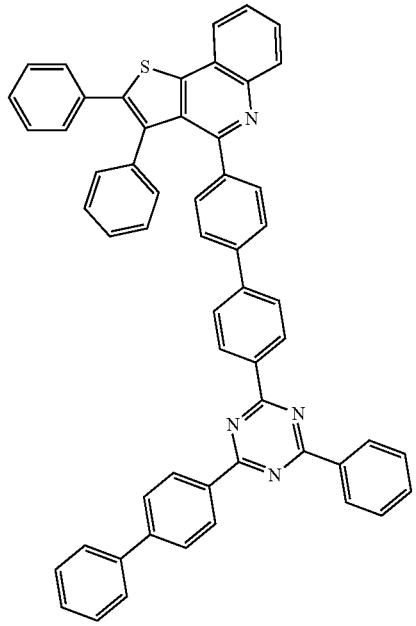
510
-continued
9
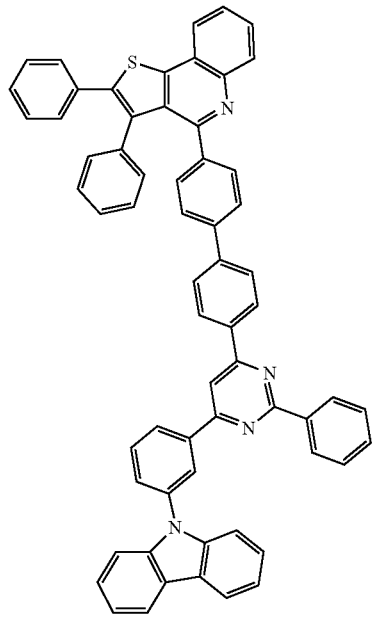
10
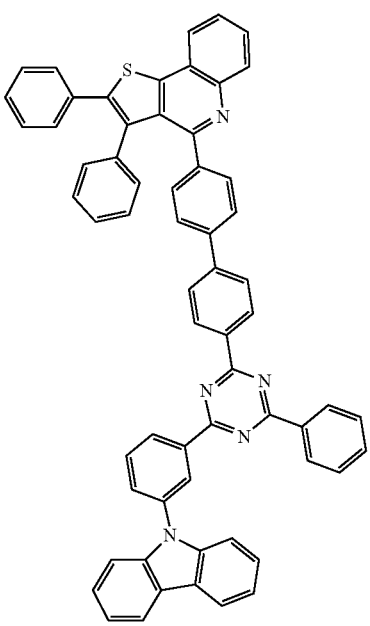

511
-continued
11
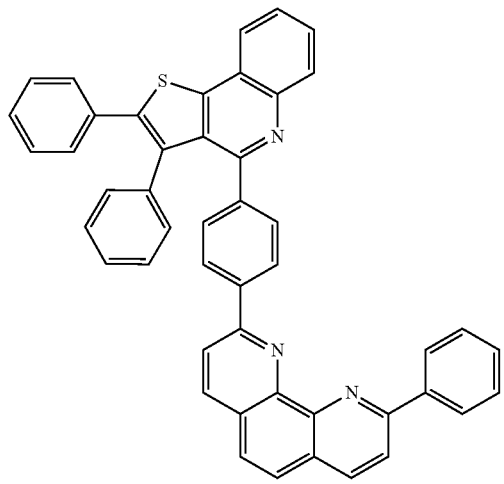
12
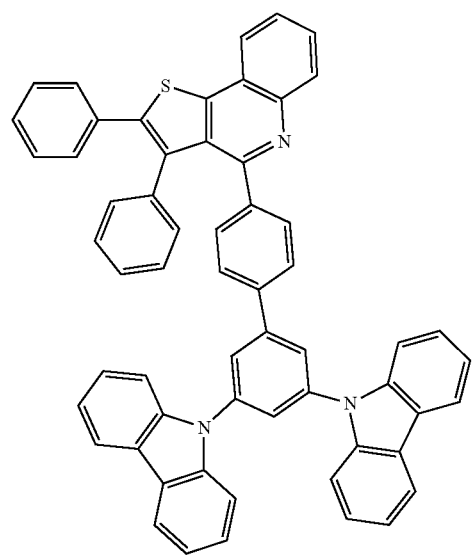
13
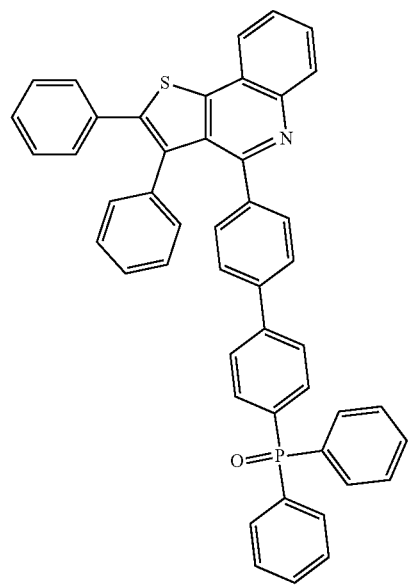
512
-continued
14
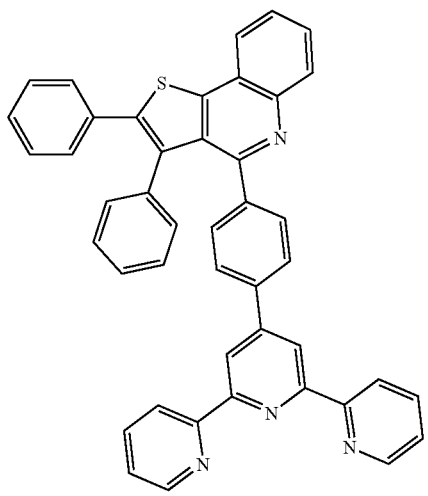
15
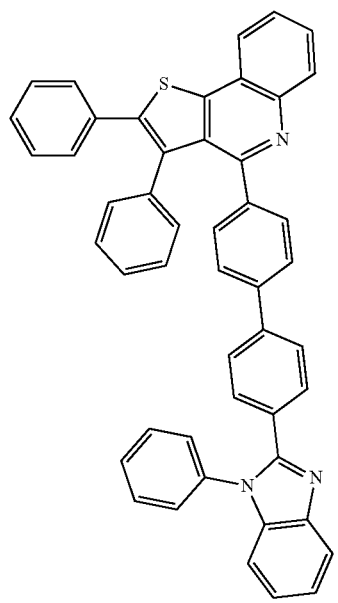
16
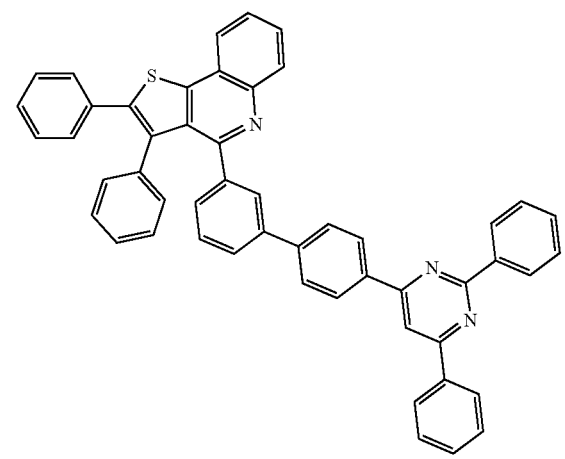

17
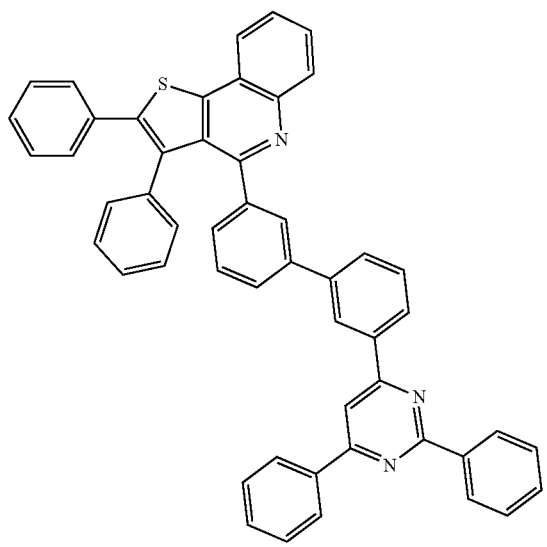
18
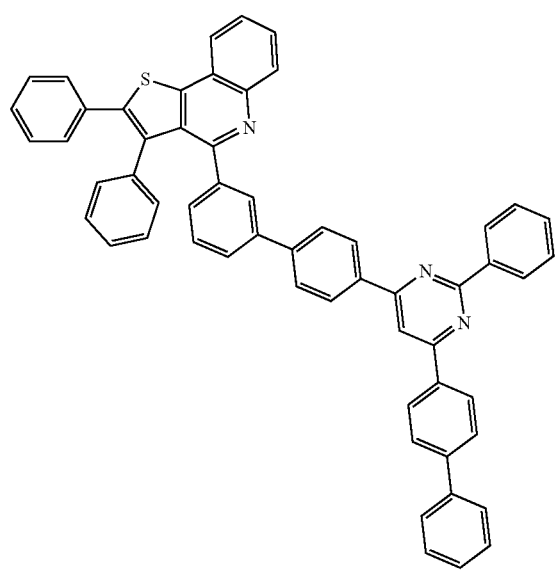
19
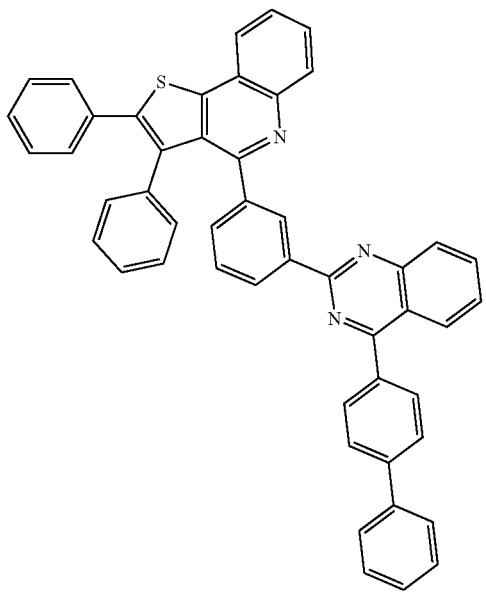
20
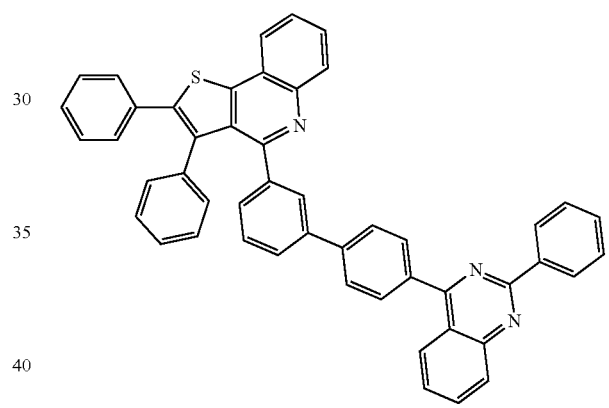
21
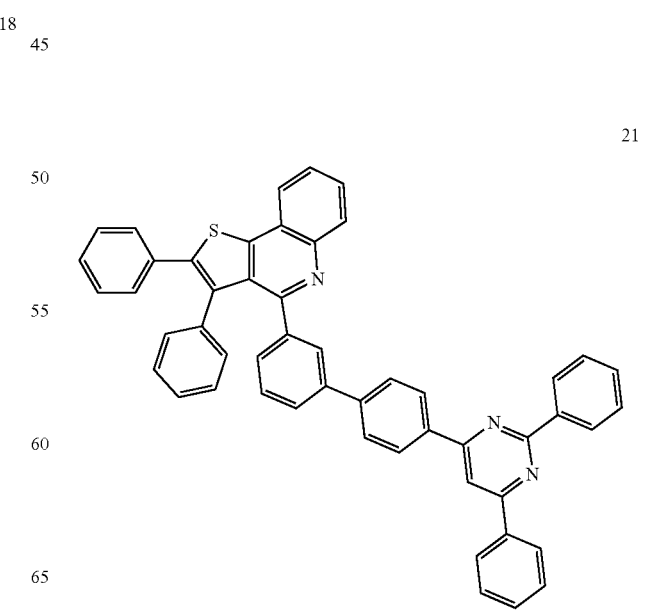

22
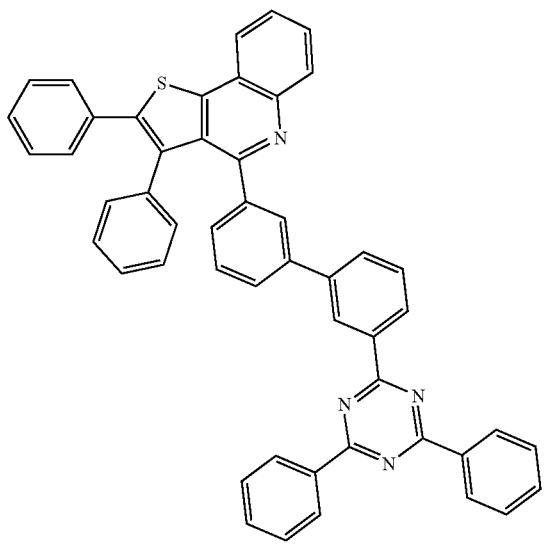
23
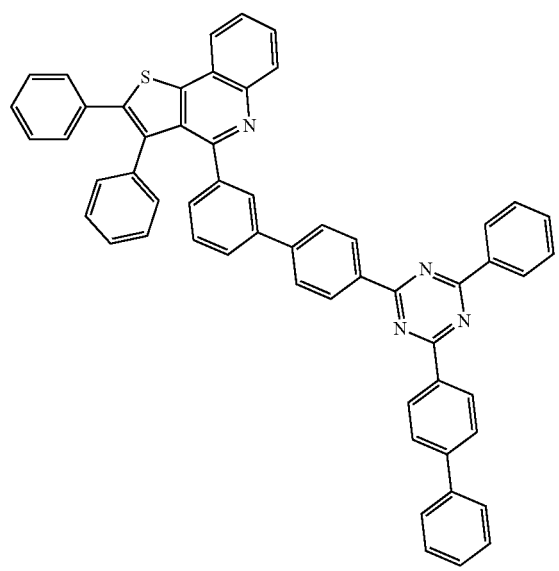
24
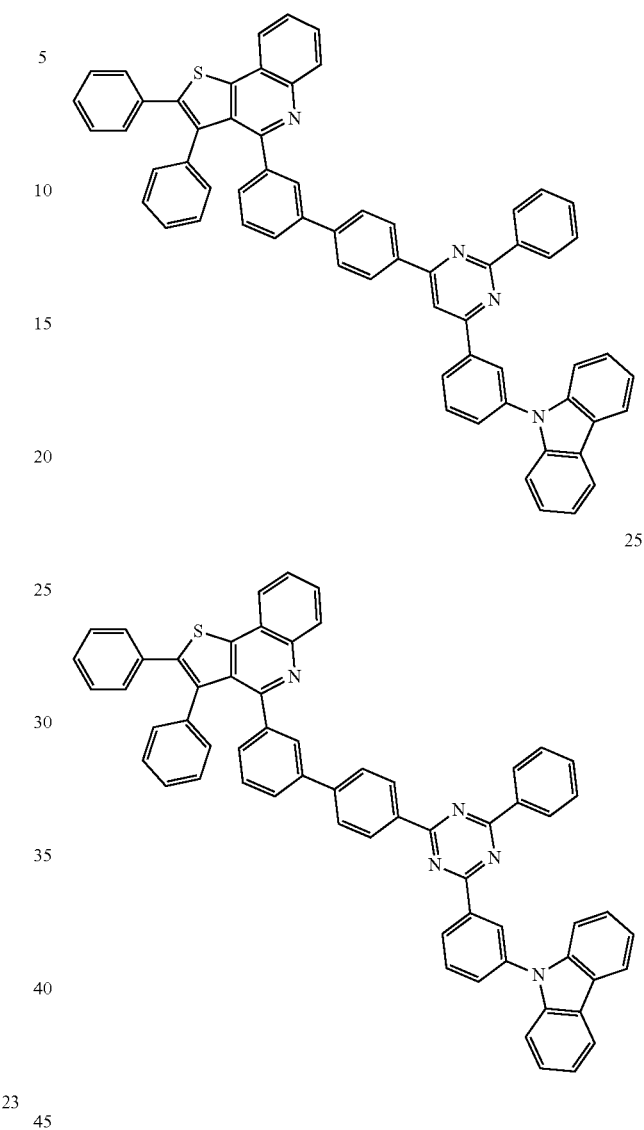
26
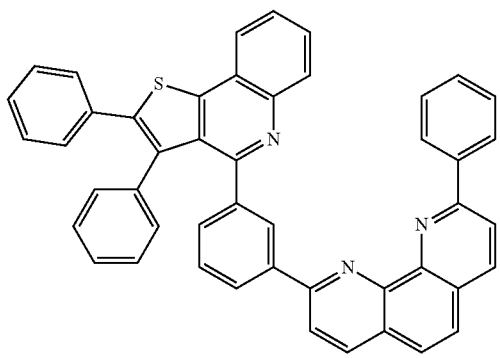

517
-continued
27
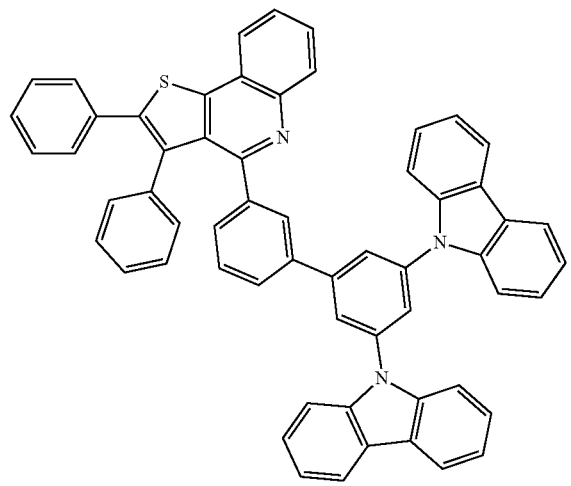
28
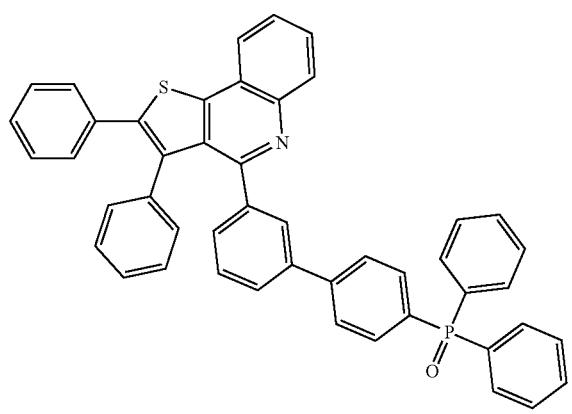
29
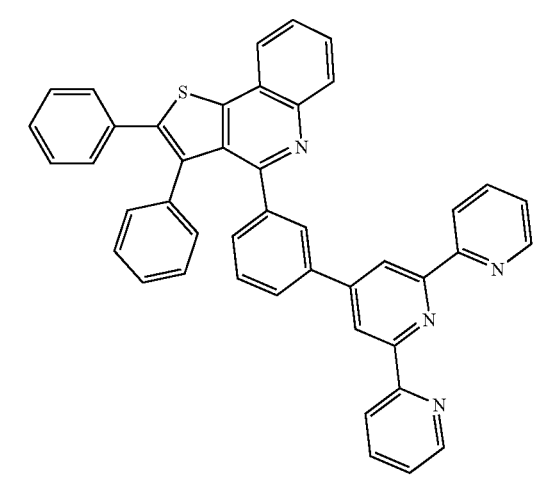
518
-continued
30
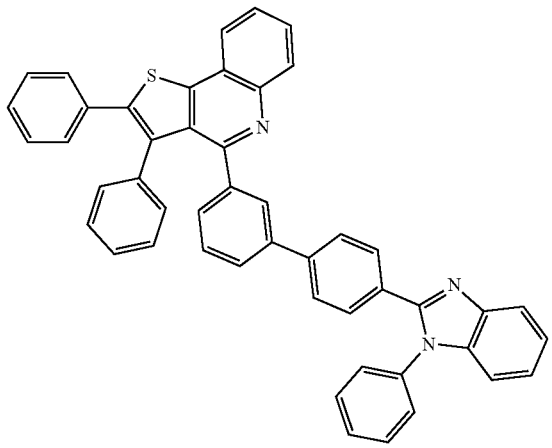
31
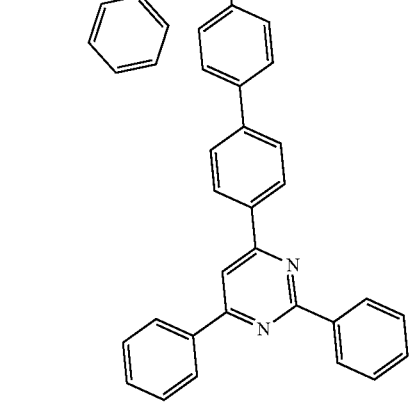
32
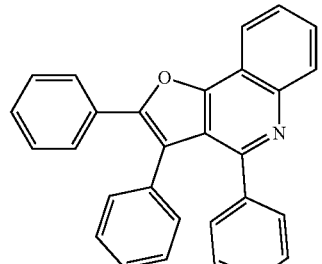

519
-continued
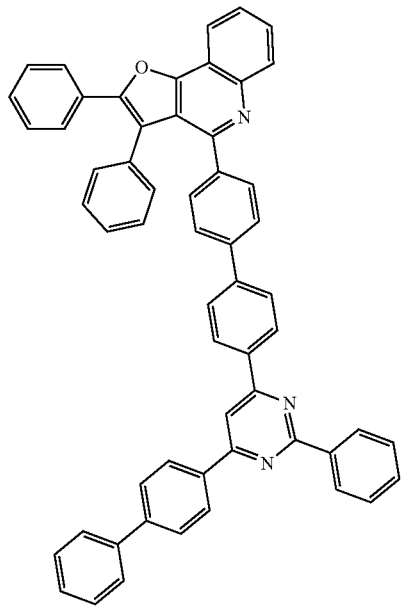
520
-continued
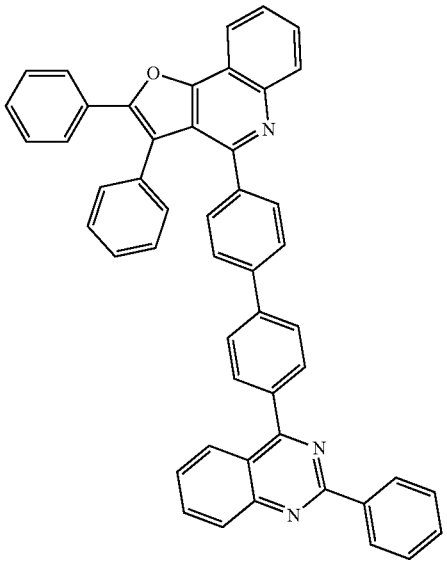
34
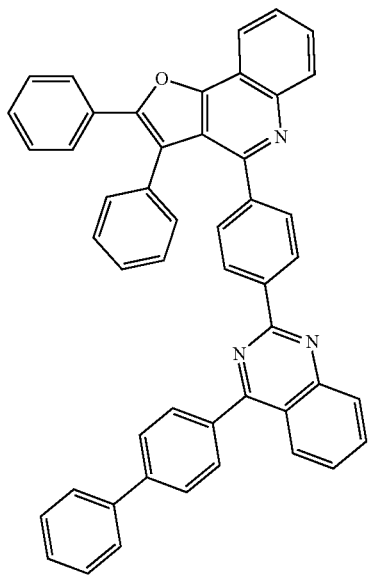
36
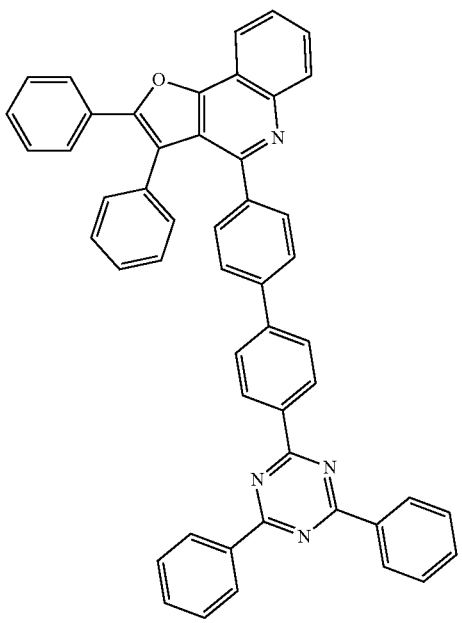

521
-continued
37
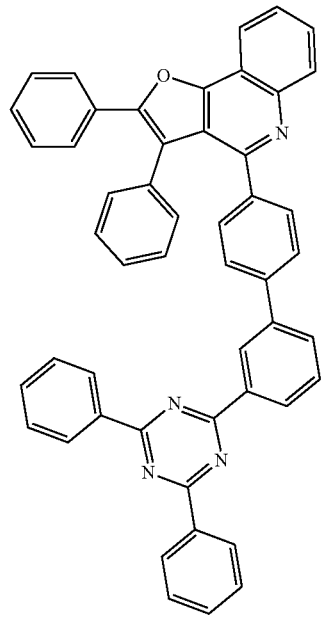
38
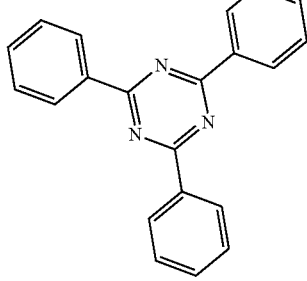
522
-continued
39
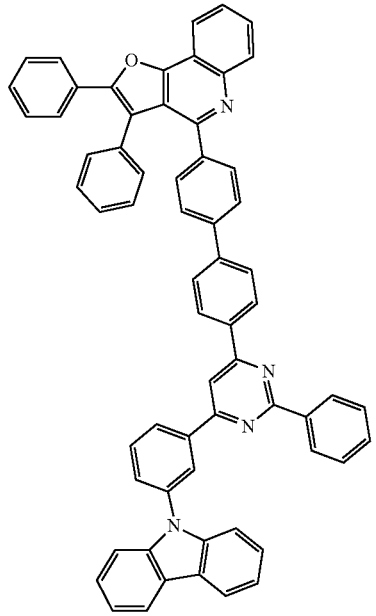
40
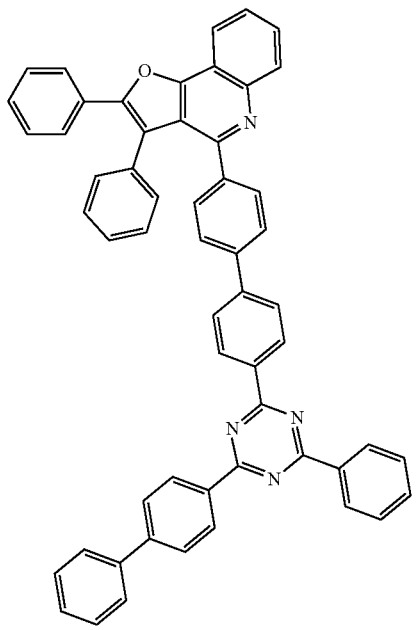

41
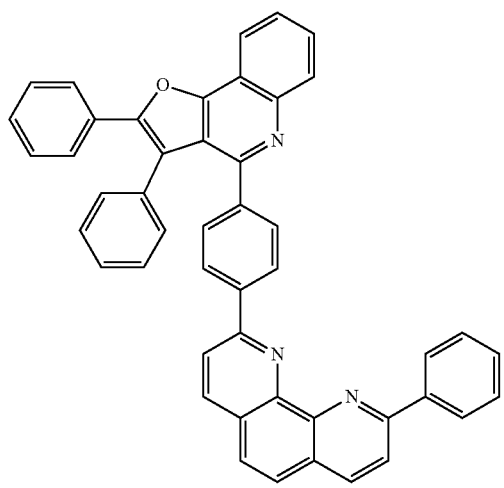
42
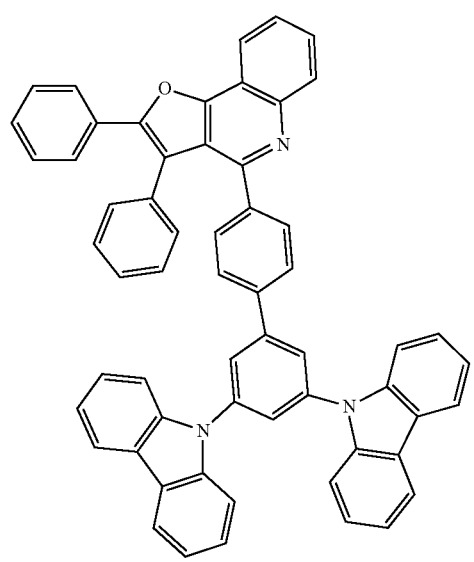
43
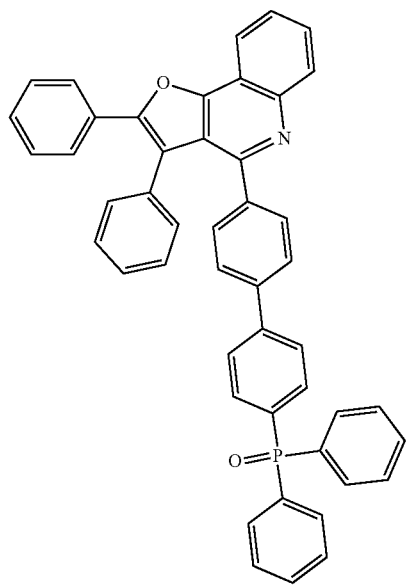
44
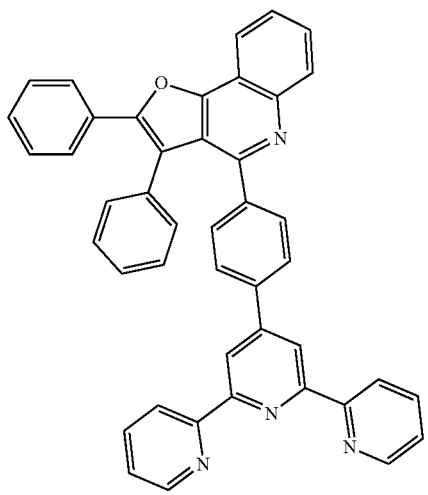
45
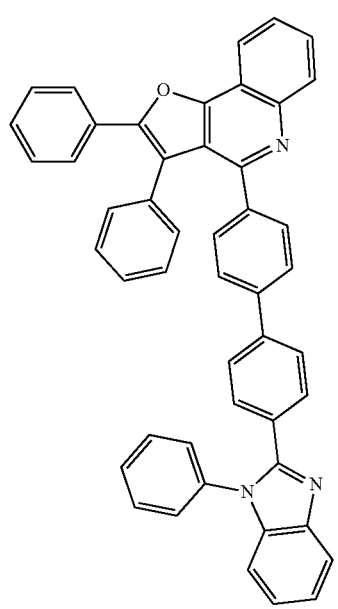
46
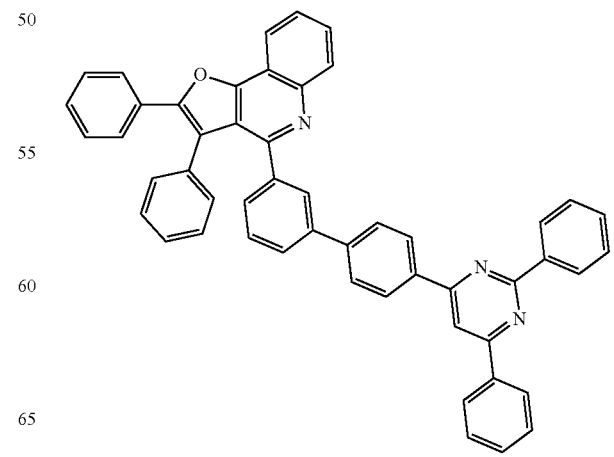

525
-continued
47
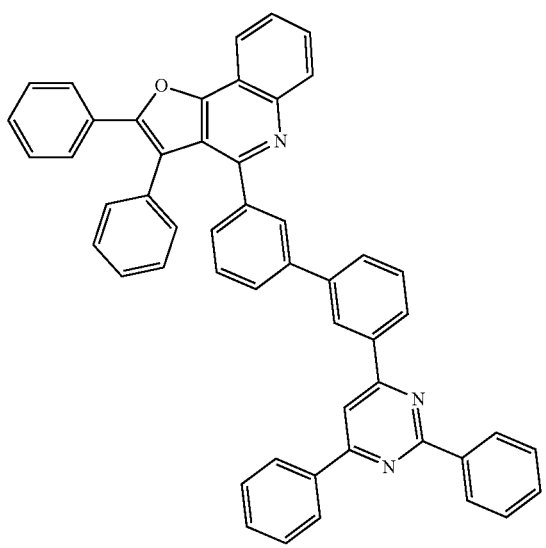
48
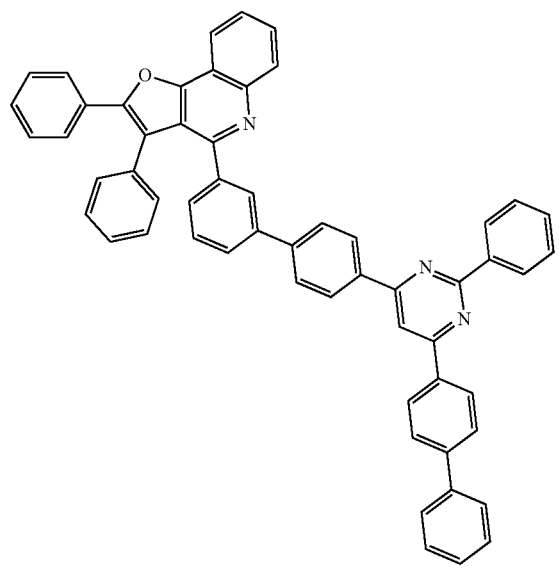
526
-continued
49
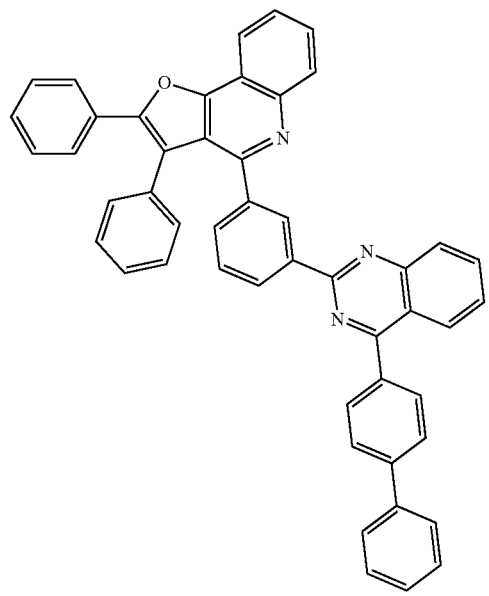
50
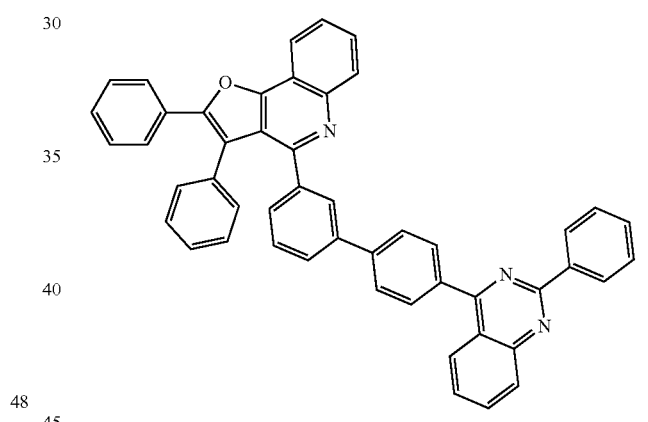
51
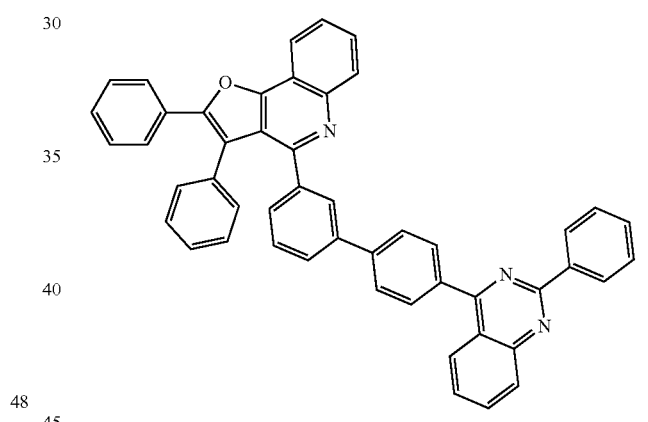

527
-continued
52
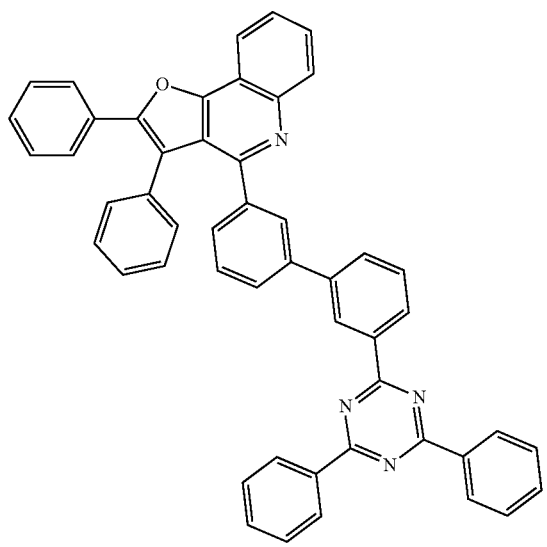
53
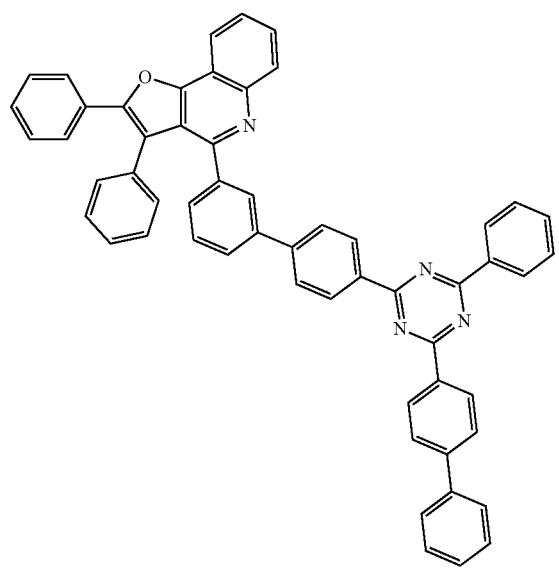
528
-continued
54
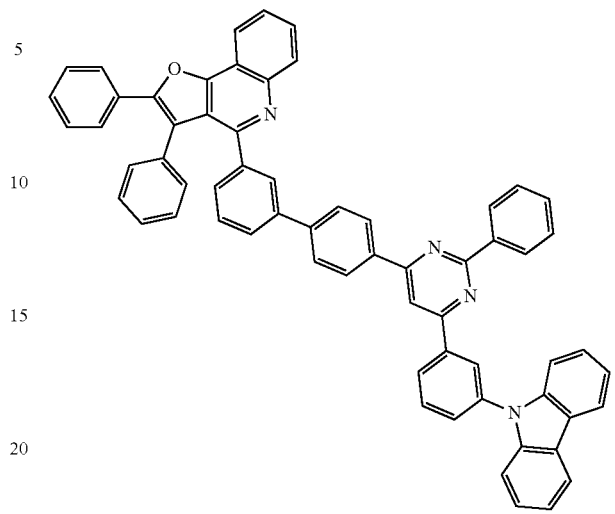
55
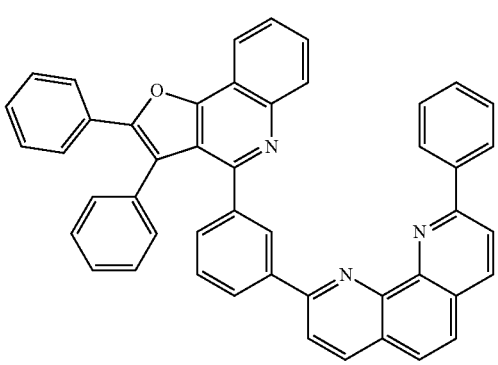
56

57
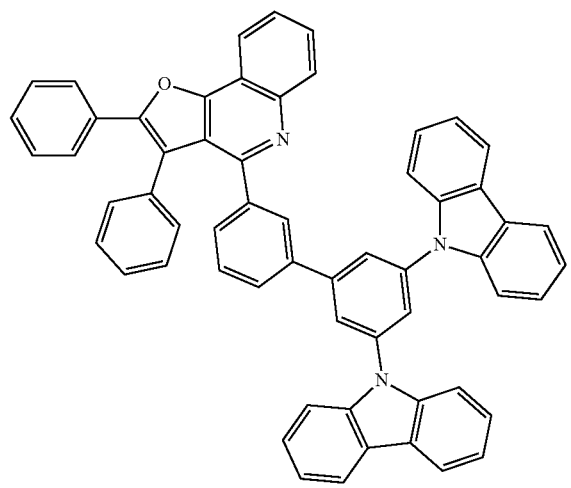
58
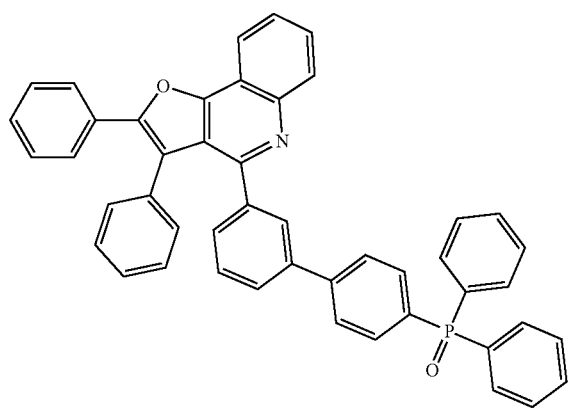
59
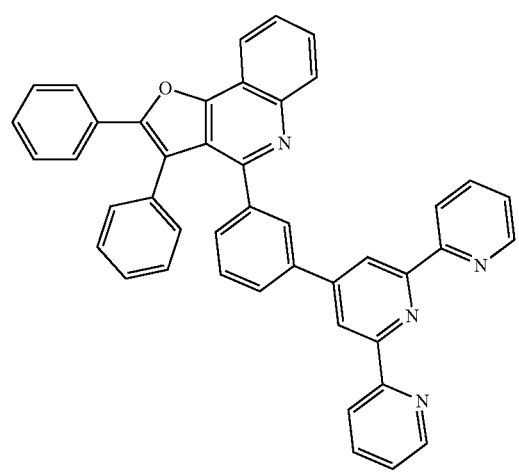
60
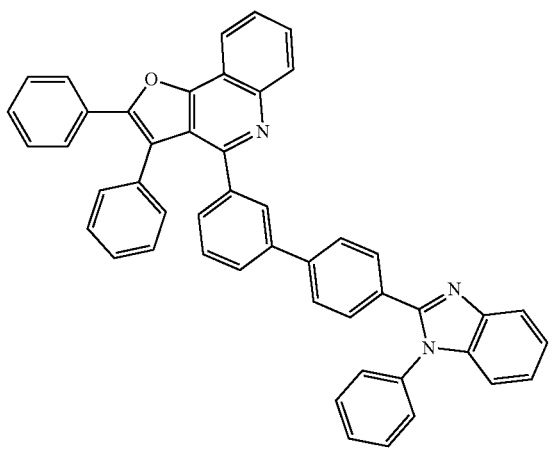
61
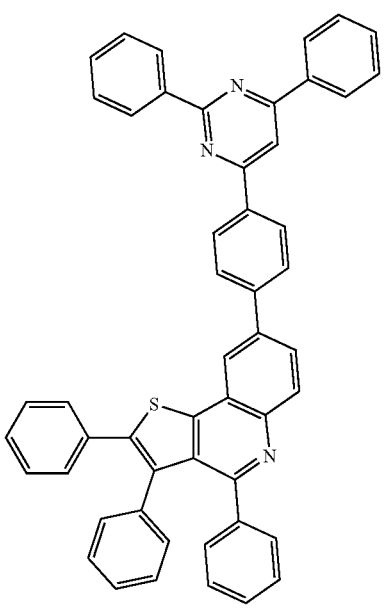

531
-continued
532
-continued
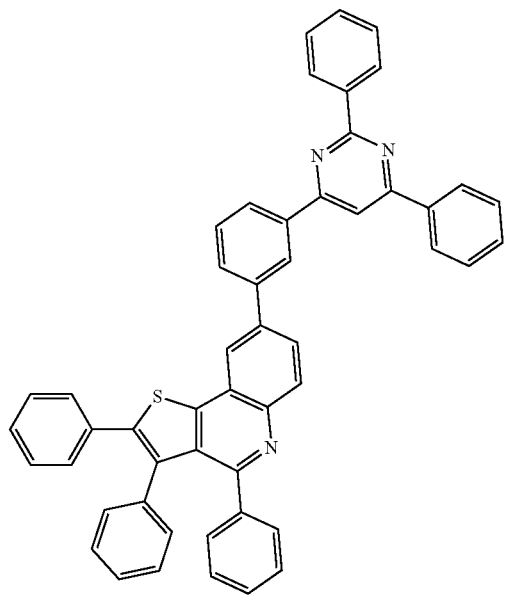
62
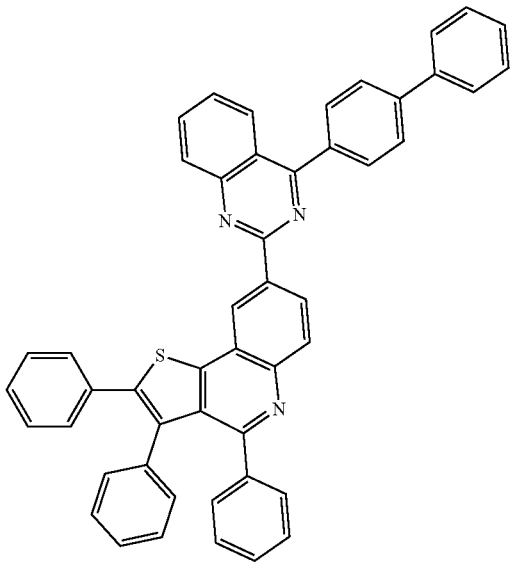
64
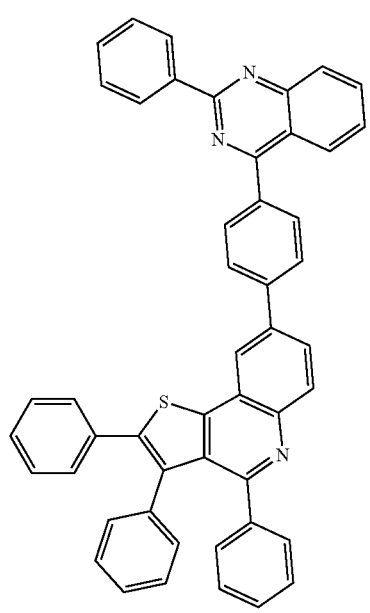
63
65

533
-continued
66
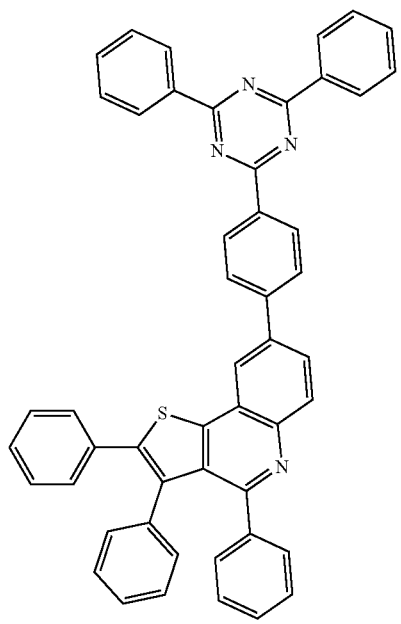
67
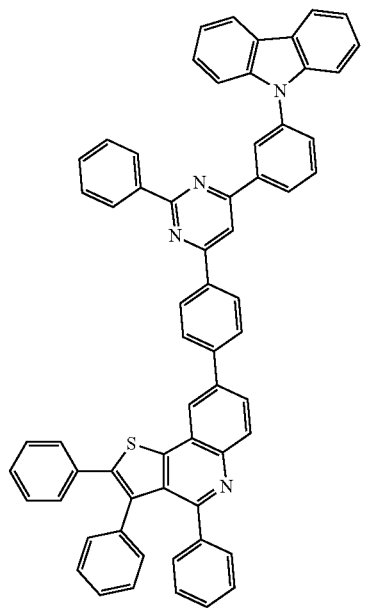
534
-continued
68
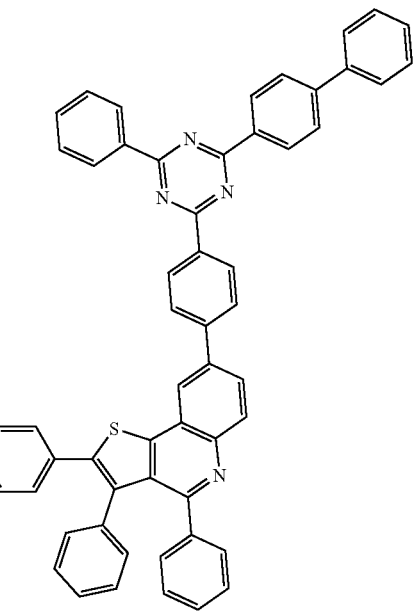
69
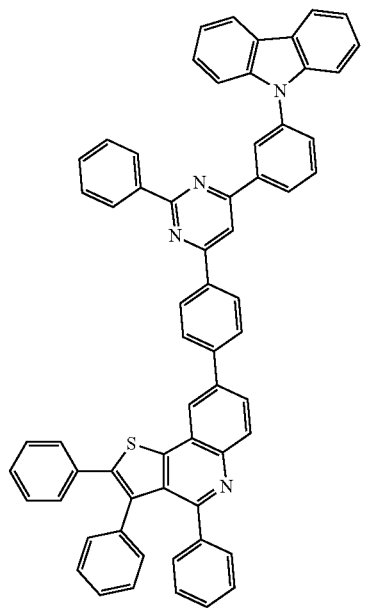

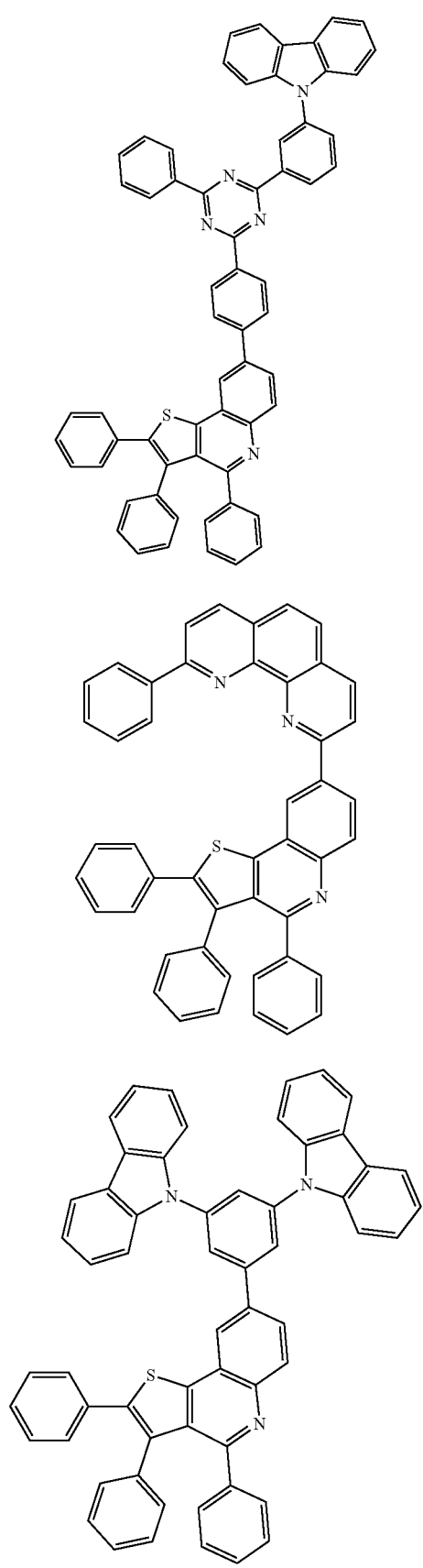
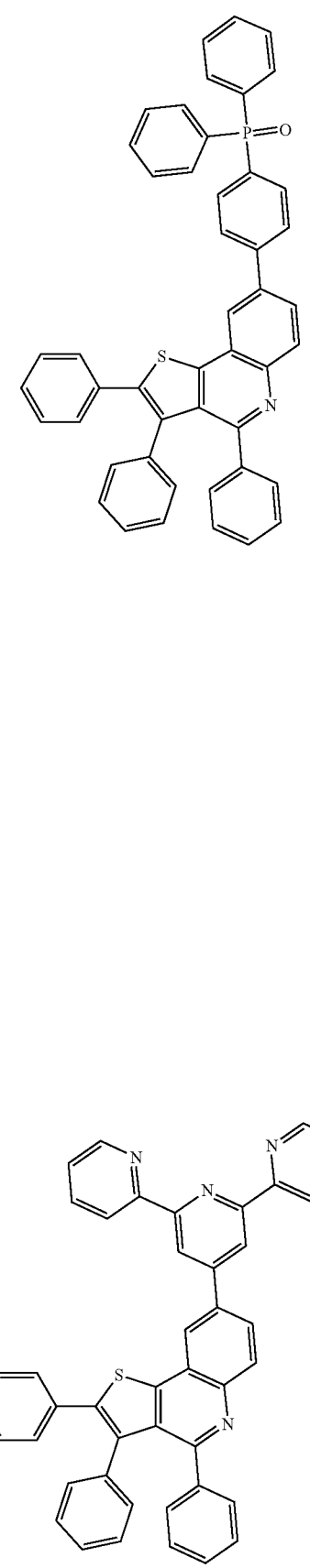

537
-continued
75
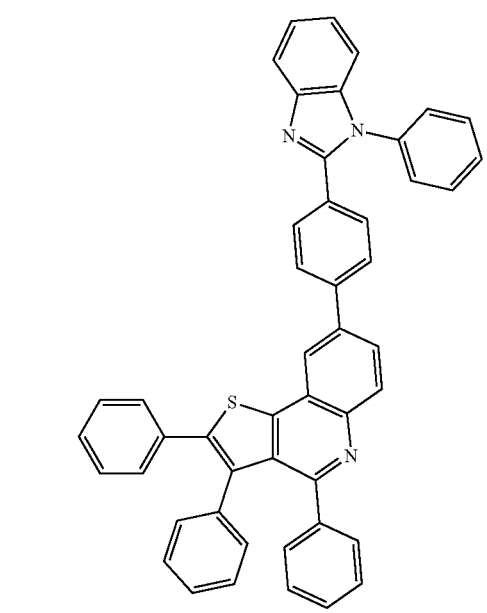
76
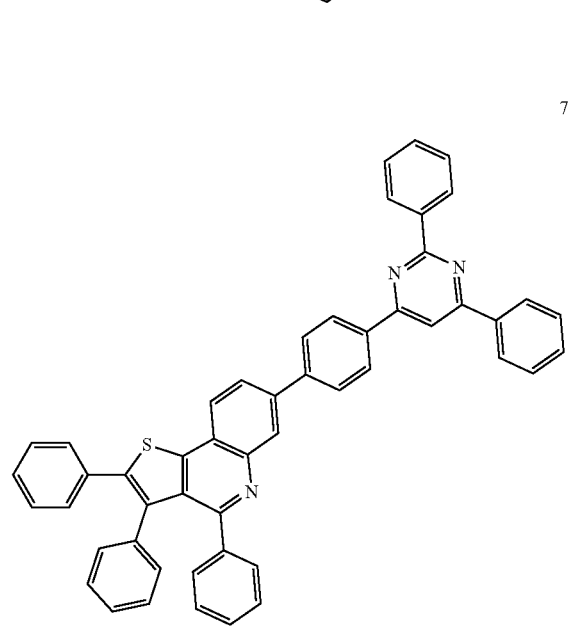
77
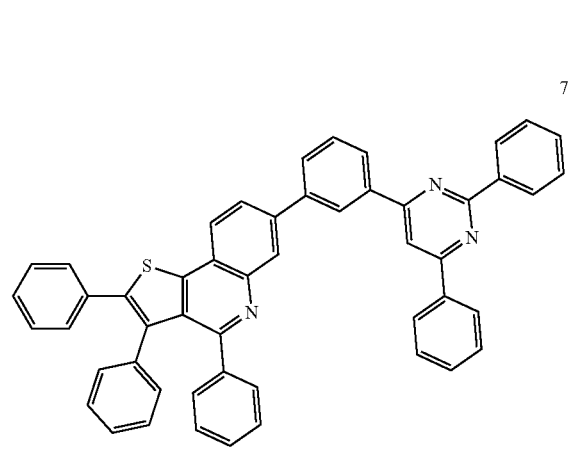
538
-continued
78
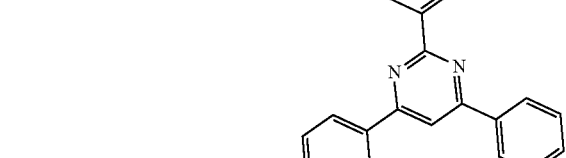
79
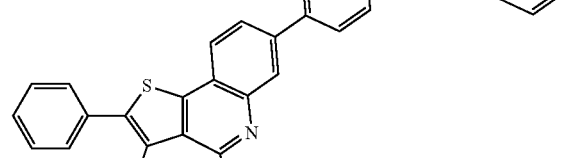
80
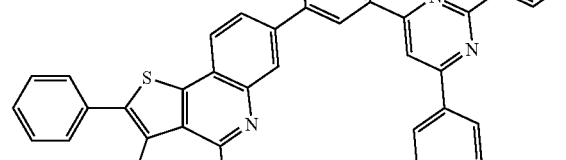

-continued
81
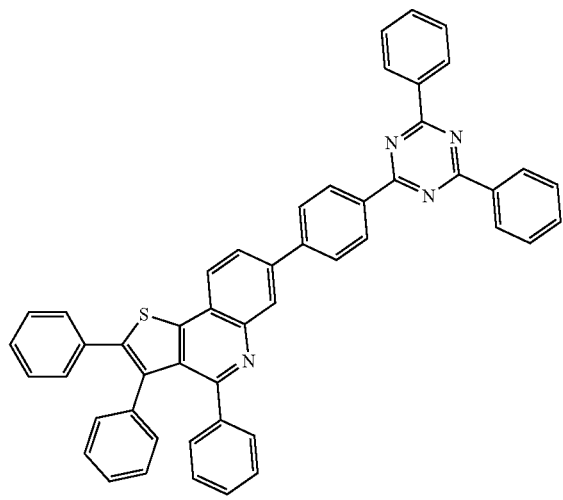
82
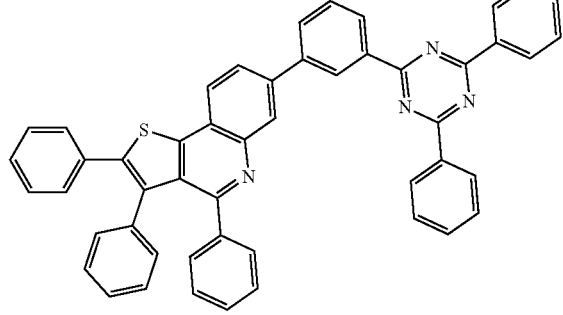
83
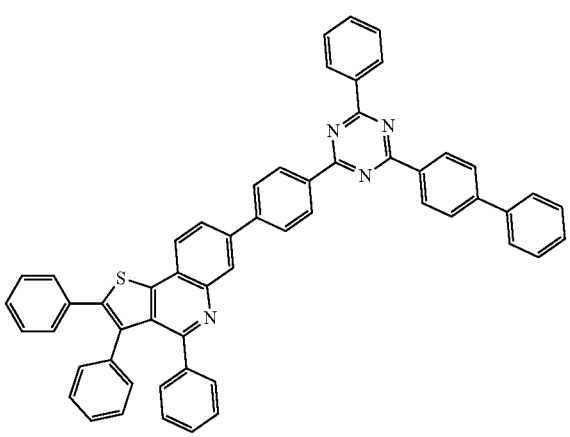
-continued
84
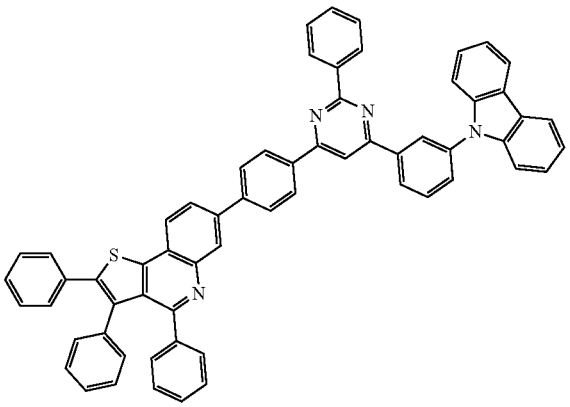
85
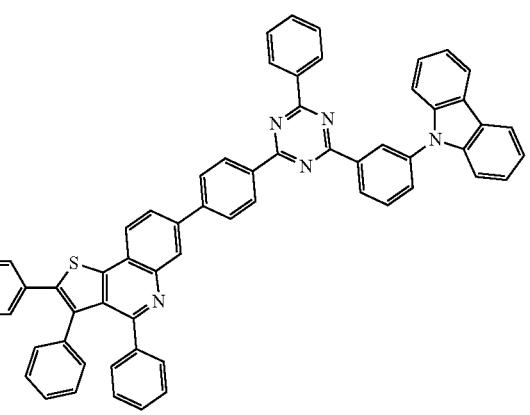
86
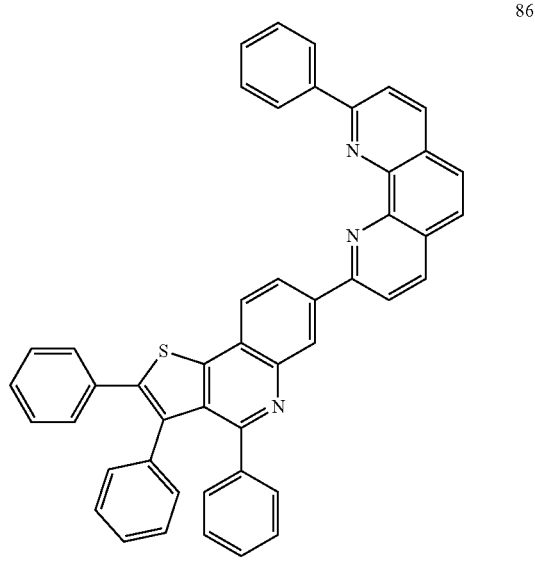

541
-continued
87
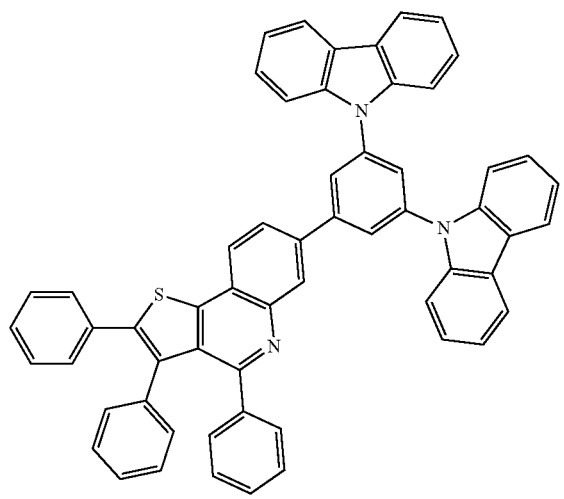
88
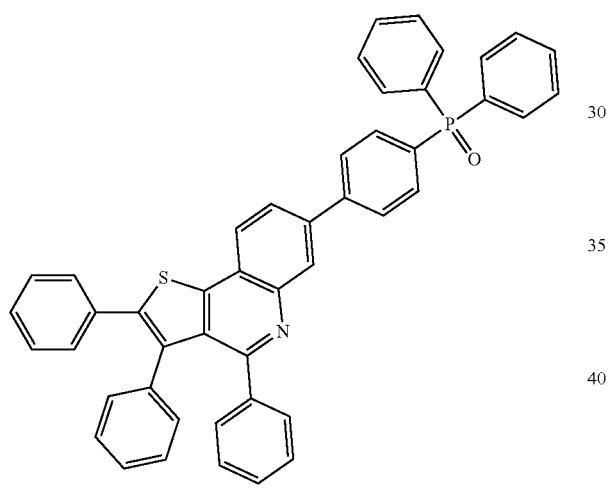
89
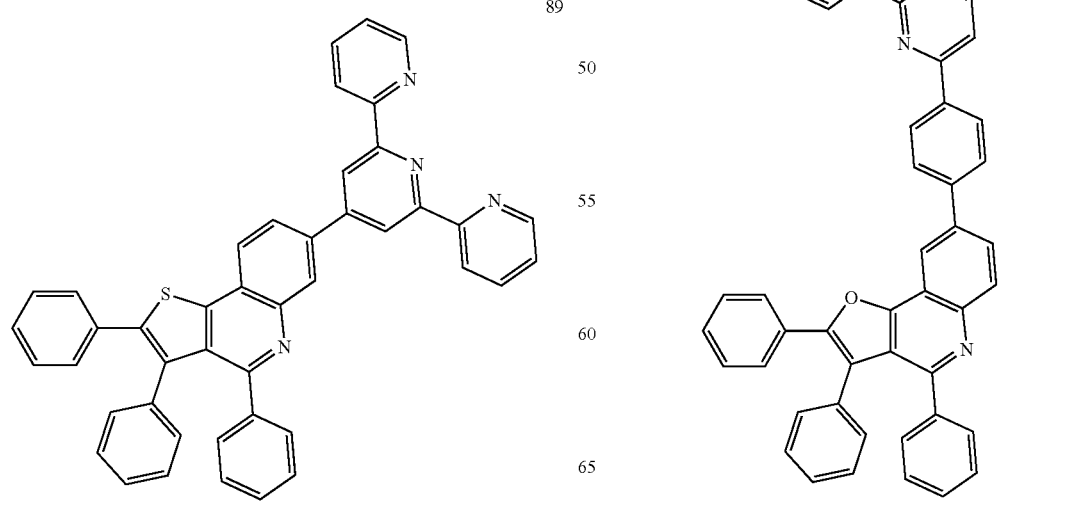
542
-continued
90
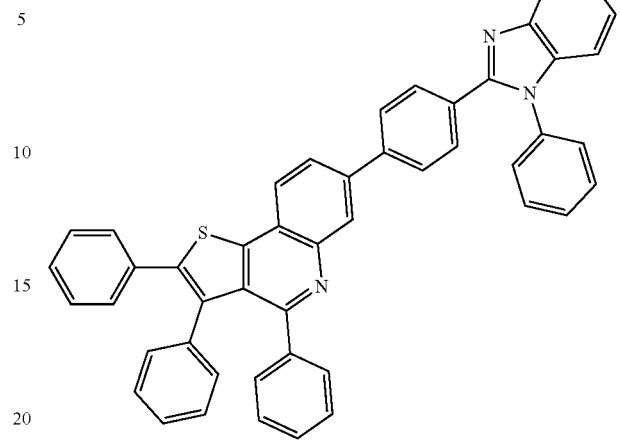
91

92
543
-continued
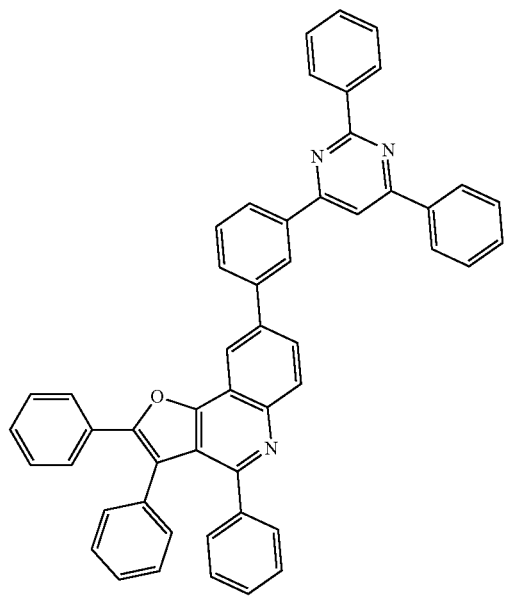
93
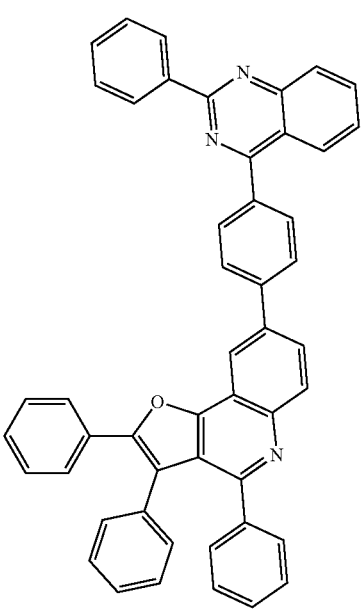
94
544
-continued
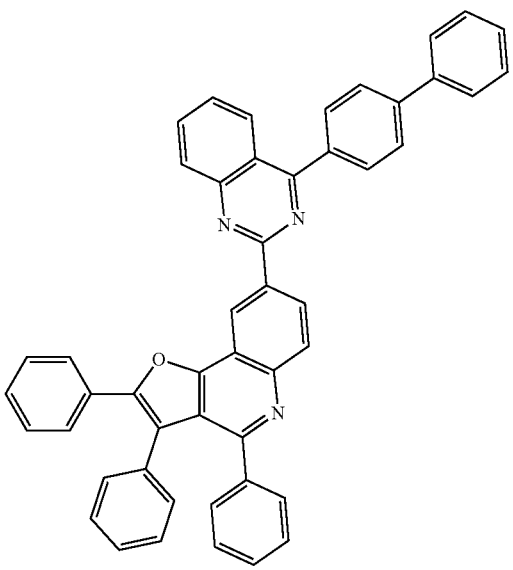
95

96
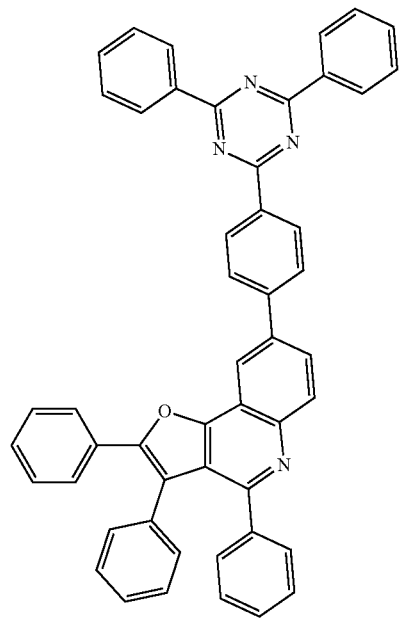
97
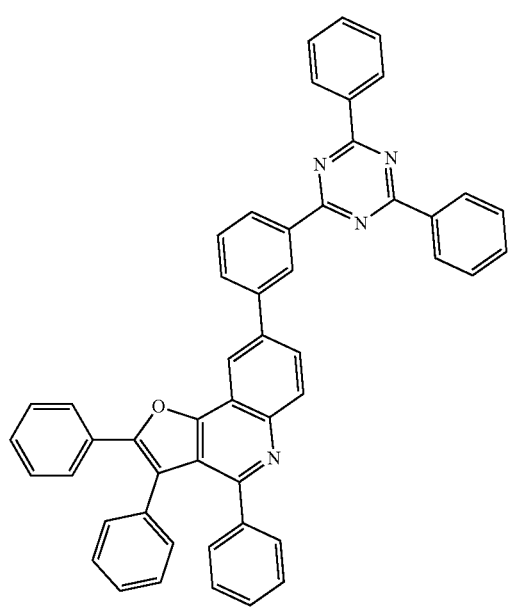
98
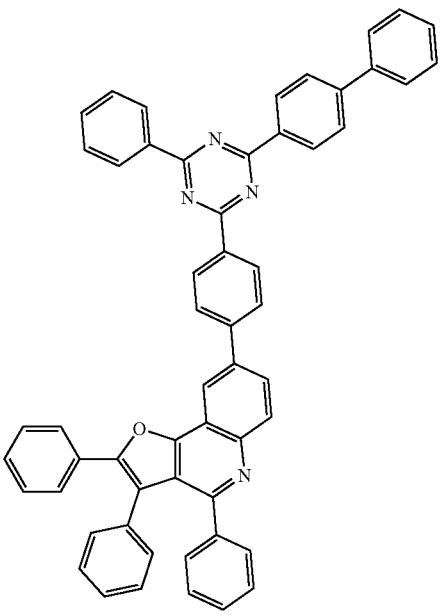
99
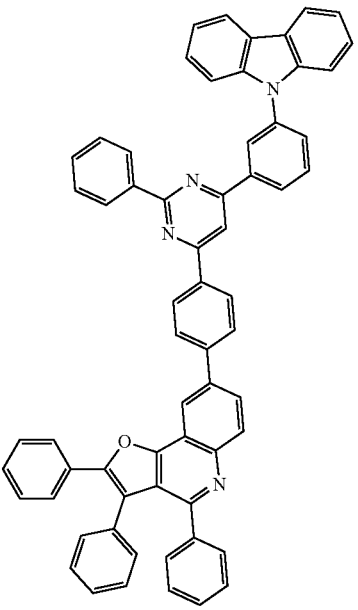

547
-continued
100
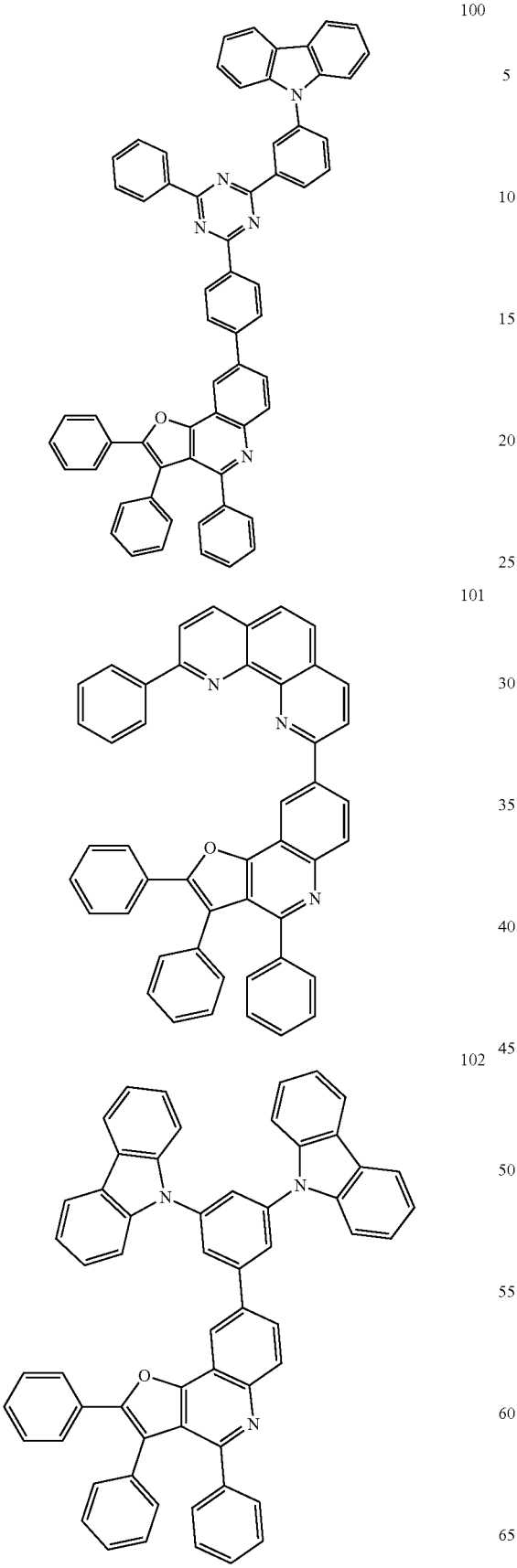
101
102
548
-continued
103
104

549
-continued
550
-continued
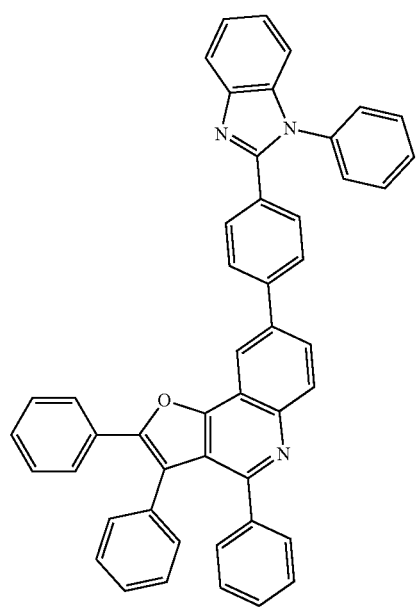
105
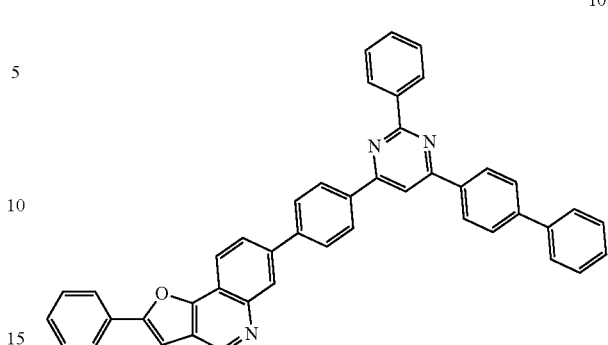
108
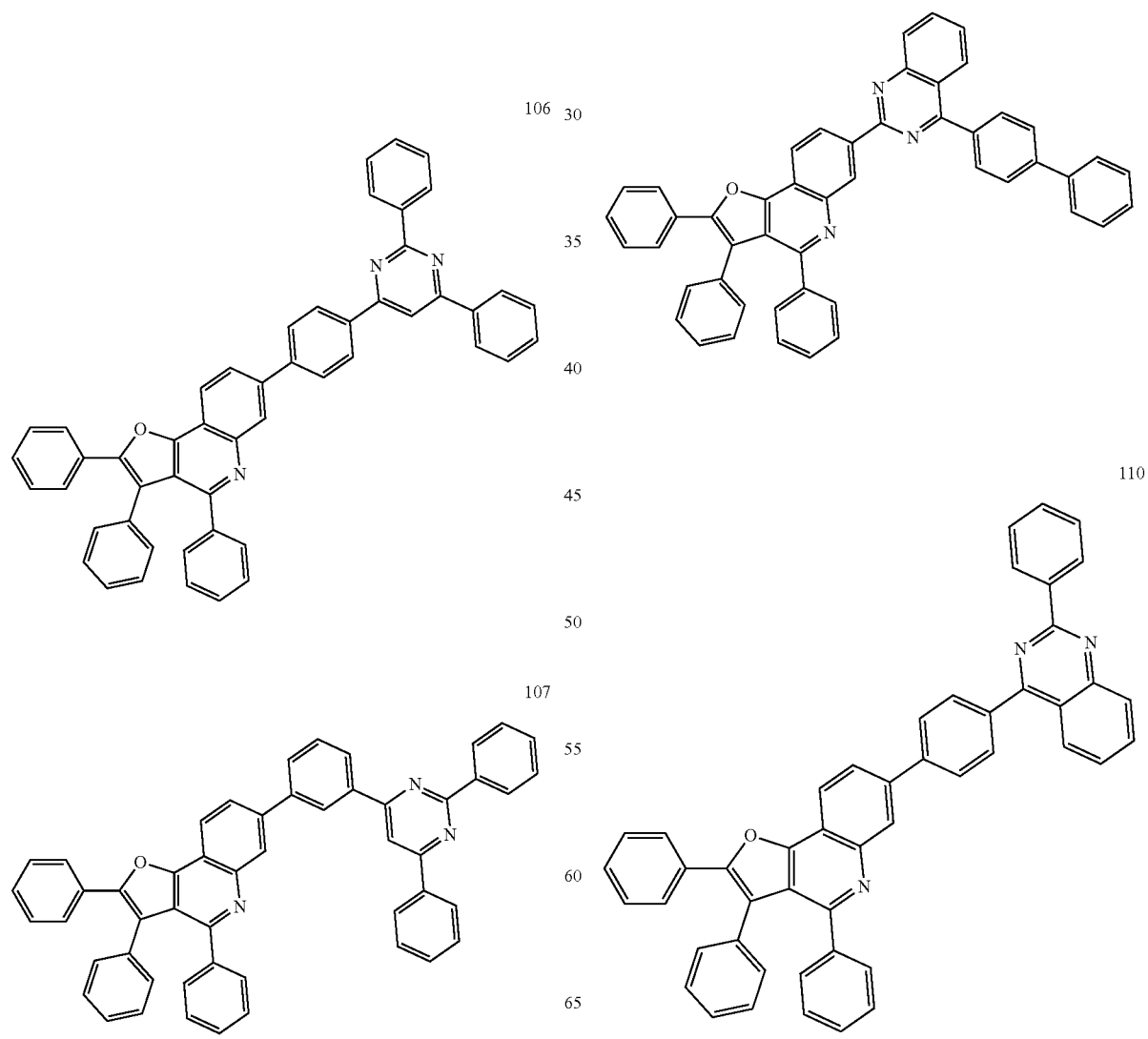

111
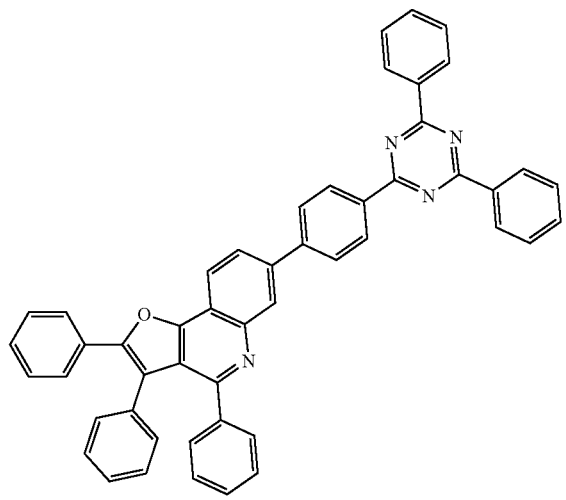
112
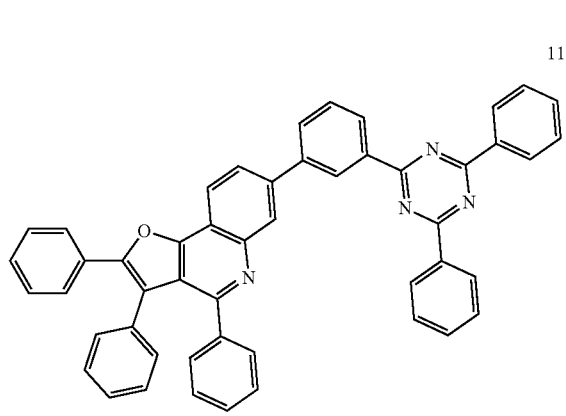
113
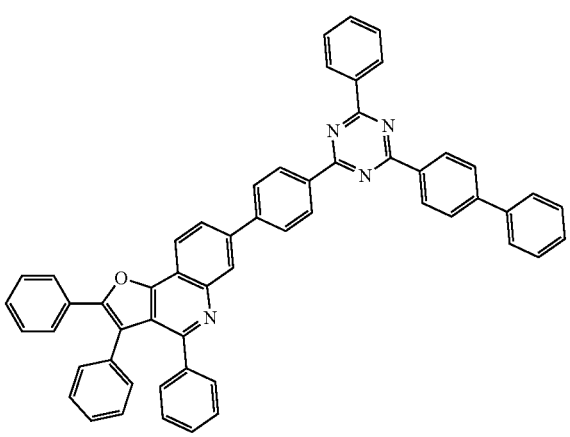
114
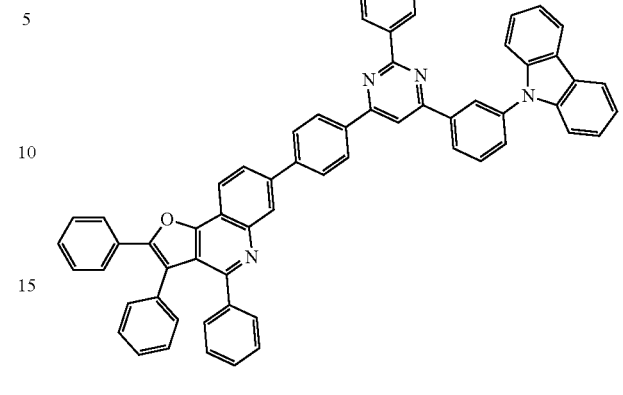
115
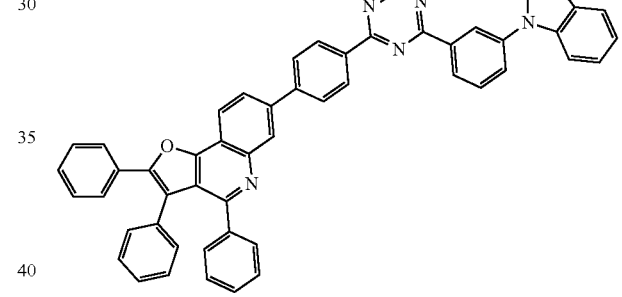
116
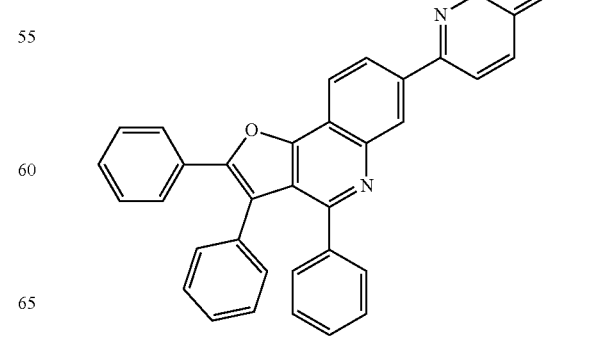

553
-continued
117
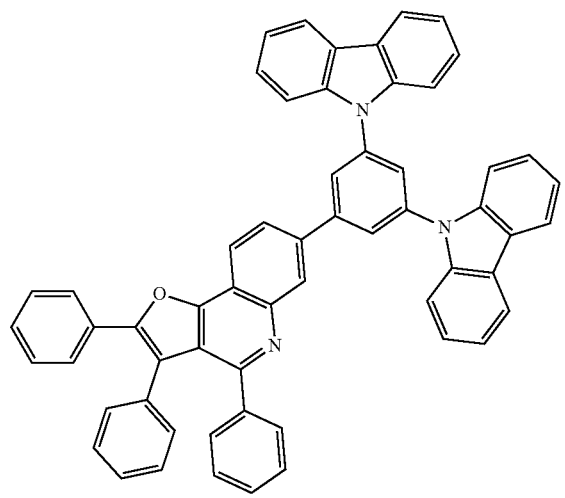
118
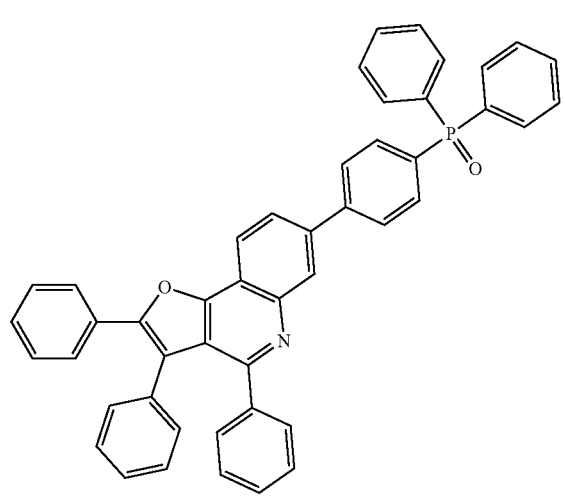
119
554
-continued
120
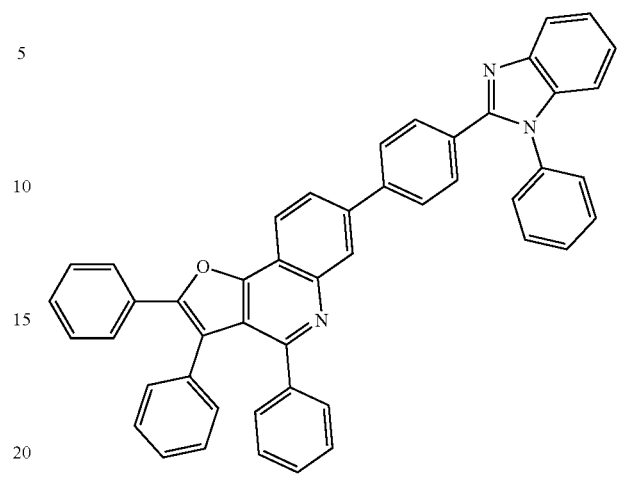
121
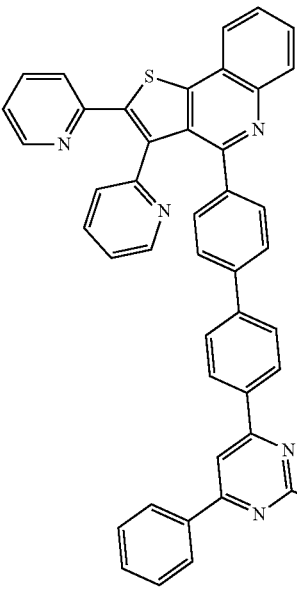

555
-continued
122
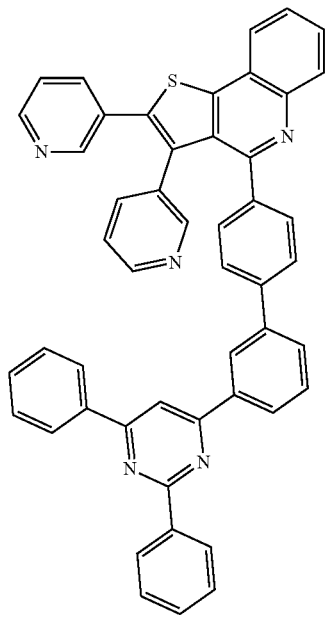
123
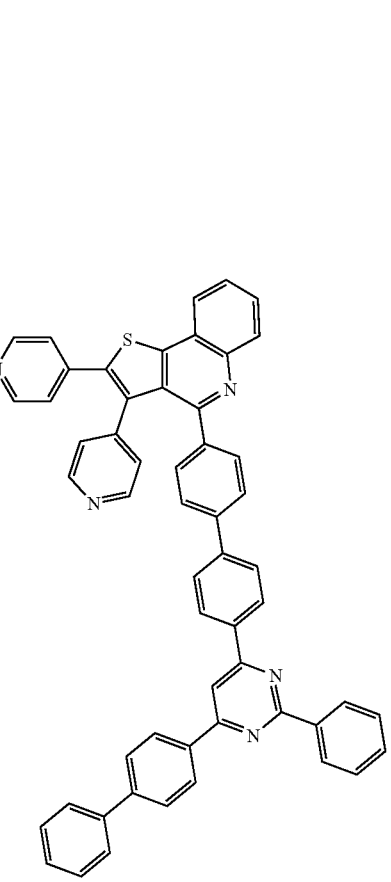
556
-continued
124
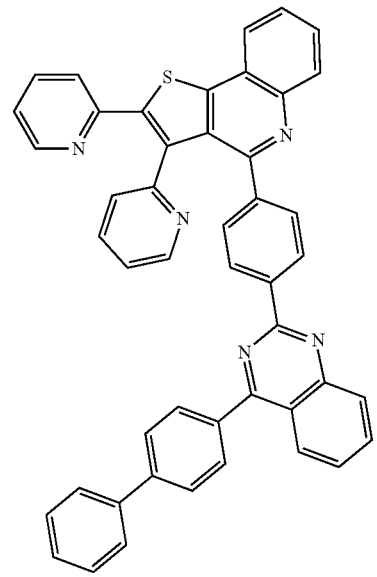
125
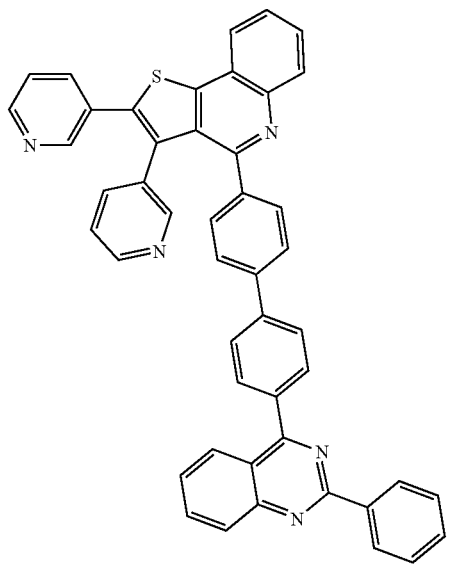

557
-continued
558
-continued
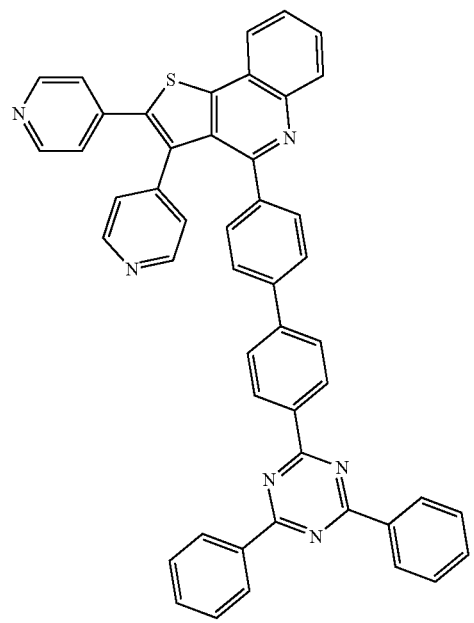
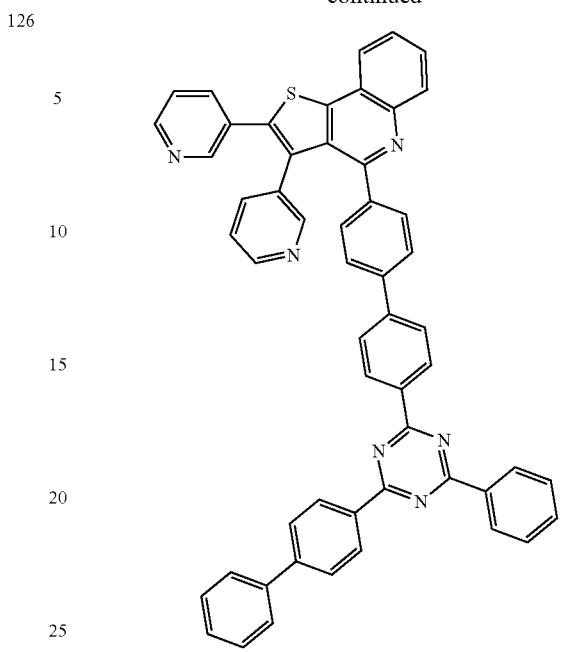

-continued
130
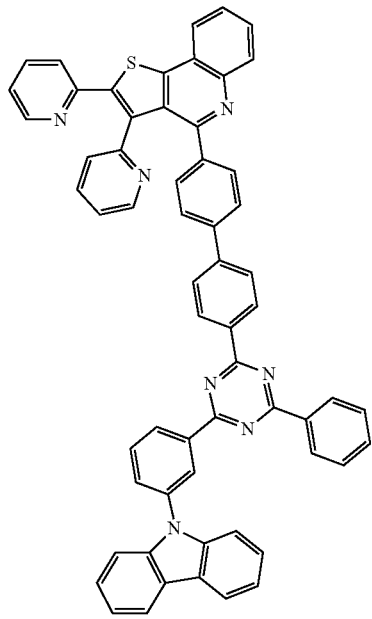
131
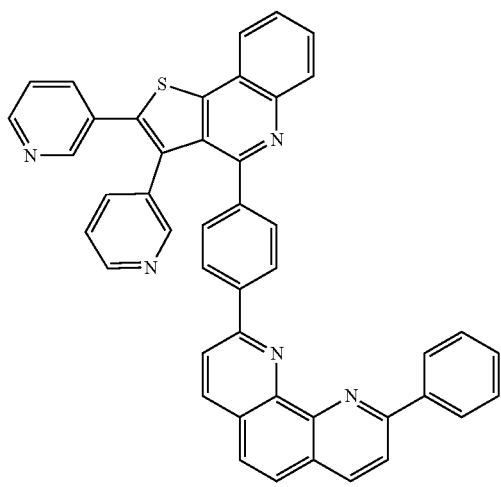
132
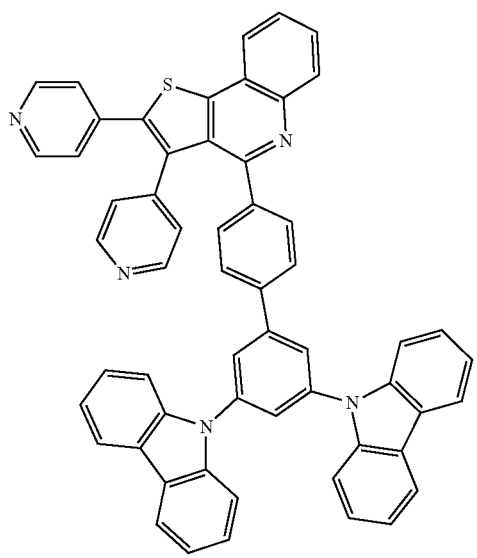
-continued
133
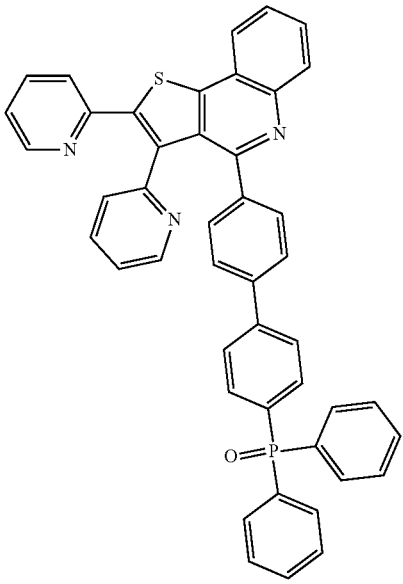
134
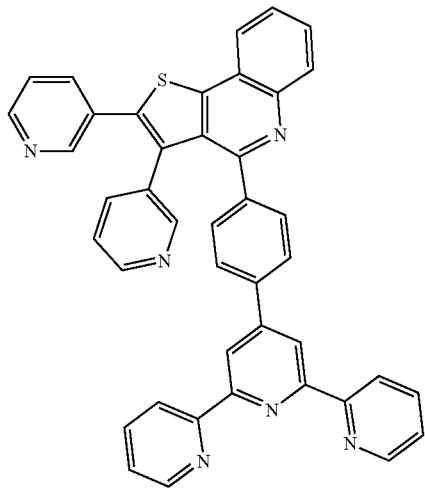
135
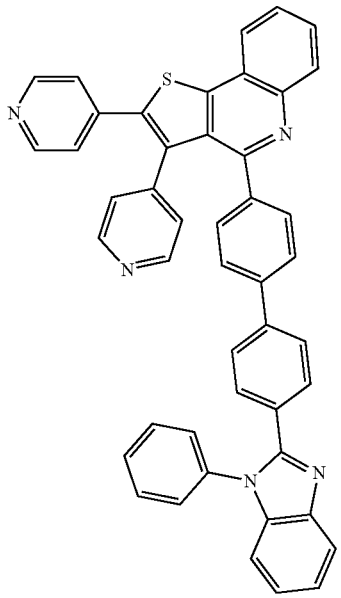

561
-continued
136
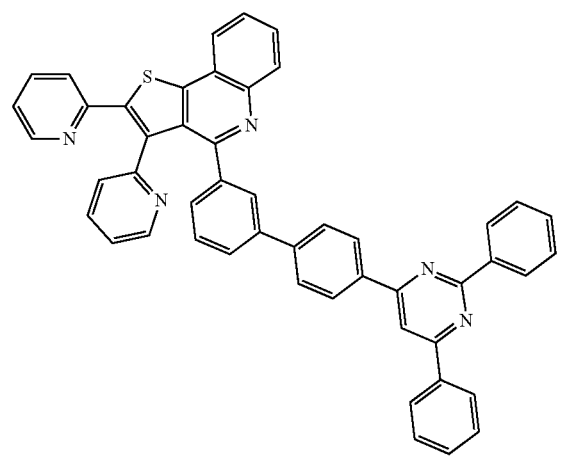
137
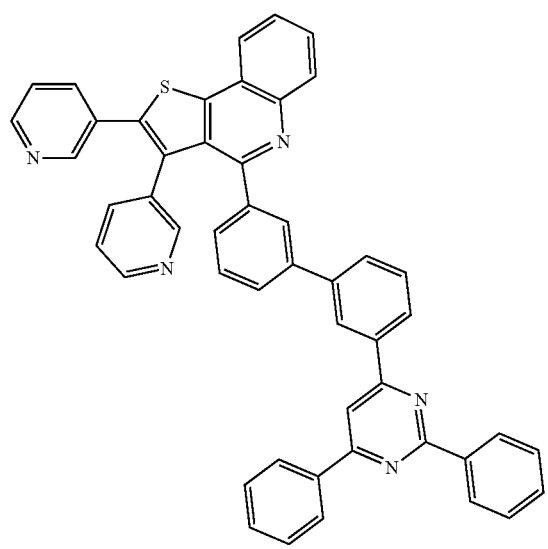
138
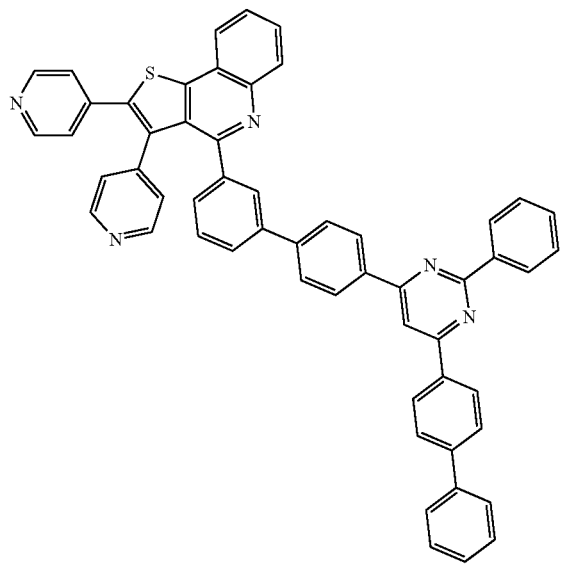
562
-continued
139
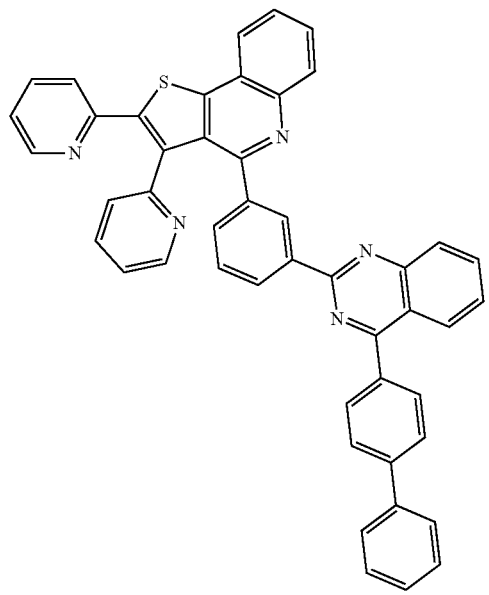
140
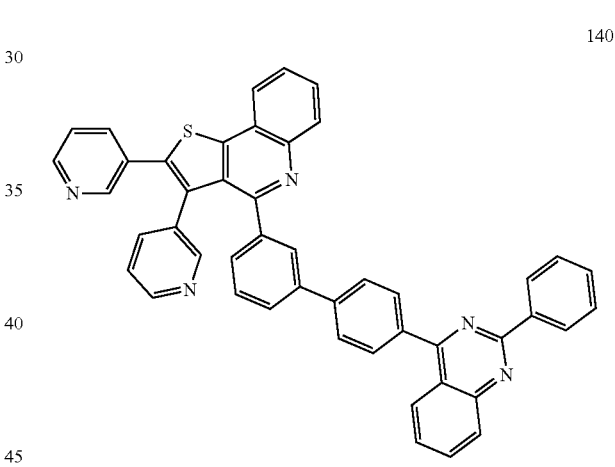
141
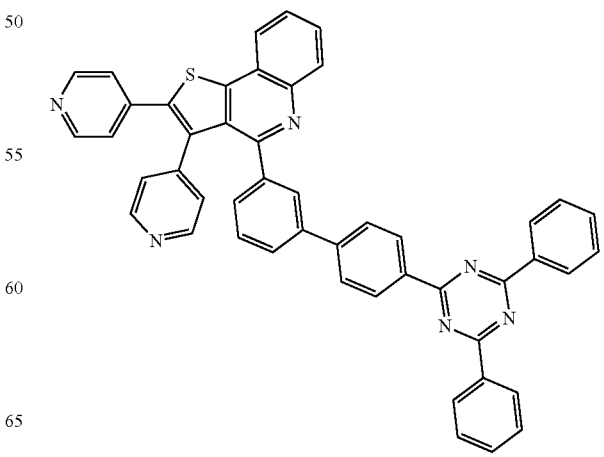

142
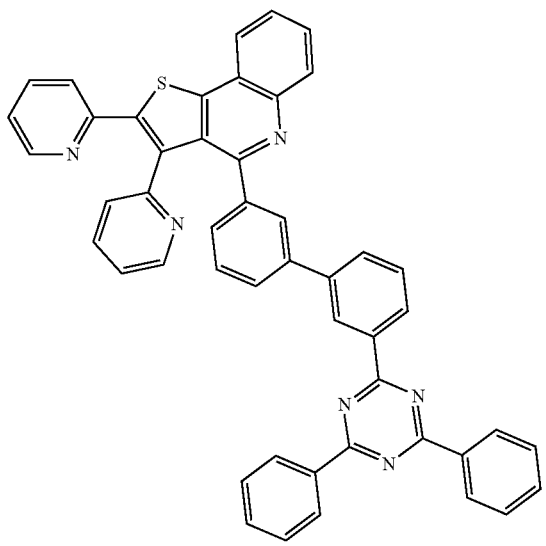
143
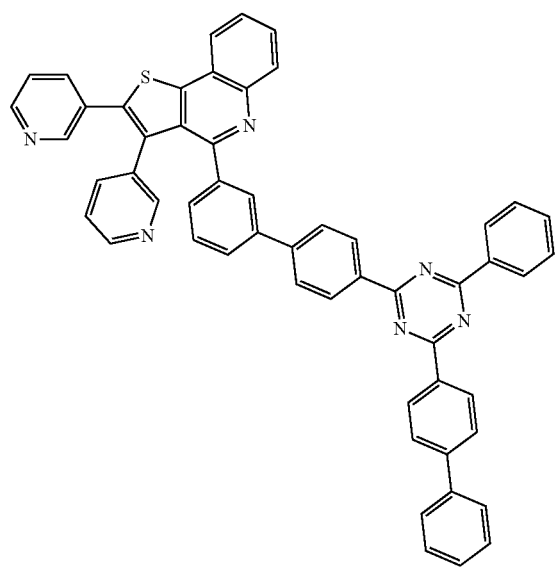
144
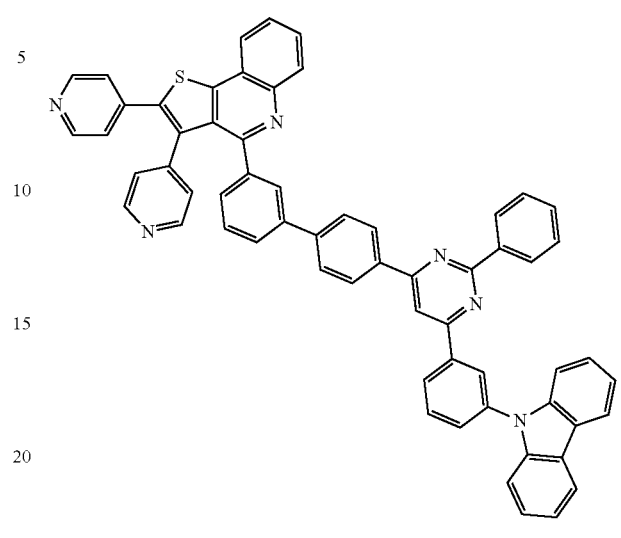
145
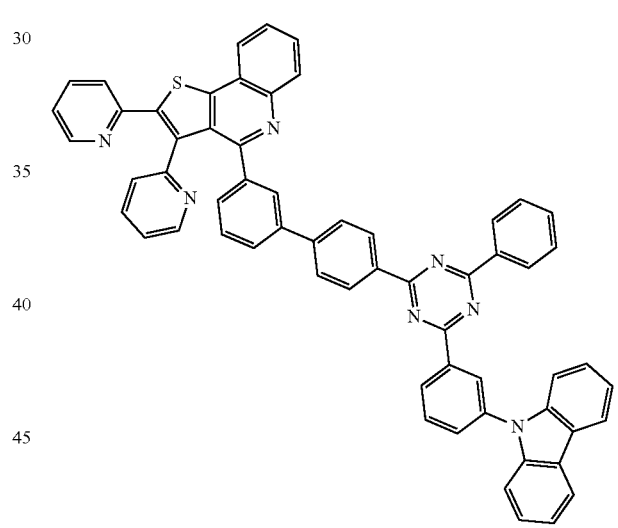
146
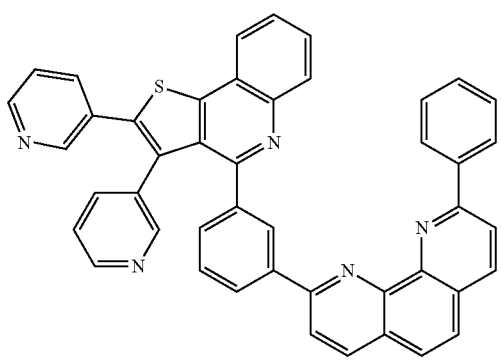

147
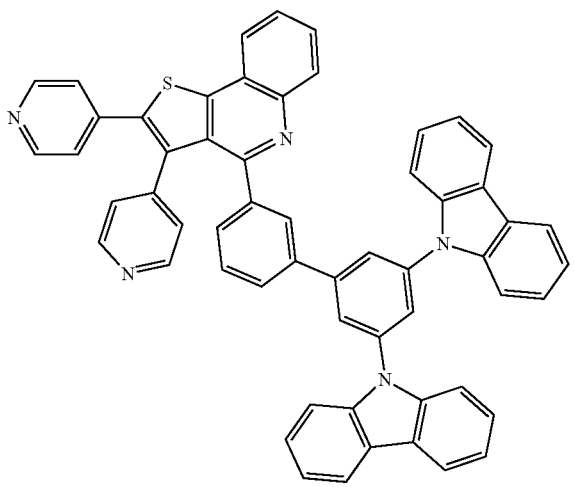
148
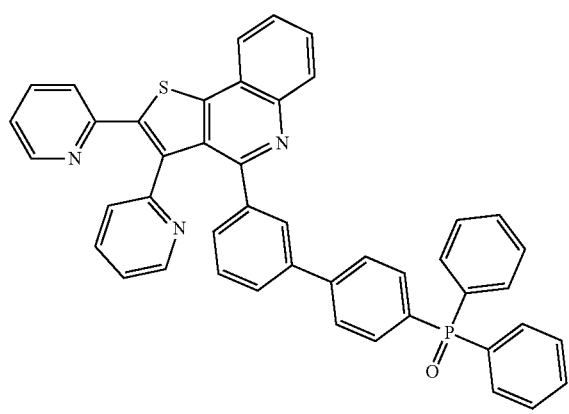
149
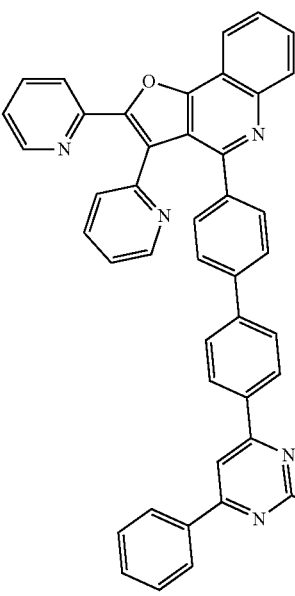
150
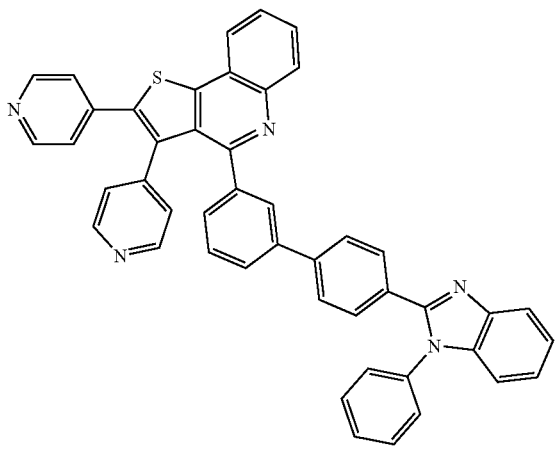
151
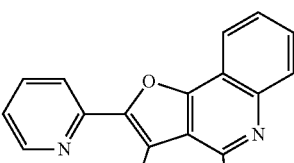
152

567
-continued
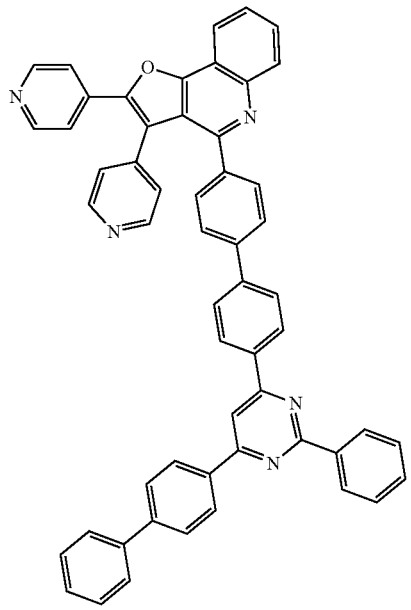
153
154
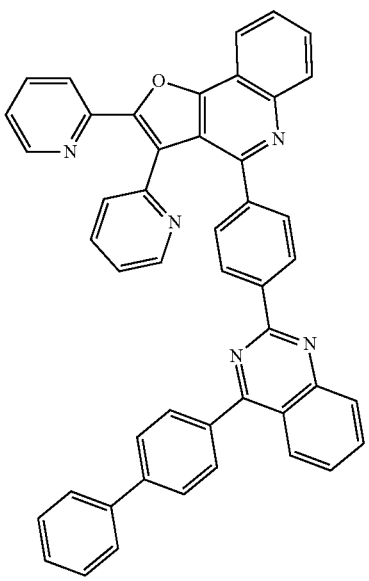
568
-continued
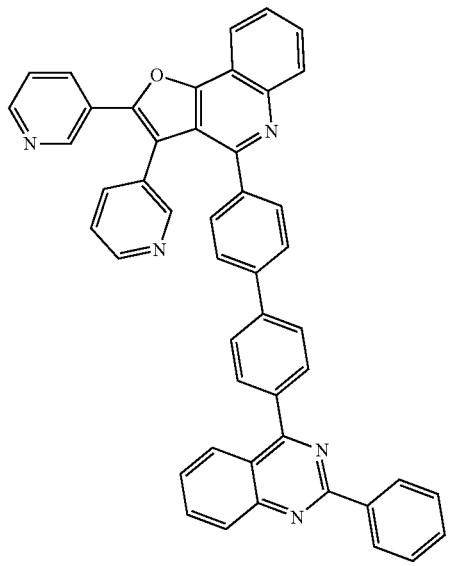
155
156
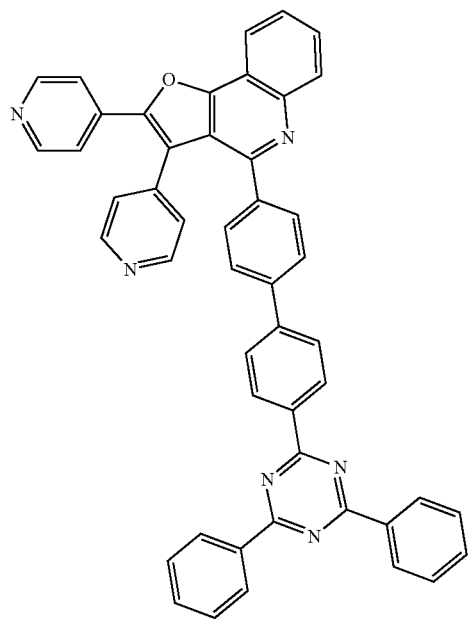

569
-continued
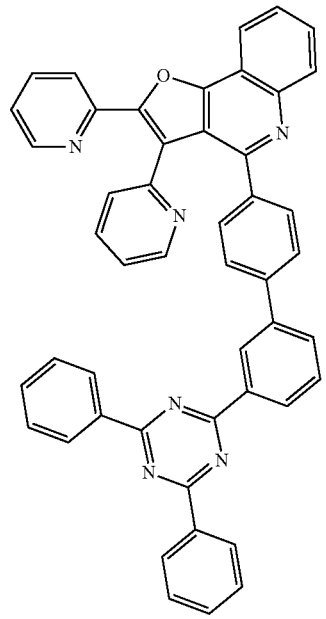
157
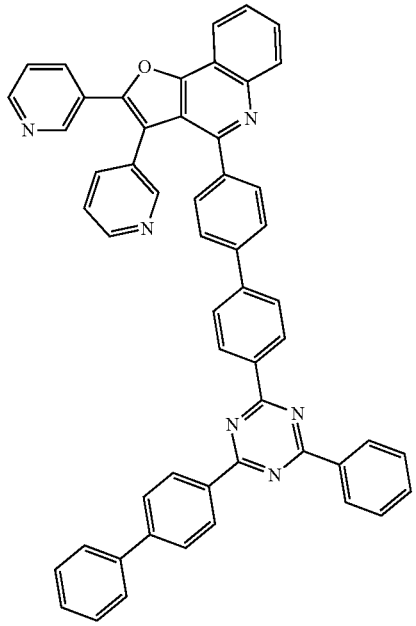
158
570
-continued
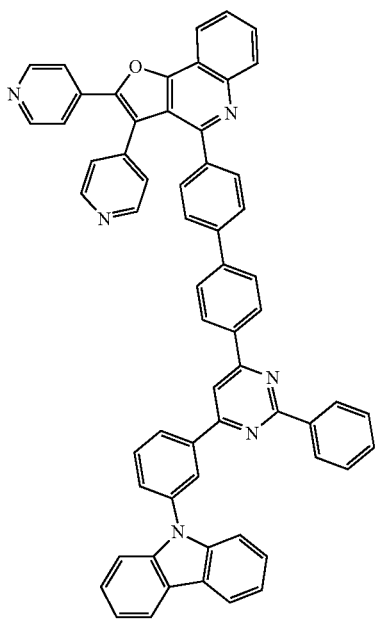
159
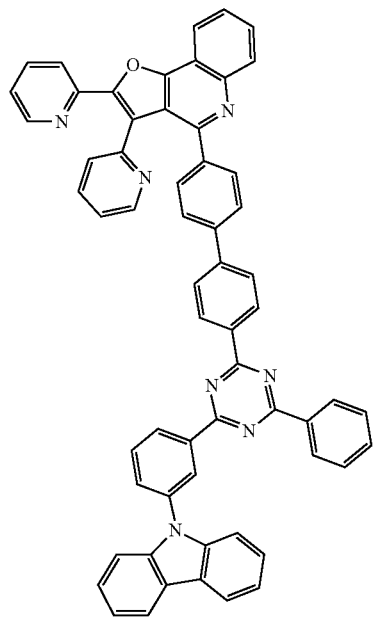
160

571
-continued
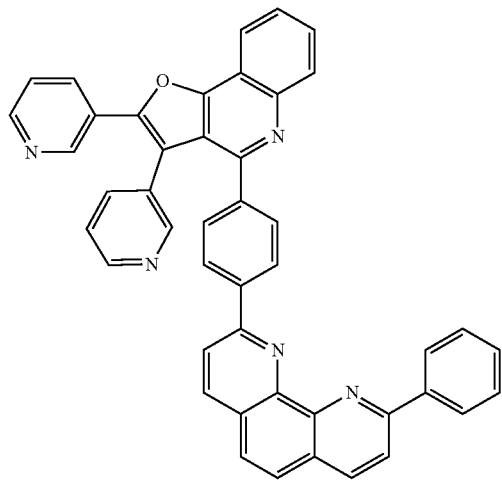
161
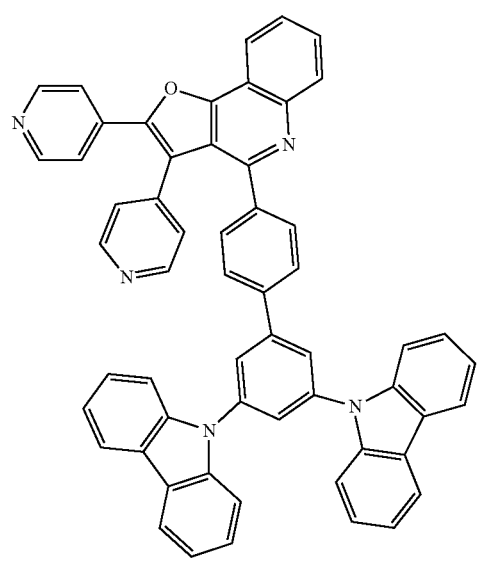
162
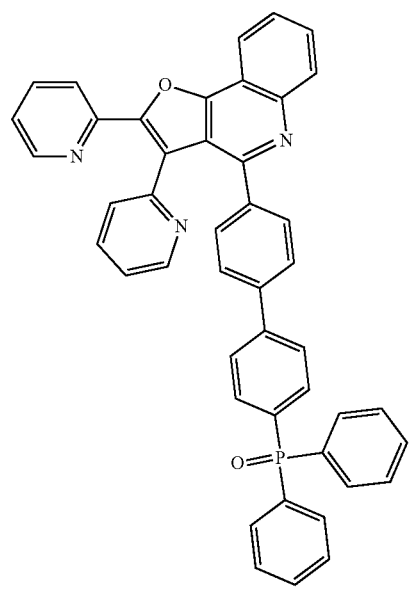
163
572
-continued
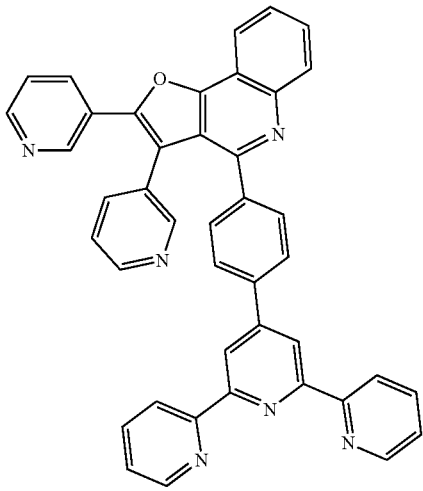
164
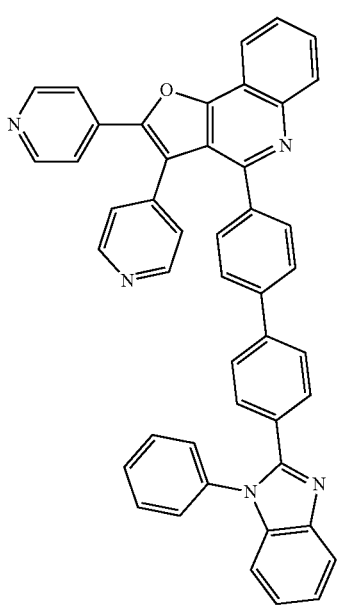
165
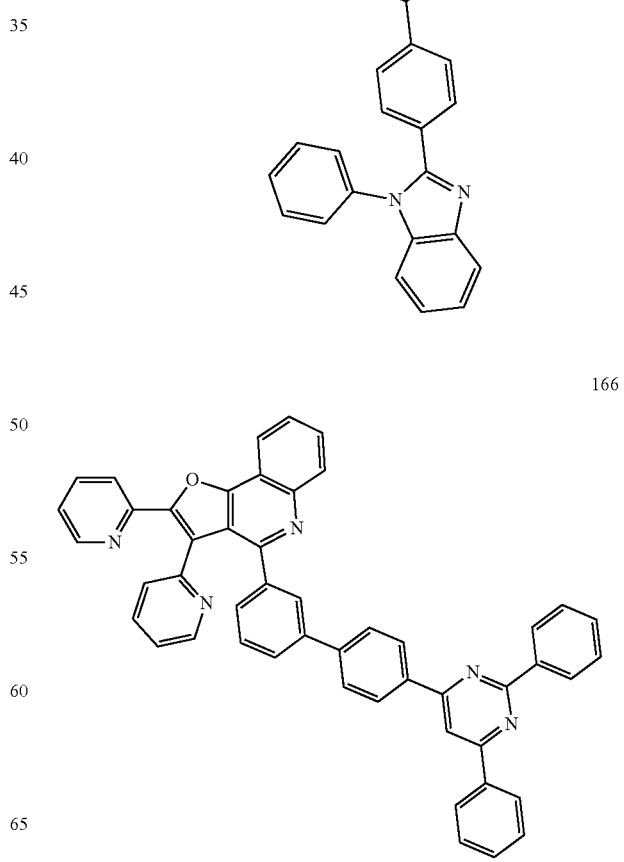
166

573
-continued
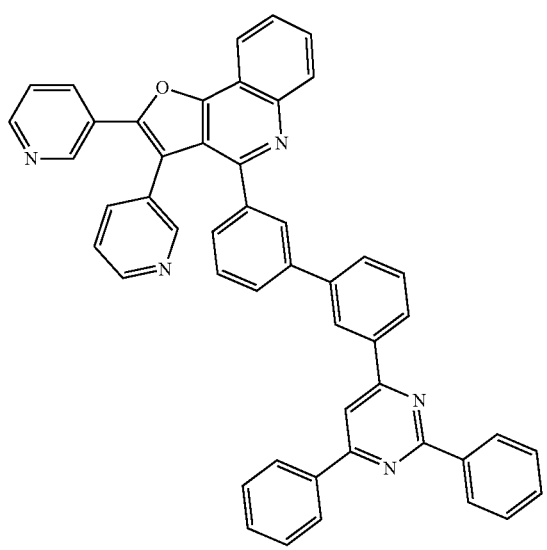
167
574
-continued
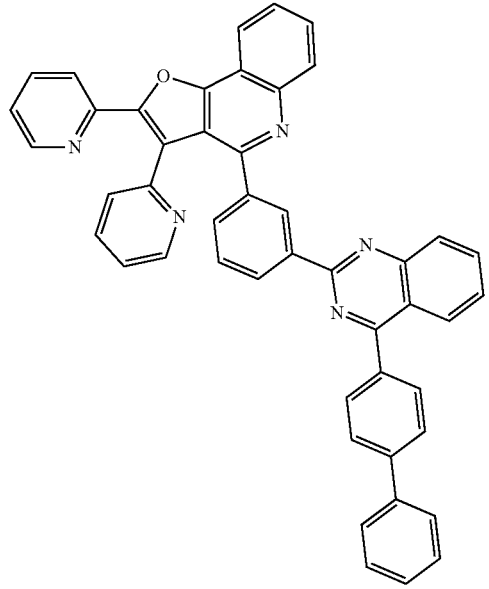
169
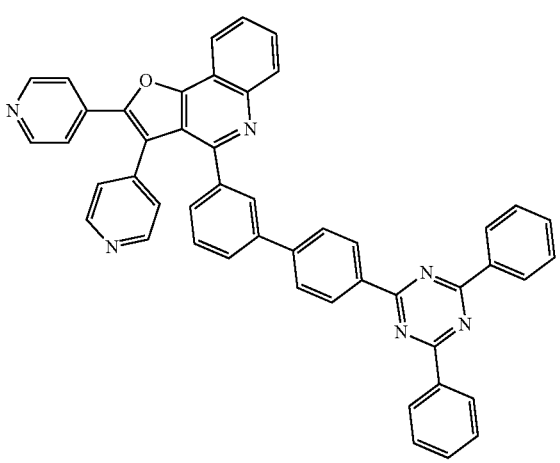
170
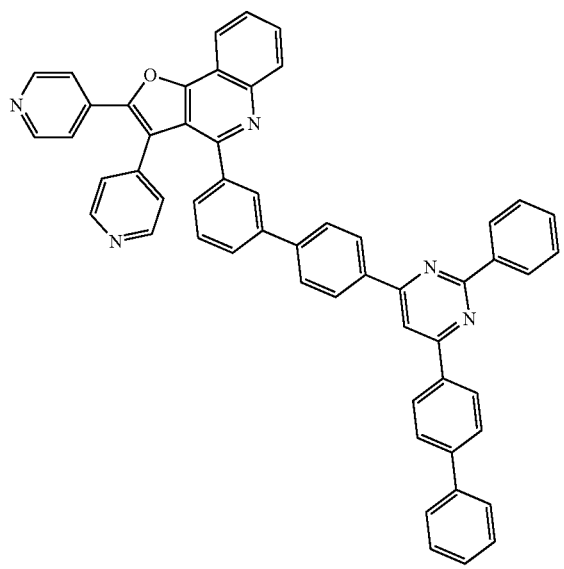
168
171

575
-continued
172
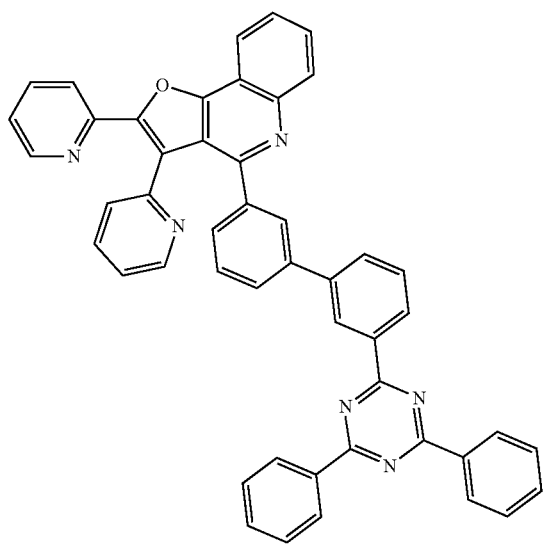
173
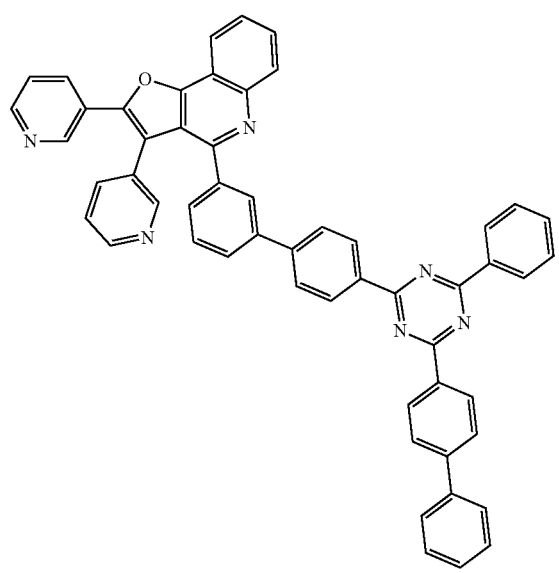
576
-continued
174
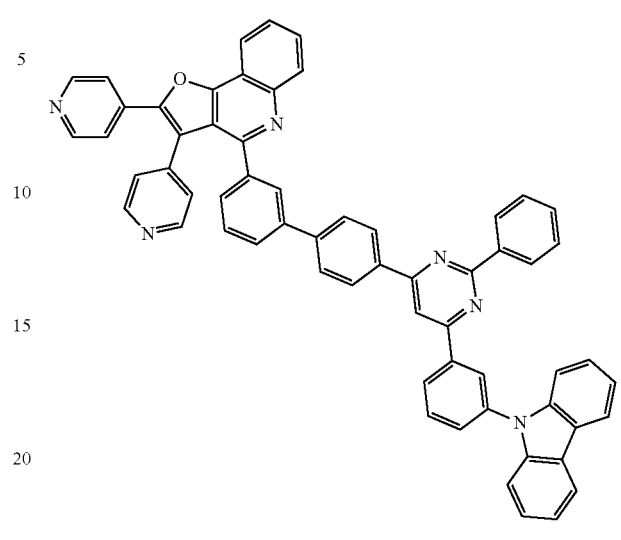
175
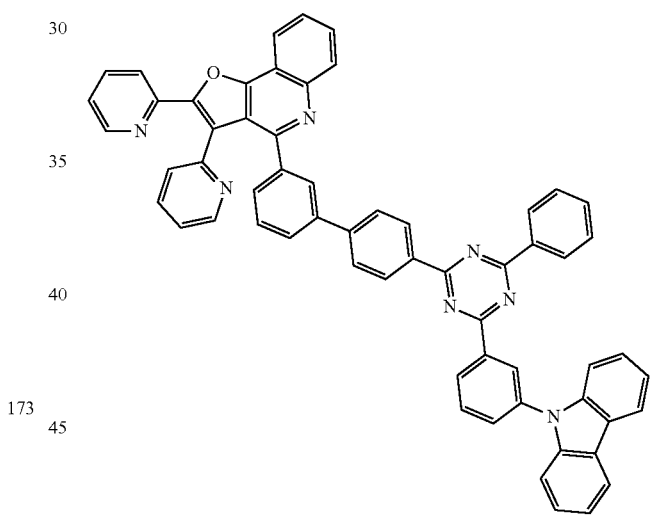
176
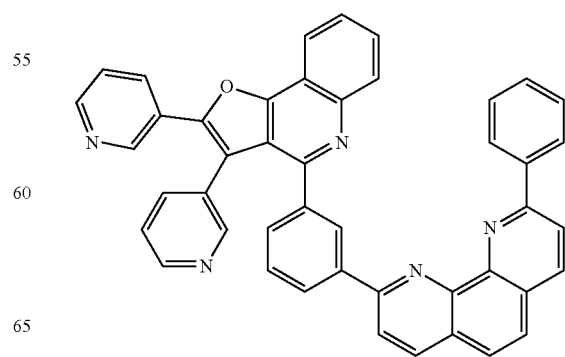

-continued
177
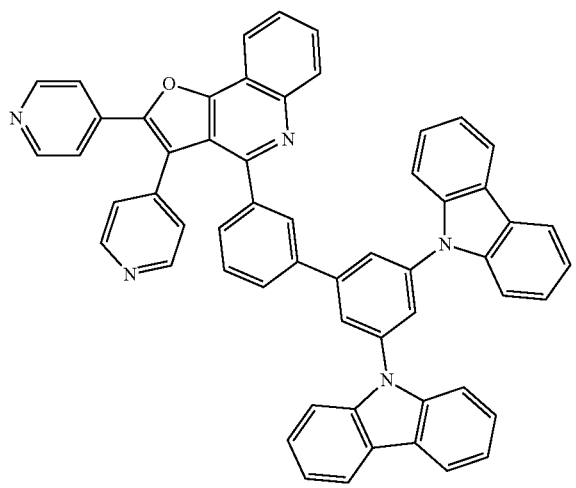
178
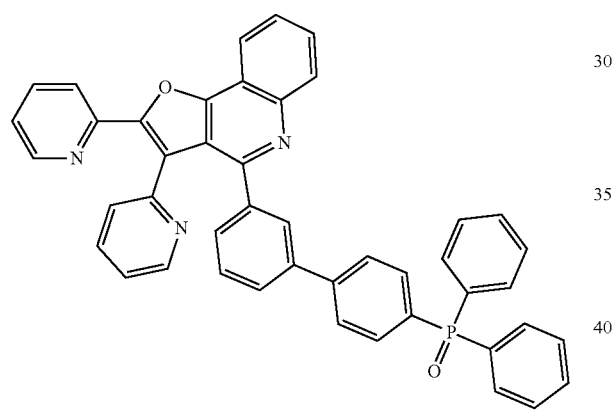
179
-continued
180
181
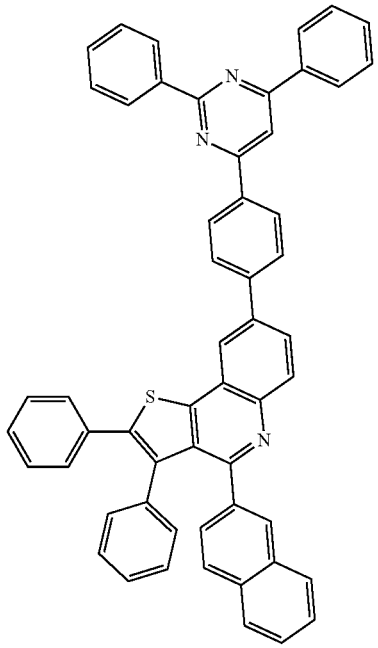

579
-continued
182
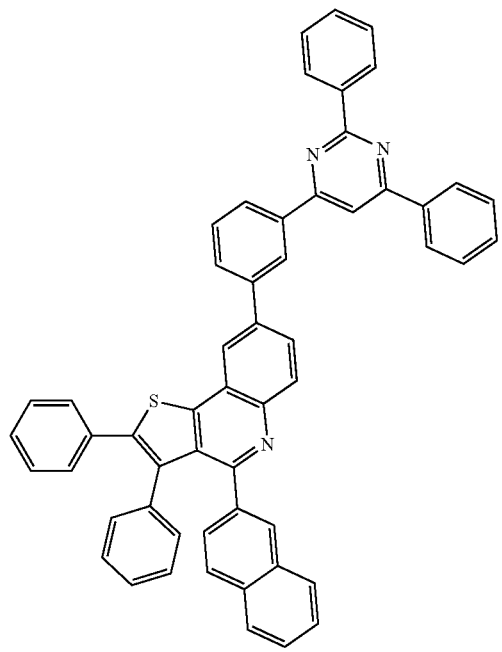
183
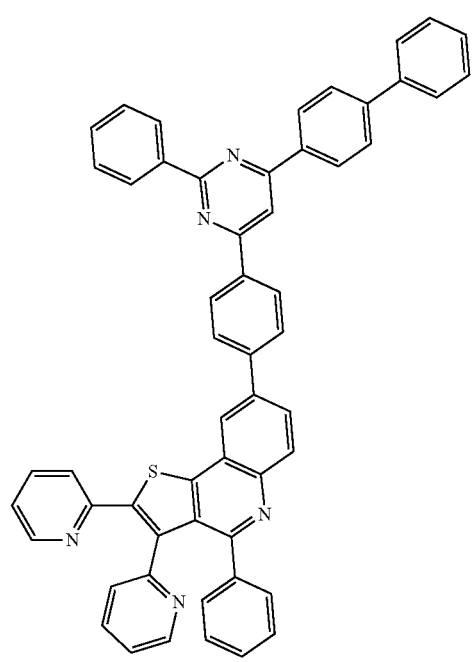
580
-continued
184
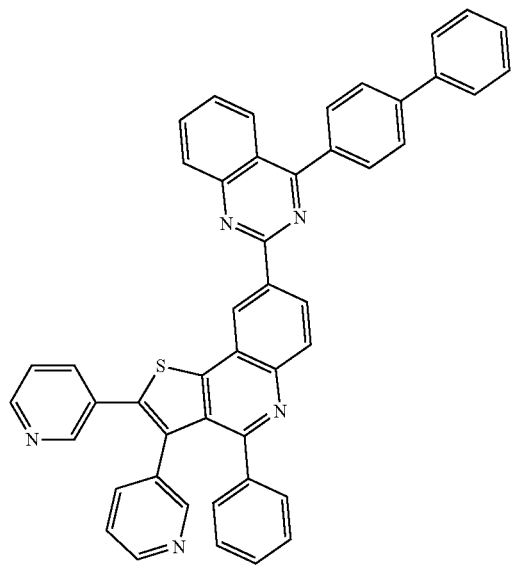
185
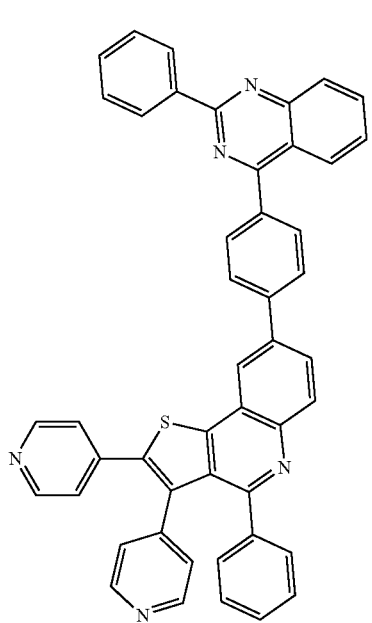

581
-continued
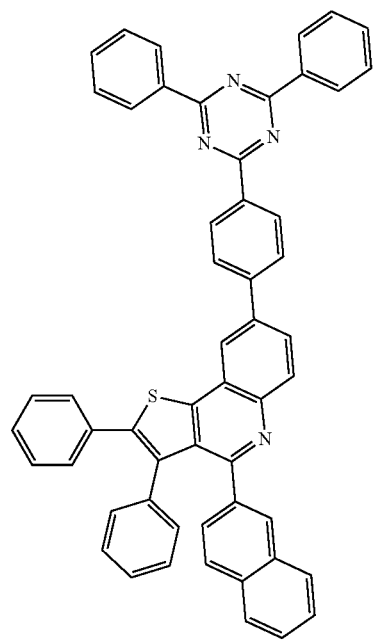
186
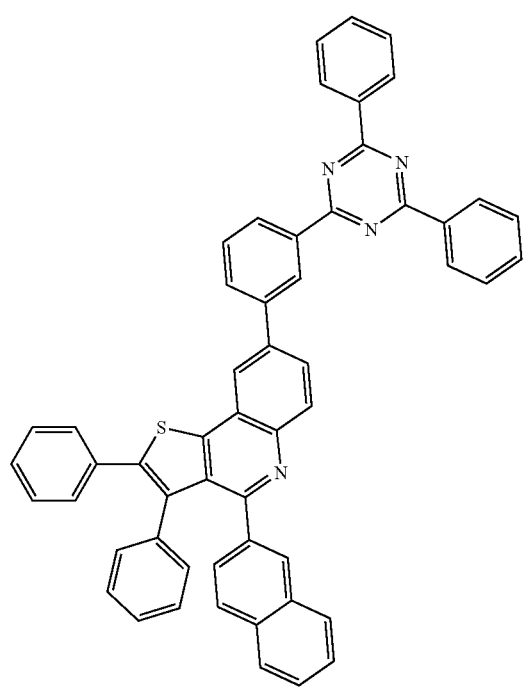
187
582
-continued
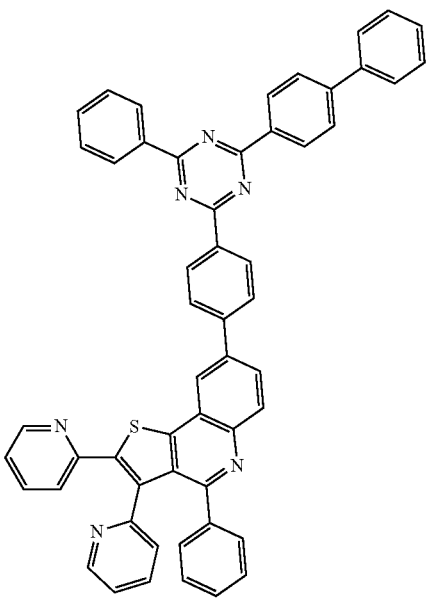
188
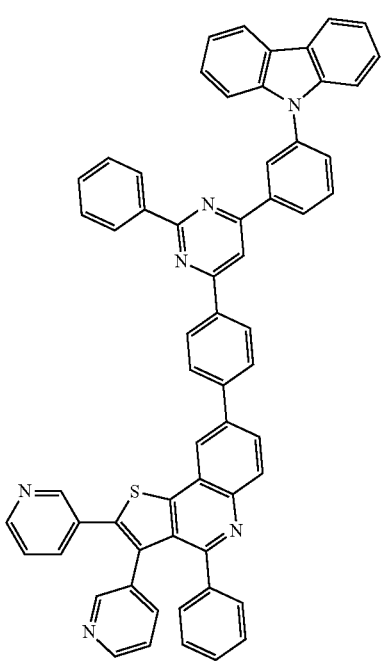
189

583
-continued
190
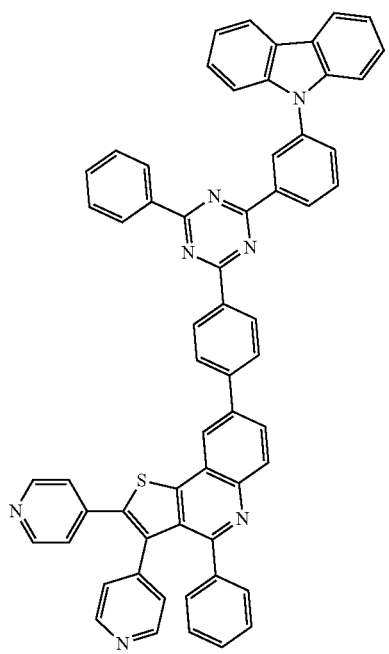
191
584
-continued
192
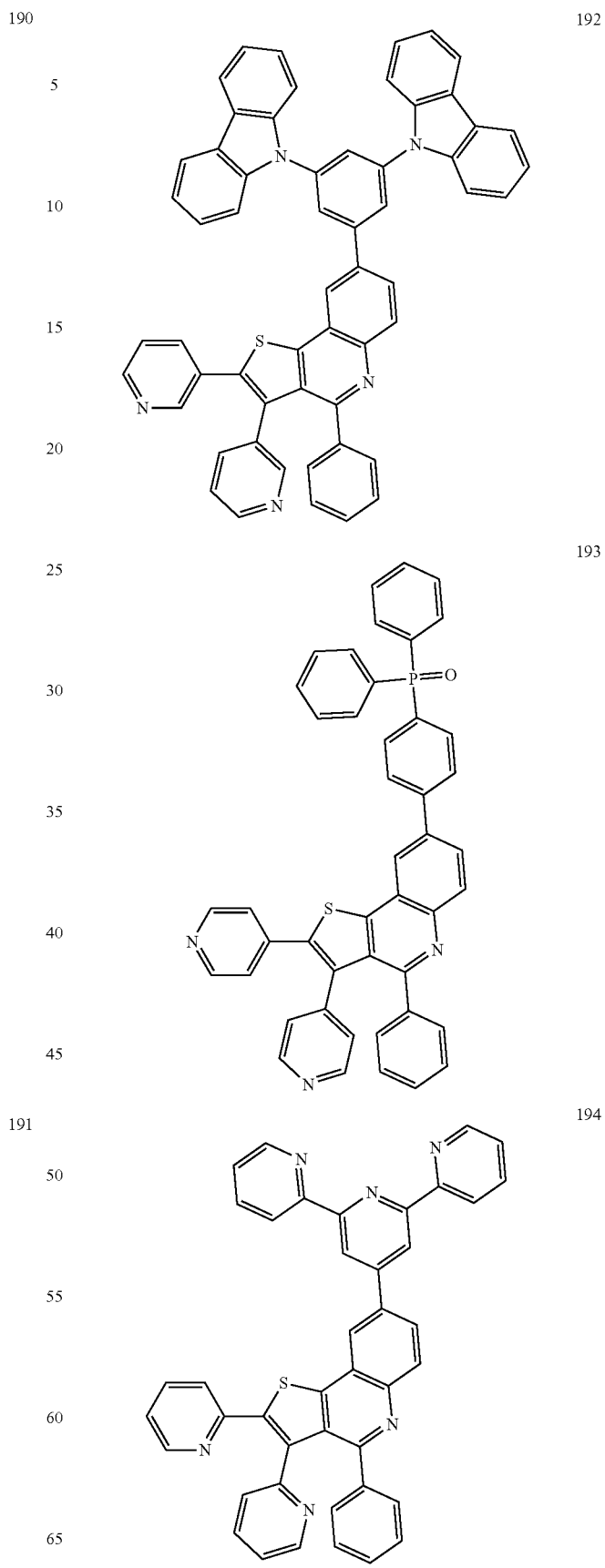
193
194

585
-continued
195
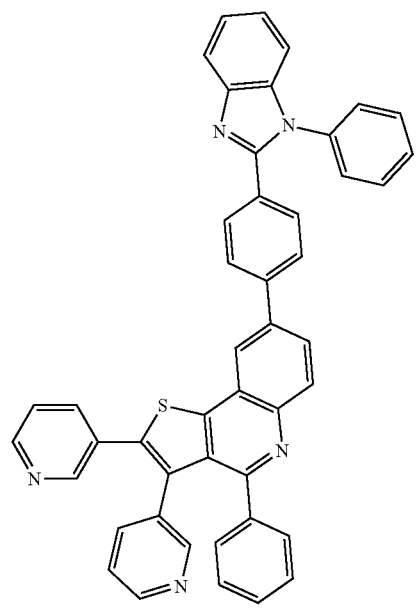
196
198
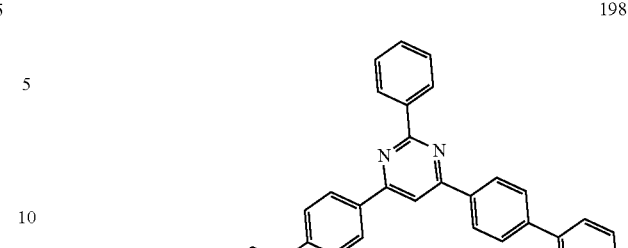
199
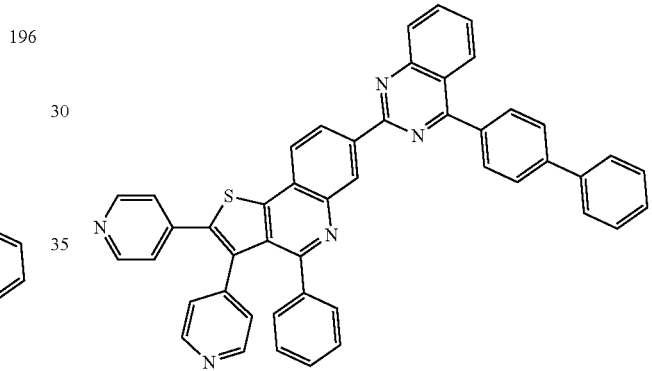
197
200
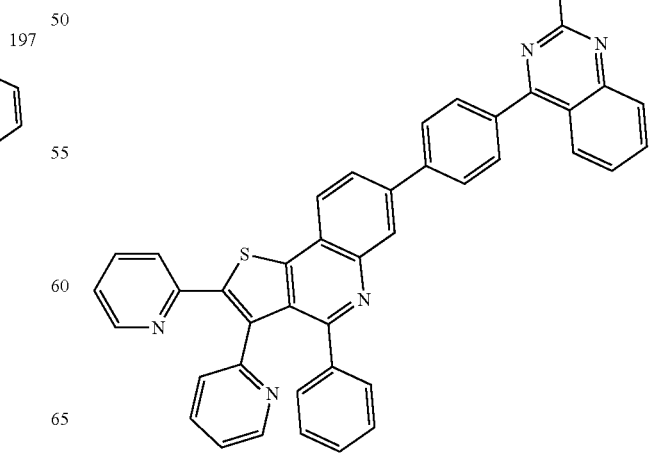
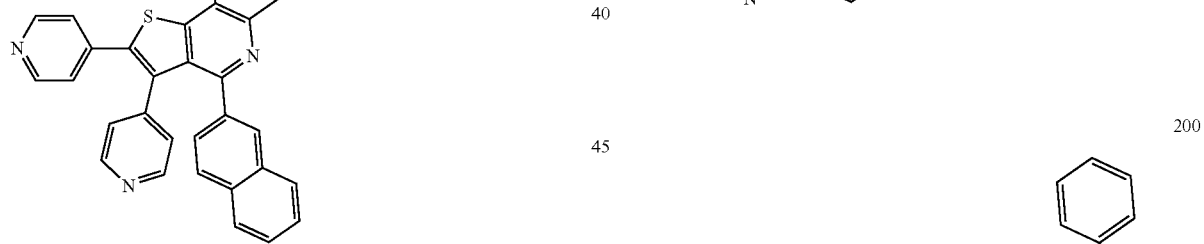

587
-continued
201
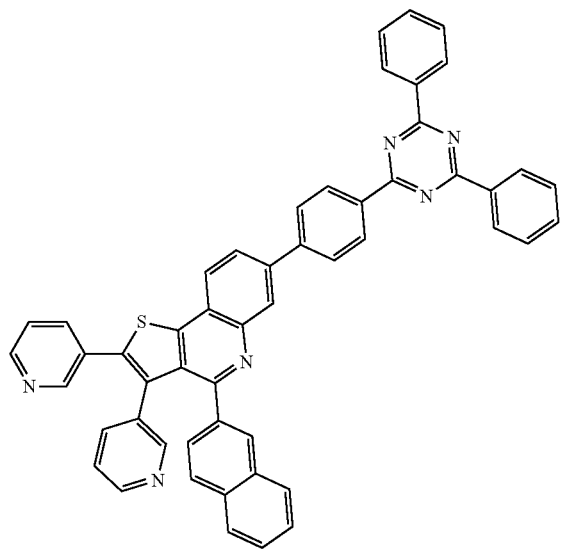
202
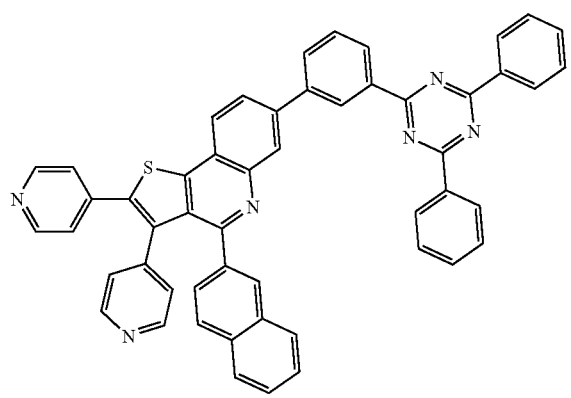
203
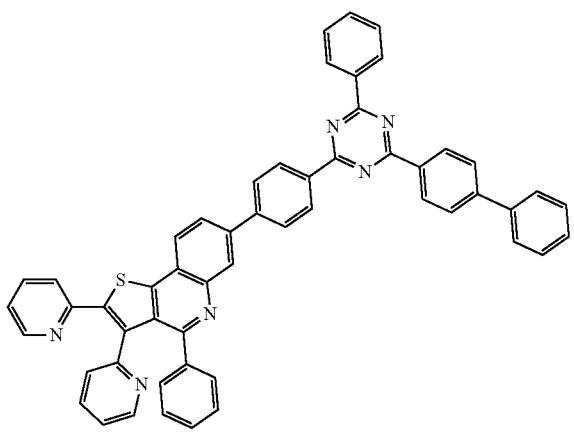
588
-continued
204
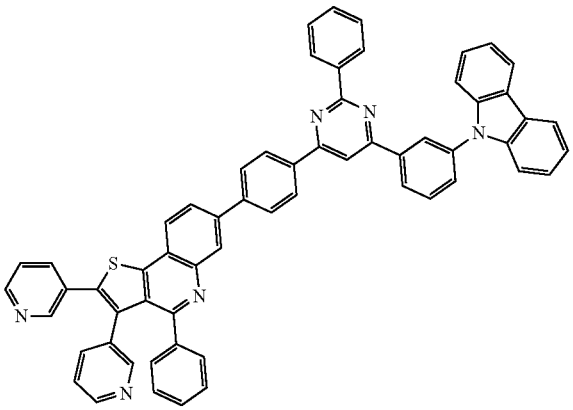
205
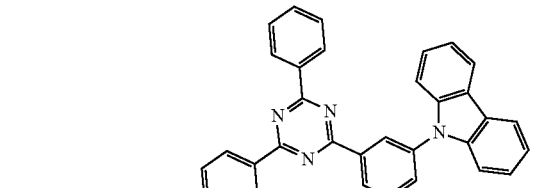
206
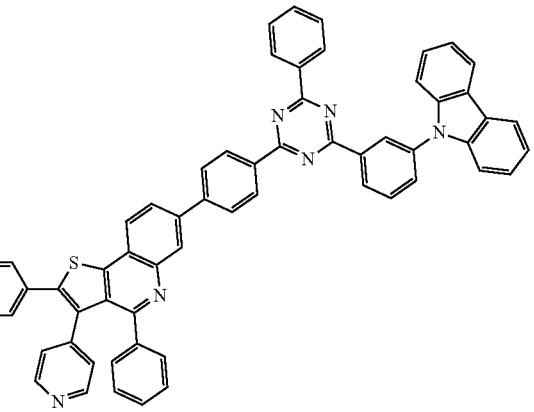

589
-continued
207
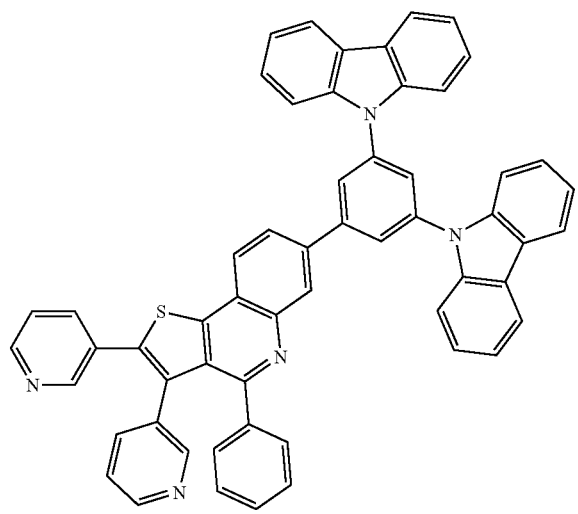
208
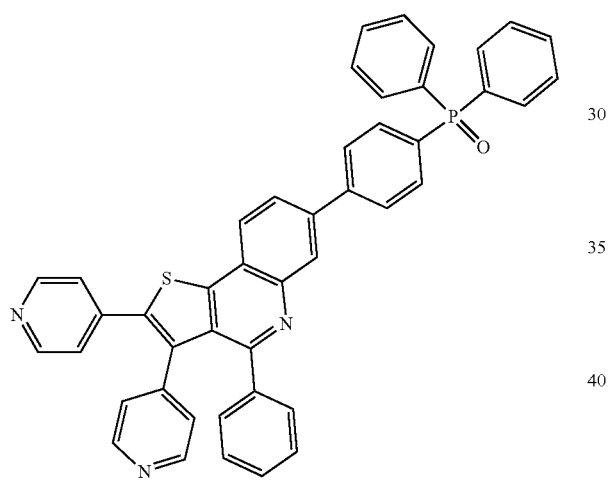
209
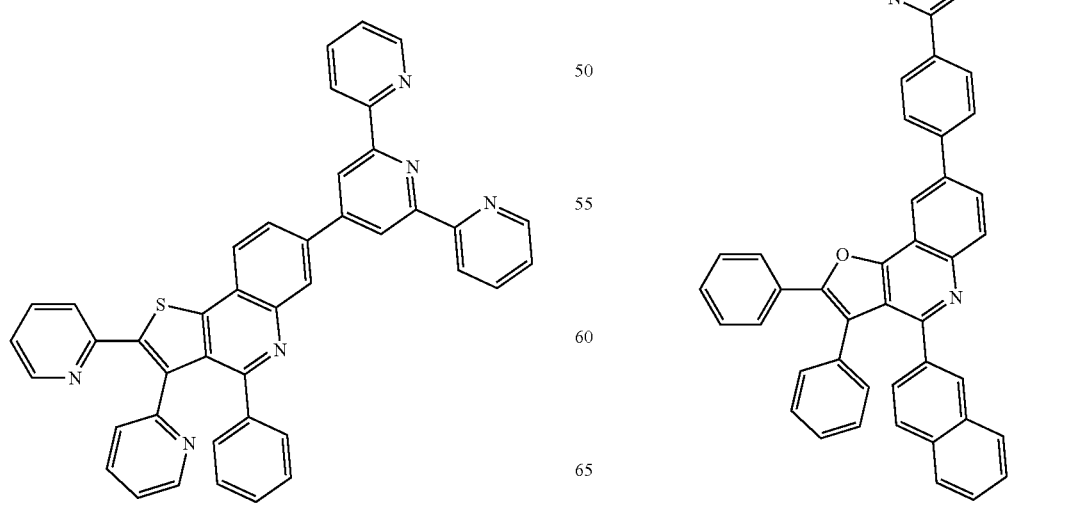
590
-continued
210
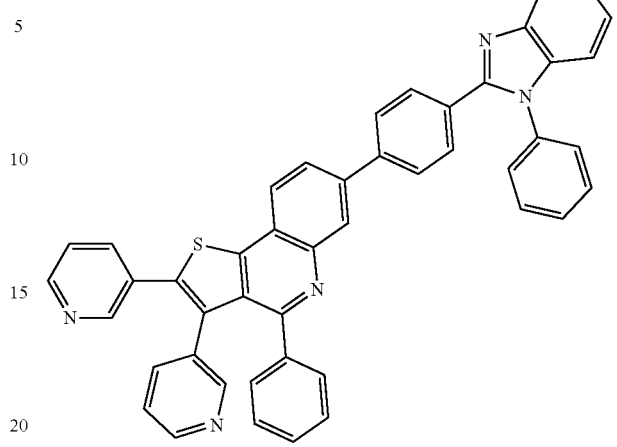
211

591
-continued
212
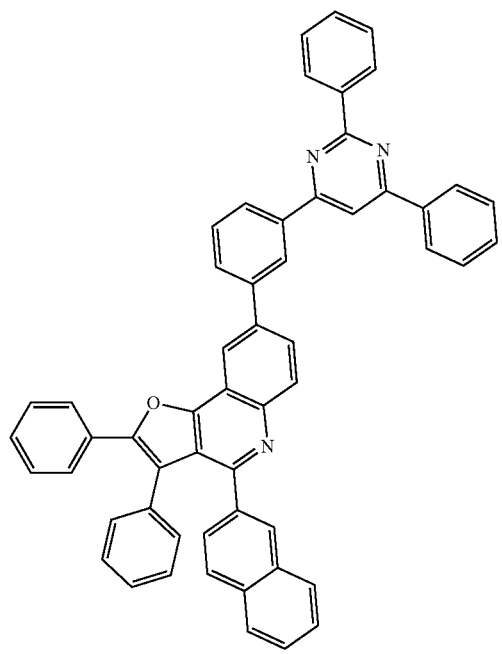
213
592
-continued
214
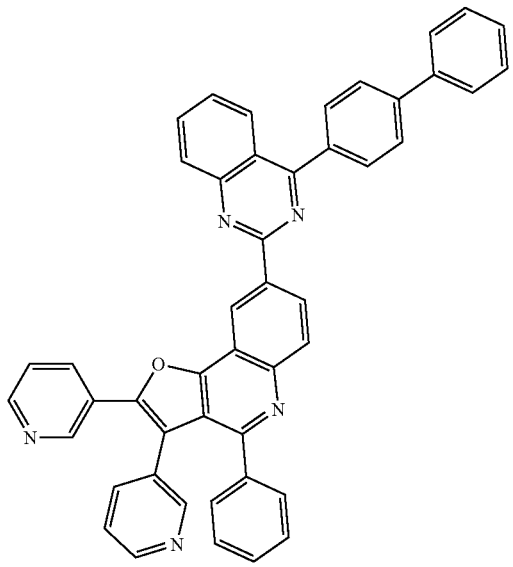
215
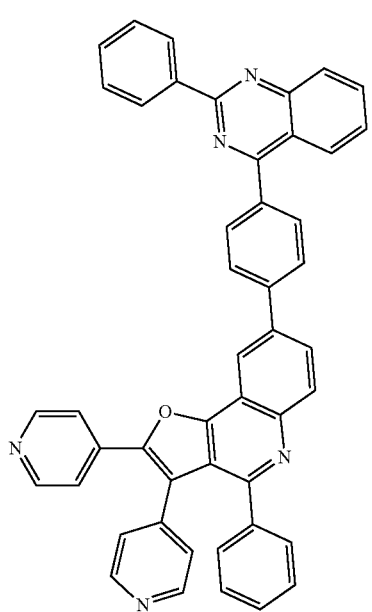

593
-continued
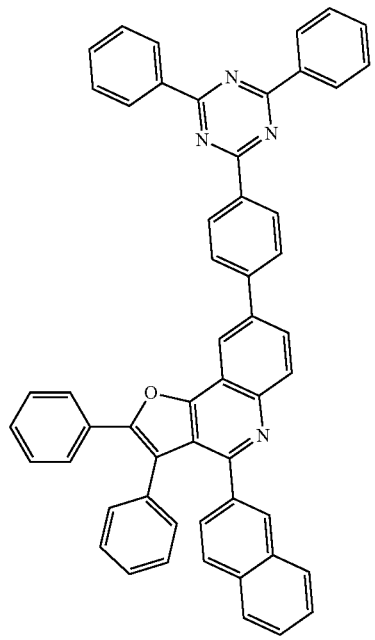
216
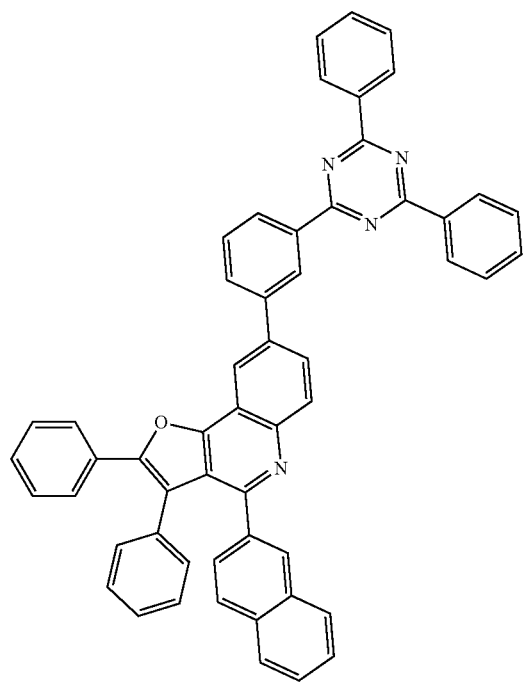
217
594
-continued
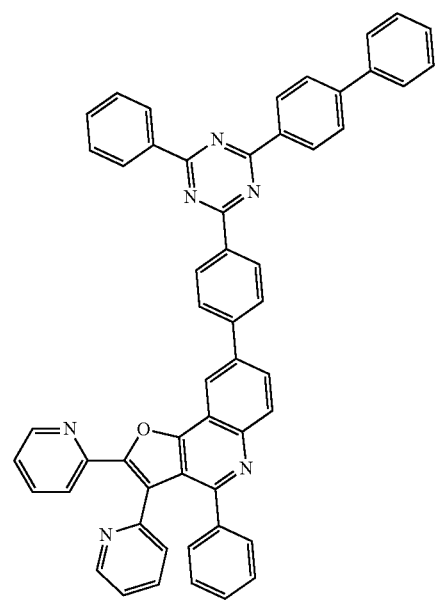
218
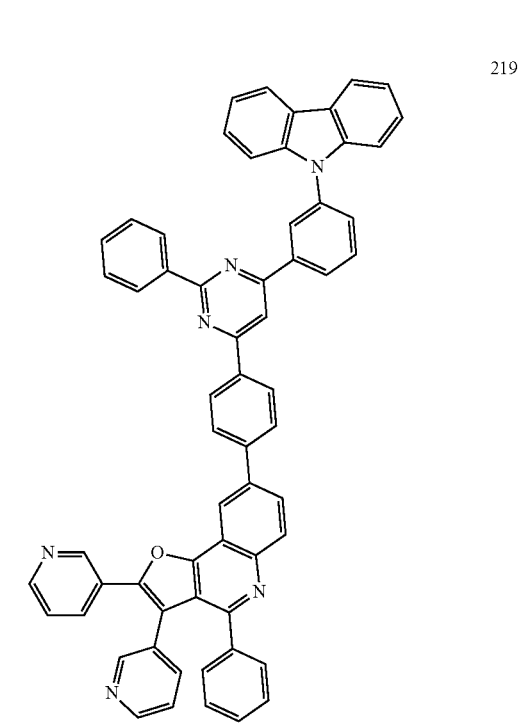
219

595
-continued
220
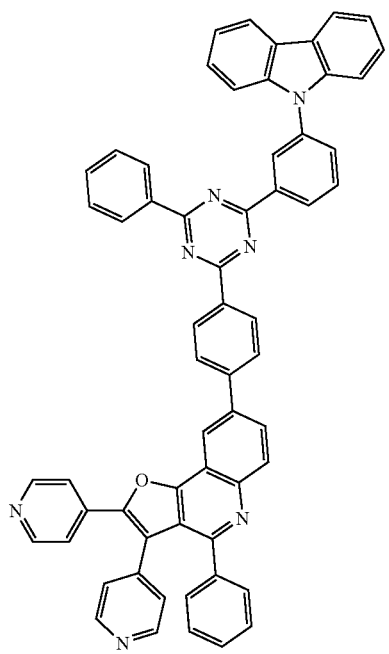
221
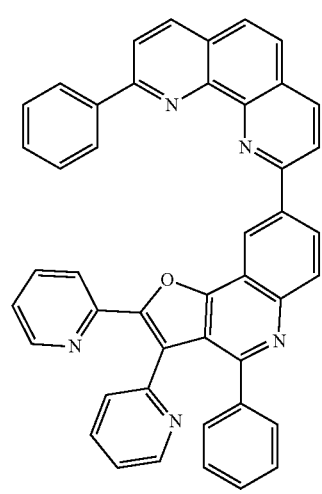
596
-continued
222
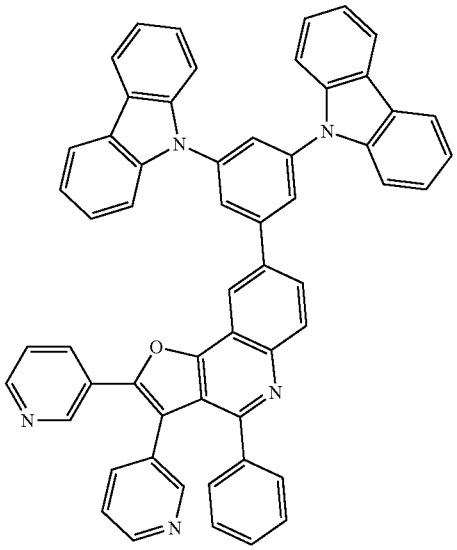
223
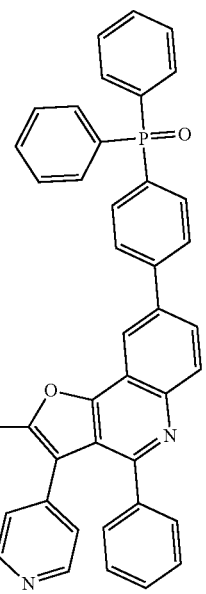
224
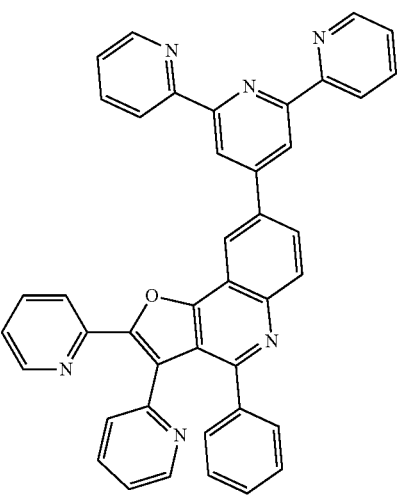

597
-continued
225
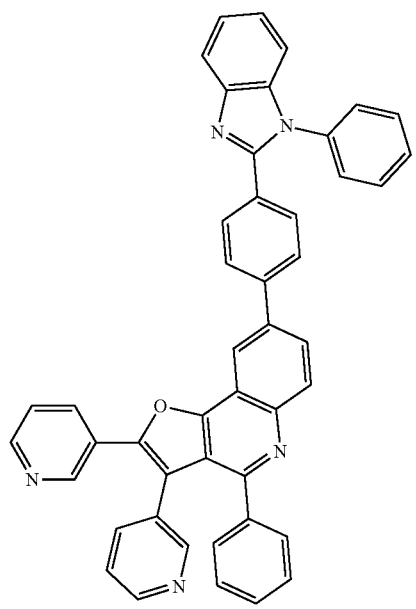
226
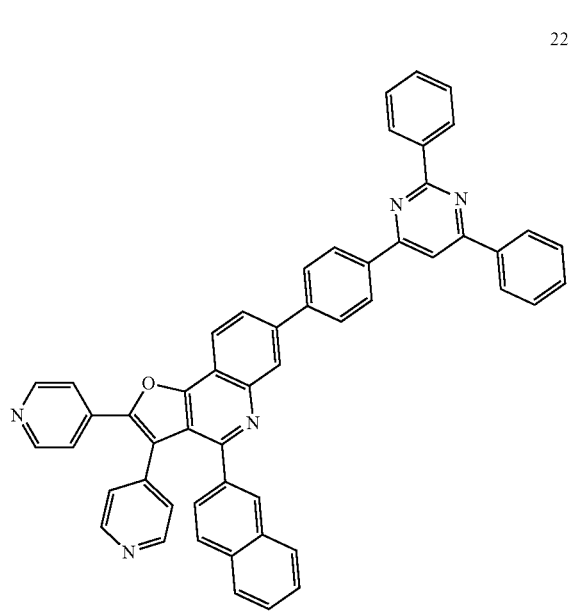
227
598
-continued
228
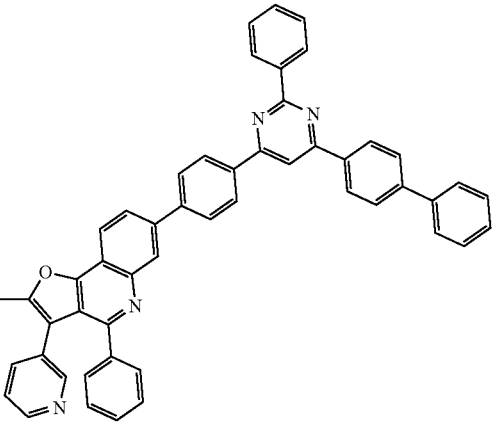
229
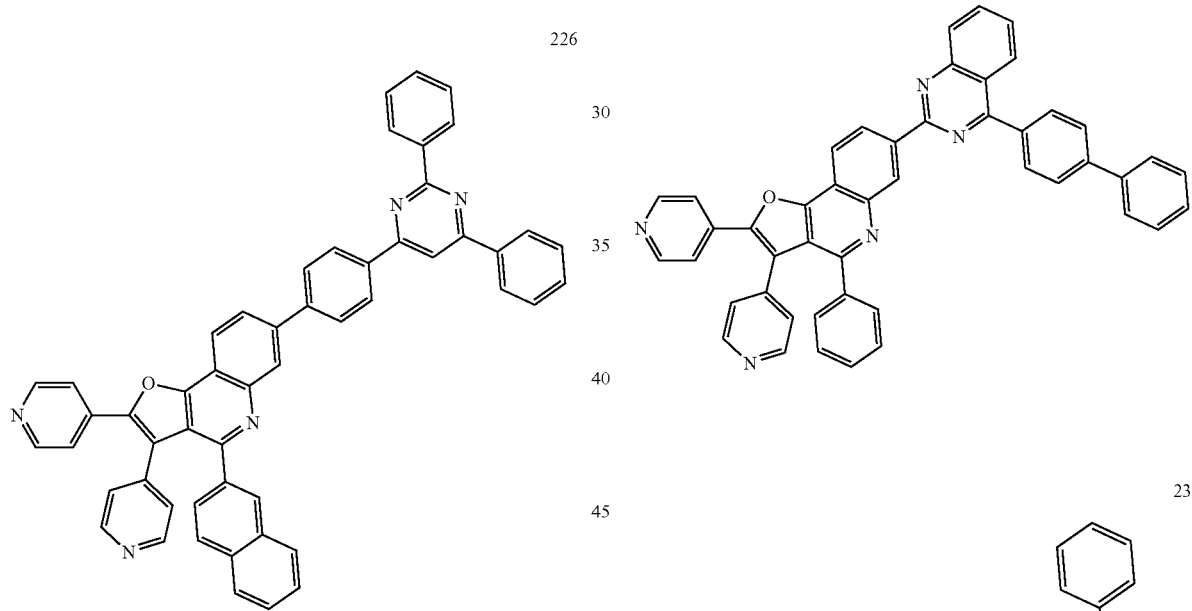
230
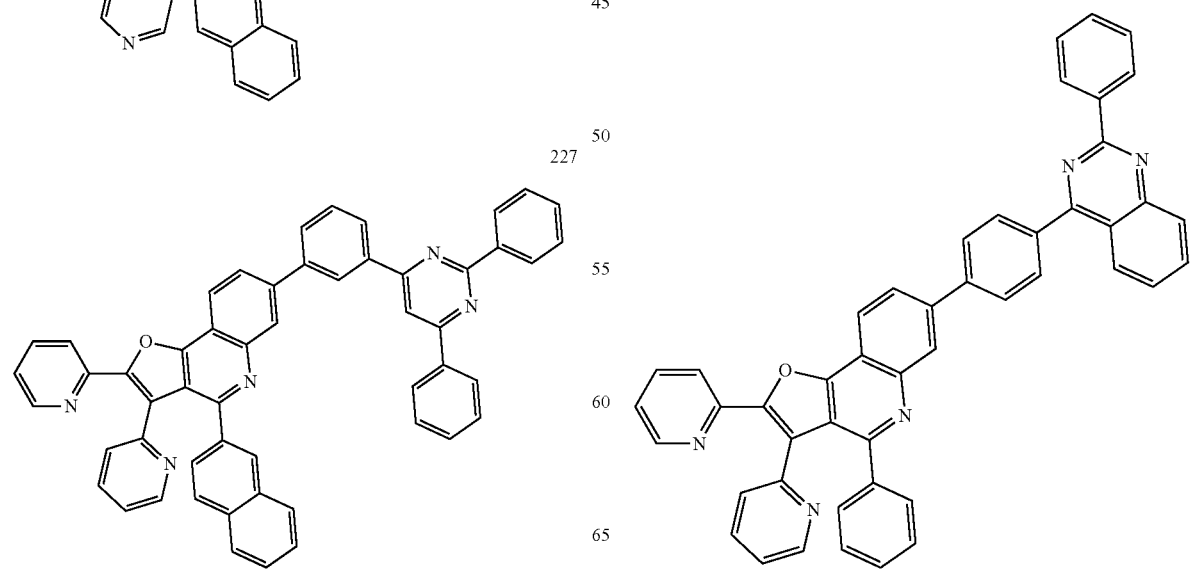

-continued
231
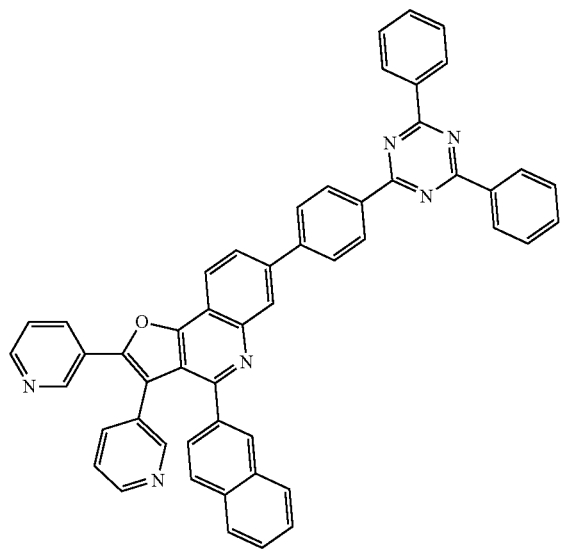
232
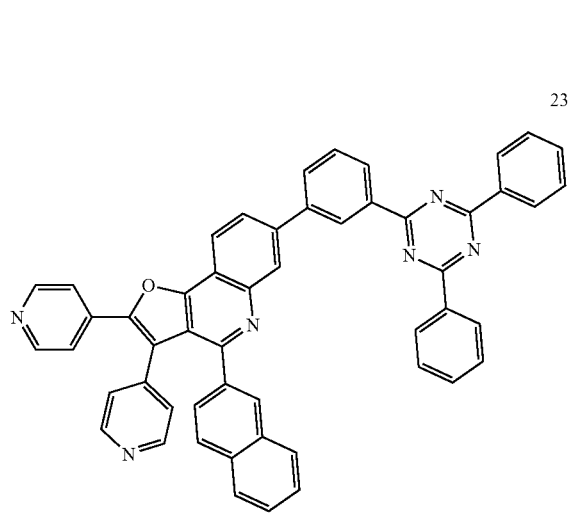
233
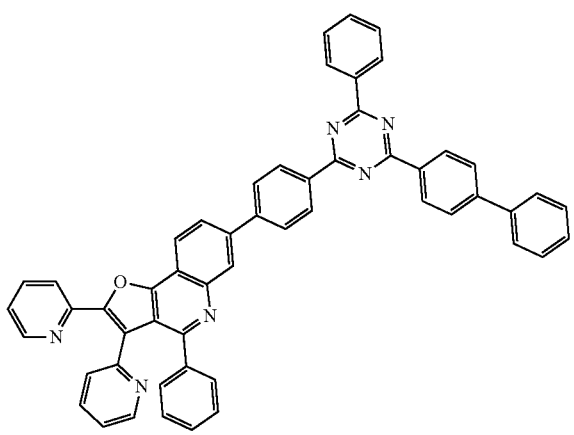
-continued
234
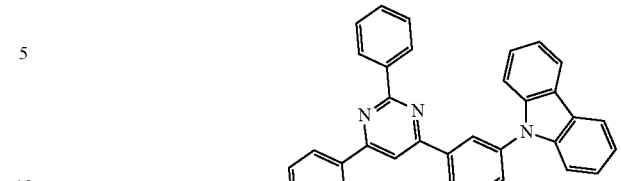
235
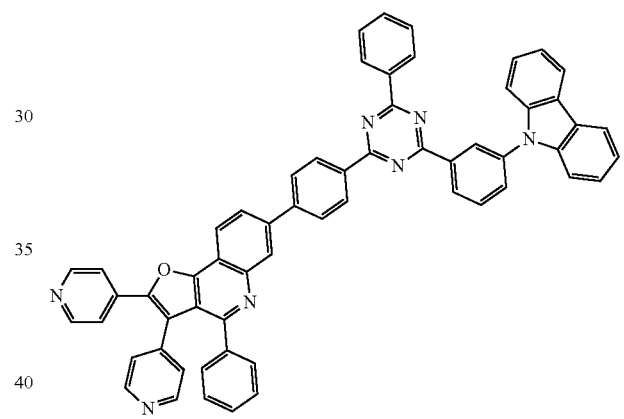
236
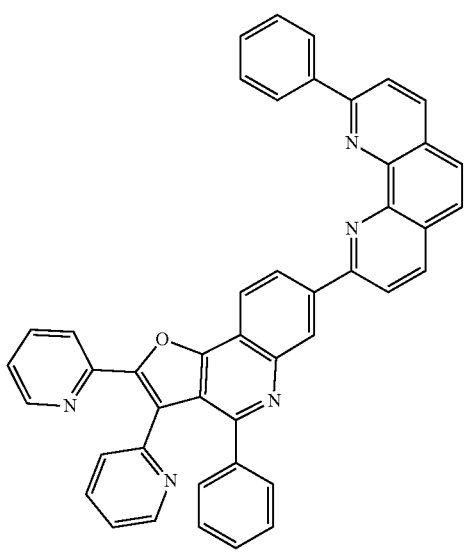

601
-continued
237
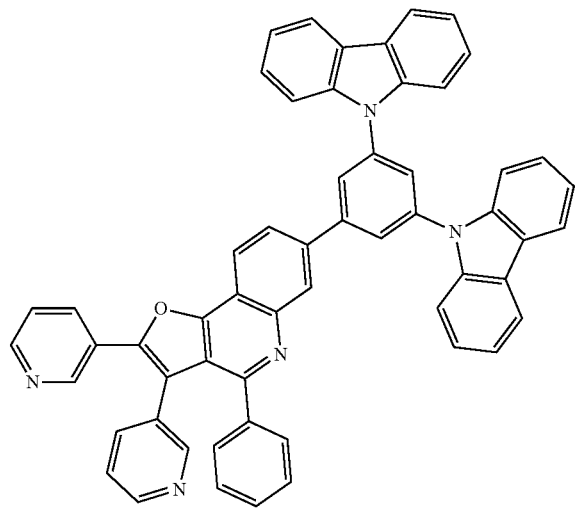
238
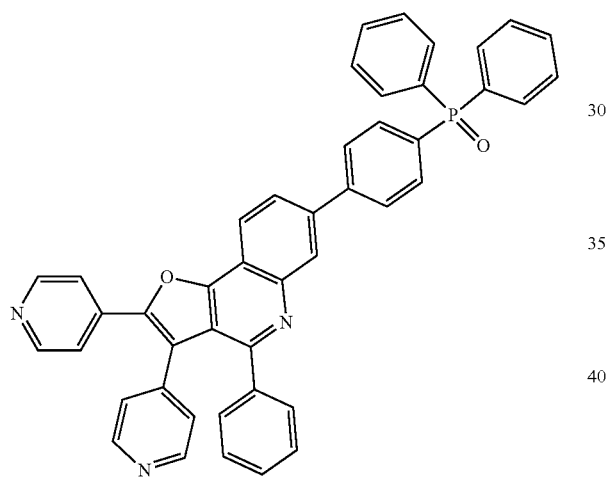
239
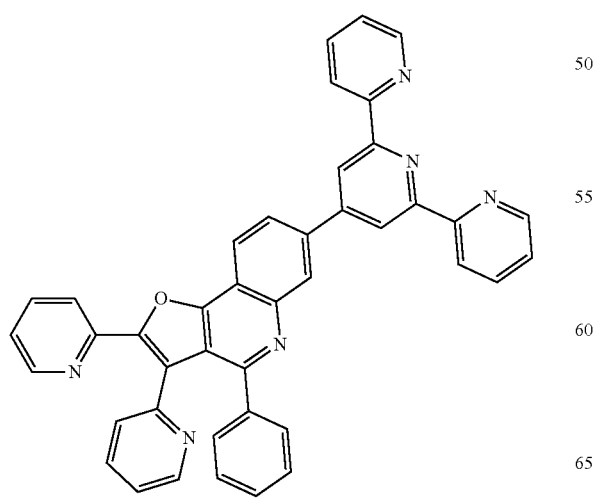
602
-continued
240
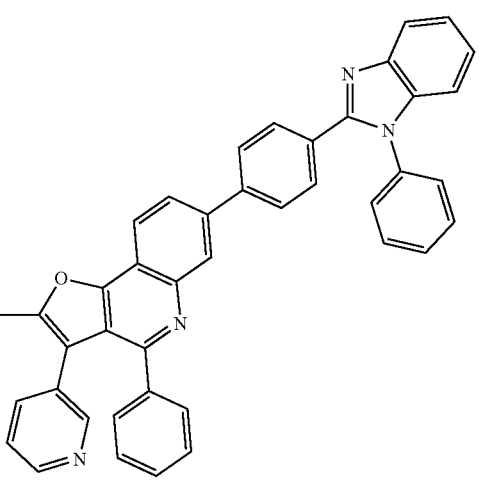
241
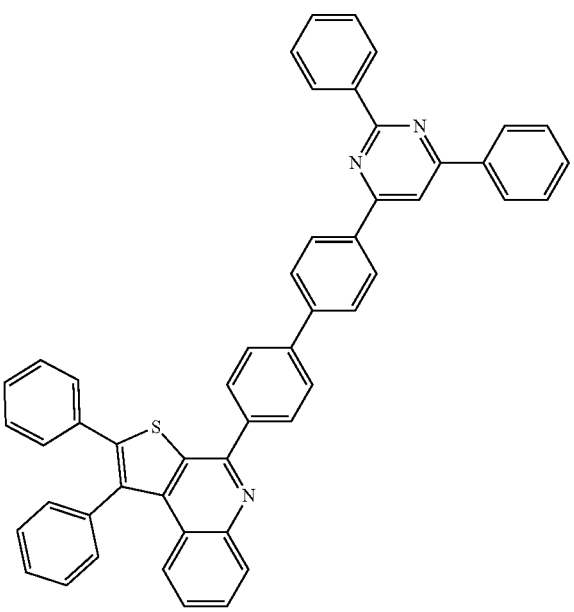

603
-continued
242
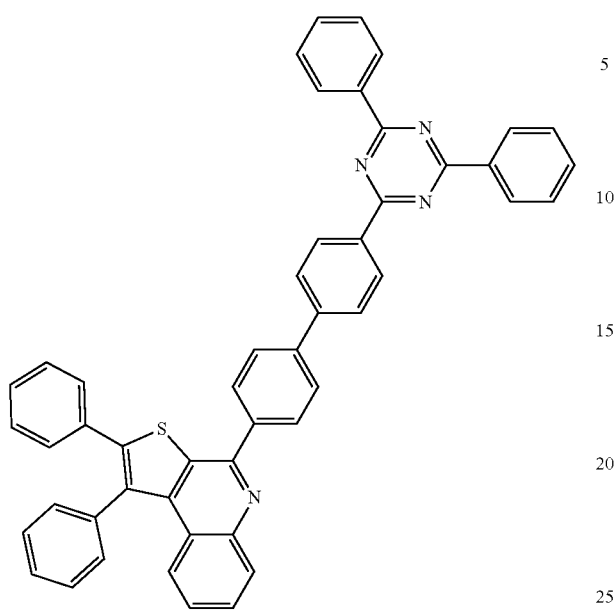
243
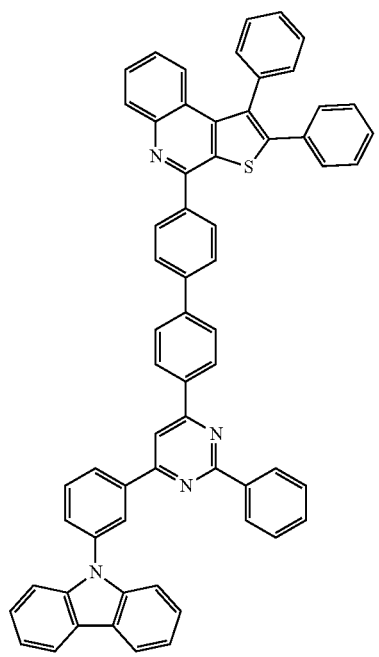
604
-continued
244
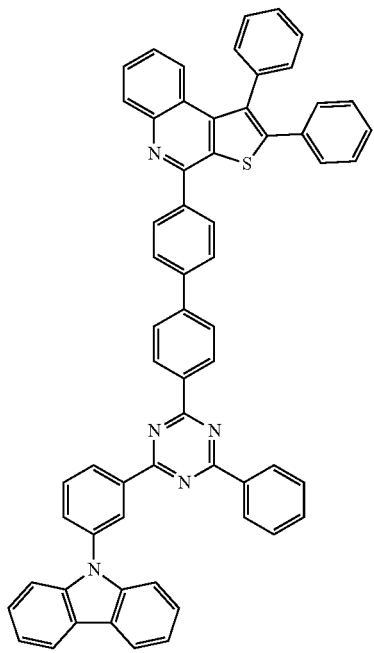
245
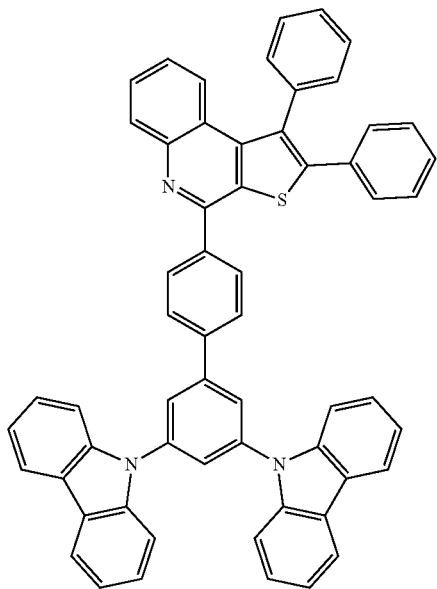

246
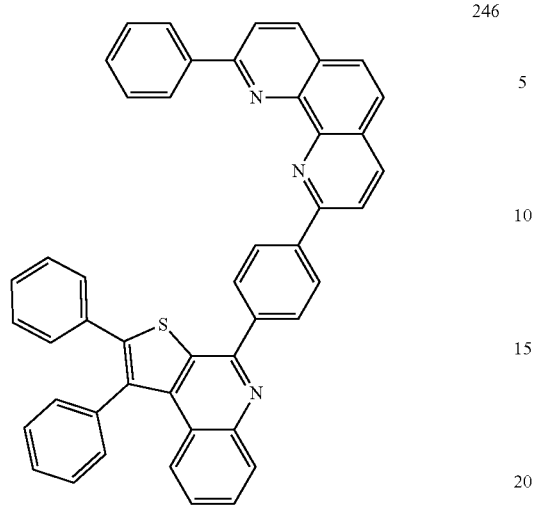
247
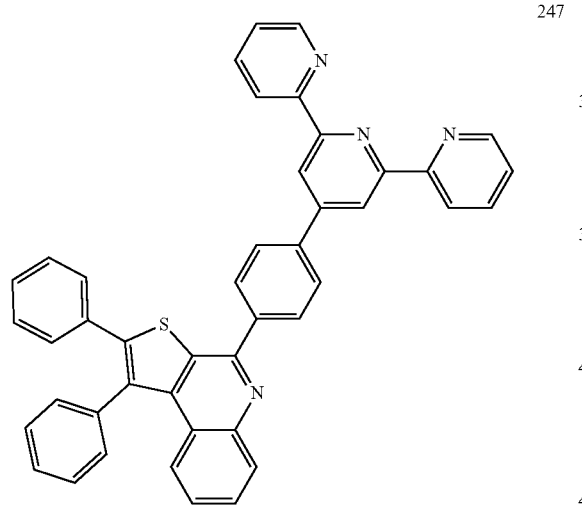
248
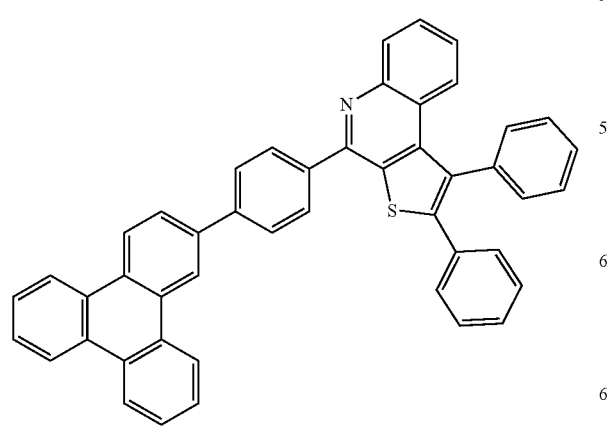
249
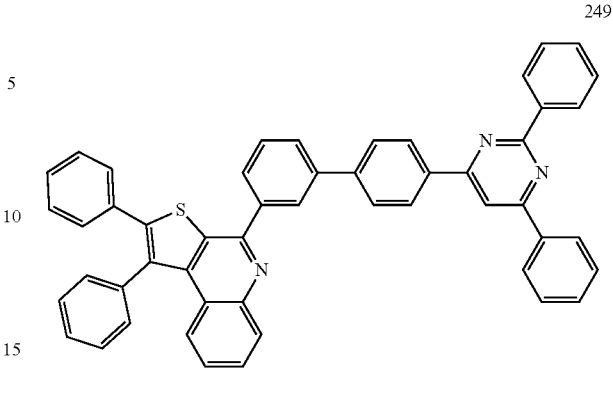
250
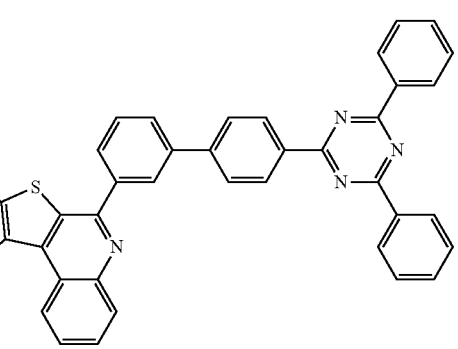
251
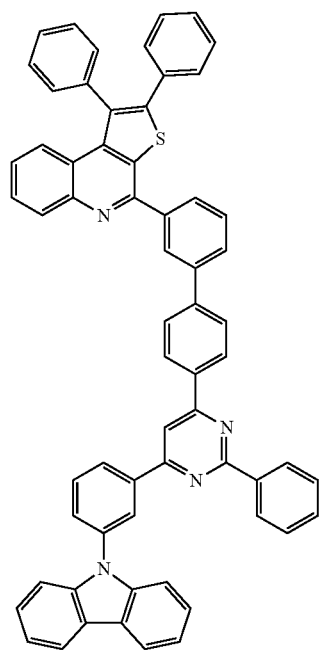

607 -continued
252
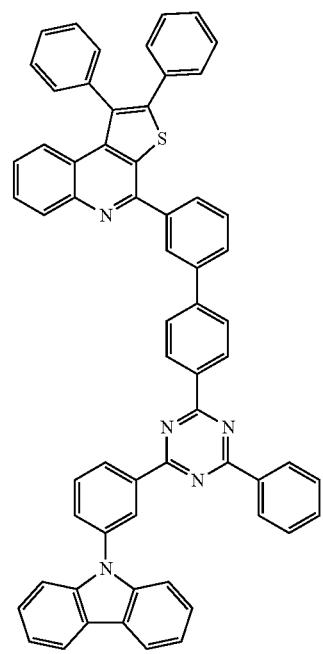
253
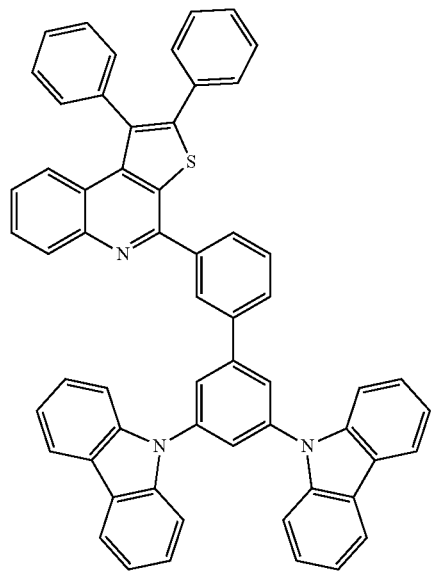
608 -continued
254
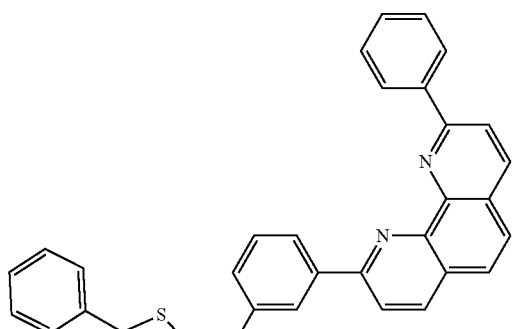
255
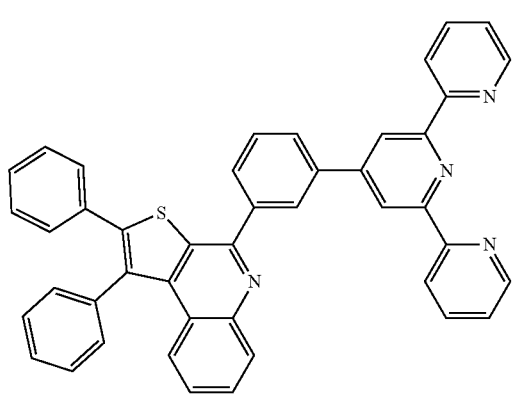
256
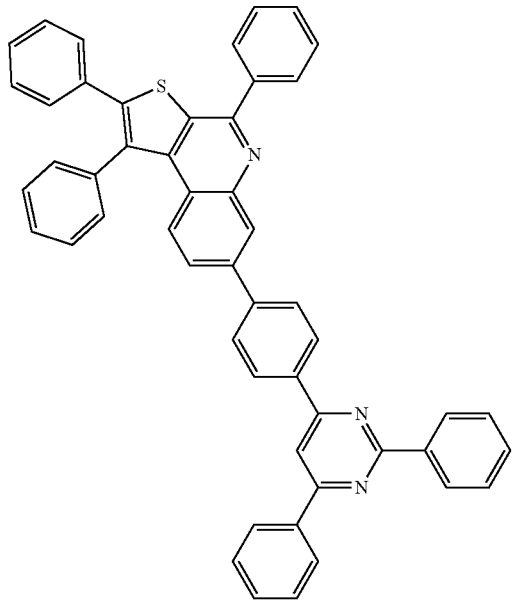

609
-continued
610
-continued
257
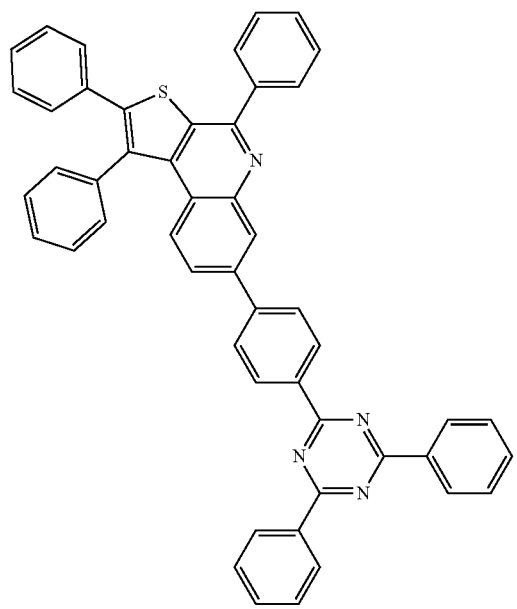
259
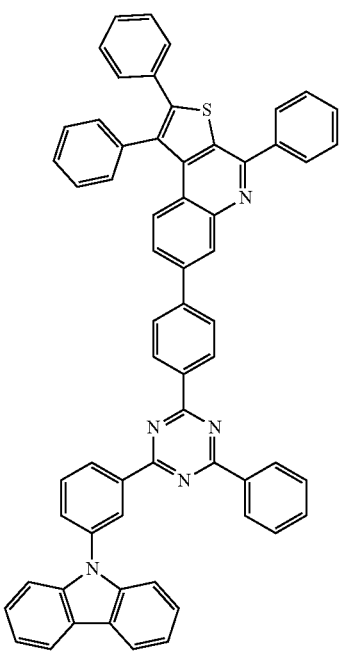
260
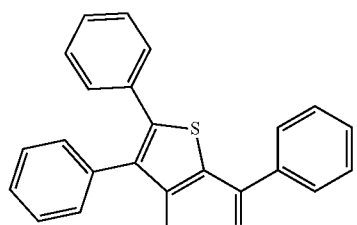
258
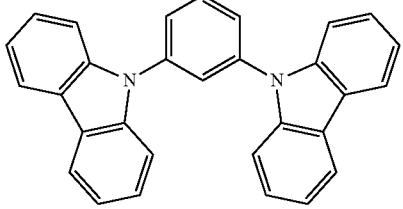
261
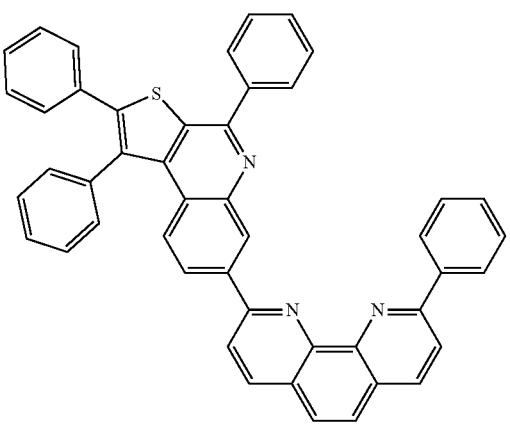

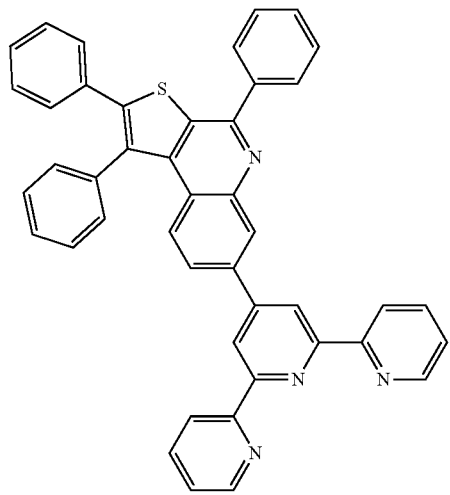
262
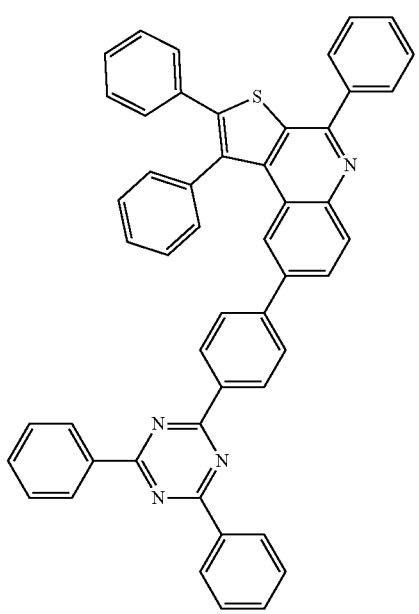
265
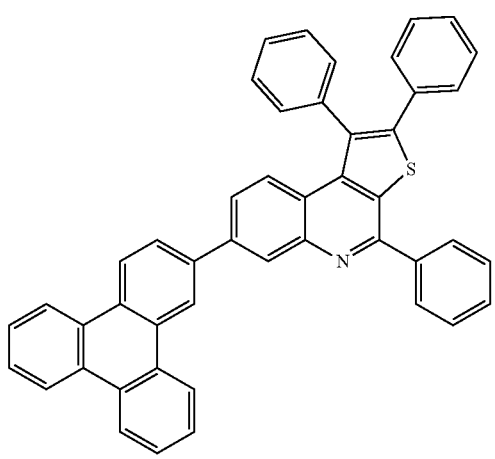
263
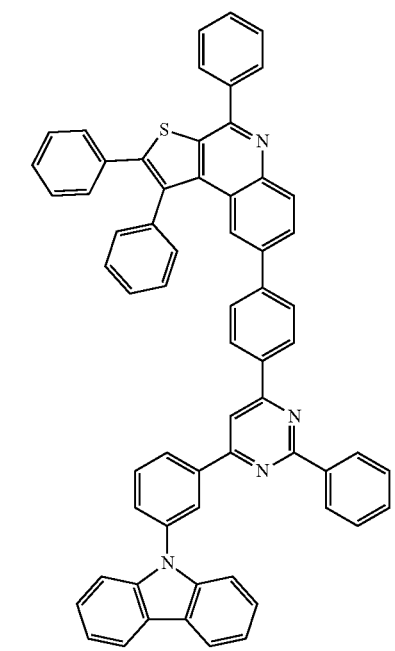
266
264

613
-continued
267
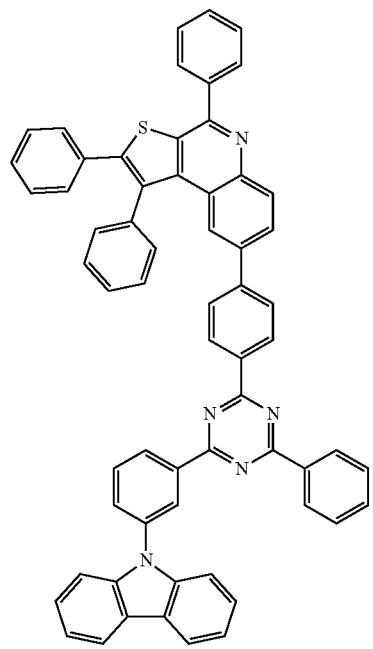
268
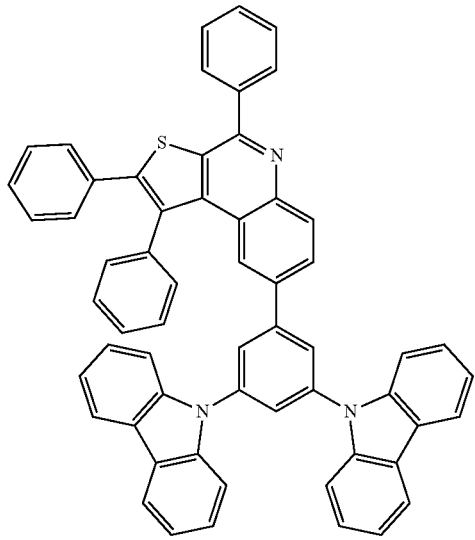
614
-continued
269
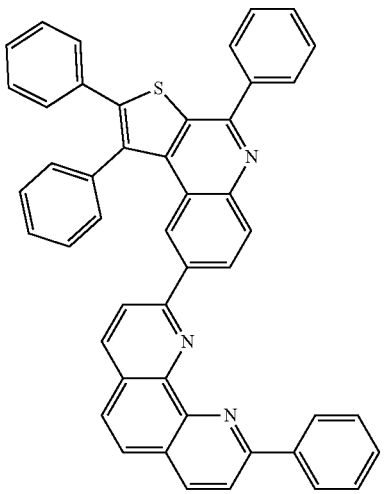
270
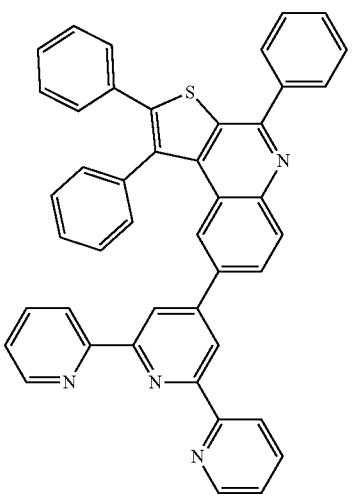
271
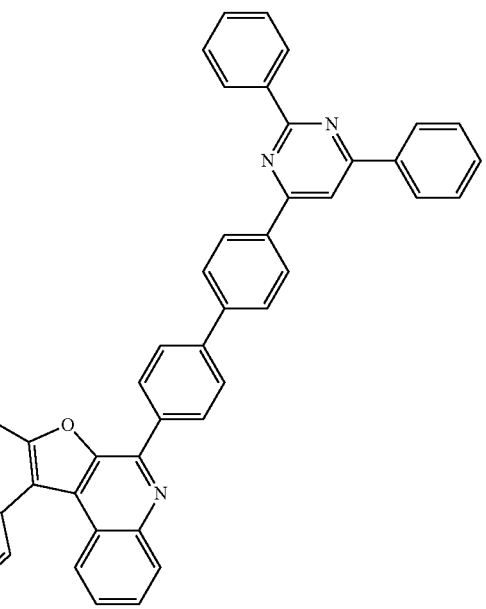

615
-continued
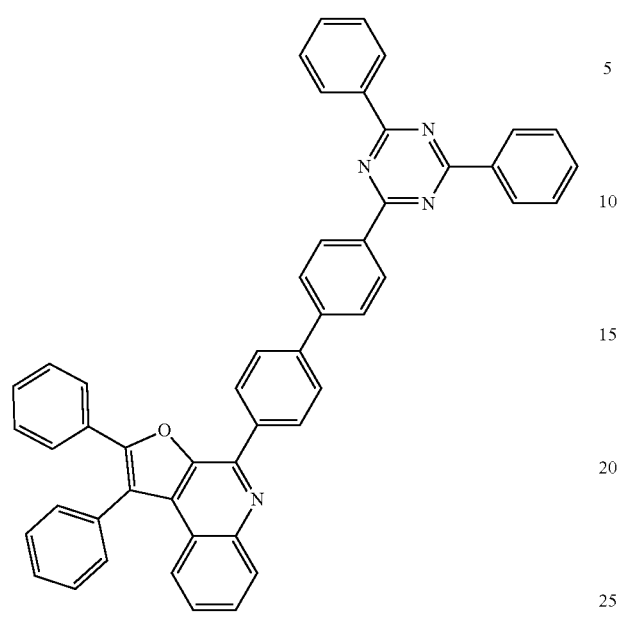
272
616
-continued
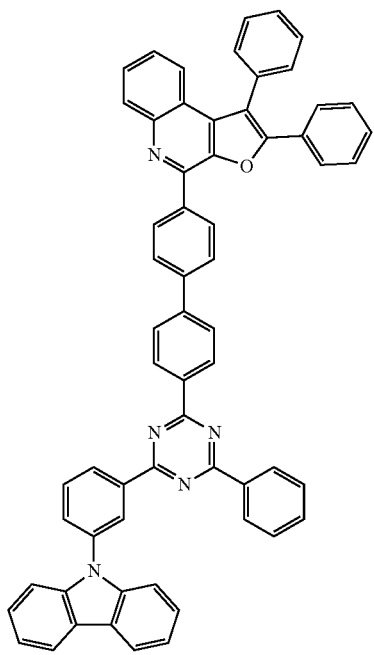
274
273
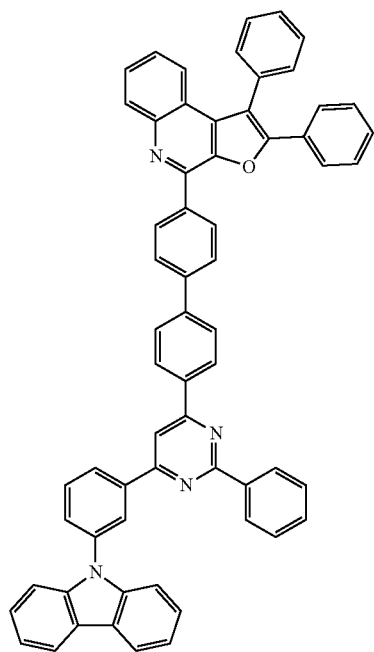
275
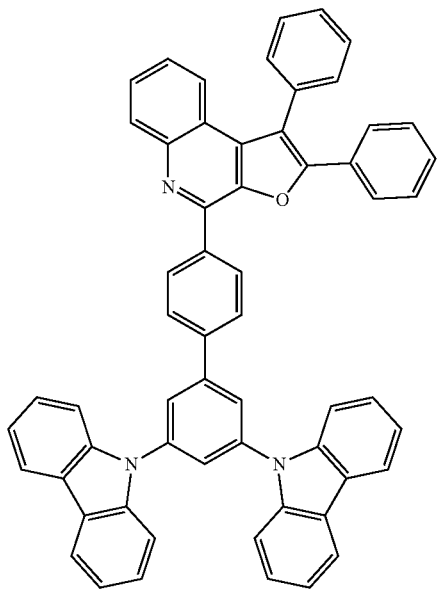

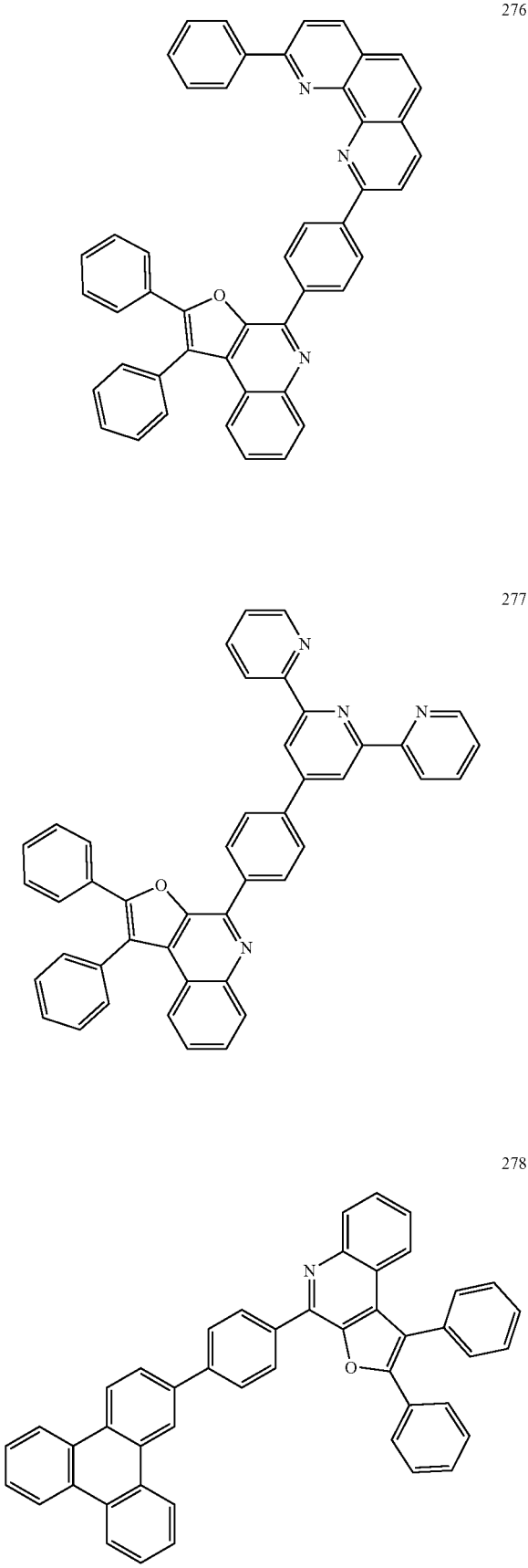
276
277
278
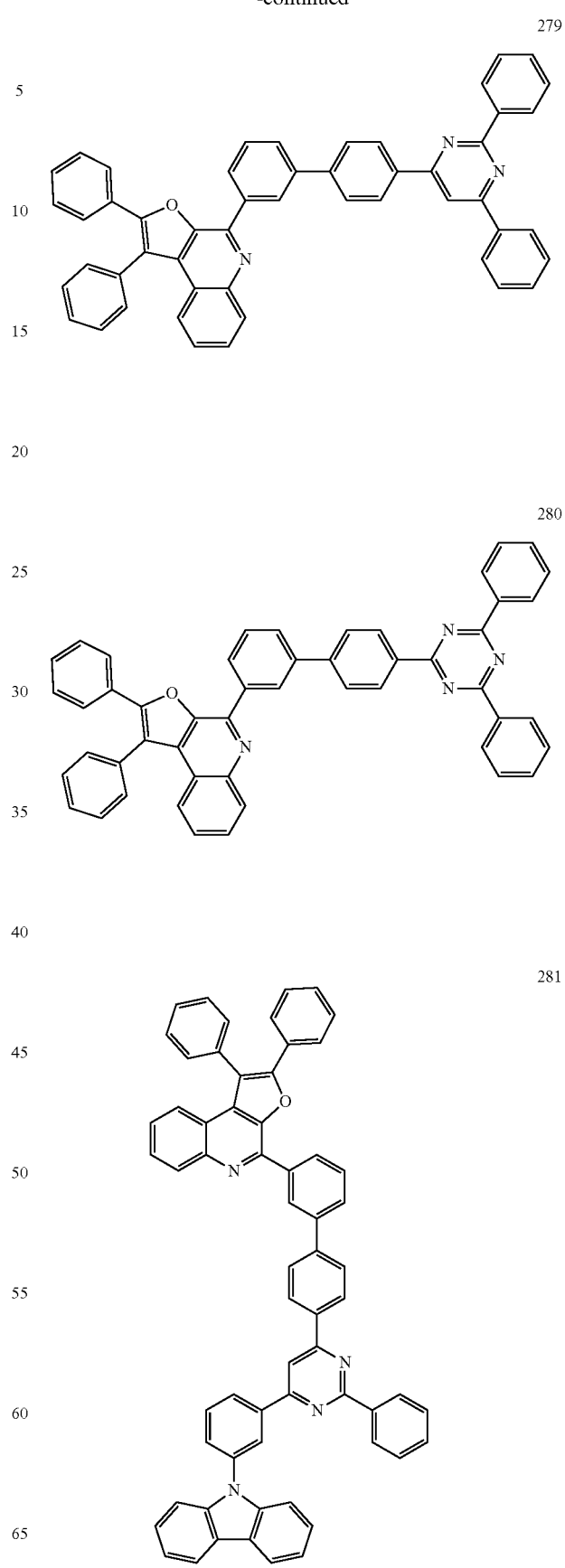
279
280
281

619
-continued
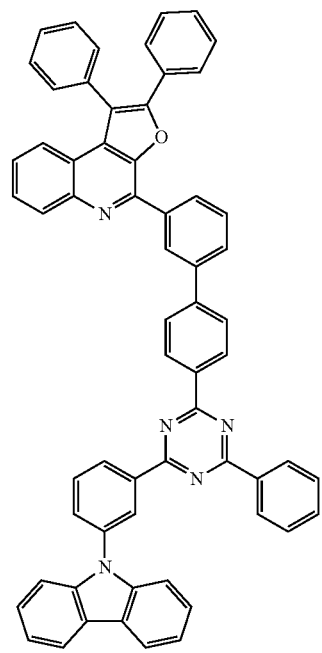
282
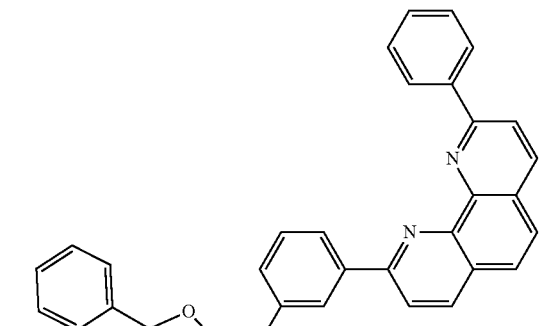
284
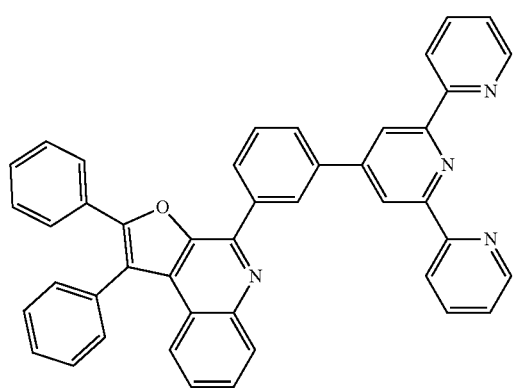
285
620
-continued
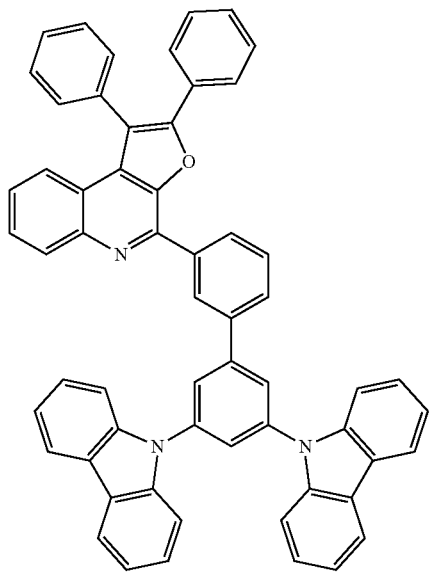
283
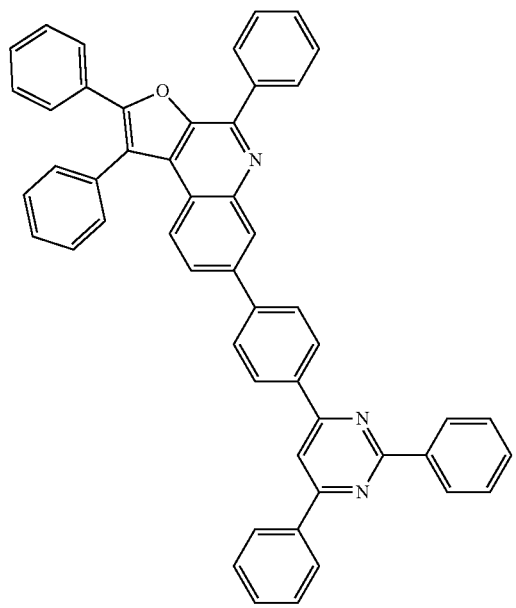
286

621
-continued
287
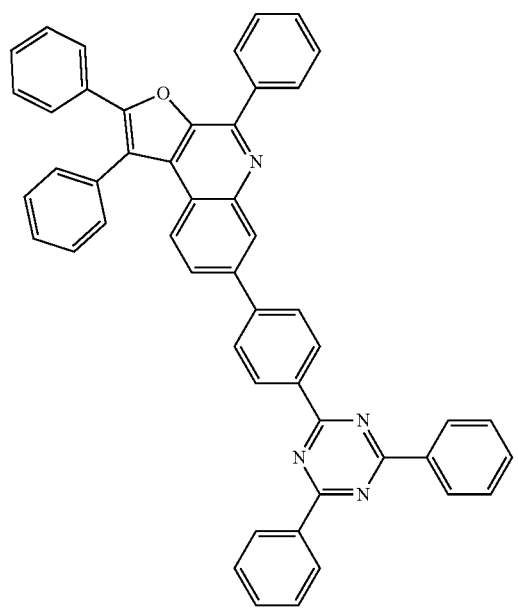
288
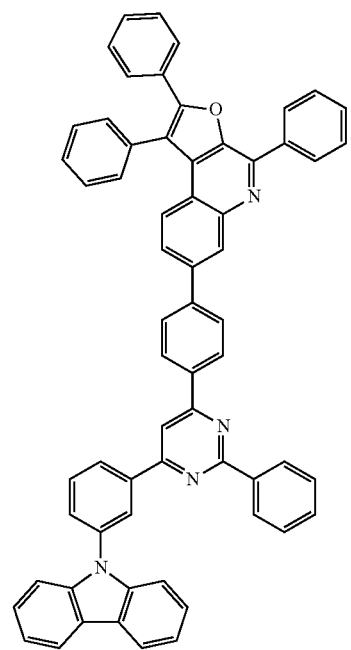
622
-continued
289
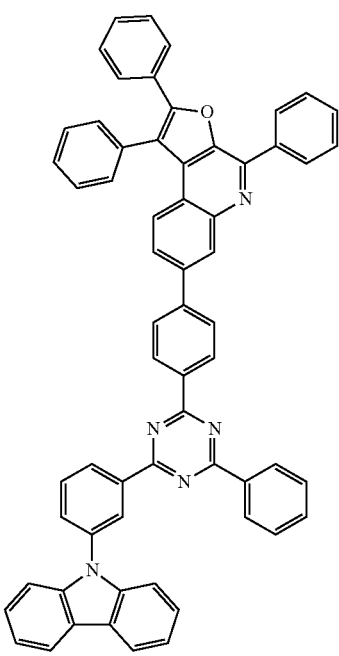
290
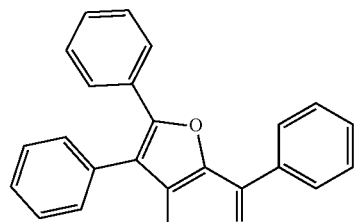
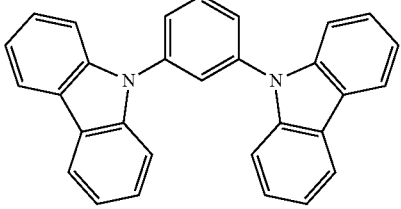
291
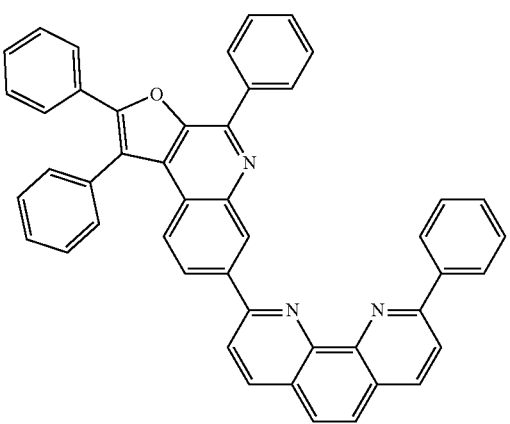

292
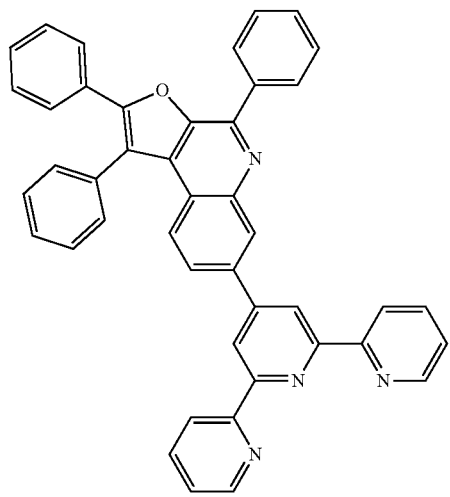
293
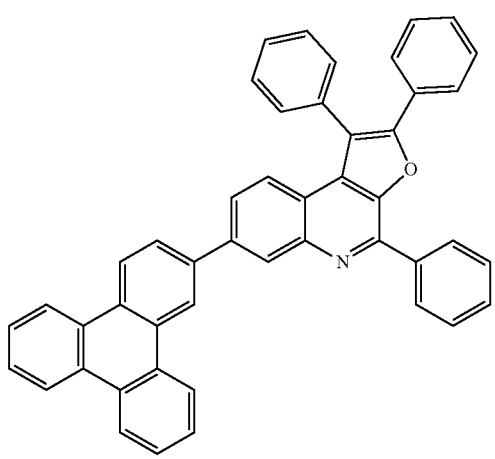
294
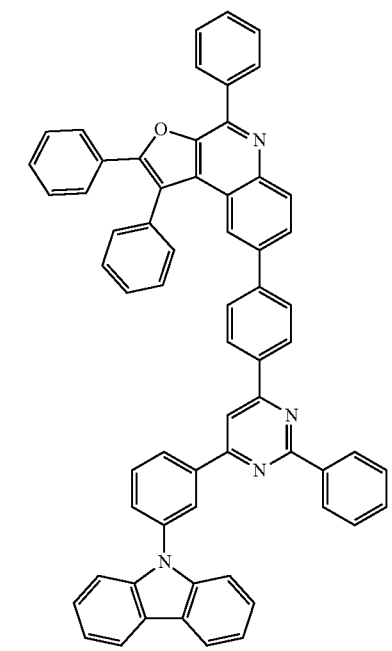
295
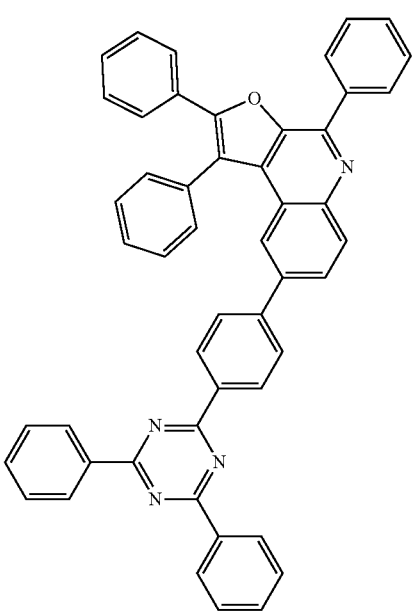
296

-continued
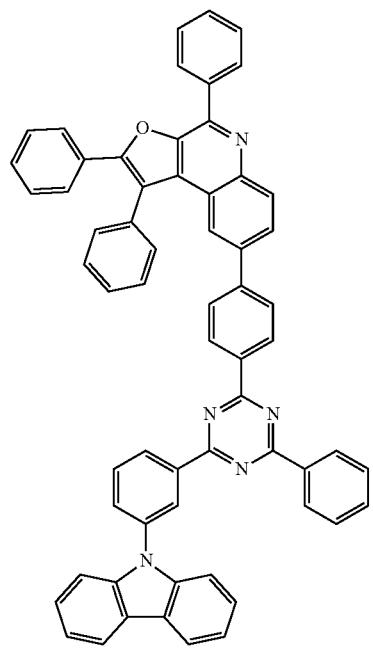
297
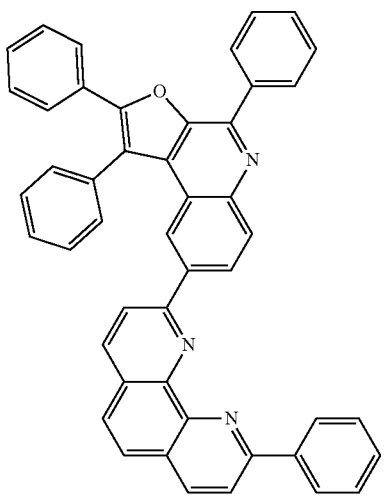
299
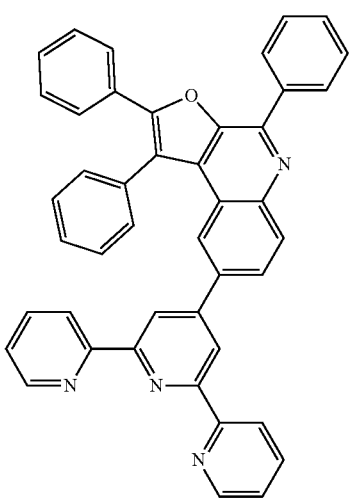
300
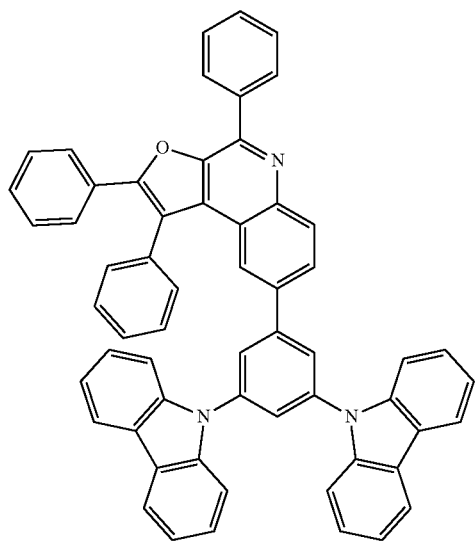
298
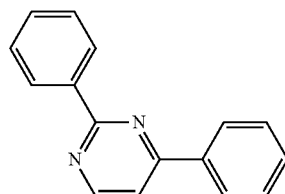
301

627
-continued
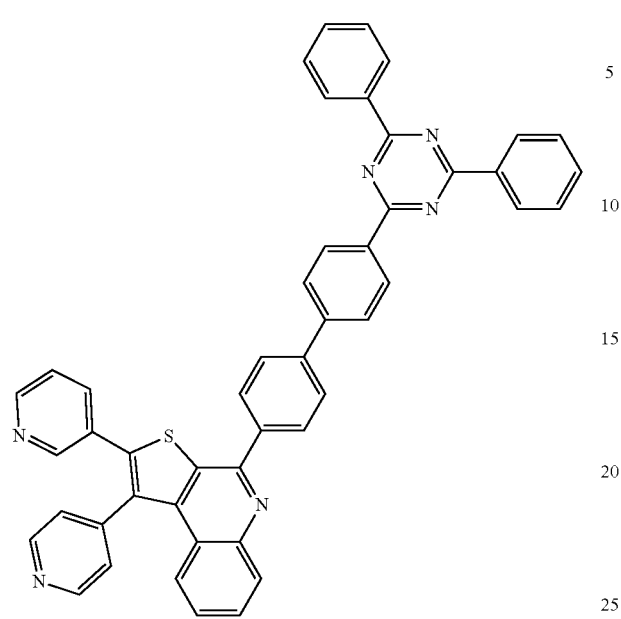
302
628
-continued
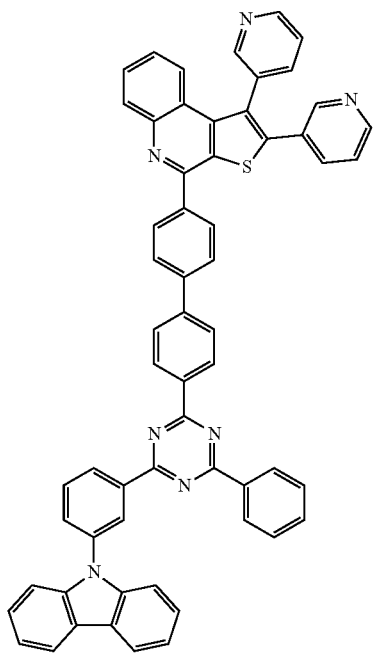
304
303
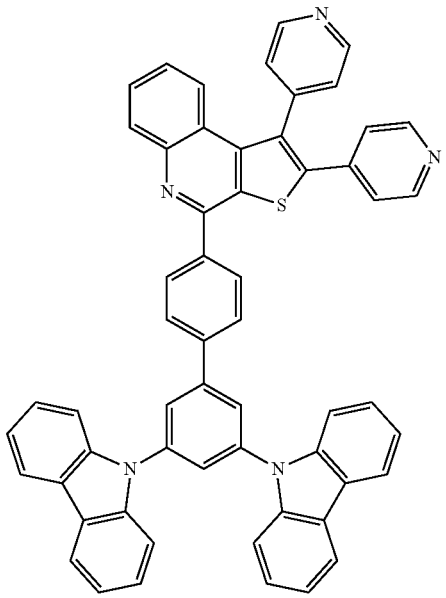
305

306
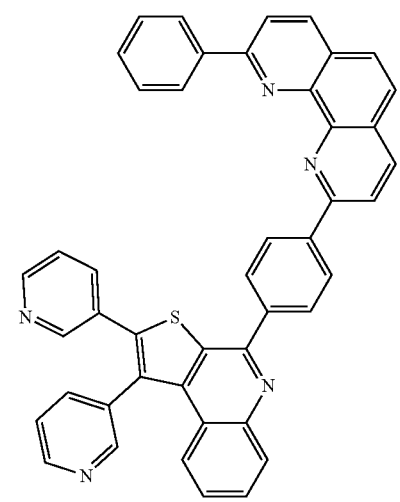
307
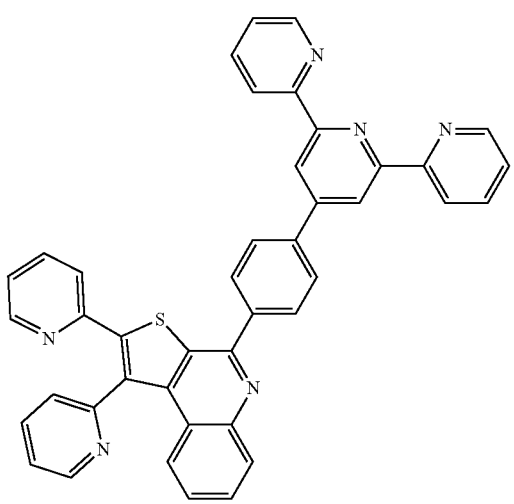
308
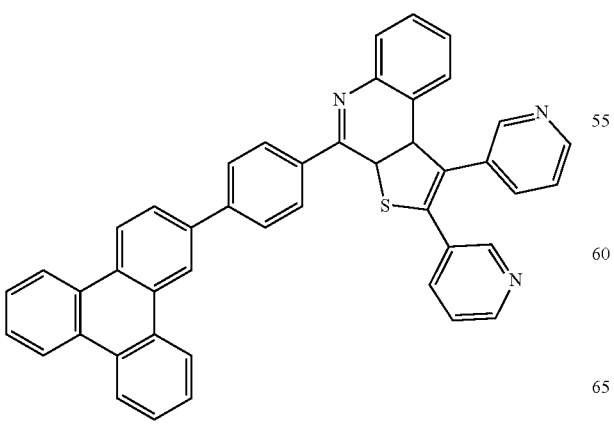
309
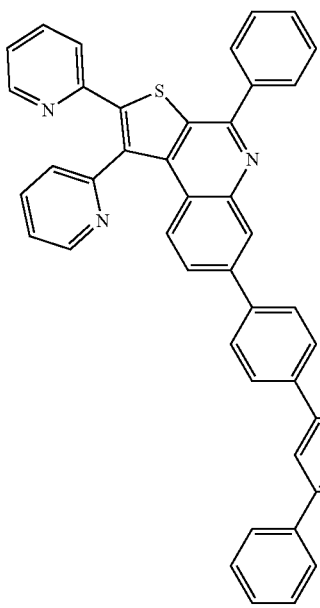
310
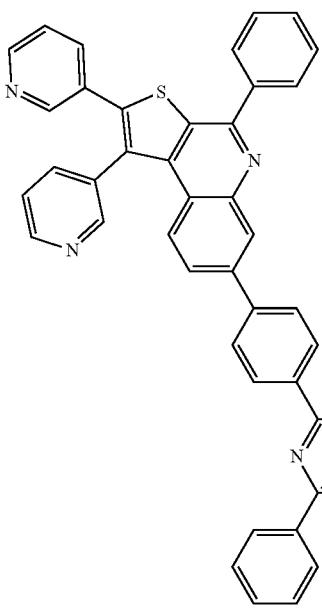

631
-continued
314
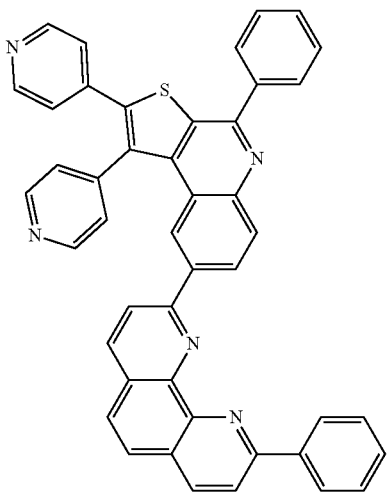
311
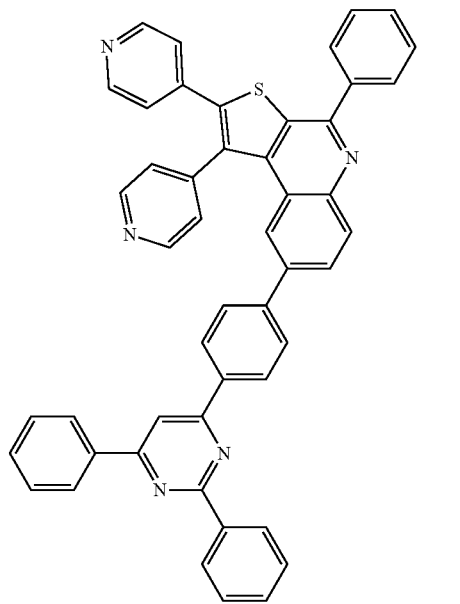
312
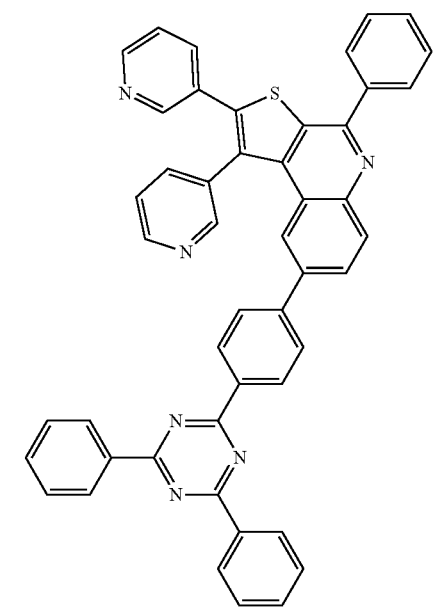
632
-continued
315
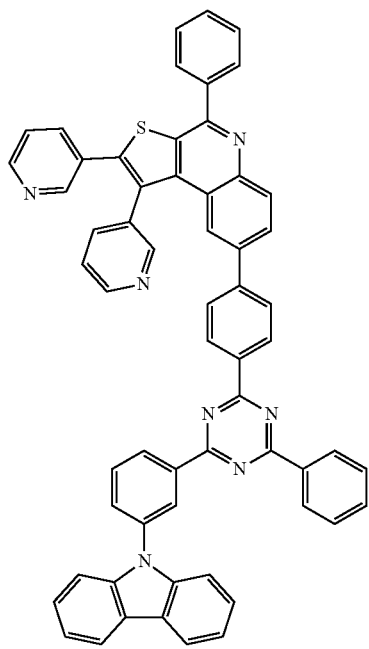
313
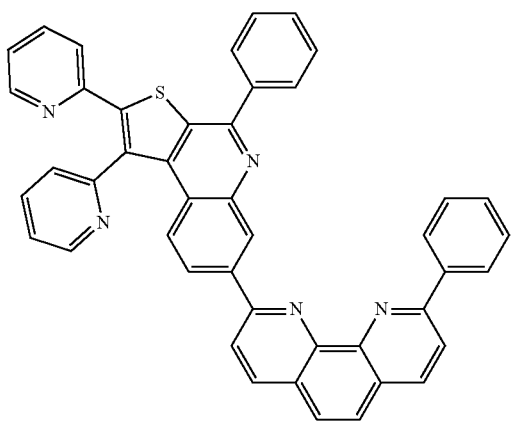

633
-continued
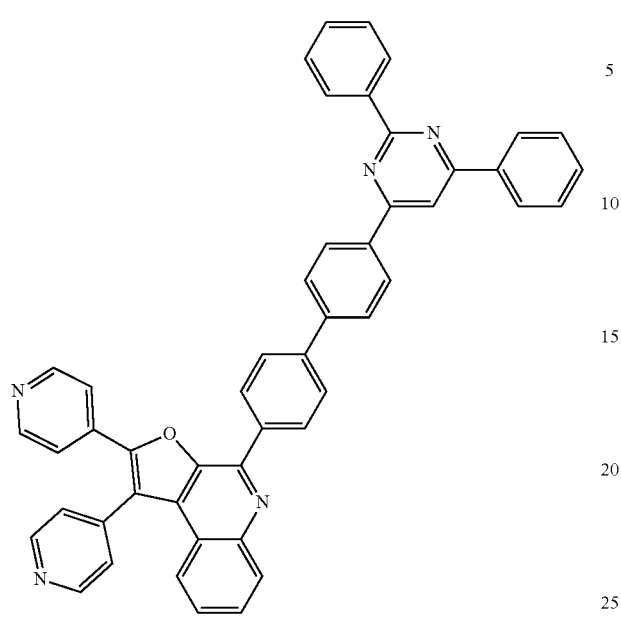
316
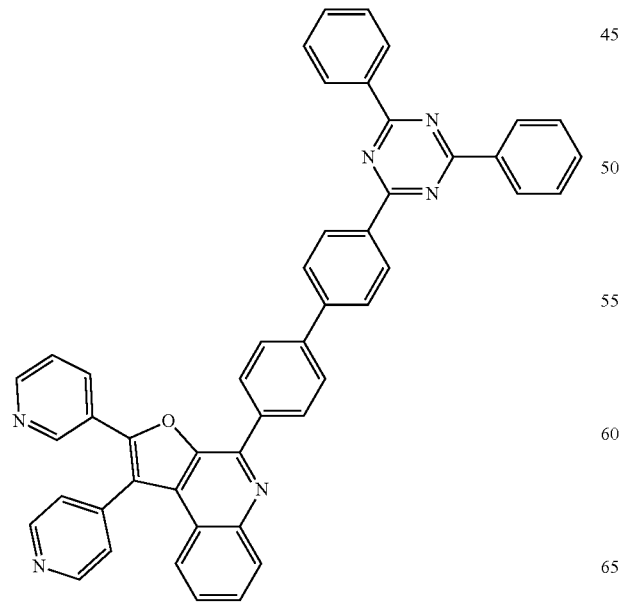
317
634
-continued
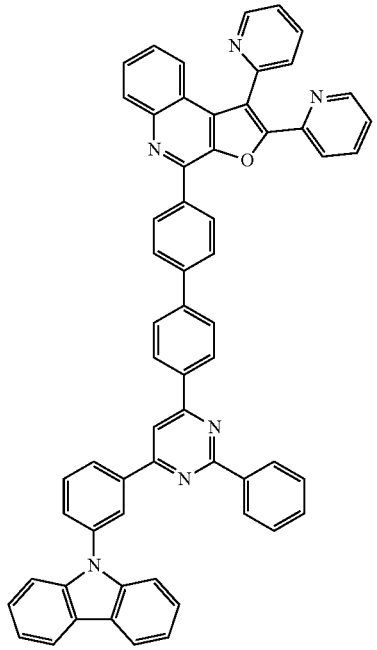
318
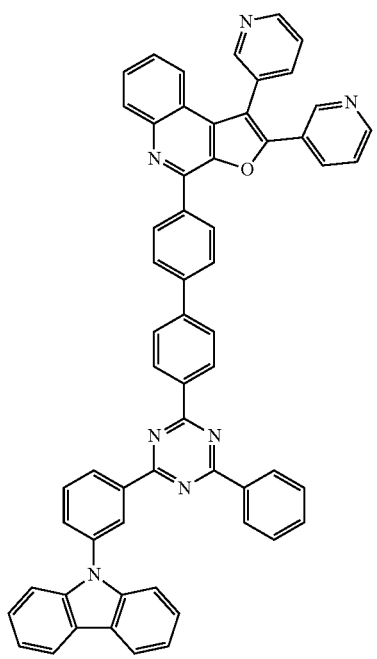
319

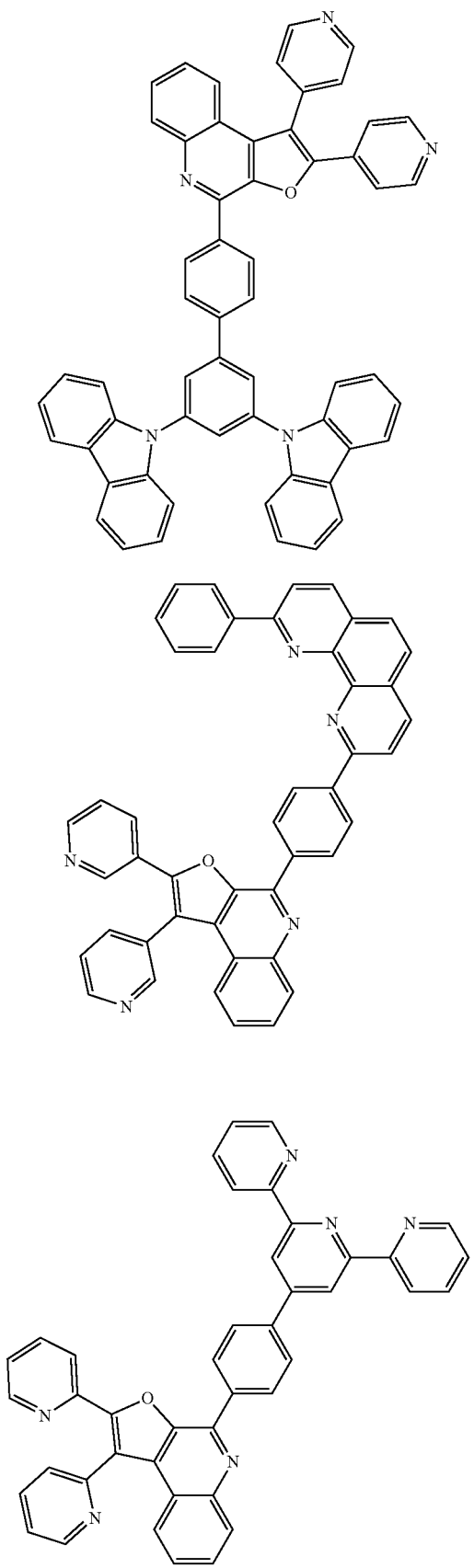
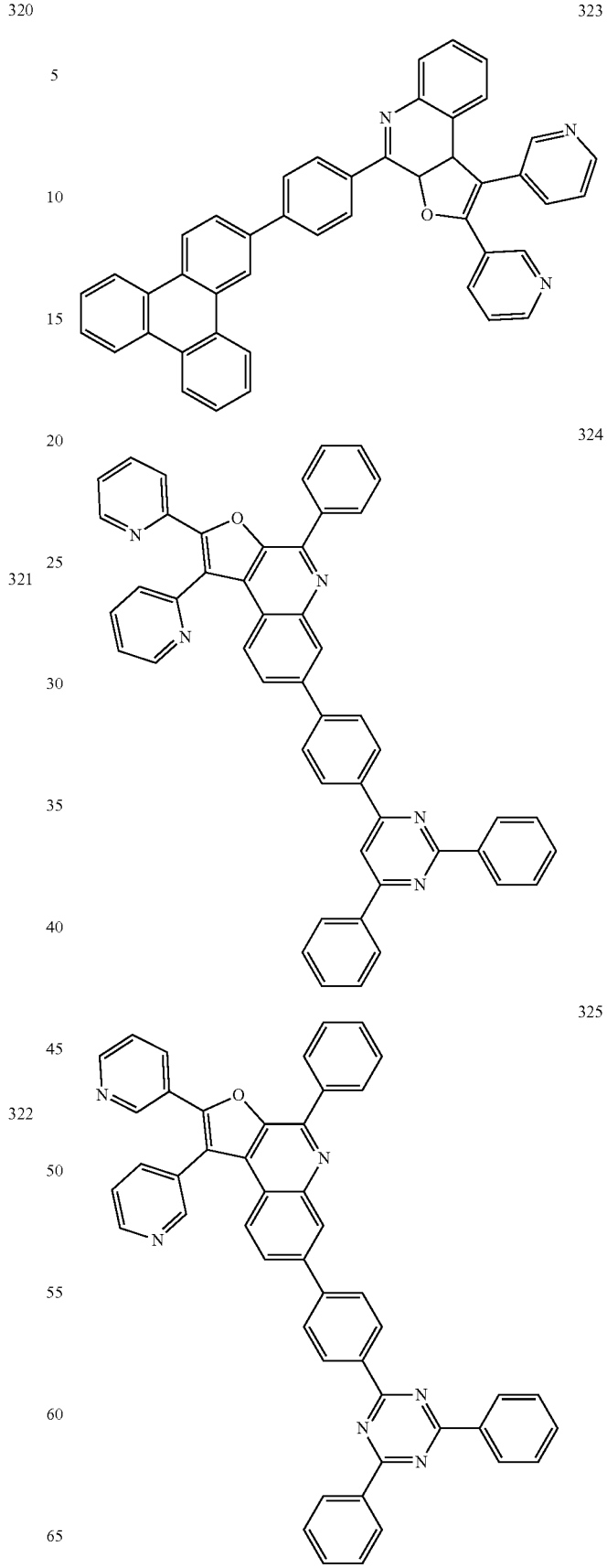

326
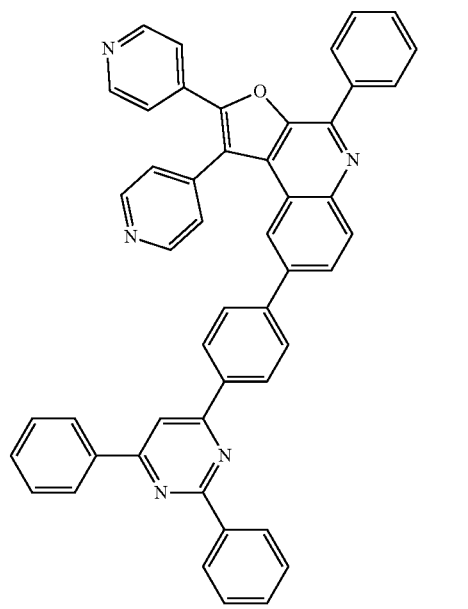
327
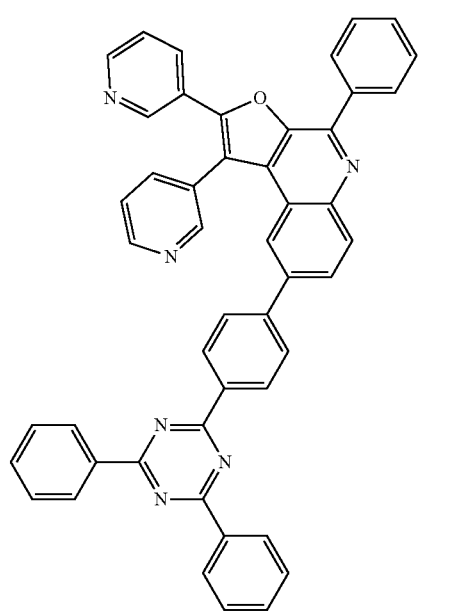
328
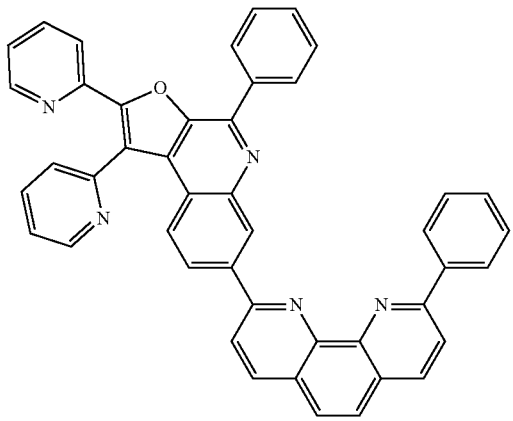
329
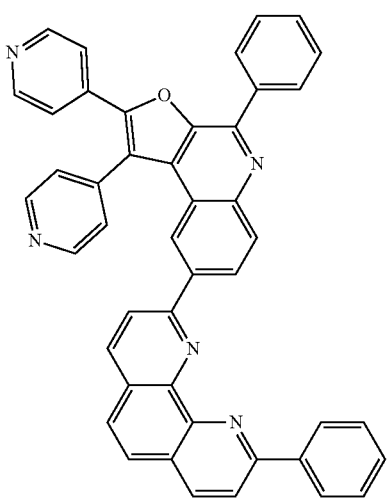
330
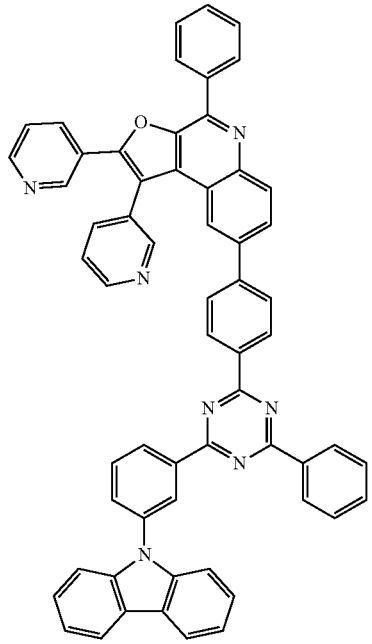
331
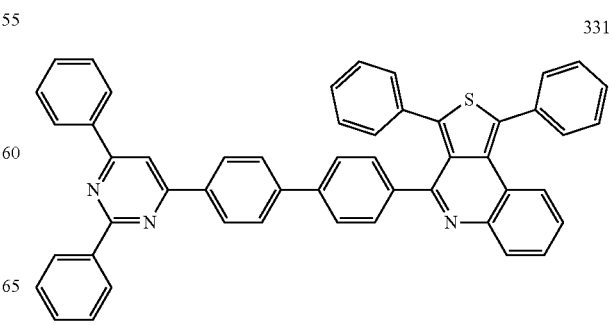

332
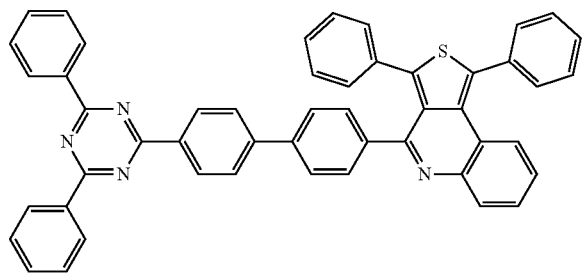
333
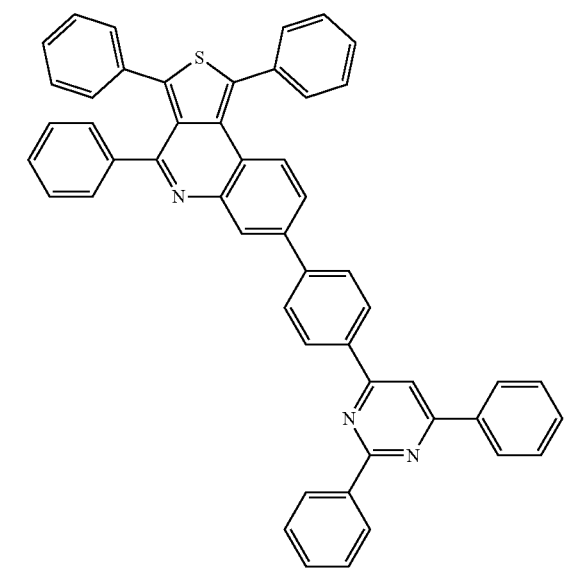
334
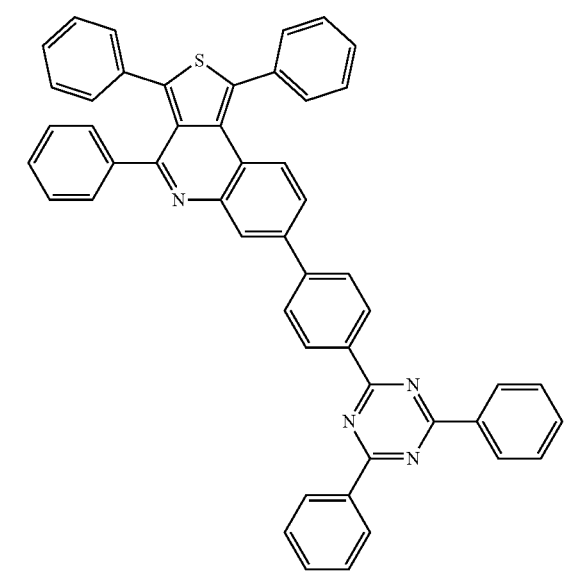
335
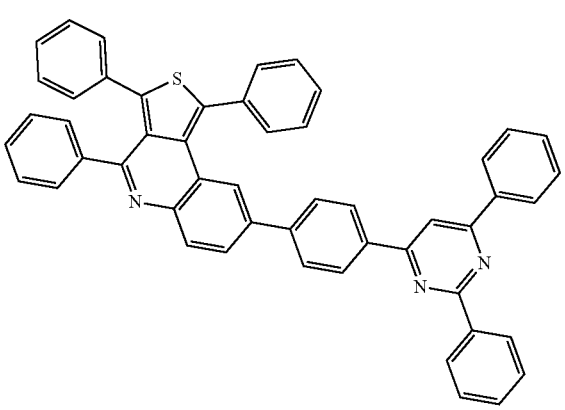
336
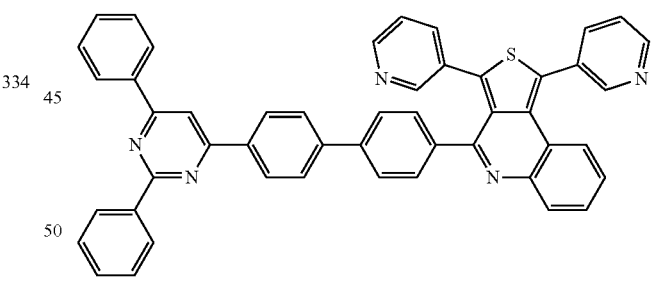
337
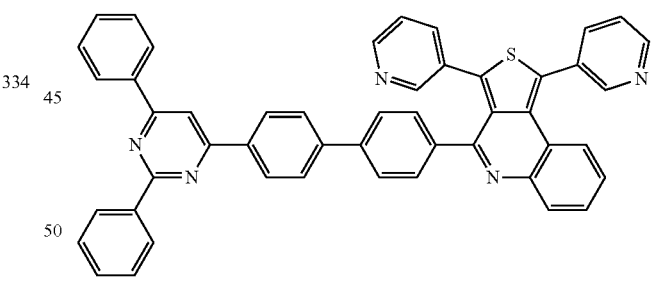
338
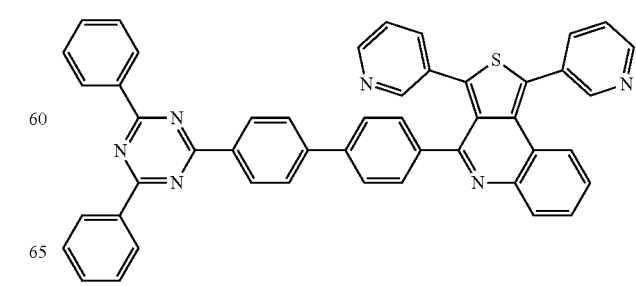

339
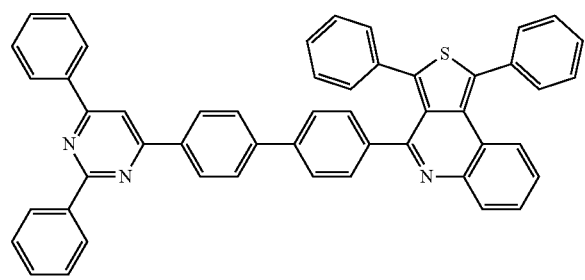
340
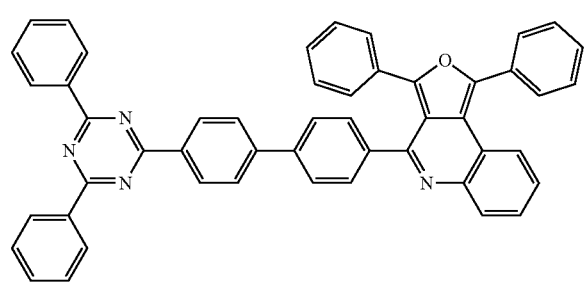
341
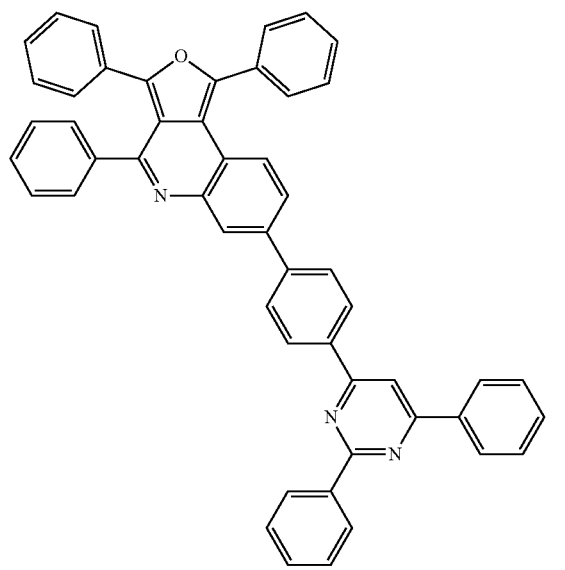
342
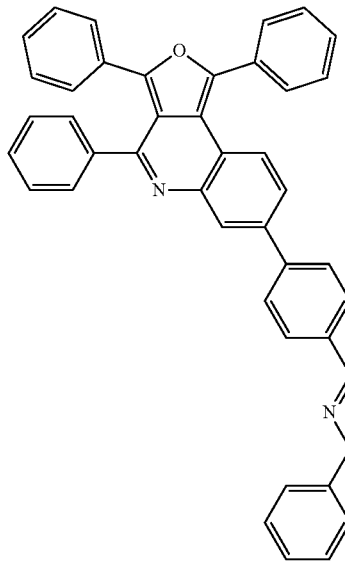
343
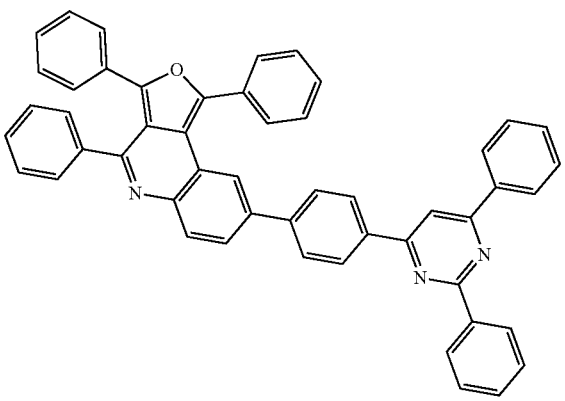
344
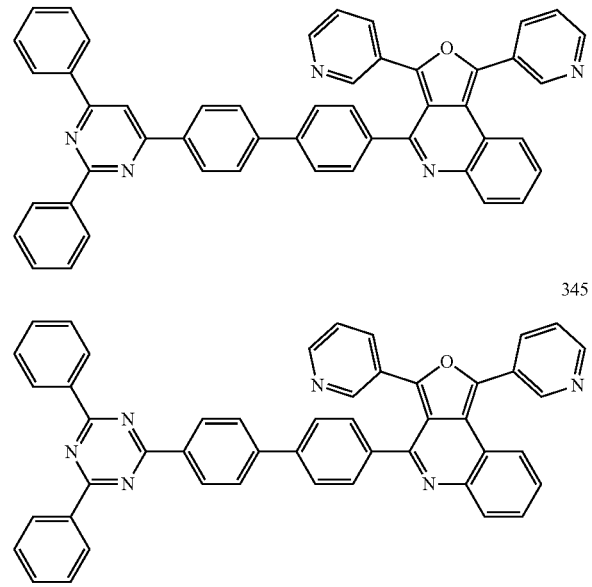
345

346
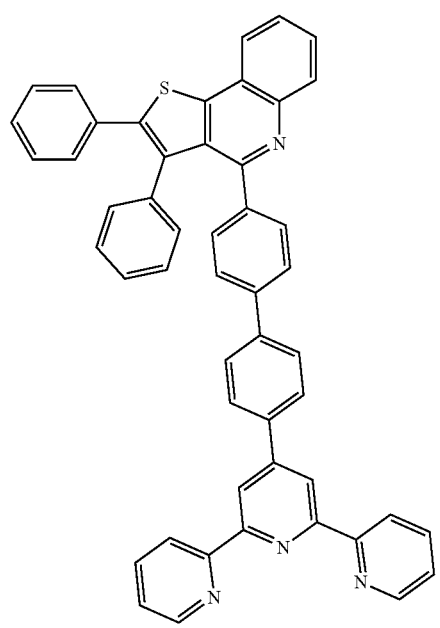
347
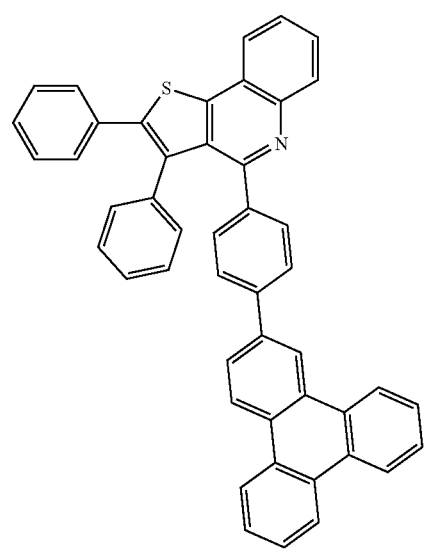
348
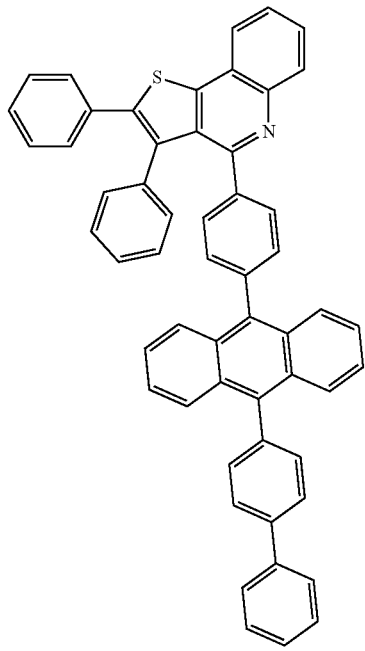
349
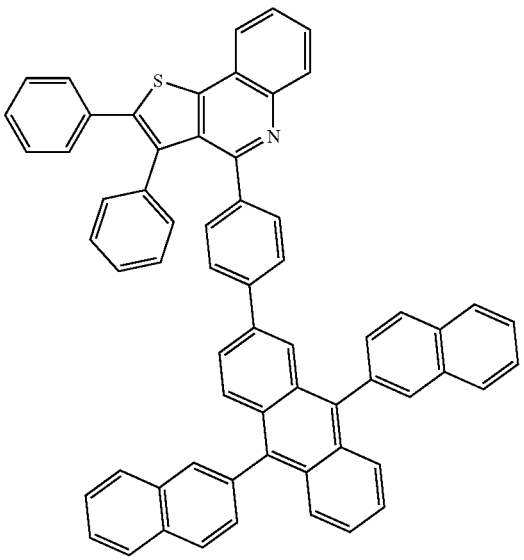

645
-continued
350
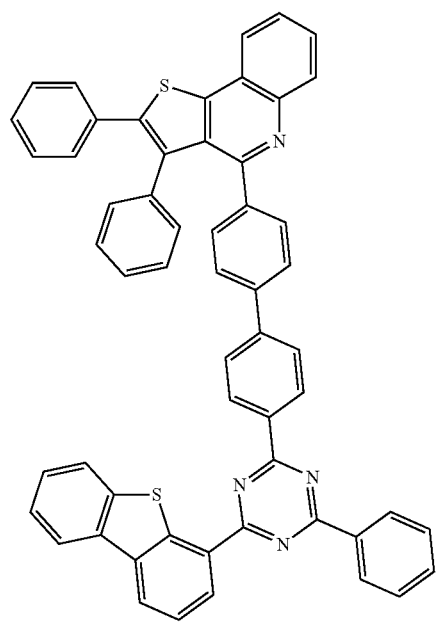
351
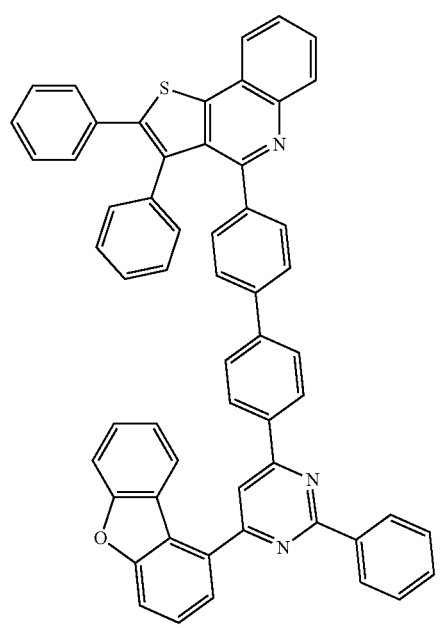
646
-continued
352
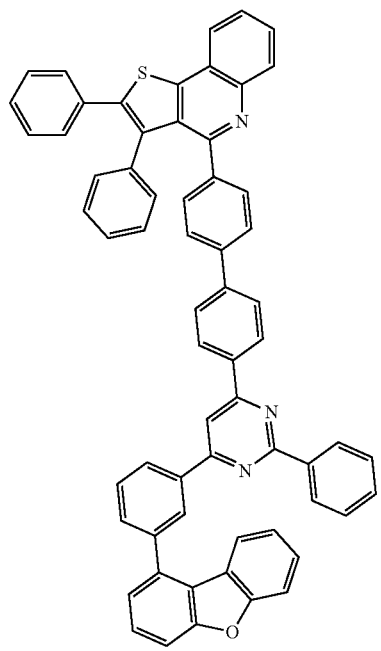
353
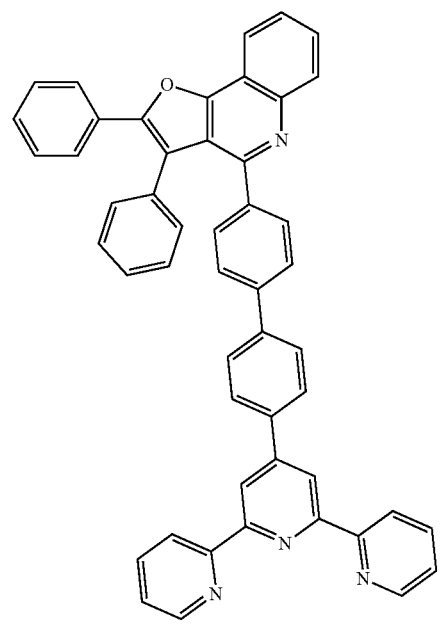

354
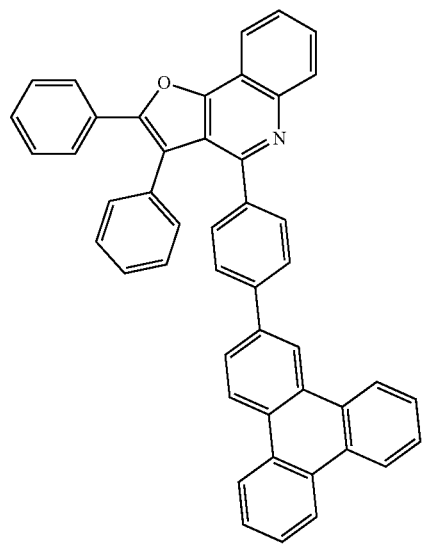
355
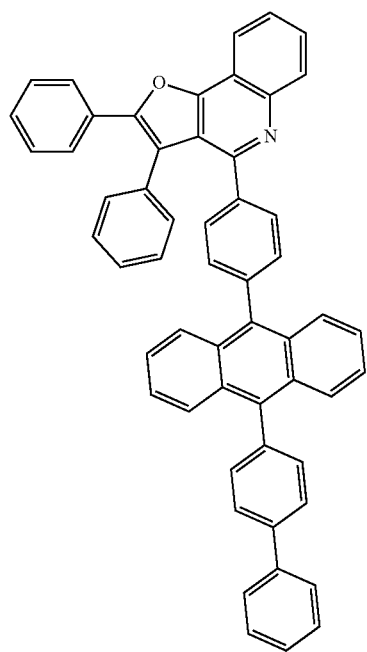
356
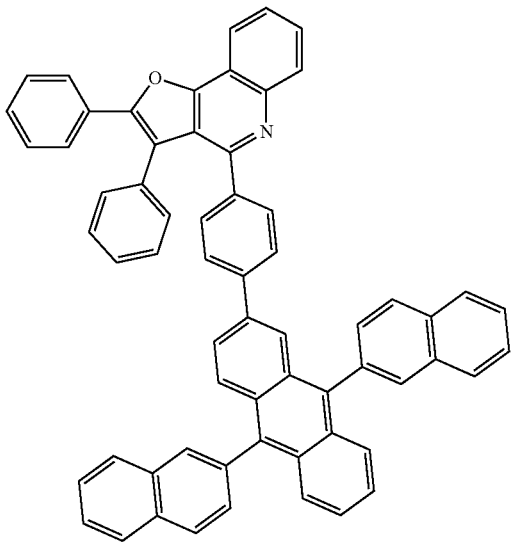
357
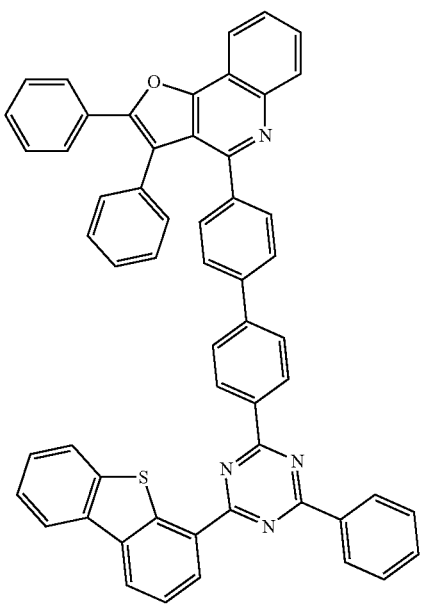

649
-continued
358
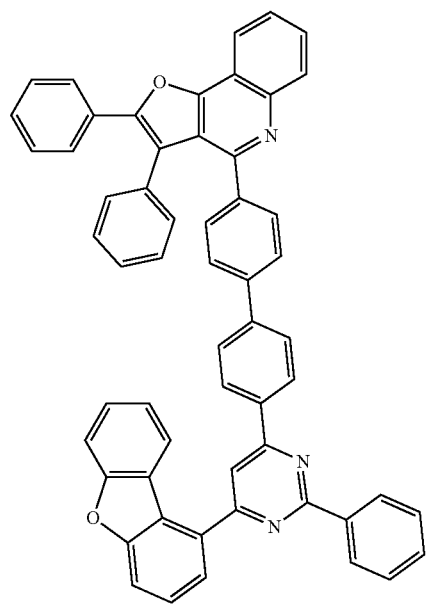
359
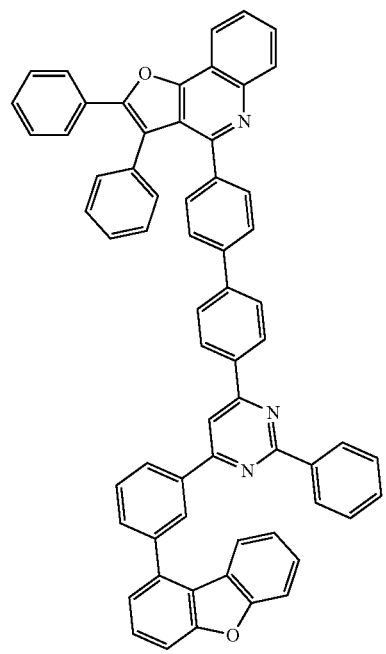
650
-continued
360
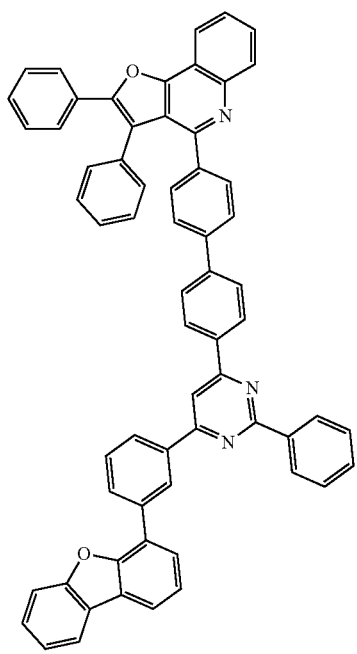
361
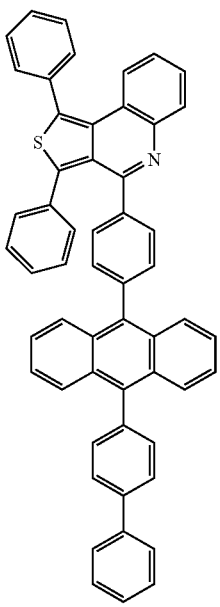

651
-continued
652
-continued
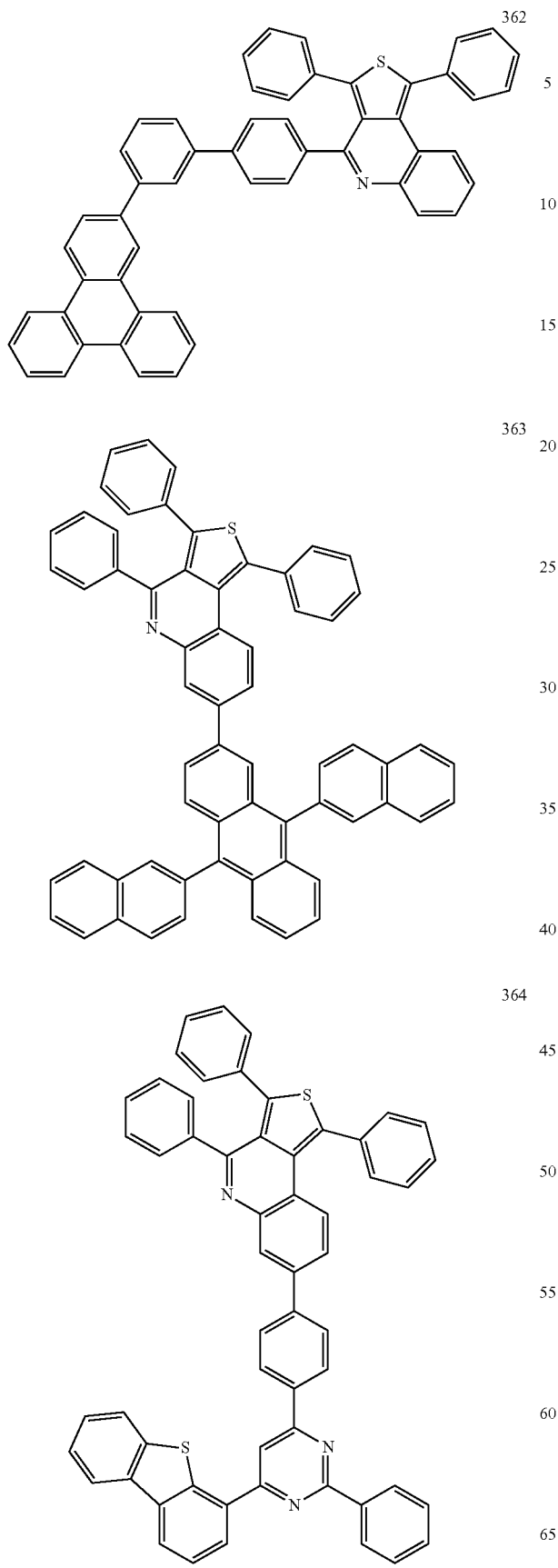

653
-continued
367
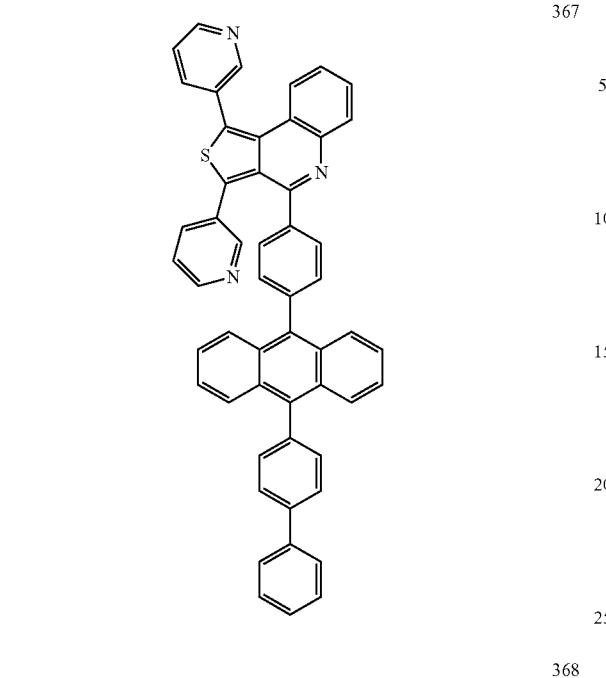
368
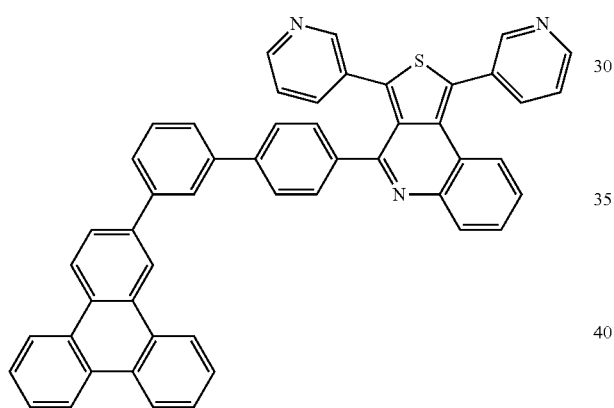
369
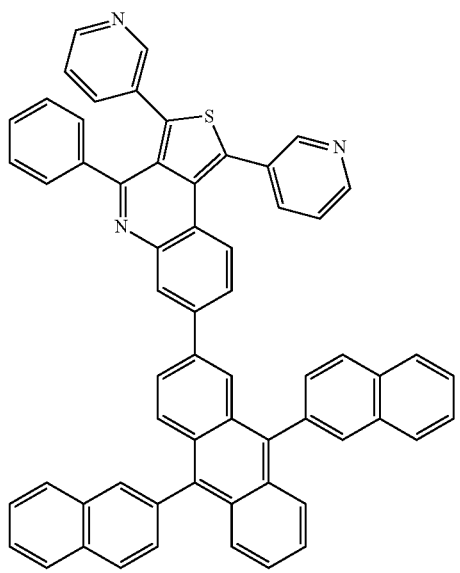
654
-continued
370
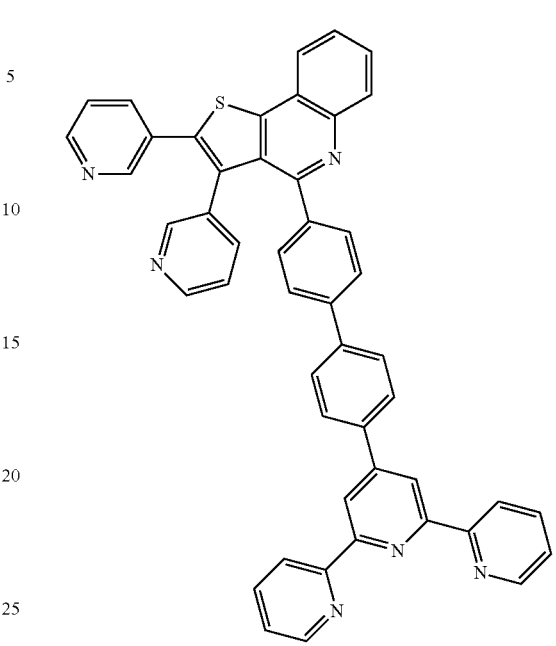
371
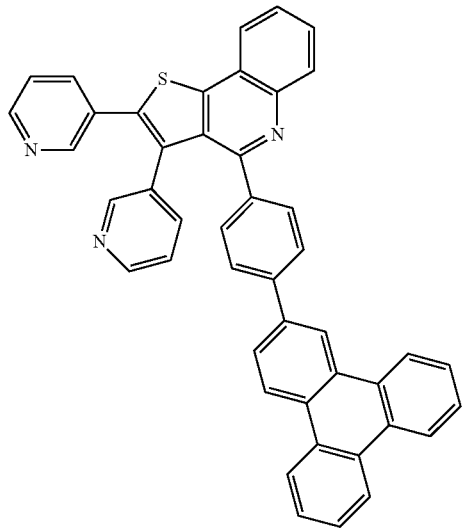

-continued
372
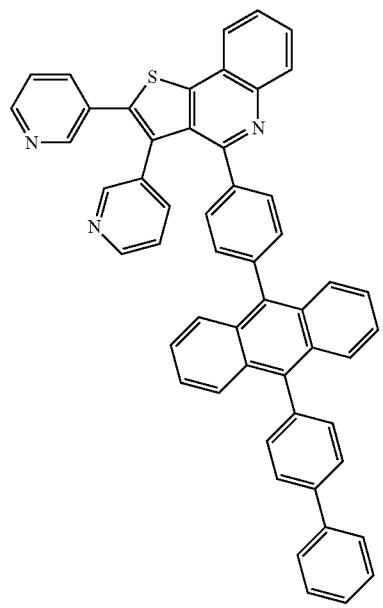
373
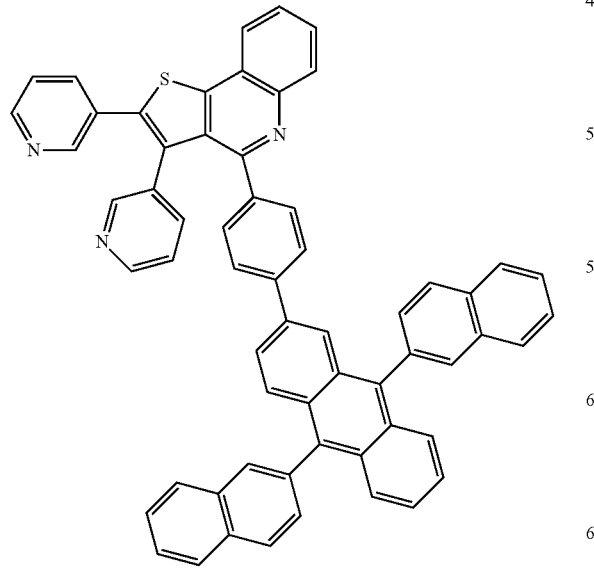
-continued
374
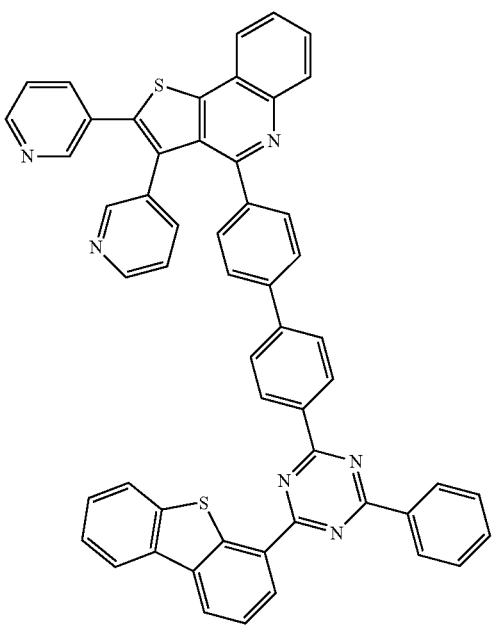
375
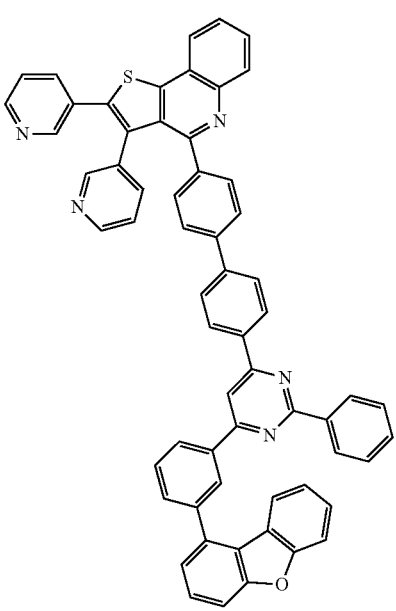

-continued
376
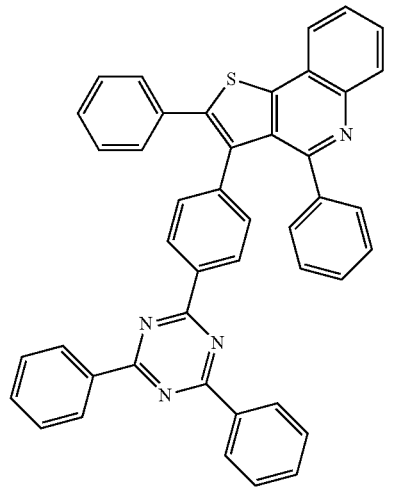
377
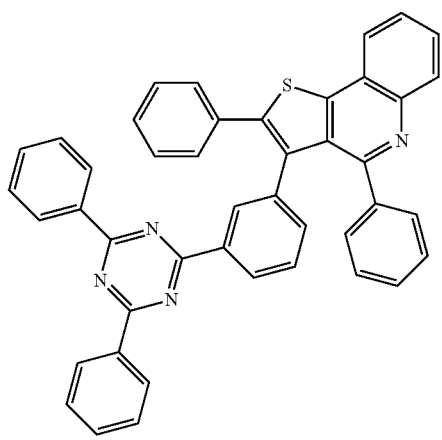
378
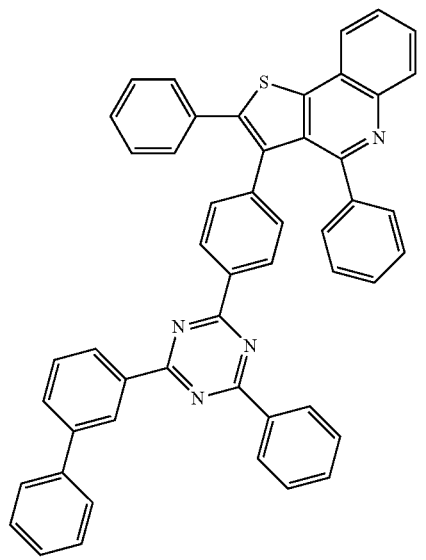
-continued
379
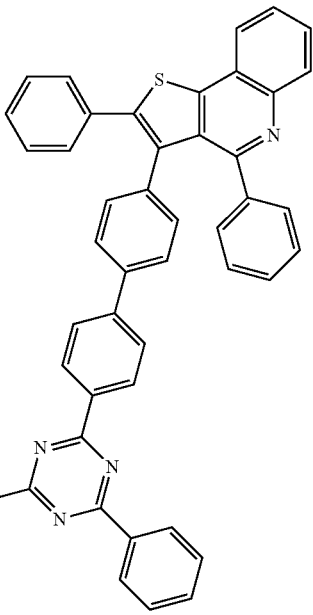
380
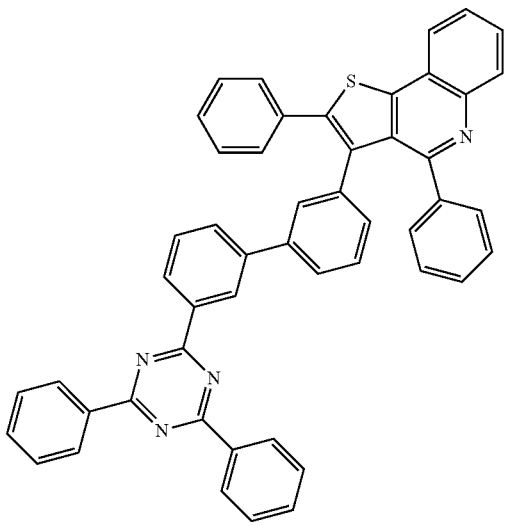
381
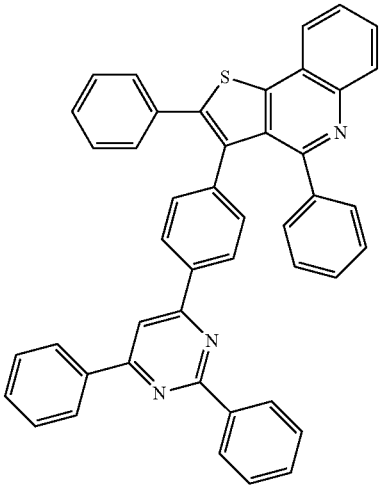

382
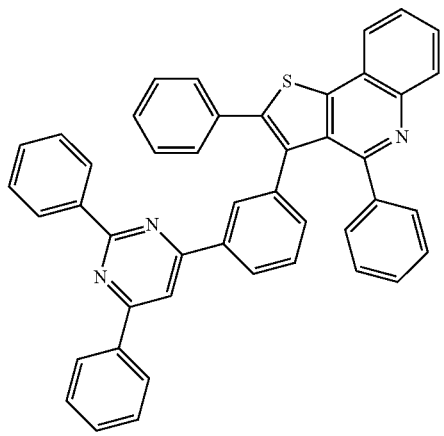
383
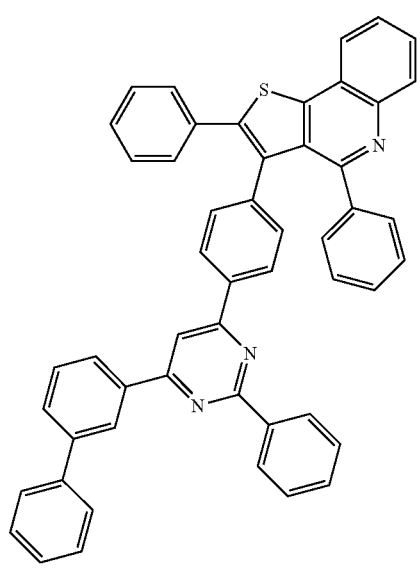
384
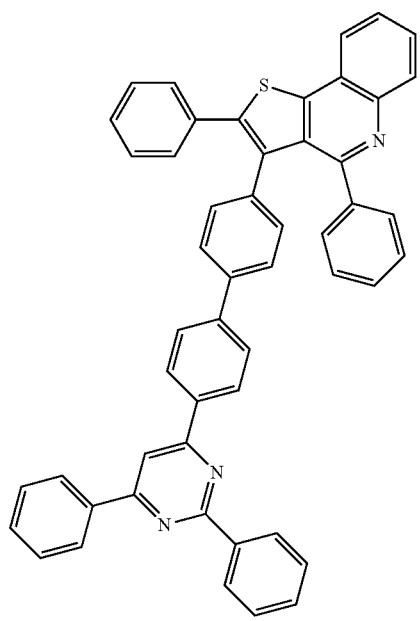
385
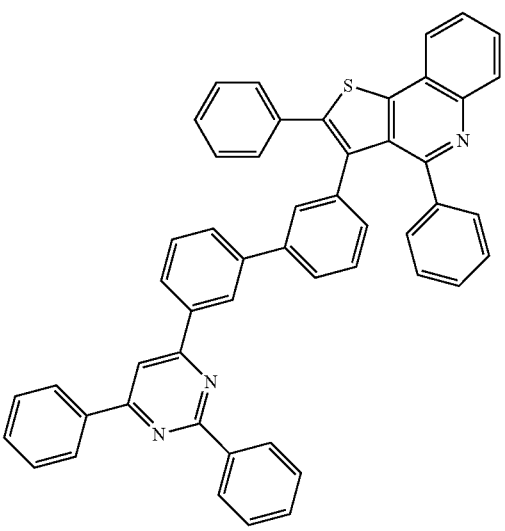
386
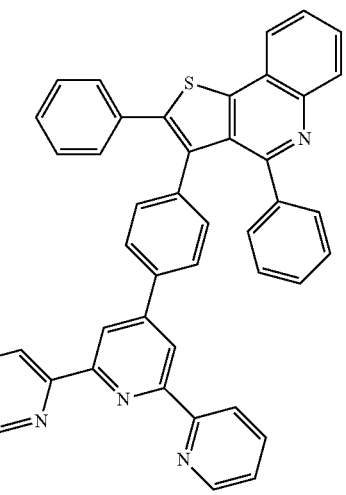
387
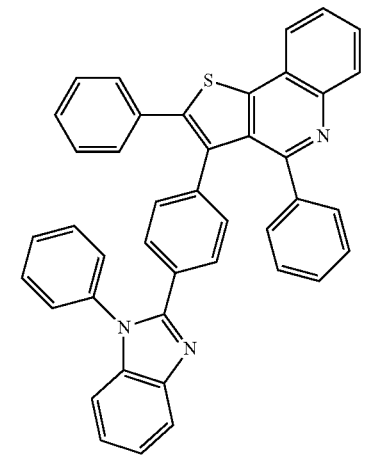

661
-continued
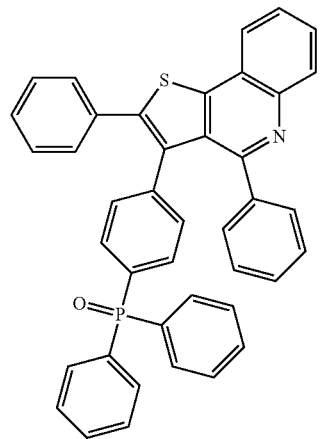
388
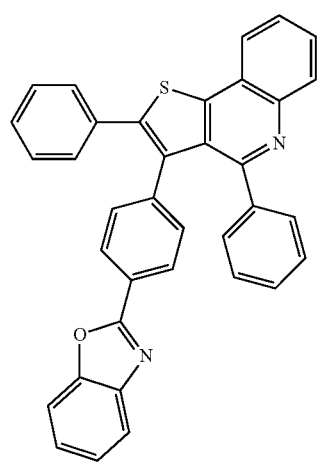
389
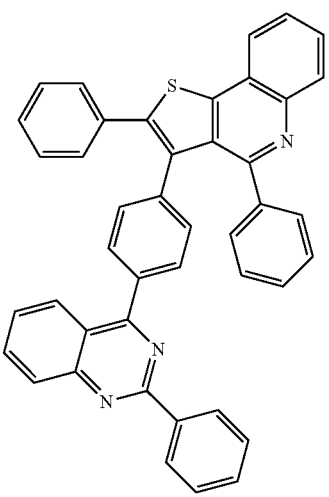
390
662
-continued
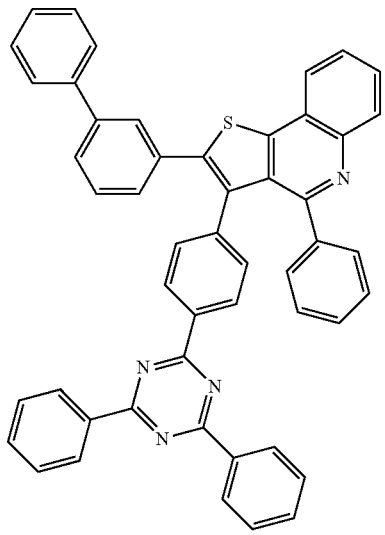
391
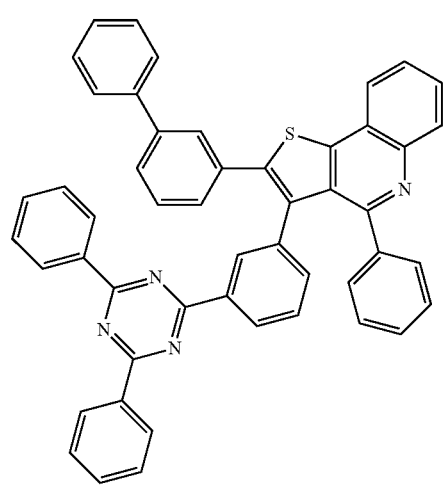
392
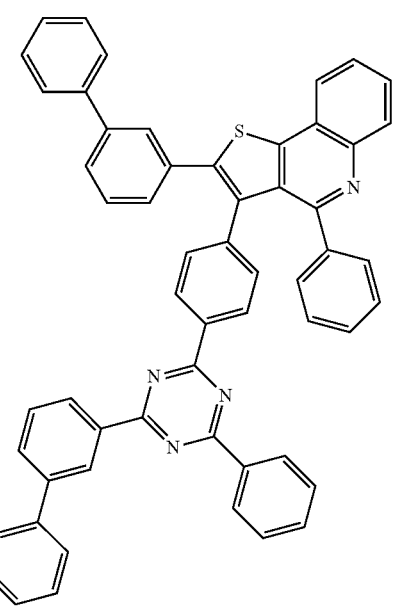
393

663
-continued
394
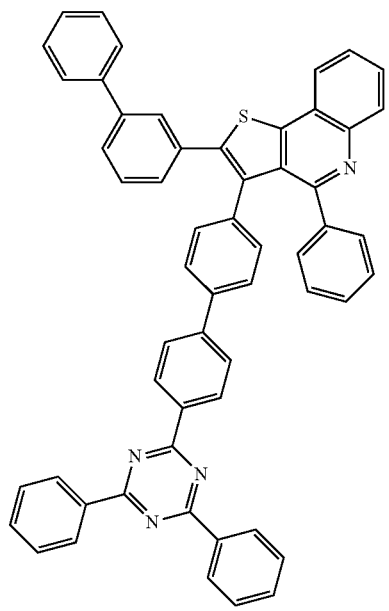
395
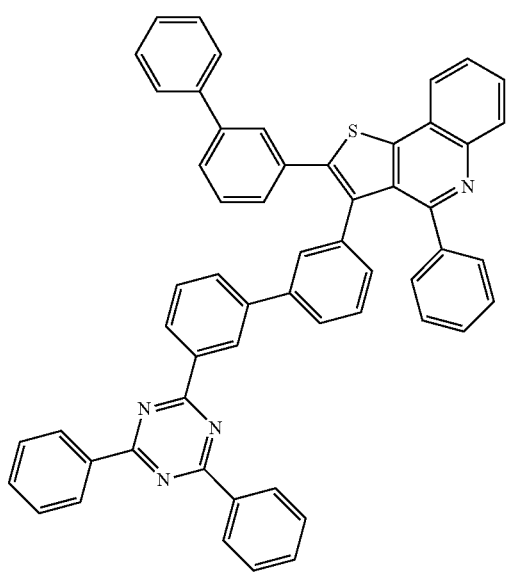
664
-continued
396
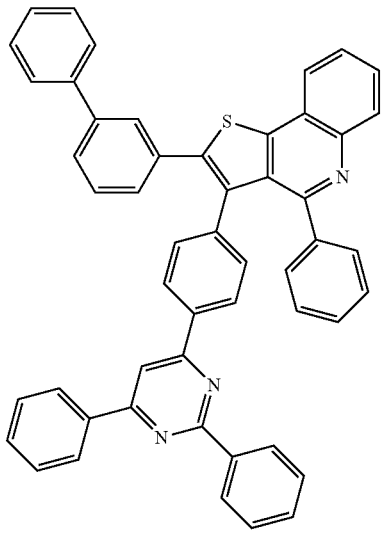
397
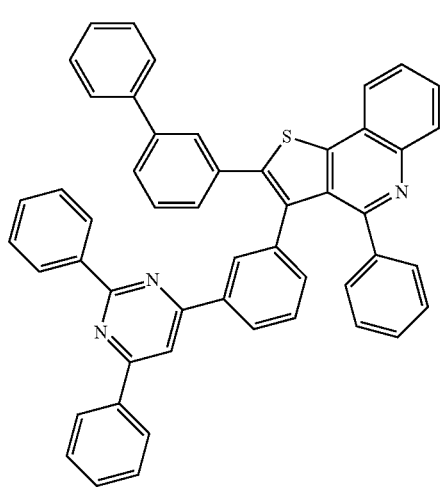
398
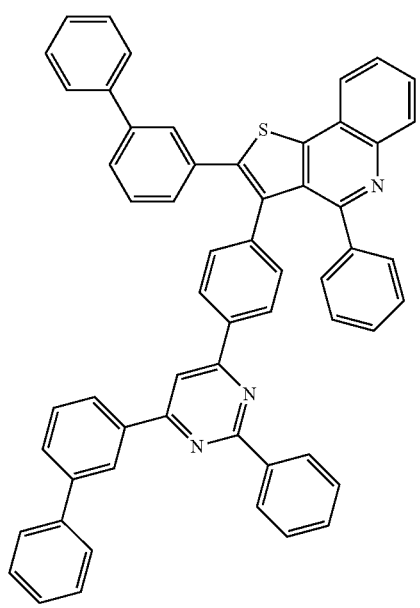

399
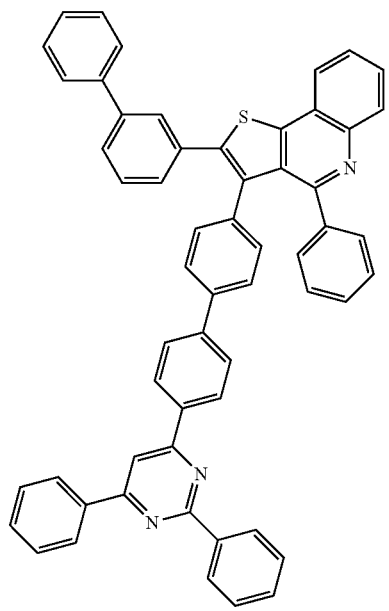
400
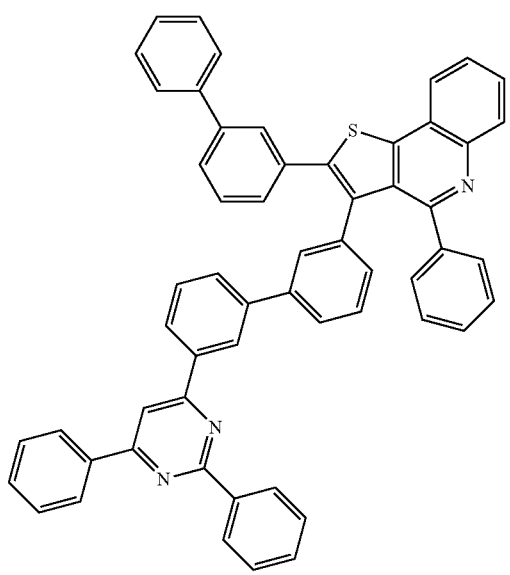
401
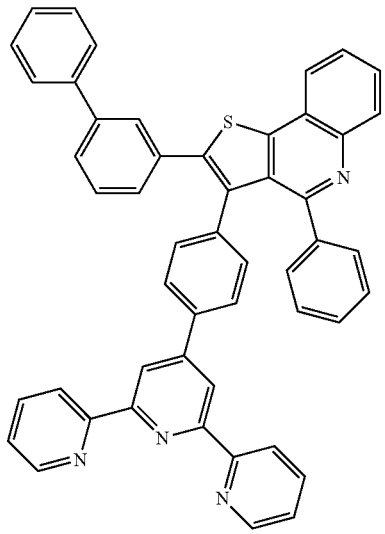
402
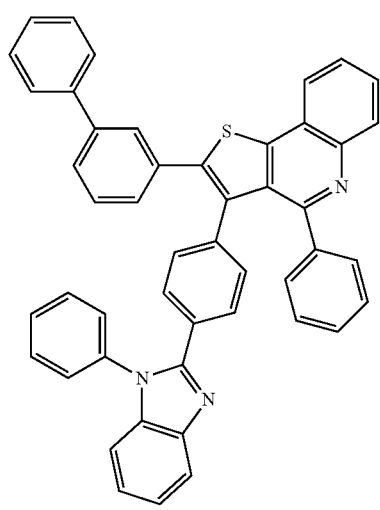
403
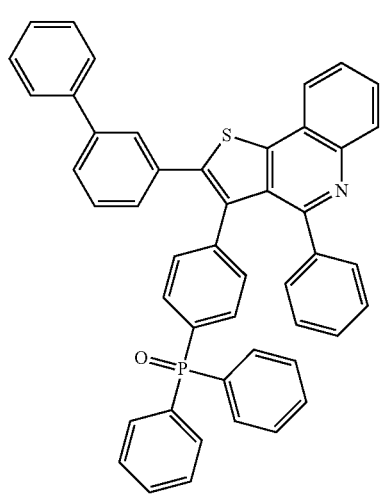

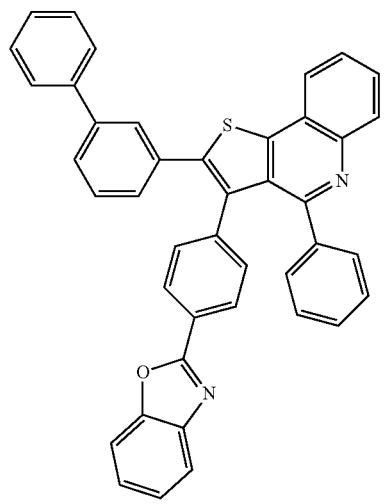
404
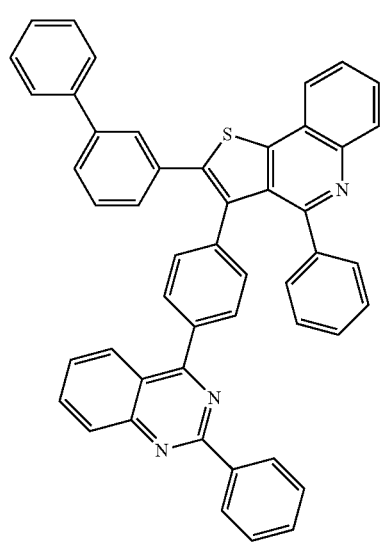
405
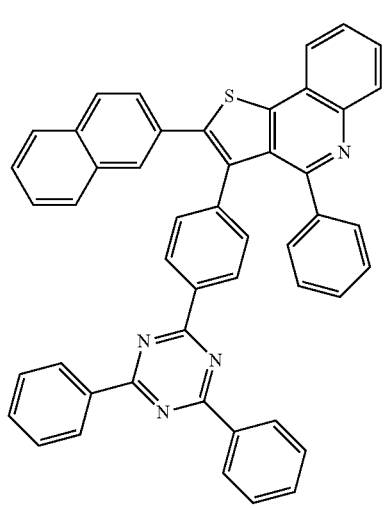
406
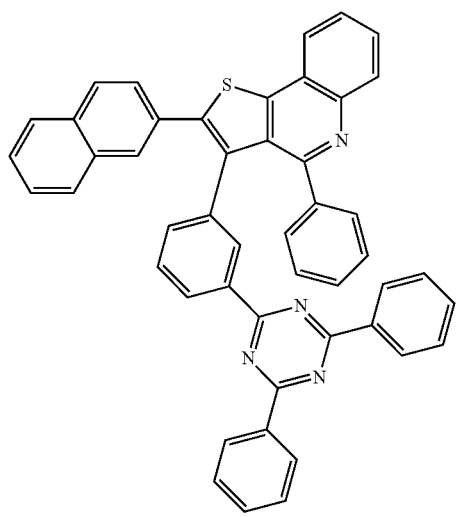
407
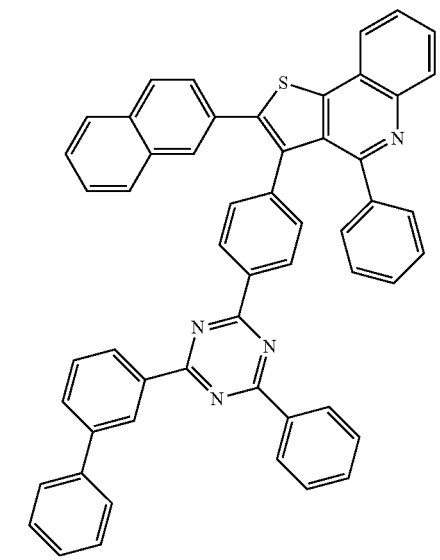
408

669
-continued
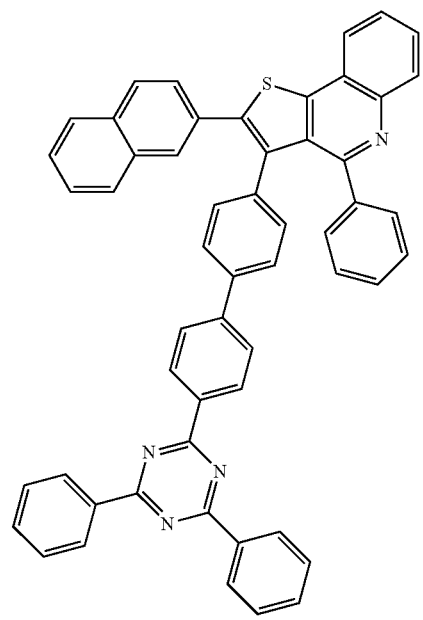
409
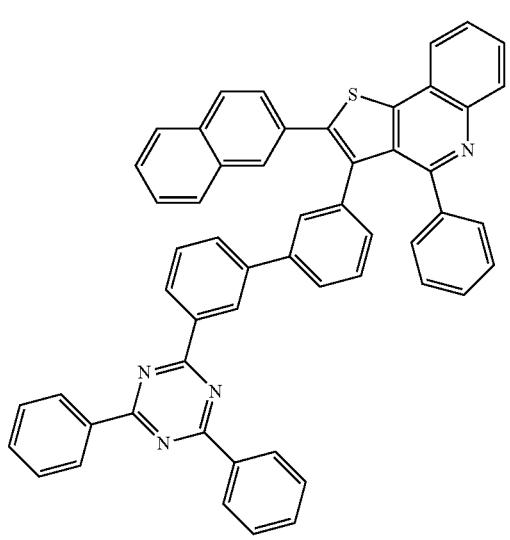
410
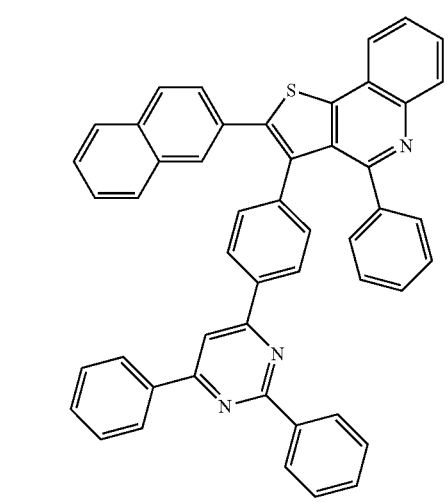
411
670
-continued
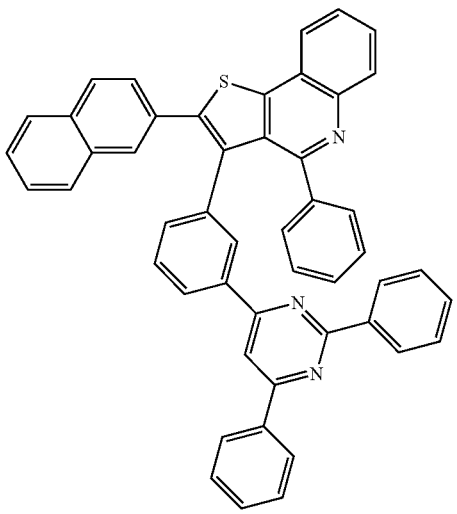
412
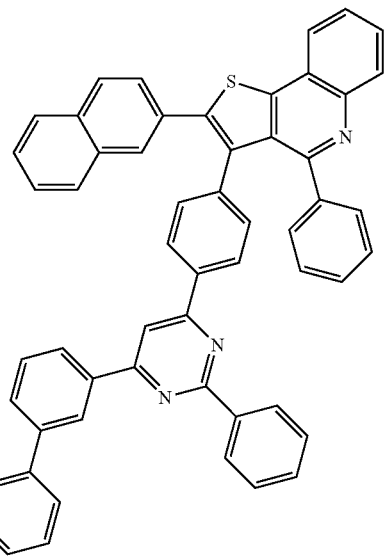
413

414
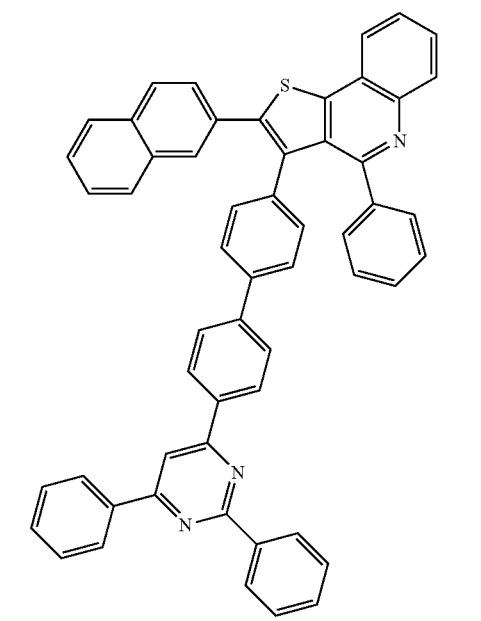
415
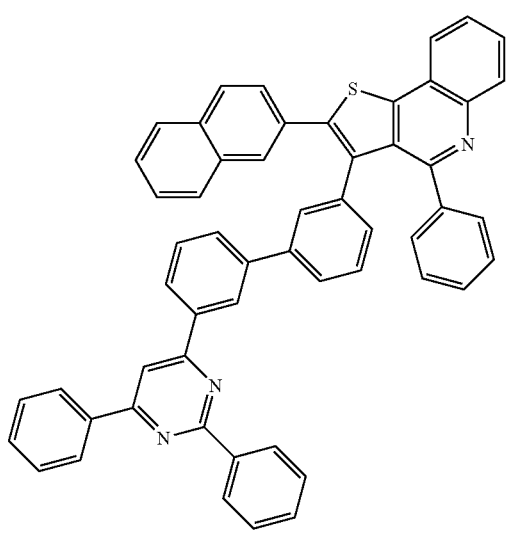
416
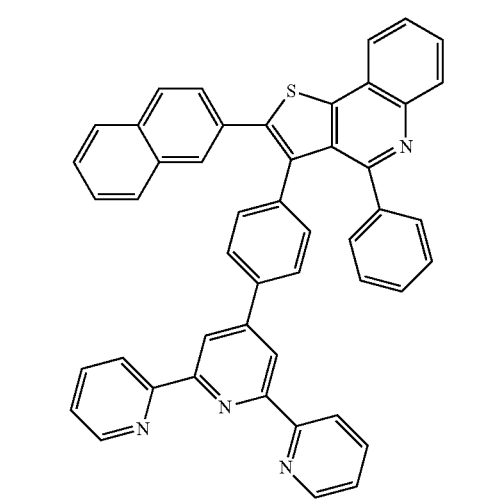
417
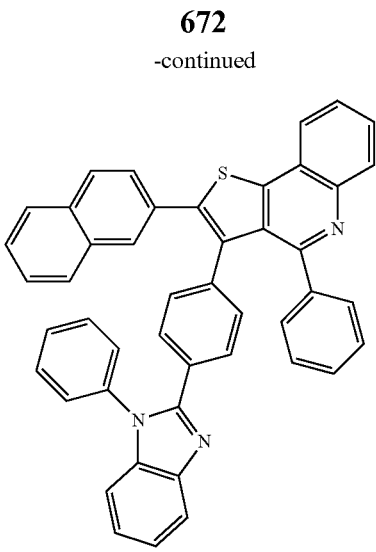
418
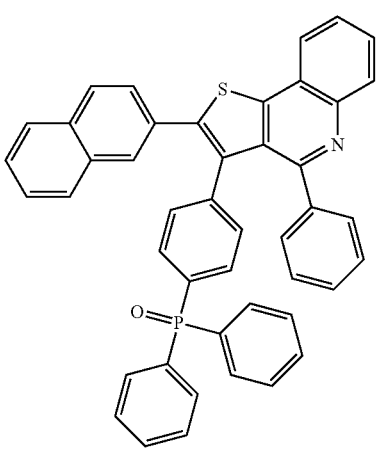
419
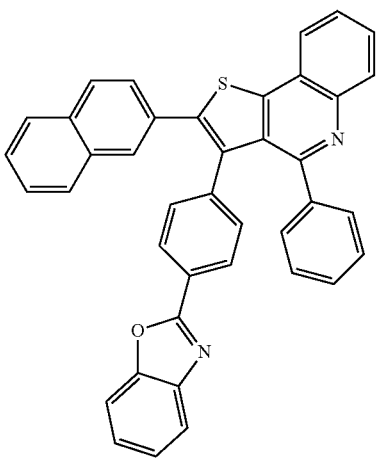

-continued
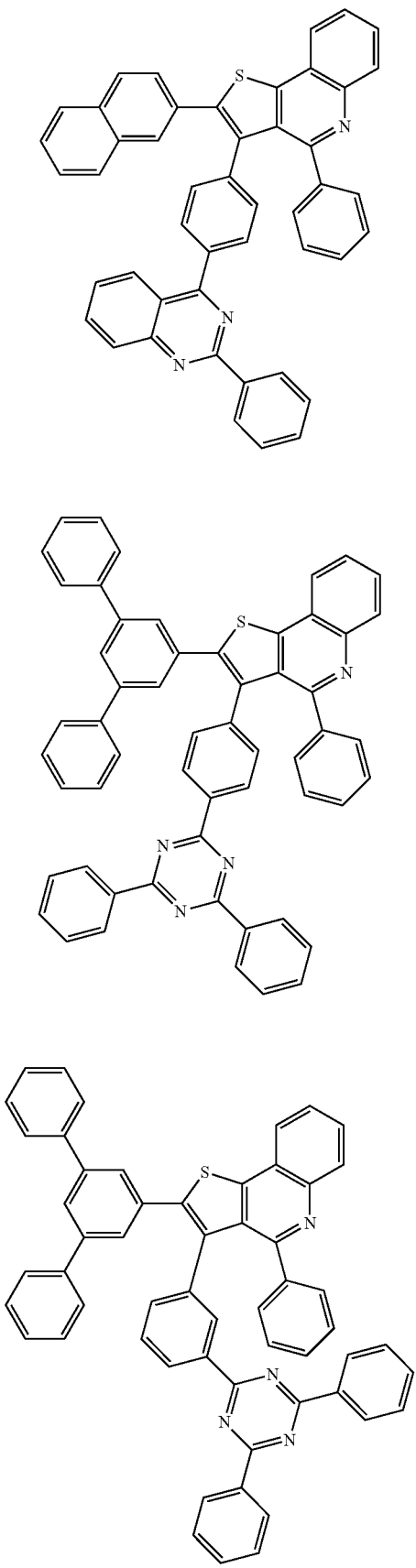
-continued

675
-continued
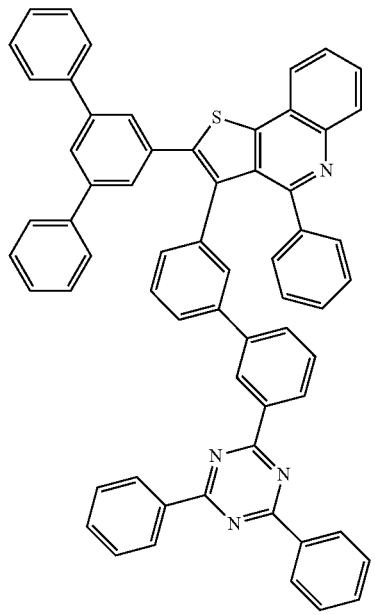
425
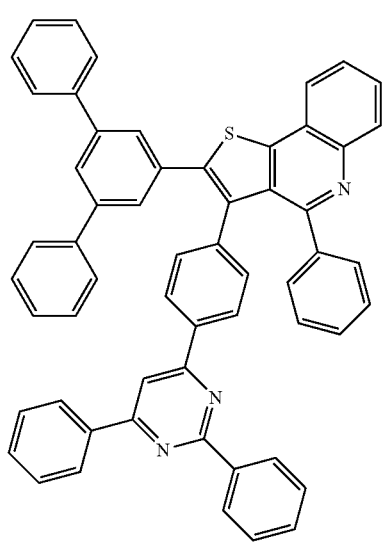
426
676
-continued
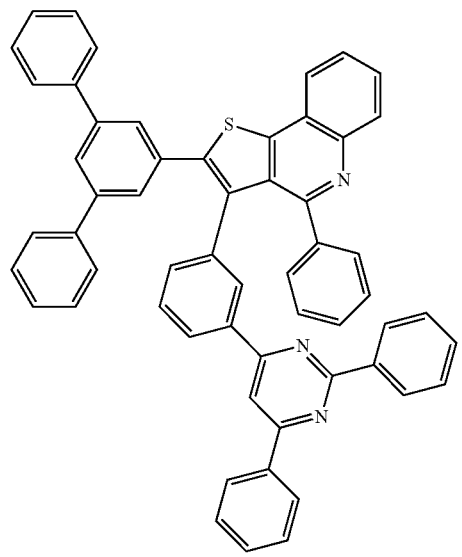
427
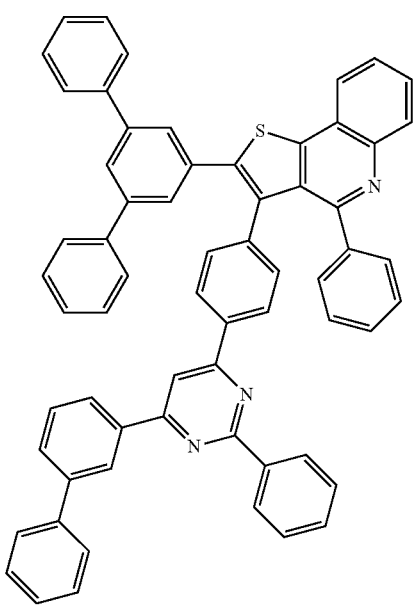
428

677
-continued
429
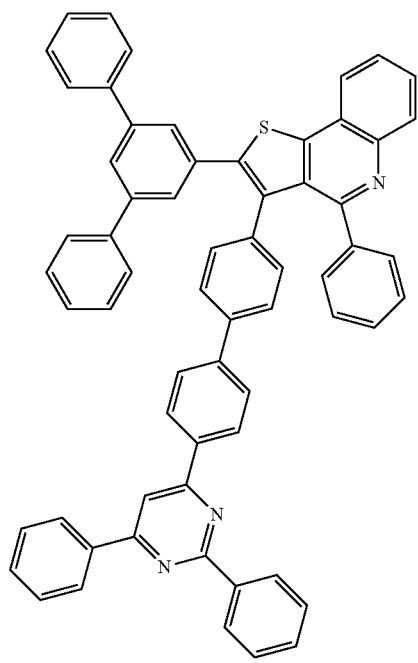
430
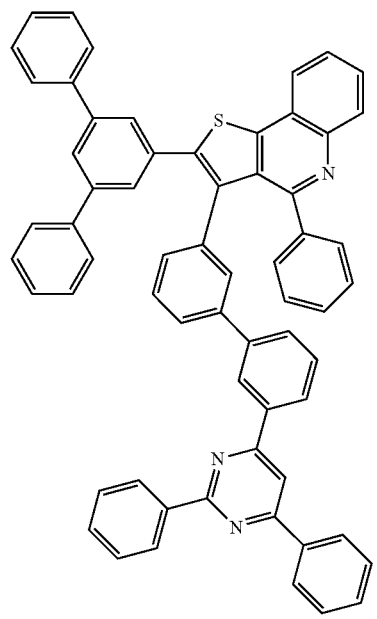
678
-continued
431
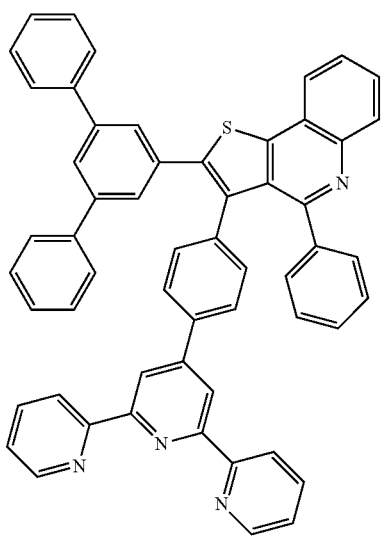
432
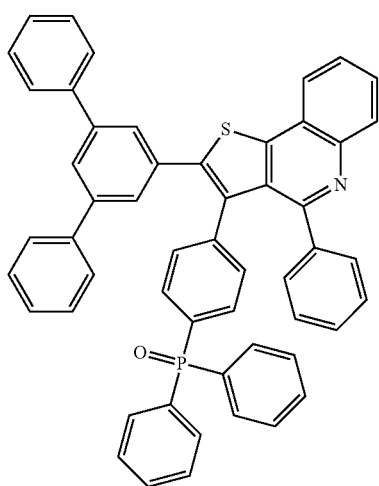
433
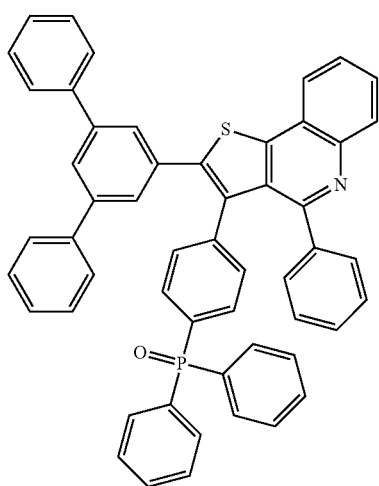

679
-continued
434
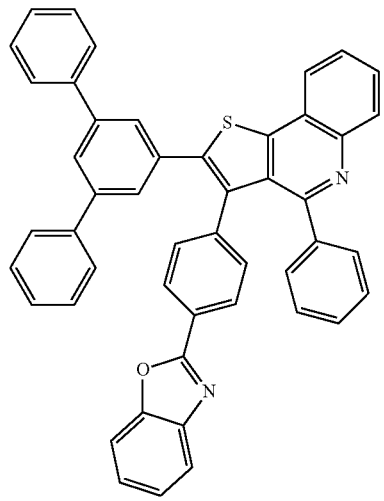
435
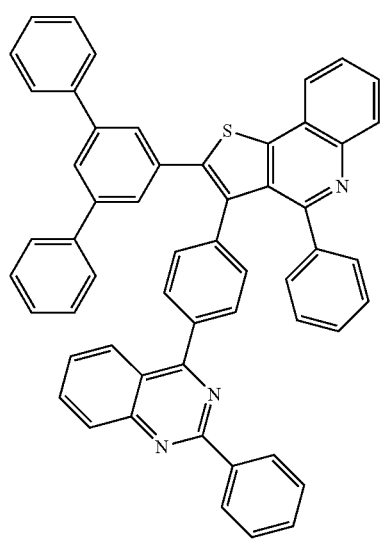
436
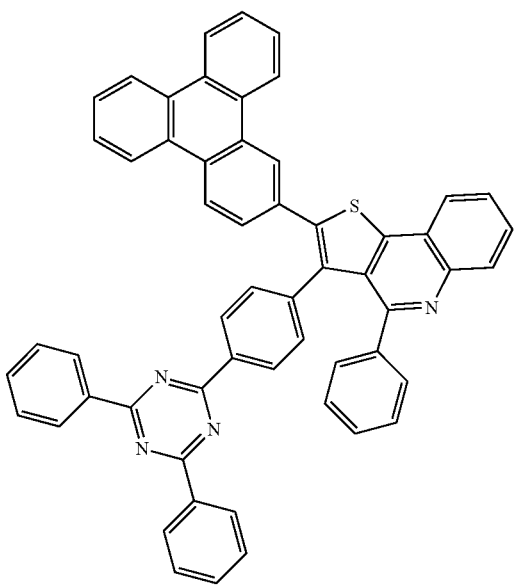
680
-continued
437
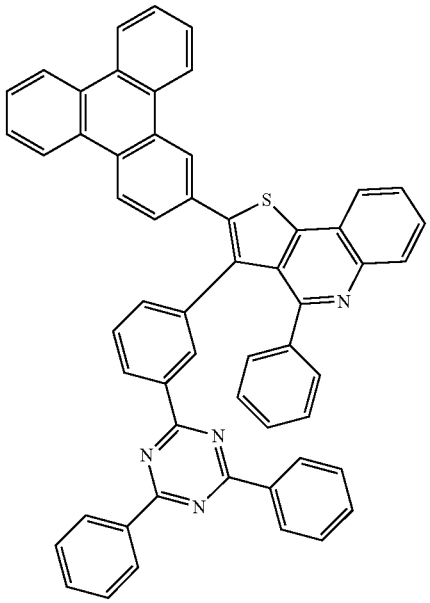
438
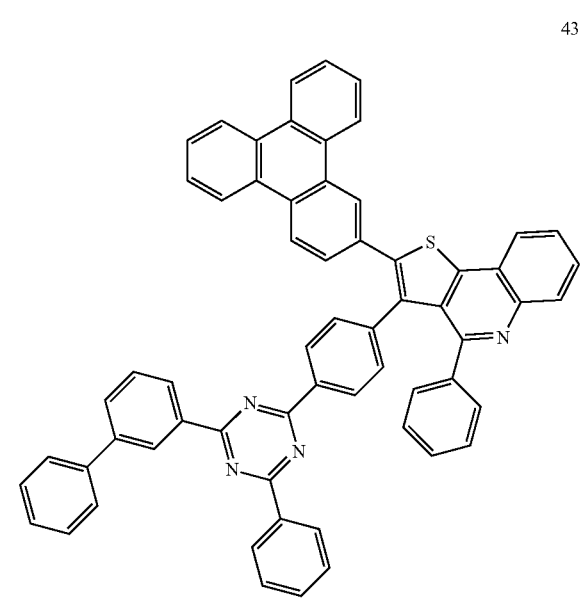

439
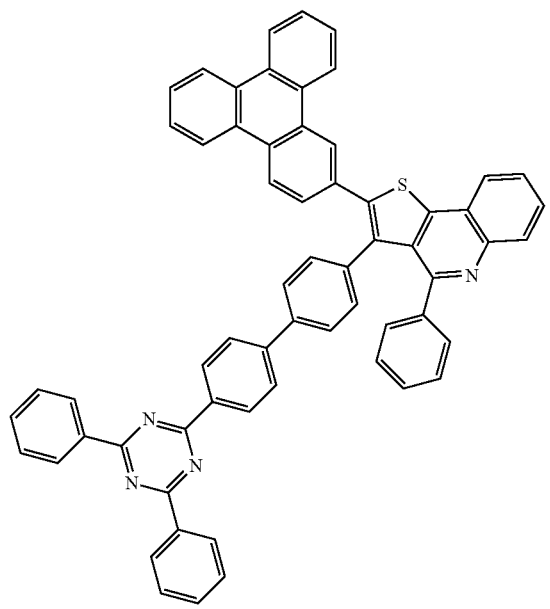
441
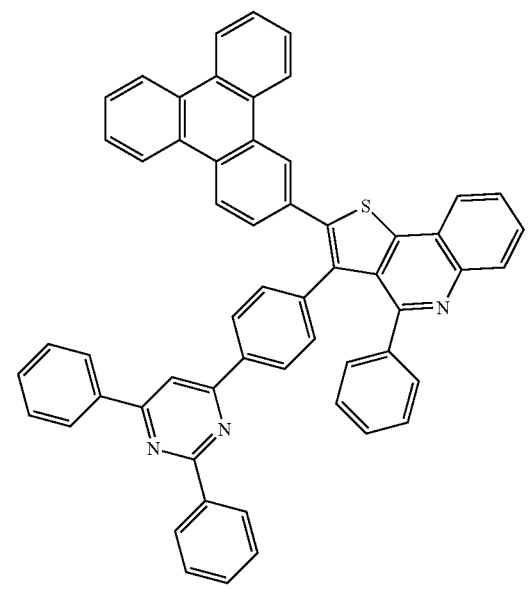
440
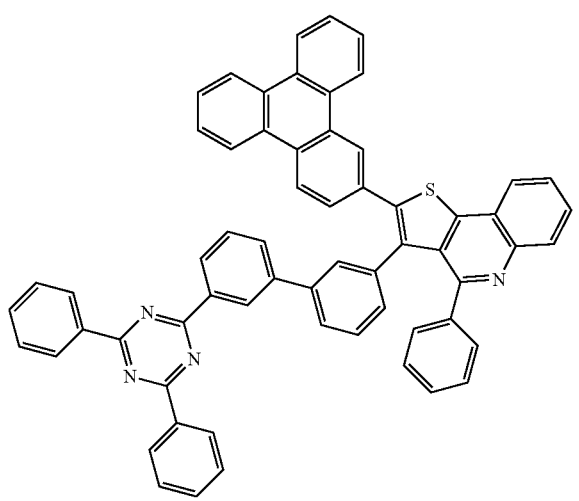
442
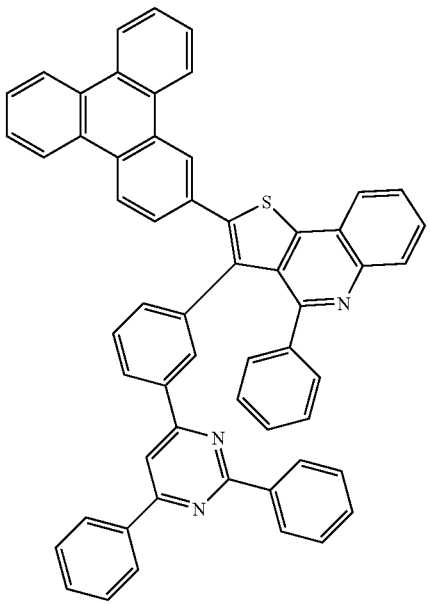

-continued
443
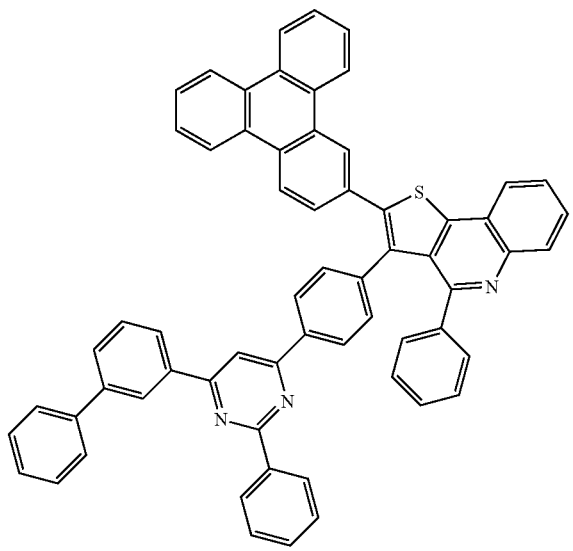
444
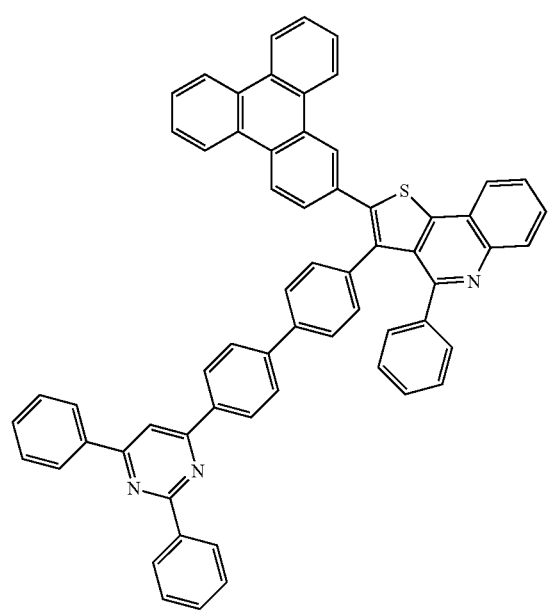
445
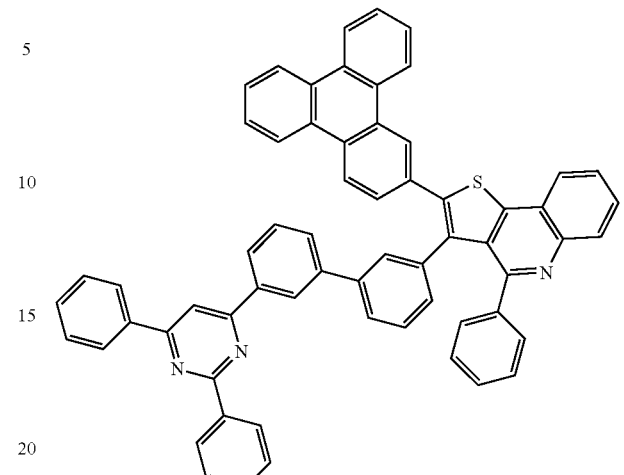
446
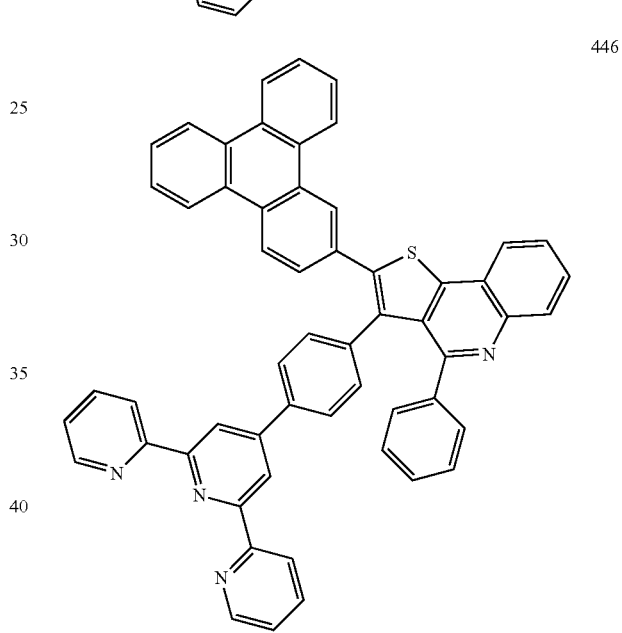
447
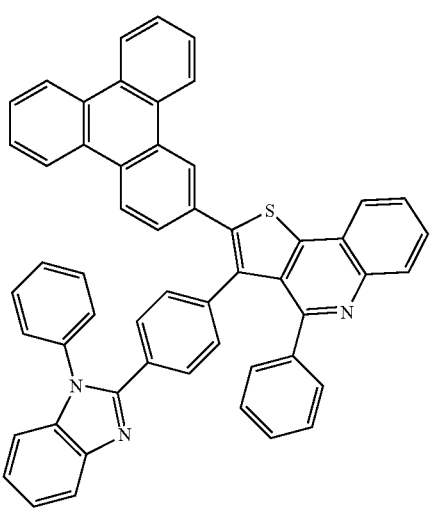

-continued
448
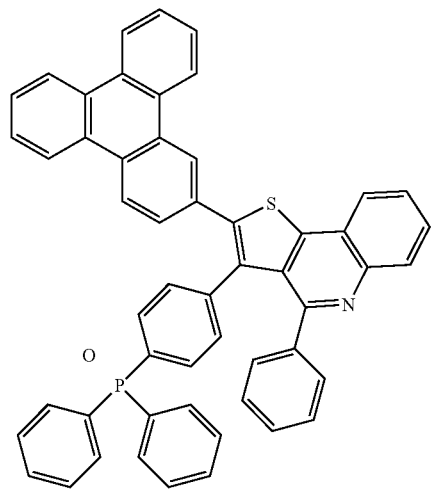
449
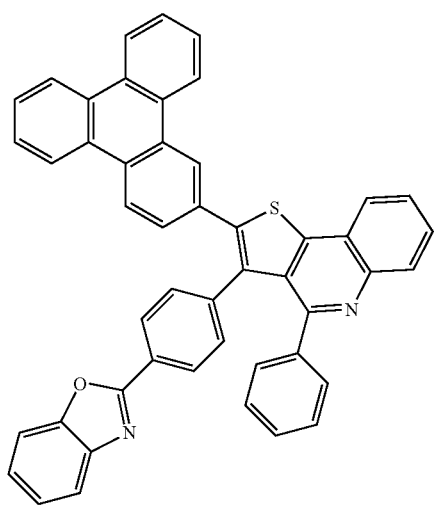
450
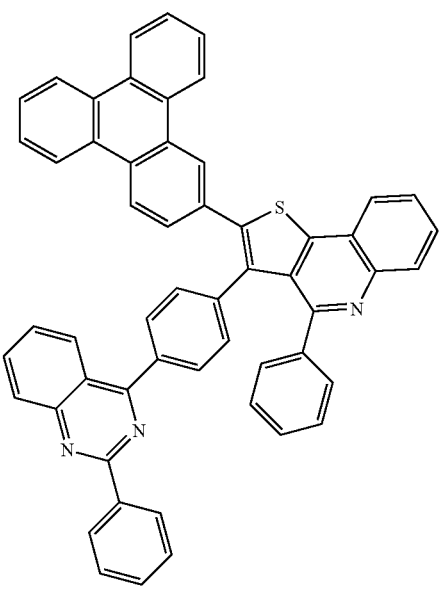
-continued
451
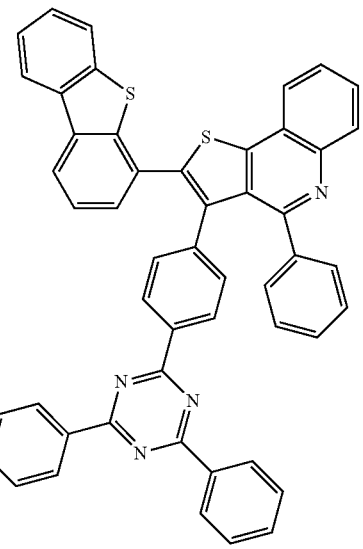
452
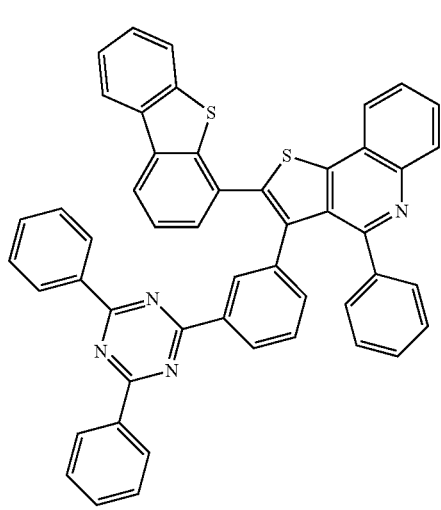
453
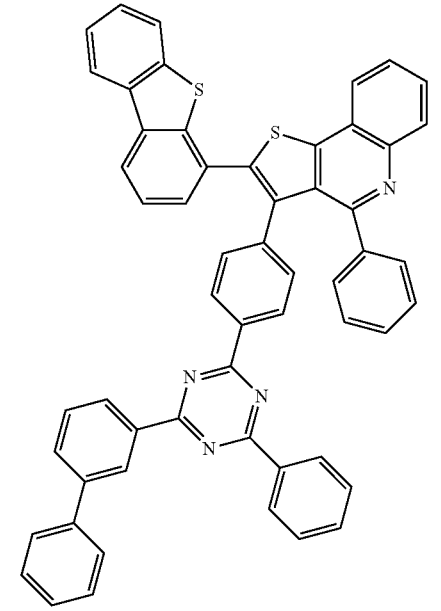

687
-continued
454
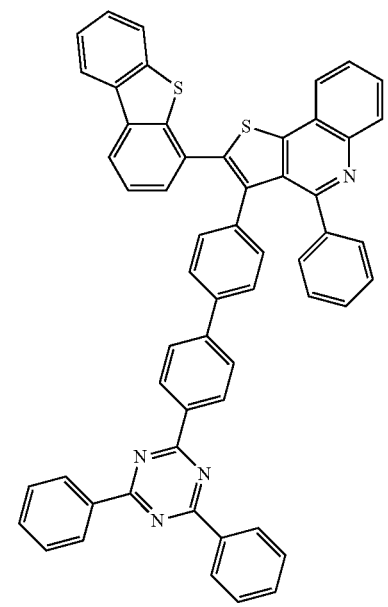
455
456
-continued
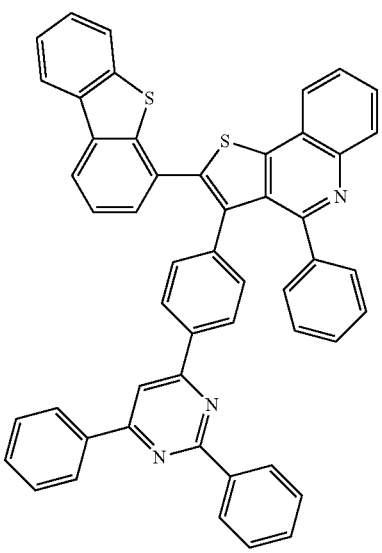
457
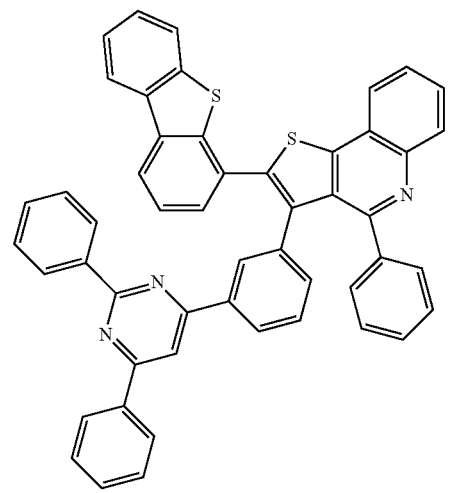
458

459
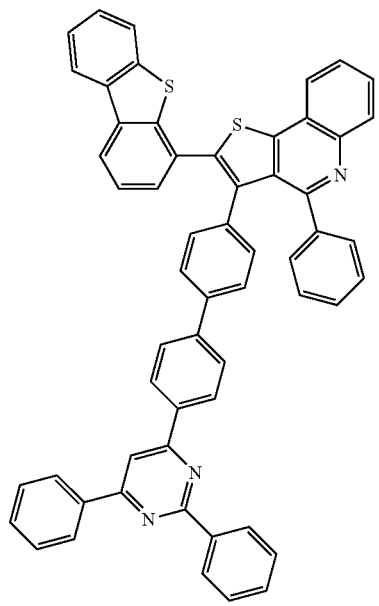
461
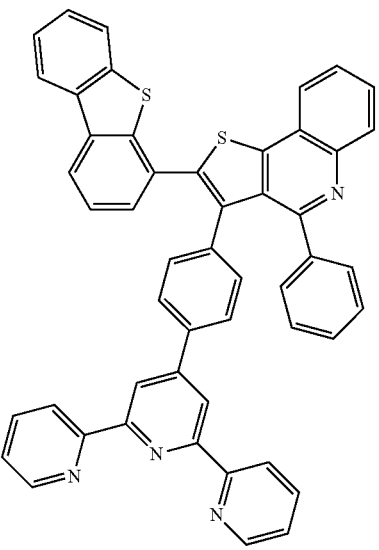
462
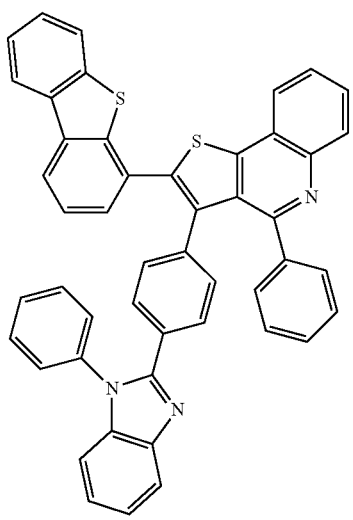
460
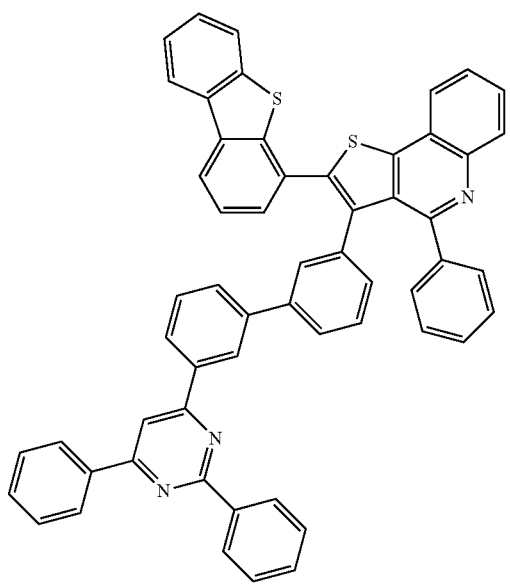
463
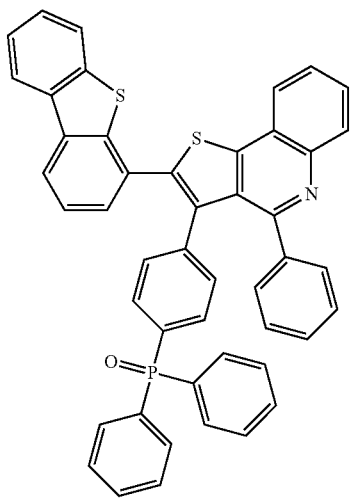

464
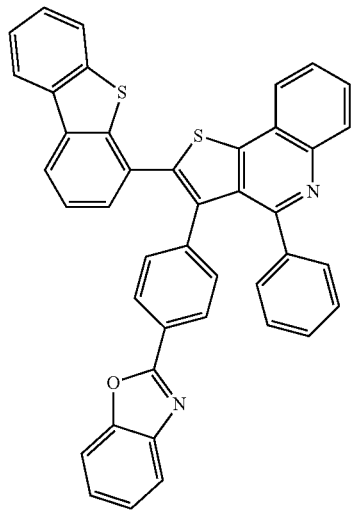
465
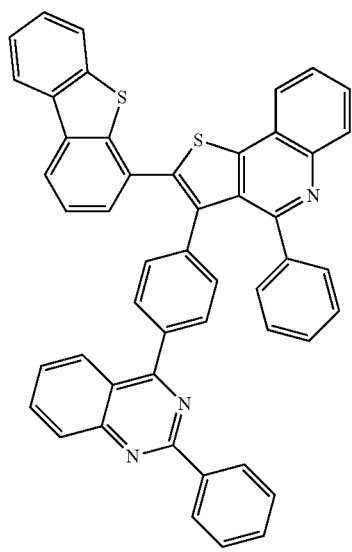
466
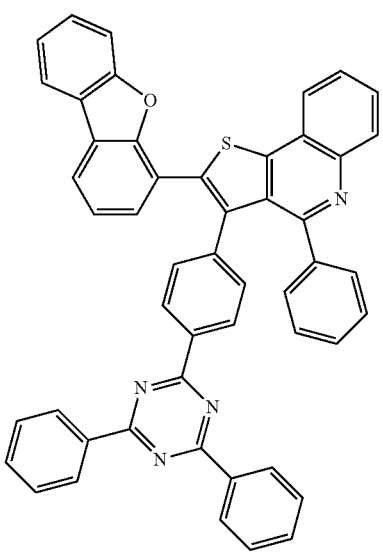
467
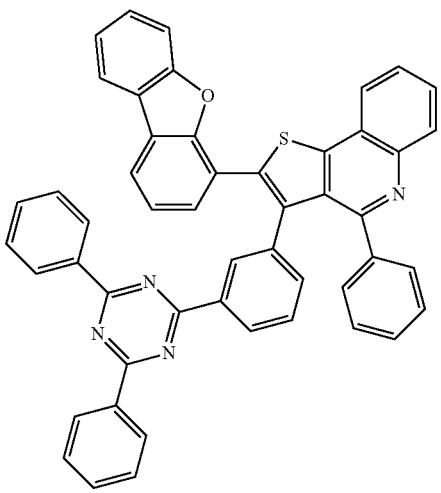
468
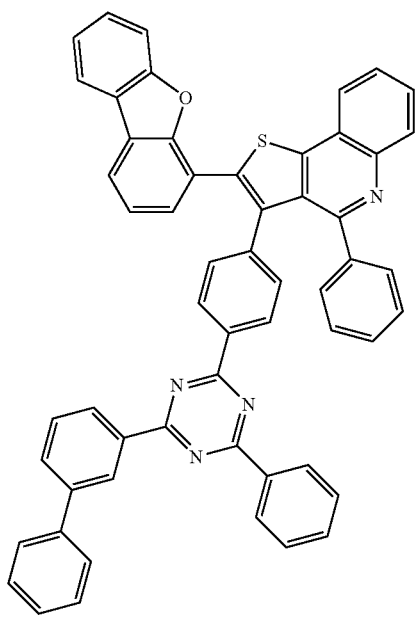

-continued
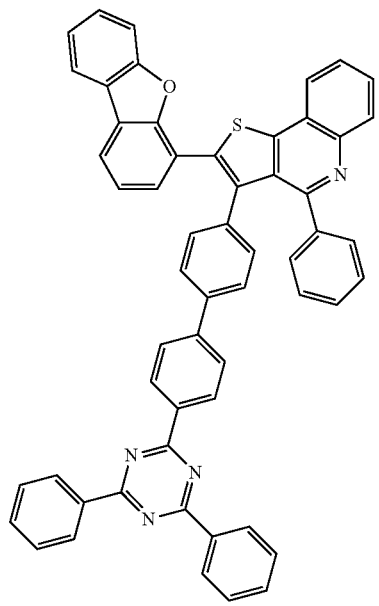
469
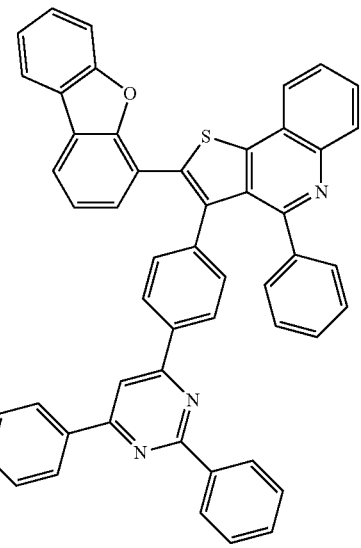
471
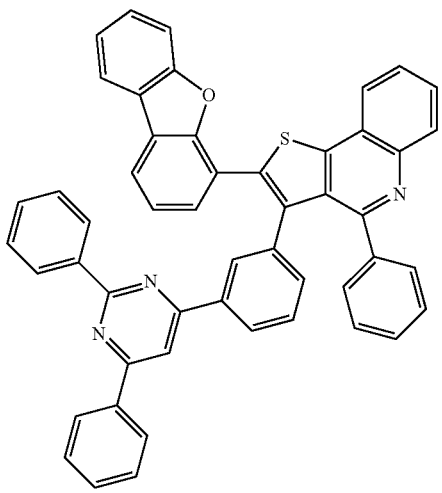
472
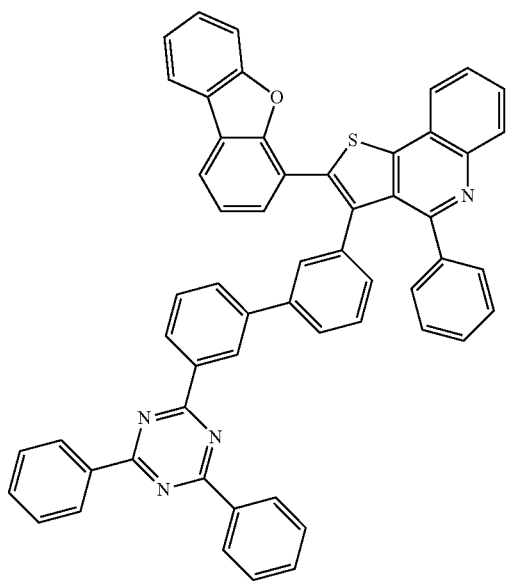
470
473

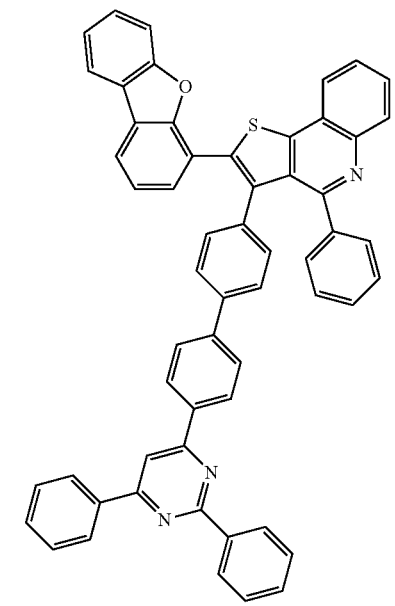
474
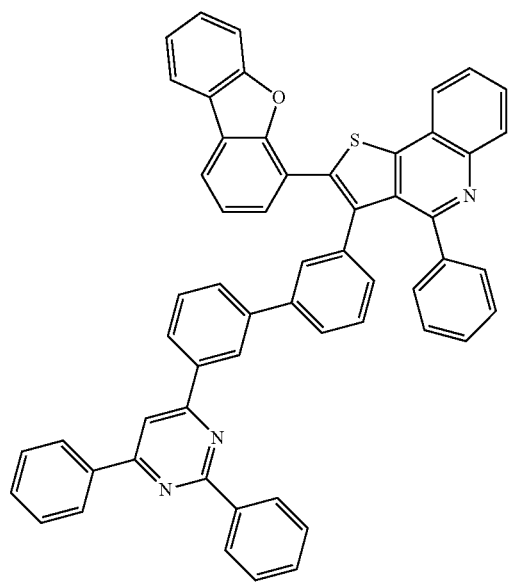
475
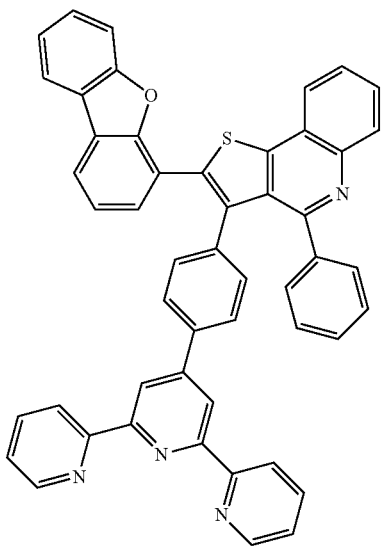
476
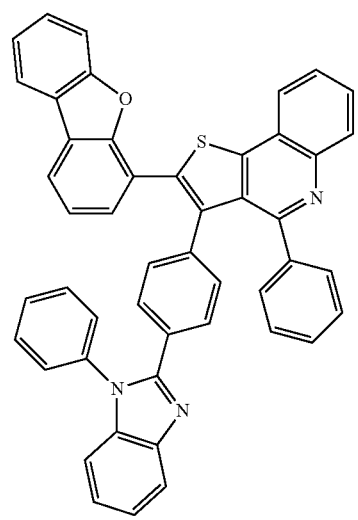
477
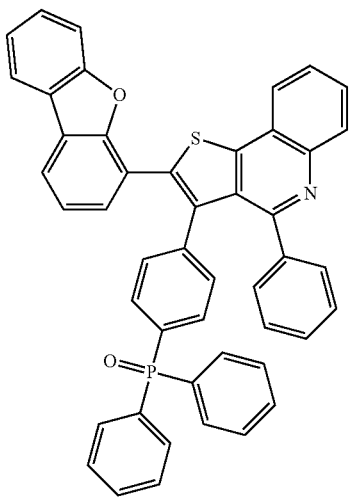
478

697
-continued
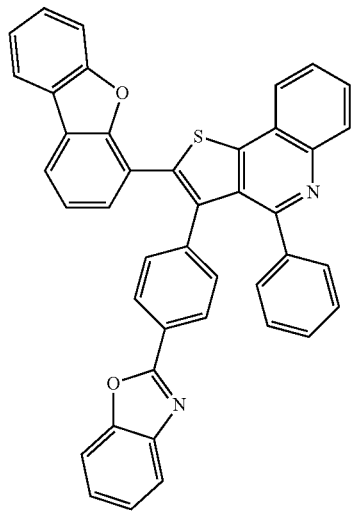
479
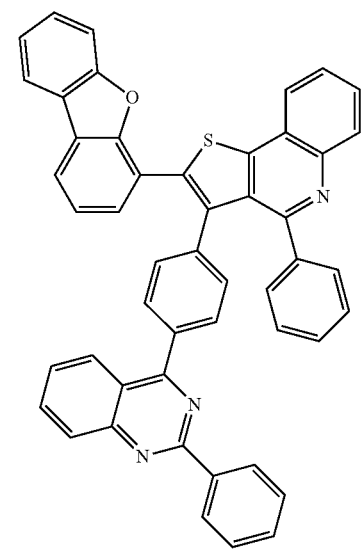
480
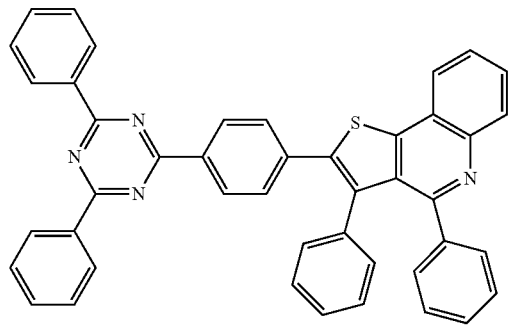
481
698
-continued
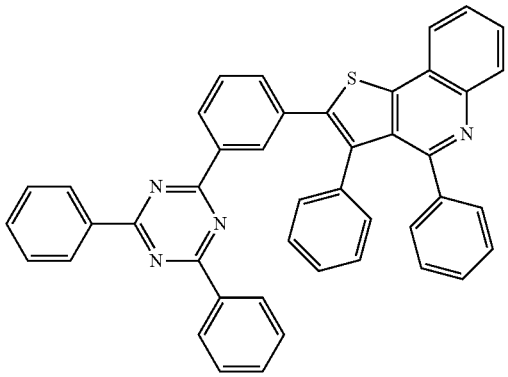
482
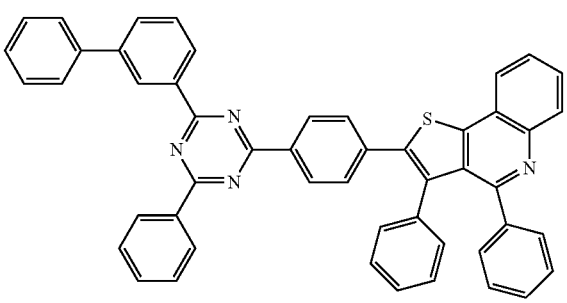
483
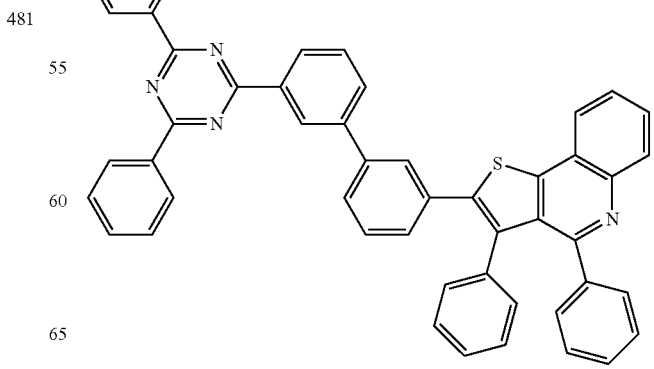
484
485

486
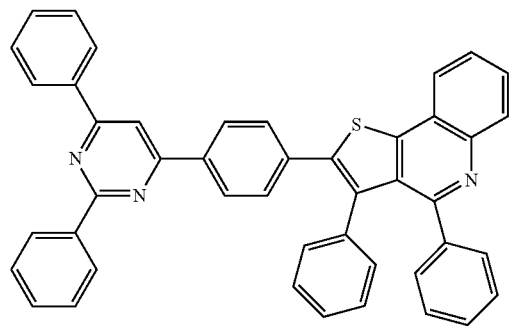
487
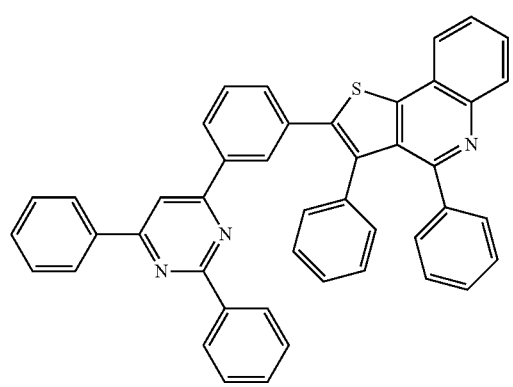
488
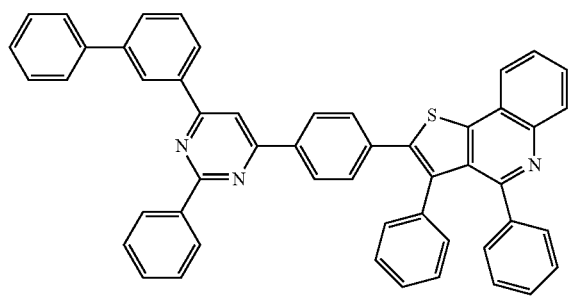
489
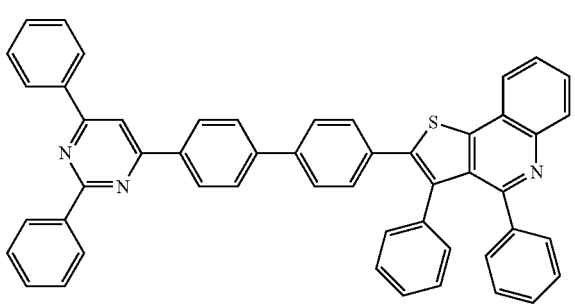
490
491
492
493
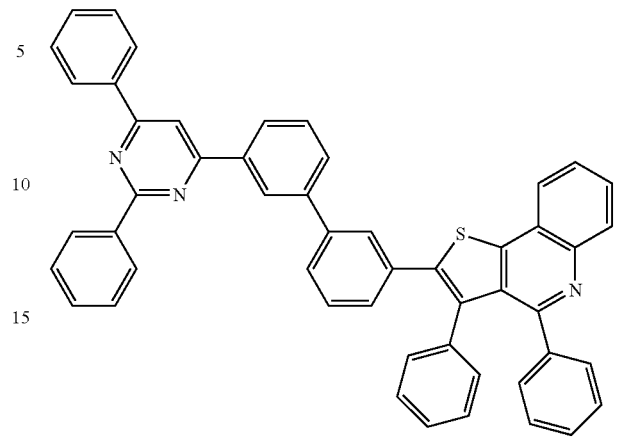
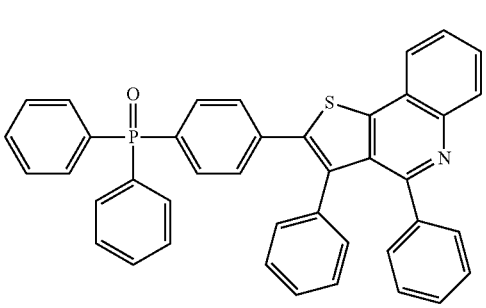

494
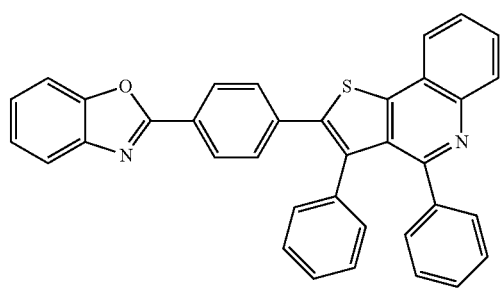
495
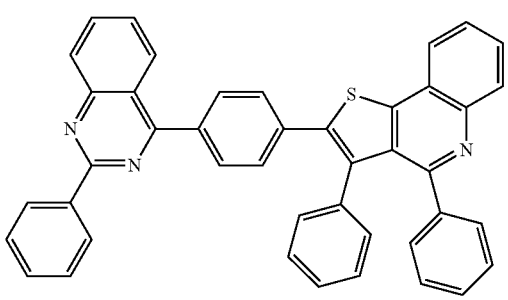
496
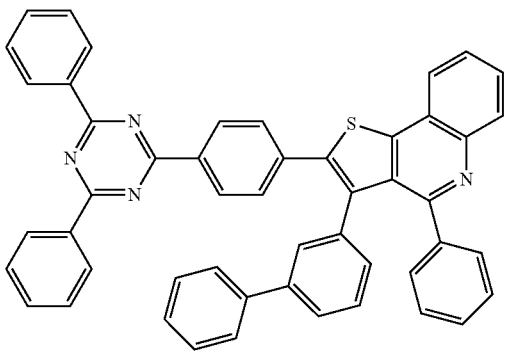
497
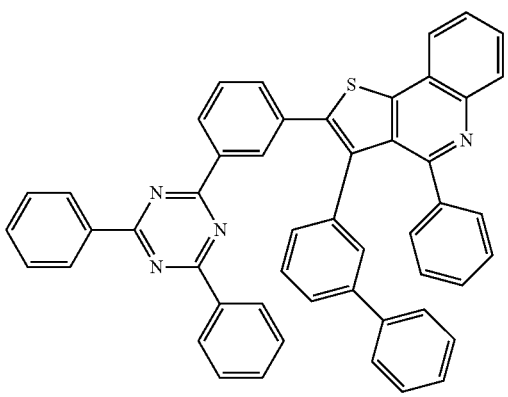
498
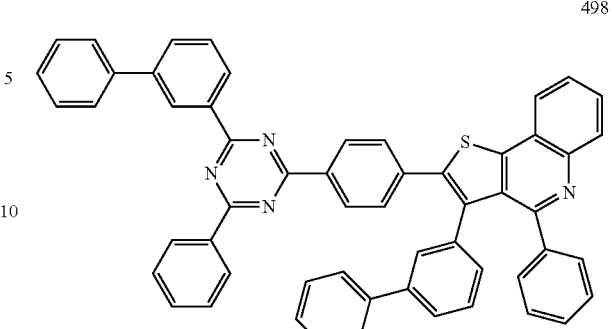
499
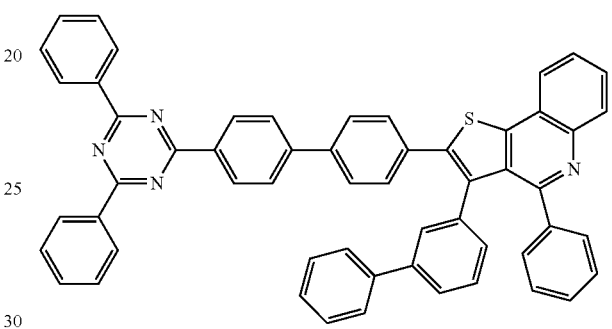
500
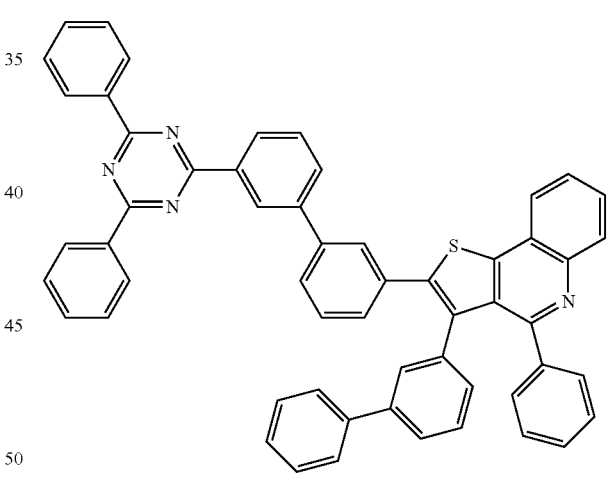
501
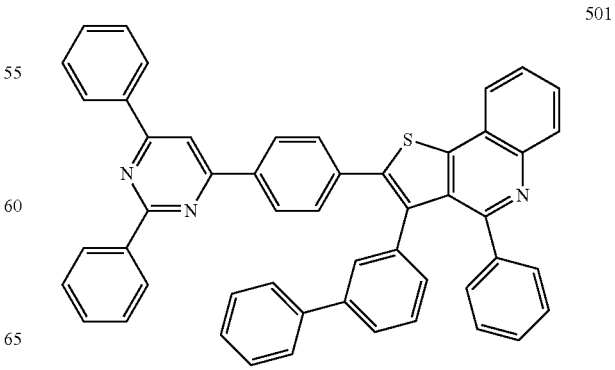

502
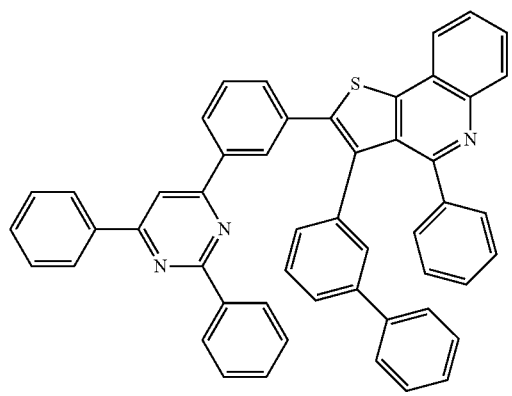
506
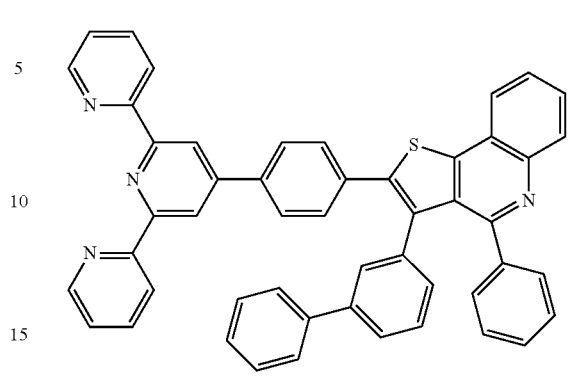
503
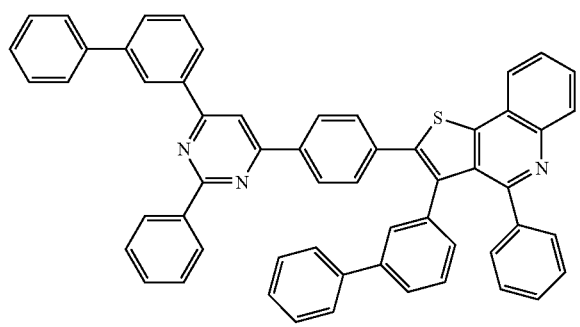
507
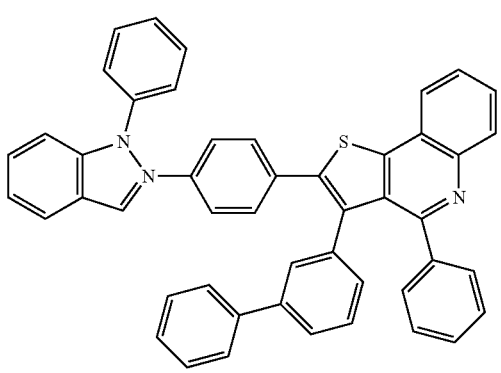
504
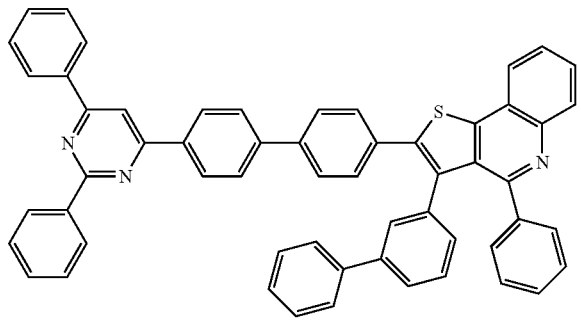
508
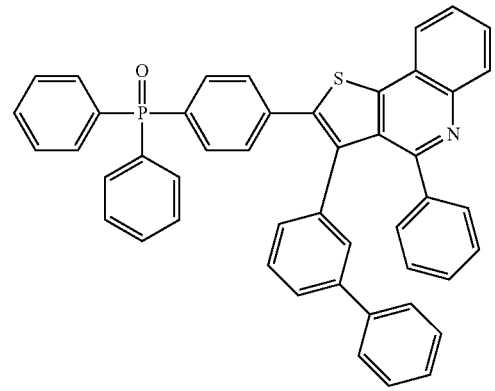
505
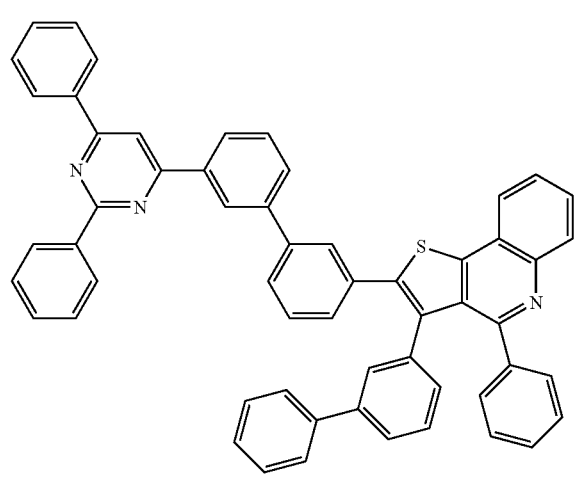
509
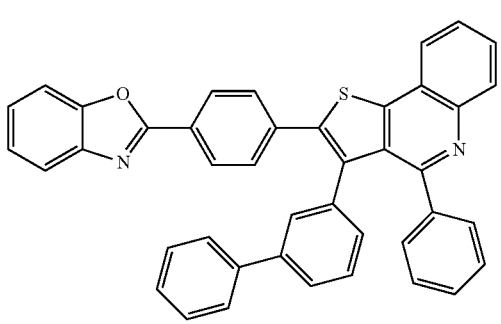

-continued
510
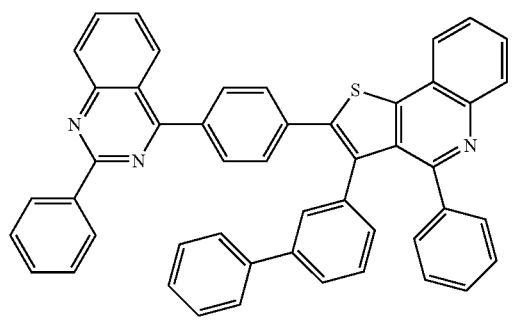
511
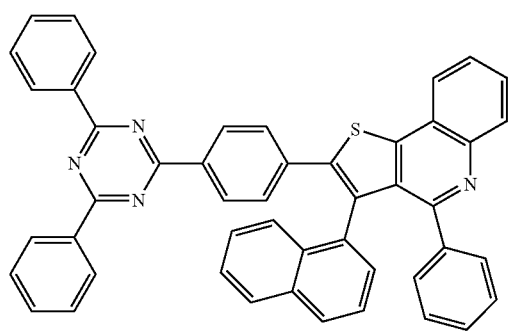
512
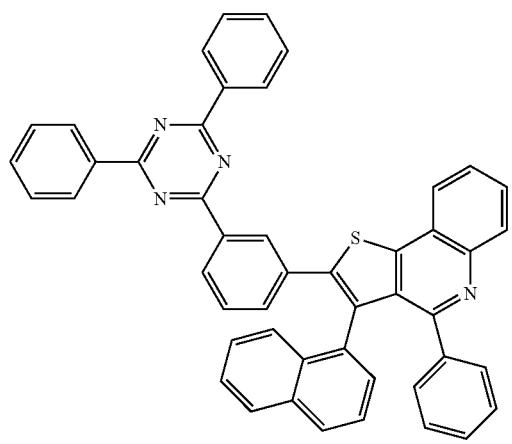
513
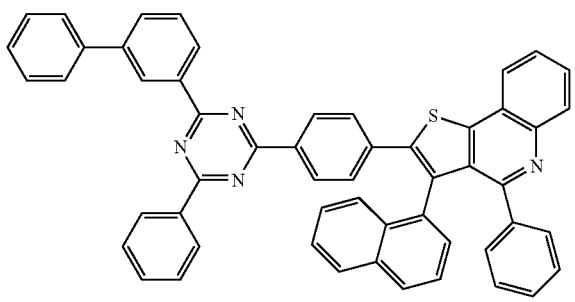
-continued
514
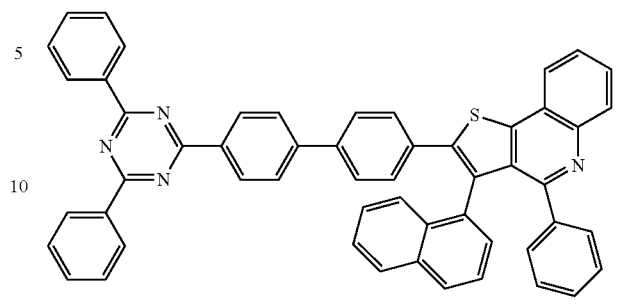
515
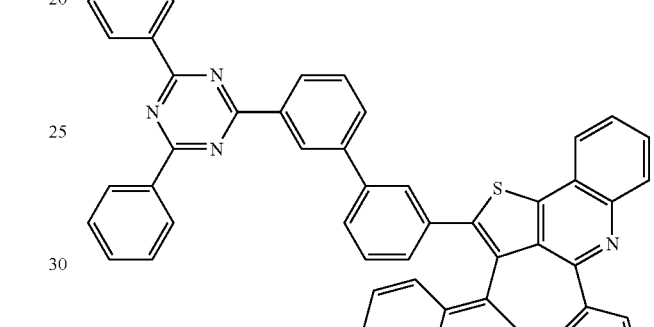
516
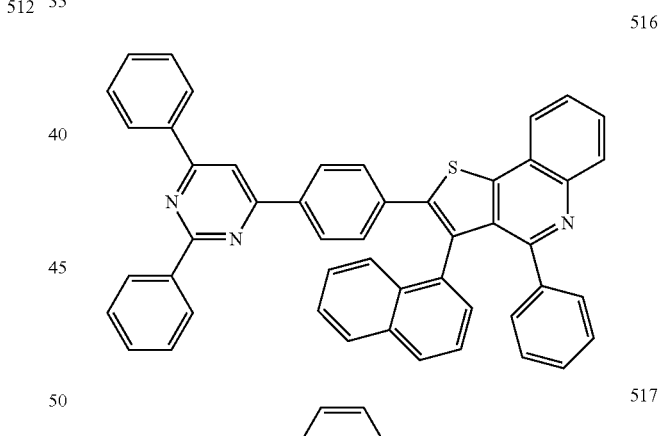
517
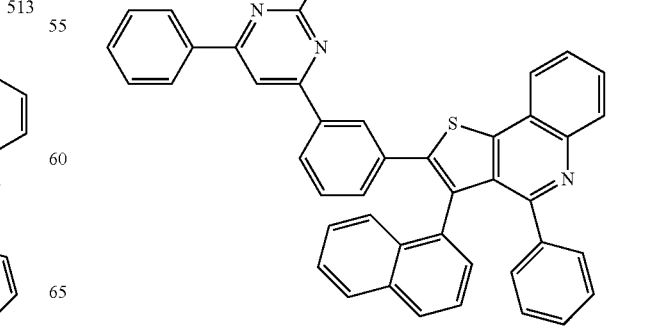

707
-continued
518
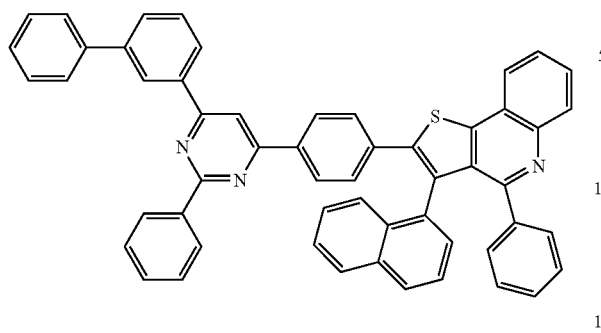
519
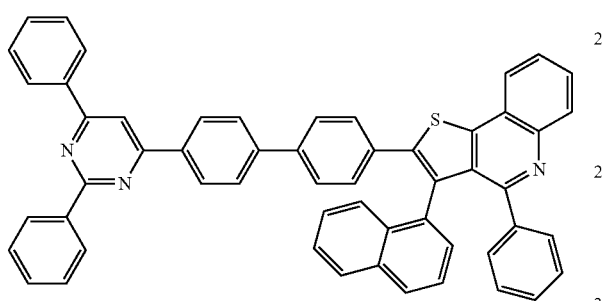
520
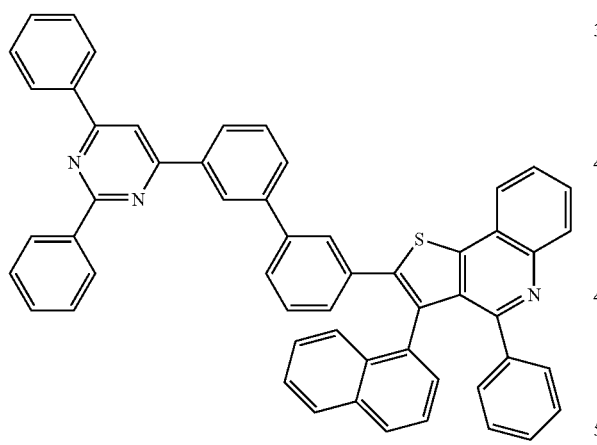
521
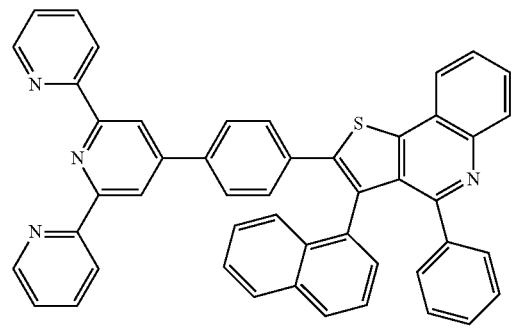
708
-continued
522
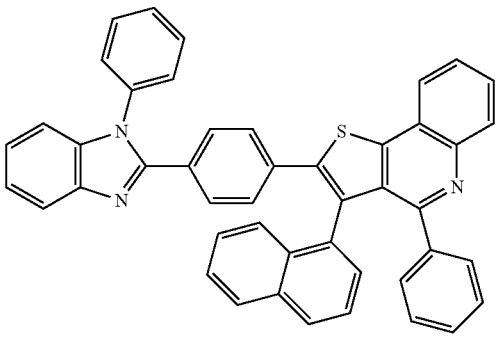
523
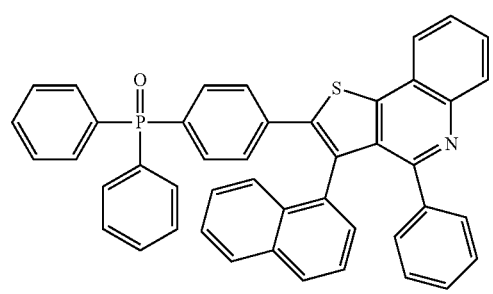
524
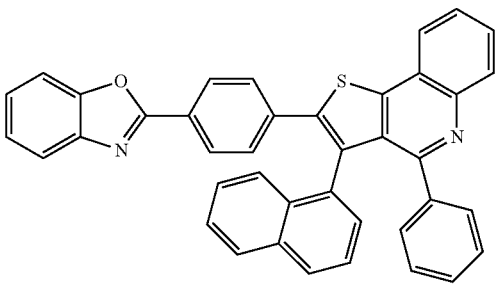
525
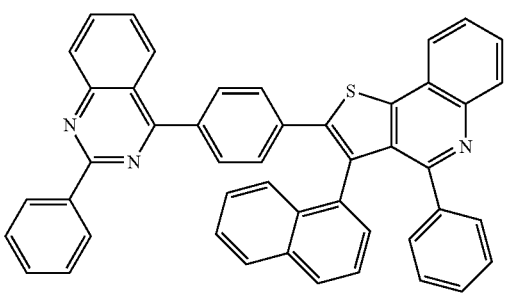

526
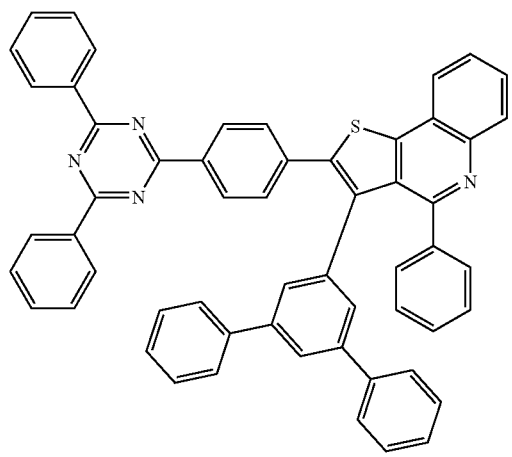
529
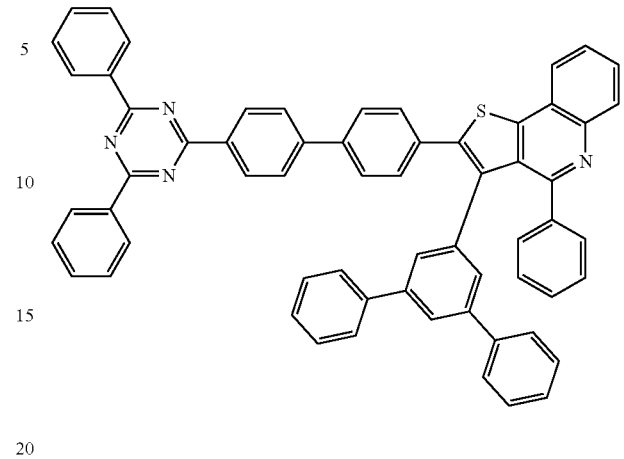
527
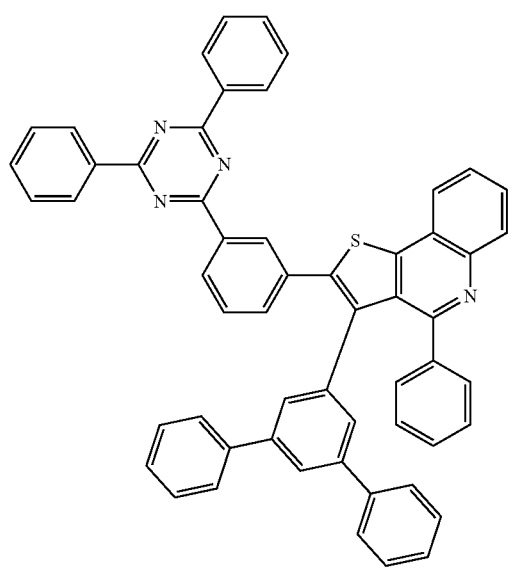
530
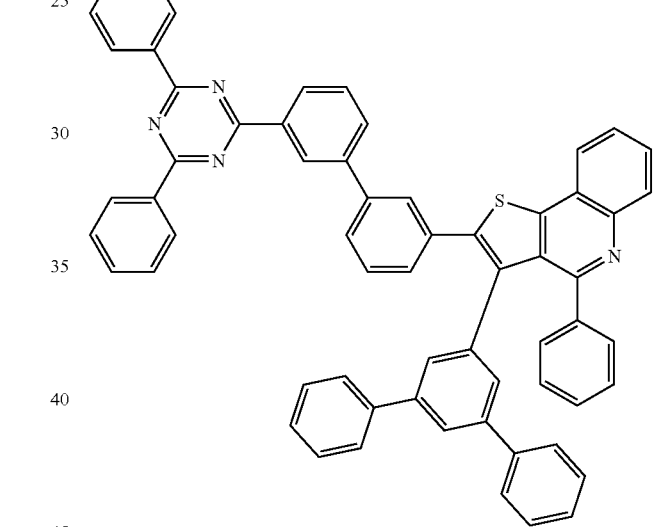
528
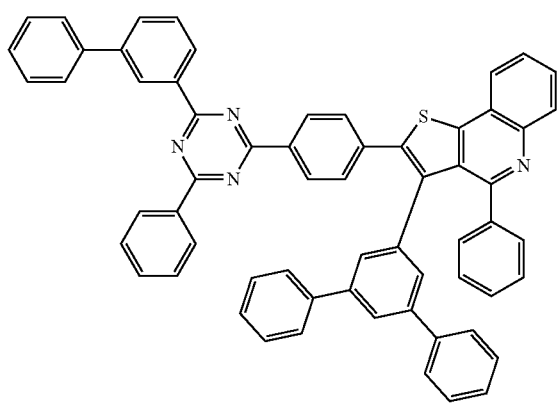
531
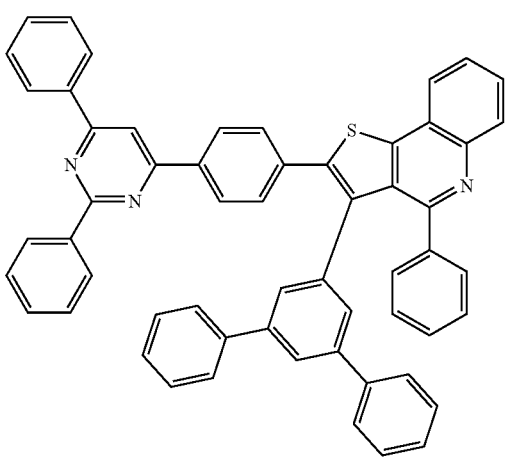

711
-continued
532
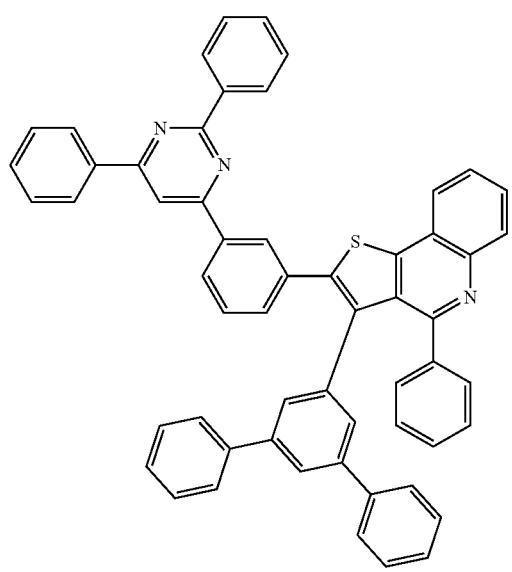
533
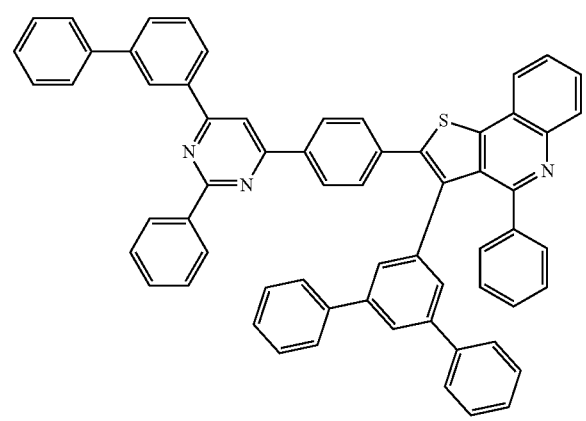
534
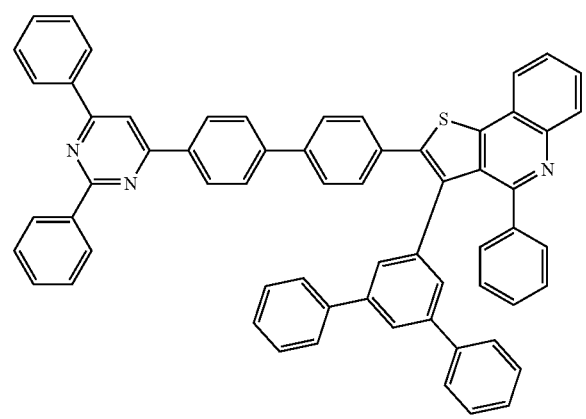
712
-continued
535
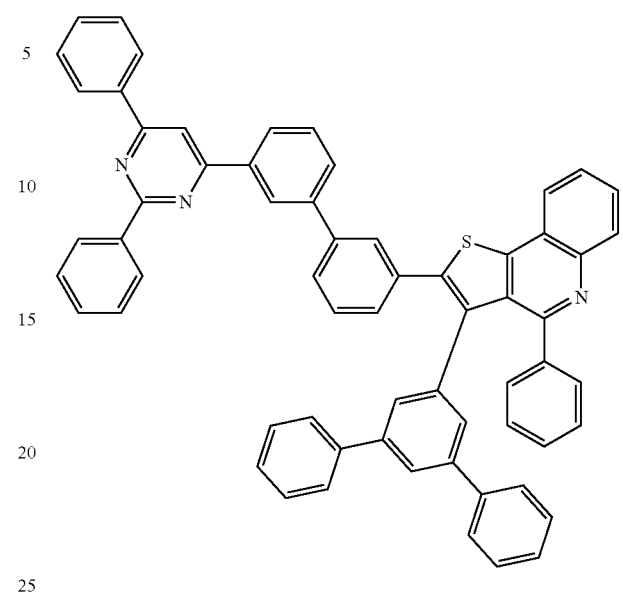
536
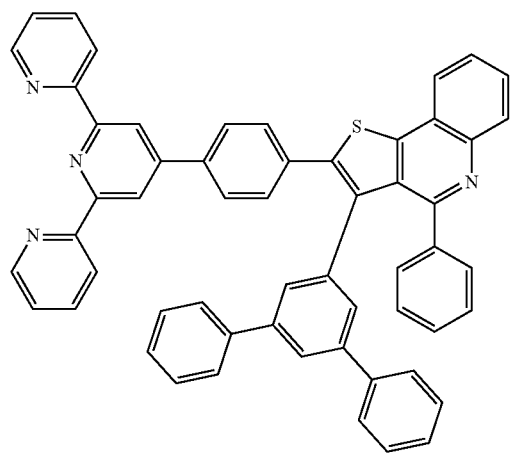
537
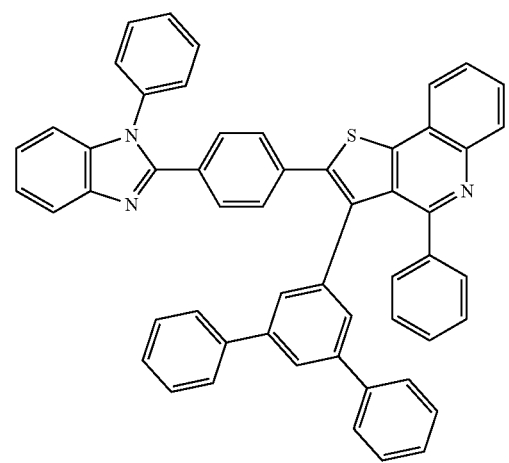

| 538 | 541 |
|---|---|
| 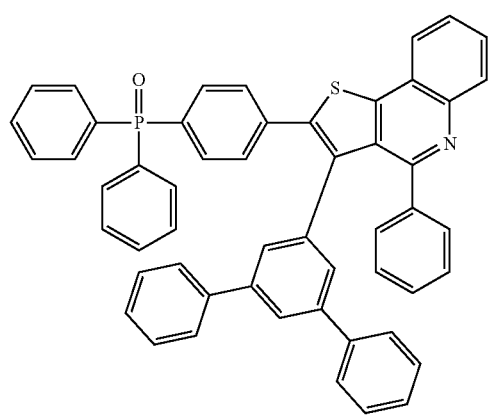 | 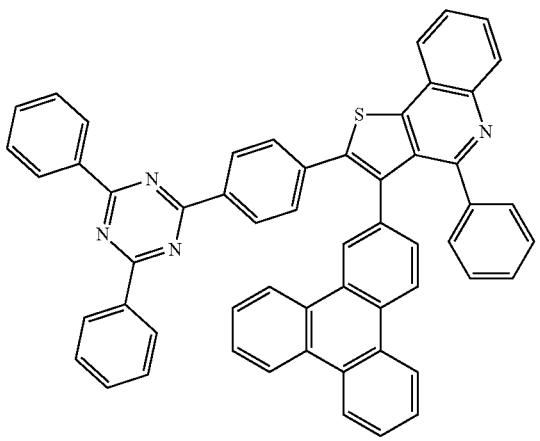 |
| 539 | 542 |
|---|---|
| 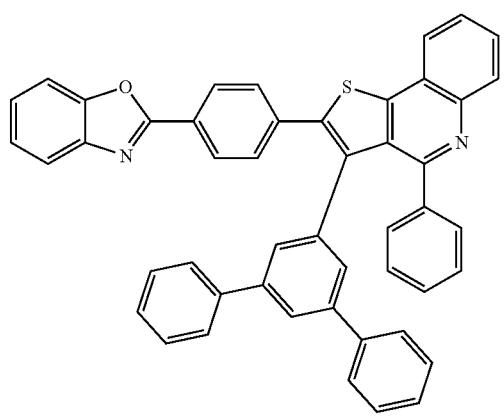 | 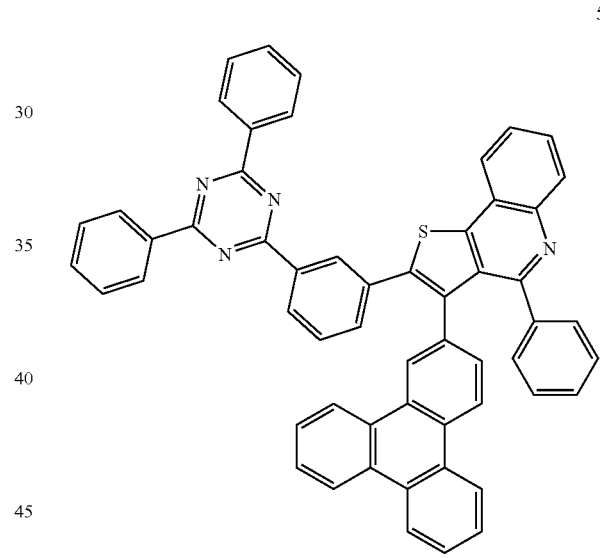 |
| 540 | 543 |
|---|---|
| 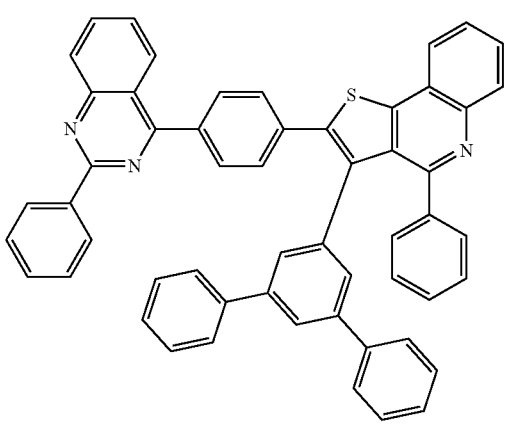 | 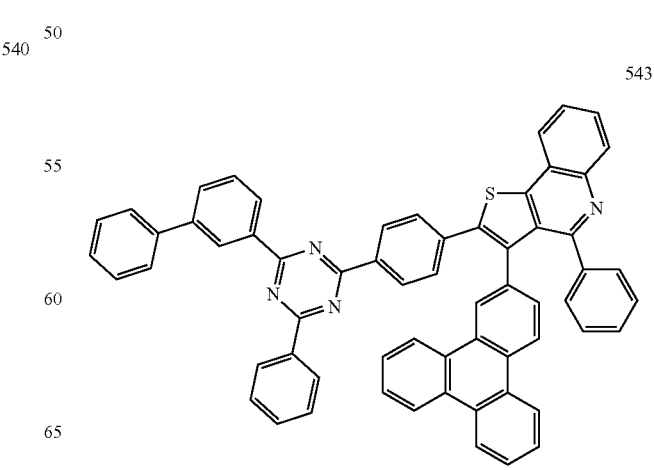 |

715
-continued
544
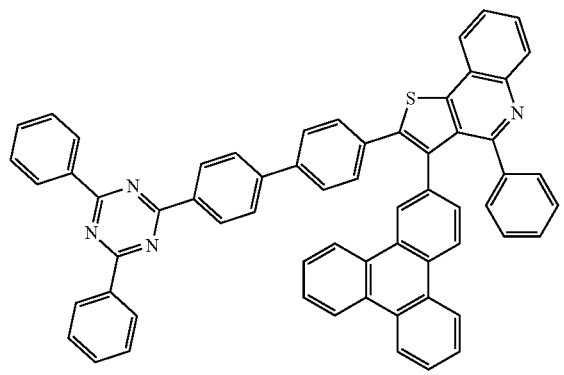
545
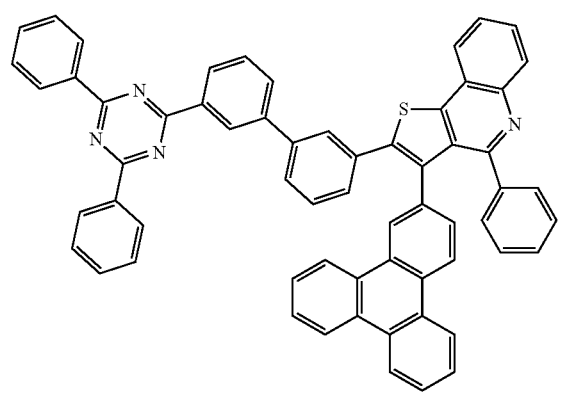
546
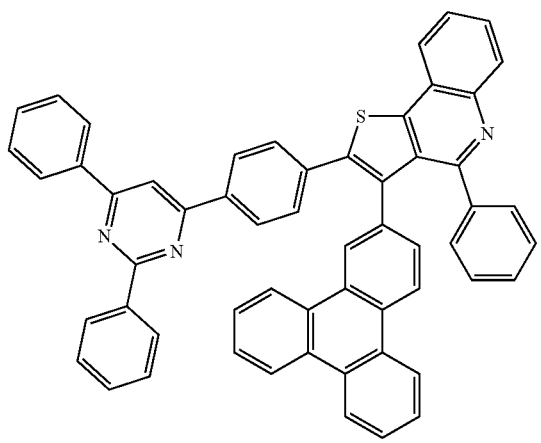
716
-continued
547
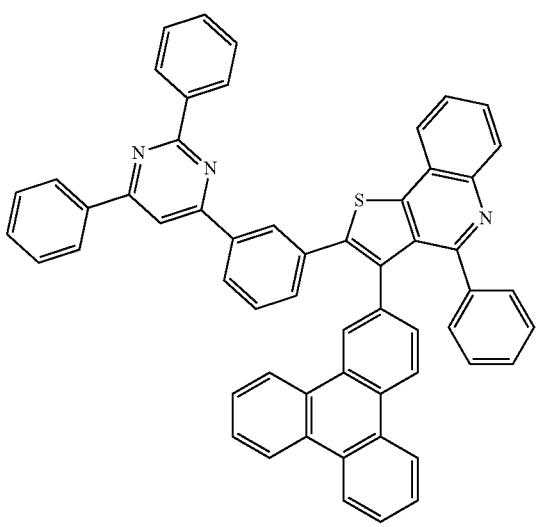
548
549
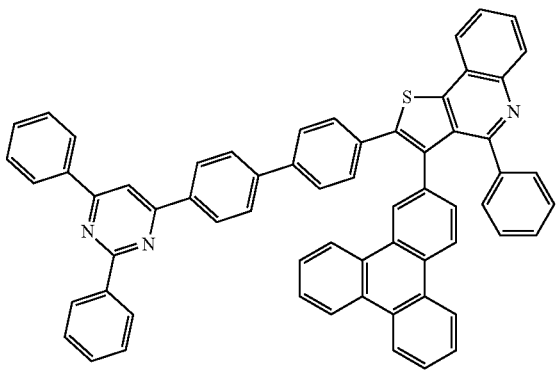

717 -continued
550
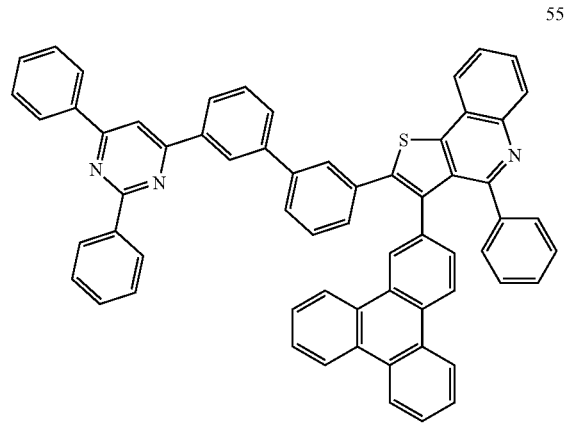
551
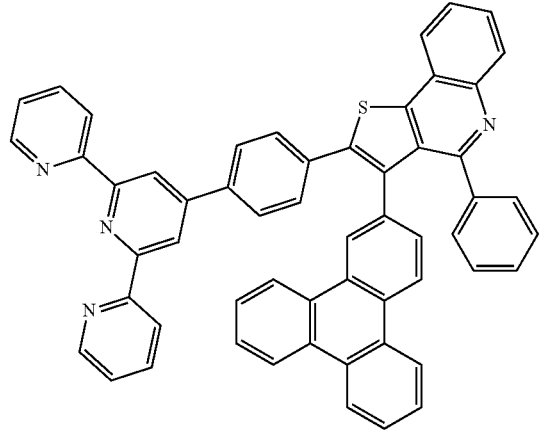
552
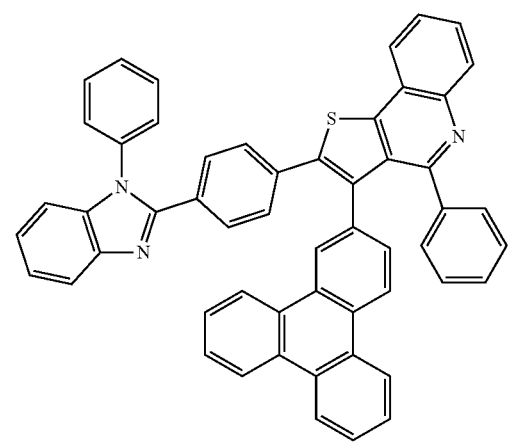
718 -continued
553
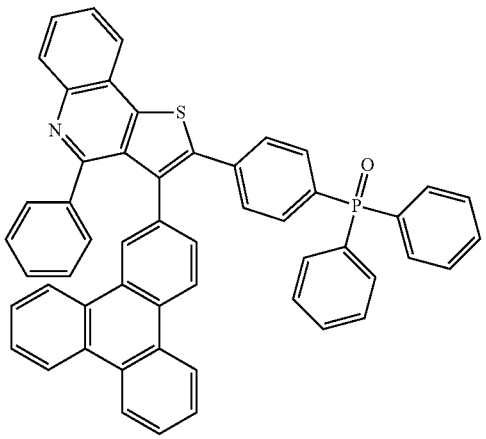
554
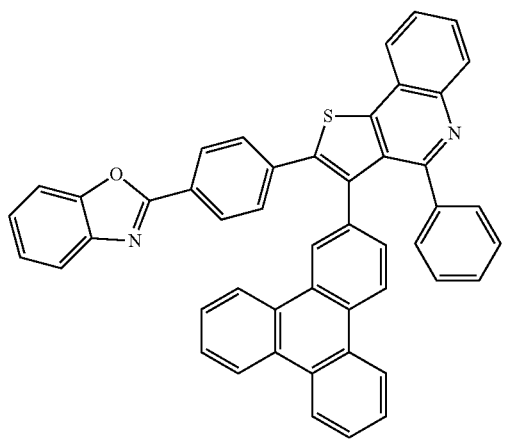
555
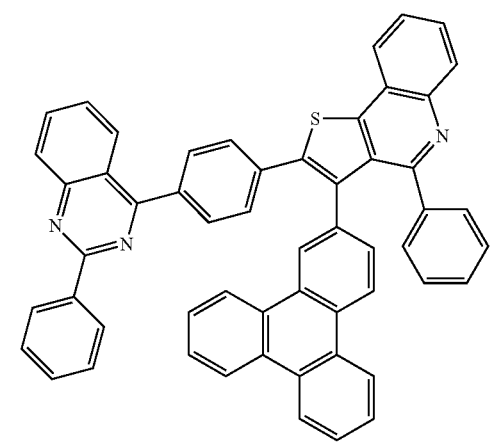
556
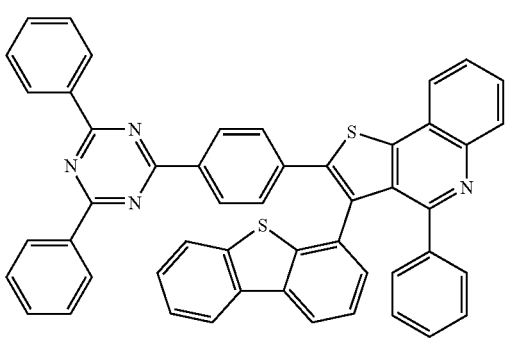

557 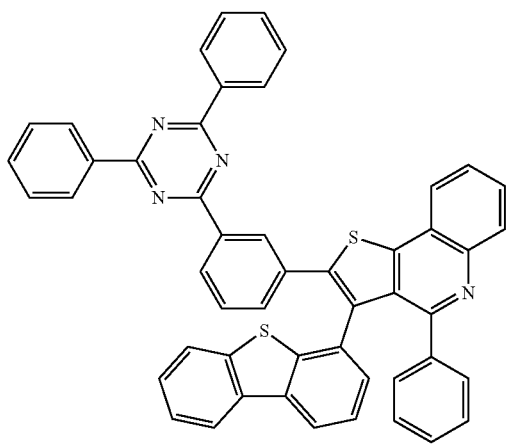
558 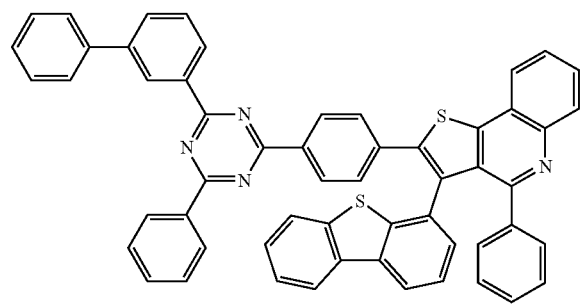
559 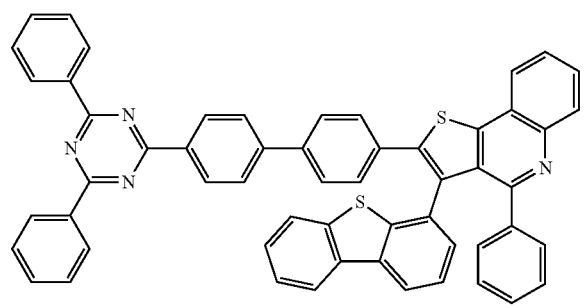
560 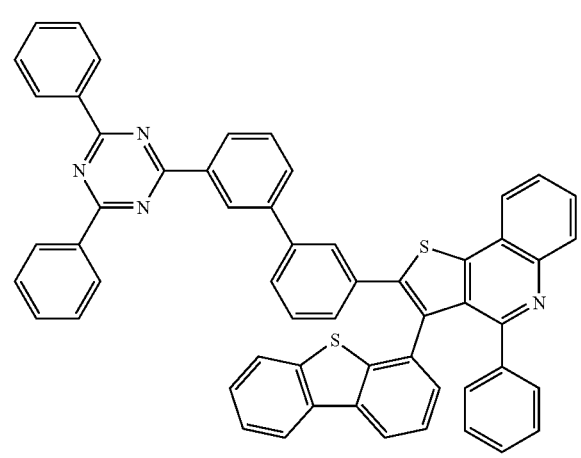
561 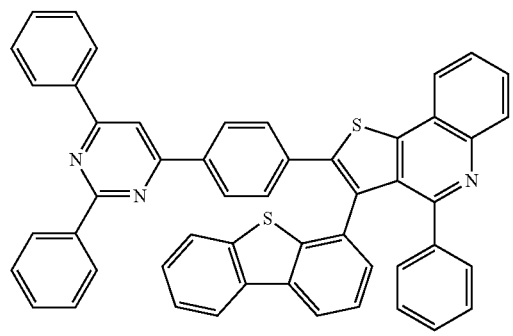
562 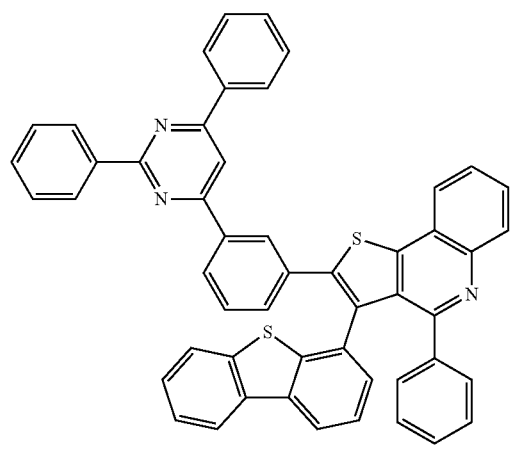
563 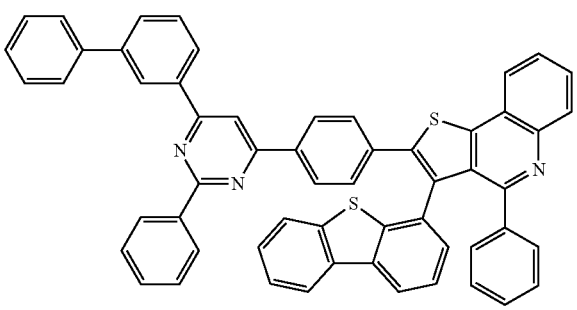
564 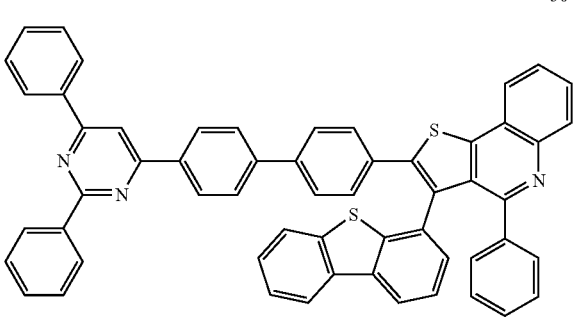

-continued
565
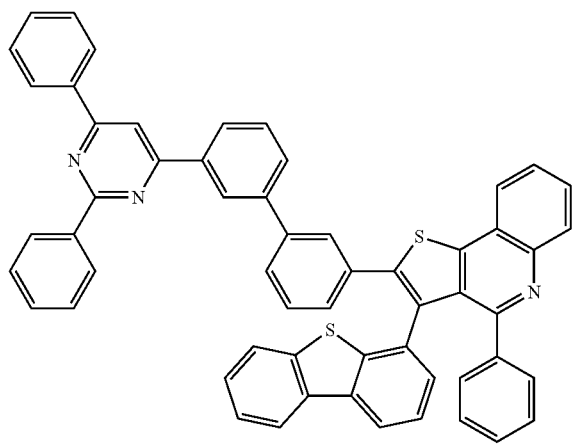
566
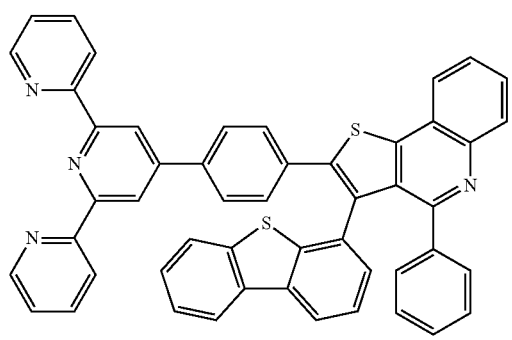
567
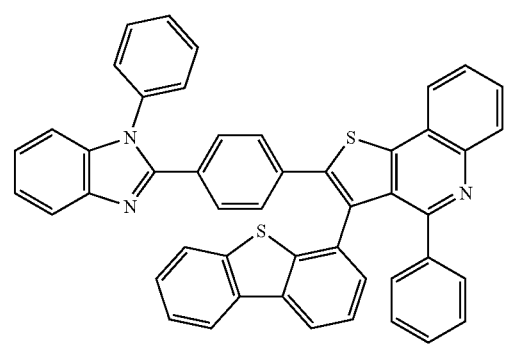
568
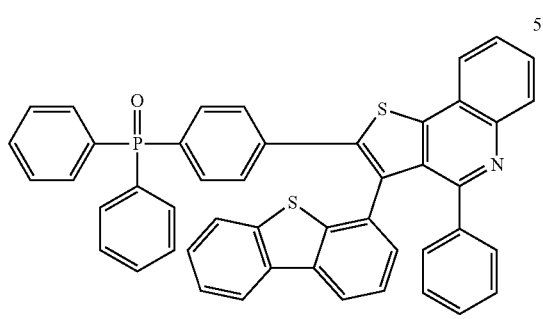
-continued
569
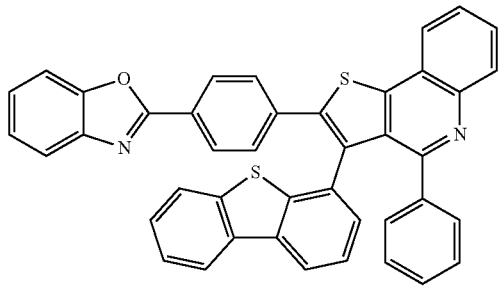
570
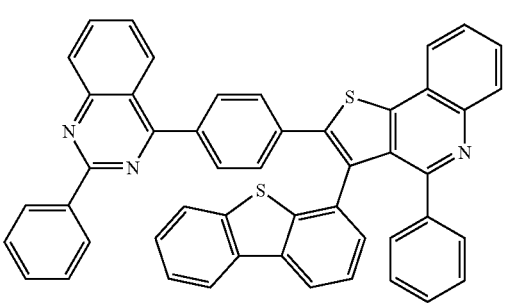
571
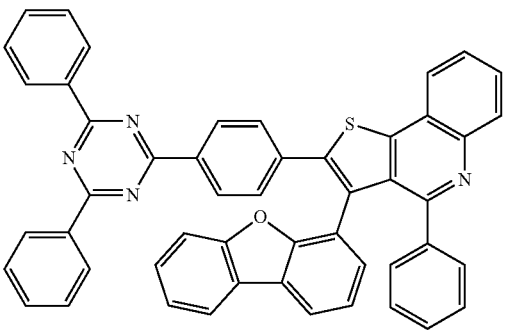
572
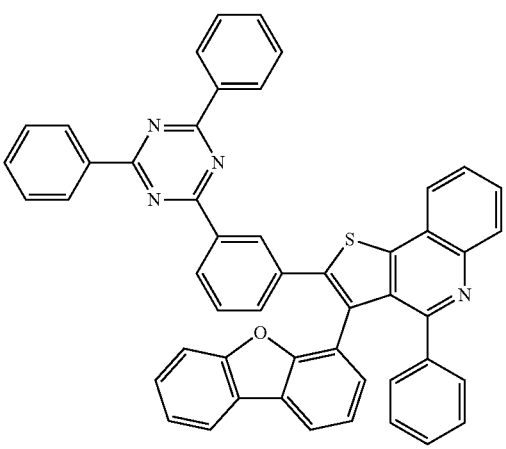

723
-continued
573
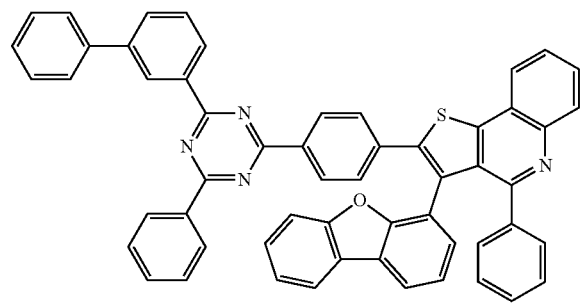
574
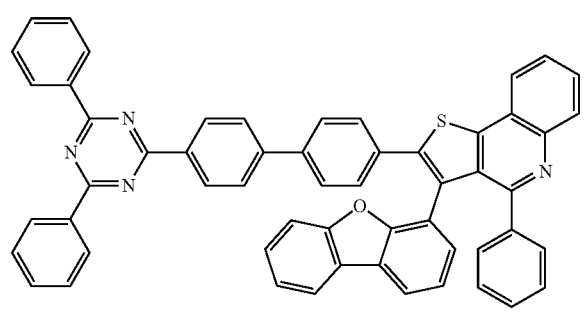
575
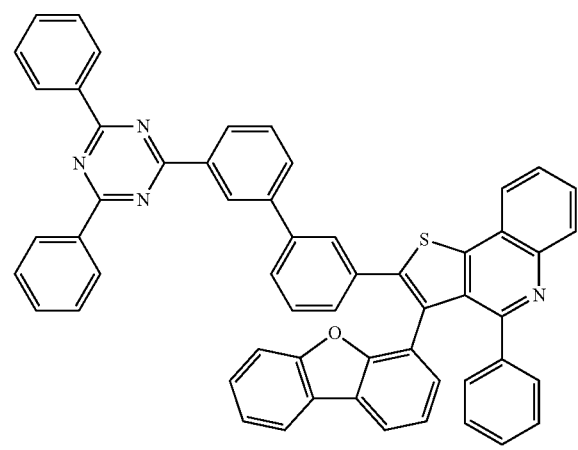
576
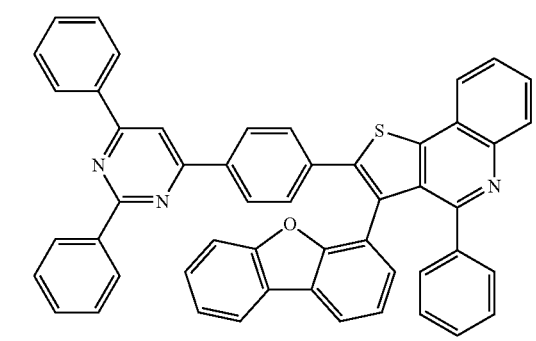
724
-continued
577
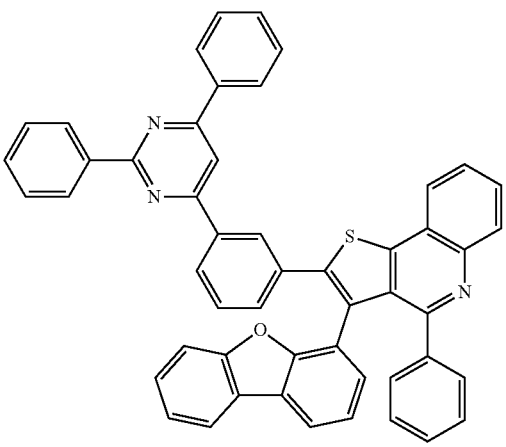
578
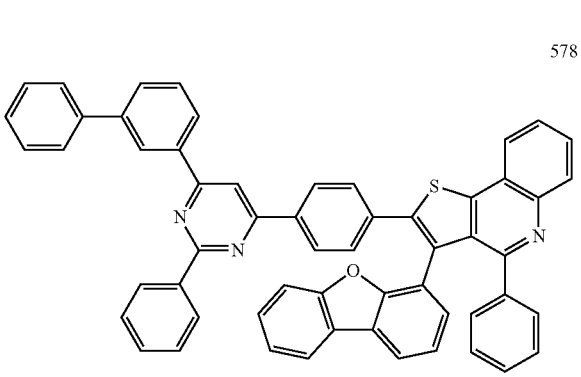
579
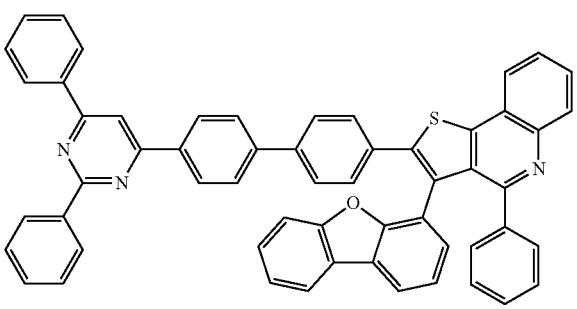
580
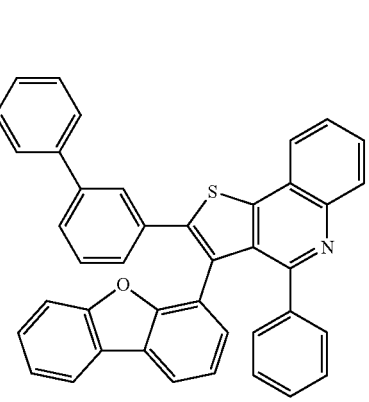

725
-continued
581
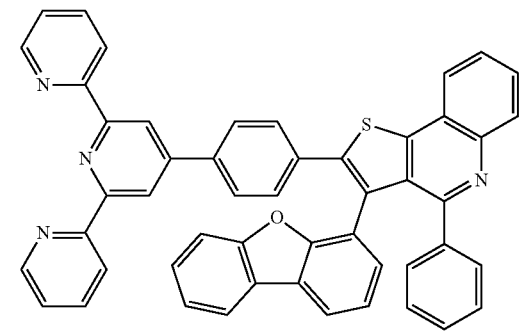
582
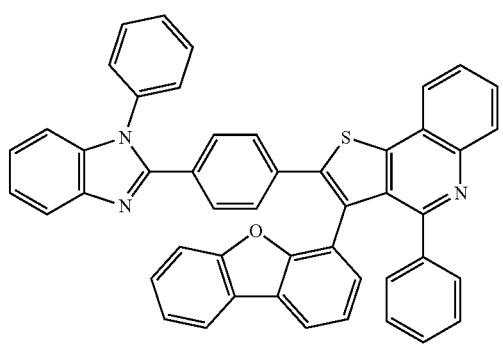
583
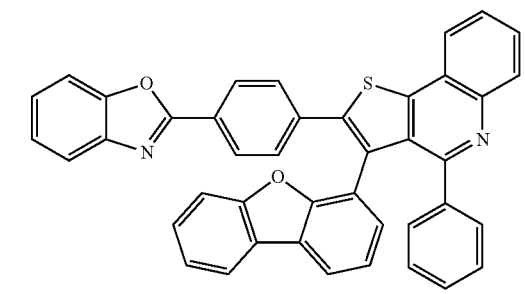
584
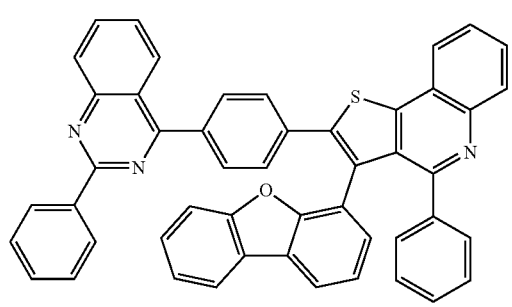
585
726
-continued
586
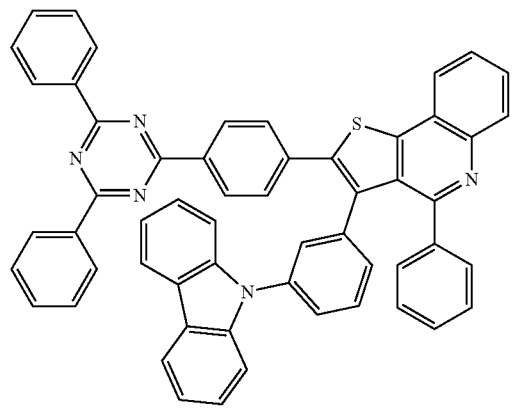
587
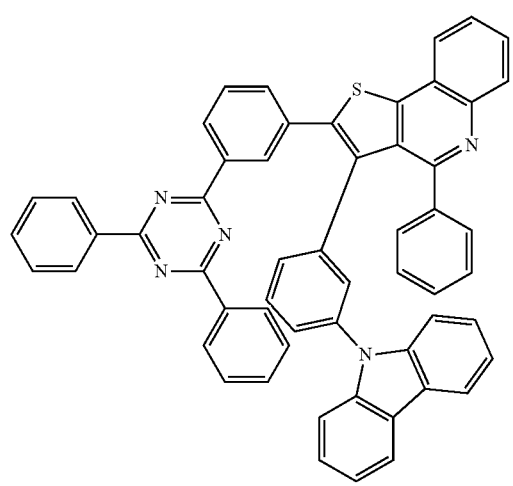
588
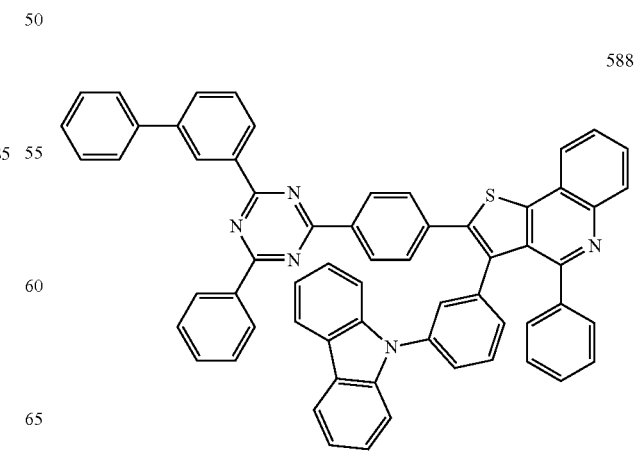

727
-continued
728
-continued
589
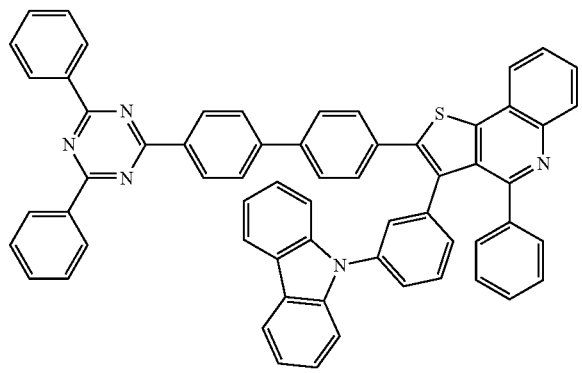
592
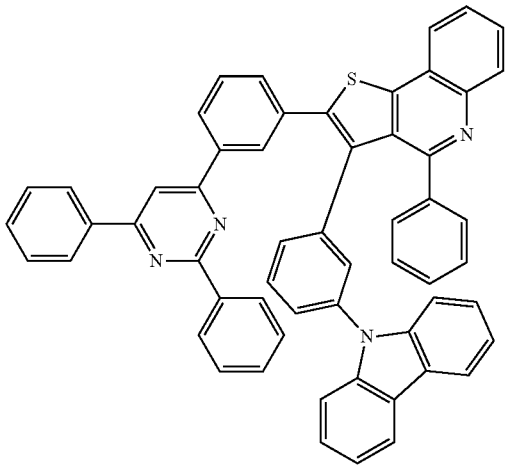
590
593
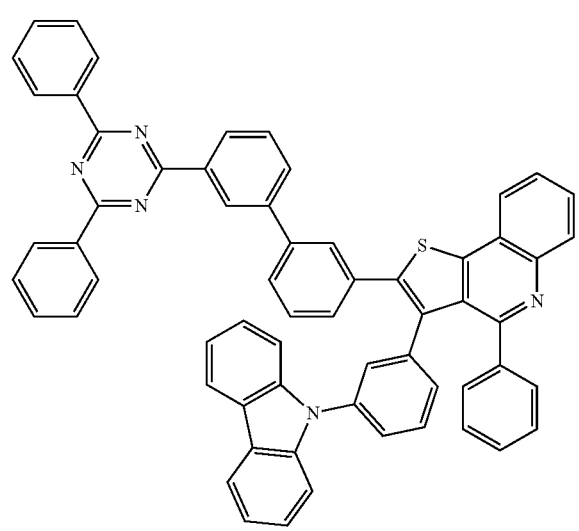
591
594
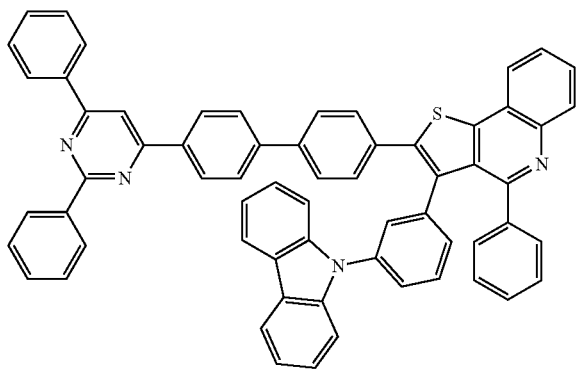
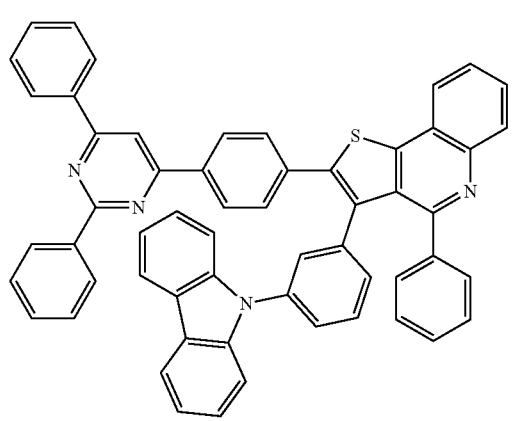

729
-continued
730
-continued
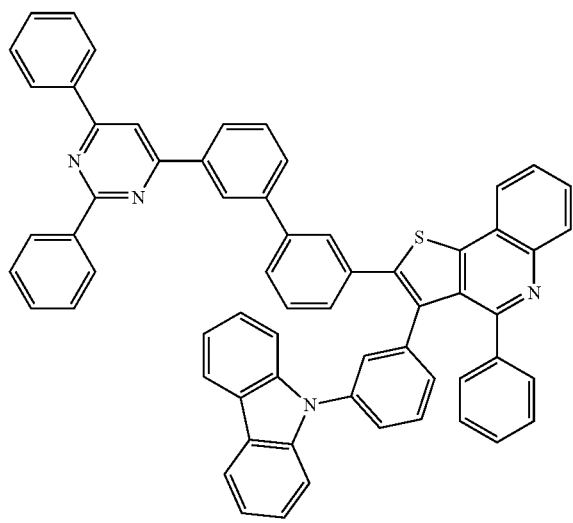
595
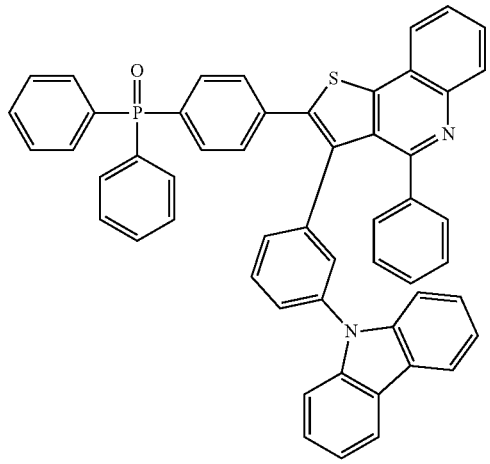
598
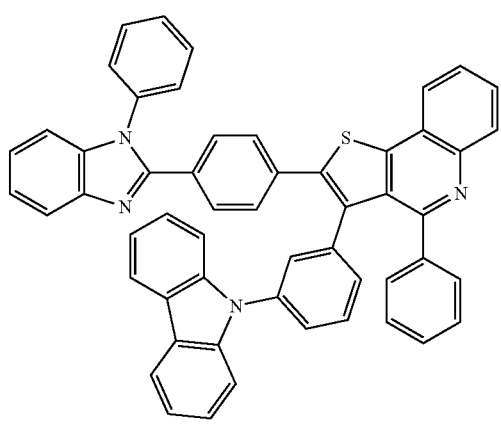
596
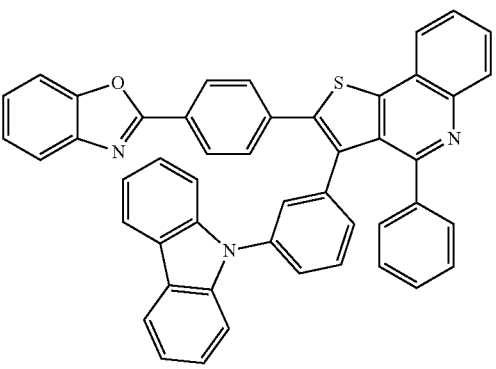
599
597
600

731
-continued
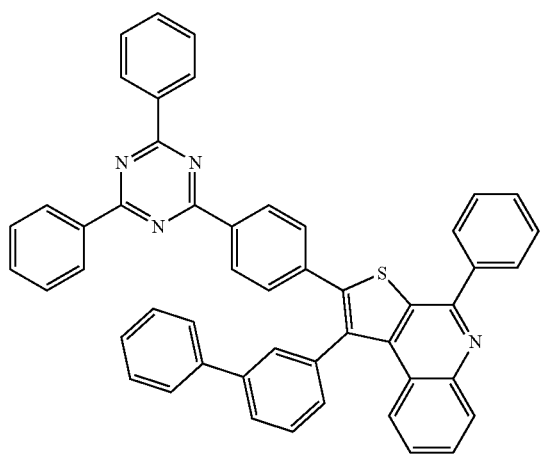
601
602
732
-continued
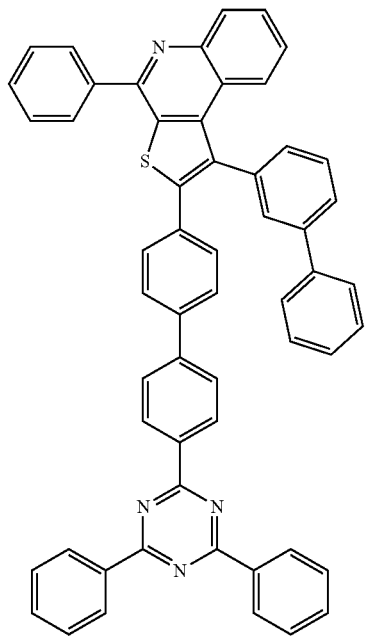
604
605
603
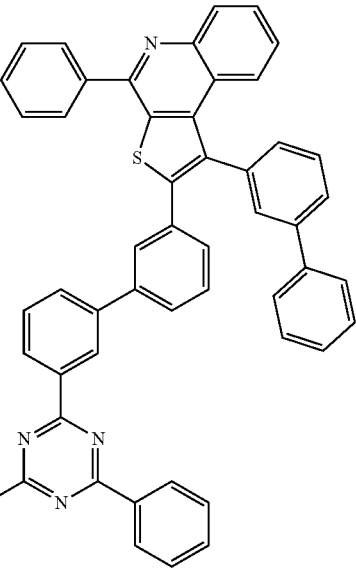

606
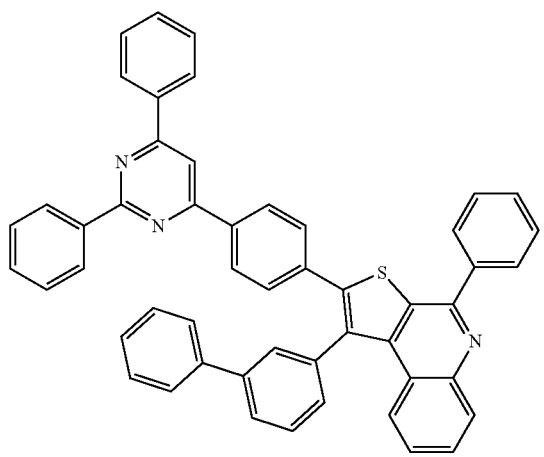
607
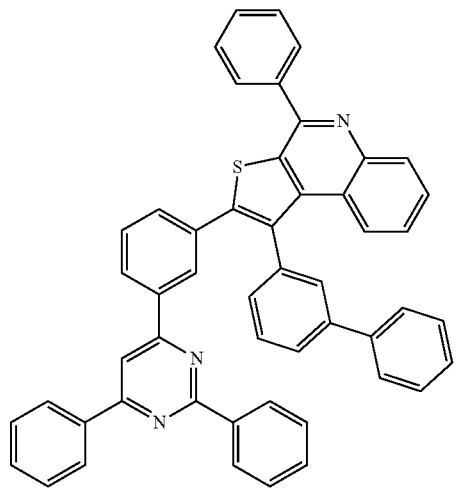
608
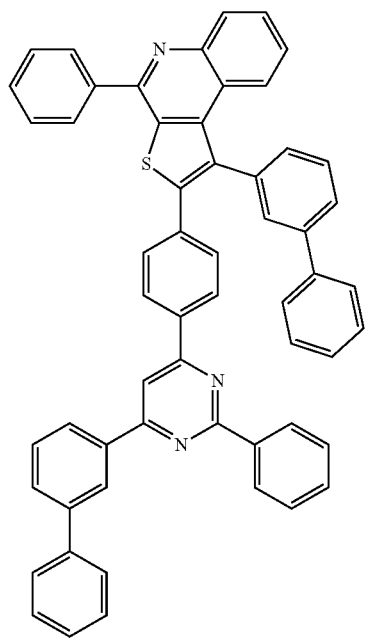
609
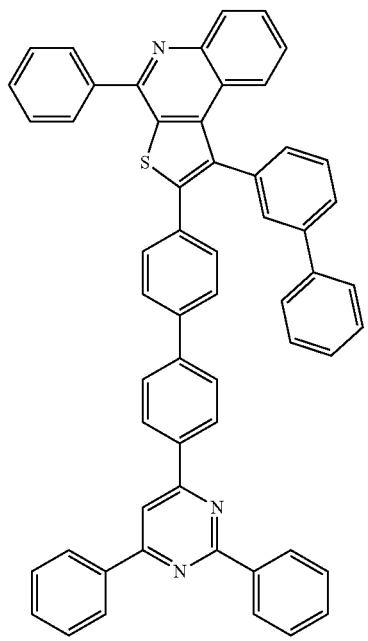
610
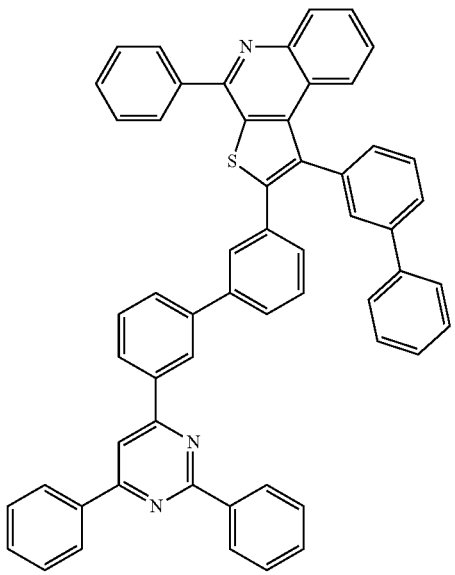

611
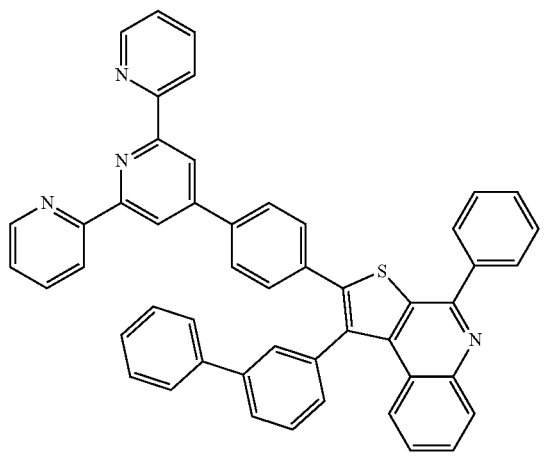
612
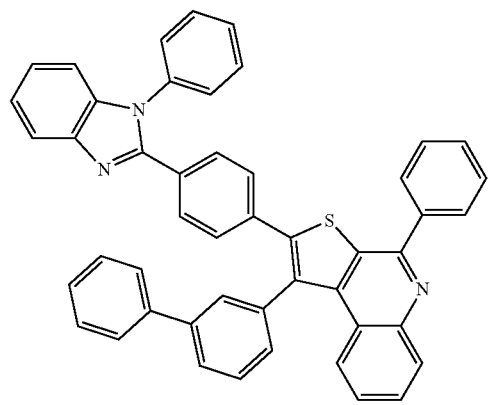
613
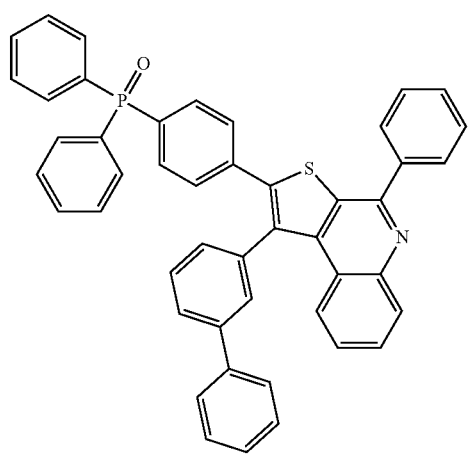
614
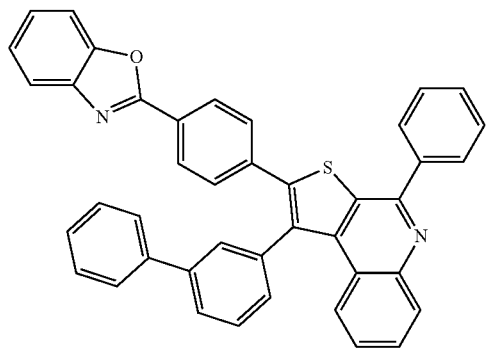
615
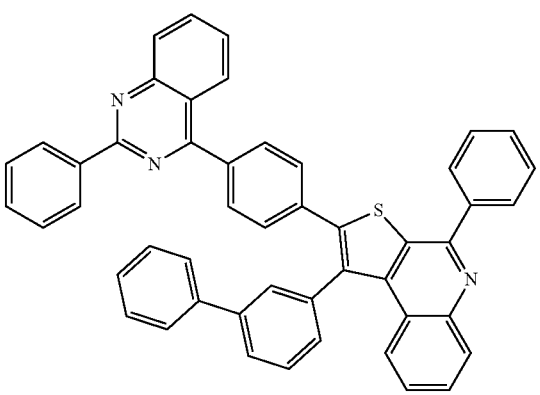
616
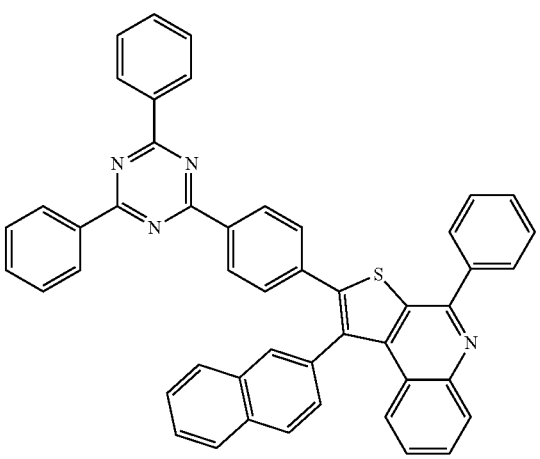

617
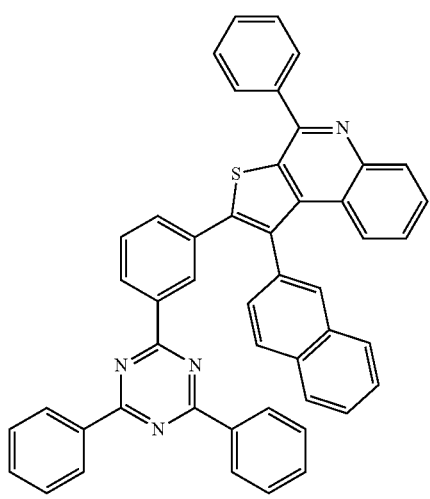
618
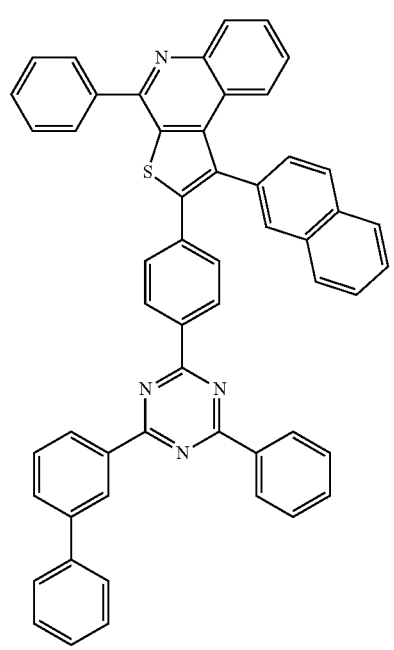
619
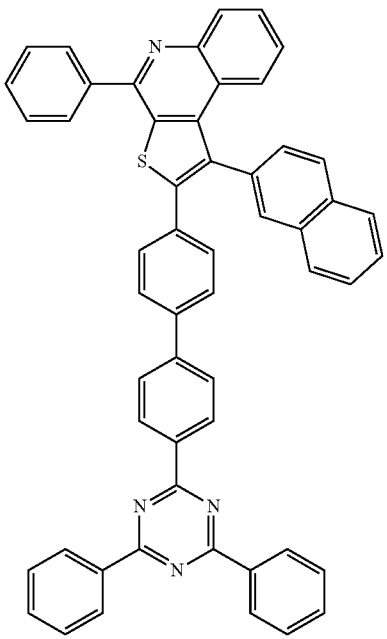
620
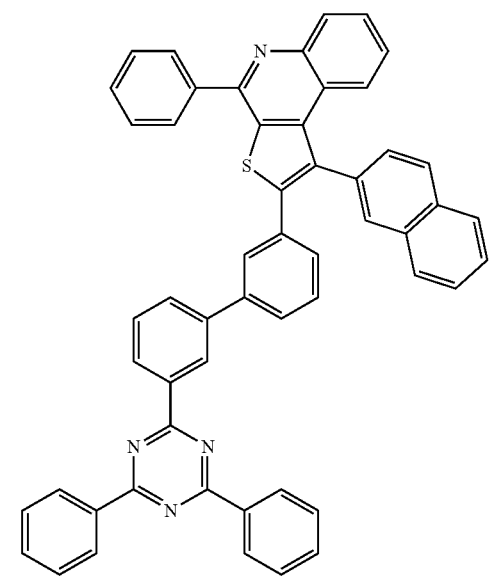

739
-continued
621
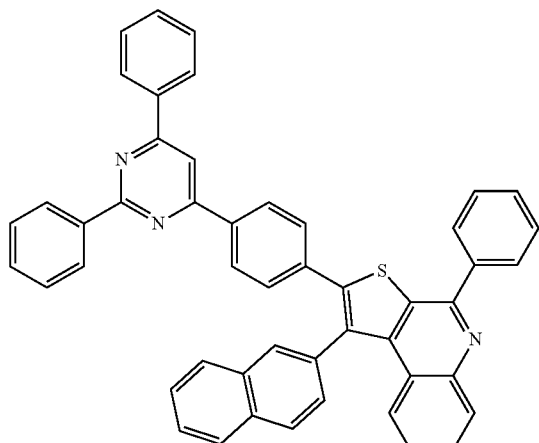
622
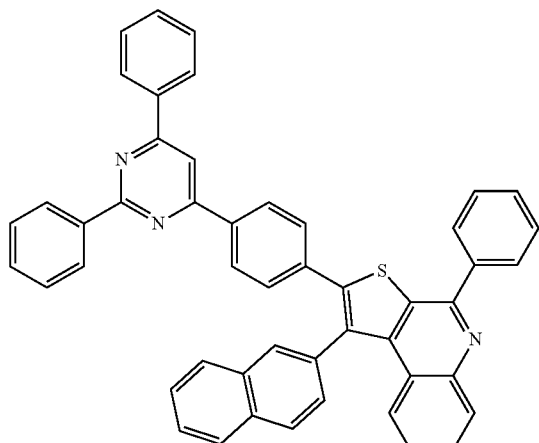
623
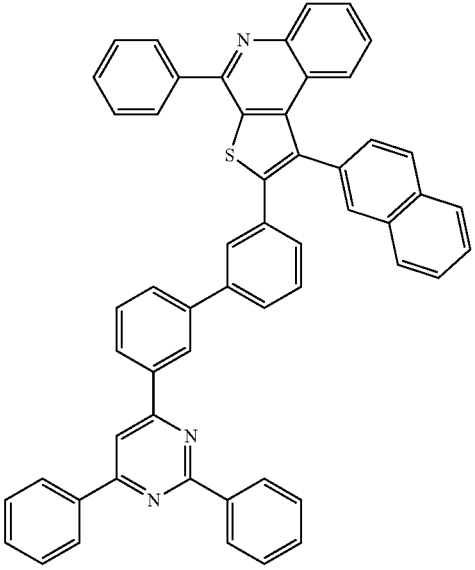
740
-continued
624
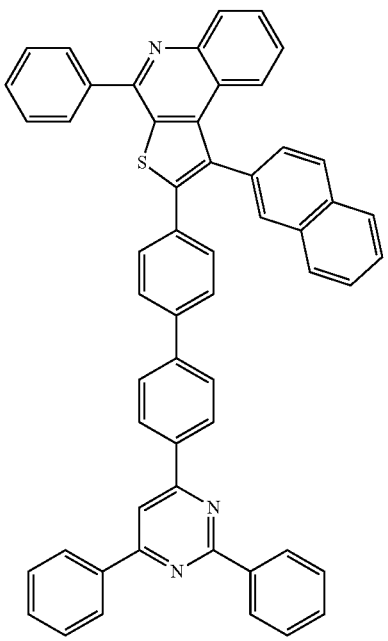
625
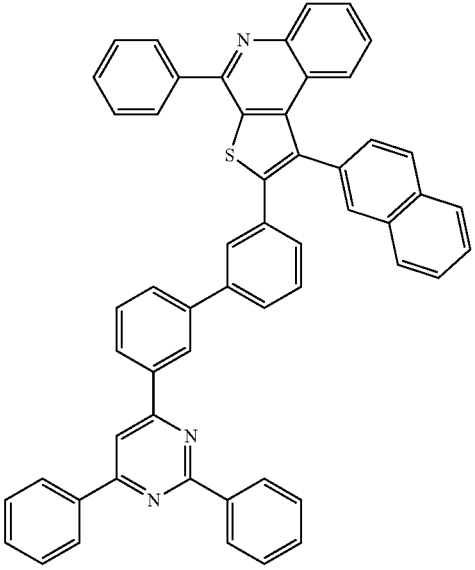

-continued
626
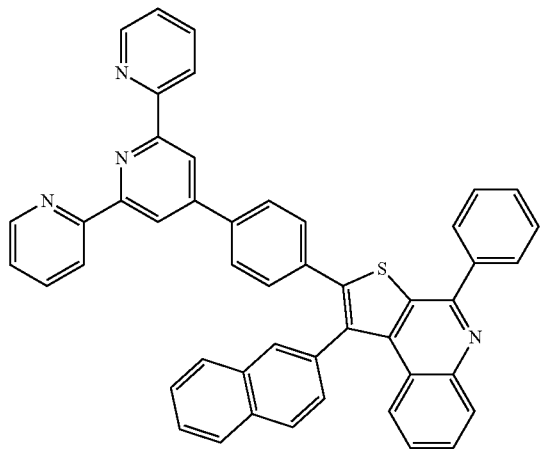
627
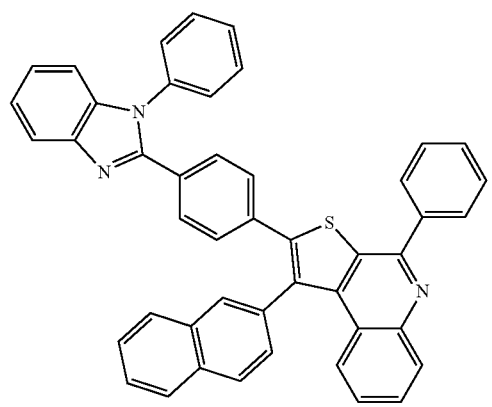
628
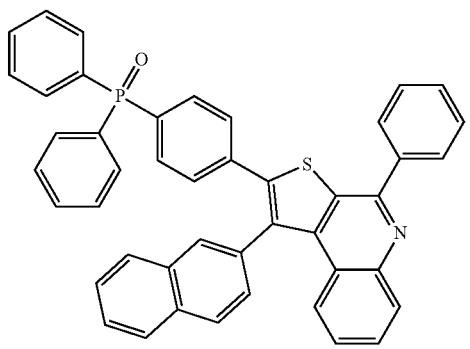
629
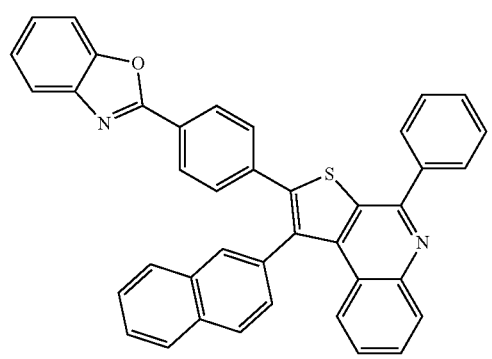
-continued
630
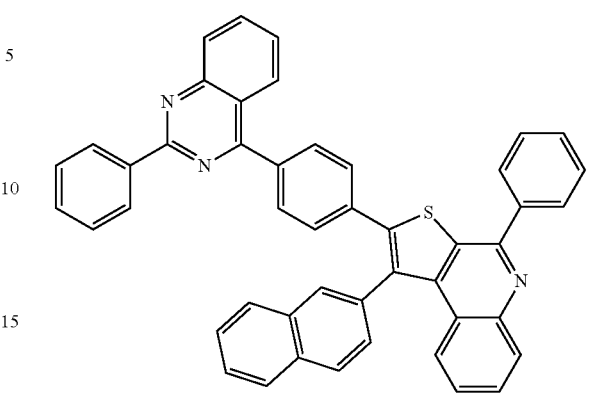
631
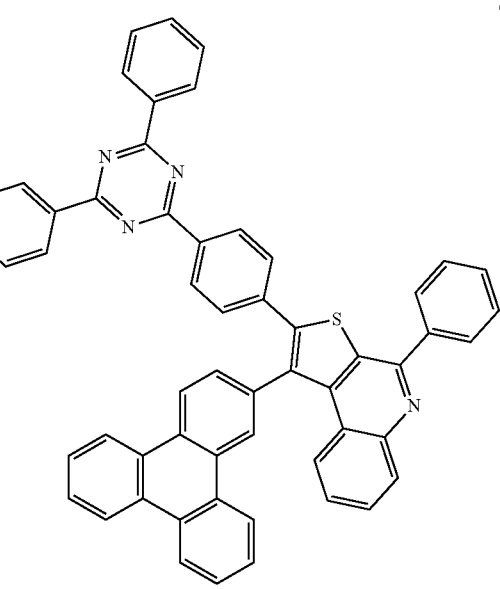
632
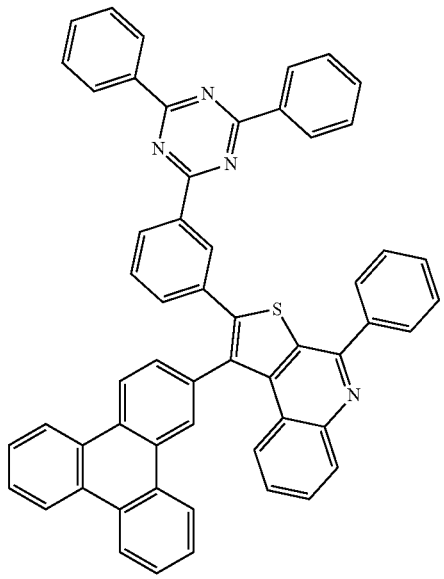

743
-continued
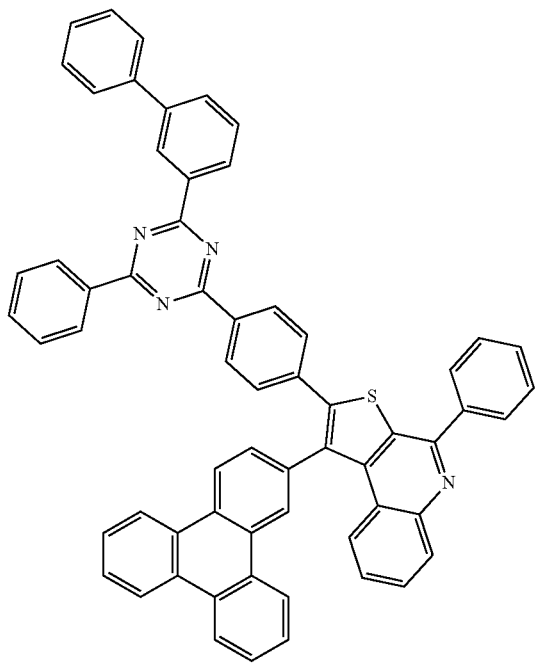
633
744
-continued
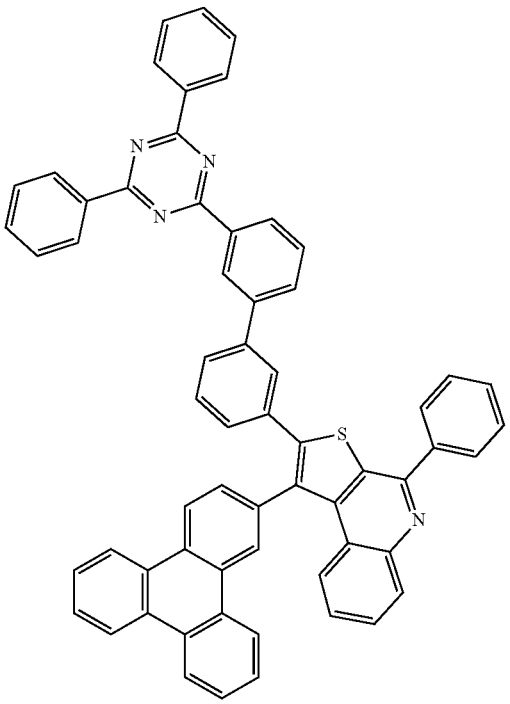
635
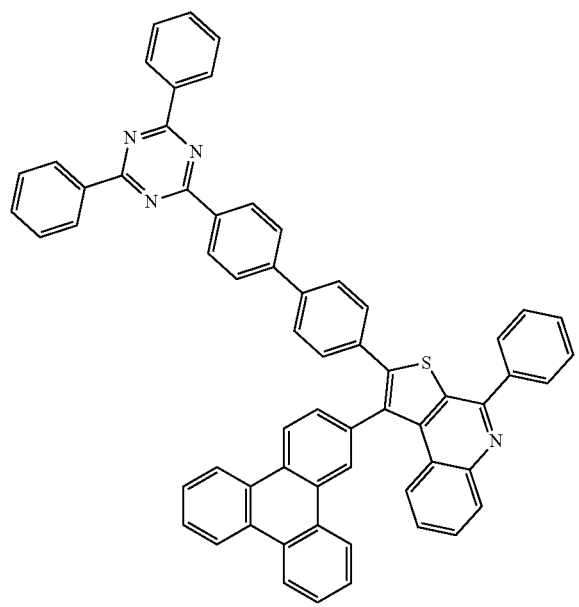
634
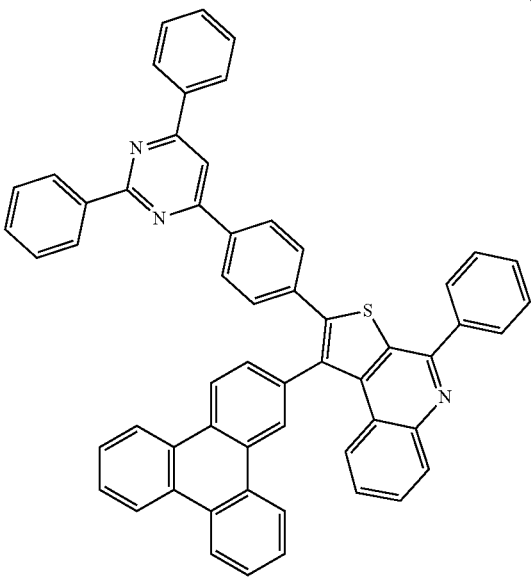
636

637
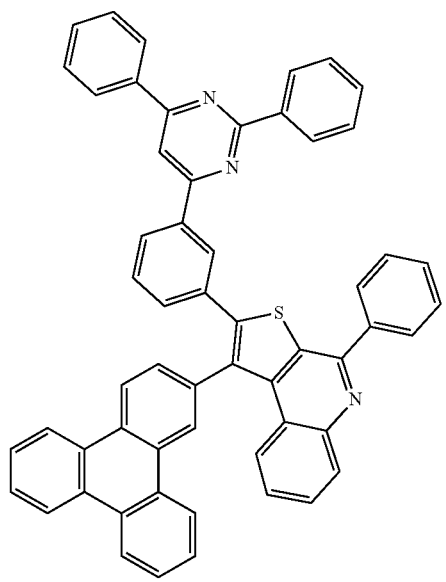
639
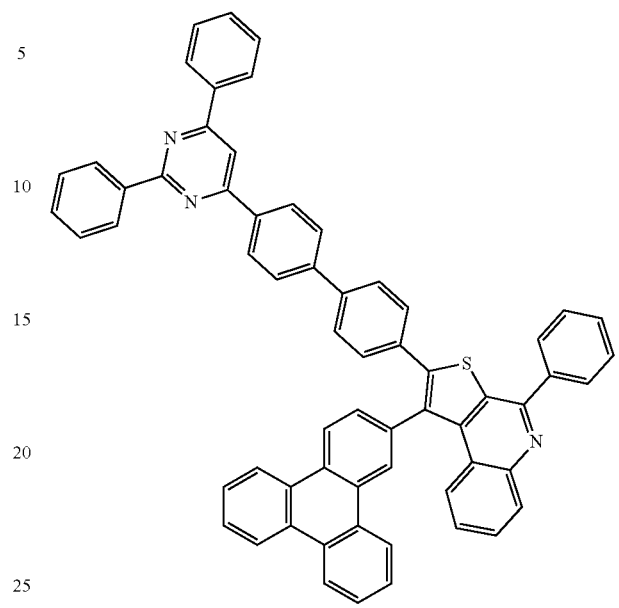
638
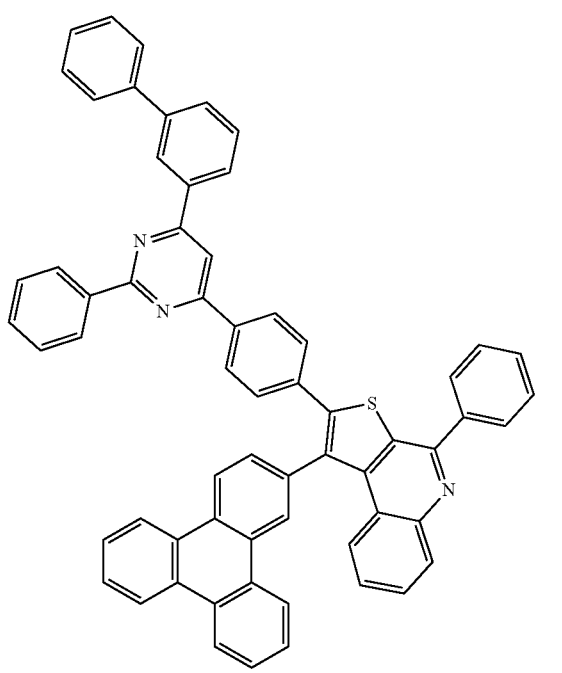
640
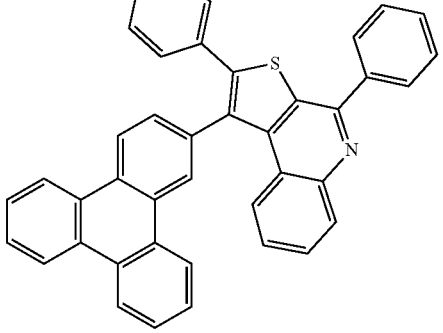

747
-continued
641
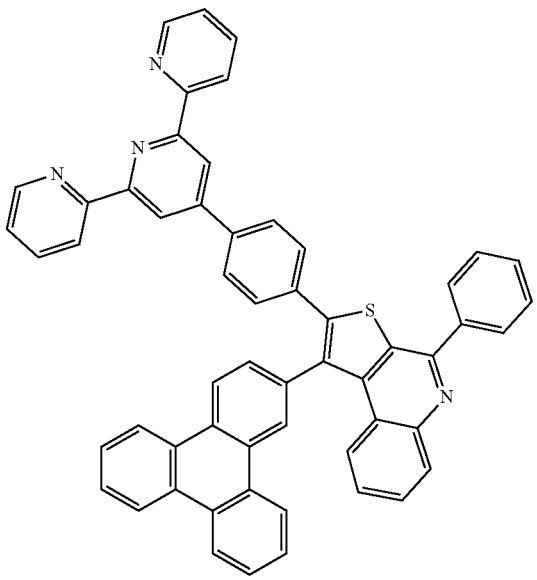
642
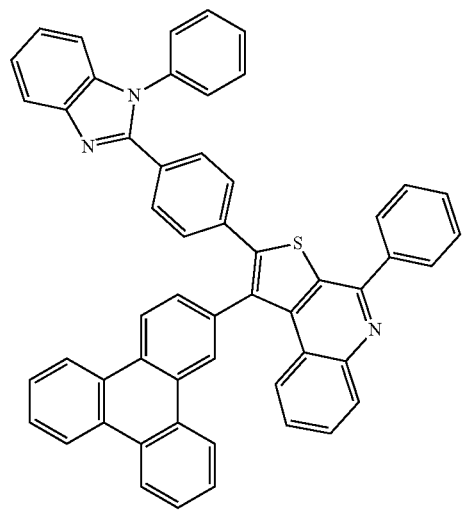
643
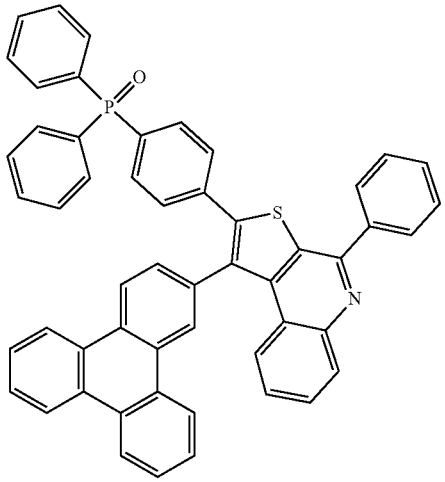
748
-continued
644
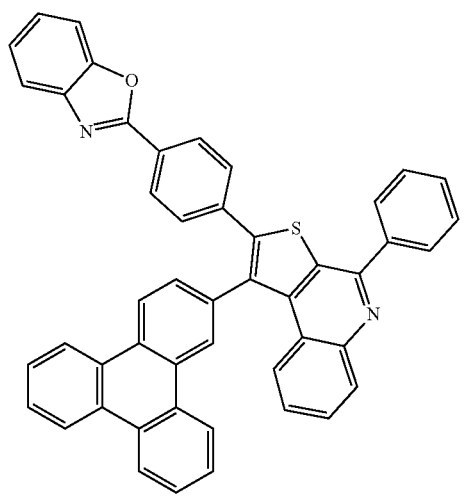
645
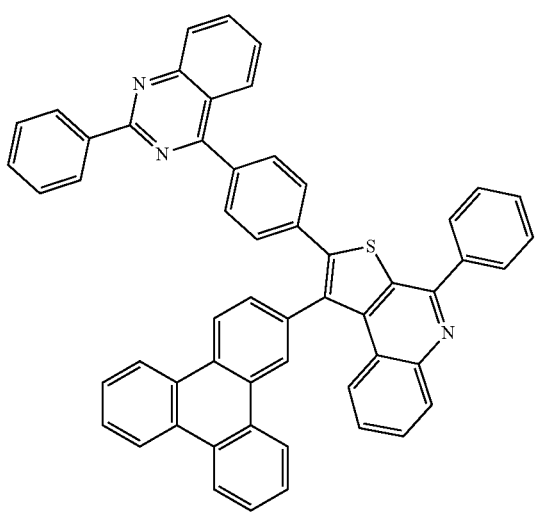
646
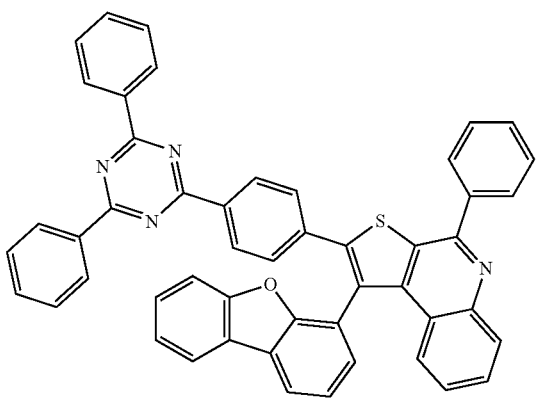

647
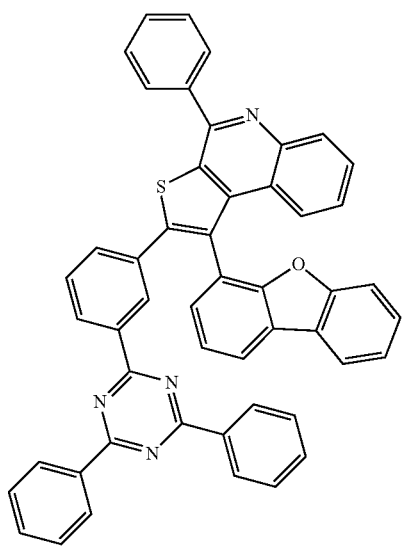
650
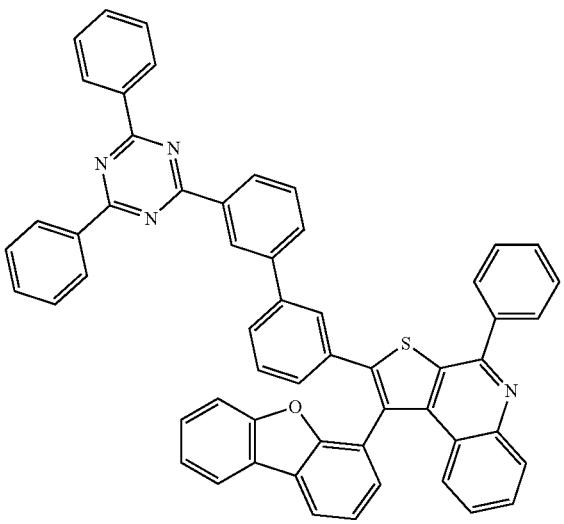
648
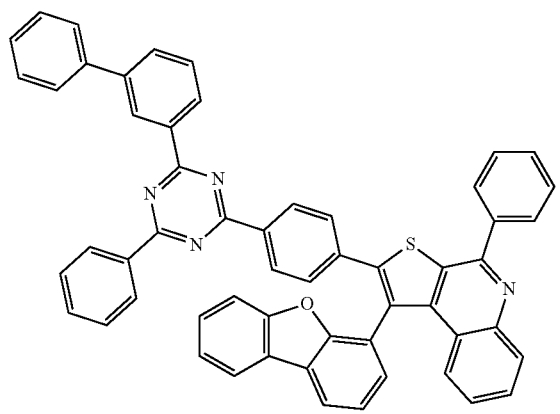
651
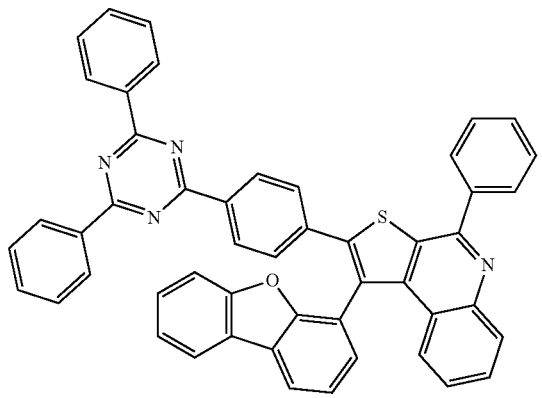
649
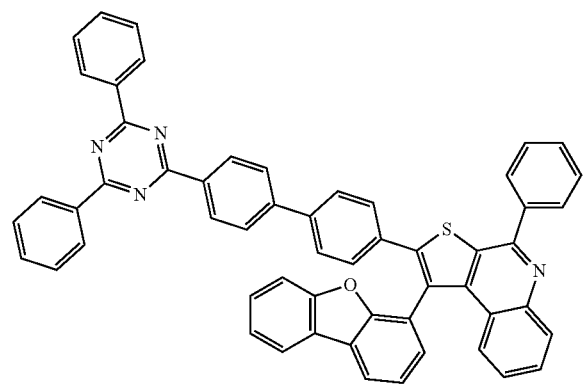
652
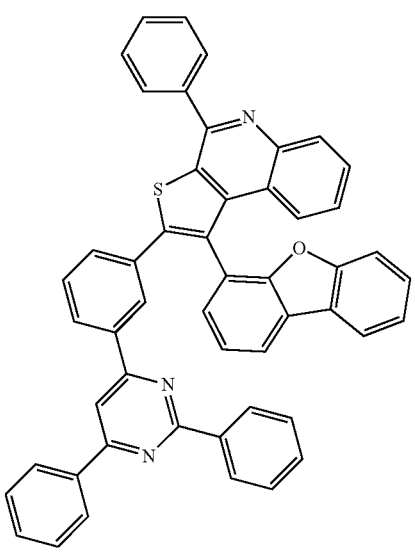

751
-continued
653
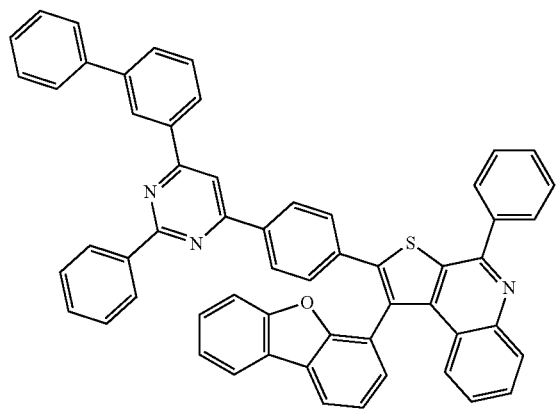
654
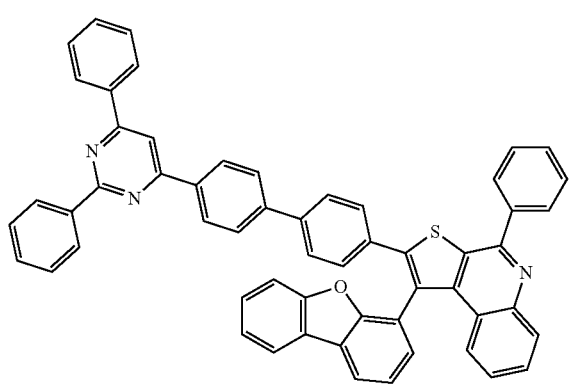
655
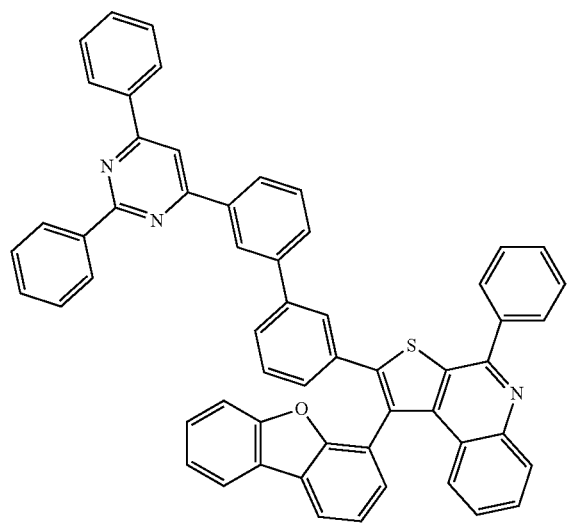
752
-continued
656
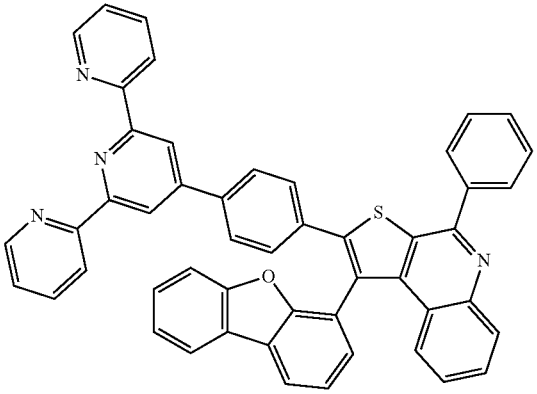
657
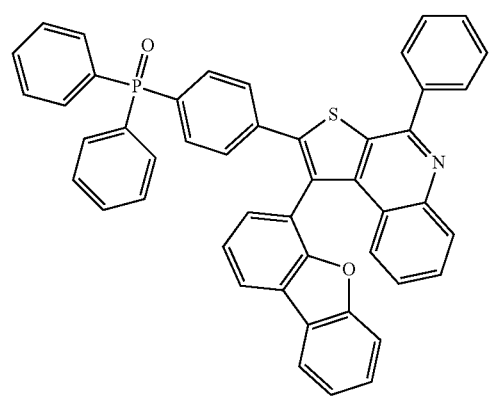
658
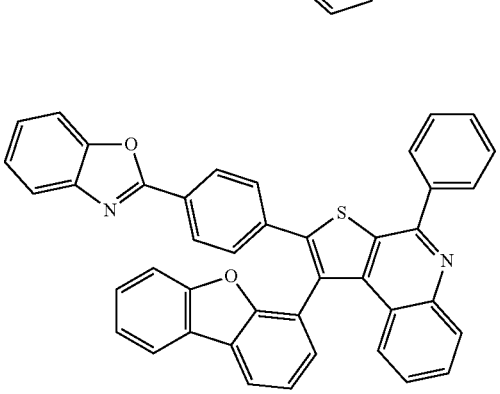
659

-continued
660
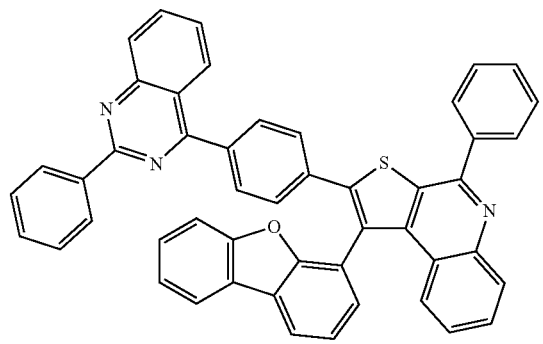
661
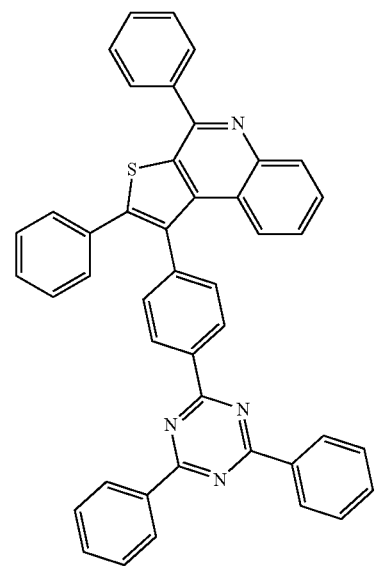
662
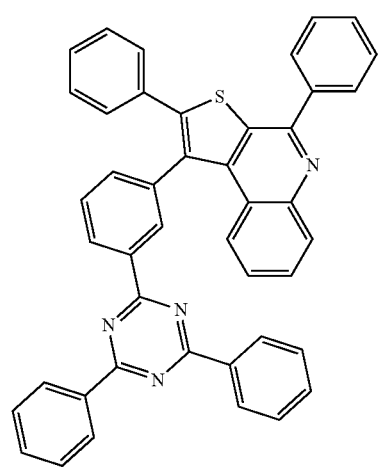
-continued
663
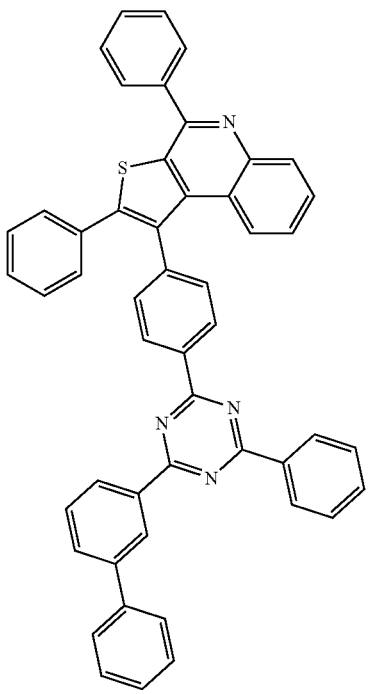
664
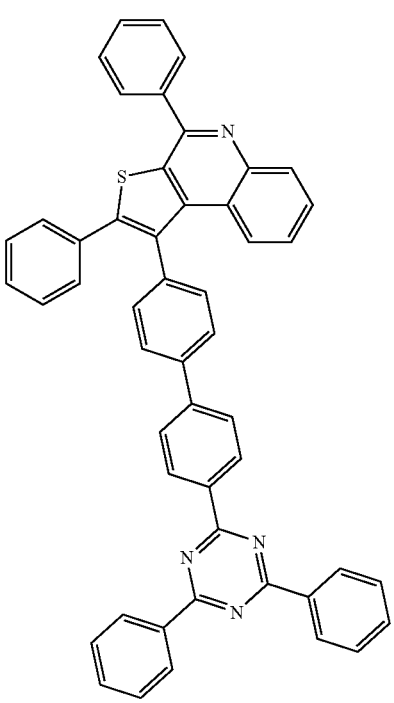

755
-continued
756
-continued
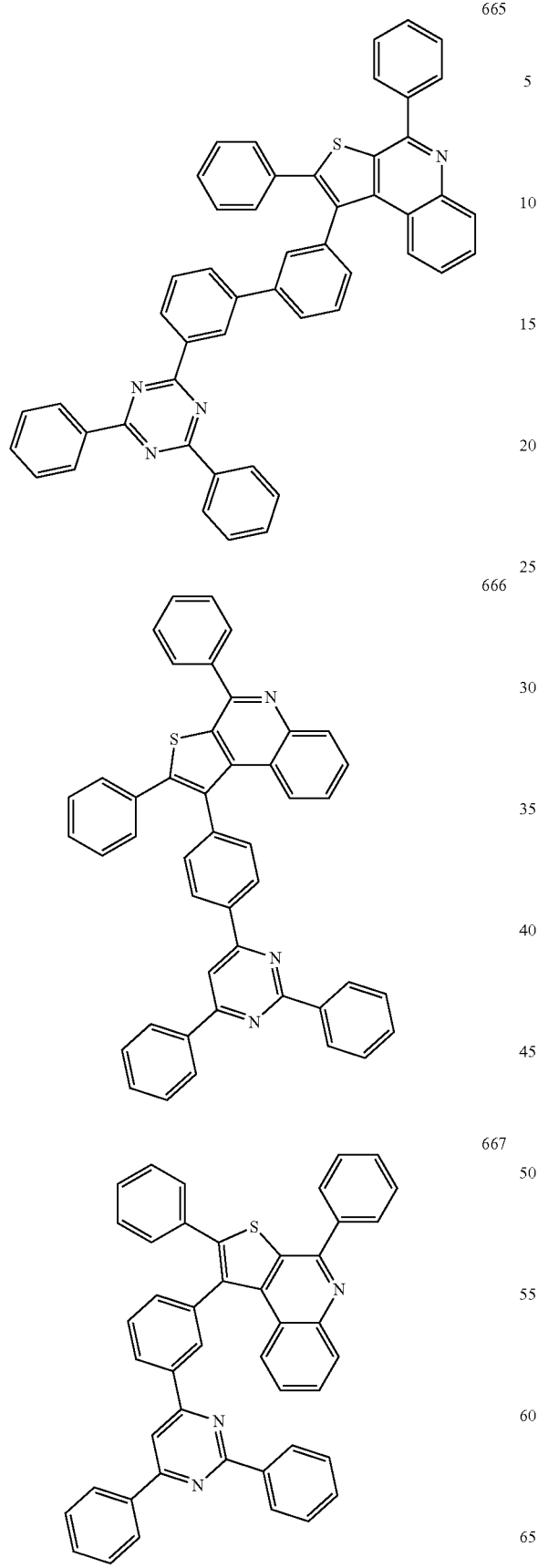
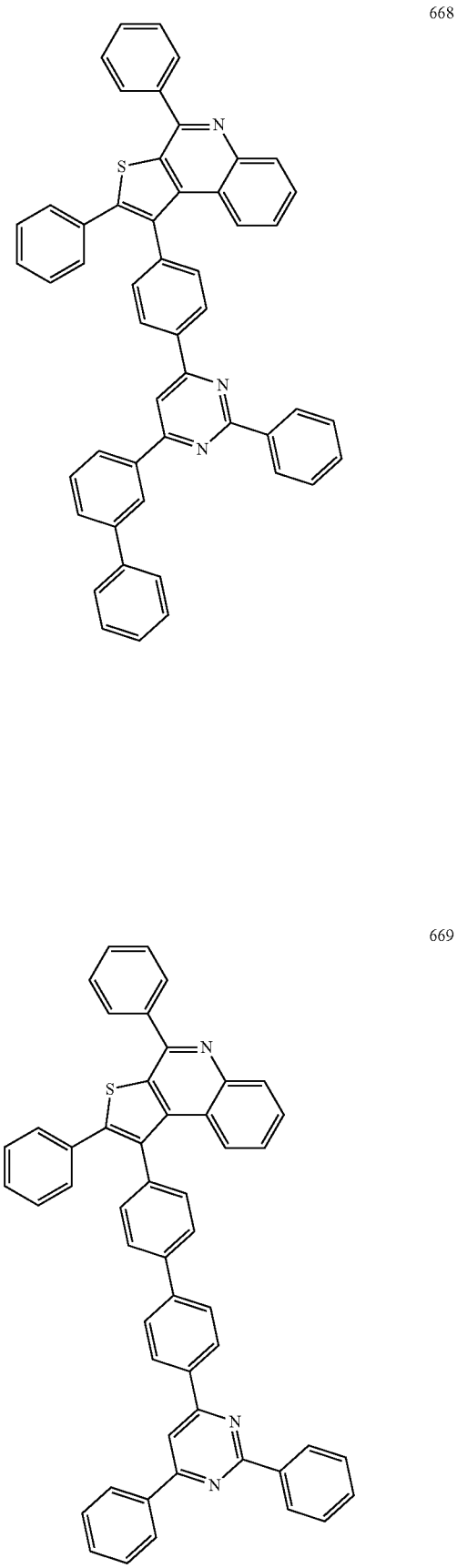

670
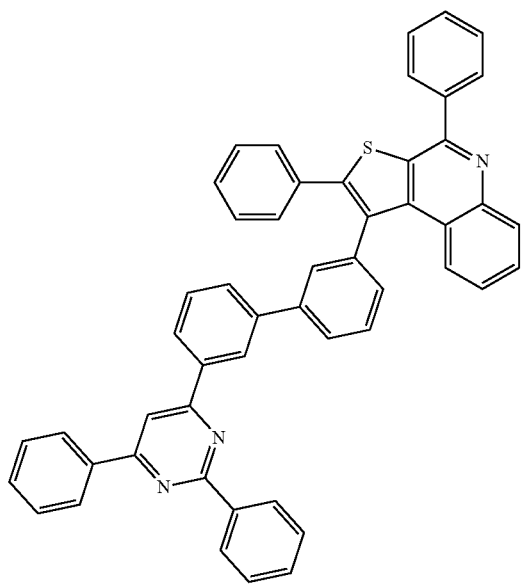
671
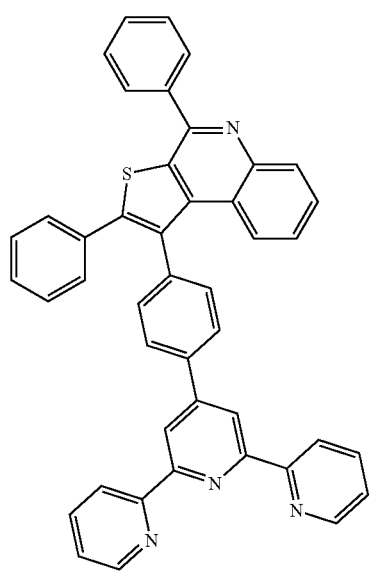
672
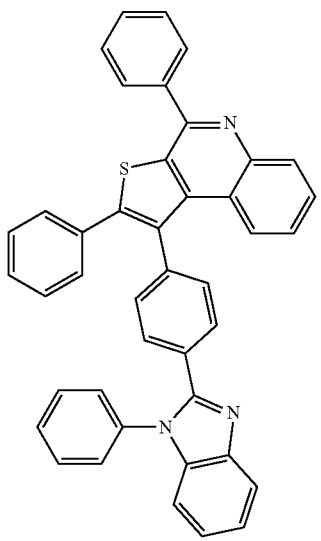
673
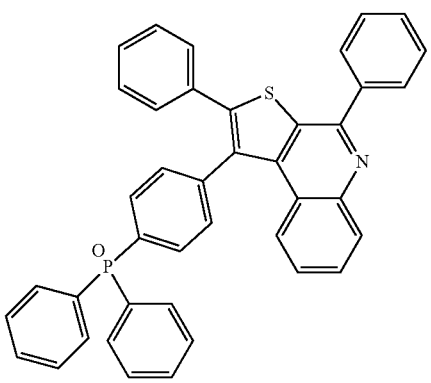
674
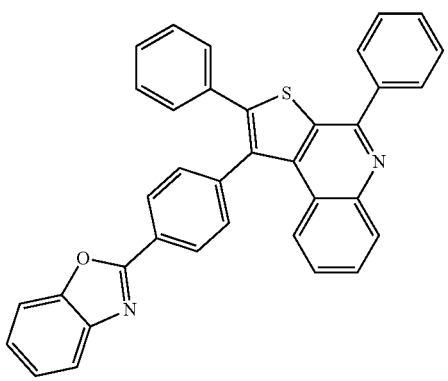

759
-continued
675
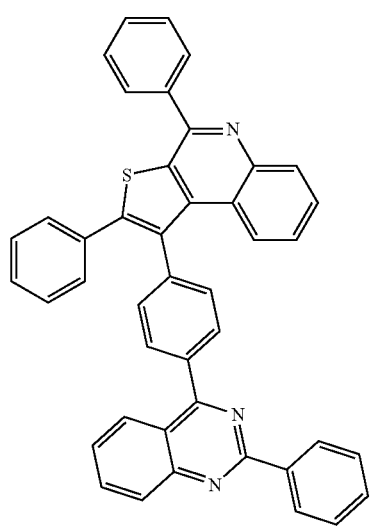
676
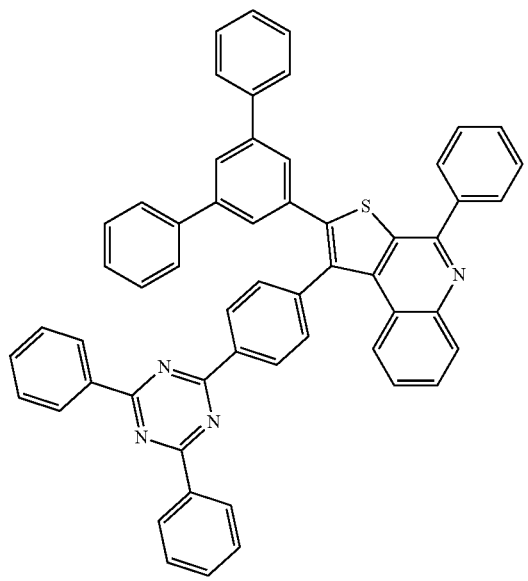
760
-continued
677
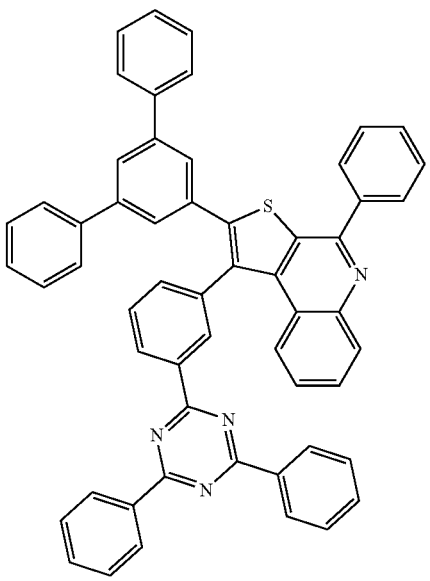
678

679
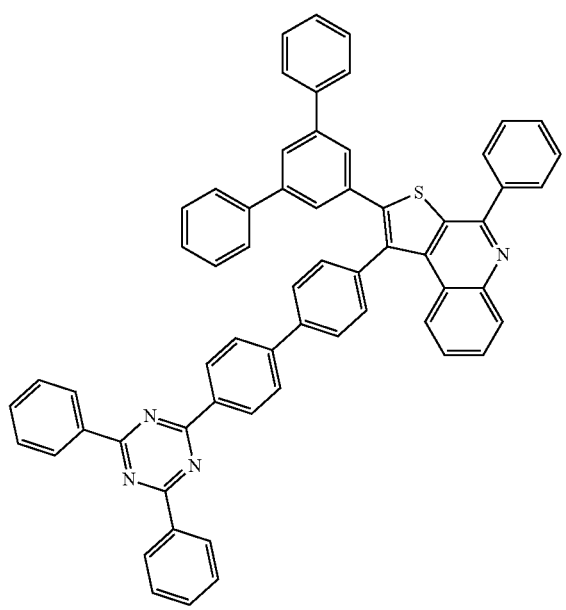
680
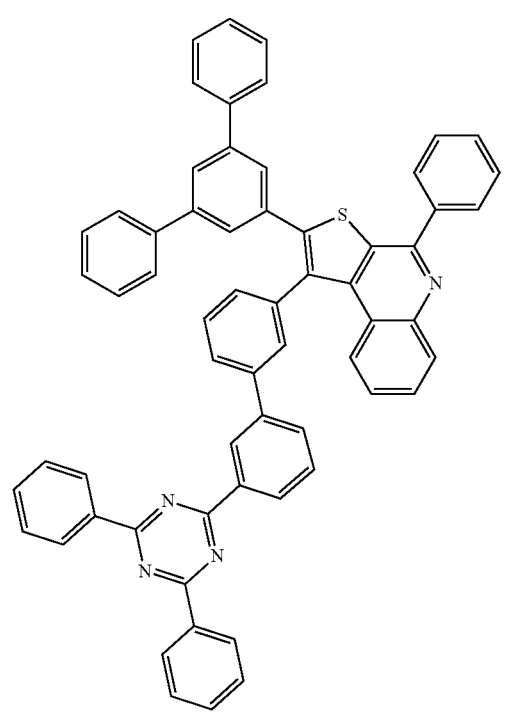
681
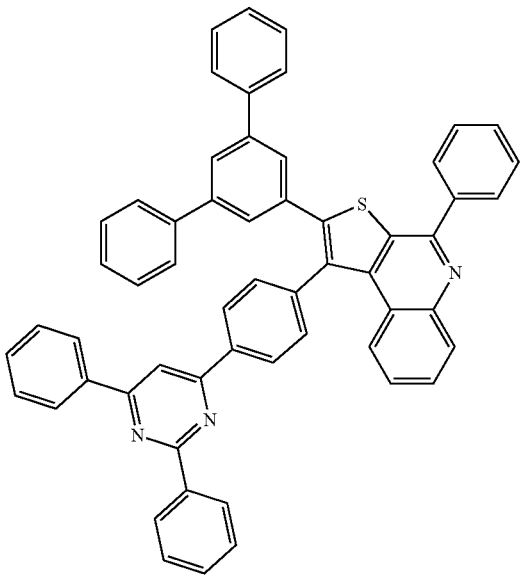
682
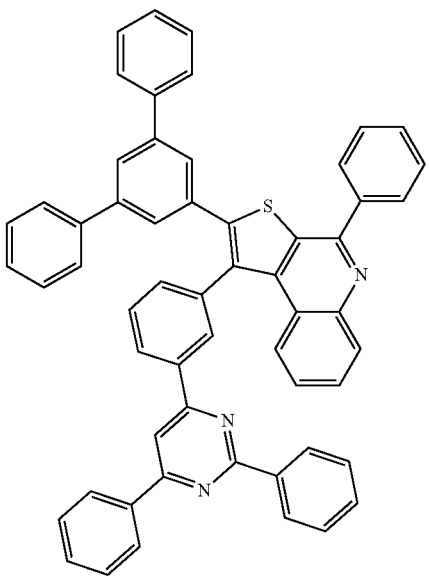

763
-continued
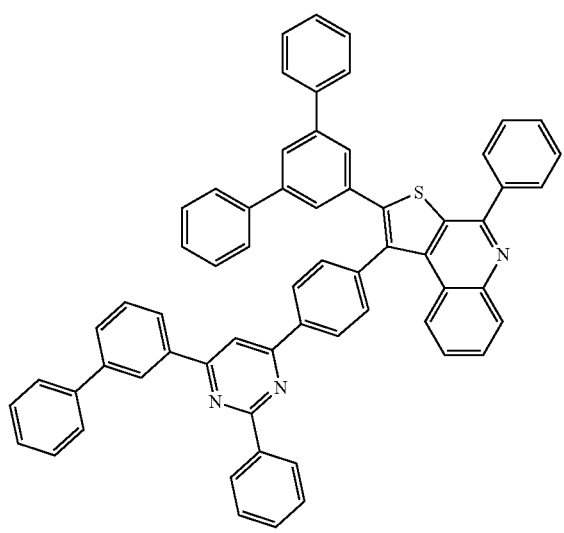
683
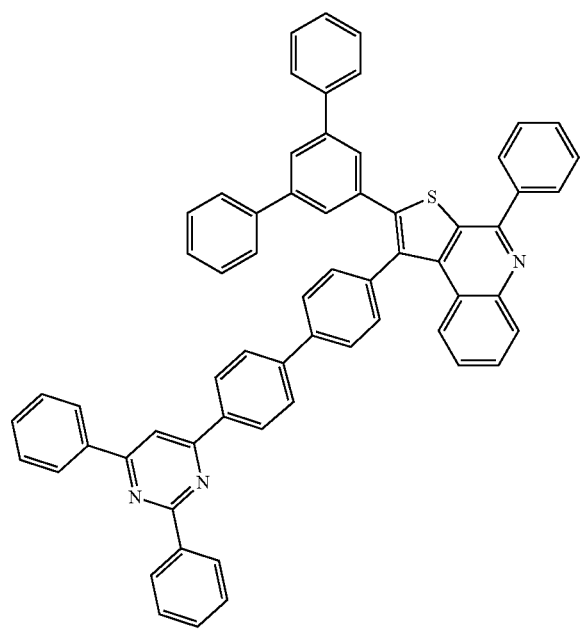
684
764
-continued
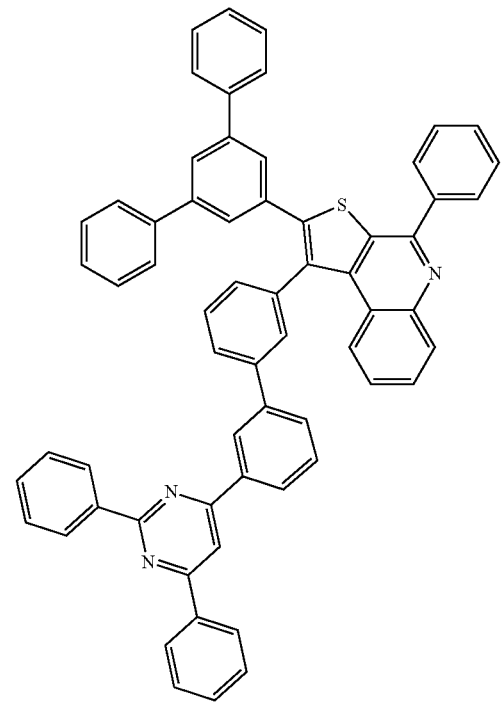
685
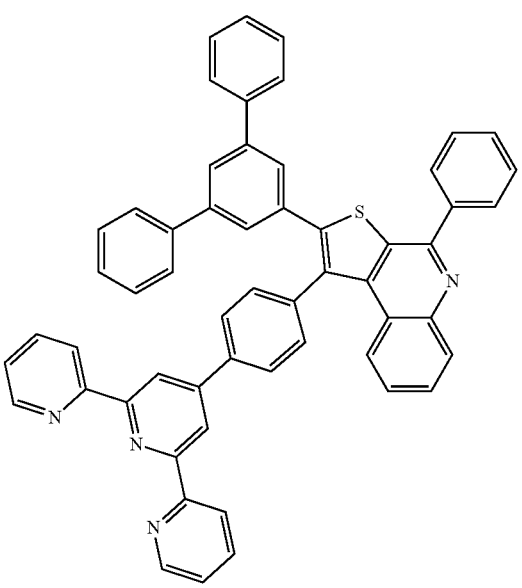
686

765
-continued
687
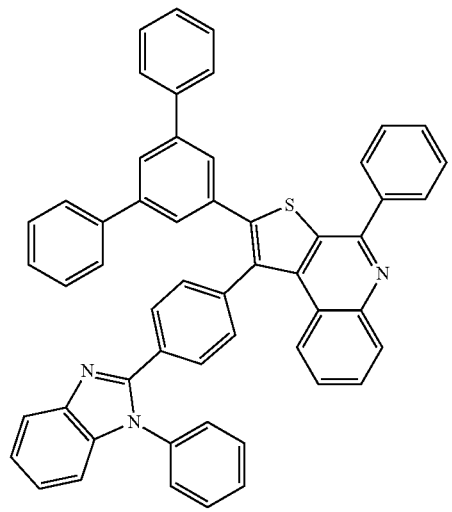
688
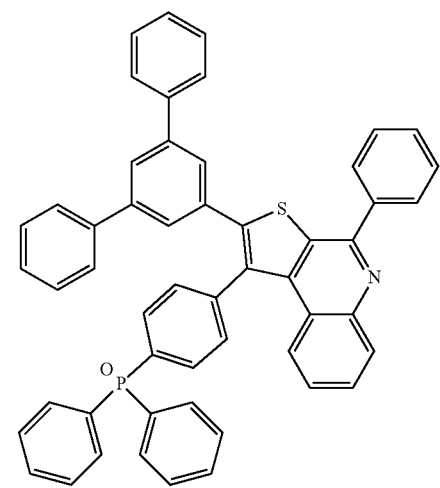
689
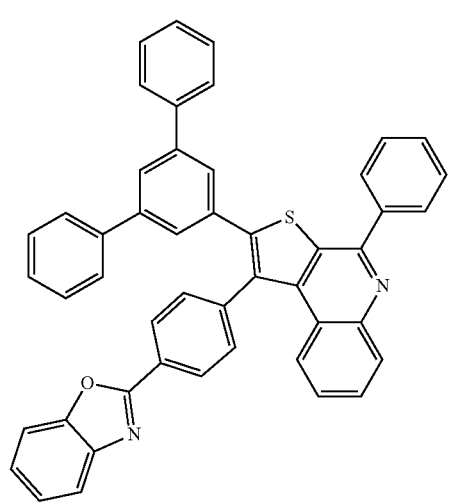
766
-continued
690
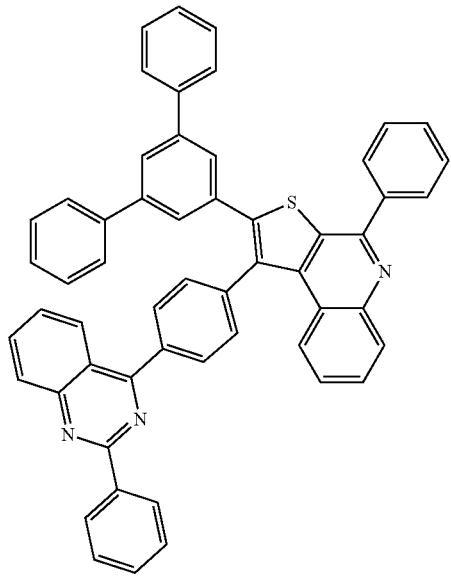
691
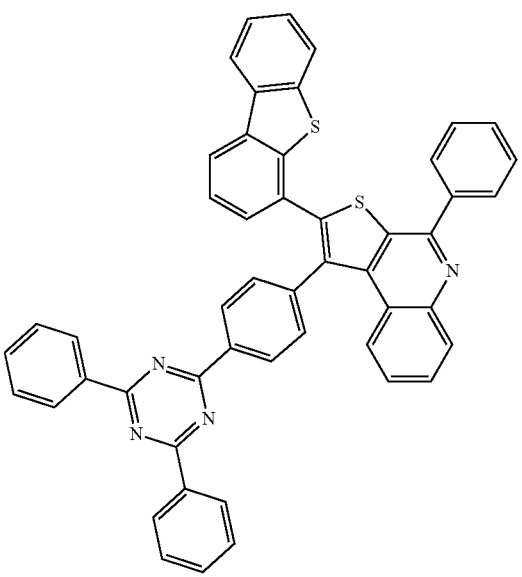

767
-continued
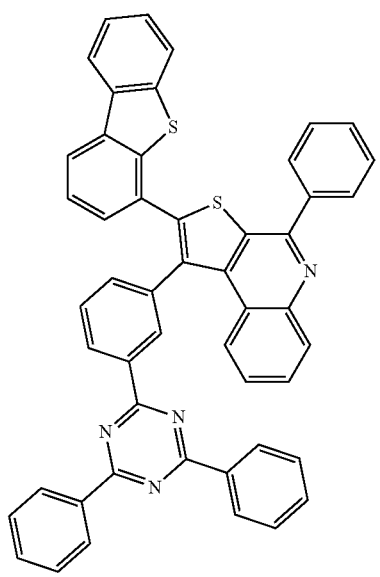
692
693
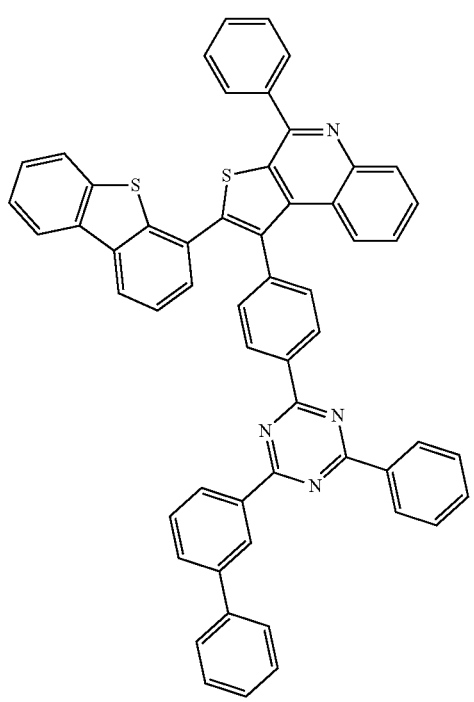
768
-continued
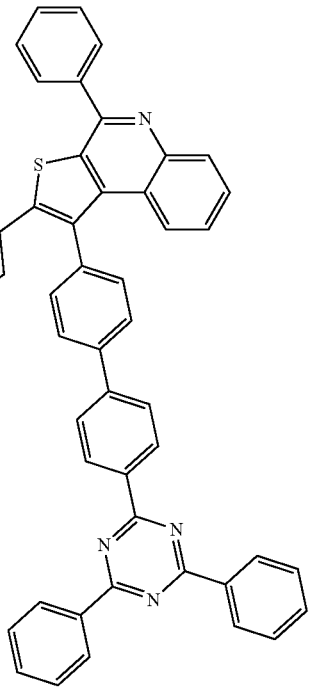
694
695
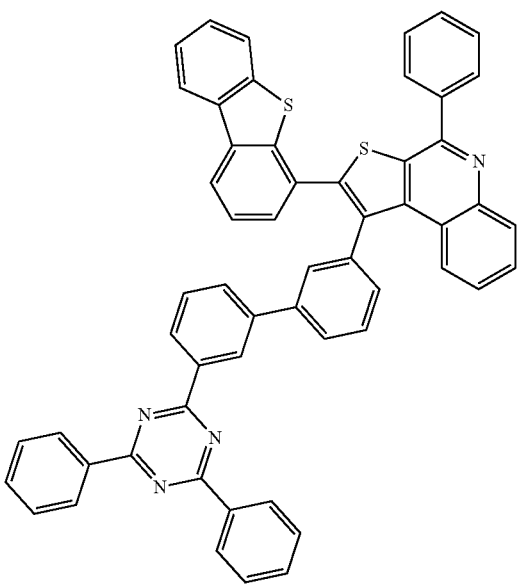

769
-continued
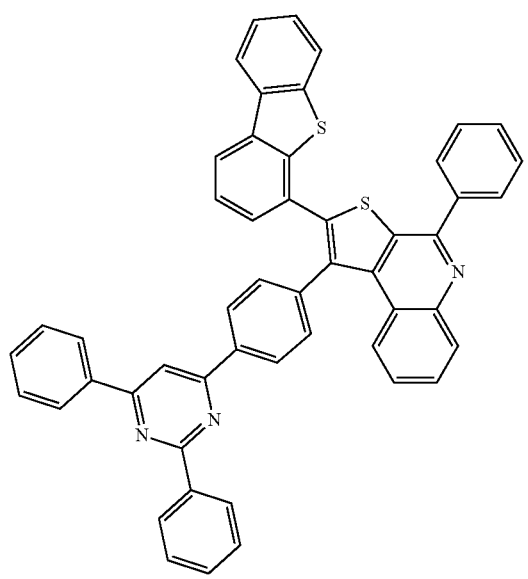
696
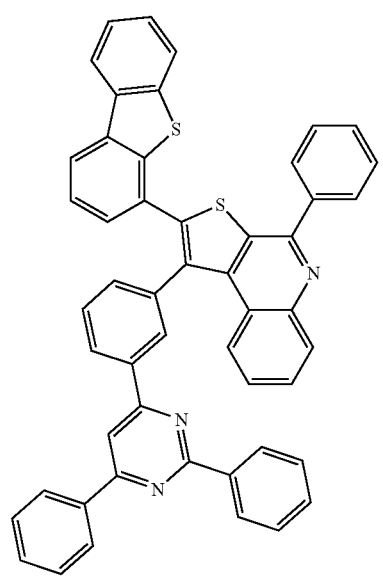
697
770
-continued
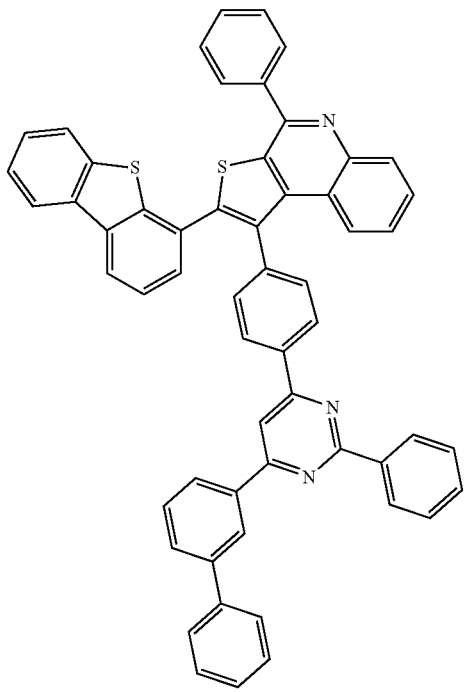
698
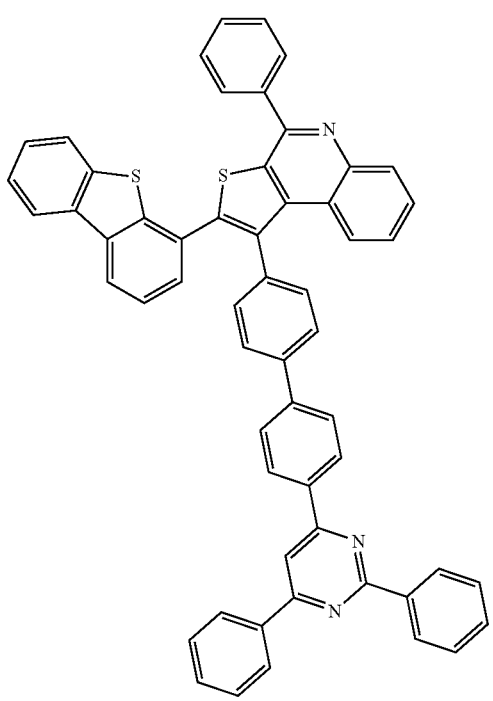
699

-continued
700
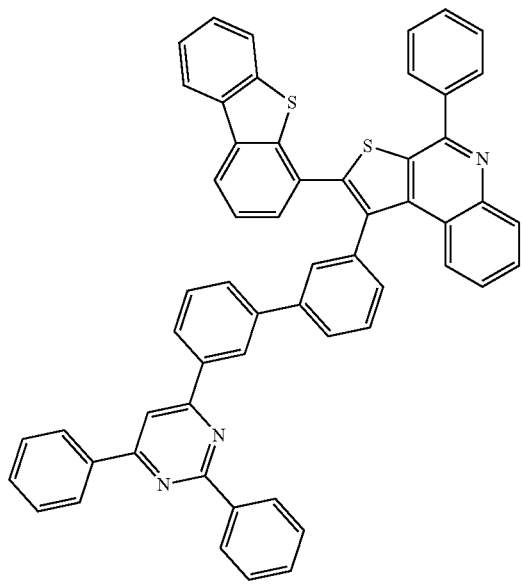
701
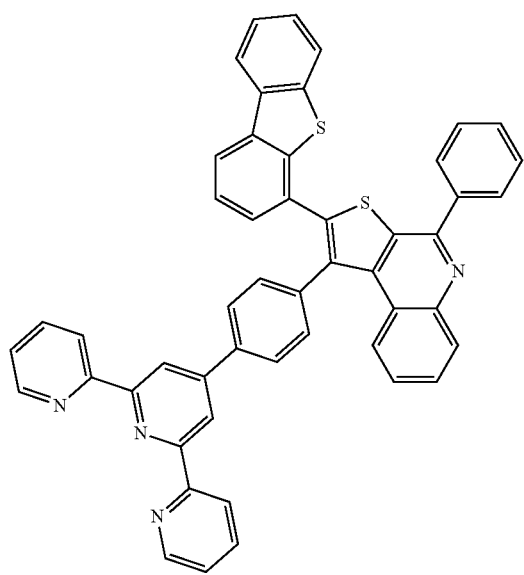
702
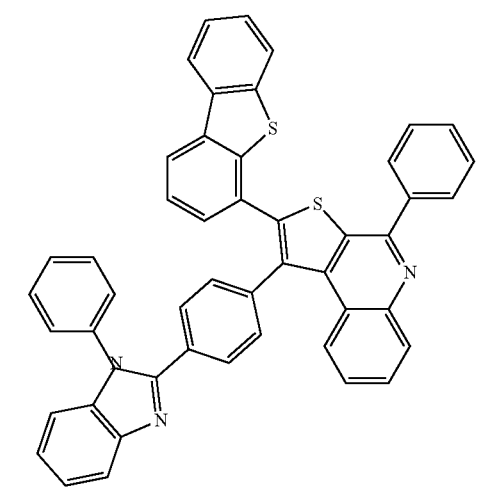
-continued
703
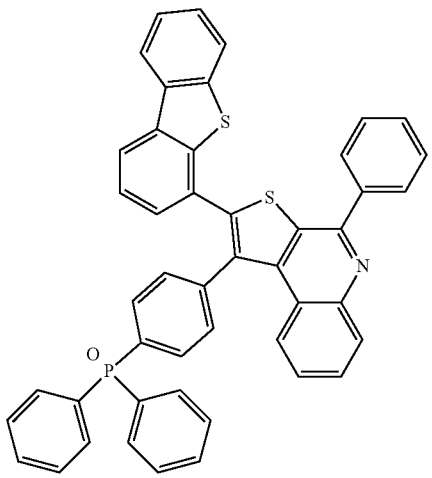
704
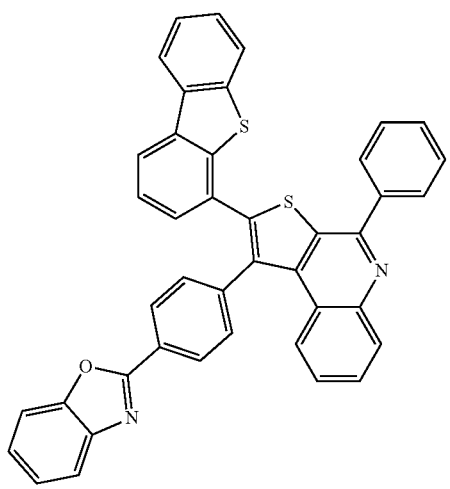
705
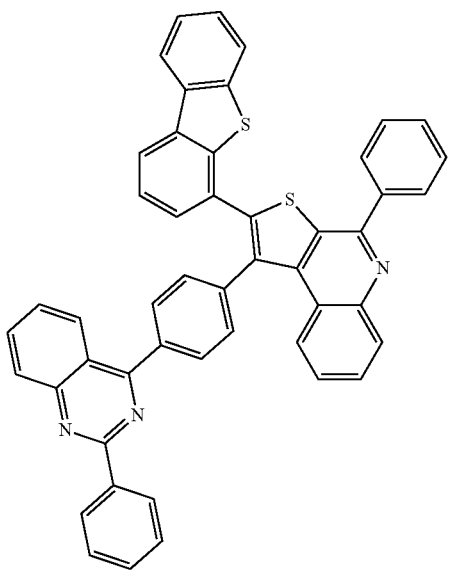

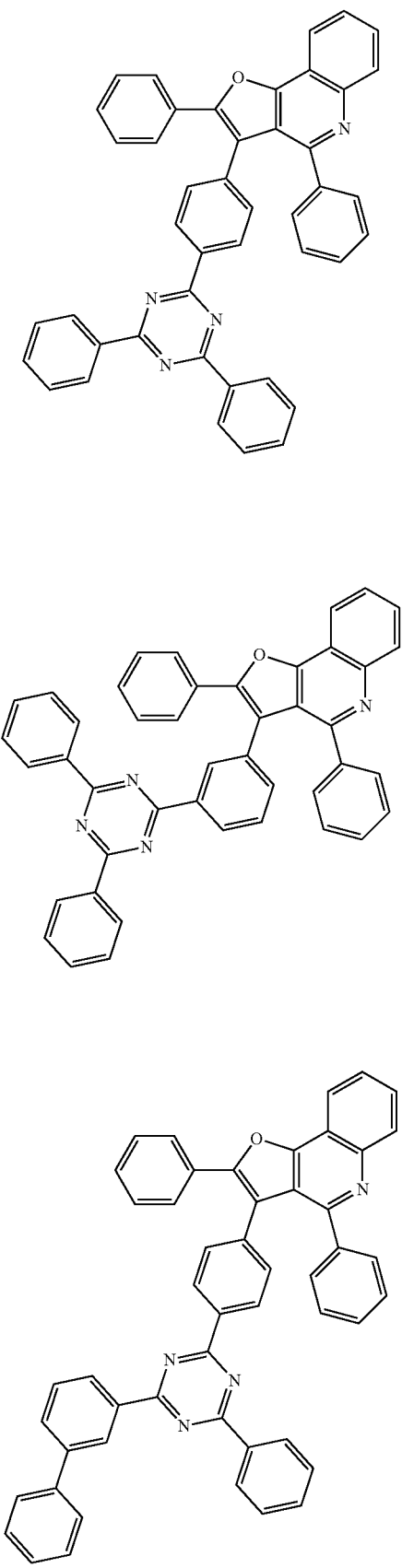
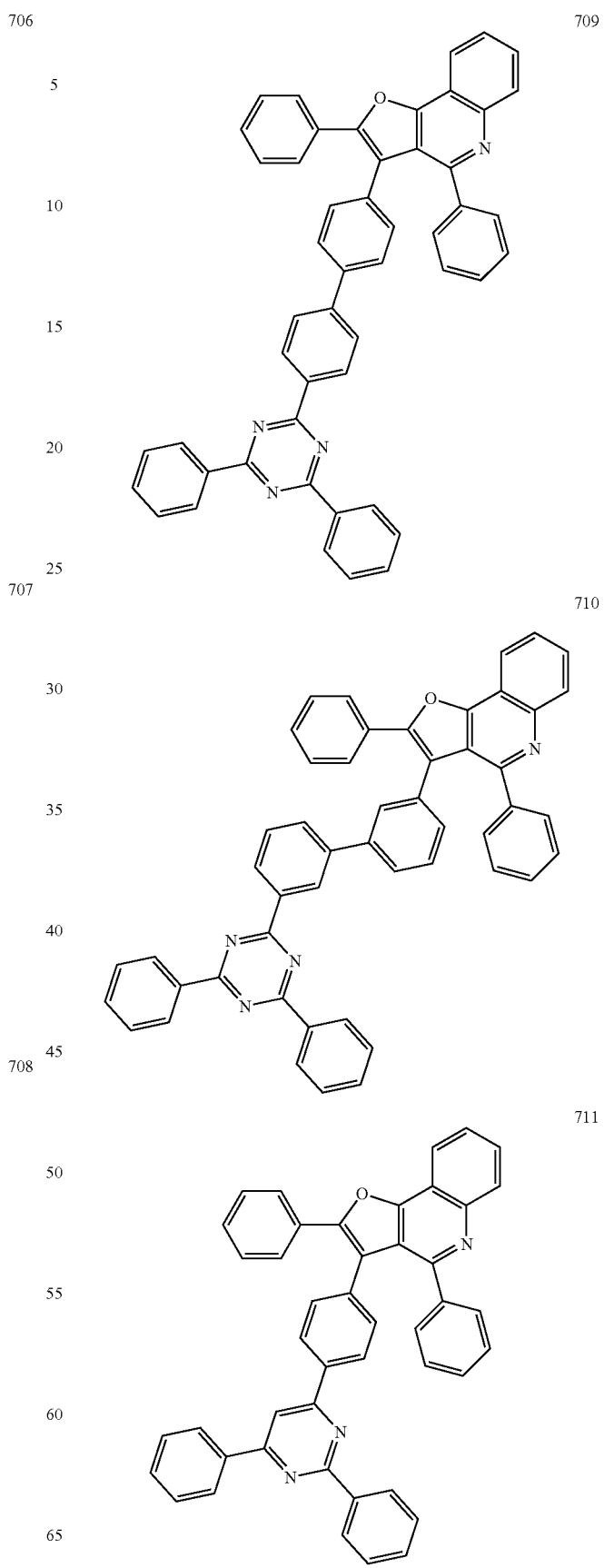

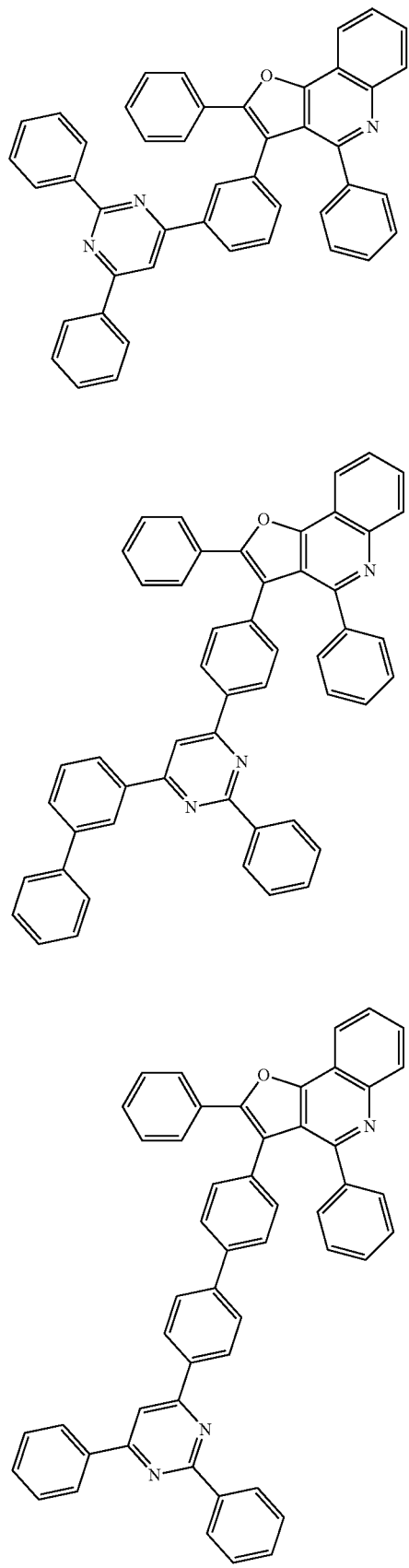
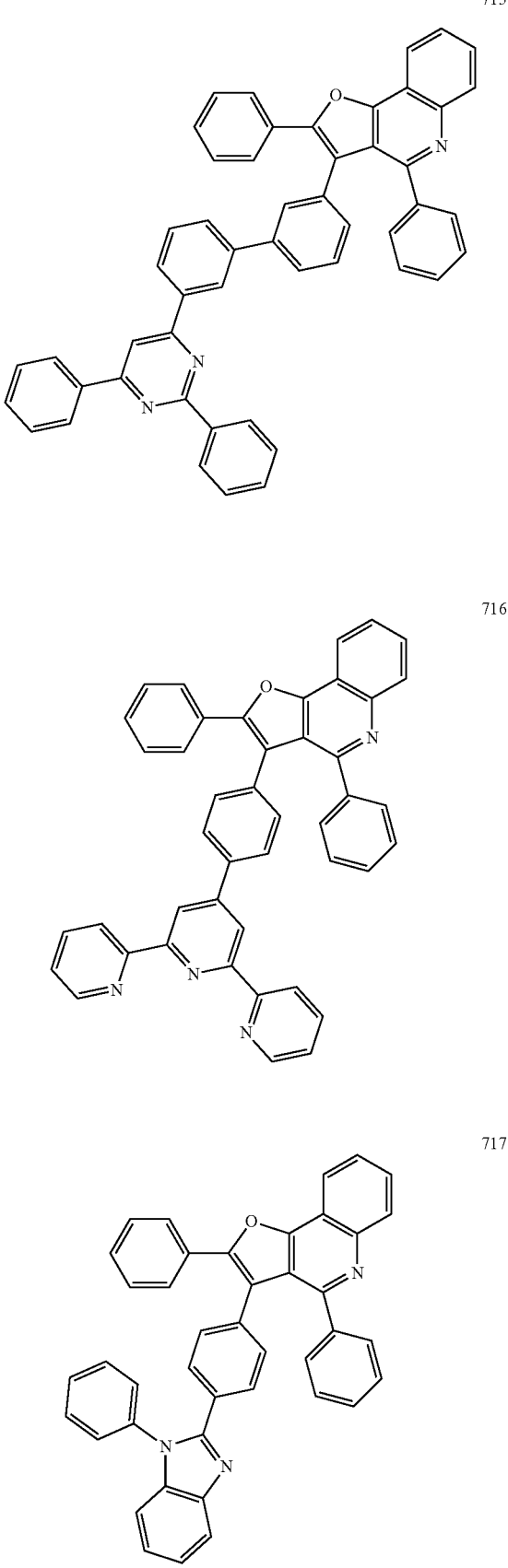

718
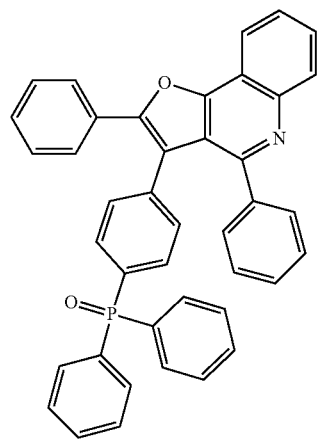
721
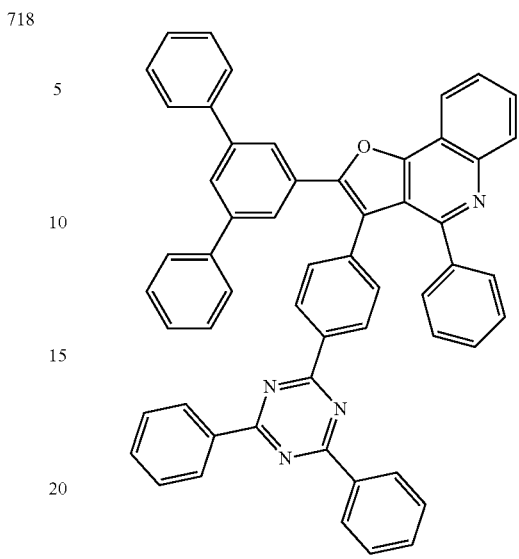
719
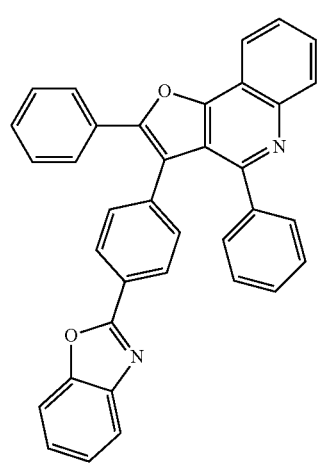
720
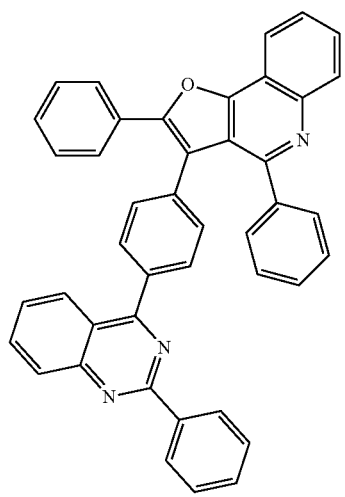
722
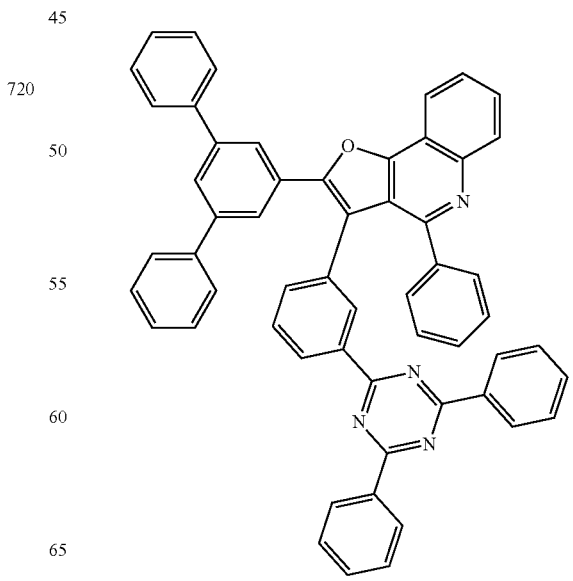

779
-continued
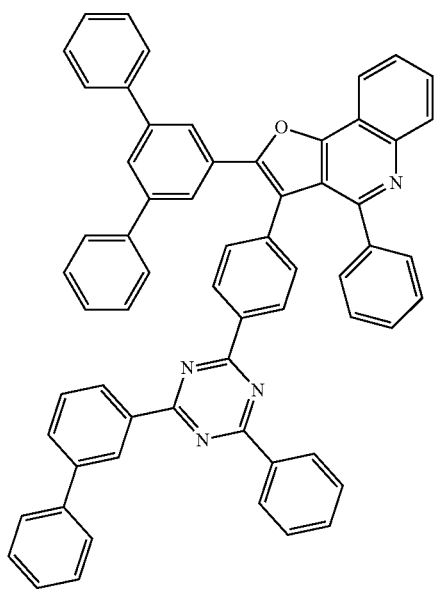
780
-continued
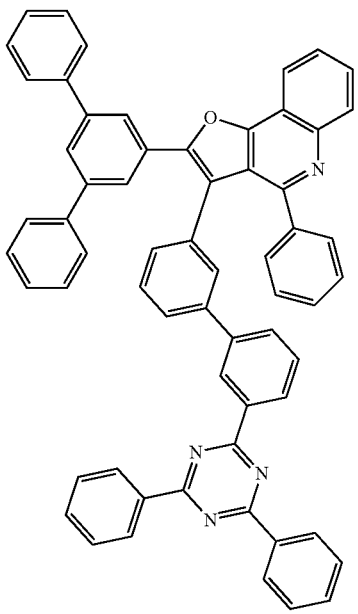
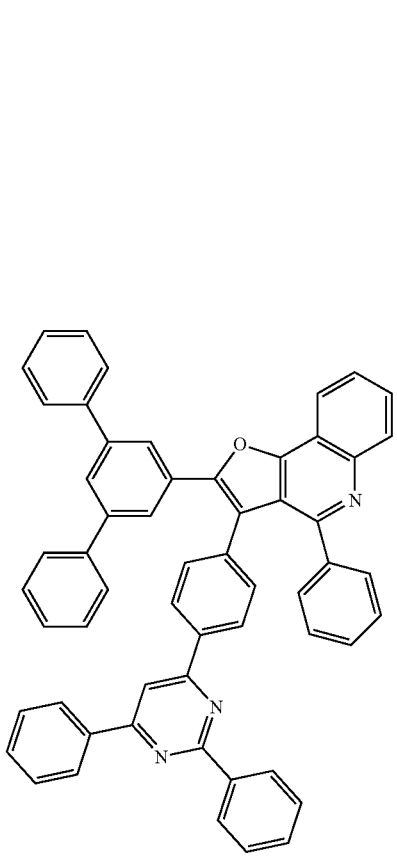

781
-continued
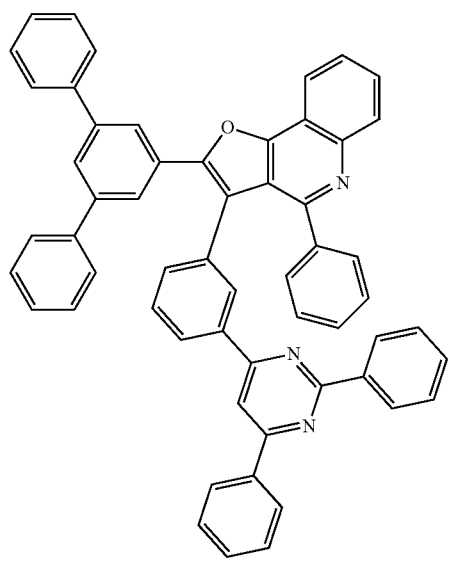
727
782
-continued
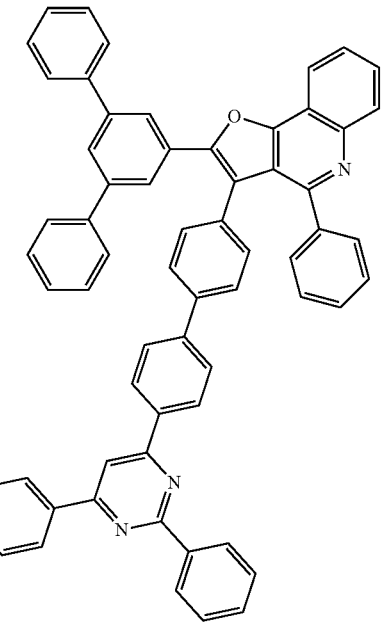
729
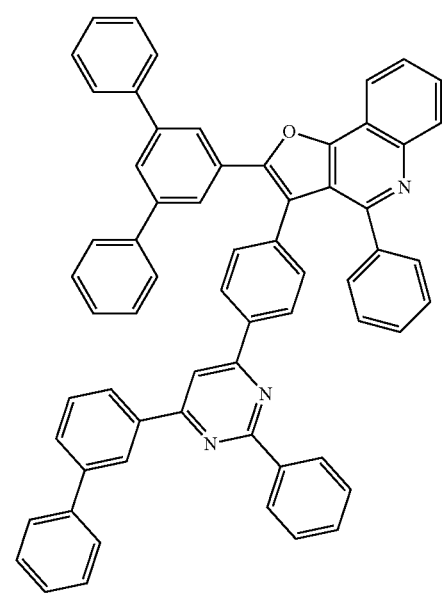
728
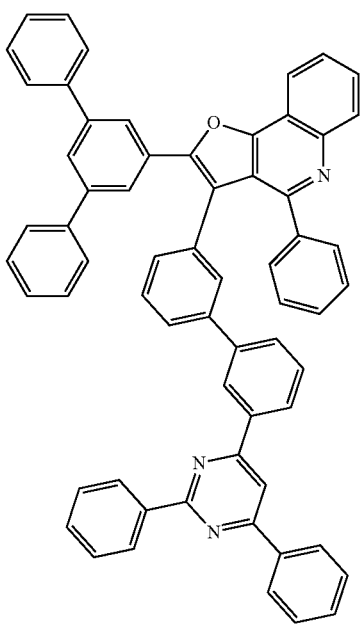
730

783
-continued
731
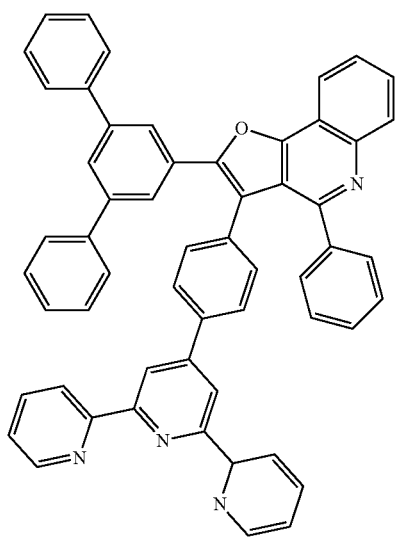
732
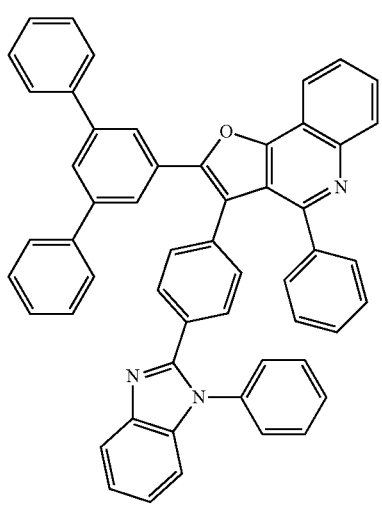
733
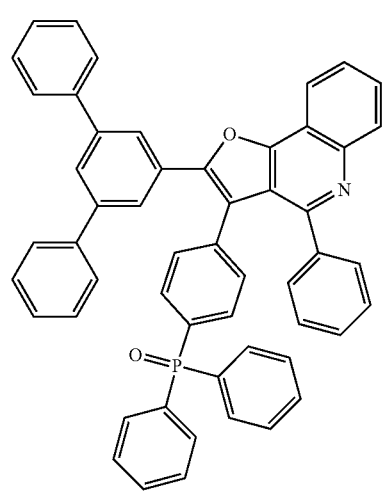
784
-continued
734
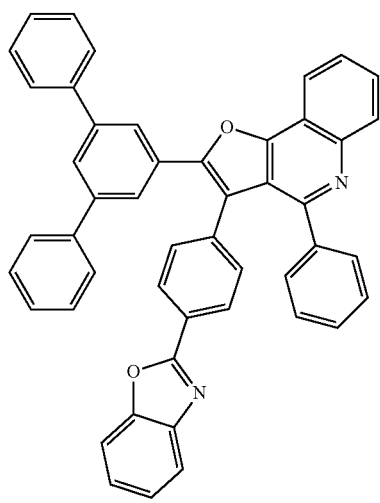
735
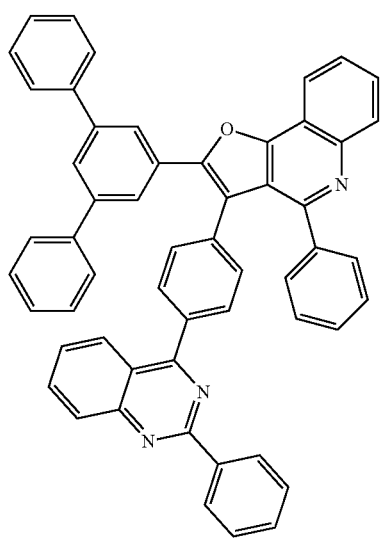
746
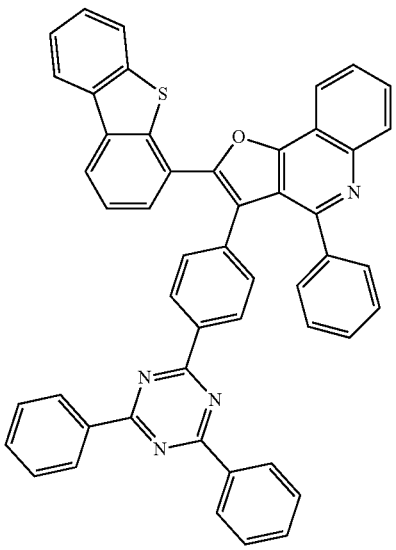

785
-continued
747
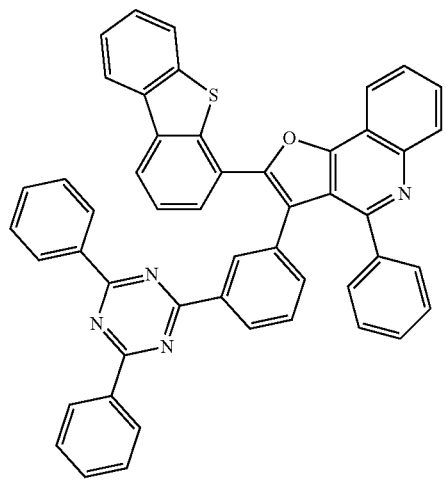
748
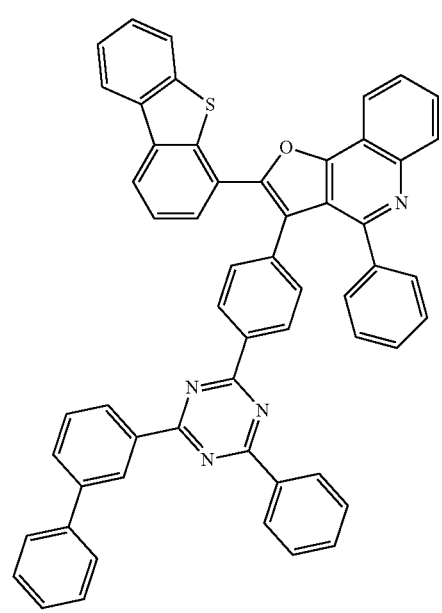
786
-continued
749
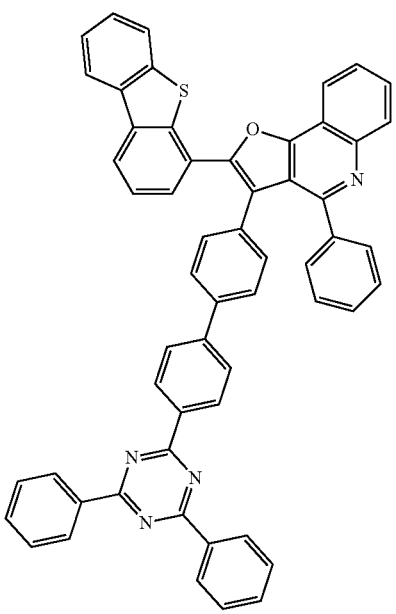
750
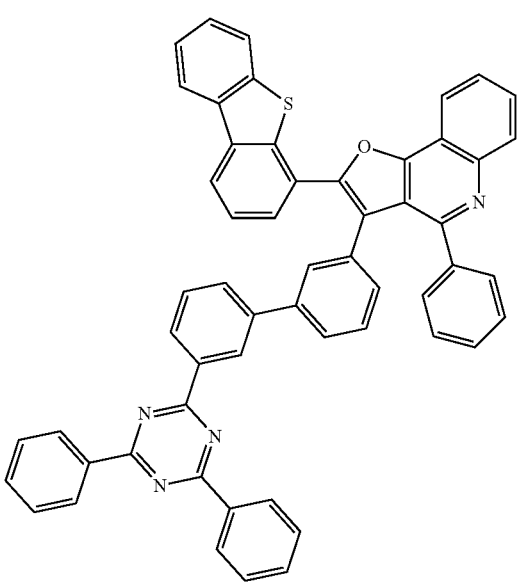

787
-continued
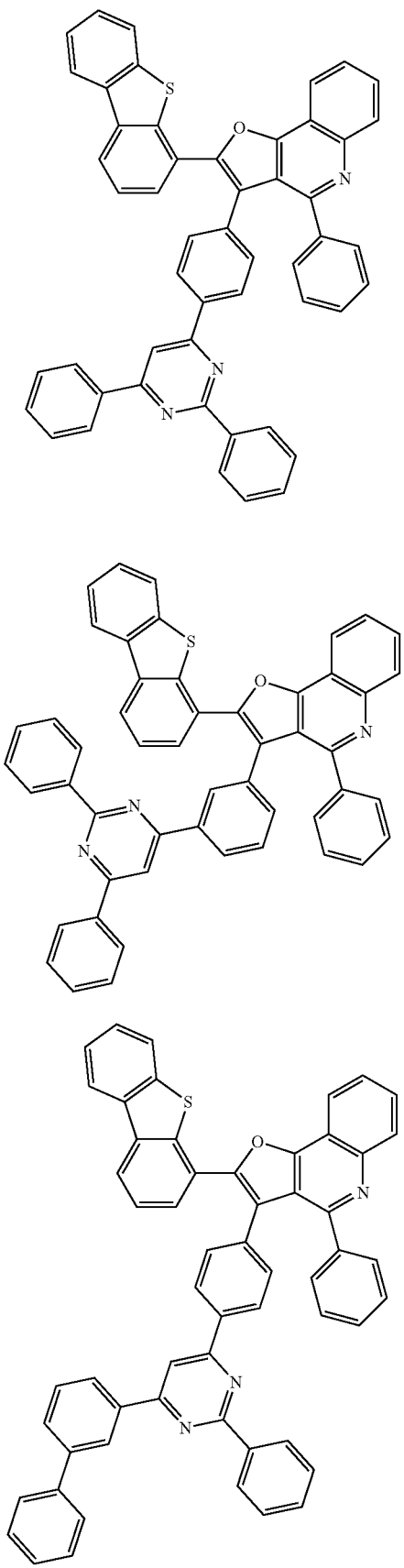
788
-continued

-continued
756
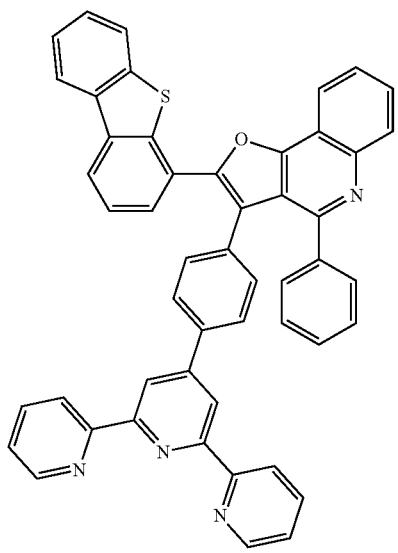
757
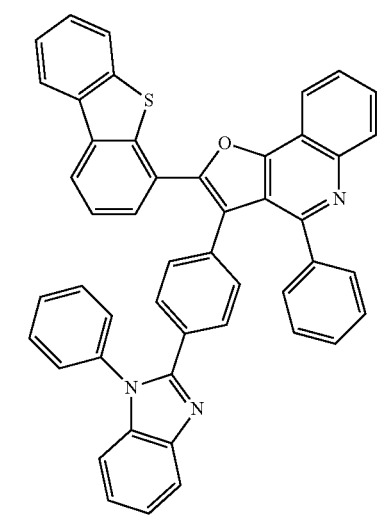
758
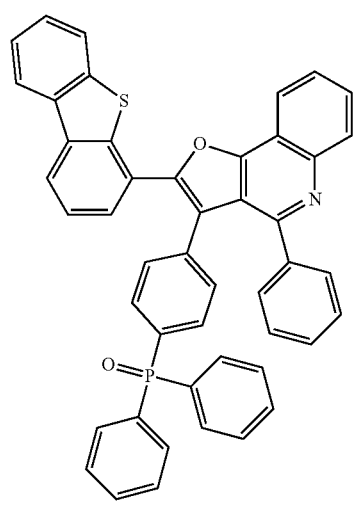
-continued
759
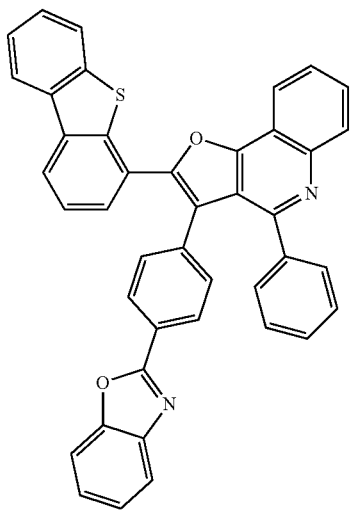
760
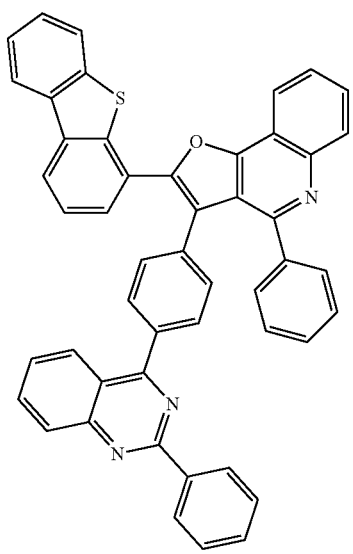
761
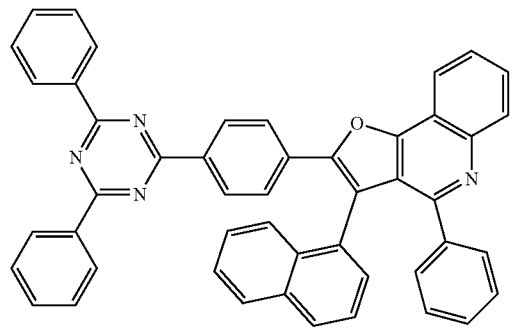

762
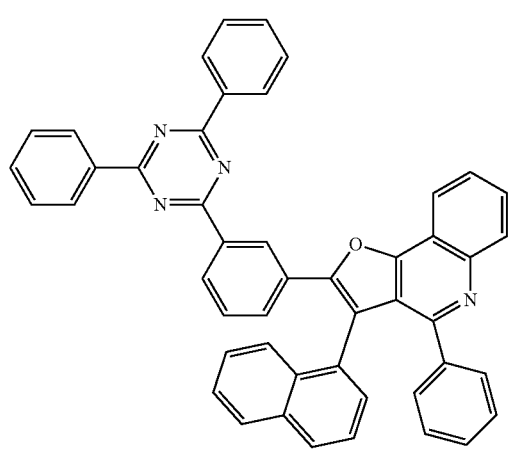
766
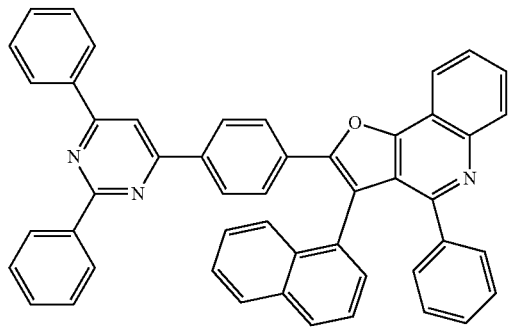
763
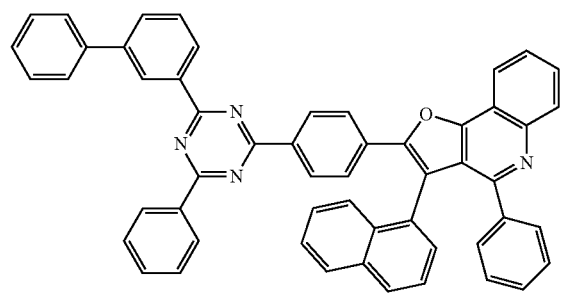
767
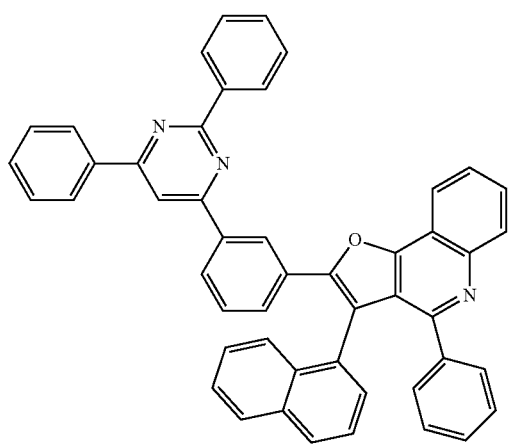
764
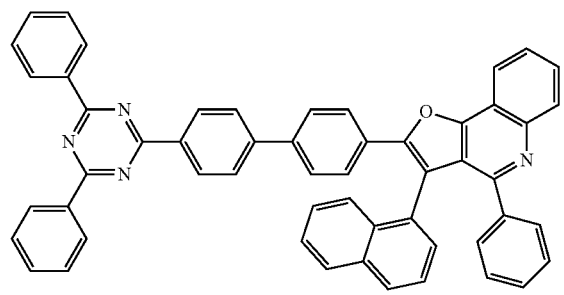
768
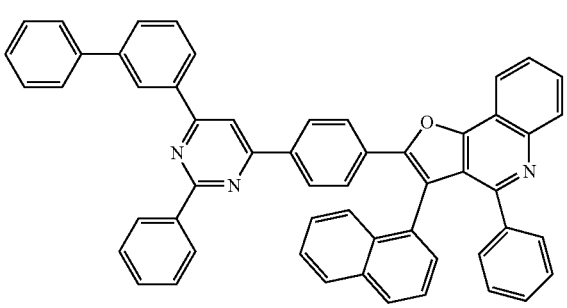
765
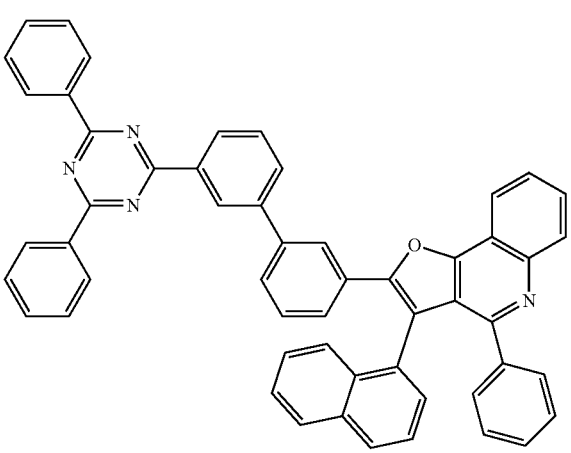
769
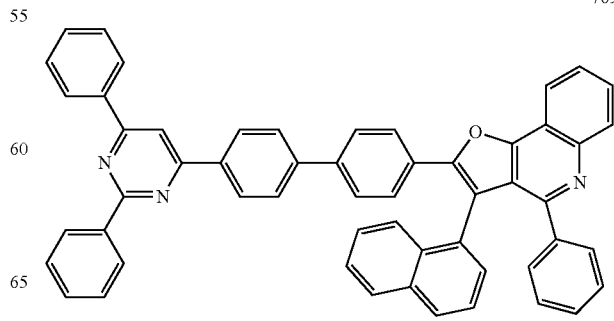

-continued
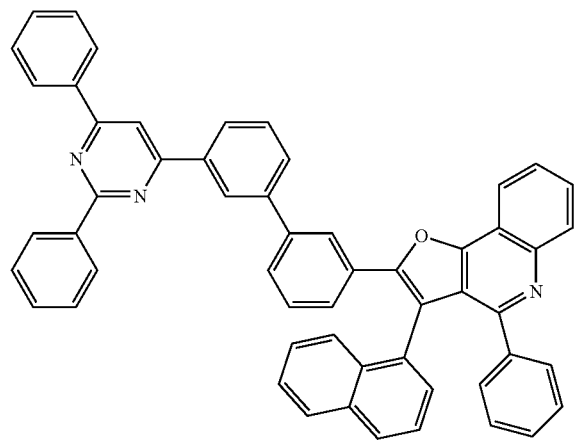
770
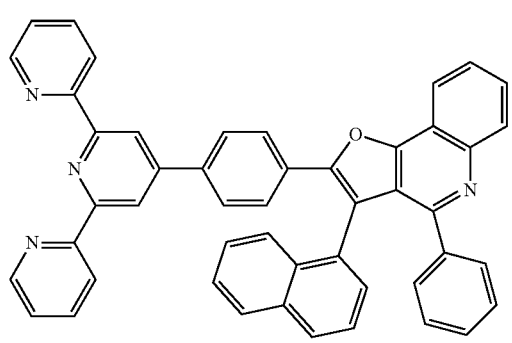
771
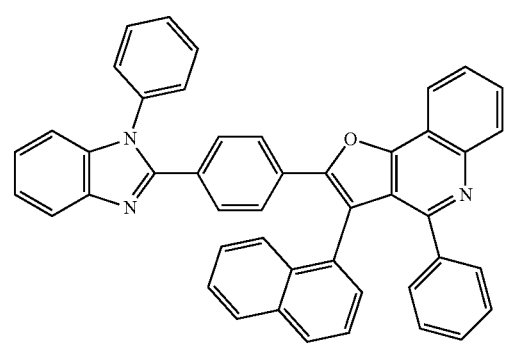
772
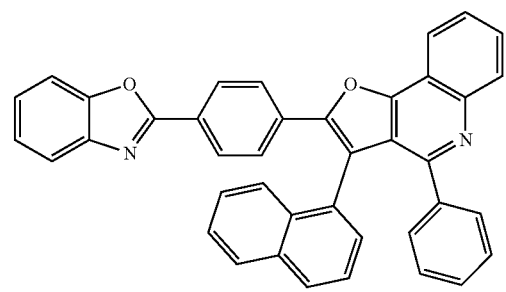
774
-continued
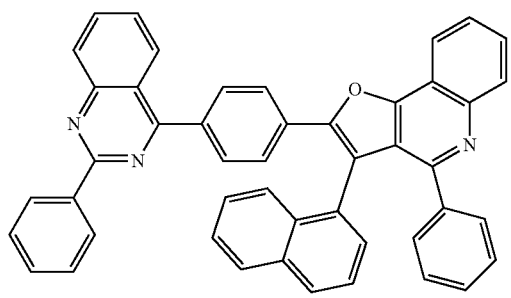
775
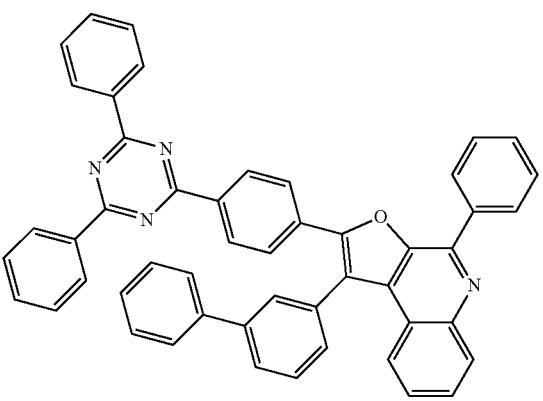
776
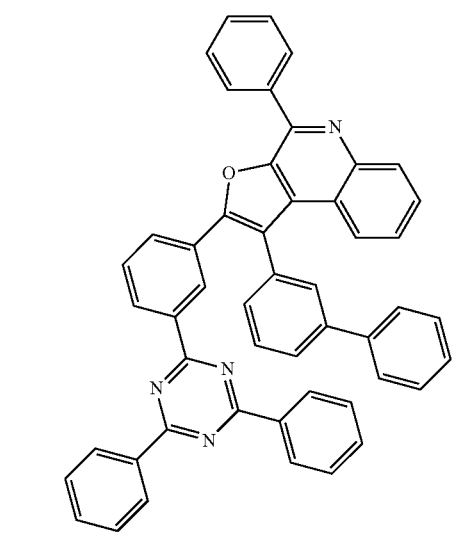
777

778
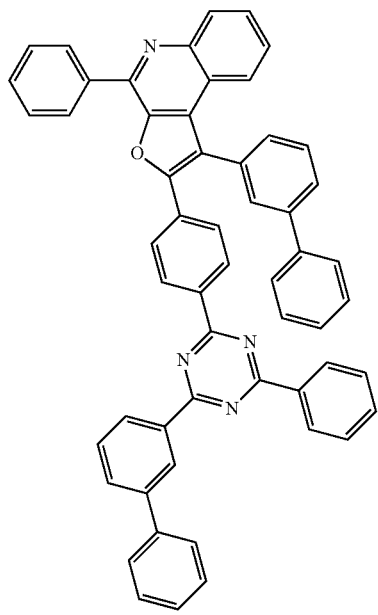
779
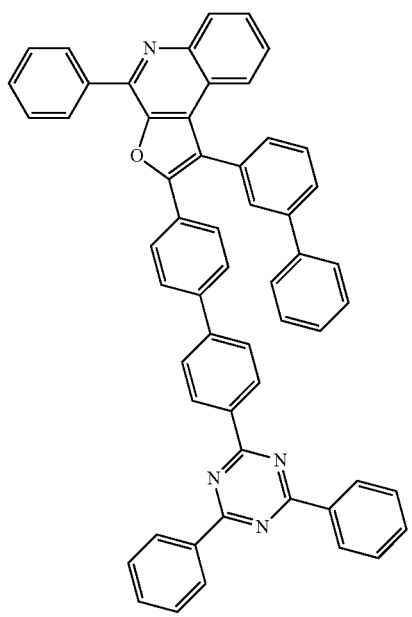
780
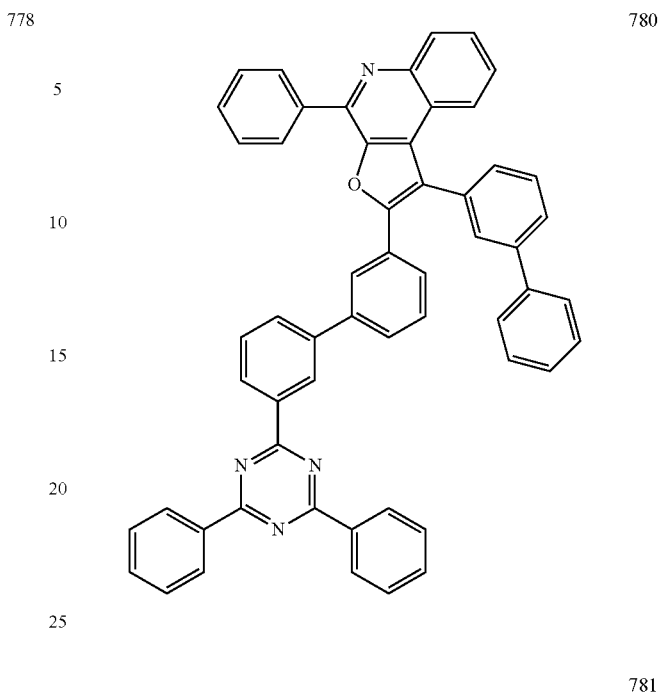
781
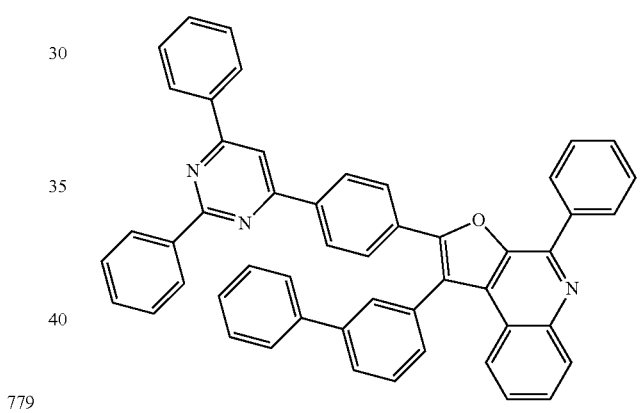
782
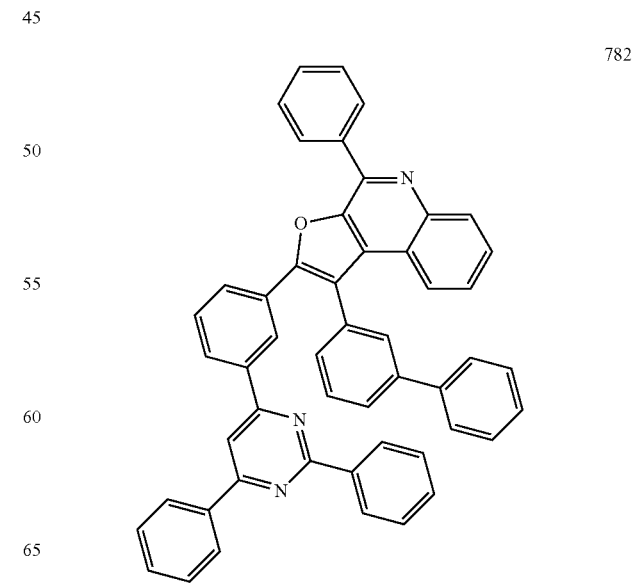

797
-continued
783
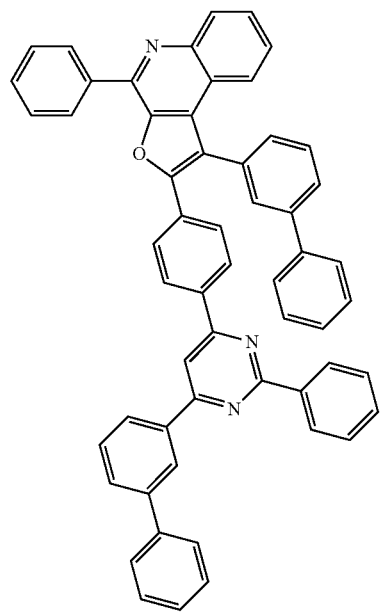
784
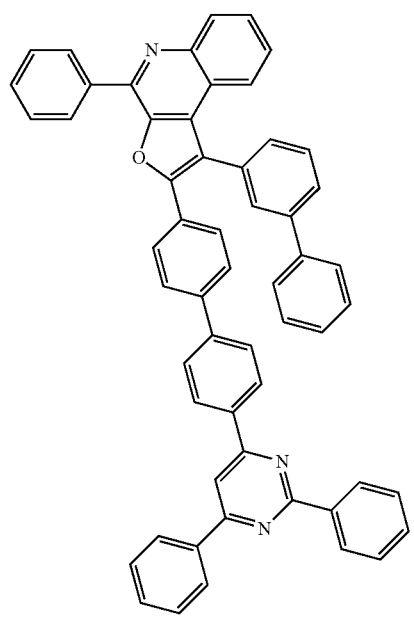
798
-continued
785
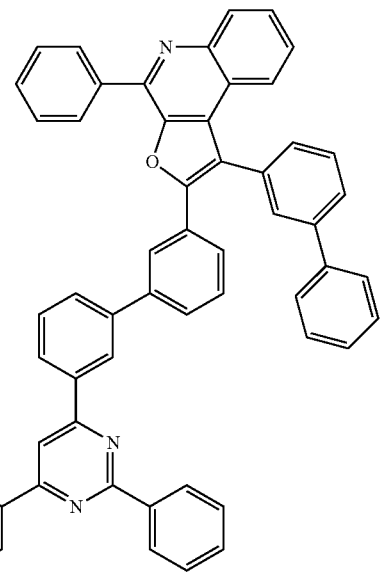
786
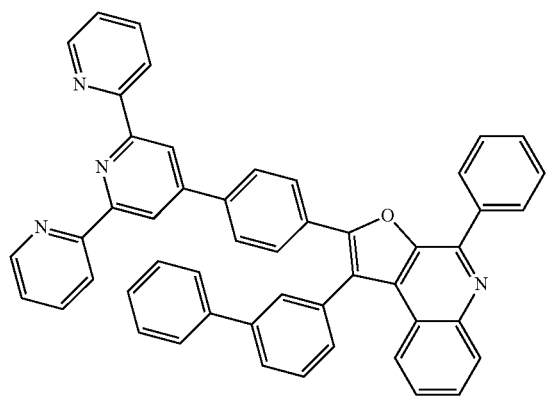
787
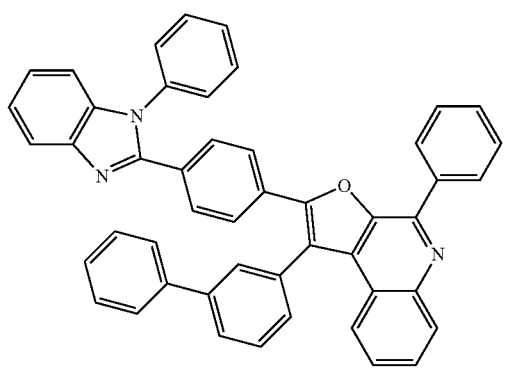

799
-continued
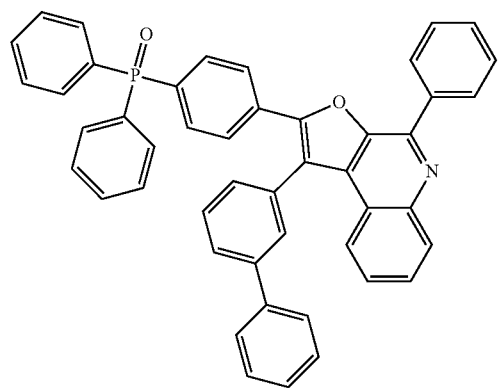
788
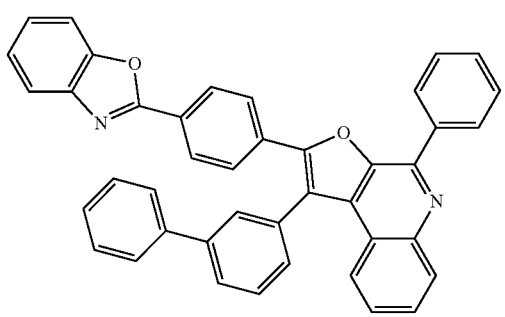
789
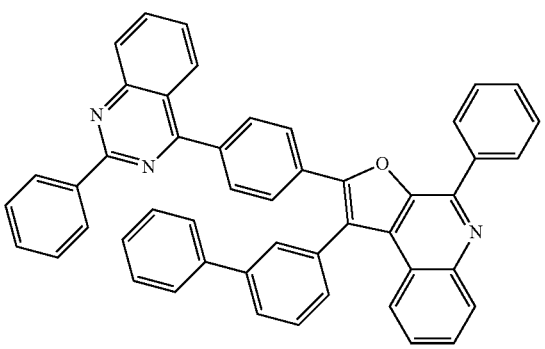
790
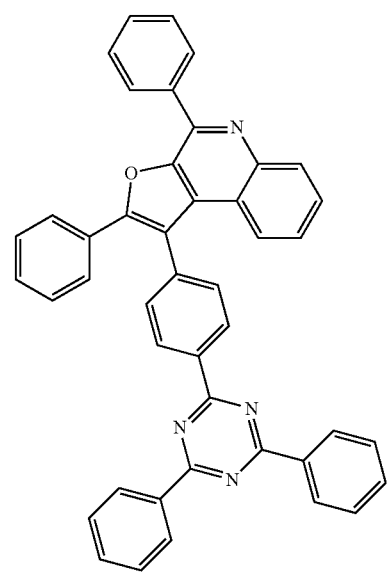
791
800
-continued
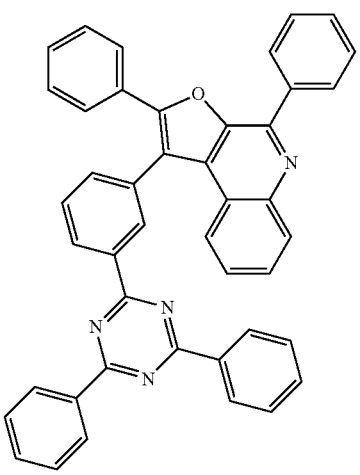
792
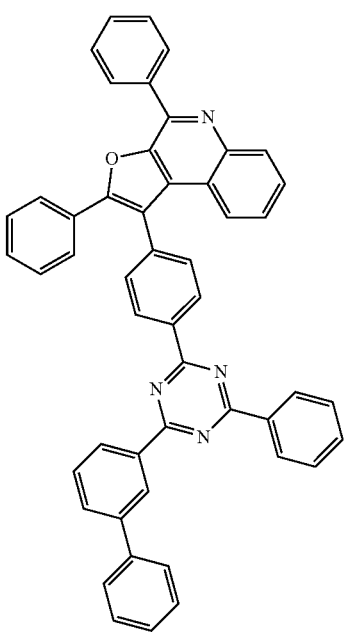
793

801
-continued
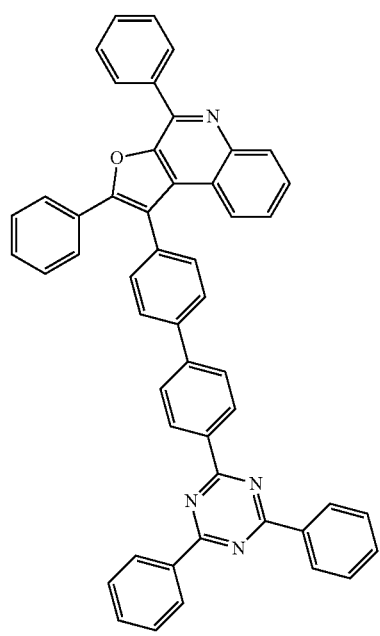
794
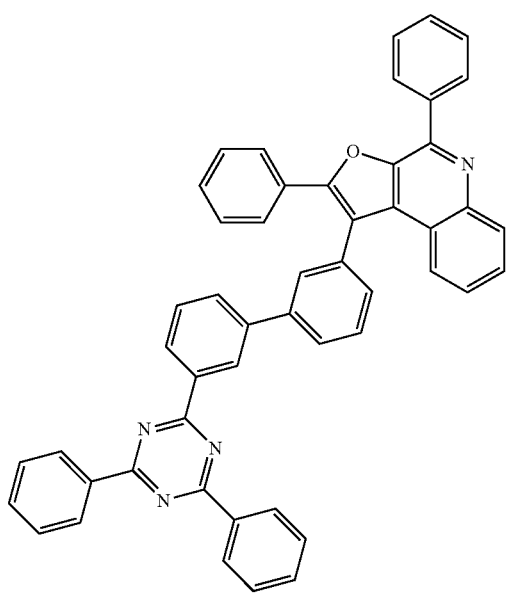
795
802
-continued
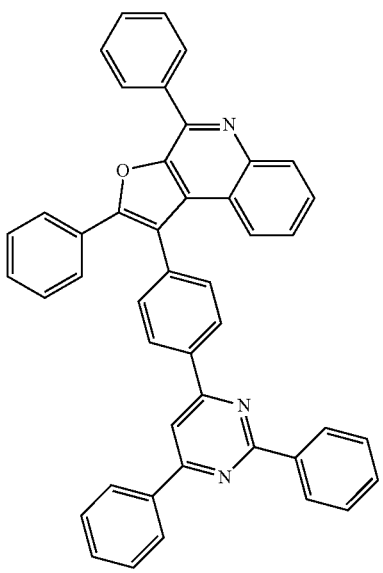
796
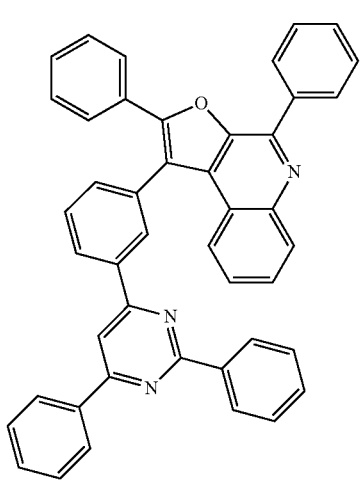
797
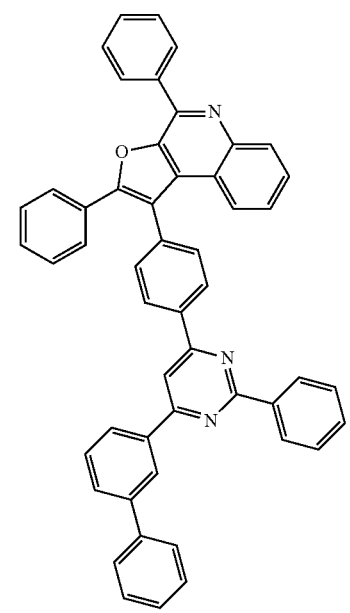
798

803
-continued
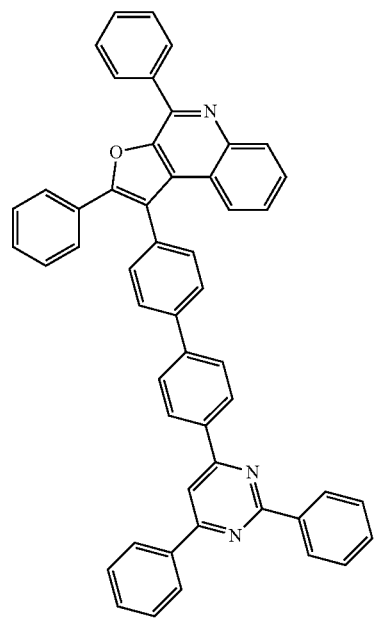
799
804
-continued
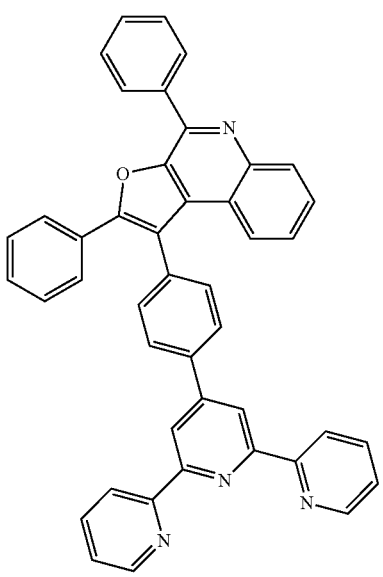
801
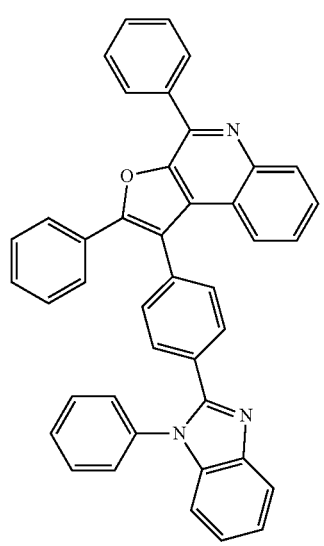
802
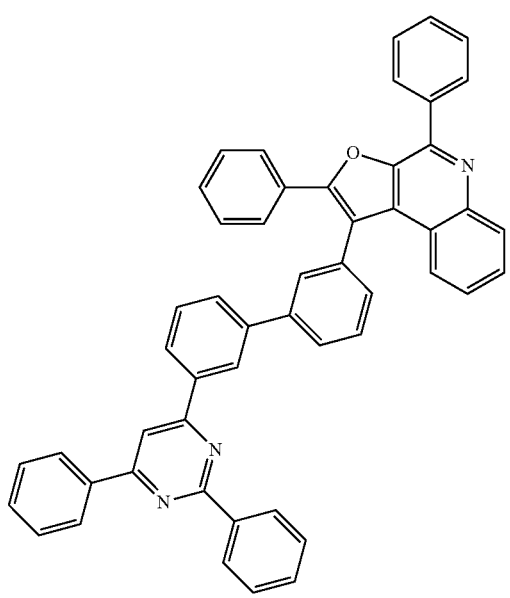
800
803

805                                806
-continued                         -continued
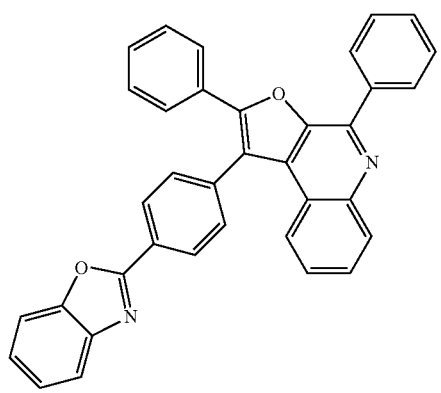
804
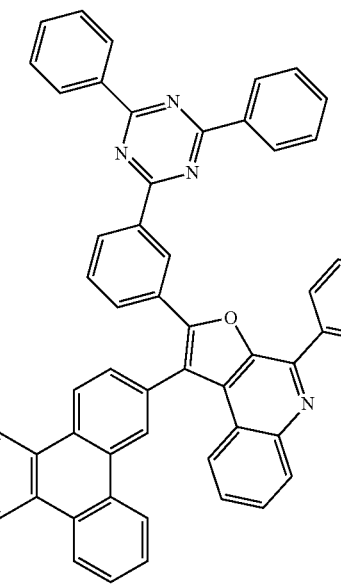
807
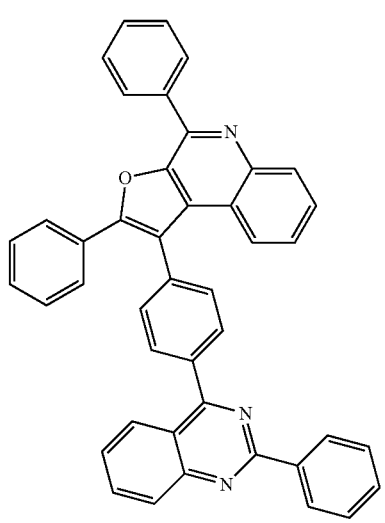
805
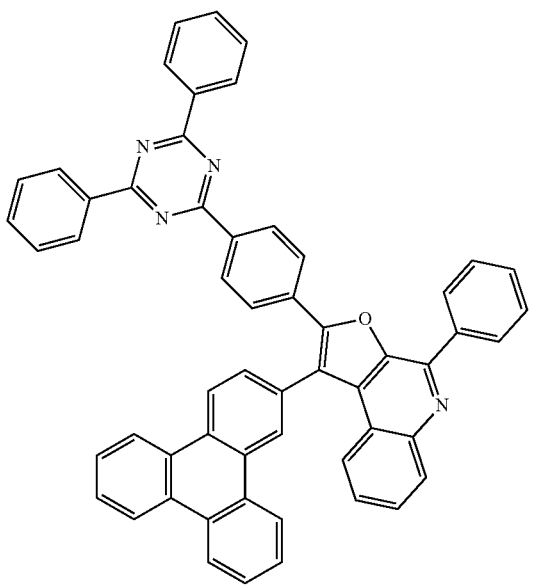
806
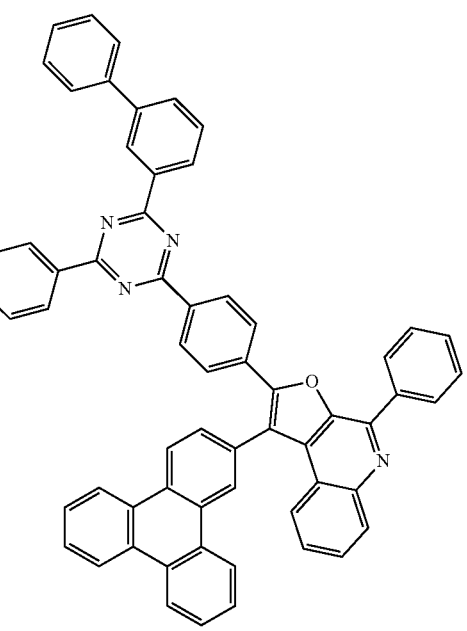
808

807
-continued
808
-continued
809
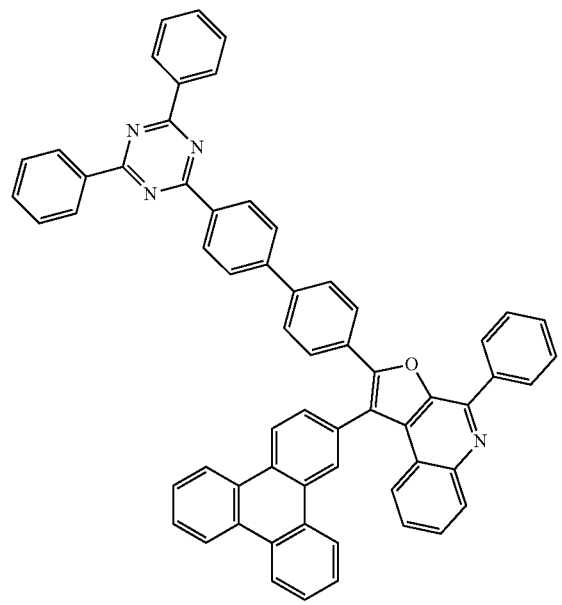
811
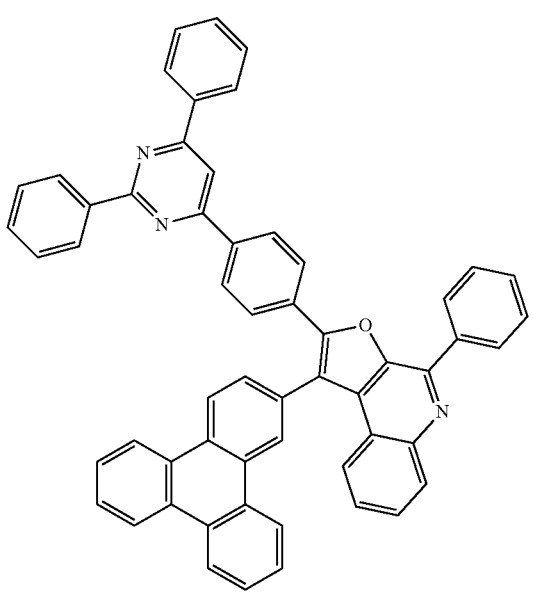
810
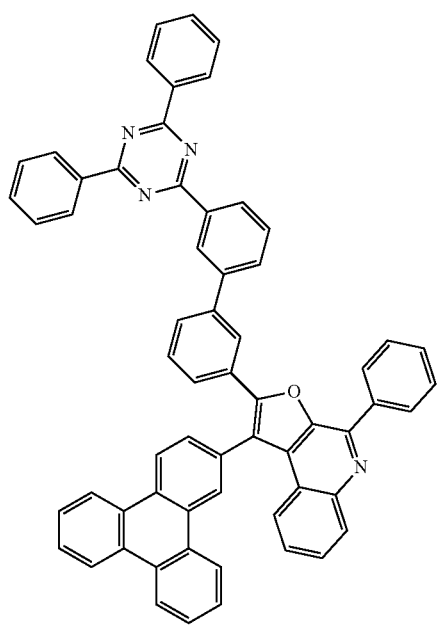
812
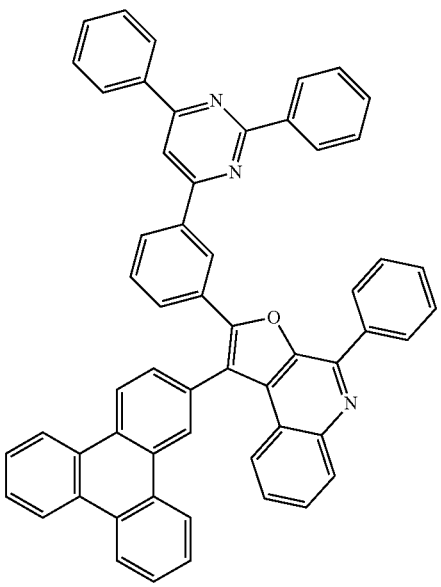

809
-continued
813
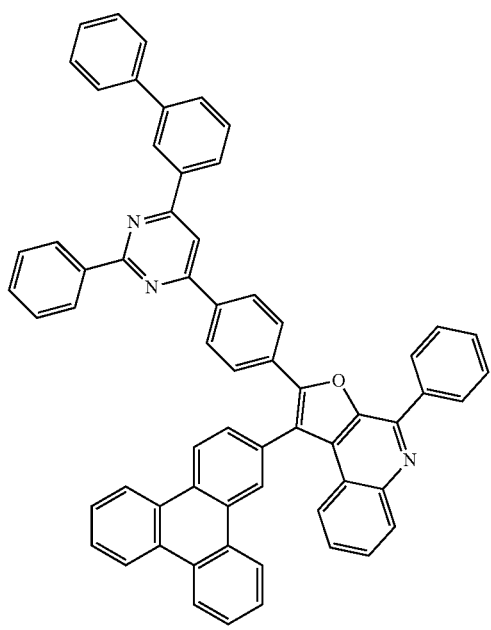
810
-continued
815
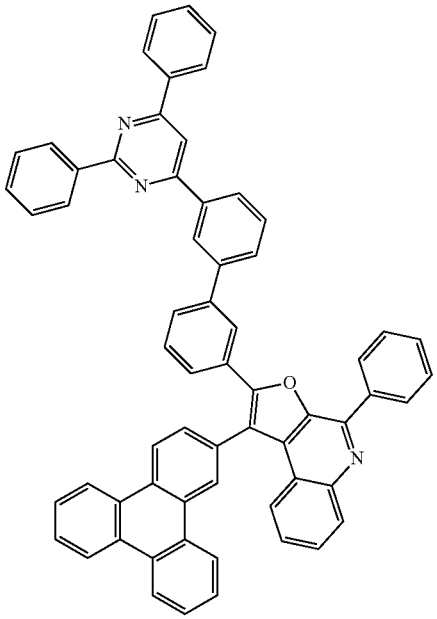
814
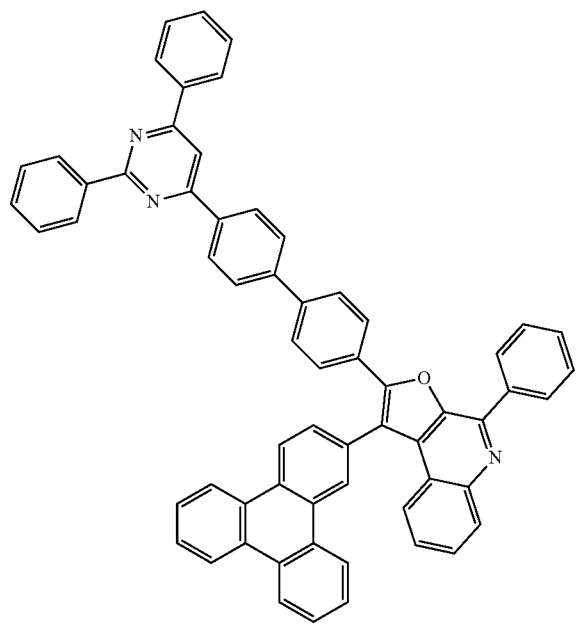
816
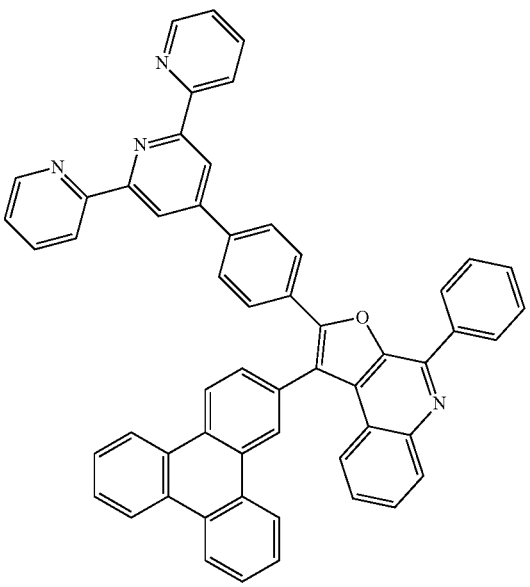

811
-continued
817
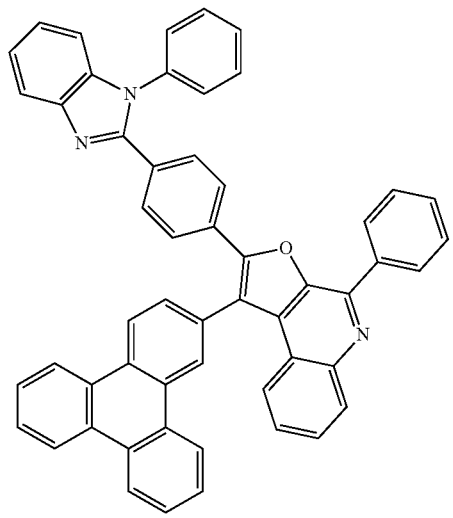
818
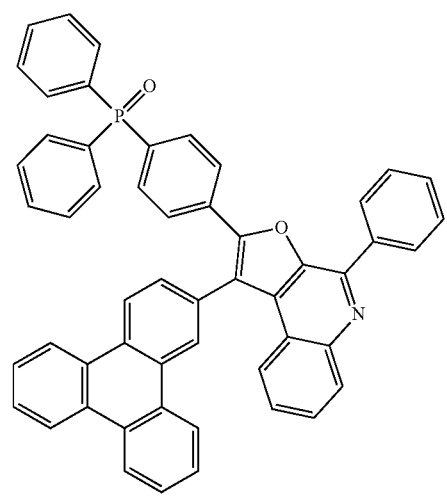
819
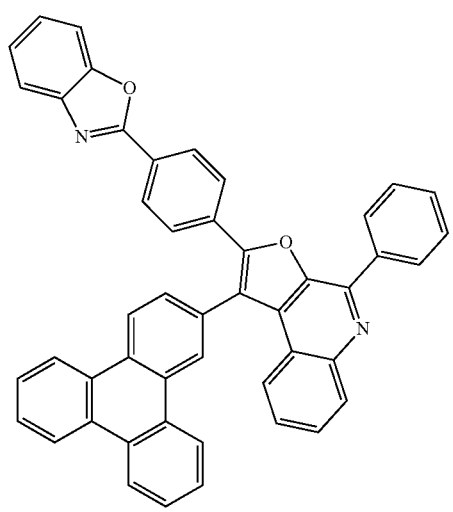
812
-continued
820
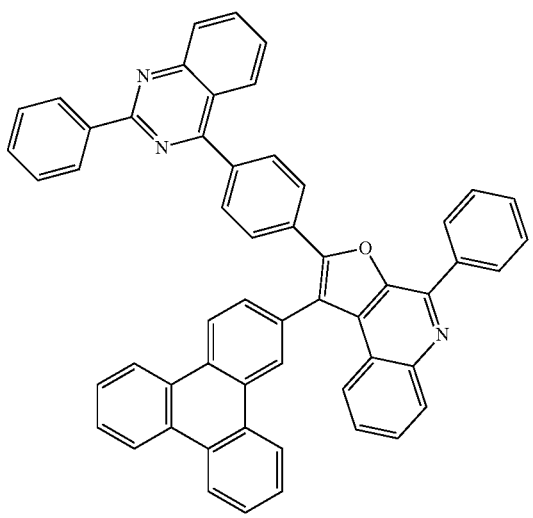
821
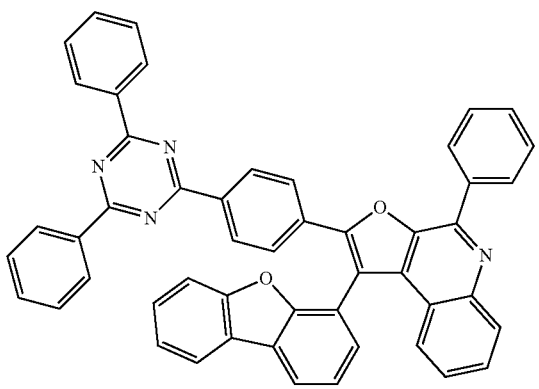
822
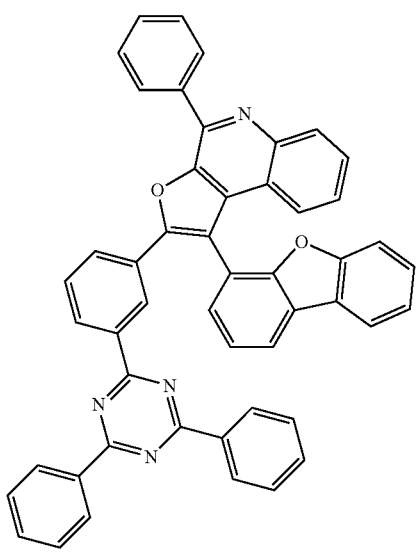

813
-continued
823
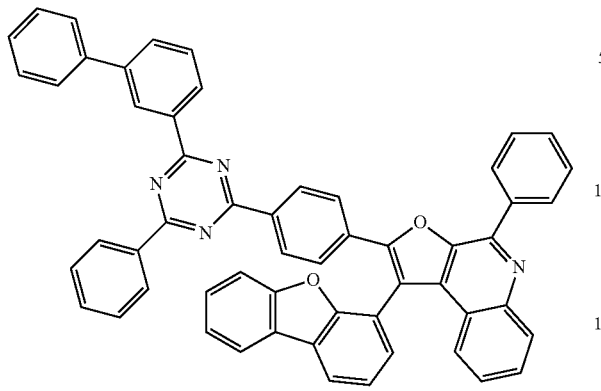
824
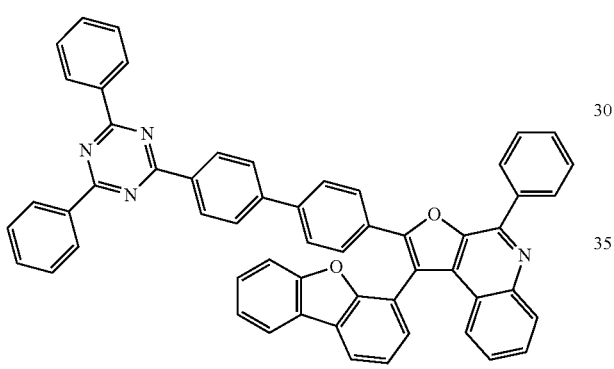
825
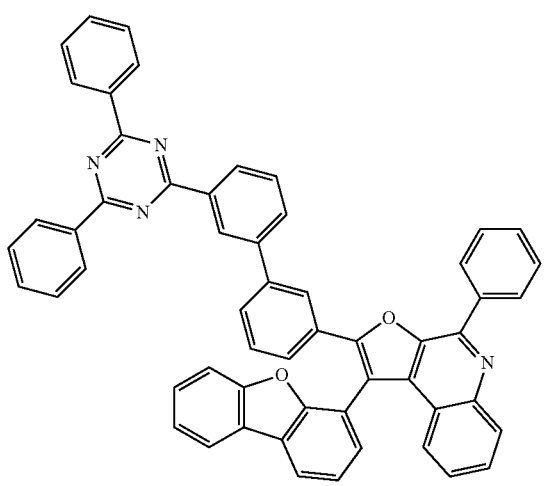
814
-continued
826
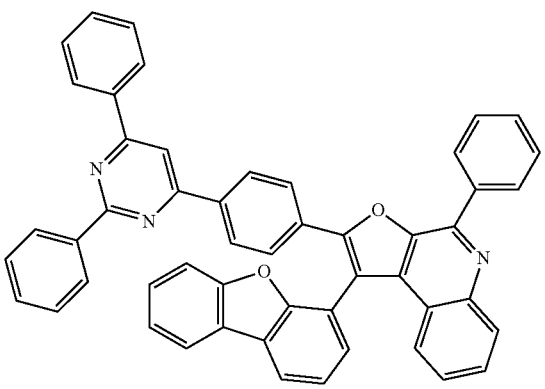
827
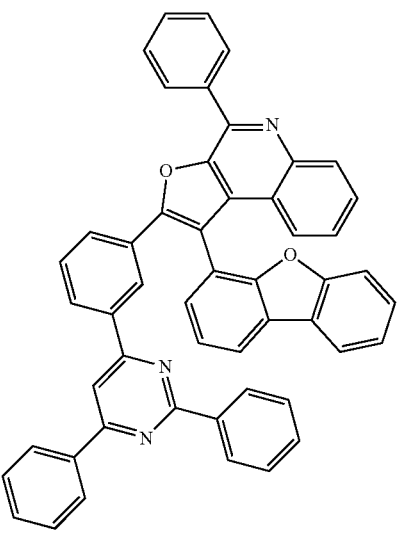
828
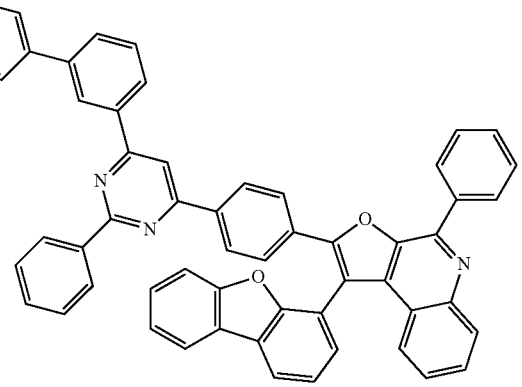

829
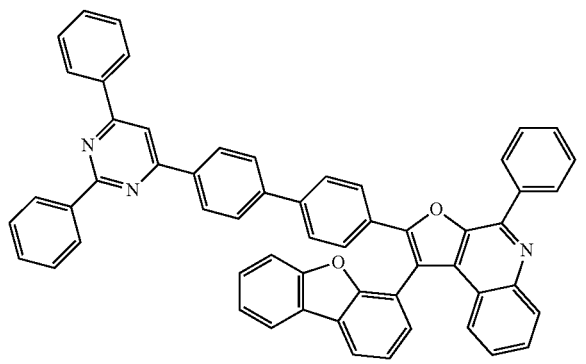
832
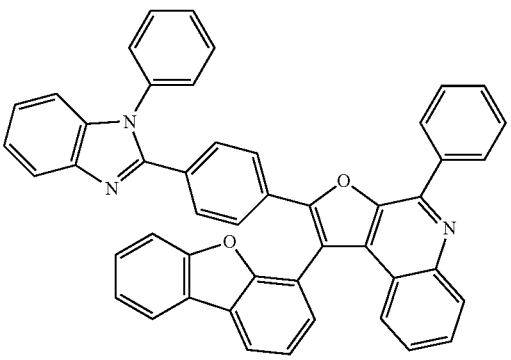
833
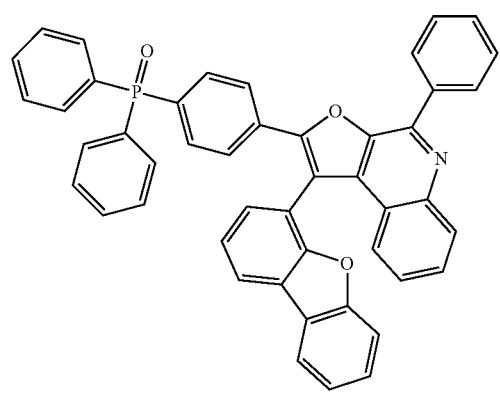
830
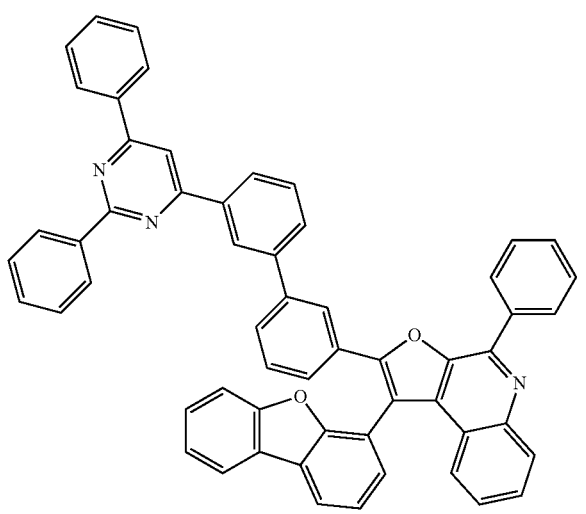
834
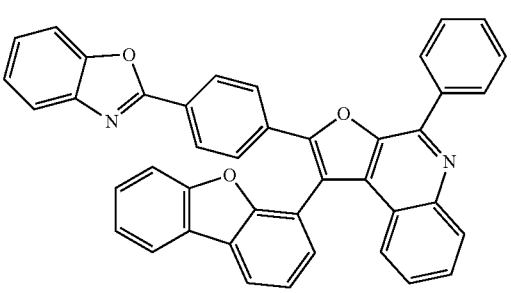
831
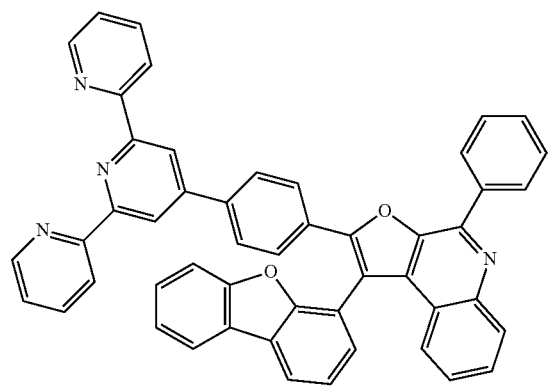
835
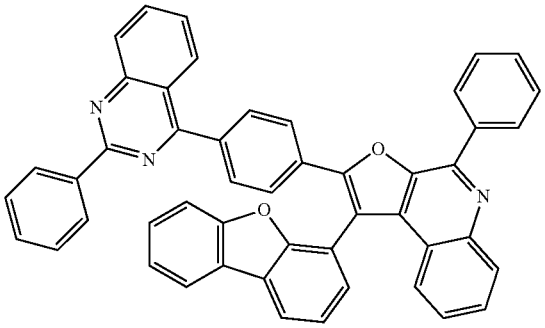

-continued
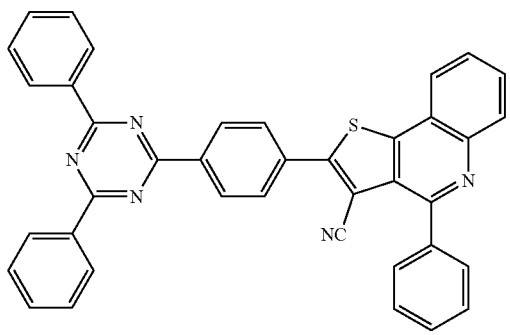
836
837
838
839
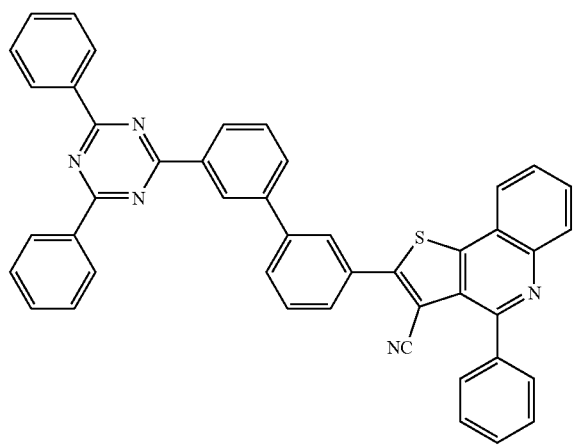
840
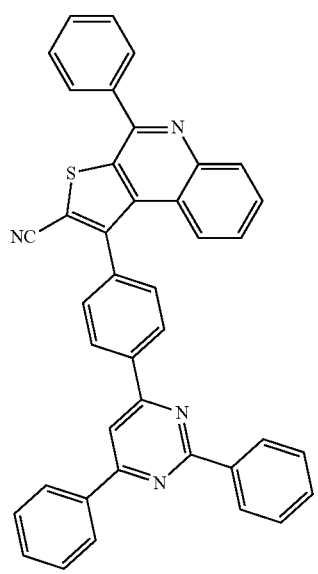
841
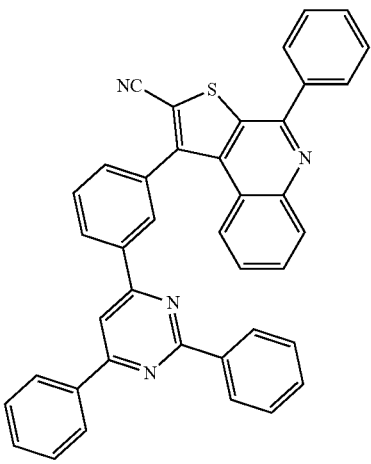
842

819
-continued
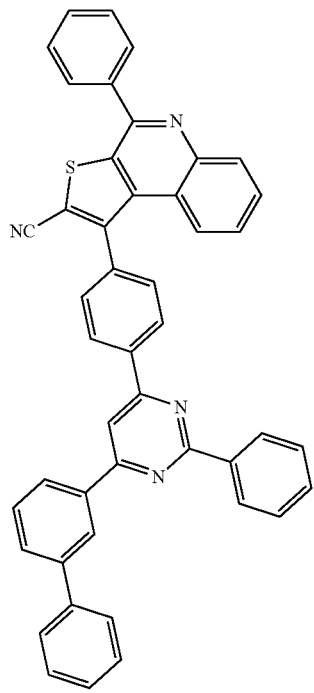
820
-continued
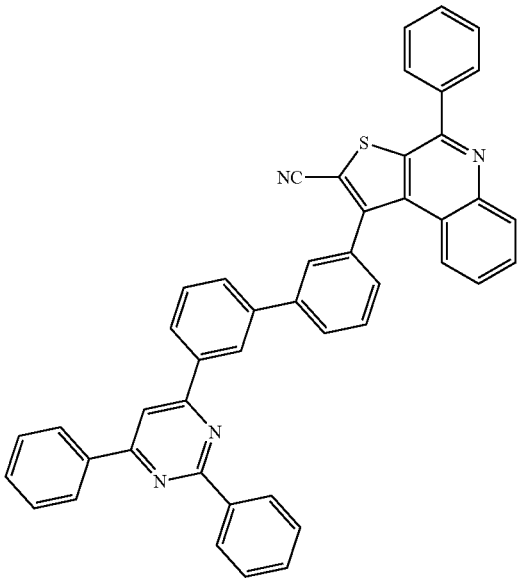
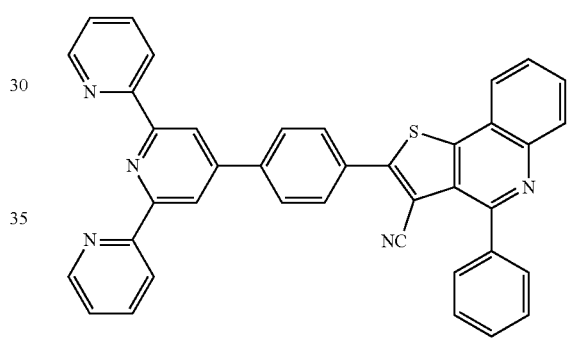
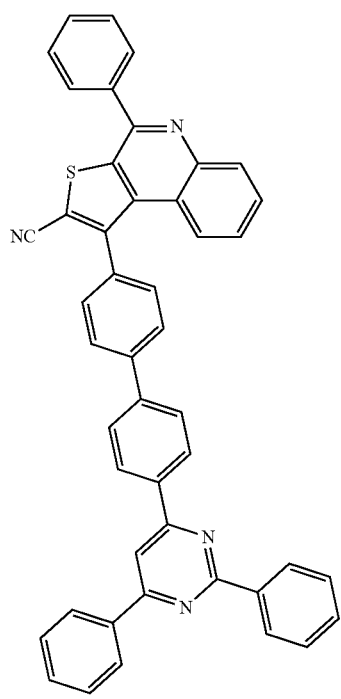
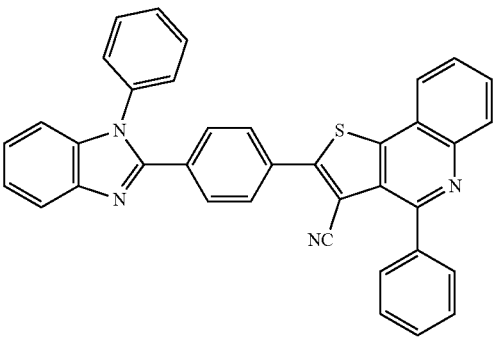
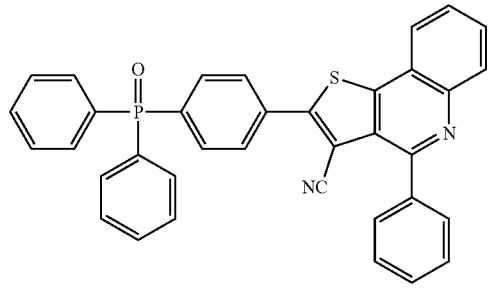

-continued
849
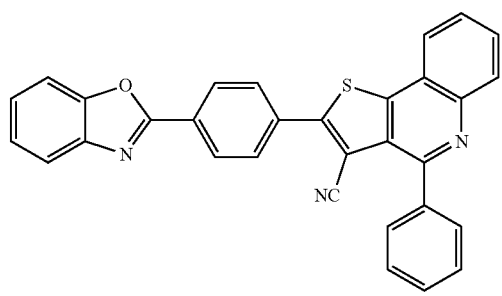
850
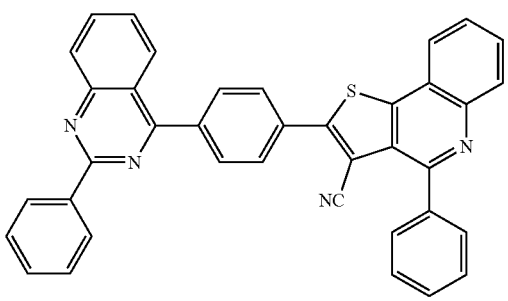
851
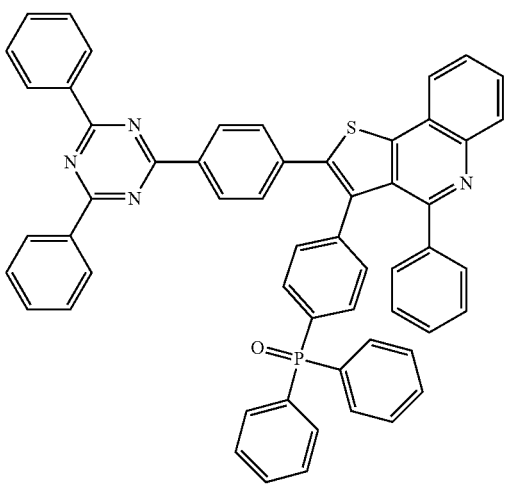
852
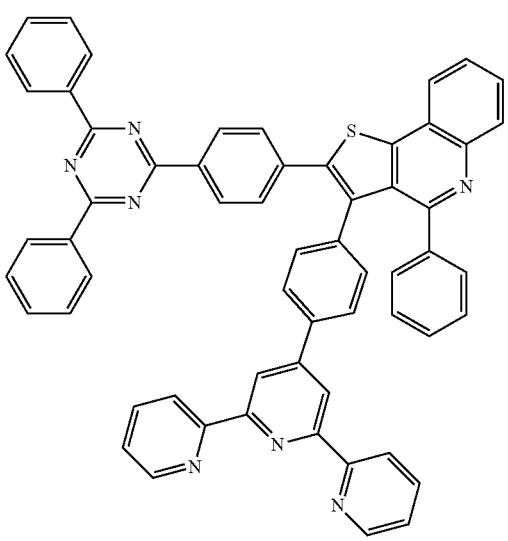
-continued
853
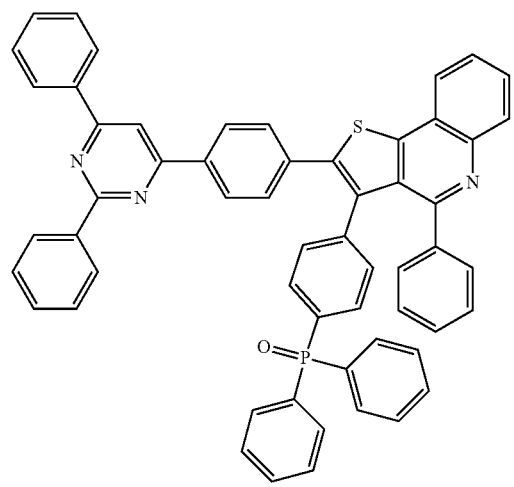
854
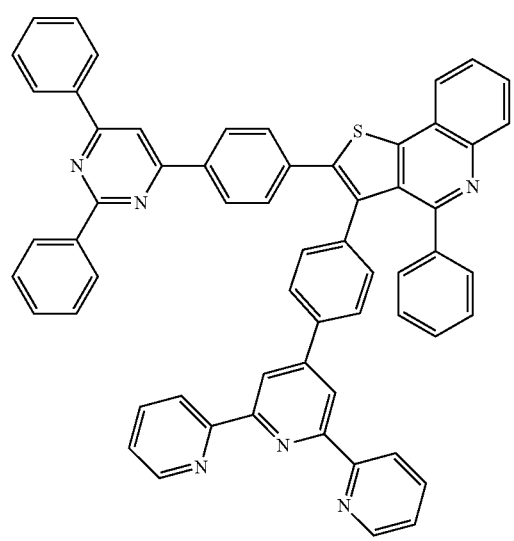
855
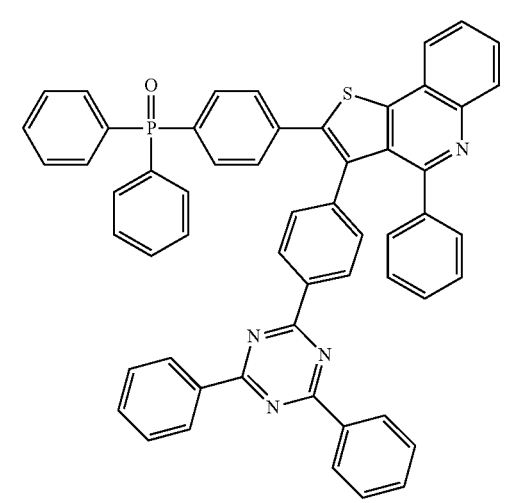

823
-continued
856
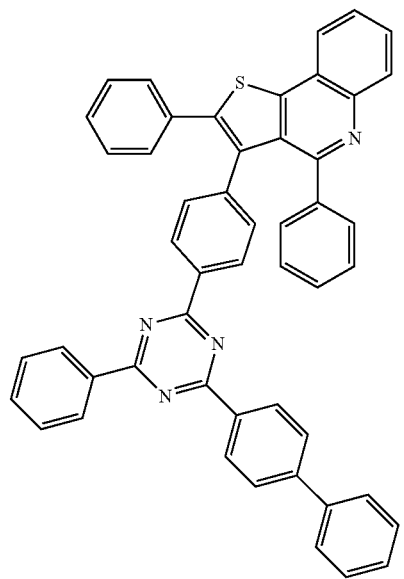
824
-continued
858
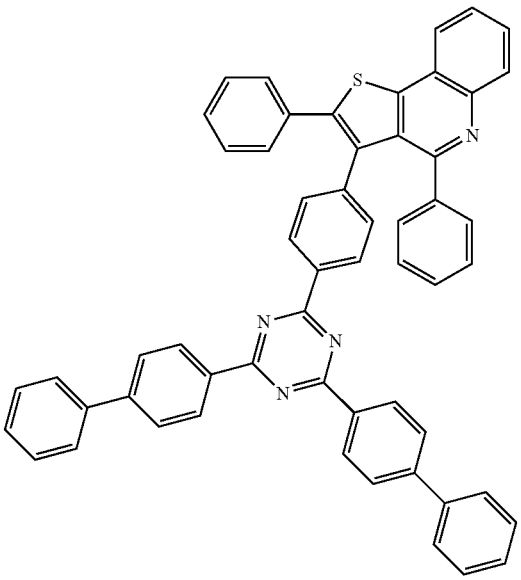
857
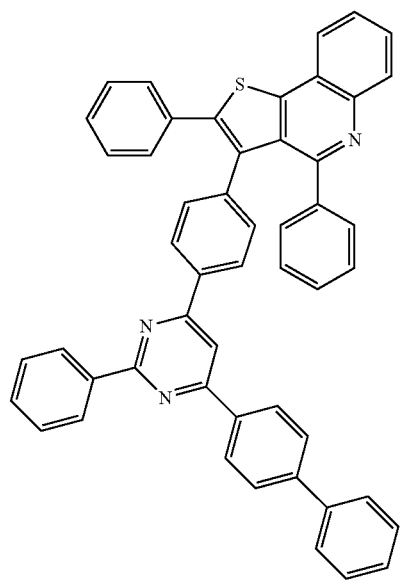
859
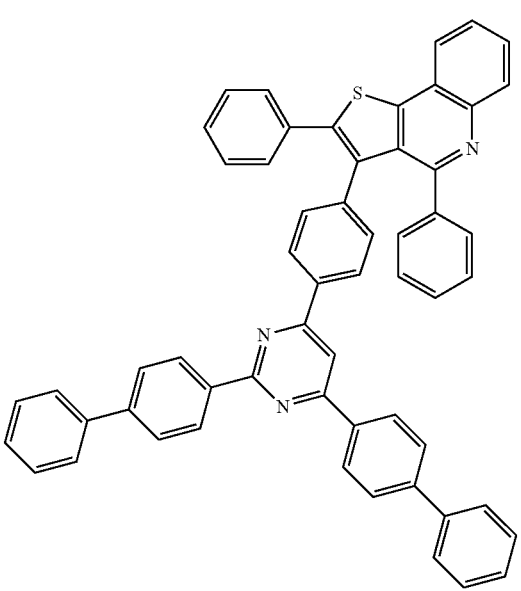

825
-continued
860
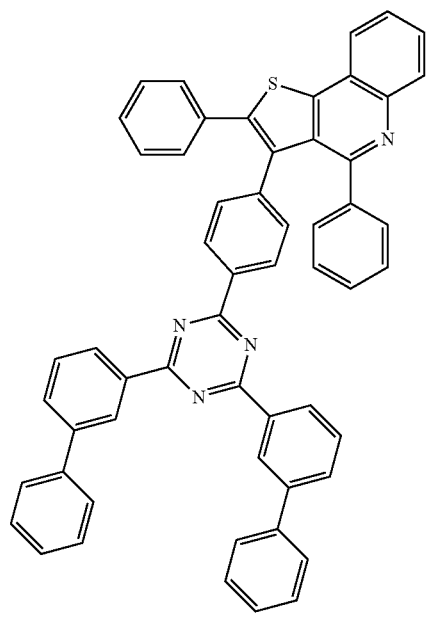
861
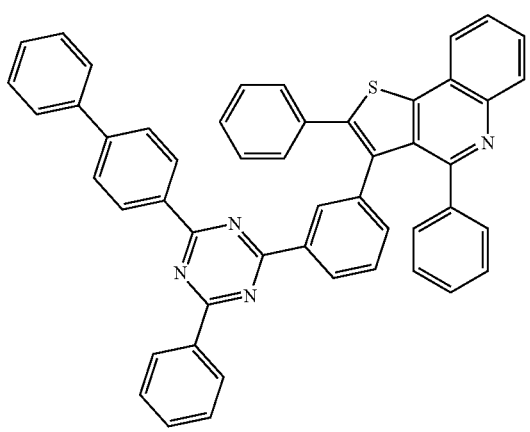
862
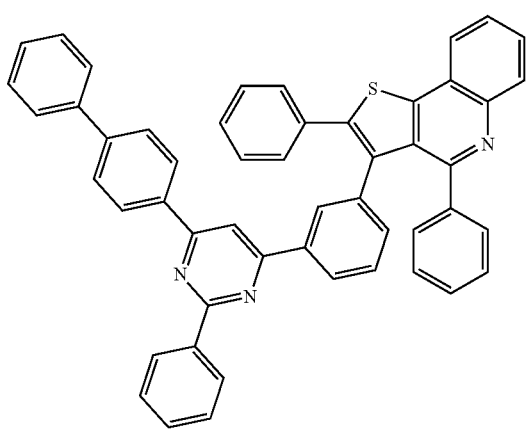
826
-continued
863
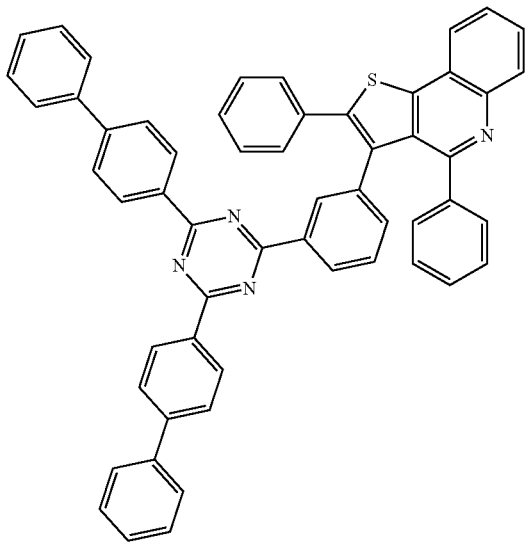
864
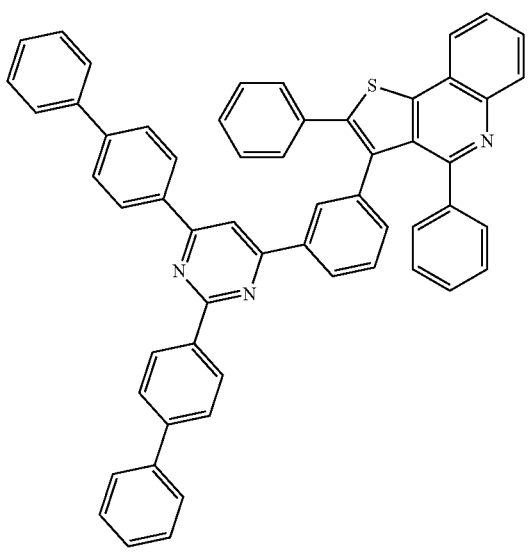
865
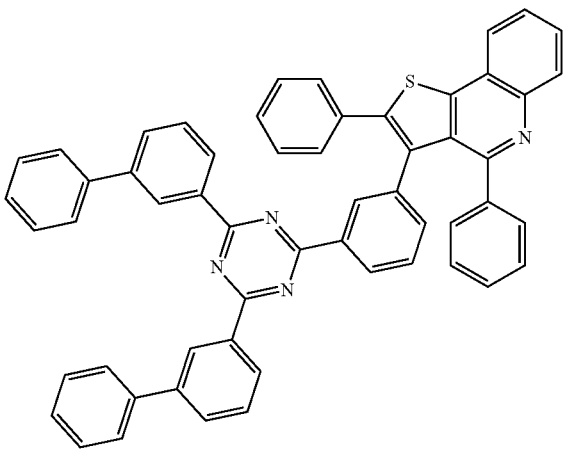

-continued
866
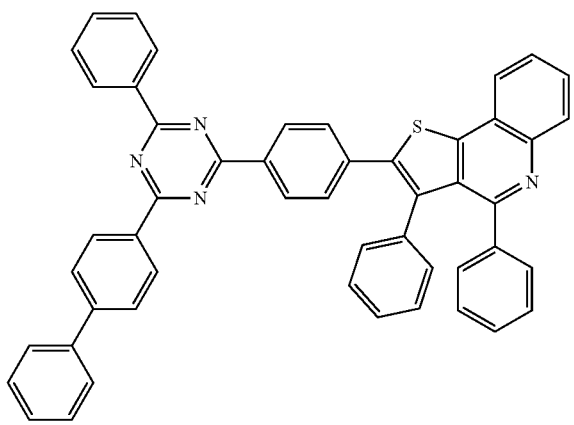
867
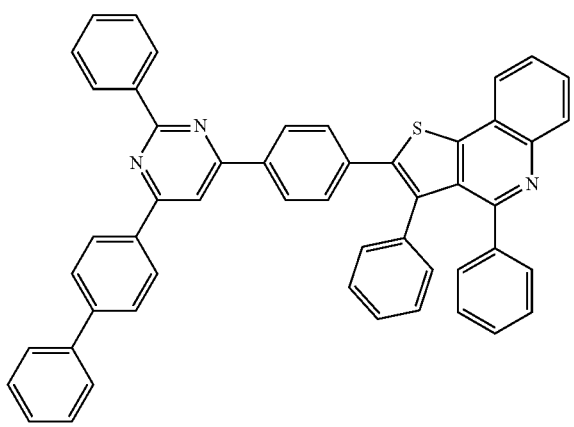
868
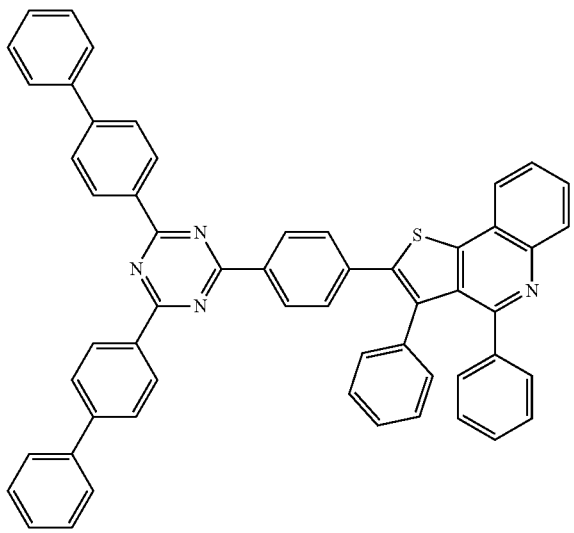
-continued
869
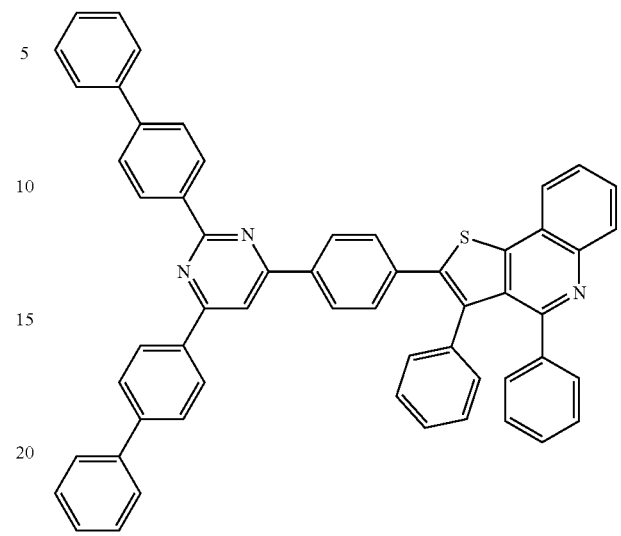
870
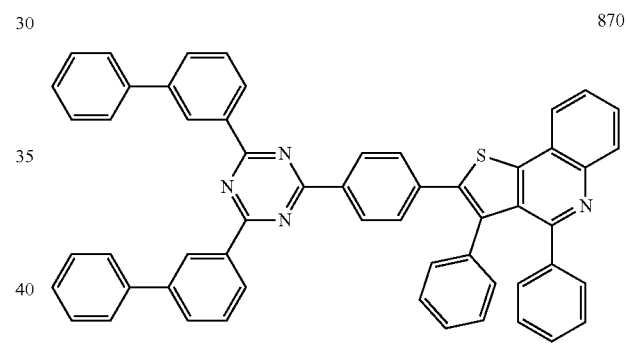
871
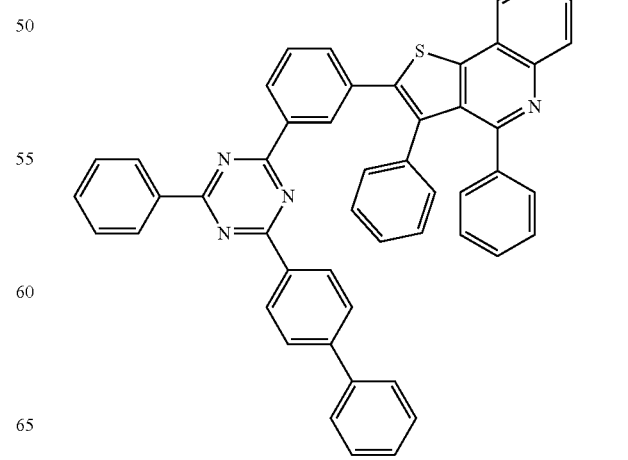

829
-continued
872
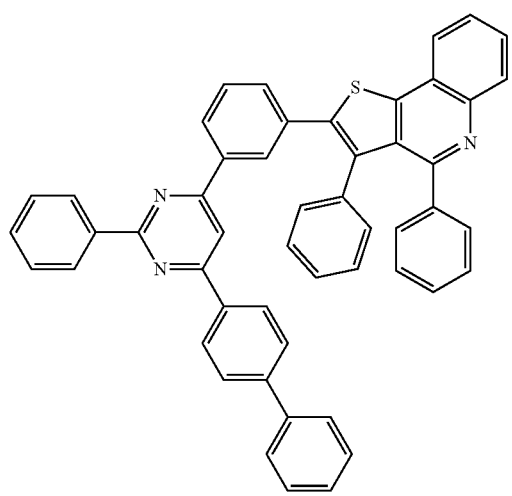
873
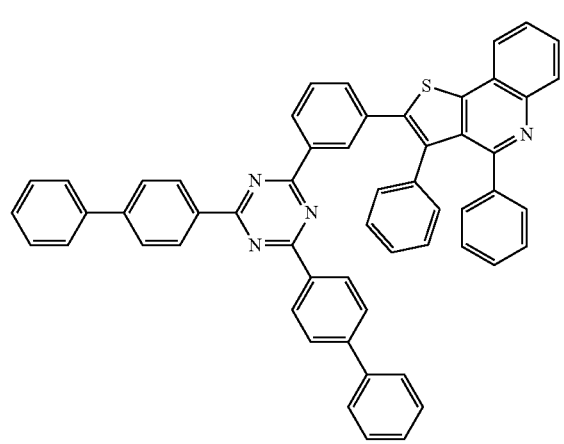
874
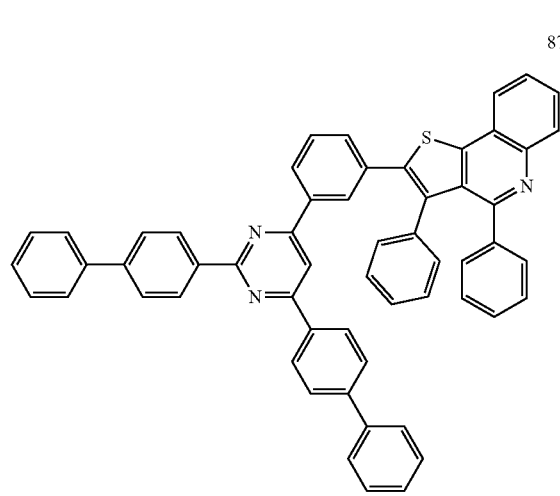
830
-continued
875
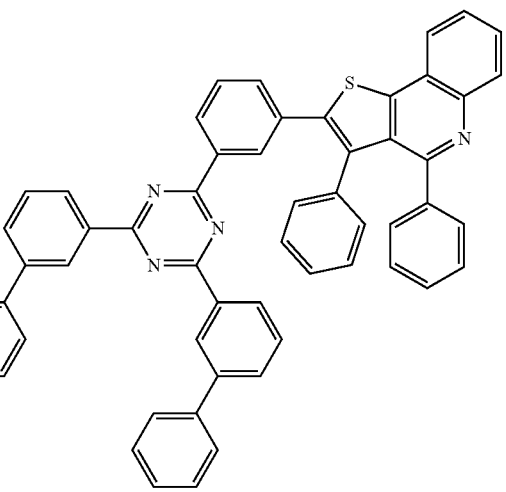
876
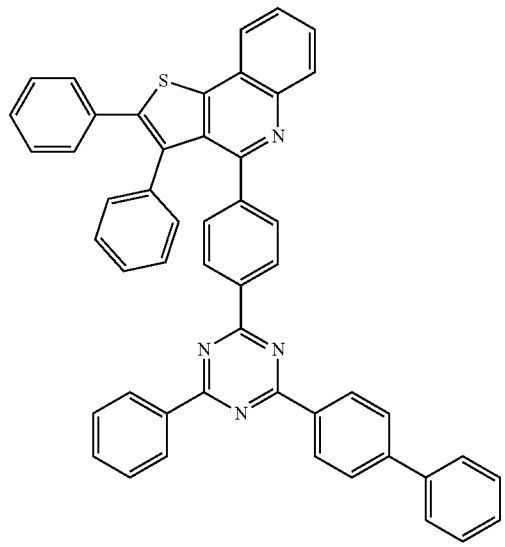
877
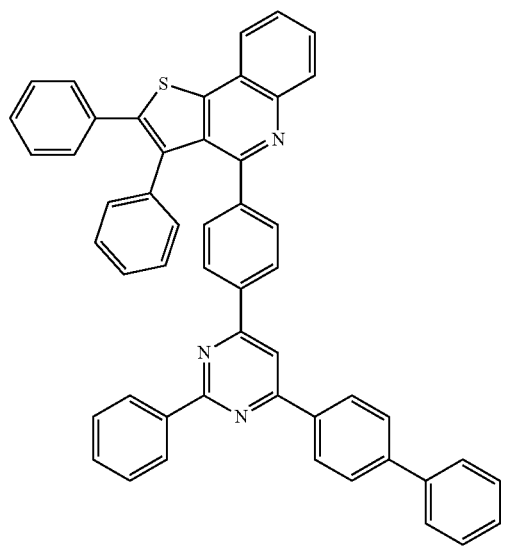

831
-continued
878
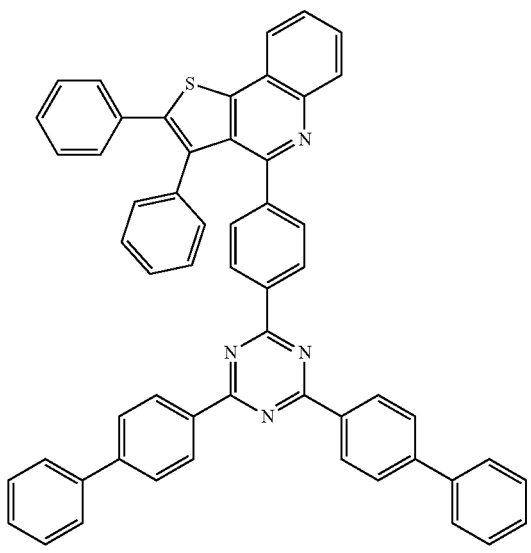
879
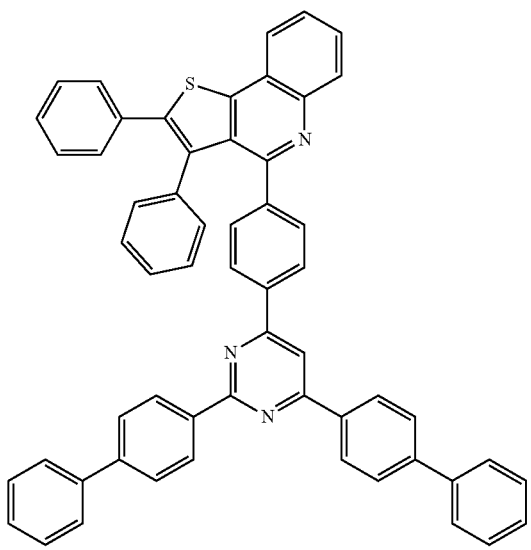
832
-continued
880
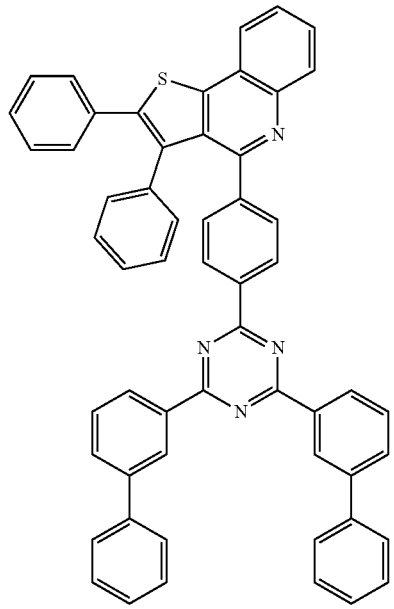
881
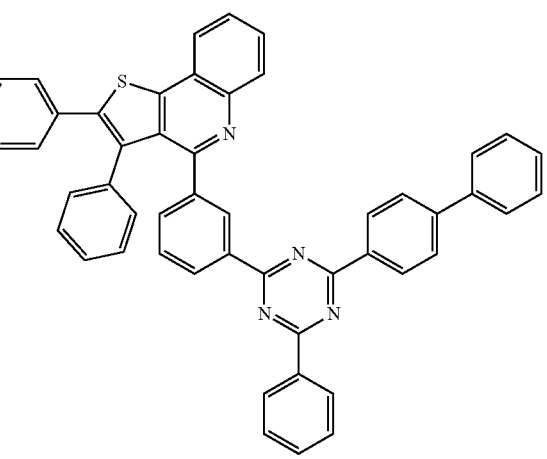
882

-continued
883
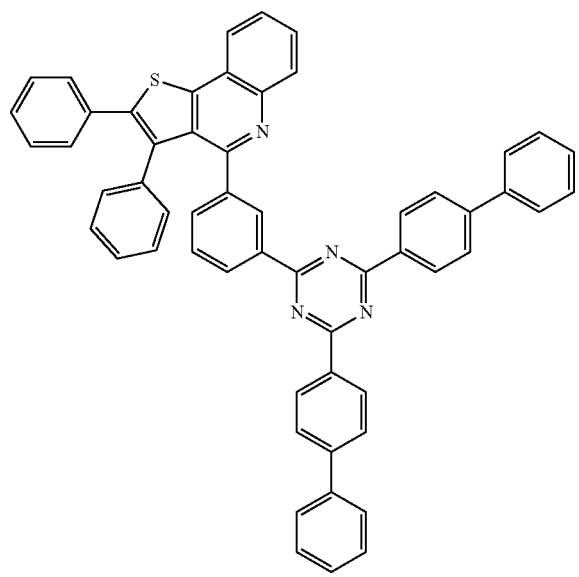
884
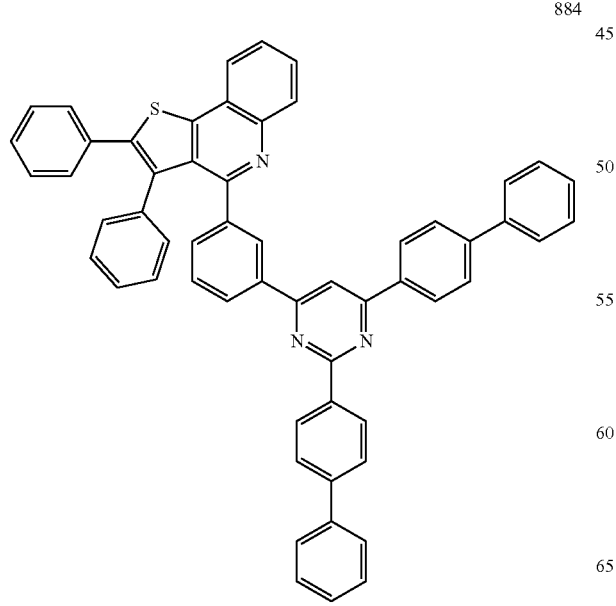
-continued
885
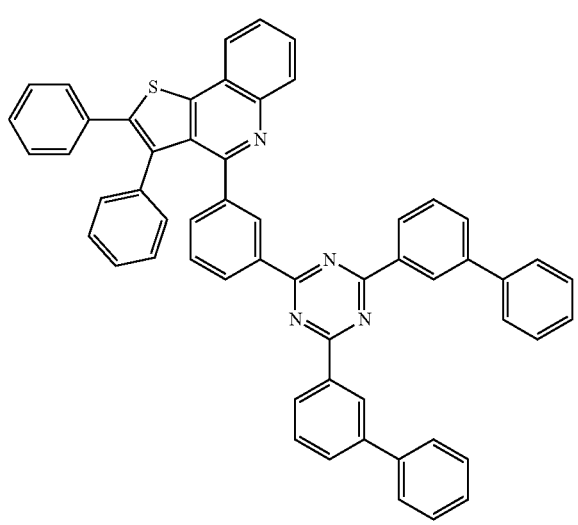
886
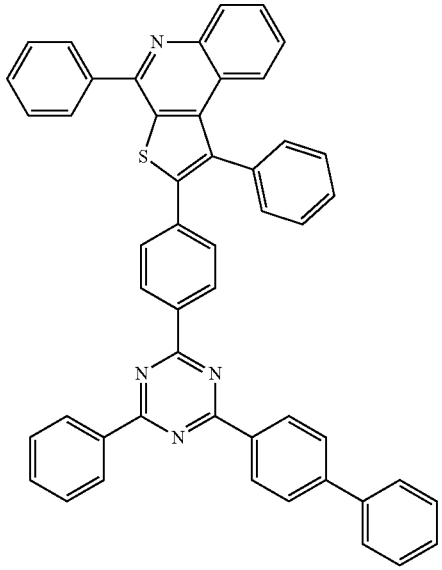

835
-continued
887
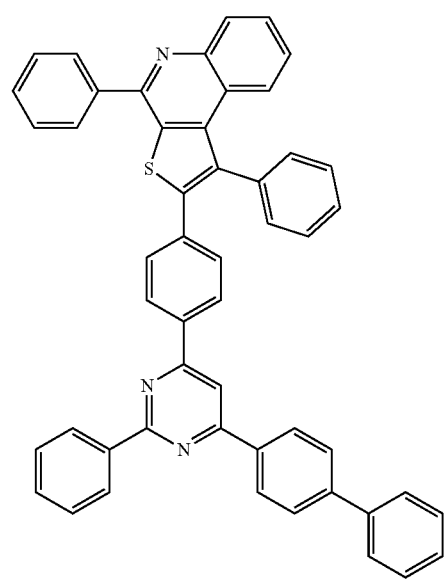
888
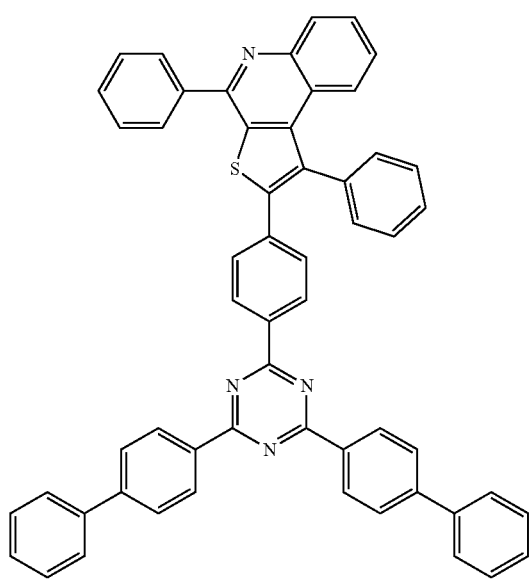
836
-continued
889
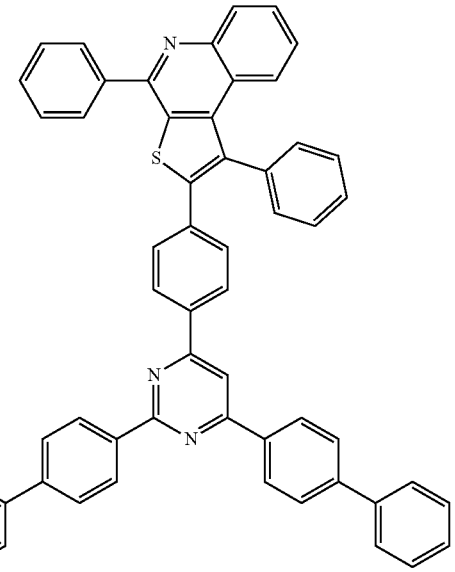
890
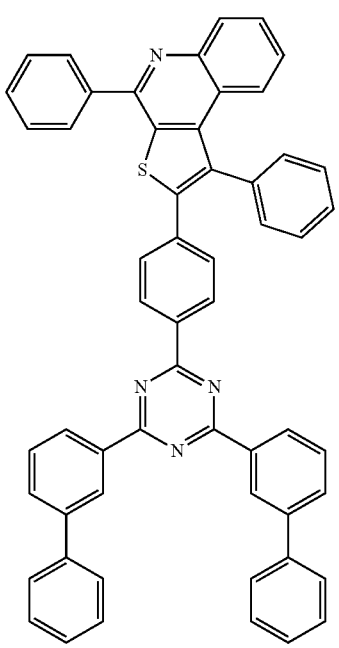

837
-continued
891
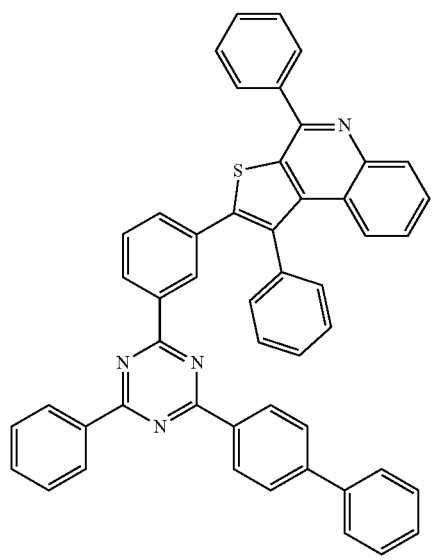
892
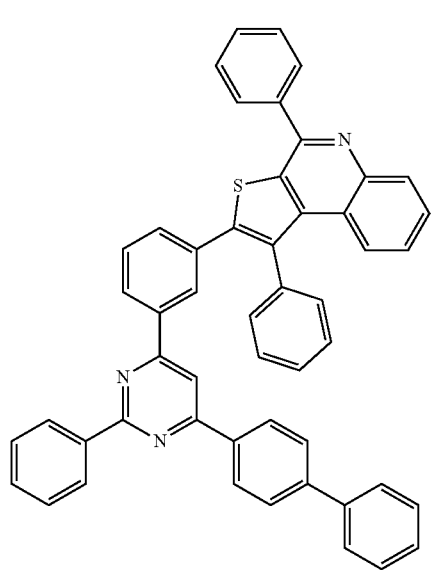
838
-continued
893
894
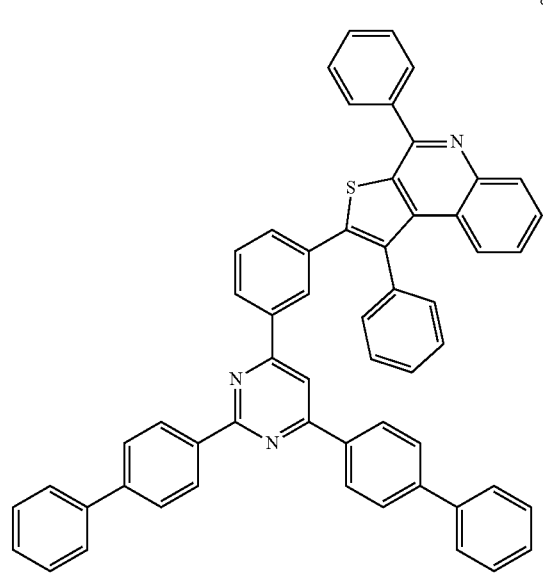

839
-continued
895
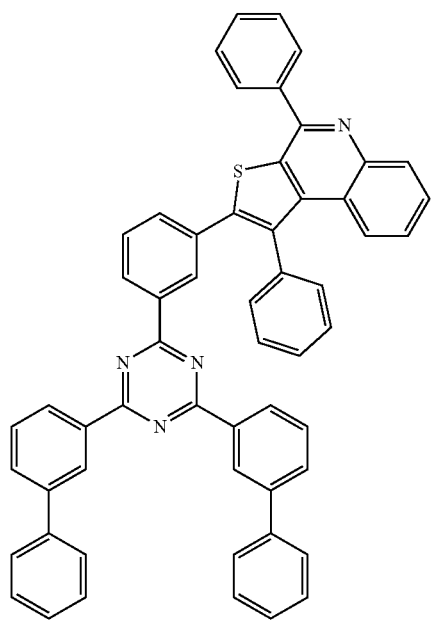
840
-continued
897
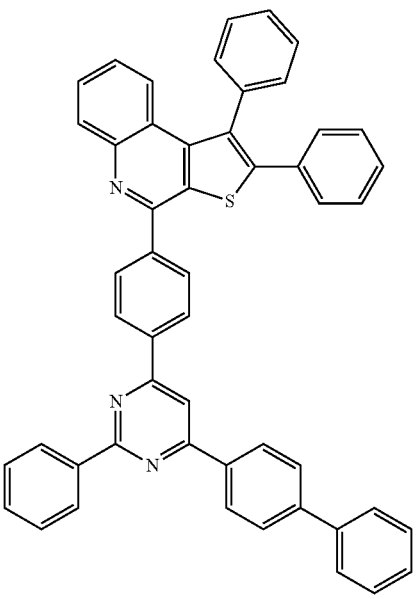
896
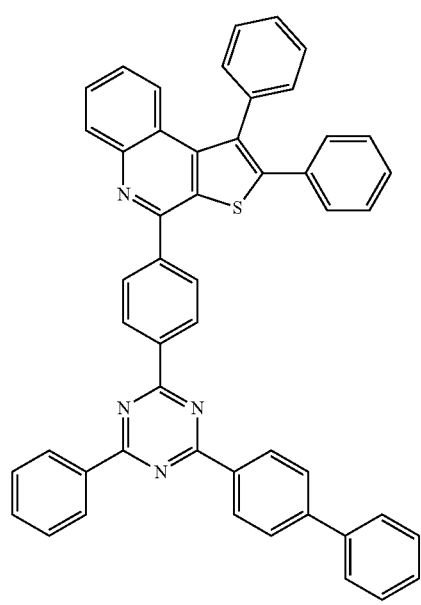
898
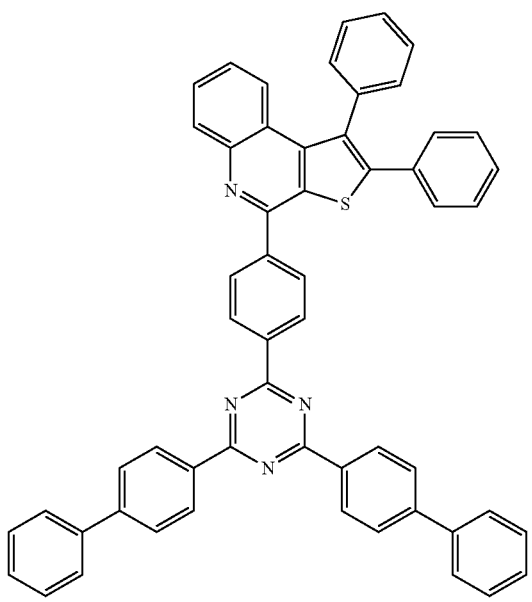

841
-continued
899
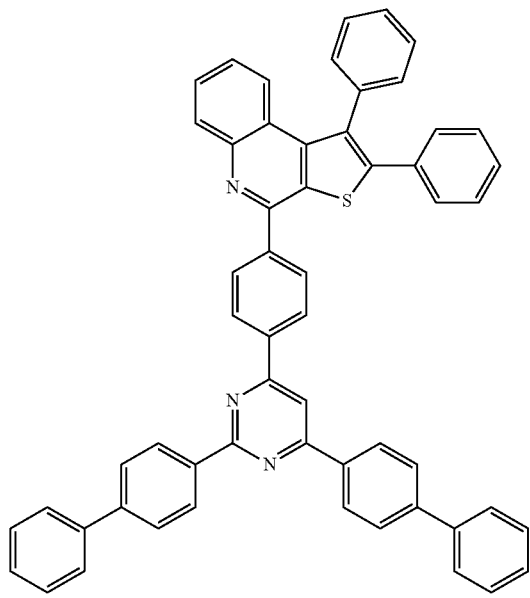
900
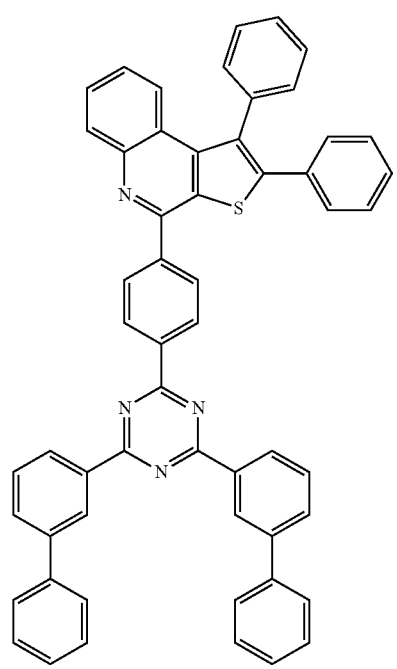
842
-continued
901
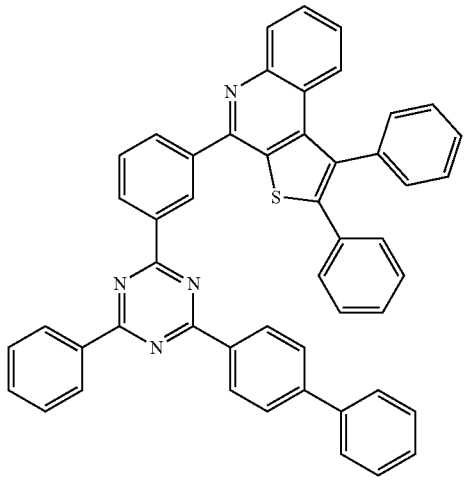
902
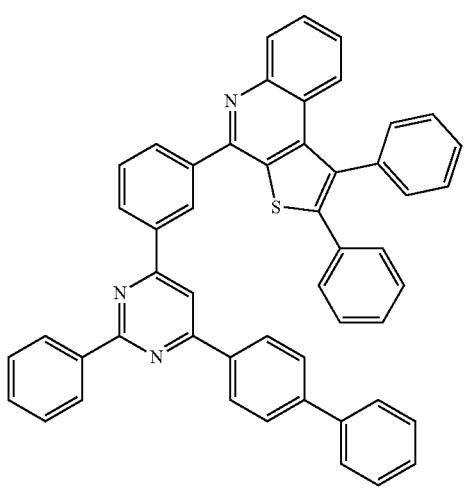
903
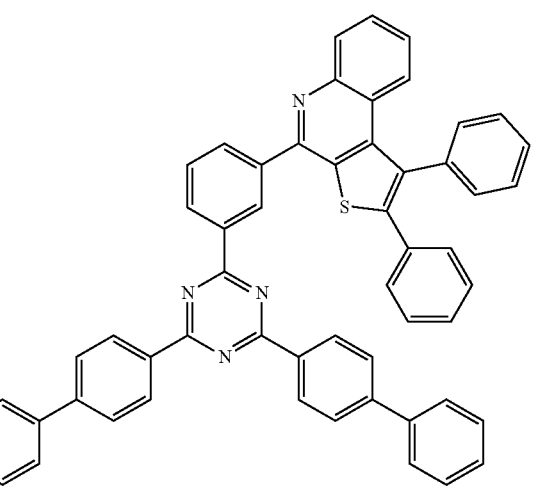

843
-continued
904
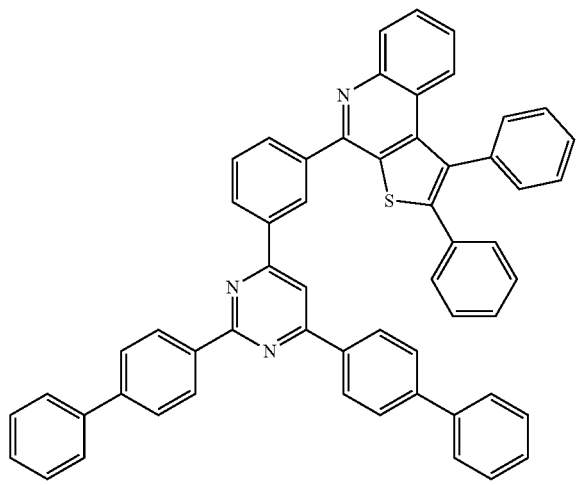
905
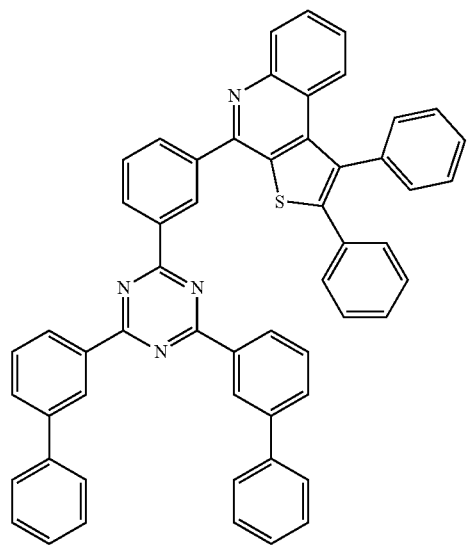
844
-continued
906
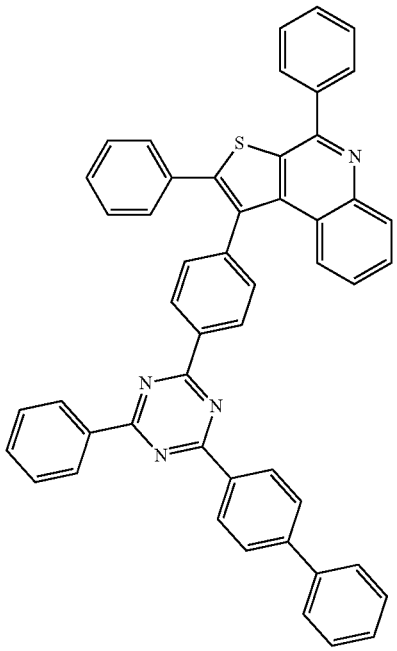
907
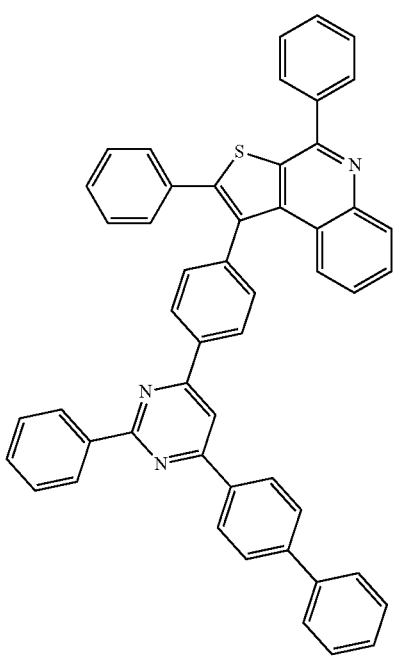

908
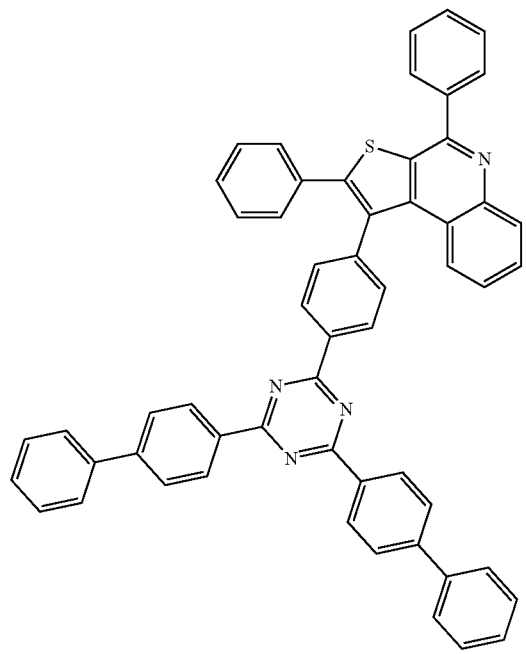
909
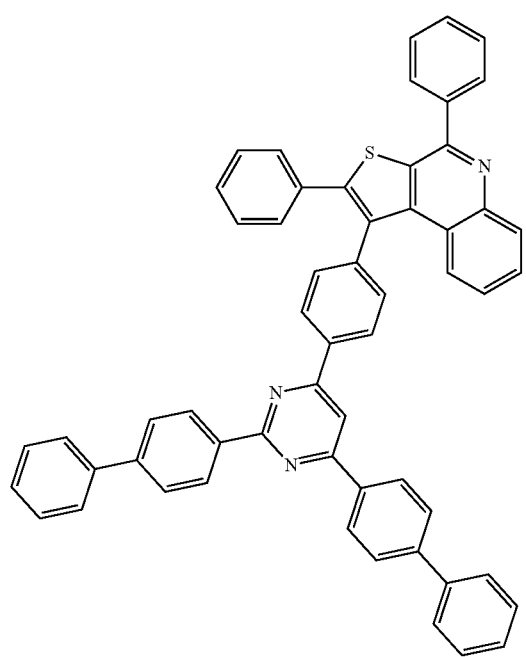
910
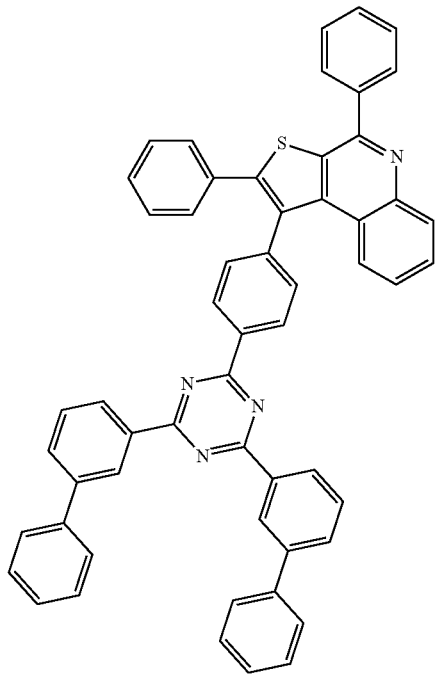
911
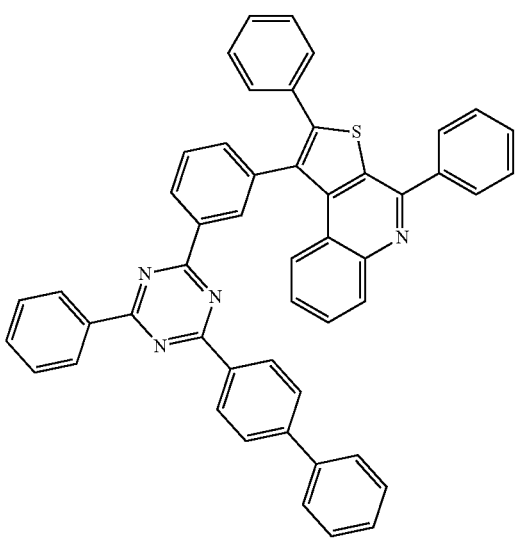

912
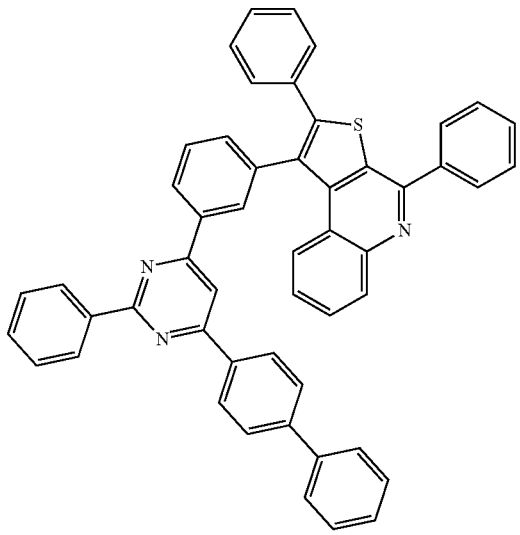
913
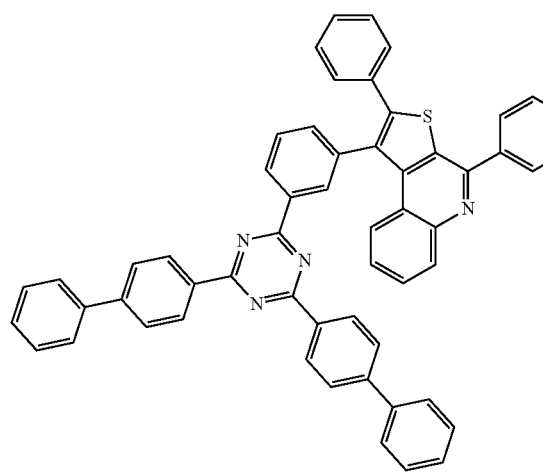
914
915
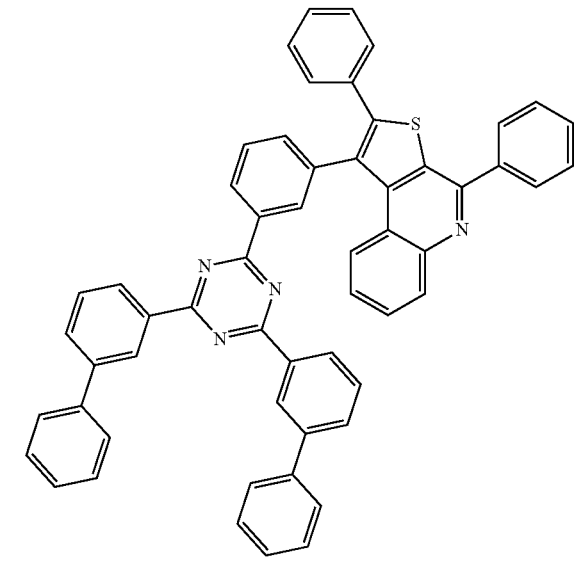
916
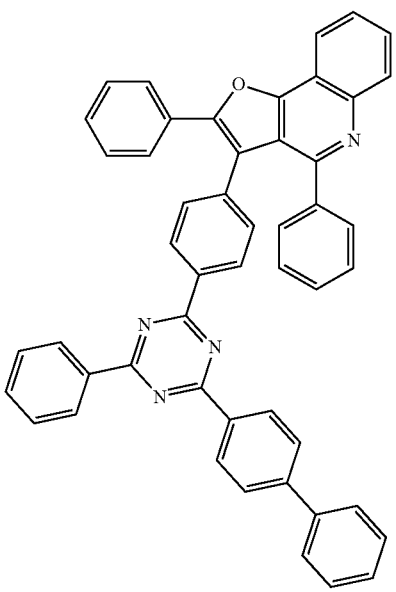

849
-continued
850
-continued
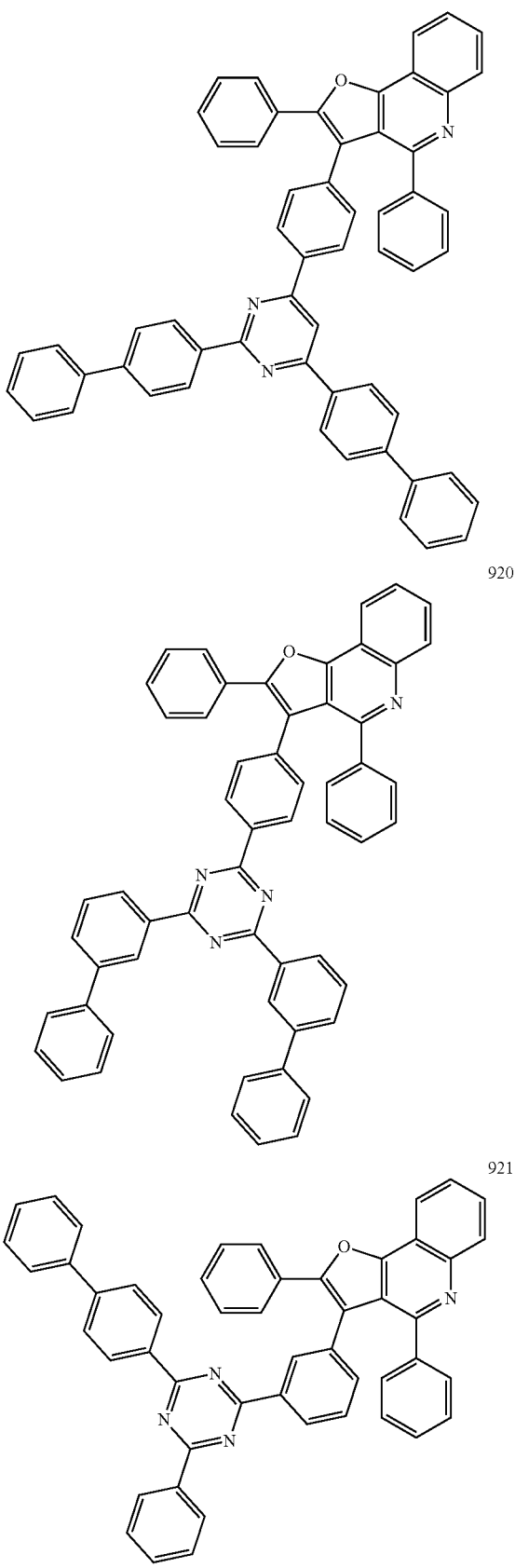

922
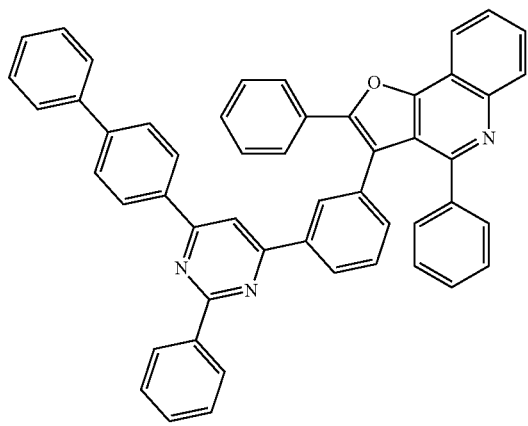
923
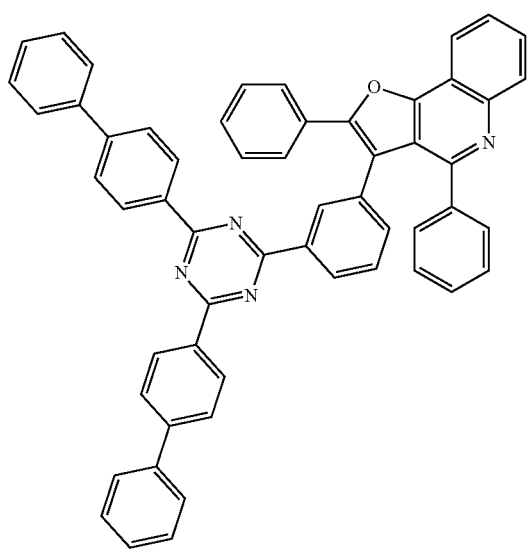
924
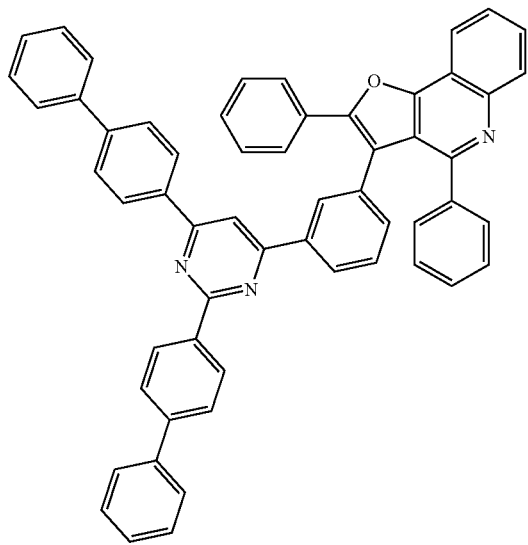
925
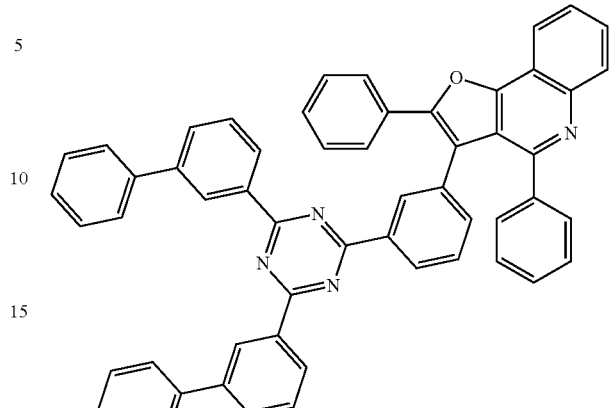
926
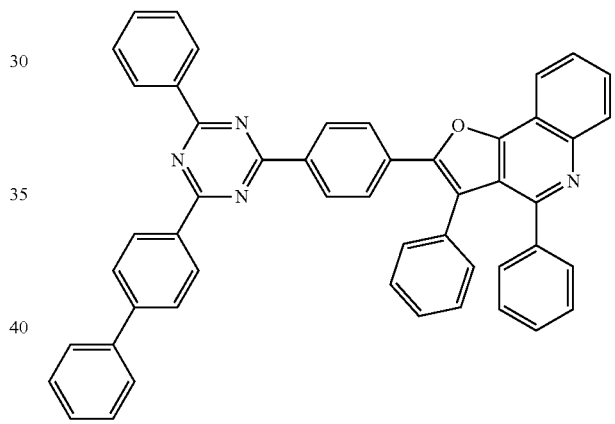
927
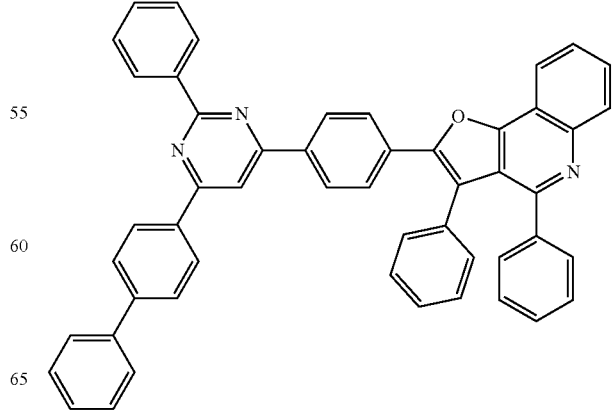

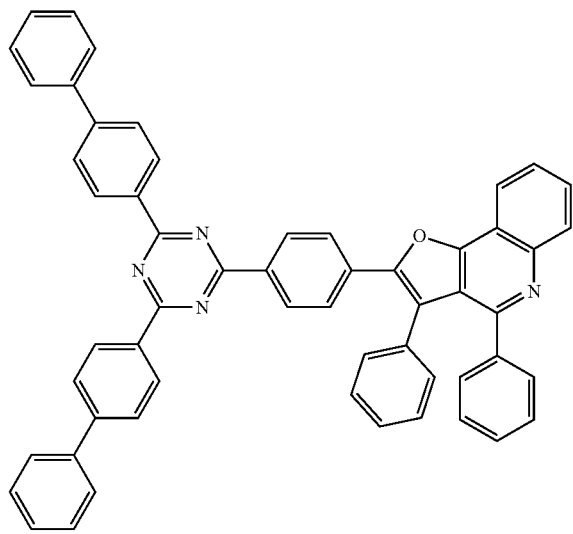
928
929
930
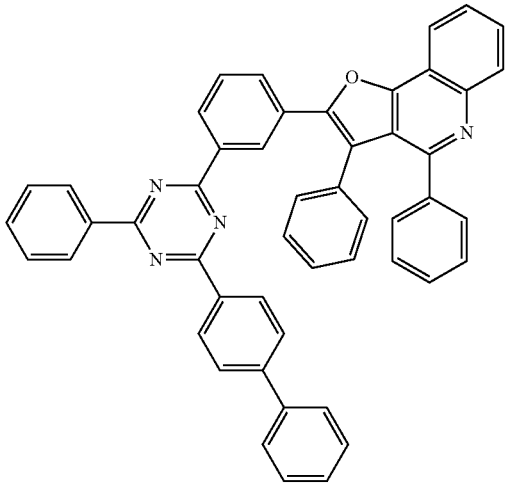
931
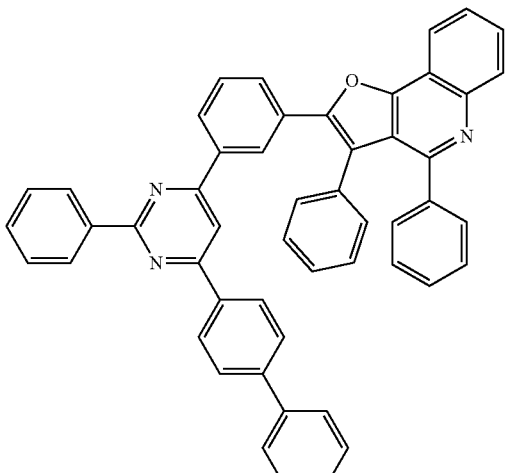
932
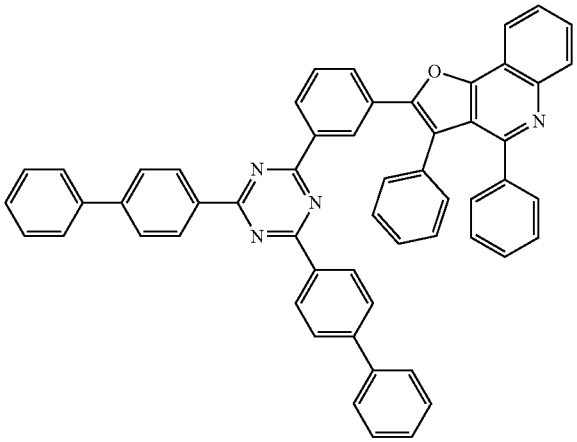
933

-continued
934
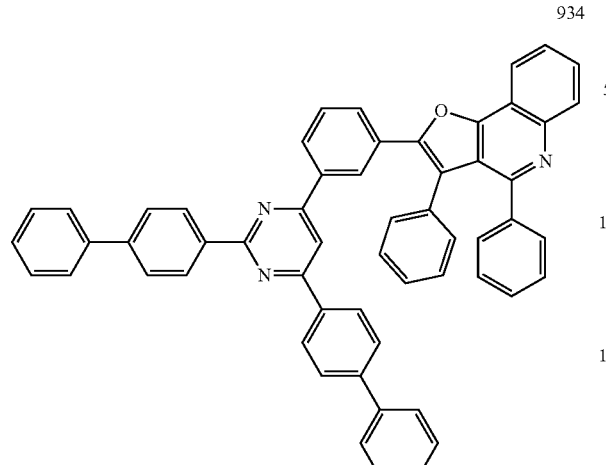
935
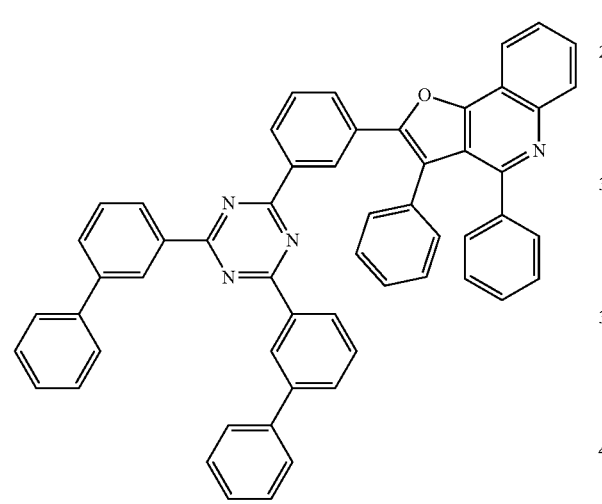
936
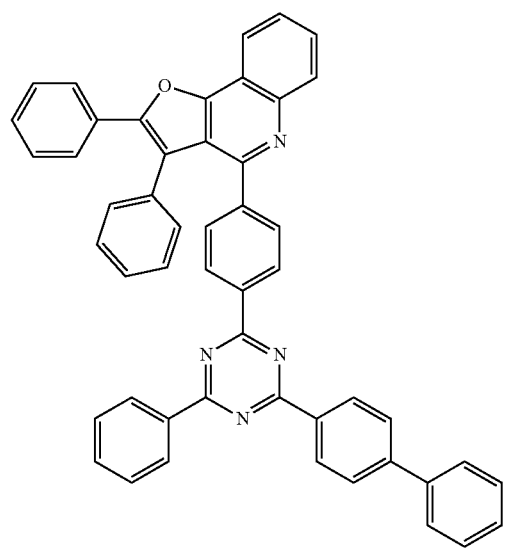
-continued
937
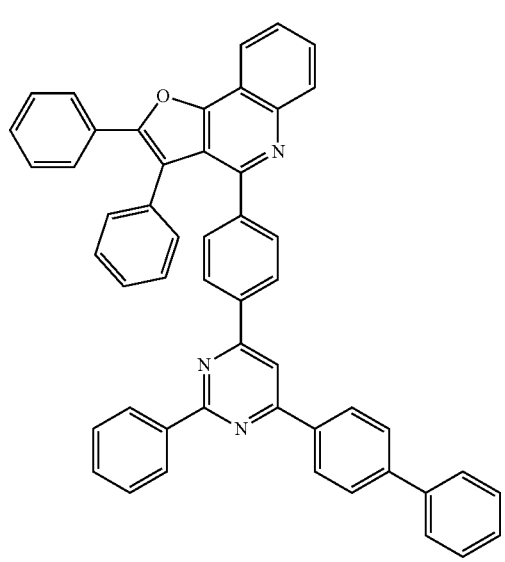
938
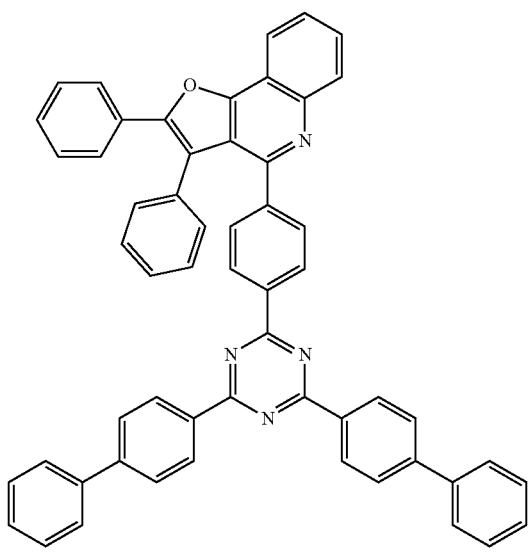

857 -continued
939
940
941
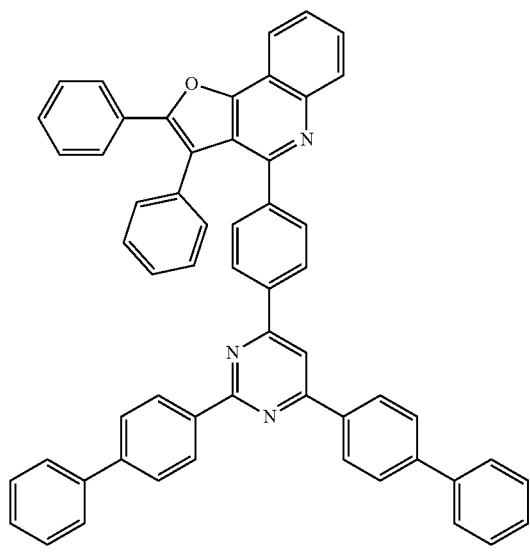
858 -continued
942
943
944
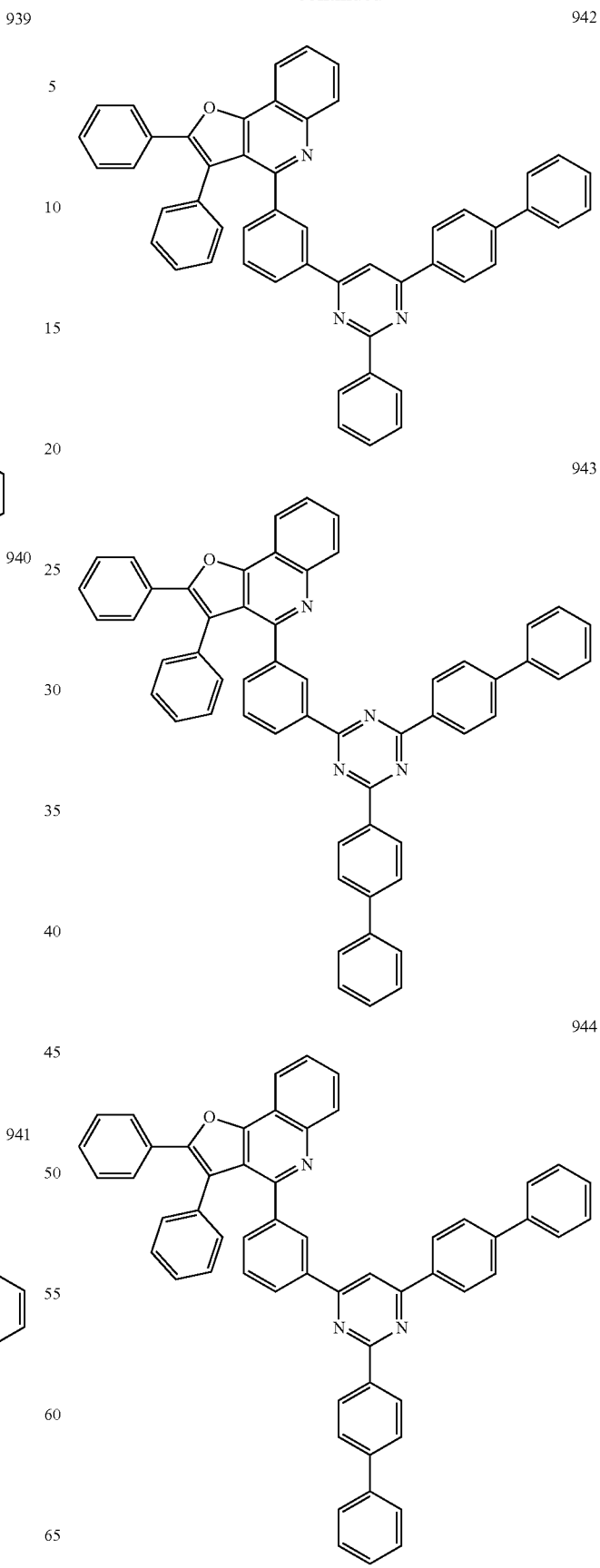

859
-continued
945
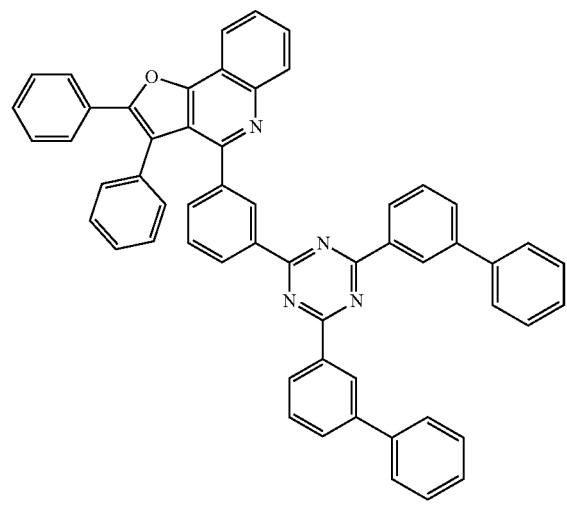
946
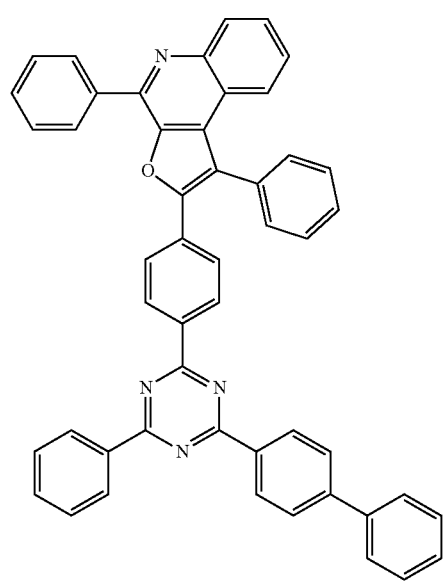
947
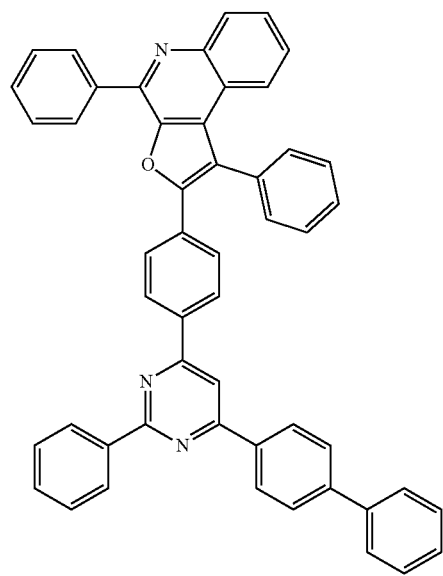
860
-continued
948
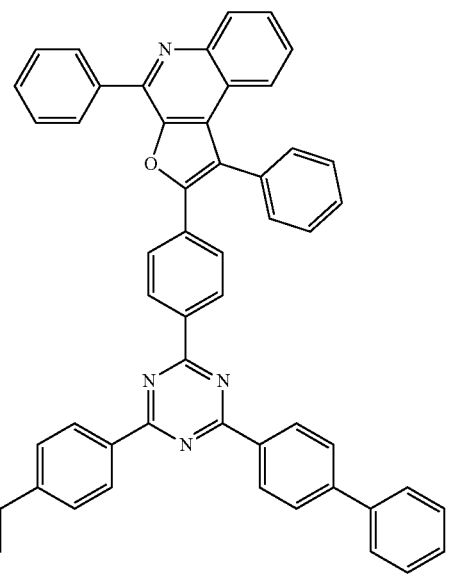
949
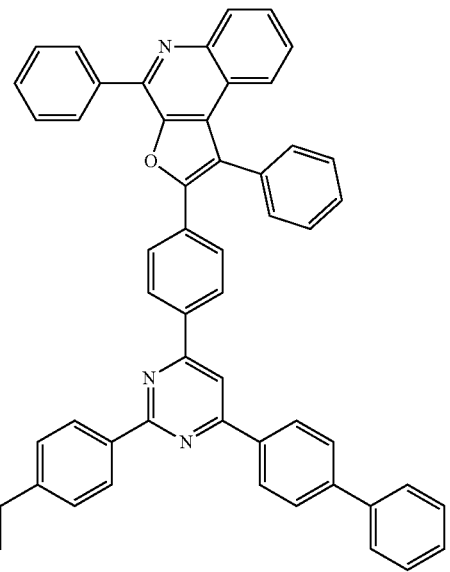

-continued
950
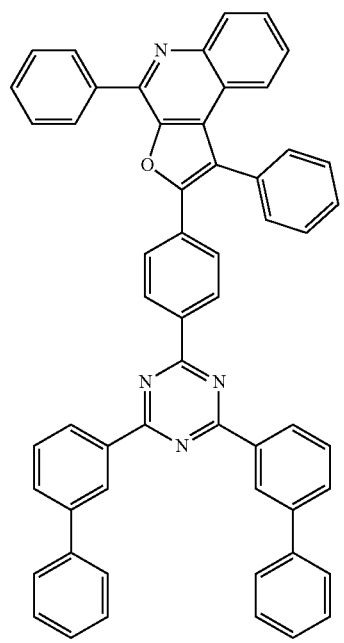
951
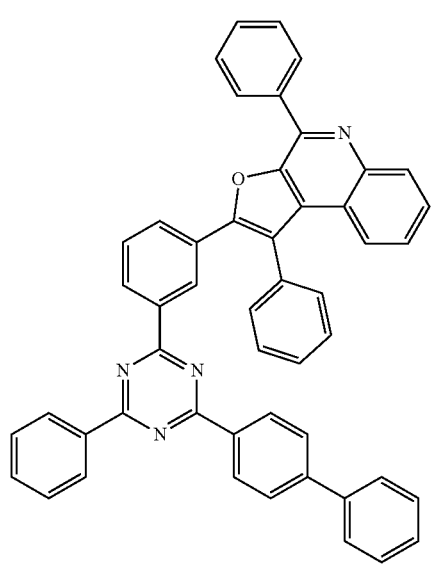
-continued
952
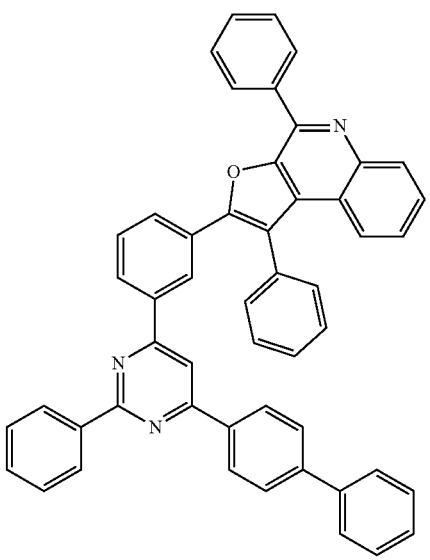
953
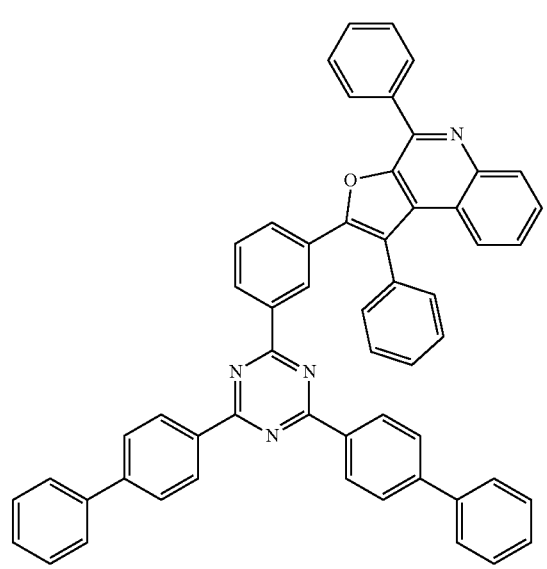

863
-continued
954
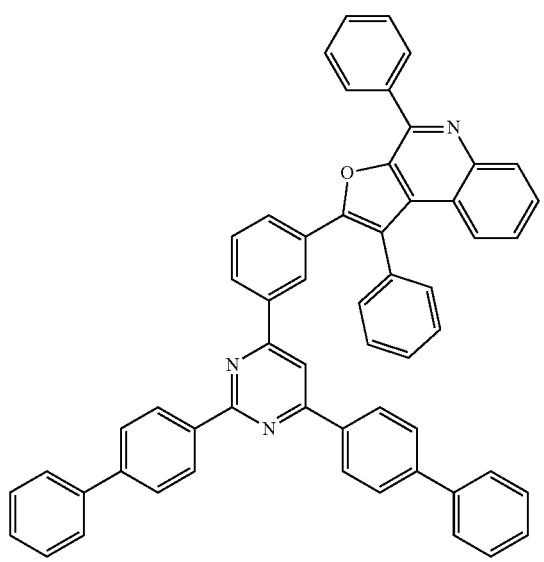
864
-continued
956
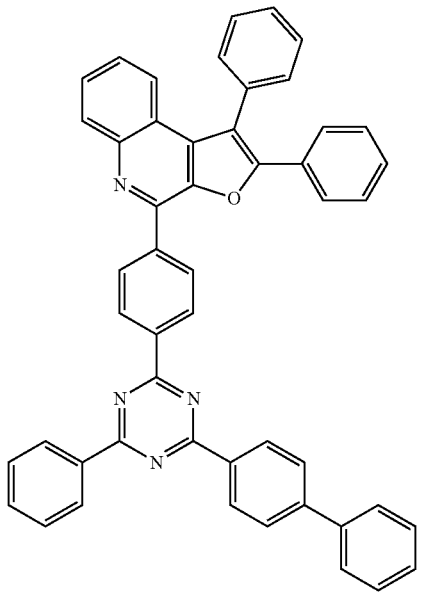
955
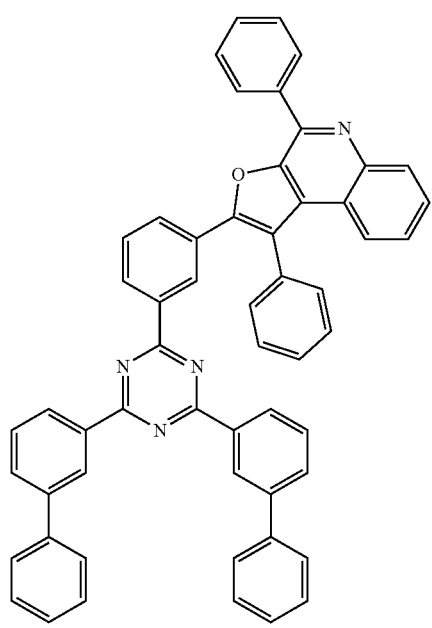
957
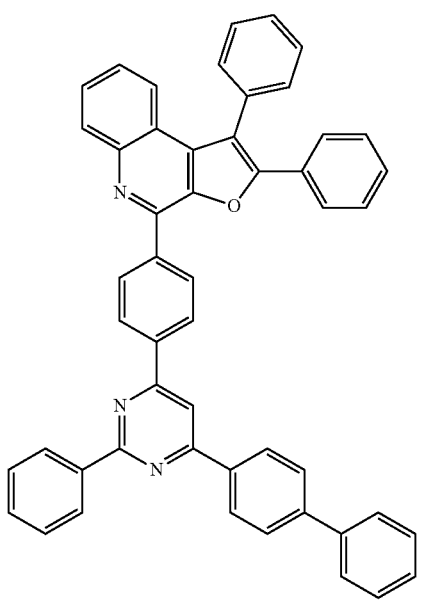

865
-continued
958
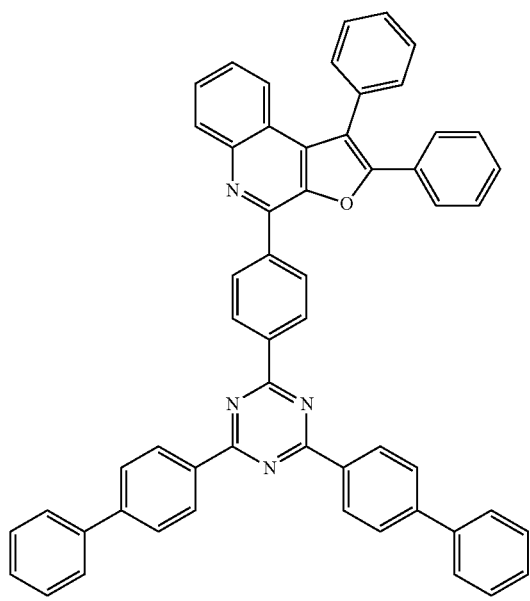
959
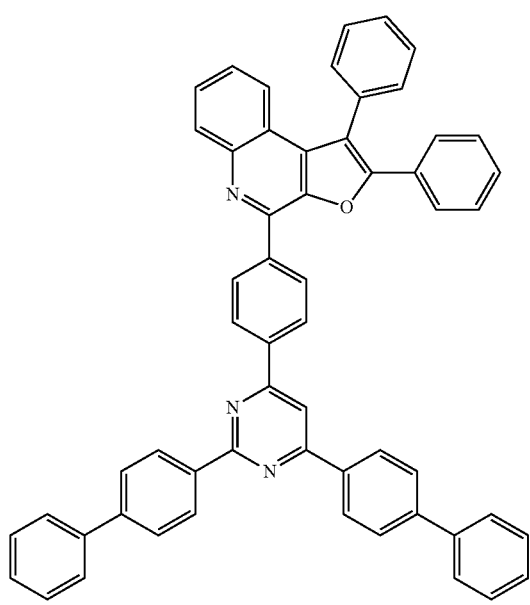
866
-continued
960
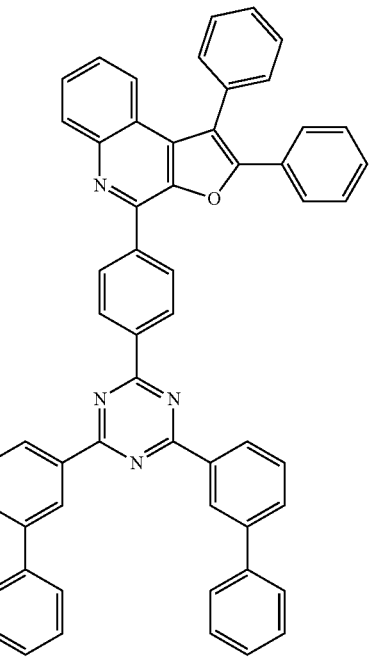
961
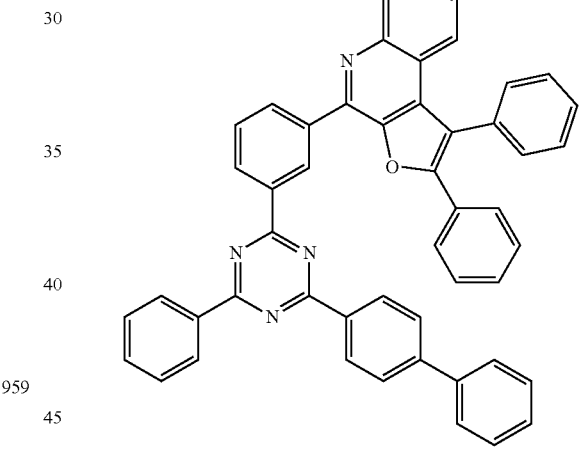
962
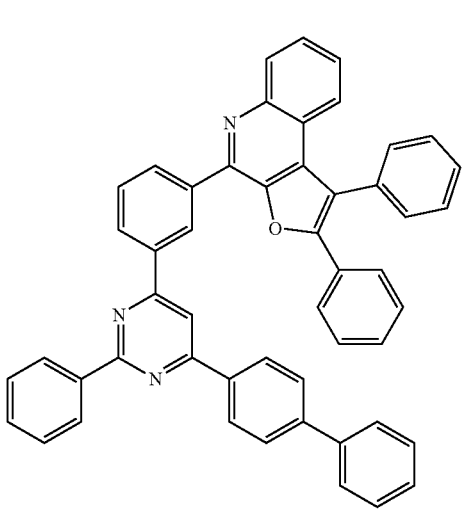

-continued
963
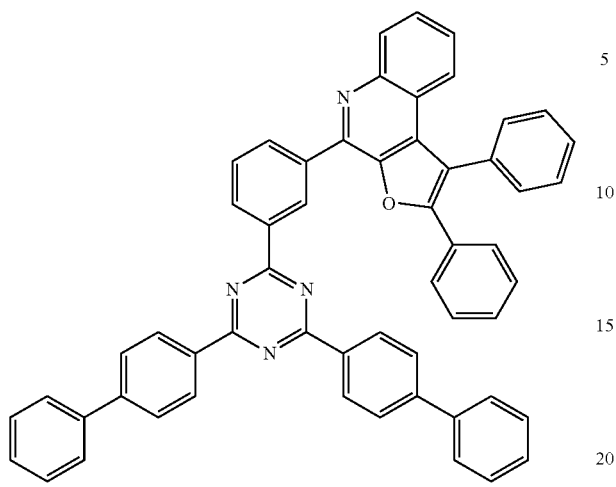
964
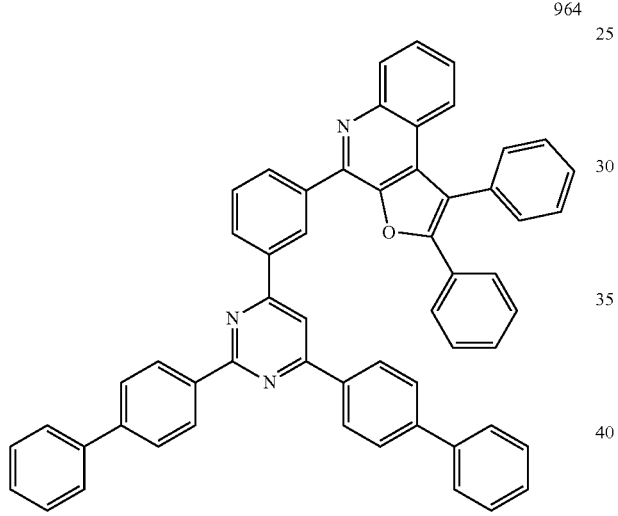
965
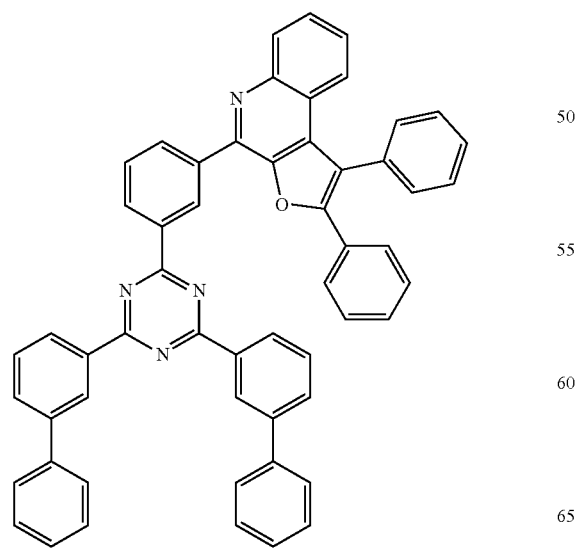
-continued
966
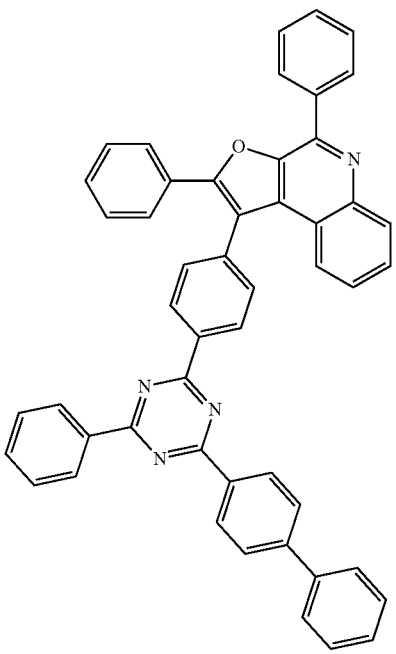
967
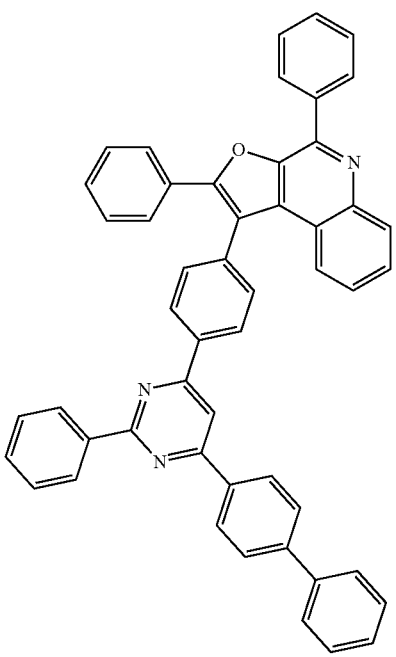

869
-continued
968
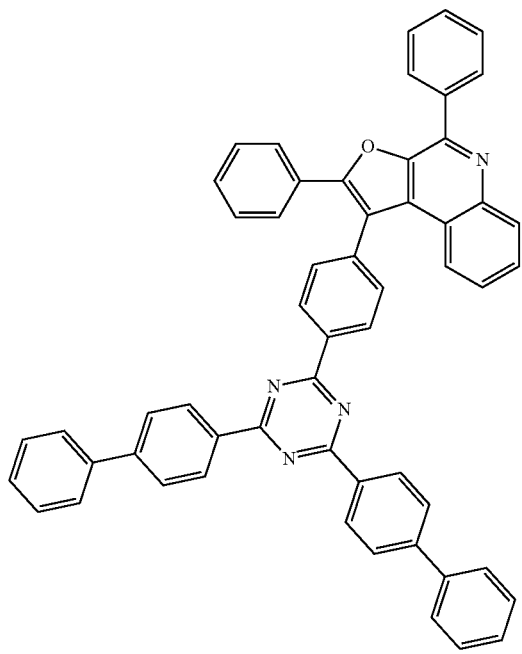
969
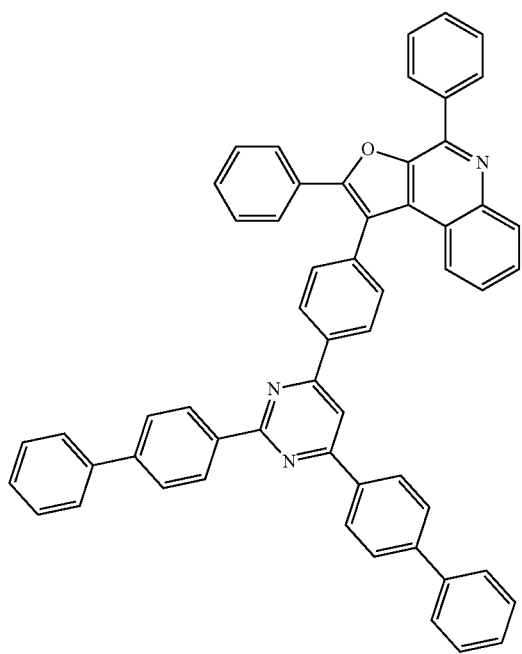
870
-continued
970
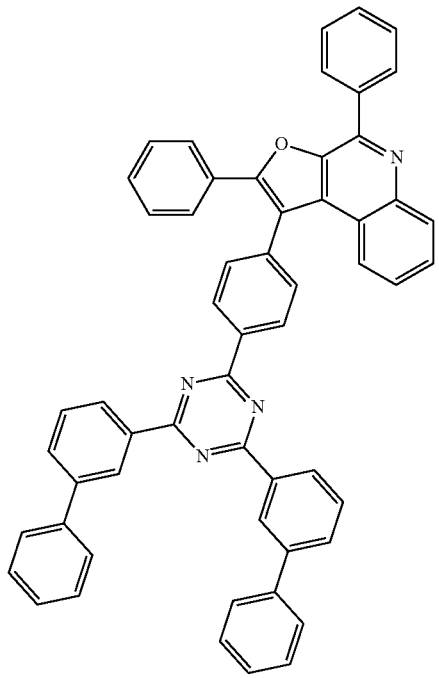
971
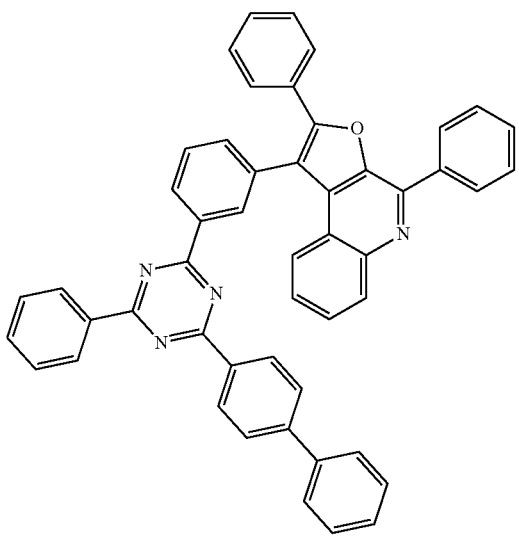

871
-continued

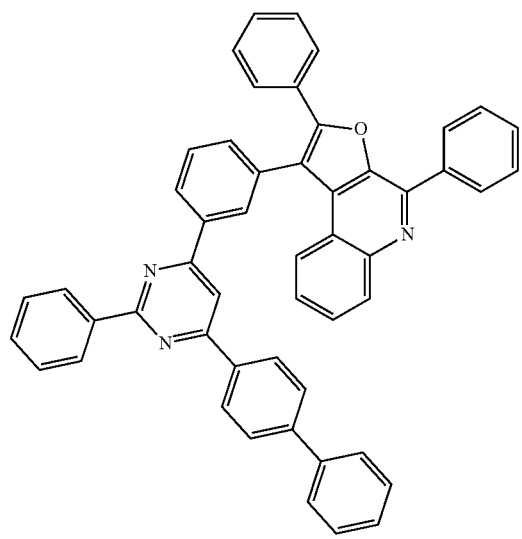
972

872
-continued

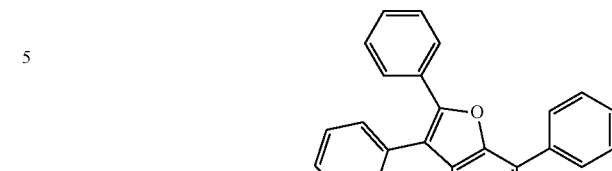
974

975

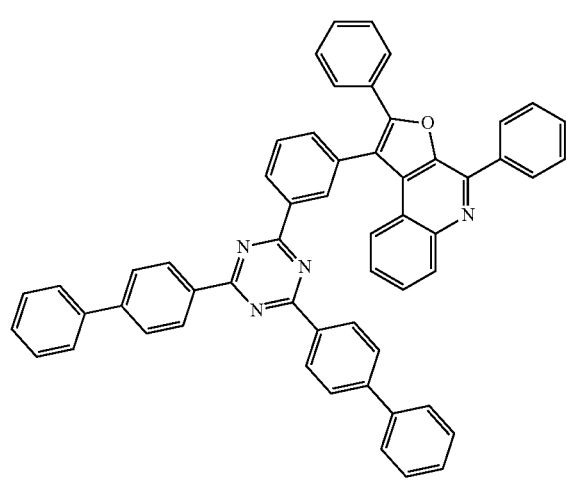
973

3. An organic optoelectronic diode comprising:
an anode and a cathode facing each other; and
at least one organic layer disposed between the anode and the cathode,
wherein the organic layer comprises the compound of claim 1.

4. The organic optoelectronic diode of claim 3, wherein the organic layer comprises an electron transfer layer, a charge generation layer, a hole blocking layer or a combination thereof, and the electron transfer layer, the charge generation layer or the hole blocking layer comprises the compound.

5. A display device comprising the organic optoelectronic diode of claim 3.

* * * * *